US009475856B2

(12) United States Patent
Mohammadi et al.

(10) Patent No.: US 9,475,856 B2
(45) Date of Patent: Oct. 25, 2016

(54) CHIMERIC FGF21 PROTEINS WITH ENHANCED BINDING AFFINITY FOR β-KLOTHO FOR THE TREATMENT OF TYPE II DIABETES, OBESITY, AND RELATED METABOLIC DISORDERS

(71) Applicant: New York University, New York, NY (US)

(72) Inventors: Moosa Mohammadi, Scarsdale, NY (US); Regina Goetz, New York, NY (US)

(73) Assignee: New York University, New York, NY (US)

( * ) Notice: Subject to any disclaimer, the term of this patent is extended or adjusted under 35 U.S.C. 154(b) by 157 days.

(21) Appl. No.: 13/784,289

(22) Filed: Mar. 4, 2013

(65) Prior Publication Data

US 2013/0231277 A1 Sep. 5, 2013

Related U.S. Application Data

(60) Provisional application No. 61/605,961, filed on Mar. 2, 2012.

(51) Int. Cl.
| | |
|---|---|
| *A61K 38/18* | (2006.01) |
| *C07K 14/50* | (2006.01) |
| *A61K 45/06* | (2006.01) |
| *G01N 33/74* | (2006.01) |
| *A61K 38/00* | (2006.01) |

(52) U.S. Cl.
CPC ............ *C07K 14/50* (2013.01); *A61K 38/1825* (2013.01); *A61K 45/06* (2013.01); *G01N 33/74* (2013.01); *A61K 38/00* (2013.01); *C07K 2319/00* (2013.01); *C07K 2319/21* (2013.01); *G01N 2333/50* (2013.01); *G01N 2500/02* (2013.01); *G01N 2800/042* (2013.01)

(58) Field of Classification Search
None
See application file for complete search history.

(56) References Cited

U.S. PATENT DOCUMENTS

| | | | |
|---|---|---|---|
| 5,132,408 A | 7/1992 | Baird et al. | |
| 5,478,804 A | 12/1995 | Calabresi et al. | |
| 6,326,484 B1 | 12/2001 | Gage et al. | |
| 6,982,170 B1 | 1/2006 | Maciag et al. | |
| 7,491,697 B2 | 2/2009 | Beals et al. | |
| 7,582,607 B2 | 9/2009 | Frye et al. | |
| 7,622,445 B2 | 11/2009 | Frye et al. | |
| 7,655,627 B2 | 2/2010 | Frye et al. | |
| 7,956,033 B2 | 6/2011 | Cheng et al. | |
| 8,168,591 B2 | 5/2012 | Takada et al. | |
| 8,642,546 B2 * | 2/2014 | Belouski et al. | 514/9.1 |
| 8,889,426 B2 | 11/2014 | Mohammadi et al. | |
| 8,889,621 B2 | 11/2014 | Mohammadi et al. | |
| 8,906,854 B2 | 12/2014 | Jonker et al. | |
| 8,951,966 B2 * | 2/2015 | Ling et al. | 514/9.1 |
| 8,999,929 B2 | 4/2015 | Mohammadi et al. | |
| 9,072,708 B2 | 7/2015 | Jonker et al. | |
| 9,272,017 B2 | 3/2016 | Mohammadi et al. | |
| 2004/0259780 A1 | 12/2004 | Glasebrook et al. | |
| 2007/0142278 A1 | 6/2007 | Beals et al. | |
| 2007/0237768 A1 | 10/2007 | Glaesner et al. | |
| 2007/0265200 A1 | 11/2007 | Glaesner et al. | |
| 2007/0293430 A1 | 12/2007 | Frye et al. | |
| 2007/0299007 A1 | 12/2007 | Frye et al. | |
| 2008/0103096 A1 | 5/2008 | Frye et al. | |
| 2008/0255045 A1 | 10/2008 | Cujec et al. | |
| 2008/0261875 A1 | 10/2008 | Etgen et al. | |
| 2009/0111742 A1 | 4/2009 | Kharitonenkov et al. | |
| 2009/0118190 A1 | 5/2009 | Beals et al. | |
| 2009/0305986 A1 | 12/2009 | Belouski et al. | |
| 2010/0062984 A1 | 3/2010 | Kumar et al. | |
| 2010/0158914 A1 | 6/2010 | Desnoyers | |
| 2010/0184665 A1 | 7/2010 | Suzuki et al. | |
| 2010/0216715 A1 | 8/2010 | Tagmose et al. | |
| 2010/0285131 A1 | 11/2010 | Belouski et al. | |
| 2010/0286042 A1 | 11/2010 | Imamura et al. | |

(Continued)

FOREIGN PATENT DOCUMENTS

| | | |
|---|---|---|
| EP | 0 645 451 B1 | 8/2001 |
| WO | 2011/047267 A1 | 4/2011 |

(Continued)

OTHER PUBLICATIONS

Presta et al., "Structure-Function Relationship of Basic Fibroblast Growth Factor: Site-Directed Mutagenesis of a Putative Heparin-Binding and Receptor-Binding Region," Biochem. Biophys. Res. Commun. 185(3):1098-1107 (1992).

Zakrzewska et al., "Increased Protein Stability of FGF1 Can Compensate for Its Reduced Affinity for Heparin," J. Biol. Chem. 284(37):25388-403 (2009).

Motomura et al., "An FGF1:FGF2 Chimeric Growth Factor Exhibits Universal FGF Receptor Specificity, Enhanced Stability and Augmented Activity Useful for Epithelial Proliferation and Radioprotection," Biochim. Biophys. Acta 1780 (12):1432-40 (2008).

(Continued)

*Primary Examiner* — Christine J Saoud
(74) *Attorney, Agent, or Firm* — LeClairRyan, a Professional Corporation

(57) ABSTRACT

The present invention relates to chimeric proteins that include an N-terminus coupled to a C-terminus, where the N-terminus includes an N-terminal portion of fibroblast growth factor 21 ("FGF21") and the C-terminus includes a C-terminal portion of fibroblast growth factor 19 ("FGF19"). The present invention also relates to pharmaceutical compositions including chimeric proteins according to the present invention, as well as methods for treating a subject suffering from diabetes, obesity, or metabolic syndrome, methods of treating a subject in need of increased FGF21-βKlotho-FGF receptor complex formation, methods of causing increased FGF21 receptor agonist-βKlotho-FGF receptor complex formation, and methods of screening for compounds with enhanced binding affinity for the βKlotho-FGF receptor complex involving the use of chimeric proteins of the present invention.

20 Claims, 18 Drawing Sheets

(56) References Cited

U.S. PATENT DOCUMENTS

| | | |
|---|---|---|
| 2010/0323954 A1 | 12/2010 | Li et al. |
| 2011/0053841 A1 | 3/2011 | Yayon et al. |
| 2011/0104152 A1 | 5/2011 | Sonoda |
| 2011/0150901 A1 | 6/2011 | Smith et al. |
| 2011/0172401 A1 | 7/2011 | Cujec et al. |
| 2011/0190207 A1 | 8/2011 | Mohammadi et al. |
| 2011/0195077 A1 | 8/2011 | Glass et al. |
| 2012/0052069 A1 | 3/2012 | Belouski et al. |
| 2012/0288886 A1 | 11/2012 | Mohammadi et al. |
| 2013/0023474 A1 | 1/2013 | Ling et al. |
| 2013/0058896 A1 | 3/2013 | Takada et al. |
| 2013/0116171 A1 | 5/2013 | Jonker et al. |
| 2013/0184211 A1 | 7/2013 | Mohammadi et al. |
| 2013/0331316 A1 | 12/2013 | Mohammadi et al. |
| 2013/0331317 A1 | 12/2013 | Mohammadi et al. |
| 2013/0331325 A1 | 12/2013 | Mohammadi et al. |
| 2014/0094406 A1 | 4/2014 | Mohammadi et al. |
| 2014/0107022 A1 | 4/2014 | Mohammadi et al. |
| 2014/0155316 A1 | 6/2014 | Mohammadi et al. |
| 2014/0171361 A1 | 6/2014 | Jonker et al. |
| 2014/0243260 A1 | 8/2014 | Mohammadi et al. |
| 2015/0111821 A1 | 4/2015 | Suh et al. |
| 2015/0343022 A1 | 12/2015 | Jonker et al. |

FOREIGN PATENT DOCUMENTS

| | | |
|---|---|---|
| WO | 2011/130729 A2 | 10/2011 |
| WO | 2013/184958 A1 | 12/2013 |
| WO | 2013/184960 A2 | 12/2013 |
| WO | 2013/184962 A1 | 12/2013 |
| WO | 2015/149069 A1 | 10/2015 |

OTHER PUBLICATIONS

Nakayama et al., "Post Treatment With an FGF Chimeric Growth Factor Enhances Epithelial Cell Proliferation to Improve Recovery From Radiation-Induced Intestinal Damage," Int. J. Radiat. Oncol. Biol. Phys. 78(3):860-7 (2010).

Kharitonenkov et al., "The Metabolic State of Diabetic Monkeys is Regulated by Fibroblast Growth Factor-21," Endocrinology 148(2):774-81 (2007).

Igarashi et al., "Characterization of Recombinant Human Fibroblast Growth Factor (FGF)-10 Reveals Functional Similarities With Keratinocyte Growth Factor (FGF-7)," J. Biol. Chem. 273(21):13230-5 (1998).

Goetz et al., "Isolated C-Terminal tail of FGF23 Alleviates Hypophosphatemia by Inhibiting FGF23-FGFR-Klotho Complex Formation," PNAS 107(1):407-412 (Epub Dec. 4, 2009).

Goetz et al., "Molecular Insights Into the Klotho-Dependent, Endocrine Mode of Action of Fibroblast Growth Factor 19 Subfamily Members," Mol. Cell. Biol. 27(9):3417-3428 (2007).

Beenken, "Structural and Biochemical Studies of FGF-FGFR Complexes," Thesis (Sep. 2011).

Ge et al., "Characterization of a FGF19 Variant With Altered Receptor Specificity Revealed a Central Role for FGFR1c in the Regulation of Glucose Metabolism," PLoS One, 7(3):e33603 (Epub Mar. 23, 2012).

Wu et al., "FGF19 Regulates Cell Proliferation, Glucose and Bile Acid Metabolism Via FGFR4-Dependent and Independent Pathways," PLoS One 6(3):e17868 (Mar. 8, 2011).

Wu et al., "Selective Activation of FGFR4 by an FGF19 Variant Does Not Improve Glucose Metabolism in OB/OB Mice," Proc. Nat'l. Acad. Sci U.S.A. 106(34):14379-84 (2009).

Mohammadi et al., "Structural Basis for Fibroblast Growth Factor Receptor Activation," Cytokine & Growth Factor Reviews 16:107-137 (2005).

Hutley et al., "Fibroblast Growth Factor 1: A Key Regulator of Human Adipogenesis," Diabetes 53:3097-3106 (2004).

Imamura et al., "Recovery of Mitogenic Activity of a Growth Factor Mutant with Nuclear Translocation Sequence," Science 249:1567-1570 (Sep. 28, 1990).

International Search Report and Written Opinion for PCT/US13/44589 (Nov. 13, 2013).

International Search Report and Written Opinion for PCT/US13/44594 (Nov. 13, 2013).

International Search Report and Written Opinion for PCT/US13/44592 (Jan. 17, 2014).

International Search Report and Written Opinion for corresponding PCT/US2013/028888 (Jul. 23, 2013).

International Search Report and Written Opinion for PCT/US14/17367 (Jun. 18, 2014).

Razzaque, "The FGF23-Klotho Axis: Endocrine Regulation of Phosphate Homeostasis," Nat. Rev. Endocrinol. 5 (11):611-19 (2009).

Yie et al., "FGF21 N- and C-Termini Play Different Roles in Receptor Interaction and Activation," FEBS Lett. 583:19-24(2009).

Andrukhova et al., "FGF23 Acts Directly on Renal Proximal Tubules to Induce Phosphaturia Through Activation of the ERK1/2-SKG1 Signaling Pathway," Bone 51(3):621-8 (Jun. 12, 2012).

Beenken et al., "Plasticity in Interactions of Fibroblast Growth Factor 1 (FGF1) N Terminus With FGF Receptors Underlies Promiscuity of FGF1," J. Biol. Chem. 287(5):3067-3078 (Nov. 4, 2011).

Jonker et al., "A PPARgamma-FGF1 Axis Is Required for Adaptive Adipose Remodelling and Metabolic Homeostasis," Nature 485(7398):391-394 (Apr. 22, 2012).

Wu et al., "A Unique FGF23 With the Ability to Activate FGFR Signaling Through Both alphaKlotho and betaKlotho," J Mol. Biol. 418:82-89 (2012).

Beenken & Mohammadi, "The Structural Biology of the FGF19 Subfamily," Adv. Exp. Med. Biol. 728:1-24 (2012).

Wu et al., "C-Terminal Tail of FGF19 Determines Its Specificity Toward Klotho Co-Receptors," J. Biol. Chem. 283 (48):33304-33309 (2008).

Goetz et al., "Conversion of a Paracrine Fibroblast Growth Factor Into an Endocrine Fibrobalst Growth Factor," J. Biol. Chem. 287(34):29134-29146 (Jun. 25, 2012).

Goetz et al., "Klotho Coreceptors Inhibit Signaling by Paracrine Fibroblast Growth Factor 8 Subfamily Ligands," Mol. Cell. Biol. 32(10):1944-1954 (Mar. 26, 2012).

Olsen et al., "Insights Into the Molecular Basis for Fibroblast Growth Factor Receptor Autoinhibition and Ligand-Binding Promiscuity," Proc. Nat'l. Acad. Sci. USA 101(4):935-940 (2004).

Wei et al., "Fibroblast Growth Factor 21 Promotes Bone Loss by Potentiating the Effects of Peroxisome Proliferator-Activated Receptor Gamma," Proc. Nat'l. Acad. Sci. USA 109(8):3143-3148 (Feb. 21, 2012).

Wu et al., "Separating Mitogenic and Metabolic Activities of Fibroblast Growth Factor 19 (FGF19)," Proc. Nat'l. Acad. Sci. USA 107(32):14158-14163 (2010).

Wu et al., "FGF19-Induced Hepatocyte Proliferation Is Mediated Through FGFR4 Activation," J. Biol. Chem. 285(8):5165-5170 (2009).

Zhang et al., "Receptor Specificity of the Fibroblast Growth Factor Family," J. Biol. Chem. 281(23):15694-15700 (2006).

PCT Search Report and Written Opinion for PCT/US2013/028888 (Jul. 23, 2013).

Abraham et al., "Human Basic Fibroblast Growth Factor: Nucleotide Sequence and Genomic Organization," EMBO J. 5(10):2523-2528 (1986).

Esch et al., "Primary Structure of Bovine Pituitary Basic Fibroblast Growth Factor (FGF) and Comparison with the Amino-Terminal Sequence of Bovine Brain Acidic FGF," PNAS 82:6507-6511 (1985).

Kurosu et al., "The Klotho Gene Family as a Regulator of Endocrine Fibroblast Growth Factors," Mol. Cel. Endocrin. 299:72-78 (2009).

Ono et al., "Novel Regulation of Fibroblast Growth Factor 2 (FGF2)-Mediated Cell Growth by Polysialic Acid," J. Biol. Chem. 287(6):3710-3722 (2012).

Schlessinger et al., "Crystal Structure of a Ternary FGF-FGFR-Heparin Complex Reveals a Dual Role for Heparin in FGFR Binding and Dimerization," Molecular Cell 6:743-750 (2000).

(56) References Cited

OTHER PUBLICATIONS

Thompson et al., "Energetic Characterization of the Basic Fibroblast Growth Factor-Heparin Interaction: Identification of the Heparin Binding Domains," Biochemistry 33:3831-3840 (1994).
5uh et al., "Endocrinization of FGF1 Produces a Neomorphic and Potent Insulin Sensitizer," Author Manuscript, Nature 513(7518):436-439 (2014).
Beenken et al., "The FGF Family: Biology, Pathophysiology and Therapy," Nat Rev Drug Discov. 8(3):235-53 (Mar. 2009).
Kurosu et al., "Tissue-specific Expression of βKlotho and Fibroblast Growth Factor (FGF) Receptor Isoforms Determines Metabolic Activity of FGF19 and FGF21," J. Biol. Chem. 282(37):26687-26695 (2007).
Micanovic et al., "Different Roles of N- and C- Termini in the Functional Activity of FGF21," J. Cell. Physiol. 219:227-234 (2009).
Kharitonenkov et al.,"FGF-21/FGF-21 Receptor Interaction and Activation is Determined by βKlotho," J. Cell. Physiol. 215:1-7 (2008).
Yao et al., "Expression and Pharmacological Evaluation of Fusion Protein FGF2I-L-Fc," Acta Pharmaceutica Sinica 46(7):787-92 (2011) (Abstract in English).
Extended European Search Report for European Application No. 13799858.9, 13 pages (dated May 3, 2016).

\* cited by examiner

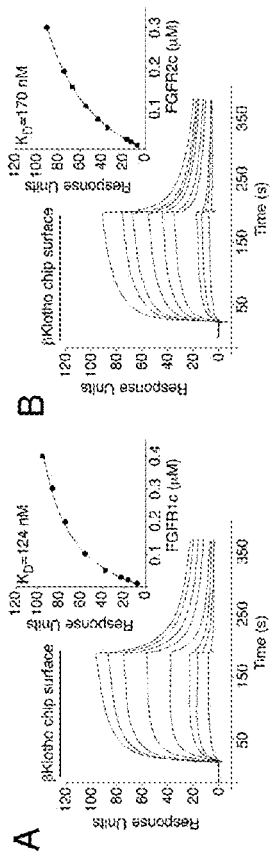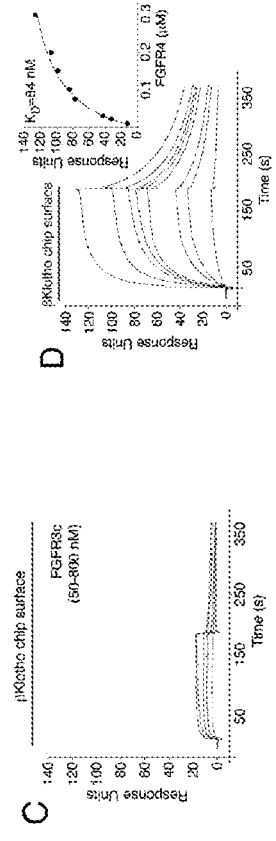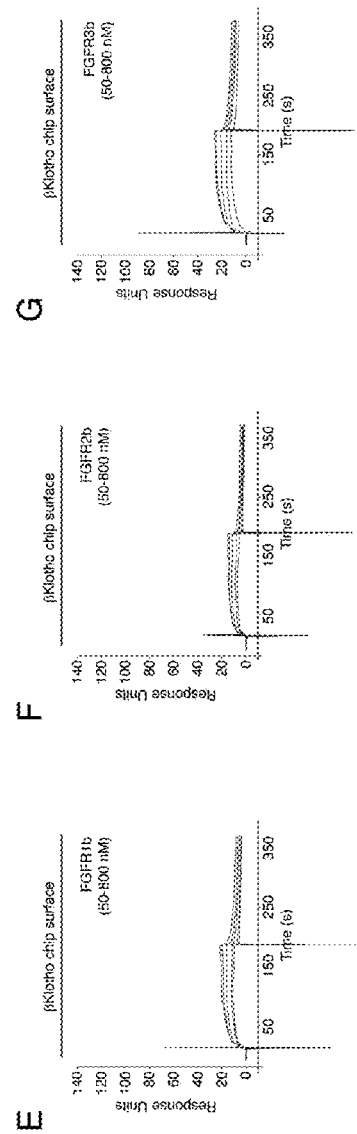
FIGS. 3A-3G

| | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| FGF19C-tail (169) | L | P | M | V | P | E | E | P | E | D | L | R | G | H | L | E | S | D | M | F | S | S | P | L | E | T | D | S | M | D | P | F | G | L | V | T | G | L | E | A | V | R | S | P | S | F | E | K | (SEQ ID NO:301) |
| FGF19C-tail/21-1 | L | P | M | V | P | E | E | P | E | D | L | R | G | H | L | E | S | D | M | F | S | S | P | L | E | T | D | S | M | D | P | F | G | L | V | T | G | L | E | A | V | R | S | P | S | F | A | K | (SEQ ID NO:302) |
| FGF19C-tail/21-2 | L | P | M | V | P | E | E | P | E | D | L | R | G | H | L | E | S | D | M | F | S | S | P | L | E | T | D | S | M | D | P | F | G | L | V | T | G | L | S | A | V | R | S | P | S | F | E | K | (SEQ ID NO:303) |
| FGF19C-tail/21-3 | L | P | M | V | P | E | E | P | E | D | L | R | G | H | L | E | S | D | M | F | S | S | P | L | E | T | D | S | M | D | P | F | G | L | V | T | G | L | E | A | V | R | S | P | S | F | E | K | (SEQ ID NO:304) |
| FGF19C-tail/21-4 | L | P | M | V | P | E | E | P | E | D | L | R | G | H | L | E | S | D | M | L | S | S | P | L | E | T | D | S | M | D | P | F | G | L | V | T | G | L | E | A | V | R | S | P | S | F | E | K | (SEQ ID NO:305) |
| FGF19C-tail/21-5 | L | P | M | V | P | E | E | P | E | D | L | R | G | H | L | E | S | D | M | F | S | S | P | L | E | T | D | S | M | D | P | F | G | M | V | T | G | L | E | A | V | R | S | P | S | F | E | K | (SEQ ID NO:306) |
| FGF19C-tail/21-6 | L | P | M | V | P | E | E | P | E | D | L | R | P | H | L | E | S | D | M | F | S | S | P | L | E | T | D | S | M | D | P | F | G | L | V | T | G | L | E | A | V | R | S | P | S | F | E | K | (SEQ ID NO:307) |
| FGF19C-tail/21-7 | L | P | M | V | P | E | E | P | E | D | L | - | - | H | L | E | S | D | M | F | S | S | P | L | E | T | D | S | M | D | P | F | G | L | V | T | G | L | E | A | V | R | S | P | S | F | E | K | (SEQ ID NO:308) |
| FGF19C-tail/21-8 | L | P | M | V | P | E | E | P | E | D | L | R | G | H | L | E | S | D | M | F | S | S | P | L | E | T | D | S | M | D | P | F | G | L | V | T | G | L | E | A | V | R | S | P | S | F | E | K | (SEQ ID NO:309) |
| FGF19C-tail/21-9 | L | P | M | V | P | A | E | P | E | D | L | R | G | H | L | E | S | D | M | F | S | S | P | L | E | T | D | S | M | D | P | F | G | L | V | T | G | L | E | A | V | R | S | P | S | F | E | K | (SEQ ID NO:310) |
| FGF19C-tail/21-10 | L | P | L | V | P | P | E | P | E | D | L | R | G | H | L | E | S | D | M | F | S | S | P | L | E | T | D | S | M | D | P | F | G | L | V | T | G | L | E | A | V | R | S | P | S | F | E | K | (SEQ ID NO:311) |
| FGF19C-tail/21-11 | L | G | M | V | P | E | E | P | E | D | L | R | G | H | L | E | S | D | M | F | S | S | P | L | E | T | D | S | M | D | P | F | G | L | V | T | G | L | E | A | V | R | S | P | S | F | E | K | |
| FGF21C-tail (168) | P | G | L | P | P | A | L | P | E | - | - | - | - | - | P | G | I | L | A | P | Q | P | P | D | V | G | S | S | D | P | L | S | M | V | - | - | G | P | S | Q | G | R | S | P | S | Y | A | S | |

FIG. 13

CHIMERIC FGF21 PROTEINS WITH ENHANCED BINDING AFFINITY FOR β-KLOTHO FOR THE TREATMENT OF TYPE II DIABETES, OBESITY, AND RELATED METABOLIC DISORDERS

This application claims the benefit of U.S. Provisional Patent Application Ser. No. 61/605,961 filed Mar. 2, 2012, which is hereby incorporated by reference in its entirety.

This invention was made with U.S. government support under DE13686, DK077276, AG019712, DK091392, and DK067158 awarded by the National Institutes of Health. The Government has certain rights in the invention.

FIELD OF THE INVENTION

This invention relates to chimeric FGF21 proteins and their use for the treatment of diabetes, obesity, and related metabolic disorders.

BACKGROUND OF THE INVENTION

Type 2 diabetes is a chronic progressive disorder, which results from end-organ resistance to the action of insulin in combination with insufficient insulin secretion from the pancreas. The metabolic abnormalities associated with insulin resistance and secretory defects, in particular the hyperglycemia, lead over the course of years to extensive irreversible damage to multiple organs including heart, blood vessels, kidney, and eye. Currently, nearly 200 million or 2.9% of the world population have type 2 diabetes (World Health Organization, Diabetes Fact Sheet No 312, January 2011; Wild et al., "Global Prevalence of Diabetes: Estimates for the Year 2000 and Projections for 2030," *Diabetes Care* 27(5):1047-1053 (2004)), and its prevalence is rising at an alarmingly fast pace in parallel with the rise in the prevalence of overweight and obesity (World Health Organization, Obesity and Overweight Fact Sheet No 311, January 2011). Until the end of the 20$^{th}$ century, type 2 diabetes was observed only in adults but what was once known as "adult-onset diabetes" is now also diagnosed in children and adolescents, and this growing incidence can be related to the increase in overweight and obesity among children and adolescents. The prevalence of pre-diabetes, an intermediate metabolic stage between normal glucose homeostasis and diabetes, is even greater than that of type 2 diabetes. Currently, nearly 80 million or 26% of the population in the United States alone have pre-diabetes (Center for Disease Control and Prevention, National Diabetes Fact Sheet 2011), and as such are at high risk for progressing to type 2 diabetes. Type 2 diabetes ranks among the ten leading causes of death worldwide, and the World Health Organization projects that mortality from diabetes (90% of which is type 2) will more than double within the next decade (World Health Organization, Diabetes Fact Sheet No 312, January 2011). Type 2 diabetes also is a major cause of disability. As a consequence of diabetic retinopathy, about 10% of all patients with diabetes in the world develop severe visual impairment and 2% become blind 15 years into the disease (World Health Organization, Diabetes Fact Sheet No 312, January 2011). Diabetic neuropathy, which affects up to half of all patients with diabetes worldwide (World Health Organization, Diabetes Fact Sheet No 312, January 2011), accounts for the majority of nontraumatic lower-limb amputations. Indeed, in its recently published first worldwide report on non-infectious diseases, the World Health Organization considers diabetes, together with other chronic non-infectious diseases like cancer and heart disease, a global economic and social burden, which exceeds that imposed by infectious diseases such as HIV/AIDS.

The current drug therapy for type 2 diabetes is focused on correcting the hyperglycemia in the patients. Although a number of small molecules and biologics with different mechanisms of anti-hyperglycemic action are available for use as mono-therapy or combination therapy, most, if not all of these have limited efficacy, limited tolerability, and significant adverse effects (Moller, "New Drug Targets for Type 2 Diabetes and the Metabolic Syndrome," *Nature* 414 (6865):821-827 (2001)). For example, treatment with sulfonylureas, glinides, thiazolidinediones, or insulin has been associated with weight gain, which is an undesired effect since overweight is considered a driving force in the pathogenesis of type 2 diabetes. Some of these treatments have also been associated with increased risk of hypoglycemia. A limitation specific to the thiazolidinediones is the potential for adverse cardiovascular effects (DeSouza et al., "Therapeutic Targets to Reduce Cardiovascular Disease in Type 2 Diabetes," *Nat Rev Drug Discov* 8(5):361-367 (2009)). A meta-analysis of clinical data on the thiazolidinedione rosiglitazone (Avandia®, which was widely used for the treatment of type 2 diabetes, found that the drug increased the risk of myocardial infarction in patients with type 2 diabetes (Nissen et al., "Effect of Rosiglitazone on the Risk of Myocardial Infarction and Death from Cardiovascular Causes," *N Engl J Med* 356(24):2457-2471 (2007)). Of all diabetic complications, cardiovascular disease is the main cause of morbidity and mortality in patients with diabetes (World Health Organization, Diabetes Fact Sheet No 312, January 2011; Center for Disease Control and Prevention, National Diabetes Fact Sheet 2011), and hence an aggravation of cardiovascular risk by drug treatment is absolutely unacceptable. In the wake of the debate about the cardiovascular safety of thiazolidinediones, the FDA issued a guidance on evaluating cardiovascular risk in new antidiabetic therapies to treat type 2 diabetes (Opar A, "Diabetes Drugs Pass Cardiovascular Risk Check," *Nat Rev Drug Discov* 8(5):343-344 (2009)). Meanwhile, thiazolidinediones lost their popularity. Even for glucagon-like peptide-1 agonists, one of the latest class of drugs introduced for the treatment of type 2 diabetes, concerns about safety have been raised, namely the potential for carcinogenicity (Opar A, "Diabetes Drugs Pass Cardiovascular Risk Check," *Nat Rev Drug Discov* 8(5):343-344 (2009)). Therefore, novel therapies that are more effective and safer than existing drugs are needed. Since the currently available drugs do not directly target complications of advanced diabetic disease, especially cardiovascular disease, therapies that are not only effective in lowering blood glucose but also reduce cardiovascular risk factors such as dyslipidemia are particularly desired.

A search conducted by Eli Lilly & Co. for potential novel biotherapeutics to treat type 2 diabetes led to the discovery of fibroblast growth factor (FGF) 21 as a protein that stimulates glucose uptake into adipocytes in an insulin-independent fashion (Kharitonenkov et al., "FGF-21 as a Novel Metabolic Regulator," *J Clin Invest* 115(6):1627-1635 (2005)). FGF21 has since emerged as a key endocrine regulator not only of glucose metabolism but also of lipid metabolism, and has become one of the most promising drug candidates for the treatment of type 2 diabetes, obesity, and metabolic syndrome. In mouse models of diabetes and obesity, pharmacologic doses of FGF21 lower plasma glucose and increase insulin sensitivity (Kharitonenkov et al., "FGF-21 as a Novel Metabolic Regulator," *J Clin Invest*

115(6):1627-1635 (2005); Coskun et al., "Fibroblast growth factor 21 corrects obesity in mice," *Endocrinology* 149(12): 6018-6027 (2008)). Concurrently, FGF21 lowers plasma triglyceride and cholesterol, enhances lipolysis and suppresses lipogenesis, and accelerates energy expenditure (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). In obese mice, FGF21 causes weight loss, in lean mice, it is weight neutral (Kharitonenkov et al., "FGF-21 as a Novel Metabolic Regulator," *J Clin Invest* 115(6):1627-1635 (2005); Coskun et al., "Fibroblast growth factor 21 corrects obesity in mice," *Endocrinology* 149(12):6018-6027 (2008)). Thus, FGF21 has some of the most desired characteristics of a drug for the treatment of type 2 diabetes; not only does it improve glycemic control, but also directly affects cardiovascular risk factors, such as hypertriglyceridemia, and reduces obesity, which is considered the single most important promoter of type 2 diabetes. Importantly, FGF21 does not induce hypoglycemia (Kharitonenkov et al., "FGF-21 as a Novel Metabolic Regulator," *J Clin Invest* 115(6):1627-1635 (2005)), a side effect that can occur with several of the current anti-diabetic therapies, including insulin. Moreover, FGF21 does not exhibit any mitogenic activity in mice (Kharitonenkov et al., "FGF-21 as a Novel Metabolic Regulator," *J Clin Invest* 115(6):1627-1635 (2005)), ruling out the possibility of a carcinogenic risk. The findings on FGF21 therapy in mouse models of diabetes have been reproduced in diabetic rhesus monkeys (Kharitonenkov et al., "The Metabolic State of Diabetic Monkeys is Regulated by Fibroblast Growth Factor-21," *Endocrinology* 148(2):774-781 (2007)), and are currently followed up with clinical trials in humans (Kharitonenkov et al., "FGF21 Reloaded: Challenges of a Rapidly Growing Field," *Trends Endocrinol Metab* 22(3):81-86 (2011)). However, there is a need for more effective FGF21 therapeutics.

The present invention overcomes these and other deficiencies in the art.

SUMMARY OF THE INVENTION

One aspect of the present invention relates to a chimeric protein that includes an N-terminus coupled to a C-terminus. The N-terminus includes an N-terminal portion of fibroblast growth factor 21 ("FGF21") having a core domain and the C-terminus includes a C-terminal portion of fibroblast growth factor 19 ("FGF19"), where either (i) the N-terminal portion of FGF21 comprises at least one amino acid residue substitution to increase stability of the FGF21 core domain compared to the wild type FGF21; (ii) the C-terminal portion of FGF19 begins at a residue corresponding to any one of residues 169 to 204 of SEQ ID NO:1 and comprises amino acid residues TGLEAV(R/N)SPSFEK (SEQ ID NO: 49); or (iii) both (i) and (ii).

Another aspect of the present invention relates to a pharmaceutical composition that includes a chimeric protein according to the present invention and a pharmaceutically acceptable carrier.

Another aspect of the present invention relates to a method of treating a subject suffering from diabetes, obesity, or metabolic syndrome. This method includes selecting a subject suffering from diabetes, obesity, or metabolic syndrome and administering to this selected subject a therapeutically effective amount of a chimeric protein according to the present invention.

Another aspect of the present invention relates to a method of treating a subject in need of increased FGF21-βKlotho-FGF receptor ("FGFR") complex formation. This method includes selecting a subject in need of increased FGF21-βKlotho-FGFR complex formation and administering to the selected subject a chimeric FGF21 protein, where the chimeric FGF21 protein comprises an FGF21 core domain and a C-terminal portion of FGF19, thereby treating a subject in need of increased FGF21-βKlotho-FGFR complex formation.

Yet another aspect of the present invention relates to a method of causing increased FGF21 receptor agonist-βKlotho-FGFR complex formation. This method comprises providing a cell comprising βKlotho and an FGFR and providing an FGF21 receptor agonist, where the agonist comprises a chimeric protein comprising a C-terminal portion of FGF19. This method also includes contacting the cell and the FGF21 receptor agonist under conditions effective to cause increased FGF21 receptor agonist-βKlotho-FGFR complex formation relative to contacting the cell with FGF21 alone, where the FGF21 has a core domain.

A further aspect of the present invention relates to a method of screening for compounds with enhanced binding affinity for βKlotho suitable for fusion to the C-terminus of an N-terminal portion of FGF21 to generate an FGF21 agonist. The method includes providing FGF21, providing βKlotho, and providing one or more candidate compounds; combining the FGF21, the βKlotho, and the candidate compounds under conditions effective for FGF21 and βKlotho to form a binary complex if present by themselves; and identifying the candidate compounds which diminish binary complex formation, compared to when the candidate compound is absent, as being potentially suitable for fusion to the C-terminus of an N-terminal portion of FGF21 to generate an FGF21 agonist.

Yet a further aspect of the present invention relates to a method of screening for compounds with enhanced binding affinity for the βKlotho-FGFR complex suitable for treatment of diabetes, obesity, or related metabolic disorders. This method includes providing FGF21, providing a binary βKlotho-FGFR complex, and providing one or more candidate compounds. This method also includes combining the FGF21, the binary βKlotho-FGFR complex, and the candidate compounds under conditions effective for the FGF21 and the βKlotho-FGFR complex to form a ternary complex if present by themselves and identifying the candidate compounds which diminish ternary complex formation compared to when the candidate compound is absent as being potentially suitable for treatment of diabetes, obesity, or related metabolic disorders.

FGF21 depends on the co-receptor βKlotho to activate its cognate FGFR (FGFR1c) in its target tissues including white adipose tissue (Ogawa et al., "βKlotho is Required for Metabolic Activity of Fibroblast Growth Factor 21," *Proc Natl Acad Sci USA* 104(18):7432-7437 (2007); Ding et al., "βKlotho is Required for Fibroblast Growth Factor 21 Effects on Growth and Metabolism," *Cell Metab* 16:387-393 (2012), which are hereby incorporated by reference in their entirety). In the course of deciphering the molecular details of how FGF21 forms a signaling complex on the cell surface with FGFR1c and βKlotho, two discoveries were made that provided the basis for the rational design of an FGF21 agonist. It was found that βKlotho promotes binding of FGF21 to its cognate FGFR by engaging ligand and receptor simultaneously through two distinct binding sites (Goetz et al., "Klotho Coreceptors Inhibit Signaling by Paracrine Fibroblast Growth Factor 8 Subfamily Ligands," *Mol Cell*

Biol 32:1944-1954 (2012), which is hereby incorporated by reference in its entirety). βKlotho plays the same role in promoting binding of FGF19, an endocrine regulator of bile acid homeostasis, to its cognate FGFR (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). The binding site for βKlotho was mapped on FGF21 and FGF19 to the C-terminal region of each ligand that follows the β-trefoil core domain (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). In the course of these studies, it was found that the C-terminal tail peptides of FGF21 and FGF19 share a common binding site on βKlotho, and that the C-terminal tail of FGF19 binds tighter than the C-terminal tail of FGF21 to this site (Goetz et al., "Klotho Coreceptors Inhibit Signaling by Paracrine Fibroblast Growth Factor 8 Subfamily Ligands," *Mol Cell Biol* 32:1944-1954 (2012), which is hereby incorporated by reference in its entirety). As described herein, chimeric FGF21 proteins were made in which C-terminal sequences in FGF21 were replaced with the corresponding sequences of FGF19, which was found to confer greater binding affinity of βKlotho to the chimeras, and, hence, enhance agonistic properties.

In another approach of engineering an FGF21 agonist, residues in the β-trefoil core domain of FGF21 were mutated in order to increase the stability of FGF21. Based on extensive knowledge of the structures of FGF ligands, including the structures of FGF19 and FGF23, Q104 of FGF21 was selected for mutagenesis. As described herein, it was found that replacing Q104 with methionine, which is found in all other FGF ligands at the corresponding position (Mohammadi et al., "Structural Basis for Fibroblast Growth Factor Receptor Activation," *Cytokine & Growth Factor Rev* 16(2):107-137 (2005), which is hereby incorporated by reference in its entirety) increases the stability of FGF21 without affecting ligand-binding affinity for receptor. This enhanced affinity for βKlotho, together with the enhanced stability, make these chimeric proteins particularly suitable for use as a therapeutic.

BRIEF DESCRIPTION OF THE DRAWINGS

FIG. 1A shows a size-exclusion chromatogram of the 1:1 FGFR1c-βKlotho complex. Arrows indicate the retention times of molecular size standards, the void volume ($V_v$) and the column volume ($V_c$). Proteins of column peak fractions were resolved on 14% SDS-polyacrylamide gels and stained with Coomassie Blue. FIG. 1B shows a size-exclusion chromatogram of the ternary FGF21-FGFR1c-βKlotho complex. Arrows indicate the retention times of molecular size standards, the void volume ($V_v$) and the column volume ($V_c$). Proteins of column peak fractions were resolved on 14% SDS-polyacrylamide gels and stained with Coomassie Blue. FIG. 1C shows a representative surface plasmon resonance (SPR) sensorgram illustrating binding of FGF21 to the binary FGFR1c-βKlotho complex. FGF21 was immobilized on a biosensor chip, and increasing concentrations of FGFR1c-βKlotho complex were passed over the chip. FIG. 1D shows a representative SPR sensorgram illustrating no interaction between FGF21 and the binary FGFR1c-αKlotho complex. FGF21 was immobilized on a biosensor chip, and two concentrations of FGFR1c-αKlotho complex were passed over the chip.

FIG. 2A shows a size-exclusion chromatogram of the 1:1 FGFR4-βKlotho complex. Arrows indicate the retention times of molecular size standards, the void volume ($V_v$) and the column volume ($V_c$). Proteins of column peak fractions were resolved on 14% SDS-polyacrylamide gels and stained with Coomassie Blue. FIG. 2B shows a size-exclusion chromatogram of the ternary FGF19-FGFR4-βKlotho complex. Arrows indicate the retention times of molecular size standards, the void volume ($V_v$) and the column volume ($V_c$). Proteins of column peak fractions were resolved on 14% SDS-polyacrylamide gels and stained with Coomassie Blue.

FIGS. 3A-3G show the FGFR binding specificity profile of βKlotho. FIG. 3A shows an overlay of SPR sensorgrams of FGFR1c binding to βKlotho, and fitted saturation binding curve. FIG. 3B shows an overlay of SPR sensorgrams of FGFR2c binding to βKlotho, and fitted saturation binding curve. FIG. 3C shows an overlay of SPR sensorgrams of FGFR3c binding to βKlotho. FIG. 3D shows an overlay of SPR sensorgrams of FGFR4 binding to βKlotho, and fitted saturation binding curve. FIG. 3E shows an overlay of SPR sensorgrams of FGFR1b binding to βKlotho. FIG. 3F shows an overlay of SPR sensorgrams of FGFR2b binding to βKlotho. FIG. 3G shows an overlay of SPR sensorgrams of FGFR3b binding to βKlotho. βKlotho ectodomain was immobilized on a biosensor chip, and increasing concentrations of the ligand-binding domain of each of the seven principal human FGFRs were passed over the chip. Where binding was observed, the dissociation constant ($K_D$) was calculated from the saturation binding curve. The data shown in FIGS. 3A-G are representative of two to five independent experiments.

FIG. 4A shows an overlay of SPR sensorgrams illustrating βKlotho binding to FGF19. FGF19 was immobilized on a biosensor chip, and increasing concentrations of βKlotho ectodomain were passed over the chip. FIG. 4B shows an overlay of SPR sensorgrams illustrating βKlotho binding to FGF21. FGF21 was immobilized on a biosensor chip, and increasing concentrations of βKlotho ectodomain were passed over the chip. Note that for any given concentration of βKlotho, the binding response is greater on the FGF19 chip surface than on the FGF21 chip surface. Also note that the FGF19-βKlotho complex dissociates more slowly than the FGF21-βKlotho complex (compare the dissociation phases of the sensorgrams shown in (A) and (B)). FIG. 4C shows an overlay of SPR sensorgrams illustrating no interaction between βKlotho and FGF23. FGF23 was immobilized on a biosensor chip, and increasing concentrations of βKlotho ectodomain were passed over the chip. FIG. 4D shows an overlay of SPR sensorgrams illustrating no interaction between αKlotho and FGF19. FGF19 was immobilized on a biosensor chip, and increasing concentrations of αKlotho ectodomain were passed over the chip. FIG. 4E shows an overlay of SPR sensorgrams illustrating no interaction between αKlotho and FGF21. FGF21 was immobilized on a biosensor chip, and increasing concentrations of αKlotho ectodomain were passed over the chip. The data shown in FIGS. 4A-E are representative of two to three independent experiments.

FIG. 5A shows an alignment of the C-terminal tail sequences of human FGF19 (SEQ ID NO:1), FGF21 (SEQ ID NO:100), and FGF23 (SEQ ID NO:223). Residue numbers are in parenthesis to the left of the alignment. Gaps (dashes) were introduced to optimize the alignment. Residues that are identical between FGF19 and FGF21 are shaded gray. Note that 40% of these residues map to the most C-terminal sequence. FIG. 5B shows an overlay of SPR sensorgrams illustrating inhibition by the FGF19 C-terminal tail peptide (M171 to K216 of SEQ ID NO:1; FGF19$^{C\text{-}tail}$) of βKlotho binding to FGF19. FGF19 was immobilized on a biosensor chip, and mixtures of a fixed concentration of βKlotho ectodomain with increasing concentrations of FGF19$^{C\text{-}tail}$ were passed over the chip. FIG. 5C shows an overlay of SPR sensorgrams illustrating inhibition by the FGF21 C-terminal tail peptide (P168 to S209 of SEQ ID NO:100; FGF21$^{C\text{-}tail}$) of βKlotho binding to FGF19. Mixtures of a fixed concentration of βKlotho ectodomain with increasing concentrations of FGF21$^{C\text{-}tail}$ were passed over a biosensor chip onto which FGF19 had been immobilized. FIG. 5D shows an overlay of SPR sensorgrams illustrating no inhibition by the FGF23 C-terminal tail peptide (S180 to I251 of SEQ ID NO:223; FGF23$^{C\text{-}tail}$) of βKlotho binding to FGF19. βKlotho ectodomain and FGF23$^{C\text{-}tail}$ were mixed at a molar ratio of 1:2, and the mixture was injected over a biosensor chip onto which FGF19 had been immobilized. FIG. 5E shows an overlay of SPR sensorgrams illustrating inhibition by the FGF21 C-terminal tail peptide (P168 to S209 of SEQ ID NO:100; FGF21$^{C\text{-}tail}$) of βKlotho binding to FGF21. FGF21 was immobilized on a biosensor chip, and mixtures of a fixed concentration of βKlotho ectodomain with increasing concentrations of FGF21$^{C\text{-}tail}$ were passed over the chip. FIG. 5F shows an overlay of SPR sensorgrams illustrating inhibition by the FGF19 C-terminal tail peptide (M171 to K216 of SEQ ID NO:1; FGF19$^{C\text{-}tail}$) of βKlotho binding to FGF21. Mixtures of a fixed concentration of βKlotho ectodomain with increasing concentrations of FGF19$^{C\text{-}tail}$ were passed over a biosensor chip onto which FGF21 had been immobilized. FIG. 5G shows an overlay of SPR sensorgrams illustrating no inhibition by the FGF23 C-terminal tail peptide (S180 to I251 of SEQ ID NO:223; FGF23$^{C\text{-}tail}$) of βKlotho binding to FGF21. βKlotho ectodomain and FGF23$^{C\text{-}tail}$ were mixed at a molar ratio of 1:2, and the mixture was injected over a biosensor chip onto which FGF21 had been immobilized. The data shown in FIGS. 5B-G are representative of two to three independent experiments.

FIG. 6A shows an immunoblot analysis for phosphorylation of FRS2α (pFRS2α) and 44/42 MAP kinase (p44/42 MAPK) in the rat hepatoma cell line H4IIE, which had been stimulated with either FGF19 or FGF19$^{C\text{-}tail}$ alone, or with mixtures of FGF19 with increasing concentrations of FGF19$^{C\text{-}tail}$. Numbers above the lanes give the amounts of protein/peptide added in ng ml$^{-1}$. To control for equal sample loading, the protein blots were probed with an antibody recognizing both phosphorylated and nonphosphorylated (total) 44/42 MAP kinase (44/42 MAPK). FIG. 6B shows an immunoblot analysis for phosphorylation of FRS2α (pFRS2α) and 44/42 MAP kinase (p44/42 MAPK) in the rat hepatoma cell line H4IIE, which had been stimulated with either FGF19 or FGF21$^{C\text{-}tail}$ alone, or with mixtures of FGF19 with increasing concentrations of FGF21$^{C\text{-}tail}$. Numbers above the lanes give the amounts of protein/peptide added in ng ml$^{-1}$. To control for equal sample loading, the protein blots were probed with an antibody recognizing both phosphorylated and nonphosphorylated (total) 44/42 MAP kinase (44/42 MAPK). The data shown in FIGS. 6A-B are representative of two independent experiments. Note that while FGF21$^{C\text{-}tail}$ can inhibit FGF19 signaling in H4IIE cells, this cell line is otherwise not responsive to FGF21.

FIG. 7A shows an overlay of SPR sensorgrams illustrating inhibition by FGF21 in solution of βKlotho binding to FGF21 immobilized on a biosensor chip. Increasing concentrations of FGF21 were mixed with a fixed concentration of βKlotho ectodomain, and the mixtures were passed over a FGF21 chip. FIG. 7B shows an overlay of SPR sensorgrams illustrating inhibition by the FGF21$^{29\text{-}190}$/FGF 19$^{197\text{-}216}$ chimera of βKlotho binding to FGF21 immobilized on a biosensor chip. Increasing concentrations of FGF21$^{29\text{-}190}$/FGF19$^{197\text{-}216}$ chimera were mixed with a fixed concentration of βKlotho ectodomain, and the mixtures were passed over a FGF21 chip. FIG. 7C shows an overlay of SPR sensorgrams illustrating inhibition by the FGF21$^{29\text{-}190}$/FGF19$^{197\text{-}216}$ chimera or FGF21 of βKlotho binding to immobilized FGF21. The figure was created from the data shown in FIGS. 7A-B, which are representative of two independent experiments.

FIG. 8A shows a schematic of the FGF21$^{29\text{-}167}$/FGF19$^{169\text{-}216}$ chimera claimed as an FGF21 agonist herein. The amino acid boundaries of each component of the chimera are labeled. The FGF19 portion of the chimera is shaded gray. FIG. 8B shows a sequence alignment of human FGF19 and FGF21. Residue numbers are in parenthesis to the left of the alignment. The secondary structure elements known for FGF19 (β1-β12, α11) are indicated above the alignment, and FGF19 residues containing these elements are boxed. A dashed line across the alignment marks the junction between the FGF homology core domain and the C-terminal tail of FGF19 and FGF21. Gaps (dashes) were introduced to optimize the sequence alignment. Residues that are identical between FGF19 and FGF21 are shaded gray.

FIG. 9 shows a sequence alignment of the FGF homology core domain and its N-terminal extension of FGF21 orthologs (including human (SEQ ID NO: 100), orangutan (SEQ ID NO: 101), chimpanzee (SEQ ID NO: 102), elephant (SEQ ID NO: 115), dog (SEQ ID NO: 103), pig (SEQ ID NO: 116), bovine (SEQ ID NO: 104), horse (SEQ ID NO: 105), panda (SEQ ID NO: 106), rabbit (SEQ ID NO: 107), squirrel (SEQ ID NO: 114), rat (SEQ ID NO: 119), and mouse (SEQ ID NO: 120)). Residue numbers are in parenthesis to the left of the alignment. Gaps (dashes) were introduced to optimize the alignment. Ortholog residues identical to human FGF21 (SEQ ID NO: 100) are shaded gray. This illustrates the high degree of sequence conservation among mammals.

FIG. 11 shows an alignment of the C-terminal tail sequences of human FGF21 (SEQ ID NO: 100), FGF19 (SEQ ID NO: 1), and variants of FGF21 harboring a single amino acid substitution or insertion for a residue unique to FGF19. Residue numbers for the sequences of native or wildtype FGF21 (SEQ ID NO: 100) and FGF19 (SEQ ID NO: 1) are in parenthesis to the left of the alignment. Gaps (dashes) were introduced to optimize the alignment. In the sequence of native or wildtype FGF19 (SEQ ID NO: 1), residues unique to FGF19 are bold and boxed, and in the sequences of the variants of the FGF21 C-terminal tail, introduced FGF19 residues are highlighted in the same manner.

FIG. 12 shows an alignment of the C-terminal tail sequences of human FGF21 (SEQ ID NO: 100), FGF19 (SEQ ID NO: 1), and variants of FGF21 in which residues unique to FGF19 progressively replace the corresponding residues of FGF21 or are inserted into the FGF21 sequence. Residue numbers for the sequences of native FGF21 (SEQ ID NO: 100) and FGF19 (SEQ ID NO: 1) are in parenthesis to the left of the alignment. Gaps (dashes) were introduced to optimize the alignment. In the sequence of native FGF19 (SEQ ID NO: 1), residues unique to FGF19 are bold and boxed, and in the sequences of variants of the FGF21 C-terminal tail, introduced FGF19 residues are highlighted in the same manner.

FIG. 13 shows an alignment of the C-terminal tail sequences of human FGF19 (SEQ ID NO: 1), FGF21 (SEQ ID NO: 100), and variants of FGF19 harboring a single amino acid deletion or substitution for a residue unique to FGF21. Residue numbers for the sequences of native FGF19 (SEQ ID NO: 1) and FGF21 (SEQ ID NO: 100) are in parenthesis to the left of the alignment. Gaps (dashes) were introduced to optimize the alignment. In the sequence of native or wildtype FGF21 (SEQ ID NO: 100), residues unique to FGF21 are bold and boxed, and in the sequences of the variants of the FGF 19 C-terminal tail, introduced FGF21 residues are also bold and boxed and deleted FGF19 residues are indicated by a dash (bold and boxed).

FIG. 14A shows an overlay of SPR sensorgrams illustrating inhibition by FGF21 in solution of FGFR1c-βKlotho binding to FGF21 immobilized on a biosensor chip. Increasing concentrations of FGF21 were mixed with a fixed concentration of FGFR1c-βKlotho complex, and the mixtures were passed over a FGF21 chip. FIG. 14B shows an overlay of SPR sensorgrams illustrating inhibition by single mutant FGF21 or wild-type FGF21 of FGFR1c-βKlotho binding to FGF21 immobilized on a biosensor chip. FIG. 14C shows an overlay of SPR sensorgrams illustrating inhibition by triple mutant FGF21 or wild-type FGF21 of FGFR1c-βKlotho binding to FGF21 immobilized on a biosensor chip. FIG. 14D shows an overlay of SPR sensorgrams illustrating inhibition by single mutant FGF21 or triple mutant FGF21 of FGFR1c-βKlotho binding to immobilized FGF21. In the experiments shown in FIGS. 14B-14C, FGFR1c-βKlotho complex was mixed with either mutant FGF21 or wild-type FGF21 at a molar ratio of 1:2 or 1:6, and the mixtures were injected over a FGF21 chip. The data shown in FIGS. 14A-14C are representative of two to three independent experiments. FIG. 14D was created from the data shown in FIGS. 14B-14C. Note that the mutants are less potent than wild-type FGF21 at inhibiting binding of the FGFR1c-βKlotho complex to immobilized FGF21. Also note that the triple mutant exhibits a greater reduction of inhibitory potency than the single mutant.

FIG. 15A shows an overlay of SPR sensorgrams illustrating inhibition by FGF21 in solution of FGFR1c-βKlotho binding to FGF21 immobilized on a biosensor chip. FIG. 15B shows an overlay of SPR sensorgrams illustrating inhibition by the FGF21$^{29-97}$/FGF19$^{204-216}$ chimera of FGFR1c-βKlotho binding to FGF21 immobilized on a biosensor chip. FIG. 15C shows an overlay of SPR sensorgrams illustrating inhibition by the FGF21$^{29-167}$/FGF19$^{169-216}$ chimera of FGFR1c-βKlotho binding to FGF21 immobilized on a biosensor chip. In the experiments shown in FIGS. 15A-15C, increasing concentrations of either an FGF21/FGF19 chimera or wild-type FGF21 were mixed with a fixed concentration of FGFR1c-βKlotho complex, and the mixtures were passed over a FGF21 chip. FIG. 15D shows an overlay of SPR sensorgrams illustrating inhibition by either of two FGF21/FGF19 chimeras or wild-type FGF21 of FGFR1c-βKlotho binding to immobilized FGF21. FIG. 15E shows an overlay of SPR sensorgrams illustrating inhibition by either of three FGF21/FGF19 chimeras of FGFR1c-βKlotho binding to immobilized FGF21. FIG. 15F shows an overlay of SPR sensorgrams illustrating inhibition by either of three FGF21/FGF19 chimeras of FGFR1c-βKlotho binding to immobilized FGF21. The data shown in FIGS. 15A-15C are representative of two to three independent experiments. FIGS. 15D-15F were created from the data shown in FIGS. 15A-15C. Included in FIGS. 15E-15F are SPR sensorgrams obtained from injecting mixtures of the FGF21$^{29-190}$/FGF19$^{197-216}$ chimera with the FGFR1c-βKlotho complex over a FGF21 chip.

FIG. 16A shows a molecular surface representation of the FGF23 crystal structure (PDB ID: 2P39; Goetz et al., "Molecular Insights into the Klotho-Dependent, Endocrine Mode of Action of Fibroblast Growth Factor 19 Subfamily Members," *Mol Cell Biol* 27:3417-3428 (2007), which is hereby incorporated by reference in its entirety). A close-up view into the hydrophobic interior core of FGF23's β-trefoil core domain showing some of the key hydrophobic side chains is shown on the right, and a view of the whole structure is shown on the left. Note that M96 makes numerous hydrophobic contacts with its neighboring residues such as I102, F115, and V136 in the β-trefoil core of FGF23. The M96T substitution would weaken these hydrophobic contacts leading to thermal instability of the FGF23 protein. FIG. 16B shows a size-exclusion chromatogram of the M96T mutant of FGF23 analyzed immediately after Ni-chelating affinity purification. FIG. 16C shows a size-exclusion chromatogram of the M96T mutant of FGF23 analyzed following incubation at 4° C. for 24 hours. FIG. 16D shows a size-exclusion chromatogram of wild-type FGF23 immediately following protein purification. FIG. 16E shows a size-exclusion chromatogram of purified wild-type FGF23 following incubation at 4° C. for 24 hours. Arrows in FIGS. 16B-16E indicate the retention times of molecular size standards, the void volume ($V_v$) and the column volume ($V_c$). Note that in contrast to wild-type FGF23, there is a substantial increase in the portion of M96T mutant protein eluting in the void volume indicating that the mutant protein unfolds over time.

FIG. 17A shows an immunoblot analysis for early growth response 1 (Egr1) expression in HEK293-βKlotho cells stimulated with $FGF21^{29-167}/FGF19^{169-216}$ chimera, $FGF21^{Q104M}$ mutant, or wild-type FGF21. Numbers above the lanes give the amounts of protein added in ng ml$^{-1}$. To control for equal sample loading, the protein blots were probed with an antibody to glyceraldehyde 3-phosphate dehydrogenase (GAPDH). The data are representative of two independent experiments. FIG. 17B shows the dose-response curve for induction of Egr1 protein expression in HEK293-βKlotho cells by the $FGF21^{29-167}/FGF19^{169-216}$ chimera or wild-type FGF21. The intensity of the protein bands on the immunoblots shown in FIG. 17A was quantified and the ratio of Egr1 to GAPDH was calculated. The ratio of Egr1 to GAPDH is plotted as a function of FGF21 ligand concentration. FIG. 17C shows the dose-response curve for induction of Egr1 protein expression in HEK293-βKlotho cells by the $FGF21^{Q104M}$ mutant or wild-type FGF21. The intensity of the protein bands on the immunoblots shown in FIG. 17A was quantified and the ratio of Egr1 to GAPDH was calculated. The ratio of Egr1 to GAPDH is plotted as a function of FGF21 ligand concentration.

FIG. 18A shows changes in blood glucose levels in healthy mice in response to injection of insulin alone or insulin plus FGF21 or vehicle. FIG. 18B shows changes in blood glucose levels in healthy mice in response to injection of insulin alone or insulin plus $FGF21^{29-167}/FGF19^{169-216}$ chimera or vehicle. FIG. 18C shows changes in blood glucose levels in healthy mice in response to injection of insulin alone or insulin plus $FGF21^{Q104M}$ mutant or vehicle. Blood glucose concentrations were measured before and at the indicated time points after the injection of protein(s) or vehicle. Blood glucose concentrations are expressed as percent of pre-injection values. Error bars denote standard deviation from mean.

DETAILED DESCRIPTION OF THE INVENTION

Figures 1A, 1B, 1C, 1D:
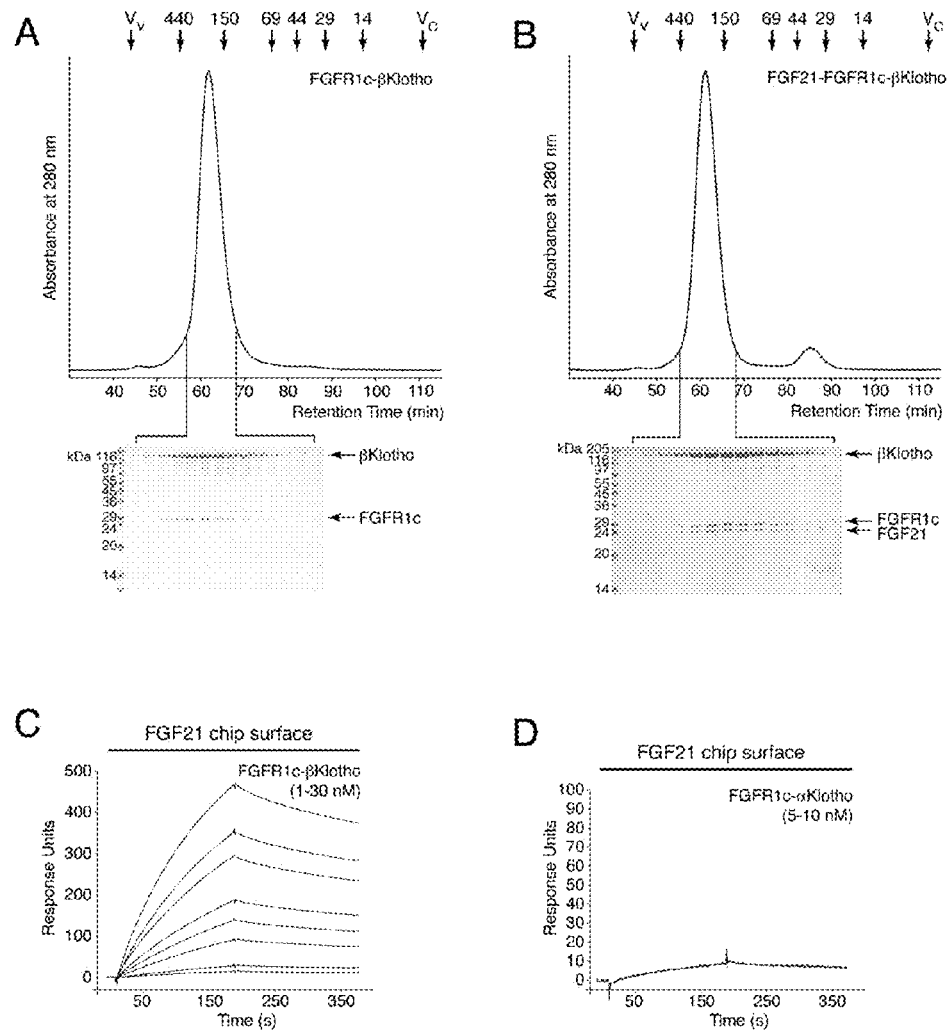
FIGS. 1A-1D show that the ternary complex of FGF21 with its cognate FGFR and βKlotho coreceptor can be reconstituted in solution using the ectodomains of βKlotho and FGFR1c.

One aspect of the present invention relates to a chimeric protein that includes an N-terminus coupled to a C-terminus. The N-terminus includes an N-terminal portion of fibroblast growth factor 21 ("FGF21") having a core domain and the C-terminus includes a C-terminal portion of fibroblast growth factor 19 ("FGF19"), where either (i) the N-terminal portion of FGF21 comprises at least one amino acid residue substitution to increase stability of the FGF21 core domain compared to the wild type FGF21; (ii) the C-terminal portion of FGF19 begins at a residue corresponding to any one of residues 169 to 204 of SEQ ID NO:1 and comprises amino acid residues TGLEAV(R/N)SPSFEK (SEQ ID NO:49); or (iii) both (i) and (ii).

As used herein, the terms "chimeric polypeptide" and "chimeric protein" encompass a polypeptide having a sequence that includes at least a portion of a full-length sequence of first polypeptide sequence and at least a portion of a full-length sequence of a second polypeptide sequence, where the first and second polypeptides are different polypeptides. A chimeric polypeptide also encompasses polypeptides that include two or more non-contiguous portions derived from the same polypeptide. A chimeric polypeptide or protein also encompasses polypeptides having at least one substitution, wherein the chimeric polypeptide includes a first polypeptide sequence in which a portion of the first polypeptide sequence has been substituted by a portion of a second polypeptide sequence.

As used herein, the term "N-terminal portion" of a given polypeptide sequence is a contiguous stretch of amino acids of the given polypeptide sequence that begins at or near the N-terminal residue of the given polypeptide sequence. An N-terminal portion of the given polypeptide can be defined by a contiguous stretch of amino acids (e.g., a number of amino acid residues). Similarly, the term "C-terminal portion" of a given polypeptide sequence is a contiguous length of the given polypeptide sequence that ends at or near the C-terminal residue of the given polypeptide sequence. A C-terminal portion of the given polypeptide can be defined by a contiguous stretch of amino acids (e.g., a number of amino acid residues).

The term "portion," when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the portion is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

As noted above, a chimeric protein according to the present invention may include an N-terminus coupled to a C-terminus. N-terminus and C-terminus are used herein to refer to the N-terminal region or portion and the C-terminal region or portion, respectively, of the chimeric protein of the present invention. In some embodiments of the present invention, the C-terminal portion and the N-terminal portion of the chimeric protein of the present invention are contiguously joined. In alternative embodiments, the C-terminal portion and the N-terminal portion of the chimeric protein of the present invention are coupled by an intervening spacer. In one embodiment, the spacer may be a polypeptide sequence of 1, 2, 3, 4, 5, 6, 7, 8, 9, 10, or more amino acid residues. In some embodiments, the C-terminal portion and/or the N-terminal portion of the chimeric protein of the present invention may include additional portion(s) coupled to the C-terminal residue and/or the N-terminal residue of the chimeric protein of the present invention, respectively. In some embodiments, the additional portion(s) may be a polypeptide sequence of 1, 2, 3, 4, 5, 6, 7, 8, 9, 10, or more amino acid residues. In some embodiments, the N-terminal portion and/or the C-terminal portion having such additional portion(s) will maintain the activity of the corresponding naturally occurring N-terminal portion of FGF21 and/or C-terminal portion of FGF19, respectively. In some embodiments, the N-terminal portion and/or the C-terminal portion having such additional portion(s) will have enhanced and/or prolonged activity compared to the corresponding naturally occurring N-terminal portion of FGF21 and/or C-terminal portion of FGF 19, respectively. In other embodiments, the C-terminal portion and/or the N-terminal portion of the chimeric protein of the present invention do not include any additional portion(s) coupled to the C-terminal residue and/or the N-terminal residue of the chimeric protein of the present invention, respectively.

As described by Goetz et al. (Goetz et al., "Molecular Insights into the Klotho-Dependent, Endocrine Mode of Action of Fibroblast Growth Factor 19 Subfamily Members," *Mol Cell Biol* 3417-3428 (2007), which is hereby incorporated by reference in its entirety), the mammalian fibroblast growth factor (FGF) family comprises 18 polypeptides (FGF1 to FGF10 and FGF16 to FGF23), which participate in a myriad of biological processes during embryo genesis, including but not limited to gastrulation, body plan formation, somitogenesis, and morphogenesis of essentially every tissue/organ such as limb, lung, brain, and kidney (Bottcher et al., "Fibroblast Growth Factor Signaling During Early Vertebrate Development," *Endocr Rev* 26:63-77 (2005), and Thisse et al., "Functions and Regulations of Fibroblast Growth Factor Signaling During Embryonic Development," *Dev Biol* 287:390-402 (2005), which are hereby incorporated by reference in their entirety).

FGFs execute their biological actions by binding to, dimerizing, and activating FGFR tyrosine kinases, which are encoded by four distinct genes (Fgfr1 to Fgfr4). Prototypical FGFRs consist of an extracellular domain composed of three immunoglobulin-like domains, a single-pass transmembrane domain, and an intracellular domain responsible for the tyrosine kinase activity (Mohammadi et al., "Structural Basis for Fibroblast Growth Factor Receptor Activation," *Cytokine Growth Factor Rev* 16:107-137 (2005), which is hereby incorporated by reference in its entirety).

The number of principal FGFRs is increased from four to seven due to a major tissue-specific alternative splicing event in the second half of the immunoglobulin-like domain 3 of FGFR1 to FGFR3, which creates epithelial lineage-specific "b" and mesenchymal lineage-specific "c" isoforms (Mohammadi et al., "Structural Basis for Fibroblast Growth Factor Receptor Activation," *Cytokine Growth Factor Rev* 16:107-137 (2005) and Ornitz et al., "Fibroblast Growth Factors," *Genome Biol* 2(3):reviews3005.1-reviews3005.12 (2001), which are hereby incorporated by reference in their entirety). Generally, the receptor-binding specificity of FGFs is divided along this major alternative splicing of receptors whereby FGFRb-interacting FGFs are produced by epithelial cells and FGFRc-interacting FGFs are produced by mesenchymal cells (Ornitz et al., "Fibroblast Growth Factors," *Genome Biol* 2(3):reviews3005.1-reviews3005.12 (2001), which is hereby incorporated by reference in its entirety). These reciprocal expression patterns of FGFs and FGFRs result in the establishment of specific paracrine FGF signaling loops between the epithelium and the mesenchyme, which is essential for proper organogenesis and patterning during embryonic development as well as tissue homeostasis in the adult organism.

Based on sequence homology and phylogenetic and structural considerations, the eighteen mammalian FGFs are grouped into six subfamilies (Itoh et al., "Fibroblast growth factors: from molecular evolution to roles in development, metabolism, and disease," *J Biochem* 149:121-130 (2011); Mohammadi et al., "Structural basis for fibroblast growth factor receptor activation," *Cytokine Growth Factor Rev* 16:107-137 (2005), which are hereby incorporated by reference in its entirety). The FGF core homology domain (approximately 120 amino acids long) is flanked by N- and C-terminal sequences that are highly variable in both length and primary sequence, particularly among different FGF subfamilies. The core region of FGF19 shares the highest sequence identity with FGF21 (38%) and FGF23 (36%), and therefore, these ligands are considered to form a subfamily.

Based on mode of action, the eighteen mammalian FGFs are grouped into paracrine-acting ligands (five FGF subfamilies) and endocrine-acting ligands (one FGF subfamily) comprising FGF19, FGF21 and FGF23 (Itoh and Ornitz, "Fibroblast Growth Factors: From Molecular Evolution to Roles in Development, Metabolism and Disease," *J. Biochem.* 149:121-130 (2011); Mohammadi et al., "Structural Basis for Fibroblast Growth Factor Receptor Activation," *Cytokine Growth Factor Rev.* 16:107-137 (2005), which are hereby incorporated by reference in their entirety).

Paracrine FGFs direct multiple processes during embryogenesis, including gastrulation, somitogenesis, organogenesis, and tissue patterning (Itoh and Ornitz, "Fibroblast Growth Factors: From Molecular Evolution to Roles in Development, Metabolism and Disease," *J. Biochem.* 149:121-130 (2011); Bottcher and Niehrs, "Fibroblast Growth Factor Signaling During Early Vertebrate Development," *Endocr. Rev.* 26:63-77 (2005); Thisse et al., "Functions and Regulations of Fibroblast Growth Factor Signaling During Embryonic Development," *Dev. Biol.* 287:390-402 (2005), which are hereby incorporated by reference in their entirety), and also regulate tissue homeostasis in the adult (Hart et al., "Attenuation of FGF Signalling in Mouse Beta-cells Leads to Diabetes," *Nature* 408:864-868 (2000); Jonker et al., "A PPARγ-FGF1 Axis is Required for Adaptive Adipose Remodelling and Metabolic Homeostasis," *Nature* 485:391-394 (2012), which is hereby incorporated by reference in its entirety).

Endocrine FGFs control major metabolic processes such as bile acid homeostasis (Inagaki et al., "Fibroblast Growth Factor 15 Functions as an Enterohepatic Signal to Regulate Bile Acid Homeostasis," *Cell Metab.* 2:217-225 (2005), which is hereby incorporated by reference in its entirety), and hepatic glucose and protein metabolism (Kir et al., "FGF19 as a Postprandial, Insulin-Independent Activator of Hepatic Protein and Glycogen Synthesis," *Science* 331: 1621-1624 (2011); Potthoff et al., "FGF15/19 Regulates Hepatic Glucose Metabolism by Inhibiting the CREB-PGC-1α Pathway," *Cell Metab.* 13:729-738 (2011), which are hereby incorporated by reference in their entirety) (FGF19), glucose and lipid metabolism (Badman et al., "Hepatic Fibroblast Growth Factor 21 Is Regulated by PPARα and Is a Key Mediator of Hepatic Lipid Metabolism in Ketotic States," *Cell Metab.* 5:426-437 (2007); Inagaki et al., "Endocrine Regulation of the Fasting Response by PPARalpha-mediated Induction of Fibroblast Growth Factor 21," *Cell Metab.* 5:415-425 (2007); Kharitonenkov et al., "FGF- 21 as a Novel Metabolic Regulator," *J. Clin. Invest.* 115: 1627-1635 (2005); Potthoff et al., "FGF21 Induces PGC-1alpha and Regulates Carbohydrate and Fatty Acid Metabolism During the Adaptive Starvation Response," *Proc. Nat'l. Acad. Sci. U.S.A.* 106:10853-10858 (2009), which are hereby incorporated by reference in their entirety) (FGF21), and phosphate and vitamin D homeostasis (White et al., "Autosomal Dominant Hypophosphataemic Rickets is Associated with Mutations in FGF23," *Nat. Genet.* 26:345-348 (2000); Shimada et al., "Targeted Ablation of Fgf23 Demonstrates an Essential Physiological Role of FGF23 in Phosphate and Vitamin D Metabolism," *J. Clin. Invest.* 113:561-568 (2004), which are hereby incorporated by reference in their entirety) (FGF23). Thus, these ligands have attracted much attention as potential drugs for the treatment of various inherited or acquired metabolic disorders (Beenken and Mohammadi, "The FGF Family: Biology, Pathophysiology and Therapy," *Nat. Rev. Drug Discov.* 8:235-253 (2009); Beenken and Mohammadi, "The Structural Biology of the FGF19 Subfamily," in *Endocrine FGFs and Klothos* (Kuro-o, M. ed.), Landes Bioscience. pp 1-24 (2012), which are hereby incorporated by reference in their entirety).

Of particular interest is FGF 19, which has been shown to target and have effects on both adipocytes and hepatocytes. For example, mice harboring a FGF19 transgene, despite being on a high-fat diet, show increased metabolic rates, increased lipid oxidation, a lower respiratory quotient and weight loss. Moreover, such mice showed lower serum levels of leptin, insulin, cholesterol and triglycerides, and normal levels of blood glucose despite the high-fat diet and without appetite diminishment (Tomlinson et al., "Transgenic Mice Expressing Human Fibroblast Growth Factor-19 Display Increased Metabolic Rate and Decreased Adiposity," *Endocrinology* 143(5), 1741-1747 (2002), which is hereby incorporated by reference in its entirety). Obese mice that lacked leptin but harbored a FGF19 transgene showed weight loss, lowered cholesterol and triglycerides, and did not develop diabetes. Obese, diabetic mice that lacked leptin, when injected with recombinant human FGF 19, showed reversal of their metabolic characteristics in the form of weight loss and lowered blood glucose (Fu et al., "Fibroblast Growth Factor 19 Increases Metabolic Rate and Reverses Dietary and Leptin-deficient Diabetes," *Endocrinology* 145(6), 2594-2603 (2004), which is hereby incorporated by reference in its entirety).

In one embodiment of the present invention, FGF19 is human FGF19 and has an amino acid sequence of SEQ ID NO: 1 (GenBank Accession No. NP_005108, which is hereby incorporated by reference in its entirety), or a portion thereof, as follows:

sponding to residues spanning residues 1 to 168 of SEQ ID NO:1. In one embodiment, the C-terminal portion of FGF19 begins at a residue corresponding to any one of residues 169, 197, or 204 of SEQ ID NO: 1.

In another embodiment, the C-terminal portion of FGF19 of the chimeric protein of the present invention comprises an amino acid sequence spanning residues corresponding to residues selected from the group consisting of from position 204 to 216 of SEQ ID NO: 1, from position 197 to 216 of SEQ ID NO: 1, and from position 169 to 216 of SEQ ID NO: 1. In yet another embodiment, the C-terminal portion of FGF19 of the chimeric protein of the present invention comprises an amino acid sequence spanning residues of SEQ ID NO:1, which correspond to residues 191 to 206 or 191 to 209 of SEQ ID NO: 100.

In one embodiment of the present invention, FGF19 or a portion thereof is from a mammalian FGF19. In one embodiment of the present invention, FGF19 or a portion thereof is or is from a vertebrate FGF19. In one embodiment, FGF19 or a portion thereof is or is from a non-human vertebrate FGF19. It will be understood that this includes orthologs of human FGF19, or a polypeptide or protein obtained from one species that is the functional counterpart of a polypeptide or protein from a different species. In one embodiment, the C-terminal portion of FGF19 of the chimeric protein of the present invention is from human FGF19. In one embodiment of the present invention, the C-terminal portion of FGF19 is from an ortholog of human FGF19 from *gorilla gorilla, pan troglodytes, macaca mulatta, pongo abelii, nomascus leucogenys, callithrix jacchus, microcebus murinus, choloepus hoffmanni, ailuropoda melanoleuca, sus scrofa, bos taurus, canis lupus familiaris, oryctolagus, pteropus vampyrus, tursiops truncates, myotis lucifugus, ornithorhynchus anatinus, monodelphis domestica, anolis carolinensis, ochotona princeps, cavia porcellus, tupaia belangeri, rattus norvegicus, mus musculus, gallus gallus, taeniopygia guttata, danio rerio, xenopus (silurana) tropicalis, otolemur garnettii, felis catus, pelodiscus sinensis, latimeria chalumnae, mustela putorius faro, takifugu rubripes, equus caballus, oryzias latipes, xiphosphorus maculatus, ictidomys tridecemlineatus, gasterosteus aculeatus, oreochromis niloticus, meleagris gallopavo, papio anubis, saimiri boliviensis boliviensis, pteropus alecto, myotis davidii, tupaia chinensis,* or *heterocephalus glaber.*

In other embodiments of the present invention, the portion of FGF19 of the chimeric protein of the present invention is from an ortholog of human FGF19 having an amino acid sequence as shown in Table 1. The portions of an ortholog of human FGF 19 of a chimeric protein according to the present invention include portions corresponding to the

```
                                                           (SEQ ID NO: 1)
  1 MRSGCVVVHV WILAGLWLAV AGRPLAFSDA GPHVHYGWGD PIRLRHLYTS GPHGLSSCFL

61 RIRADGVVDC ARGQSAHSLL EIKAVALRTV AIKGVHSVRY LCMGADGKMQ GLLQYSEEDC

121 AFEEEIRPDG YNVYRSEKHR LPVSLSSAKQ RQLYKNRGFL PLSHFLPMLP MVPEEPEDLR

181 GHLESDMFSS PLETDSMDPF GLVTGLEAVR SPSFEK
```

Figure 10:
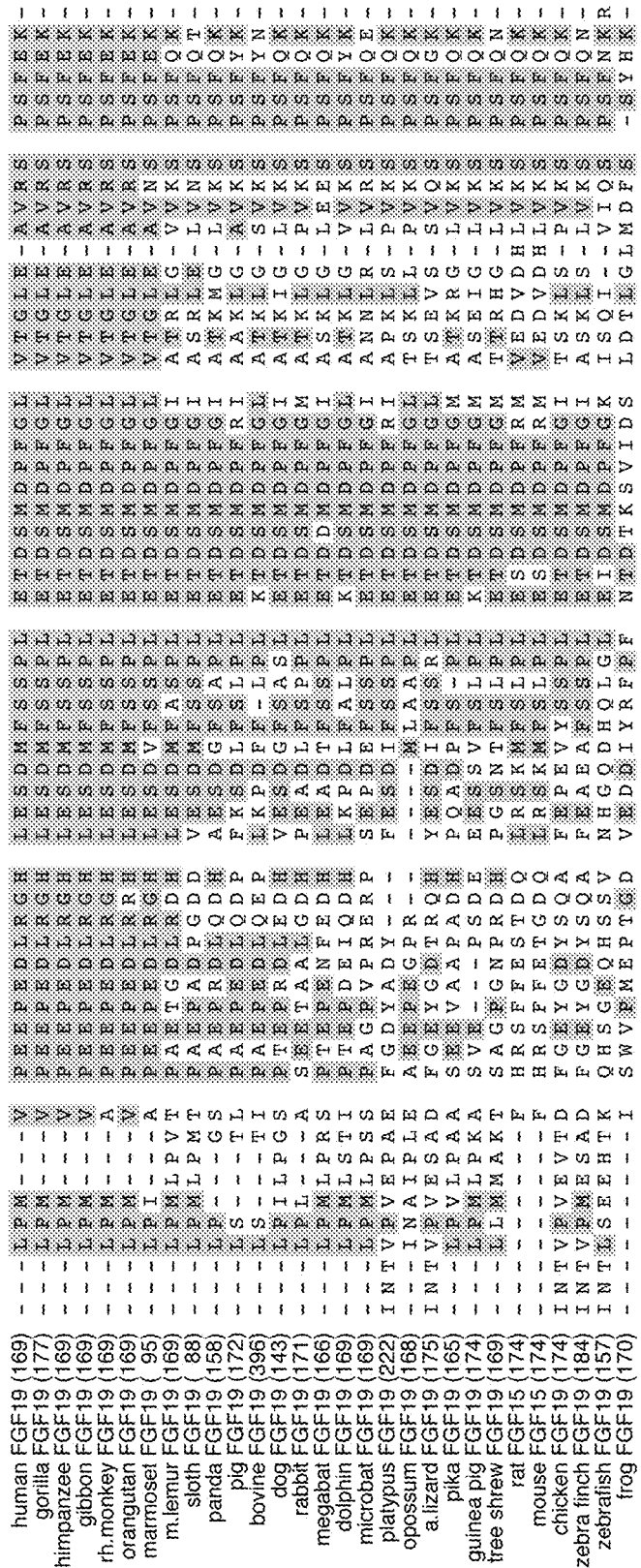
FIG. 10 shows a sequence alignment of the C-terminal tail of FGF19 orthologs (including human (SEQ ID NO: 1), gorilla (SEQ ID NO: 2), chimpanzee (SEQ ID NO: 3), gibbon (SEQ ID NO: 6), rhesus monkey (SEQ ID NO: 4), orangutan (SEQ ID NO: 5), marmoset (SEQ ID NO: 7), mouse lemur (SEQ ID NO: 8), sloth (SEQ ID NO: 9), panda (SEQ ID NO: 10), pig (SEQ ID NO: 11), bovine (SEQ ID NO: 12), dog (SEQ ID NO: 13), rabbit (SEQ ID NO: 14), megabat (SEQ ID NO: 15), dolphin (SEQ ID NO: 16), microbat (SEQ ID NO: 17), platypus (SEQ ID NO: 18), opossum (SEQ ID NO: 19), anole lizard (SEQ ID NO: 20), pika (SEQ ID NO: 21), guinea pig (SEQ ID NO: 22), tree shrew (SEQ ID NO: 23), rat (SEQ ID NO: 24), mouse (SEQ ID NO: 25), chicken (SEQ ID NO: 26), zebra finch (SEQ ID NO: 27), zebrafish (SEQ ID NO: 28), and frog (SEQ ID NO: 29)). Residue numbers are in parenthesis to the left of the alignment. Gaps (dashes) were introduced to optimize the alignment. Ortholog residues identical to human FGF19 are shaded gray.

In one embodiment, the C-terminal portion of FGF 19 of the chimeric protein of the present invention does not include any of residues 1 to 168 of SEQ ID NO: 1. In certain embodiments of the present invention, the chimeric protein of the present invention does not include residues correabove-identified amino acid sequences of human FGF 19. Corresponding portions may be determined by, for example, sequence analysis and structural analysis. The high degree of FGF19 sequence conservation among orthologs is shown in FIG. 10.

TABLE 1

Gorilla gorilla (gorilla) FGF19 (Ensembl Accession No.
ENSGGOP00000021055, which is hereby incorporated by reference in its
entirety) (SEQ ID NO: 2)
```
  1 MRSGCVVVHV WILAGLWLAV AGRPLAFSDA GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

Pan troglodytes (chimpanzee) FGF19 (Ensembl Accession No.
ENSPTRP00000006877, which is hereby incorporated by reference in its
entirety) (SEQ ID NO: 3)
```
  1 MRNGCVVVHV WILAGLWLAV AGRPLAFSDA GRHVHYCWGD PIPLRHLYTS GPHGLSSCFL
 61 RIPANCVMNC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

Macaca mulatta (Rhesus monkey) FGF19 (GenBank Accession No.
XP_001100825, which is hereby incorporated by reference in its
entirety) (SEQ ID NO: 4)
```
  1 MRSGCVVVHA WILASLWLAV AGRPLAFSDA GPHVHYGWGD PIRLRHLYTS GPHGLSSCFL
 61 RIRTDGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MAPEEPEDLR
181 GHLESDMFSS PLETDSMDPF GLVTGLEAVR SPSFEK
```

Pongo abelii (Sumatran orangutan) FGF19 (GenBank Accession No.
XP_002821459, which is hereby incorporated by reference in its
entirety) (SEQ ID NO: 5)
```
  1 MRSGCVVVHA WILAGLWLAV AGRPLAFSDS GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 RHLESDMFSS PLETDSMDPF GLVTGLEAVR SPSFEK
```

Nomascus leucogenys (Northern white-cheeked gibbon) FGF19 (Genbank
Accession No. XP_003278071, which is hereby incorporated by reference
in its entirety) (SEQ ID NO: 6)
```
  1 MRSECVVVHA WILAGLWLAV AGRPLAFSDA GPHVHYGWGD PIRLRHLYTS GPHGLSSCFL
 61 RIRADGVVDC ARGQSAHSLL EIKAVALRTV AIKGVHSVRY LCMGADGKMQ GLLQYSEEDC
121 AFEEEIRPDG YNVYRSEKHR LPVSLSSAKQ RQLYKNRGFL PLSHFLPMLP MVPEEPEDLR
181 GHLESDMFSS PLETDSMDPF GLVTGLEAVR SPSFEK
```

Callithrix jacchus (white-tufted-ear marmoset) FGF19 (GenBank
Accession No. XP_002763730, which is hereby incorporated by reference
in its entirety) (SEQ ID NO: 7)
```
  1 MWKATAGGQQ GQSEAQMSTC PHVPRPLWIA QSCLFSLQLQ YSEEDCAFEE EIRPDGYNVY
 61 WSEKHRLPVS LSSAKQRQLY KKRGFLPLSH FLPMLPIAPE EPEDLRGHLE SDVFSSPLET
121 DSMDPFGLVT GLEAVNSPSF EK
```

Microcebus murinus (mouse lemur) FGF19 (Ensembl Accession No.
ENSMICP00000002788, which is hereby incorporated by reference in its
entirety) (SEQ ID NO: 8)
```
  1 MPSGQSGCVA ARALILAGLW LTAAGRPLAF SDAGPHVHYG WGEPIRLRHL YTAGPHGLSS
 61 CFLRIRADGS VDCARGQSAH SLLEIRAVAL RTVAIKGVHS VRYLCMGADG RMQGLLRYSE
121 EDCAFEEEIR PDGYNVYRSE KHRLPVSLSS ARQRQLYKGR GFLPLSHFLP MLPVTPAETG
181 DLRDHLESDM FASPLETDSM DPFGIATRLG VVKSPSFQK
```

Choloepus hoffmanni (sloth) FGF19 (Ensembl Accession No.
ENSCHOP00000002044, which is hereby incorporated by reference in its
entirety) (SEQ ID NO: 9) (partial amino acid sequence corresponding to
human FGF19 residues 79 to 216)
```
  1 LLEMKAVALR AVAIKGVHSA LYLCMNADGS LHGLPRYSAE DCAFEEEIRP DGYNVYWSRK
 61 HGLPVSLSSA KQRQLYKGRG FLPLSHFLPM LPMTPAEPAD PGDDVESDMF SSPLETDSMD
121 PFGIASRLEL VNSPSFQT
```

Ailuropoda melanoleuca (giant panda) FGF19 (GenBank Accession No.
XP_002927952, which is hereby incorporated by reference in its
entirety) (SEQ ID NO: 10) (partial amino acid sequence corresponding
to human FGF19 residues 12 to 216)
```
124    VLAGLCL AVAGRPLAFS DAGPHVHYGW GEPIRLRHLY TAGPHGLSSC FLRIRADGGV
181 DCARGQSAHS LVEIRAVALR TVAIKGVHSV RYLCMGADGR MQGLPQYSAG DCAFEEEIRP
241 DGYNVYRSKK HRLPVSLSGA KQRQLYKDRG FLPLSHFLPM LPGSPAEPRD LQDHAESDGF
301 SAPLETDSMD PFGIATKMGL VKSPSFQK
```

Sus scrofa (pig) FGF19 (Ensembl Accession No. ENSSSCP00000013682,
which is hereby incorporated by reference in its entirety)
(SEQ ID NO: 11)
```
  1 MRSAPSRCAV VRALVLAGLW LAAAGRPLAF SDAGPHVHYG WGESVRLRHL YTASPHGVSS
 61 CFLRIHSDGP VDCAPGQSAH SLMEIRAVAL STVAIKGERS RYLCMGADGK MQGQTQYSDE
121 DCAFEEEIRP DGYNVYWSKK HHLPVSLSSA RQRQLYKGRG FLPLSHFLPM LSTLPAEPED
181 LQDPFKSDLF SLPLETDSMD PFRIAAKLGA VKSPSFYK
```

TABLE 1-continued

*Bos taurus* (bovine) FGF19 (GenBank Accession No. XP_599739, which is hereby incorporated by reference in its entirety) (SEQ ID NO: 12)
```
136                 MRSAP SRCAVARALV LAGLWLAAAG RPLAFSDAGP HVHYGWGESV
181 RLRHLYTAGP QGLYSCFLRI HSDGAVDCAQ VQSAHSLMEI RAVALSTVAI KGERSVLYLC
241 MDADGKMQGL TQYSAEDCAF EEEIRPDGYN VYWSRKHHLP VSLSSSRQRQ LFKSRGFLPL
301 SHFLPMLSTI PAEPEDLQEP LKPDFFLPLK TDSMDPFGLA TKLGSVKSPS FYN
```

*Canis lupus* familiaris (dog) FGF19 (GenBank Accession No. XP_540802, which is hereby incorporated by reference in its entirety) (SEQ ID NO: 13) (partial amino acid sequence corresponding to human FGF19 residues 25 to 216)
```
  1 LAFSDAGPHV HSFWGEPIRL RHLYTAGPHG LSSCFLRIRA DGGVDCARGQ SAHSLMEMRA
 61 VALRTVAIKG VHSGRYLCMG ADGRMQGLPQ YSAGDCTFEE EIRPDGYNVY WSKKHHLPIS
121 LSSAKQRQLY KGRGFLPLSH FLPILPGSPT EPRDLEDHVE SDGFSASLET DSMDPFGIAT
181 KIGLVKSPSF QK
```

*Oryctolagus cuniculus* (rabbit) FGF19 (GenBank Accession No. XP_002724495, which is hereby incorporated by reference in its entirety) (SEQ ID NO: 14)
```
  1 MRRAPSGGAA ARALVLAGLW LAAAARPLAL SDAGPHLHYG WGEPVRLRHL YATSAHGVSH
 61 CFLRIRADGA VDCERSQSAH SLLEIRAVAL RTVAFKGVHS SRYLCMGADG RMRGQLQYSE
121 EDCAFQEEIS SGYNVYRSTT HHLPVSLSSA KQRHLYKTRG FLPLSHFLPV LPLASEETAA
181 LGDHPEADLF SPPLETDSMD PFGMATKLGP VKSPSFQK
```

*Pteropus vampyrus* (megabat) FGF19 (Ensembl Accession No. ENSPVAP00000009339, which is hereby incorporated by reference in its entirety) (SEQ ID NO: 15)
```
  1 MRSPCAVARA LVLAGLWLAS AAGPLALSDA GPHVHYGWGE AIRLRHLYTA GPHGPSSCFL
 61 RIRADGAVDC ARGQSAHSLV EIRAVALRNV AIKGVHSVRY LCMGADGRML GLLQYSADDC
121 AFEEEIRPDG YNVYHSKKHH LPVSLSSAKQ RQLYKDRGFL PLSHFLPMLP RSPTEPENFE
181 DHLEADTFSS LETDDMDPFG IASKLGLEES PSFQK
```

*Tursiops truncatus* (dolphin) FGF19 (Ensembl Accession No. ENSTTRP00000000061, which is hereby incorporated by reference in its entirety) (SEQ ID NO: 16)
```
  1 MRSAPSRCAV ARALVLAGLW LAAAGRPLAF SDAGPHVHYG WGESVRLRHL YTAGPQGLSS
 61 CFLRIHSDGA VDCAPVQSAH SLMEIRAVAL STVAIKGERS VLYLCMGADG KMQGLSQYSA
121 EDCAFEEEIR PDGYNVYWSK KHHLPVSLSS ARQRQLFKGR GFLPLSHFLP MLSTIPTEPD
181 EIQDHLKPDL FALPLKTDSM DPFGLATKLG VVKSPSFYK
```

*Myotis lucifugus* (microbat) FGF19 (Ensembl Accession No. ENSMLUP00000002279, which is hereby incorporated by reference in its entirety) (SEQ ID NO: 17)
```
  1 MQSAWSRRVV ARALVLASLG LASAGGPLGL SDAGPHVHYG WGESIRLRHL YTSGPHGPSS
 61 CFLRIRADGA VDCARGQSAH SLVEIRAVAL RKVAIKGVHS ALYLCMGGDG RMLGLPQFSP
121 EDCAFEEEIR PDGYNVYRSQ KHQLPVSLSS ARQRQLFKAR GFLPLSHFLP MLPSSPAGPV
181 PRERPSEPDE FSSPLETDSM DPFGIANNLR LVRSPSFQE
```

*Ornithorhynchus anatinus* (platypus) FGF19 (GenBank Accession No. XP_001506714, which is hereby incorporated by reference in its entirety) (SEQ ID NO: 18) (partial amino acid sequence corresponding to human FGF19 residues 79 to 216)
```
  1 MLSCVVLPSL LEIKAVAVRT VAIKGVHISR YLCMEEDGKT PWARLLEIKA VAVRTVAIKG
 61 VHSSRYLCME EDGKLHGQIW YSAEDCAFEE EIRPDGYNVY KSKKYGVPVS LSSAKQRQQF
121 KGRDFLPLSR FLPMINTVPV EPAEFGDYAD YFESDIFSSP LETDSMDPFR IAPKLSPVKS
181 PSFQK
```

*Monodelphis domestica* (opossum) FGF19 (GenBank Accession No. XP_001506714, which is hereby incorporated by reference in its entirety) (SEQ ID NO: 19)
```
  1 MAQLLAPLLT LAALWLAPTA RARPLVDAGP HVYYGWGEPI RLRHLYTANR HGLASFSFLR
 61 IHRDGRVDGS RSQSALSLLE IKAVALRMVA IKGVHSSRYL CMGDAGKLQG SVRFSAEDCT
121 FEEQIRPDGY NVYQSPKYNL PVSLCTDKQR QQAHGKEHLP LSHFLPMINA IPLEAEEPEG
181 PRMLAAPLET DSMDPFGLTS KLLPVKSPSF QK
```

*Anolis carolinensis* (anole lizard) FGF19 (GenBank Accession No. XP_003214715, which is hereby incorporated by reference in its entirety) (SEQ ID NO: 20)
```
  1 MCRRALPLLG ALLGLAAVAS RALPLTDAGP HVSYGWGEPV RLRHLYTAGR QGLFSQFLRI
 61 HADGRVDGAG SQNRQSLLEI RAVSLRAVAL KGVHSSRYLC MEEDGRLRGM LRYSAEDCSF
121 EEEMRPDGYN IYKSKKYGVL VSLSNARQRQ QFKGKDFLPL SHFLPMINTV PVESADFGEY
181 GDTRQHYESD IFSSRLETDS MDPFGLTSEV SSVQSPSFGK
```

*Ochotona princeps* (pika) FGF19 (Ensembl Accession No. ENSOPRP00000009838, which is hereby incorporated by reference in its entirety) (SEQ ID NO: 21) (partial amino acid sequence corresponding to human FGF19 residues 12 to 77 and 113 to 216)
```
  1 VRSRGAMARA LVLATLWLAA TGRPLALSDA GPHLHYGWGE PIRLRHLYAT SAHGLSHCFL
 61 RIRTDGTVDC ERSQSAH--- ---------- ---------- ---------- --LQYSEEDC
```

TABLE 1-continued

```
121 AFEEEISSGY NVYRSRRYQL PVSLGSARQR QLQRSRGFLP LSHFLPVLPA ASEEVAAPAD
181 HPQADPFSPL ETDSMDPFGM ATKRGLVKSP SFQK
```

*Cavia porcellus* (guinea pig) FGF19 (Ensembl Accession No. ENSCPOP00000007325, which is hereby incorporated by reference in its entirety) (SEQ ID NO: 22)
```
  1 MWSAPSGCVV IRALVLAGLW LAVAGRPLAR RSLALSDQGP HLYYGWDQPI RLRHLYAAGP
 61 YGRSRCFLRI HTDGAVDCVE EQSEHCLLEI RAVALETVAI KDINSVRYLC MGPDGRMRGL
121 PWYSEEDCAF KEEISYPGYS VYRSQKHHLP IVLSSVKQRQ QYQSKGVVPL SYFLPMLPKA
181 SVEPSDEEES SVFSLPLKTD SMDPFGMASE IGLVKSPSFQ K
```

*Tupaia belangeri* (tree shrew) FGF19 (Ensembl Accession No. ENSTBEP00000000264, which is hereby incorporated by reference in its entirety) (SEQ ID NO: 23) (partial amino acid sequence corresponding to human FGF19 (residues 1 to 112 and 136 to 216)
```
  1 MRRTPSGFAV ARVLFLGSLW LAAAGSPLAL SDAGPHVNYG WDESIRLRHL YTASPHGSTS
 61 CFLRIRDDGS VDCARGQSLH SLLEIKAVAL QTVAIKGVYS VRYLCMDADG RMQGL-----
121 ---------- --------ST KHGLPVSLSS AKQRQLLTVR GFPSLPHFLL MMAKTSAGPG
181 NPRDHPGSNT FSLPLETDSM DPFGMTTRHG LVKSPSFQN
```

*Rattus norvegicus* (Norway rat) FGF15 (GenBank Accession No. NP_570109, which is hereby incorporated by reference in its entirety) (SEQ ID NO: 24)
```
  1 MARKWSGRIV ARALVLATLW LAVSGRPLVQ QSQSVSDEGP LFLYGWGKIT RLQYLYSAGP
 61 YVSNCFLRIR SDGSVDCEED QNERNLLEFR AVALKTIAIK DVSSVRYLCM SADGKIYGLI
121 RYSEEDCTFR EEMDCLGYNQ YRSMKHHLHI IFIKAKPREQ LQGQKPSNFI PIFHRSFFES
181 TDQLRSKMFS LPLESDSMDP FRMVEDVDHL VKSPSFQK
```

*Mus musculus* (house mouse) FGF15 (GenBank Accession No. NP_032029, which is hereby incorporated by reference in its entirety) (SEQ ID NO: 25)
```
  1 MARKWNGRAV ARALVLATLW LAVSGRPLAQ QSQSVSDEDP LFLYGWGKIT RLQYLYSAGP
 61 YVSNCFLRIR SDGSVDCEED QNERNLLEFR AVALKTIAIK DVSSVRYLCM SADGKIYGLI
121 RYSEEDCTFR EEMDCLGYNQ YRSMKHHLHI IFIQAKPREQ LQDQKPSNFI PVFHRSFFET
181 GDQLRSKMFS LPLESDSMDP FRMVEDVDHL VKSPSFQK
```

*Gallus gallus* (chicken) FGF19 (GenBank Accession No. NP_990005, which is hereby incorporated by reference in its entirety) (SEQ ID NO: 26)
```
  1 MGPARPAAPG AALALLGIAA AAAAARSLPL PDVGGPHVNY GWGEPIRLRH LLHRPGKHGL
 61 FSCFLRIGGD GRVDAVGSQS PQSLLEIRAV AVRTVAIKGV QSSRYLCMDE AGRLHGQLSY
121 SIEDCSFEEE IRPDGYNVYK SKKYGISVSL SSAKQRQQFK GKDFLPLSHF LPMINTVPVE
181 VTDFGEYGDY SQAFEPEVYS SPLETDSMDP FGITSKLSPV KSPSFQK
```

*Taeniopygia guttata* (zebra finch) FGF19 (GenBank Accession No. XP_002194493, which is hereby incorporated by reference in its entirety) (SEQ ID NO: 27)
```
  1 MVIISNLYLM QNDVMMNMRR APLRVHAARS SATPASALPL PPPDAGPHLK YGWGEPIRLR
 61 HLYTASKHGL FSCFLRIGAD GRVDAAGSQS PQSLLEIRAV AVRTVAIKGV QSSRYLCMDE
121 AGRLHGQLRN STEDCSFEEE IRPDGYNVYR SKKHGISVSL SSAKQRQQFK GKDFLPLSHF
181 LPMINTVPME SADFGEYGDY SQAFEAEAFS SPLETDSMDP FGIASKLSLV KSPSFQN
```

*Danio rerio* (zebrafish) FGF19 (GenBank Accession No. NP_001012246, which is hereby incorporated by reference in its entirety) (SEQ ID NO: 28)
```
  1 MLLLLFVTVC GSIGVESLPL PDSGPHLAND WSEAVRLRHL YAARHGLHLQ INTDGEIIGS
 61 TCKARTVSLM EIWPVDTGCV AIKGVASSRF LCMERLGNLY GSHIYTKEDC SFLERILPDG
121 YNVYFSSKHG ALVTLSGAKN KLHSNDGTSA SQFLPMINTL SEEHTKQHSG EQHSSVNHGQ
181 DHQLGLEIDS MDPFGKISQI VIQSPSFNKR
```

*Xenopus* (*Silurana*) *tropicalis* (western clawed frog) FGF19 (GenBank Accession No. NP_001136297, which is hereby incorporated by reference in its entirety) (SEQ ID NO: 29)
```
  1 MWKTLPWILV PMMVAVLYFL GGAESLPLFD AGPHMQNGWG ESIRIRHLYT ARRFGHDSYY
 61 LRIHEDGRVD GDRQQSMHSL LEIRAIAVGI VAIKGYRSSL YLCMGSEGKL YGMHSYSQDD
121 CSFEEELLPD GYNMYKSRKH GVAVSLSKEK QKQQYKGKGY LPLSHFLPVI SWVPMEPTGD
181 VEDDIYRFPF NTDTKSVIDS LDTLGLMDFS SYHKK
```

*Otolemur garnettii* (bushbaby) FGF19 (Ensembl Accession No. ENSOGAP00000017975, which is hereby incorporated by reference in its entirety) (SEQ ID NO: 30)
```
  1 MPSGLRGRVV AGALALASFW LAVAGRPLAF SDAGPHVHYG WGEPIRLRHL YTAGPHGLSS
 61 CFLRVRTDGA VDCARGQSAH SLLEIRAVAL RTVAIKGVHS ARYLCMGADG RMQGLPQYSE
121 EDCAFEEEIR PDGYNVYWSE KHRLPVSLSS ARQRQLYKGR GFLPLSHFLP MLPVTPAEPG
181 DLRDHLESDM FSLPLETDSM DPFGIATRLG VVKSPSFQK
```

*Felis catus* (cat) FGF19 (Ensembl Accession No. ENSFCAP00000022548, which is hereby incorporated by reference in its entirety) (SEQ ID NO: 31)
```
  1 MRSAPSQCAV TRALVLAGLW LAAAGRPLAF SDAGPHVHYG WGEPIRLRHL YTAGPHGLSS
 61 CFLRIRADGG VDCARSQSAH SLVEIRAVAL RTVAIKGVHS VRYLCMGADG RMQGLLQYSA
```

TABLE 1-continued

```
121 GDCAFQEEIR PDGYNVYRSE KHRLPVSLSS AIQRQLYKGR GFLPLSHFLP MLPGSPAEPR
181 DLQDHVESER FSSPLETDSM DPFGIATKMG LVKSPSFQK
```

*Pelodiscus sinensis* (Chinese softshell turtle) FGF19 (Ensembl Accession No. ENSPSIP00000010374, which is hereby incorporated by reference in its entirety) (SEQ ID NO: 32)
```
  1 MWRSLCKSHT SLALLGLCFA VVVRSLPFSD AGPHVNYGWG EPIRLRHLYT ASRHGLFNYF
 61 LRISSDGKVD GTSIQSPHSL LEIRAVAVRT VAIKGVHSSR YLCMEEDGKL HGLLRYSTED
121 CSFEEEIRPD GYNVYKSKKY GISVSLSSAK QRQQFKGKDF LPLSHFLPMI NTVPVESMDF
181 GEYGDYSHTF ESDLFSSPLE TDSMDPFGIT SKISPVKSPS FQK
```

*Latimeria chalumnae* (coelacanth) FGF19 (Ensembl Accession No. ENSLACP00000014596, which is hereby incorporated by reference in its entirety) (SEQ ID NO: 33)
```
  1 MLQALYNLCT ALVLFKLPFA MVGYTLPSAN EGPHLNYDWG ESVRLKHLYT SSKHGLISYF
 61 LQINDDGKVD GTTTRSCYSL LEIKSVGPGV LAIKGIQSSR YLCVEKDGKL HGSRTYSADD
121 CSFKEDILPD GYTIYVSKKH GSVVNLSNHK QKRQRNRRTL PPFSQFLPLM DTIRVECMNC
181 GEHCDDNLHD ELETGLSMDP FESTSKKSFQ SPSFHNR
```

*Mustela putorius furo* (ferret) FGF19 (Ensembl Accession No. ENSMPUP00000004571, which is hereby incorporated by reference in its entirety) (SEQ ID NO: 34)
```
  1 MRSAASRCAV ARALVLAGLW LAAAGRPLAF SDAGPHVHYG WGEPIRLRHL YTAGPHGLSS
 61 CFLRIRADGG VDCARGQSAH SLVEIRAVAL RTVAIKGVYS DRYLCMGADG RMQGLPQYSA
121 GDCAFEEEIR PDGYNVYRSK KHRLPVSLSS AKQRQLYKDR GFLPLSHFLP MLPGSLAEPR
181 DLQDHVEADG FSAPLETDSM DPFGIATKMG LVKSPSFQK
```

*Takifugu rubripes* (fugu) FGF19 (Ensembl Accession No. ENSTRUP00000007110, which is hereby incorporated by reference in its entirety) (SEQ ID NO: 35)
```
  1 SSTRISGNMV LLMLPITVAN LFLCAGVLSL PLLDQGSHFP QGWEQVVRFR HLYAASAGLH
 61 LLITEEGSIQ GSADPTLYSL MEIRPVDPGC VVIRGAATTR FLCIEGAGRL YSSQTYSKDD
121 CTFREQILAD GYSVYRSVGH GALVSLGNYR QQLRGEDWSV PTLAQFLPRI SSLDQDFKAA
181 LDETEKPEQT APQRSEPVDM VDSFGKLSQI IHSPSFHK
```

*Equus caballus* (horse) FGF19 (Ensembl Accession No. ENSECAP00000017705, which is hereby incorporated by reference in its entirety) (SEQ ID NO: 36); partial sequence corresponding to human FGF19 residues 20 to 113
```
  1 AAGRPLALSD AGPHVHYGWG EPIRLRHLYT AGPHGLSSCF LRIRADGAVD CARGQSAHSL
 61 VEIRAVALRT VAIKGVHSVR YLCMGADGRM QGLV
```

*Oryzias latipes* (medaka) FGF19 (Ensembl Accession No. ENSORLP00000000352, which is hereby incorporated by reference in its entirety) (SEQ ID NO: 37)
```
  1 TMLLIVVTIS TMVFSDSGVS SMPLSDHGPH ITHSWSQVVR LRHLYAVKPG QHVQIREDGH
 61 IHGSAEQTLN SLLEIRPVAP GRVVFRGVAT SRFLCMESDG RLFSSHTFDK DNCVFREQIL
121 ADGYNIYISD QHGTLLSLGN HRQRQQGLDR DVPALAQFLP RISTLQQGVY PVPDPPHQMR
181 TMQTEKTLDA TDTFGQLSKI IHSPSFNKR
```

*Xiphophorus maculatus* (platyfish) FGF19 (Ensembl Accession No. ENSXMAP00000001516, which is hereby incorporated by reference in its entirety) (SEQ ID NO: 38)
```
  1 MFVFILCIAG ELFTLGVFCM PMMDQGPLVT HGWGQVVRHR HLYAAKPGLH LLISEDGQIH
 61 GSADQTLYSL LEIQPVGPGR VVIKGVATTR FLCMESDGRL YSTETYSRAD CTFREQIQAD
121 GYNVYTSDSH GALLSLGNNQ QRHSGSDRGV PALARFLPRL NTLQQAVPTE PDVPDQLSPE
181 KVQQTVDMVA SFGKLSHIIH SPSFHKR
```

*Ictidomys tridecemlineatus* (squirrel) FGF19 (Ensembl Accession No. ENSSTOP00000021639, which is hereby incorporated by reference in its entirety) (SEQ ID NO: 39)
```
  1 MRSAPSGRAL ARALVLASLW LAVAGRPLAR RSLALSDQGP HLYYGWDQPI RLRHLYAAGP
 61 YGFSNCFLRI RTDGAVDCEE KQSERSLMEI RAVALETVAI KDINSVRYLC MGADGRIQGL
121 PRYSEEECTF KEEISYDGYN VYRSQKYHLP VVLSSAKQRQ LYQSKGVVPL SYFLPMLPLA
181 SAETRDRLES DVFSLPLETD SMDPFGMASE VGLKSPSFQK
```

*Gasterosteus aculeatus* (stickleback) FGF19 (Ensembl Accession No. ENSGACP00000018732, which is hereby incorporated by reference in its entirety) (SEQ ID NO: 40)
```
  1 MLLLLVPAYV ASVFLALGVV CLPLTDQGLH MADDWGQSVR LKHLYAASPG LHLLIGEDGR
 61 IQGSAQQSPY SLLEISAVDP GCVVIRGVAT ARFLCIEGDG RLYSSDTYSR DDCTFREQIL
121 PDGYSVYVSH GHGALLSLGN HRQRLQGRDH GVPALAQFLP RVSTMDQASA PDAPGQTATE
181 TEEPVDSFGK LSQIIHSPSF HER
```

*Oreochromis niloticus* (tilapia) FGF19 (Ensembl Accession No. ENSONIP00000022796, which is hereby incorporated by reference in its entirety) (SEQ ID NO: 41)
```
  1 MLLLLIVSIV NMLFGVGMVC MPLSDNGPHI AHGWAQVVRL RHLYATRPGM HLLISEGGQI
 61 RGSAVQTLHS LMEIRPVGPG RVVIRGVATA RFLCIEDDGT LYSSHAYSRE DCIFREQILP
```

TABLE 1-continued

```
121 DGYNIYISDR HGVLLSLGNH RQRLQGLDRG DPALAQFLPR ISTLNQIPSP GANIGDHMKV
181 AKTEEPVDTI DSFGKFSQII DSPSFHKR

Meleagris gallopavo (turkey) FGF19 (Ensembl Accession No.
ENSMGAP00000010265, which is hereby incorporated by reference in its
entirety) (SEQ ID NO: 42); partial sequence corresponding to human
FGF19 residues 71 to 216
  1 VGNQSPQSIL EITAVDVGIV AIKGLFSGRY LAMNKRGRLY ASLSYSIEDC SFEEEIRPDG
 61 YNVYKSKKYG ISVSLSSAKQ RQQFKGKDFL PLSHFLPMIN TVPVEVTDFG EYGDYSQAFE
121 PEVYSSPLET DSMDPFGITS KLSPVKSPSF QK Papio anubis (olive baboon) FGF19 (GenBank Accession No.
XP_003909471, which is hereby incorporated by reference in its
entirety) (SEQ ID NO: 43)
  1 MRSGCVVVHA WILASLWLAV AGRPLAFSDA GPHVHYGWGD PIRLRHLYTS GPHGLSSCFL
 61 RIRTDGVVDC ARGQSAHSLL EIKAVALRTV AIKGVHSVRY LCMGADGKMQ GLLQYSEEDC
121 AFEEEIRPDG YNVYRSQKHR LPVSLSSAKQ RQLYKNRGFL PLSHFLPMLP MAPEEPEDLR
181 GPLESDMFSS PLETDSMDPF GLVTGLEAVR SPSFEK Saimiri boliviensis boliviensis (Bolivian squirrel monkey) FGF19
(GenBank Accession No. XP_003941214, which is hereby incorporated by
reference in its entirety) (SEQ ID NO: 44)
  1 MRSGCVVVHA WILAGLWLAV VGRPLAFSDA GPHVHYGWGD PIRLRHLYTS SPHGLSSCFL
 61 RIRSDGVVDC ARGQSAHSLL EIKAVALRTV AIKGVHSSRY LCMGADGRLQ GLFQYSEEDC
121 AFEEEIRPDG YNVYLSEKHR LPVSLSSAKQ RQLYKKRGFL PLSHFLPMLP RAPEEPDDLR
181 GHLESDVFSS PLETDSMDPF GLVTGLEAVN SPSFEK Pteropus alecto (black flying fox) FGF19 (GenBank Accession No.
ELK13233, which is hereby incorporated by reference in its entirety)
(SEQ ID NO: 45)
  1 MRSPCAVARA LVLAGLWLAS AAGPLALSDA GPHVHYGWGE AIRLRHLYTA GPHGPSSCFL
 61 RIRADGAVDC ARGQSAHSLV EIRAVALRNV AIKGVHSVRY LCMGADGRML GLLQYSADDC
121 AFEEEIRPDG YNVYHSKKHH LPVSLSSAKQ RQLYKDRGFL PLSHFLPMLP RSPTEPENFE
181 DHLEADTFSS PLETDDMDPF GIASKLGLEE SPSFQK Myotis davidii (David's myotis) FGF19 (GenBank Accession No.
ELK24234, which is hereby incorporated by reference in its entirety)
(SEQ ID NO: 46)
  1 MSGQNSGRHG SRPGLDEEPE PGPLELRALG STRADPQLCD FLENHFLGYT CLELDICLAT
 61 YLGVSHWGES IRLRHLYTSG PHGPSSCFLR IRVDGAVDCA RGQSAHSLVE IRAVALRKVA
121 IKGVHSALYL CMEGDGRMRG LPQFSPEDCA FEEEIRPDGY NVYRSQKHQL PVSLSSARQR
181 QLFKARGFLP LSHFLPMLPS SPAEPVHRER PLEPDAFSSP LETDSMDPFG IANNLRLVKS
241 PSFQK Tupaia chinensis (Chinese tree shrew) FGF19 (GenBank Accession No.
ELW64990, which is hereby incorporated by reference in its entirety)
(SEQ ID NO: 47); residues 1-257, excluding 13-19
  1 MRRTWSGFAV AT-------R AGSPLALADA GPHVNYGWDE SIRLRHLYTA SLHGSTSCFL
 61 RIRDDGSVGC ARGQSMHSLL EIKAVALQTV AIKGVYSVRY LCMDTDGRMQ GLPQYSEEDC
121 TFEEEIRSDG HNVYRSKKHG LPVSLSSAKQ RQLYKGRGFL SLSHFLLMMP KTSAGPGNPR
181 DQRNPRDQRD PNTFSLPLET DSMDPFGMTT RHGLLLDSCC ASLVLLNIST DGEFSPYGNI
241 LRPSFRFKLF KMKKVTN Heterocephalus glaber (naked mole-rat) FGF19 (GenBank Accession No.
EHB12332, which is hereby incorporated by reference in its entirety)
(SEQ ID NO: 48)
  1 MRFSKSTCGF FNHQRLQALW LSLSSVKWVL DAAVEGRPIR LRHLYAAGPY GRSRCFLRIH
 61 TDGAVDCVEE QSEHCLLEIR AVALETVAIK DINSVRYLCM GPDGRMQGLP WYSEEDCAFK
121 EEISYPGYSV YRSQKHHLPI VLSSVKQRQQ YQSKGVVPLS YFLPMLPKAS VEPGDEEESA
181 FSLPLKTDSM DPFGMASEIG LAKSPSFQK
```

In one embodiment, a C-terminal portion of FGF19 of the chimeric protein of the present invention comprises the conserved amino acid sequence TGLEAV(R/N)SPSFEK (SEQ ID NO: 49). In one embodiment, a C-terminal portion of FGF19 comprises the conserved amino acid sequence MDPFGLVTGLEAV(R/N)SPSFEK (SEQ ID NO: 50). In one embodiment, the C-terminal portion of FGF19 of the chimeric protein of the present invention comprises the conserved amino acid sequence LP(M/I)(V/A)PEEPEDLR(G/R)HLESD(M/V)FSSPLETDSMDPFGLVTGLEAV(R/N)SPSFEK (SEQ ID NO: 51).

In one embodiment, the C-terminal portion of FGF 19 of the chimeric protein of the present invention consists of an amino acid sequence selected from the group consisting of TGLEAV(R/N)SPSFEK (SEQ ID NO: 49); MDPF-GLVTGLEAV(R/N)SPSFEK (SEQ ID NO: 50); and LP(M/I)(V/A)PEEPEDLR(G/R)HLESD(MN)FSSPLETDSMDP-FGLVTGLEAV(R/N)SPSFEK (SEQ ID NO: 51).

In certain embodiments according to the present invention, the C-terminal portion of FGF19 of the chimeric protein of the present invention includes a polypeptide sequence that has at least 80%, at least 85%, at least 90%, at least 95%, at least 97%, or at least 99% amino acid sequence identity to the amino acid sequences of any of SEQ ID NOs: 49 to 51. In certain embodiments according to the present invention, the C-terminal portion of FGF19 of the chimeric protein of the present invention includes a polypeptide sequence that has at least 80%, at least 85%, at least 90%, at least 95%, at least 97%, or at least 99% amino acid sequence homology to the amino acid sequences of any of SEQ ID NOs: 49 to 51.

Percent (%) amino acid sequence identity with respect to a given polypeptide sequence identified herein is defined as the percentage of amino acid residues in a candidate sequence that are identical to the amino acid residues in the reference sequence, after aligning the sequences and introducing gaps, if necessary, to achieve the maximum percent sequence identity, and not considering any conservative substitutions as part of the sequence identity. Percent (%) amino acid sequence homology with respect to a given polypeptide sequence identified herein is the percentage of amino acid residues in a candidate sequence that are identical to or strongly similar to the amino acid residues in the reference sequence, after aligning the sequences and introducing gaps, if necessary, to achieve the maximum percent sequence homology. Strongly similar amino acid residues may include, for example, conservative amino acid substitutions known in the art. Alignment for purposes of determining percent amino acid sequence identity and/or homology can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

It will be understood that the portion from FGF19 of the chimeric protein of the present invention may be from a nucleotide sequence that encodes an FGF19 protein (e.g., those encoding orthologs) from a mammal or even a non-mammalian species. For example, a nucleotide sequence encoding a mammalian or non-mammalian FGF19 protein according to the present invention may include, but is not limited to, those FGF-encoding nucleotide sequences shown in Table 2.

TABLE 2

```
Human FGF19 gene coding sequence (SEQ ID NO: 52) (GenBank Accession No.
NM_005117, which is hereby incorporated by reference in its entirety)
 464      ATGCGGA GCGGGTGTGT GGTGGTCCAC GTATGGATCC TGGCCGGCCT CTGGCTGGCC
 521 GTGGCCGGGC GCCCCCTCGC CTTCTCGGAC GCGGGGCCCC ACGTGCACTA CGGCTGGGGC
 581 GACCCCATCC GCCTGCGGCA CCTGTACACC TCCGGCCCCC ACGGGCTCTC CAGCTGCTTC
 641 CTGCGCATCC GTGCCGACGG CGTCGTGGAC TGCGCGGGGG GCCAGAGCGC GCACAGTTTG
 701 CTGGAGATCA AGGCAGTCGC TCTGCGGACC GTGGCCATCA AGGGCGTGCA CAGCGTGCGG
 761 TACCTCTGCA TGGGCGCCGA CGGCAAGATG CAGGGGCTGC TTCAGTACTC GGAGGAAGAC
 821 TGTGCTTTCG AGGAGGAGAT CCGCCCAGAT GGCTACAATG TGTACCGATC CGAGAAGCAC
 881 CGCCTCCCGG TCTCCCTGAG CAGTGCCAAA CAGCGGCAGC TGTACAAGAA CAGAGGCTTT
 941 CTTCCACTCT CTCATTTCCT GCCCATGCTG CCCATGGTCC CAGAGGAGCC TGAGGACCTC
1001 AGGGGCCACT TGGAATCTGA CATGTTCTCT TCGCCCCTGG AGACCGACAG CATGGACCCA
1061 TTTGGGCTTG TCACCGGACT GGAGGCCGTG AGGAGTCCCA GCTTTGAGAA GTAA Gorilla FGF19 gene coding sequence (SEQ ID NO: 53) (Ensembl Accession
No. ENSGGOT00000028361, which is hereby incorporated by reference in
its entirety)
 463      ATGCGGAG CGGGTGTGTG GTGGTCCACG TCTGGATCCT GGCCGGCCTC TGGCTGGCCG
 521 TGGCCGGGCG CCCCCTCGCC TTCTCGGACG CGGGGCCCCA CGTGCACTAC GGCTGGGGCG
 581 ACCCCATCCG CCTGCGGCAC CTGTACACCT CCGGCCCCCA CGGGCTCTCC AGCTGCTTCC
 641 TGCGCATCCG TGCCGACGGC GTCGTGGACT GCGCGCGGGG CCAGAGCGCG CACAGTTTGC
 701 TGGAGATCAA GGCAGTCGCT CTGCGGACCG TGGCCATCAA GGGCGTGCAC AGCGTGCGGT
 761 ACCTCTGCAT GGGCGCCGAC GGCAAGATGC AGGGGCTGCT TCAGTACTCG GAGGAAGACT
 821 GTGCTTTCGA GGAGGAGATC CGCCCAGATG GCTACAATGT GTACCGATCT GAGAAGCACC
 881 GCCTCCCGGT CTCCCTGAGC AGTGCCAAAC AGCGGCAGCT GTACAAGAAC AGAGGCTTTC
 941 TTCCGCTCTC TCATTTCCTG CCCATGCTGC CCATGGTCCC AGAGGAGCCT GAGGACCTCA
1001 GGGGCCACTT GGAATCTGAC ATGTTCTCTT CACCCCTGGA GACCGACAGC ATGGACCCAT
1061 TTGGGCTTGT CACCGGACTG GAGGCCGTGA GGAGTCCTAG CTTTGAGAAG TAA Pan troglodytes gene coding sequence (chimpanzee) FGF19 (SEQ ID NO:
54) (Ensembl Accession No. ENSPTRT00000007454, which is hereby
incorporated by reference in its entirety)
   1 ATGCGGAACG GGTGTGTGGT GGTCCACGTC TGGATCCTGG CCGGCCTCTG GCTGGCCGTG
  61 GCCGGGCGCC CCCTCGCCTT CTCGGACGCG GGGCGCCACG TGCACTACTG CTGGGGCGAC
 121 CCCATCCCCC TGCGGCACCT GTACACCTCC GGCCCCCATG GGCTCTCCAG CTGCTTCCTG
 181 CGCATCCCTG CGAACTGCGT CATGAACTGC GCGCGGGGCC AGAGCGCGCA CAGTTTGCTG
 241 GAGATCAAGG CAGTCGCTCT GCGGACCGTG GCCATCAAGG GCGTGCACAG CGTGCGGTAC
 301 CTCTGCATGG GCGCCGACGG CAAGATGCAG GGGCTGCTTC AGTACTCGGA GGAAGACTGT
 361 GCTTTCGAGG AGGAGATCCG CCCAGATGGC TACAATGTGT ACCGATCCGA AGCACCGC
 421 CTCCCGGTCT CCCTGAGCAG TGCCAAACAG CGGCAGCTGT ACAAGAACAG AGGCTTTCTT
 481 CCACTCTCTC ATTTCCTGCC CATGCTGCCC ATGGTCCCAG AGGAGCCTGA GGACCTCAGG
 541 GGCCACTTGG AATCTGACAT GTTCTCTTCG CCCCTGGAGA CCGACAGCAT GGACCCATTT
 601 GGGCTTGTCA CCGGACTGGA GGCCGTGAGG AGTCCCAGCT TTGAGAAGTA A Macaca mulatta gene coding sequence (Rhesus monkey) FGF19 (SEQ ID NO:
55) (GenBank Accession No. XM_001100825, which is hereby incorporated
by reference in its entirety)
 758         ATG AGGAGCGGGT GTGTGGTGGT CCACGCCTGG ATCCTGGCCA GCCTCTGGCT
 811 GGCCGTGGCC GGGCGTCCCC TCGCCTTCTC GGACGCGGGG CCCCACGTGC ACTACGGCTG
 871 GGGCGACCCC ATCCGCCTGC GGCACCTGTA CACCTCCGGC CCCATGGGC TCTCCAGCTG
 931 CTTCCTGCGC ATCCGCACCG ACGGCGTCGT GGACTGCGCG CGGGGCCAAA GCGCGCACAG
 991 TTTGCTGGAG ATCAAGGCAG TAGCTCTGCG GACCGTGGCC ATCAAGGGCG TGCACAGCGT
1051 GCGGTACCTC TGCATGGGCG CCGACGCAA GATGCAGGGG CTGCTTCAGT ACTCAGAGGA
1111 AGACTGTGCT TTCGAGGAGG AGATCCGCCC TGATGGCTAC AATGTATACC GATCCGAGAA
1171 GCACCGCCTC CCGGTCTCTC TGAGCAGTGC CAAACAGAGG CAGCTGTACA AGAACAGAGG
1231 CTTTCTTCCG CTCTCTCATT TCCTACCCAT GCTGCCCATG GCCCAGAGG AGCCTGAGGA
```

TABLE 2-continued

1291 CCTCAGGGGC CACTTGGAAT CTGACATGTT CTCTTCGCCC CTGGAGACTG ACAGCATGGA
1351 CCCATTTGGG CTTGTCACCG GACTGGAGGC GGTGAGGAGT CCCAGCTTTG AGAAATAA

*Pongo abelii* gene coding sequence (Sumatran orangutan) FGF19 (SEQ ID
NO: 56) (GenBank Accession No. XM_002821413, which is hereby
incorporated by reference in its entirety)
 763    ATGCGGAG CGGGTGTGTG GTGGTCCACG CCTGGATCCT GGCCGGCCTC TGGCTGGCCG
 821 TGGCCGGGCG CCCCCTCGCC TTCTCGGACT CGGGGCCCCA CGTGCACTAC GGCTGGGGCG
 881 ACCCCATCCG CCTGCGGCAC CTGTACACCT CCGGCCCCCA CGGGCTCTCC AGCTGCTTCC
 941 TGCGCATCCG TGCCGACGGC GTCGTGGACT GCGCGCGGGG CCAGAGCGCG CACAGTTTGC
1001 TGGAGATCAA GGCAGTCGCT CTGCGGACCG TGGCCATCAA GGGCGTGCAC AGCGTGCGGT
1061 ACCTCTGCAT GGGCGCCGAC GGCAAGATGC AGGGGCTGCT TCAGTACTCG GAGGAAGACT
1121 GTGCTTTCGA GGAGGAGATC CGCCCAGATG GCTACAATGT GTACCGATCC GAGAAGCACC
1181 GCCTCCCGGT CTCCCTGAGC AGTGCCAAAC AGCGGCAGCT GTACAAGAAC AGGGGCTTTC
1241 TTCCGCTCTC TCATTTCCTG CCCATGCTGC CCATGGTCCC AGAGGAGCCT GAGGACCTCA
1301 GGCGCCACTT GGAATCCGAC ATGTTCTCTT CGCCCCTGGA GACCGACAGC ATGGACCCAT
1361 TTGGGCTTGT CACCGGACTG GAGGCCGTGA GGAGTCCCAG CTTTGAGAAA TAA

*Nomascus leucogenys* gene coding sequence (Northern white-cheeked
gibbon) FGF19 (SEQ ID NO: 57) (Genbank Accession No. XM_003278023,
which is hereby incorporated by reference in its entirety)
 456      ATGCG GAGCGAGTGT GTGGTGGTCC ACGCCTGGAT CCTGGCCGGC CTCTGGCTGG
 511 CAGTGGCCGG GCGCCCCCTC GCCTTTTCGG ACGCGGGGCC CCACGTGCAC TACGGCTGGG
 571 GCGACCCCAT CCGTCTGCGG CACCTGTACA CCTCCGGCCC CCACGGGCTC TCCAGCTGCT
 631 TCCTGCGCAT CCGTGCCGAC GGCGTCGTGG ACTGCGCGCG GGGCCAGAGC GCGCACAGTT
 691 TGCTGGAGAT CAAGGCAGTC GCTCTGCGGA CCGTGGCCAT AAAGGGCGTG CACAGCGTGC
 751 GGTACCTCTG CATGGGCGCC GACGGCAAGA TGCAGGGGCT GCTTCAGTAT TCGGAGGAAG
 811 ACTGTGCTTT CGAGGAGGAG ATCCGCCCAG ATGGCTACAA TGTGTACCGA TCCGAGAAGC
 871 ACCGCCTCCC CGTCTCCCTG AGCAGTGCCA AACAGCGGCT GTGTATAAG AACAGAGGCT
 931 TTCTTCCACT CTCTCATTTC CTGCCCATGC TGCCCATGGT CCCAGAGGAG CCTGAGGACC
 991 TCAGGGGCCA CTTGGAATCT GACATGTTCT CTTCGCCCCT GGAGACCGAC AGCATGGACC
1051 CATTTGGGCT TGTCACCGGA CTGGAGGCCG TGAGGAGTCC CAGCTTTGAG AAATAA

*Callithrix jacchus* gene coding sequence (white-tufted-ear marmoset)
FGF19 (SEQ ID NO: 58) (GenBank Accession No. XM_002763684, which is
hereby incorporated by reference in its entirety)
   1 ATGTGGAAGG CCACCGCTGG TGGCCAGCAG GGACAGTCCG AAGCACAAAT GTCCACATGT
  61 CCCCATGTTC CTCGTCCTCT GTGGATTGCT CAGAGCTGCC TGTTTTCTCT GCAGCTCCAG
 121 TACTCGGAGG AAGACTGTGC TTTCGAGGAG GAGATCCGCC CTGATGGCTA CAATGTGTAC
 181 TGGTCCGAGA AGCACCGCCT CCCGGTCTCC CTGAGCAGCG CCAAACAGCG GCAGCTGTAC
 241 AAGAAACGAG GCTTTCTTCC ACTGTCCCAT TTCCTGCCCA TGCTGCCCAT AGCCCCAGAA
 301 GAGCCTGAGG ACCTCAGGGG ACACCTGGAA TCTGACTGTG TCTCTTCACC CCTGGAGACT
 361 GACAGCATGG ACCCATTTGG GCTTGTCACG GGACTGGAGG CGGTGAACAG TCCCAGCTTT
 421 GAGAAGTAA

*Microcebus murinus* gene coding sequence (mouse lemur) FGF19 (SEQ ID
NO: 59) (Ensembl Accession No. ENSMICT00000003065, which is hereby
incorporated by reference in its entirety)
   1 ATGCCGAGCG GGCAAAGCGG TTGTGTGGCG GCCCGCGCCC TGATCCTGGC CGGCCTCTGG
  61 CTGACCGCGG CCGGGCGCCC GCTGGCCTTC TCCGACGCGG GCCCGCACGT GCACTACGGC
 121 TGGGGCGAGC CCATCCGCCT GCGGCACCTG TACACCGCCG GCCCCCACGG CCTCTCCAGC
 181 TGCTTCCTGC GCATCCGCGC AGACGGCTCC GTGGACTGCG CGCGGGGCCA GAGCGCACAC
 241 AGTTTGCTGG AGATCAGGGC GGTCGCTCTT CGGACTGTGG CCATCAAGGG CGTGCACAGC
 301 GTGCGGTACC TCTGCATGGG CGCAGACGGC AGGATGCAGG GGCTGCTCCG GTACTCGGAG
 361 GAAGACTGTG CCTTCGAGGA GGAGATCCGC CCCGATGGCT ACAACGTGTA CCGGTCTGAG
 421 AAGCACCGCC TGCCGGTGTC TCTGAGCAGC GCCAGGCAGA GGCAGCTGTA CAAGGGCAGG
 481 GGCTTCCTGC CGCTCTCTCA CTTCCTGCCC ATGCTGCCCG TGACCCCGGC AGAGACCGGG
 541 GACCTCAGGG ACCACTTGGA GTCCGACATG TTCGCTTCGC CCTGGAGAC CGACAGCATG
 601 GACCCGTTTG GGATCGCCAC CAGACTTGGG GTGGTGAAGA GTCCCAGCTT TCAGAAATGA

*Choloepus hoffmanni* gene coding sequence (sloth) FGF19 (SEQ ID NO: 60)
(Ensembl Accession No. ENSCHOT00000002324, which is hereby
incorporated by reference in its entirety)
   1 TTGCTCGAAA TGAAGGCAGT GGCGCTGCGG GCCGTGGCCA TCAAGGGCGT GCACAGTGCT
  61 CTGTACCTCT GCATGAACGC CGACGGCAGT CTGCACGGGC TGCCTCGGTA CTCTGCAGAA
 121 GACTGTGCTT TTGAGGAGGA AATCCGCCCC GACGGCTACA ATGTGTACTG GTCTAGGAAG
 181 CACGGCCTCC CTGTCTCTTT GAGCAGTGCA AAACAGAGGC AGCTGTACAA AGGCAGAGGC
 241 TTTCTGCCCC TGTCCCACTT CCTGCCCATG CTGCCCATGA CGCCGGCCGA GCCCGCAGAC
 301 CCCGGGGATG ACGTGGAGTC GGACATGTTC TCTTCACCTC TGGAAACCGA CAGCATGGAT
 361 CCTTTTGGAA TTGCCTCCAG ACTTGAGCTT GTGAACAGTC CAGCTTTCAG CATAA

*Ailuropoda melanoleuca* gene coding sequence (giant panda) FGF19 (SEQ
ID NO: 61) (GenBank Accession No. XM_002927906, which is hereby
incorporated by reference in its entirety)
  69         GG TCCTAGCCGG CCTCTGCCTG GCGGTAGCCG GGCGCCCCCT AGCCTTCTCG
 421 GACGCGGGGC CGCACGTGCA CTACGGCTGG GGTGAGCCCA TCCGCCTACG GCACCTGTAC
 481 ACCGCCGCC CCCACGGCCT CTCCAGCTGC TTCCTGCGCA TCCGTGCCGA CGGCGGGGTT
 541 GACTGCGCGC GGGGCCAGAG CGCGCACAGT TTGGTGGAGA TCAGGGCAGT CGCTCTGCGG
 601 ACCGTGGCCA TCAAGGGTGT GCACAGCGTC CGGTACCTCT GCATGGCGC GGACGGCAGG
 661 ATGCAAGGGC TGCCTCAGTA CTCTGCAGGG GACTGTGCTT TCGAGGAGGA GATCCGCCCC TABLE 2-continued

```
721 GACGGCTACA ATGTGTACCG GTCCAAGAAG CACCGTCTCC CCGTCTCTCT GAGCGGTGCC
781 AAACAGAGGC AGCTTTACAA AGACAGAGGC TTTCTGCCCC TGTCCCACTT CTTGCCCATG
841 CTGCCCGGGA GCCCAGCAGA GCCCAGGGAC CTCCAGGACC ATGCGGAGTC GGACGGGTTT
901 TCTGCACCCC TAGAAACAGA CAGCATGGAC CCTTTTGGGA TCGCCACCAA AATGGGACTA
961 GTGAAGAGTC CCAGCTTCCA GAAATAA
```

Sus scrofa gene coding sequence (pig) FGF19 (SEQ ID NO: 62) (Ensembl Accession No. ENSSSCT00000014068, which is hereby incorporated by reference in its entirety)

```
  1 ATGCGGAGCG CTCCGAGCCG GTGCGCGGTG GTCCGCGCCC TGGTCCTGGC CGGCCTCTGG
 61 CTGGCCGCAG CCGGGCGCCC CCTAGCCTTC TCGGATGCTG GGCCGCACGT GCACTACGGC
121 TGGGGCGAGT CGGTCCGCCT GCGGCACCTG TACACTGCGA GTCCCCACGG CGTCTCCAGC
181 TGCTTCCTGC GCATCCACTC AGACGGCCCC GTGGACTGCG CGCCGGGACA GAGCGCGCAC
241 AGTTTGATGG AGATCAGGGC AGTCGCGCTG AGTACCGTGG CGATCAAGGG CGAGCGCAGC
301 GGCCGTTACC TCTGCATGGG CGCCGACGGC AAGATGCAAG GGCAGACTCA GTACTCGGAT
361 GAGGACTGTG CTTTCGAGGA GGAGATCCGC CCTGATGGCT ACAACGTGTA CTGGTCCAAG
421 AAACACCATC TGCCCGTCTC TCTGAGCAGC GCCAGGCAGA GGCAGCTGTA CAAAGGCAGG
481 GGCTTCCTGC CGCTGTCCCA CTTTCTGCCC ATGCTGTCCA CTCTCCCAGC CGAGCCGGAG
541 GACCTCCAGG ACCCCTTCAA GTCCGACCTG TTTTCTTTGC CCTGGAAAC GGACAGCATG
601 GACCCTTTCC GGATCGCCGC CAAACTGGGA GCGGTGAAGA GTCCCAGCTT CTATAAATAA
```

Bos taurus gene coding sequence (bovine) FGF19 (SEQ ID NO: 63) (GenBank Accession No. XM_599739, which is hereby incorporated by reference in its entirety)

```
406                                                      ATGCG GAGCGCTCCG
421 AGCCGGTGCG CCGTGGCCCG CGCCCTGGTC CTGGCTGGCC TCTGGCTGGC CGCAGCCGGG
481 CGCCCCCTGG CCTTCTCGGA TGCGGGGCCG CACGTGCACT ACGGCTGGGG CGAGTCGGTT
541 CGCTTGCGGC ACCTGTATAC CGCGGGCCCG CAGGGCCTCT ACAGCTGCTT TCTGCGCATC
601 CACTCCGACG GCGCCGTGGA CTGCGCGCAG GTCCAGAGCG CGCACAGTTT GATGGAGATC
661 AGGGCGGTCG CTCTGAGCAC CGTAGCCATC AAGGGCGAGC GCAGCGTGCT GTACCTCTGC
721 ATGGACGCCG ACGGCAAGAT GCAAGGACTG ACCCAGTACT CAGCCGAGGA CTGTGCTTTC
781 GAGGAGGAGA TCCGTCCTGA CGGCTACAAC GTGTACTGGT CCAGGAAGCA CCATCTCCCG
841 GTCTCCCTGA GCAGCTCCAG GCAGAGGCAG CTGTTCAAAA GCAGGGGCTT CCTGCCGCTG
901 TCTCACTTCC TGCCCATGCT GTCCACCATC CCAGCCGAAC CTGAAGACCT CCAGGAACCC
961 CTGAAGCCTG ATTTCTTTCT GCCCCTGAAA ACAGATAGCA TGGACCCTTT CGGGGCTCGCC
1021 ACCAAACTGG GATCGGTGAA GAGTCCCAGC TTCTATAATT AA
```

Canis lupus familiaris gene coding sequence (dog) FGF19 (SEQ ID NO: 64) (GenBank Accession No. XM_540802, which is hereby incorporated by reference in its entirety)

```
  1 CTAGCCTTCT CCGACGCGGG GCCGCACGTG CACTCCTTCT GGGGGGAGCC CATCCGCCTG
 61 CGGCACCTGT ACACCGCCGG CCCCCACGGC CTCTCCAGCT GCTTCCTGCG CATCCGCGCC
121 GACGCGGGG TGGACTGCGC GCGGGGCCAG AGCGCGCACA GTCTGATGGA GATGAGGGCG
181 GTCGCTCTGC GGACCGTGGC CATCAAGGGC GTGCACAGCG GCCGGTACCT CTGCATGGGC
241 GCCGACGGCA GGATGCAAGG GCTGCCTCAG TACTCCGCCG GAGACTGTAC TTTCGAGGAG
301 GAGATCCGTC CCGATGGCTA CAATGTGTAC TGGTCCAAGA AGCACCATCT CCCCATCTCT
361 CTGAGTAGTG CCAAACAGAG GCAGCTCTAC AAGGGCAGGG GCTTTTTGCC CCTGTCCCAC
421 TTCTTACCTA TCTTGCCCGG GAGCCCAACA GAGCCCAGGG ACCTGGAAGA CCATGTGGAG
481 TCTGACGGGT TTTCTGCATC CCTGGAAACA GACAGCATGG ACCCTTTTGG GATCGCCACC
541 AAAAATTGGAC TAGTGAAGAG TCCCAGTTTC AAAAATAA
```

Oryctolagus cuniculus gene coding sequence (rabbit) FGF19 (SEQ ID NO: 65) (GenBank Accession No. XM_002724449, which is hereby incorporated by reference in its entirety)

```
  1 ATGCGCCGCG CGCCGAGCGG AGGTGCCGCG GCCCGCGCCT TGGTCCTGGC CGGCCTCTGG
 61 CTGGCCGCGG CCGCGCGCCC CTTGGCCTTG TCCGACGCGG GCCCGCATCT GCACTACGGC
121 TGGGGCGAGC CCGTCCGCCT GCGGCACCTG TACGCCACCA GCGCCCACGG CGTCTCGCAC
181 TGCTTCCTGC GTATACGCGC CGACGGCGCC GTGGACTGCG AGCGGAGCCA GAGCGCACAC
241 AGCTTGCTGG AGATCCGAGC GGTCGCCCTG CGCACCGTGG CCTTCAAGGG CGTGCACACA
301 TCCCGCTACC TCTGCATGGG CGCCGACGGC AGGATGCGGG GGCAGCTGCA GTACTCGGAG
361 GAGGACTGTG CCTTCCAGGA GGAGATCAGC TCCGGCTACA ACGTGTACCG CTCCACGACG
421 CACCACCTGC CCGTGTCTCT GAGCAGTGCC AAGCAGAGAC ACCTGTACAA GACCAGAGGC
481 TTCCTGCCCC TCTCCCACTT CCTGCCCGTG CTGCCCCTGG CCTCCGAGGA GACCGCGCCG
541 CTCGGCGACC ACCCTGAAGC CGACCTGTTC TCCCCGCCCC TGGAAACCGA CAGCATGGAC
601 CCCTTCGGCA TGGCCACCAA GCTCGGGCCG GTGAAGAGCC CCAGCTTTCA GAAGTAG
```

Pteropus vampyrus gene coding sequence (megabat) FGF19 (SEQ ID NO: 66) (Ensembl Accession No. ENSPVAT00000009907, which is hereby incorporated by reference in its entirety)

```
  1 ATGCGGAGCC CGTGCGCTGT GGCCCGCGCC TTGGTCCTGG CCGGCCTCTG GCTGGCCTCA
 61 GCTGCGGGCC CCCTCGCCCT CTCGGACGCG GGGCCGCACG TGCACTACGG CTGGGGCGAG
121 GCCATCCGCC TGCGGCACCT GTACACCGCC GGCCCCCACG GCCCCTCCAG CTGCTTCCTG
181 CGCATCCGCG CGGATGGGGC GGTGGACTGC GCGCGGGGCC AGAGCGCGCA CAGTTTGGTG
241 GAAATCCGGG CTGTCGCCCT GCGGAACGTG GCTATCAAGG GCGTGCACAG CGTCCGATAC
301 CTCTGCATGG GAGCCGACGG CAGGATGCTA GGGCTGCTTC AGTACTCCGC TGACGACTGA
361 GCCTTCGAGG AGGAGATCCG CCCGGACGGC TACAACGTGT ACCACTCCAA GAAGCACCAC
421 CTCCCGGTCT CTCTGAGCAG TGCCAAGCAG AGGCAACTGT ACAAGGACAG GGGCTTCCTG
481 CCCCTGTCCC ATTTCCTGCC CATGCTGCCC AGGAGCCCGA CAGAGCCCGA GAACTTCGAA
541 GACCACTTGG AGGCCGAGAC GTTTTCCTCG CCCCTGGAGA CAGACGACAT GGACCCTTTT
601 GGGATTGCCA GTAAATTGGG GCTGGAGGAA AGTCCCAGCT TCCAGAAGTA A
```

TABLE 2-continued

*Tursiops truncatus* gene coding sequence (dolphin) FGF19 (SEQ ID NO: 67) (Ensembl Accession No. ENSTTRT00000000066, which is hereby incorporated by reference in its entirety)
```
  1 ATGCGGAGCG CTCCGAGCCG GTGCGCCGTG GCCCGCGCCC TGGTCCTGGC CGGCCTCTGG
 61 CTGGCTGCAG CCGGGCGCCC CCTAGCCTTC TCGGATGCCG GGCCGCACGT GCACTACGGC
121 TGGGGCGAGT CCGTCCGCCT GCGGCACCTG TACACCGCGG GTCCCCAGGG CCTCTCCAGC
181 TGCTTCCTGC GCATCCACTC AGACGGCGCC GTGGACTGCG CGCCGGTTCA GAGCGCGCAC
241 AGTTTGATGG AGATCAGGGC AGTCGCTCTG AGTACCGTGG CCATCAAGGG CGAACGCAGC
301 GTCCTGTACC TCTGCATGGG CGCCGACGGC AAAATGCAAG GGCTGAGTCA GTACTCAGCT
361 GAGGACTGTG CCTTTGAGGA GGAAATCCGT CCGGACGGCT ACAACGTGTA CTGGTCCAAG
421 AAACACCACC TCCCGGTGTC CCTGAGCAGC GCCAGGCAGC GGCAGCTGTT CAAAGGCAGG
481 GGTTTCCTGC CGCTGTCTCA CTTCCTTCCC ATGCTGTCCA CCATCCCCAC AGAGCCCGAT
541 GAAATCCAGG ACCACTTGAA GCCCGATTTG TTTGCTTTGC CCCTGAAAAC AGATAGCATG
601 GACCCATTTG GGCTCGCCAC CAAACTGGGA GTGGTGAAGA GTCCCAGCTT CTATAAGTAA
```

*Myotis lucifugus* gene coding sequence (microbat) FGF19 (SEQ ID NO: 68) (Ensembl Accession No. ENSMLUT00000002508, which is hereby incorporated by reference in its entirety)
```
  1 ATGCAAAGCG CGTGGAGCCG ACGCGTTGTG GCCCGAGCCC TGGTCTTGGC CAGCCTCGGG
 61 CTGGCCTCAG CCGGGGGGCC CCTCGGTCTT TCGGACGCTG GGCCGCACGT GCACTACGGC
121 TGGGGGGAGT CCATCCGCCT GCGCCACCTG TACACCTCCG GCCCCCACGG CCCATCCAGC
181 TGCTTCCTGC GCATCCGCGC TGACGGCGCA GTGGACTGCG CGCGGGGCCA GAGCGCGCAC
241 AGTTTGGTGG AGATCAGGGC CGTCGCCTTG CGGAAAGTGG CCATCAAGGG CGTGCACAGC
301 GCCCTGTACC TCTGCATGGG AGGCGACGGC AGGATGCTGG GGCTGCCTCA GTTCTCGCCC
361 GAGGACTGTG CTTTCGAGGA GGAGATCCGC CCGGACGGCT ACAACGTGTA CCGGTCCCAG
421 AAGCACCAGC TGCCCGTCTC GCTGAGCAGT GCCCGGCAGA GGCAGCTGTT CAAGGCCCGG
481 GGCTTCCTGC CGCTGTCCCA CTTCCTGCCC ATGCTGCCCA GCAGCCCCGC GGGACCCGTG
541 CCCCGAGAGC GCCCCTCGGA GCCGGACGAG TTCTCTTCGC CCTGGAAAC AGACAGCATG
601 GACCCTTTTG GGATTGCCAA CAACCTGAGG CTGGTGAGAA GTCCCAGCTT TCAGGAATAA
```

*Ornithorhynchus anatinus* gene coding sequence (platypus) FGF19 (SEQ ID NO: 69) (GenBank Accession No. XM_001506664, which is hereby incorporated by reference in its entirety)
```
  1 ATGCTTTCCT GTGTGGTTTT GCCTAGTCTG CTGGAGATCA AGGCGGTGGC CGTGCGCACG
 61 GTGGCCATCA AAGGGGTCCA CATCTCTCGG TACCTCTGCA TGGAAGAGGA TGGGAAAACT
121 CCATGGGCAC GTCTGCTGGA GATCAAGGCG GTGGCCGTGC GCACGGTGGC CATCAAAGGG
181 GTCCACAGCT CTCGGTACCT CTGCATGGAA GAGGATGGAA AACTCCATGG GCAGATTTGG
241 TATTCTGCAG AAGACTGTGC TTTTGAAGAG GAAATACGTC CAGATGGCTA CAATGTGTAT
301 AAATCTAAGA AATATGGTGT TCCTGTTTCT TTAAGCAGCG CCAAACAAAG GCAGCAATTC
361 AAAGGAAGAG ACTTTCTGCC TCTTTCTCGT TTCTTGCCAA TGATCAACAC AGTGCCTGTG
421 GAGCCAGCAG AGTTTGGGGA CTATGCCGAT TACTTTGAAT CAGATATATT TTCCTCACCT
481 CTGGAAACTG ACAGCATGGA CCCATTTAGA ATTGCCCCTA AACTGTCCCC TGTAAAGAGC
541 CCCAGCTTTC AGAAATAA
```

*Monodelphis domestica* gene coding sequence (opossum) FGF19 (SEQ ID NO: 70) (GenBank Accession No. XM_001373653, which is hereby incorporated by reference in its entirety)
```
  1 ATGGCCCAGC TCCTGGCCCC GCTCCTCACC CTGGCTGCTC TCTGGCTGGC CCCGACGGCG
 61 CGTGCCCGAC CGCTGGTGGA CGCCGGGCCT CACGTCTACT ACGGCTGGGG GGAGCCCATT
121 CGTCTGCGGC ATCTCTACAC GGCCAATCGG CACGGGCTCG CCAGCTTCTC CTTCCTCCGG
181 ATCCACCGCG ACGGCCGCGT GGACGGCAGC CGGAGTCAGA GCGCGCTCAG TTTGCTGGAG
241 ATCAAGGCGG TAGCTCTTCG GATGGTGGCG ATCAAAGGTG TCCATAGCTC TCGGTACCTG
301 TGTATGGGAG ACGCCGGGAA ACTCCAGGGA TCGGTGAGGT TCTCGGCCGA GGACTGCACC
361 TTCGAGGAGC AGATTCGCCC CGACGGCTAC AACGTGTACC AGTCCCCAA GTACAACCTC
421 CCCGTCTCGC TCTGCACTGA CAAGCAGAGG CAGCAGGCCC ACGCCAAGGA GCACCTGCCC
481 CTGTCCCACT TCCTGCCCAT GATCAATGCT ATTCCTTTGG AGGCCGAGGA GCCCGAGGGC
541 CCCAGGATGT TGGCGGCGCC TCTGGAGACG GACAGCATGG ACCCCTTCGG CCTCACCTCC
601 AAGCTGTTGC CGGTCAAGAG CCCCAGCTTT CAGAAATAA
```

*Anolis carolinensis* gene coding sequence (anole lizard) FGF19 (SEQ ID NO: 71) (GenBank Accession No. XM_003214667, which is hereby incorporated by reference in its entirety)
```
  1 ATGTGTCGGC GGGCGTTGCC TCTGCTGGGG GCCCTTCTGG GCTTGGCGGC CGTGGCCTCC
 61 CGCGCCCTCC CGCTCACCGA CGCCGGGCCC CACGTCAGCT ACGGCTGGGG GGAGCCCGTC
121 CGGCTCAGGC ACCTCTACAC CGCGGGGCGG CAGGGCCTCT TCAGCCAGTT CCTCCGCATC
181 CACGCCGACG GGAGAGTCGA CGGCGCCGGC AGCCAGAACC GGCAGAGTTT GCTGGAGATC
241 CGCGCGGTCT CGTTGCGCGC CGTGGCCCTC AAAGGCGTGC ACAGCTCCCG CTACCTCTGC
301 ATGGAGGAGG ACGCCGGGCT CCGCGGGATG CTCAGATATT CTGCAGAAGA CTGTTCCTTT
361 GAAGAGGAGA TGCGTCCAGA TGGCTACAAT ATCTACAAGT CAAAGAAATA CGGAGTTTTG
421 GTCTCCCTAA GTAATGCCAA ACAAGACAG CAATTCAAAG GGAAAGATTT TCTTCCTTTG
481 TCTCATTTCT TGCCGATGAT CAACACTGTG CCAGTGGAGT CTGCAGACTT TGGAGAGTAT
541 GGTGACACCA GGCAGCATTA TGAATCGGAT ATTTTCAGTT CACGTCTTGA AACTGACAGC
601 ATGGACCCTT TGGCCTCAC TTCAGAAGTG TCATCAGTAC AAAGTCCTAG CTTTGGGAAA
661 TAA
```

*Ochotona princeps* gene coding sequence (pika) FGF19 (SEQ ID NO: 72) (Ensembl Accession No. ENSOPRT00000010769, which is hereby incorporated by reference in its entirety) (1-214, excluding 78-112)
```
  1 GTGCGGAGCA GGGGAGCCAT GGCCCGCGCT CTGGTTCTAG CCACTCTCTG GCTGGCCGCG
 61 ACGGGGCGGC CGCTGGCCTT GTCCGACGCG GGGCCGCACC TGCACTACGG CTGGGGCGAG
```

TABLE 2-continued

```
121  CCCATCCGCC TGCGGCACCT GTACGCCACC AGCGCCCACG GCCTCTCGCA CTGCTTTTTG
181  CGCATCCGTA CCGACGGCAC CGTGGACTGC GAGCGCAGCC AGAGCGCGCA CA--------
     ---------- ---------- ---------- ---------- ---------- ----------
242  ---------- ---------- ---------- ------CTAC AGTACTCGGA GGAGGACTGC
266  GCCTTCGAAG AGGAGATCAG CTCTGGCTAT AACGTGTACC GCTCCAGGAG GTACCAGCTG
326  CCCGTGTCCC TGGGCAGCGC CAGGCAGAGG CAGCTGCAGC GGAGCCGTGG CTTCCTGCCC
386  CTGTCCCACT TCCTGCCGGT GCTGCCCGCG GCCTCGGAGG AGGTGGCGGC CCCCGCTGAC
446  CACCCGCAAG CAGACCCTTT CTCGCCCCTG GAGACCGACA GCATGGACCC ATTTGGAATG
506  GCCACCAAGC GGGGGCTGGT GAAGAGCCCC AGCTTCCAGA GTGA
```

*Cavia porcellus* gene coding sequence (guinea pig) FGF19 (SEQ ID NO: 73) (Ensembl Accession No. ENSCPOT00000008222, which is hereby incorporated by reference in its entirety)

```
  1  ATGTGGAGTG CGCCGAGCGG ATGTGTGGTG ATCCGCGCCC TGGTCCTGGC TGGCCTGTGG
 61  CTGCGGTGG CGGGGCGCCC CCTGGCCCGG CGGTCTCTCG CGCTATCTGA CCAGGGGCCG
121  CACTTGTACT ACGGCTGGGA CCAGCCGATC CGCCTTCGGC ACCTGTACGC CGCGGGCCCC
181  TACGGCCGCT CGCGCTGCTT CCTGCGCATT CACACGGACG GCGCGGTGGA CTGCGTCGAG
241  GAACAGAGCG AGCACTGTTT GCTGGAGATC AGAGCAGTCG CTCTGGAGAC CGTGGCCATC
301  AAGGACATAA ACAGCGTCCG GTACCTGTGC ATGGGCCCCG ACGGCAGGAT GCGGGGCCTG
361  CCCTGGTATT CGGAGGAGGA CTGTGCCTTC AAGGAAGAGA TCAGCTACCC GGGCTACAGC
421  GTGTACCGCT CCCAGAAGCA CCACCTCCCC ATCGTGCTGA GCAGTGTCAA GCAGAGGCAG
481  CAGTACCAGA GCAAGGGGGT GGTGCCCCTG TCCTACTTCC TGCCCATGCT GCCCAAGGCC
541  TCTGTGGAGC CCAGCGACGA GGAGGAATCC AGCGTGTTCT CGTTGCCCCT GAAGACGGAC
601  AGCATGGACC CCTTTGGGAT GGCCAGTGAG ATCGGGCTGG TGAAGAGTCC CAGCTTTCAG
661  AAGTAA
```

*Tupaia belangeri* gene coding sequence (tree shrew) FGF19 (SEQ ID NO: 74) (from Ensembl Accession No. ENSTBET00000000307, which is hereby incorporated by reference in its entirety) (1-219, excluding 116-138)

```
  1  ATGAGGAGAA CACCGAGCGG GTTTGCAGTG GCCCGTGTCC TCTTCCTGGG CAGCCTTTGG
 61  CTGGCCGCAG CCGGGAGCCC CTTGGCCCTG TCCGACGCCG GGCCGCATGT GAACTACGGC
121  TGGGATGAGT CCATACGCCT GCGACACTTG TACACCGCCA GCCCGCACGG CTCCACCAGC
181  TGCTTCTTGC GCATCCGTGA CGACGGCTCA GTGGACTGCG CGCGGGGCCA GAGTTTGCAC
241  AGTTTGCTGG AGATCAAGGC AGTCGCTTTG CAGACCGTGG CCATCAAAGG CGTGTACAGT
301  GTCCGCTACC TCTGCATGGA CGCCGACGGC AGGATGCAGG GGCTG----- ----------
361  ---------- ---------- ---------- ---------- ---------- NNGGTCCACG
369  AAGCACGGCC TCCCAGTCTC CCTGAGCAGT GCCAAGCAGA GGCAGCTGTT AACGGTTAGG
429  GGCTTTCCTT CCCTTCCCCA CTTCCTGCTC ATGATGGCCA AGACTTCAGC AGGGCCTGGA
489  AACCCCAGGG ACCACCCAGG GTCTAACACT TTCTCGTTGC CCCTGGAAAC TGATAGCATG
549  GACCCATTTG GGATGACCAC CAGACATGGG CTGGTGAAGA GTCCCAGCTT TCAAAACTAA
```

*Rattus norvegicus* gene coding sequence (Norway rat) FGF15 (SEQ ID NO: 75) (GenBank Accession No. NM_130753, which is hereby incorporated by reference in its entirety) (SEQ ID NO: 56)

```
  1  ATGGCGAGAA AGTGGAGTGG GCGTATTGTG GCCCGAGCTC TGGTCCTGGC CACTCTGTGG
 61  CTGGCCGTGT CTGGGCGTCC CCTGGTCCAG CAATCCCAGT CTGTGTCGGA TGAAGGTCCA
121  CTCTTTCTCT ATGGCTGGGG CAAGATTACC CGCCTGCAGT ACCTGTACTC TGCTGGTCCC
181  TACGTCTCCA ACTGCTTCCT GCGTATCCGG AGTGACGGCT CTGTGGACTG CGAGGAGGAC
241  CAGAACGAAC GAAATCTGTT GGAGTTCCGC GCGGTTGCTC TGAAGACAAT TGCCATCAAG
301  GACGTCAGCA GCGTGCGGTA CCTCTGCATG AGCGCCGAGC GCAAGATATA CGGGCTGATT
361  CGCTACTCGG AGGAAGACTG TACCTTCAGG GAGGAAATGG ACTGTTTGGG CTACAACCAG
421  TACAGGTCCA TGAAGCACCA CCTCCACATC ATCTTCATCA AGGCCAAGCC CAGAGAGCAG
481  CTCCAGGGCC AGAAACCTTC AAACTTTATC CCCATATTTC ACCGGTCTTT CTTTGAATCC
541  ACGGACCAGC TGAGGTCTAA AATGTTCTCT CTGCCCCTGG AGAGCGACAG CATGGATCCG
601  TTCAGAATGG TGGAGGATGT GGACCACCTA GTGAAGAGTC CCAGCTTCCA GAAATGA
```

*Mus musculus* gene coding sequence (house mouse) FGF15 (SEQ ID NO: 76) (GenBank Accession No. NM_008003, which is hereby incorporated by reference in its entirety)

```
148                      ATG GCGAGAAAGT GGAACGGGCG TGCGGTGGCC
181  CGAGCCCTGG TCCTGGCCAC TCTGTGGCTG GCTGTGTCTG GCGTCCCCT GGCTCAGCAA
241  TCCCAGTCTG TGTCAGATGA AGATCCACTC TTTCTCTACG GCTGGGCAA GATTACCCGC
301  CTGCAGTACC TGTACTCCGC TGGTCCCTAT GTCTCCAACT GCTTCCTCCG AATCCGGAGC
361  GACGGCTCTG TGGACTGCGA GGAGGACCAA AACGAACGAA ATTTGTTGGA ATTCCGCGCG
421  GTCGCTCTGA AGACGATTGC CATCAAGGAC GTCAGCAGCG TGCGGTACCT CTGCATGAGC
481  GCGGACGGCA AGATATACGG GCTGATTCGC TACTCGGAGG AAGACTGTAC CTTCAGGGAG
541  GAAATGGACT GTTTAGGCTA CAACCAGTAC AGCACCATCT CCATATCATC
601  TTCATCCAGG CCAAGCCCAG AGAACAGCTC CAGGACCAGA AACCCTCAAA CTTTATCCCC
661  GTGTTTCACC GCTCCTTCTT TGAAACCGGG GACCAGCTGA GGTCTAAAAT GTTCTCCCTG
721  CCCCTGGAGA GTGACAGCAT GGATCCGTTC AGGATGGTGG AGGATGTAGA CCACCTAGTG
781  AAGAGTCCCA GCTTCCAGAA ATGA
```

*Gallus gallus* gene coding sequence (chicken) FGF19 (SEQ ID NO: 77) (GenBank Accession No. NM_204674, which is hereby incorporated by reference in its entirety)

```
127         ATGG GGCCGGCCCG CCCCGCCGCA CCCGGCGCTG CCCTGGCGCT GCTGGGGATC
181  GCCGCCGCCG CCGCCGCCGC CAGGTCCCTG CCGCTGCCCG ACGTCGGGGG TCCGCACGTC
241  AACTACGGCT GGGGGGAACC CATCCGGCTG CGGCACCTAC TACACCGCCC AGGCAAGCAC
301  GGGCTCTTCA GCTGCTTCCT GCGCATCGGC GGCGACGGCC GGGTGGACGC TGTCGGTAGC
361  CAGAGCCCGC AGAGTCTGTT GGAGATCCGC GCCGTGGCGG TGCGCACCGT GGCCATCAAG
```

TABLE 2-continued

```
421  GGCGTGCAGA GCTCCCGCTA CCTCTGCATG GACGAGGCGG GGCGGCTGCA CGGGCAGCTC
481  AGCTATTCCA TTGAGGACTG TTCCTTTGAA GAGGAGATTC GTCAGACGG CTACAACGTG
541  TATAAATCAA AGAAATACGG GATATCGGTG TCTTTGAGCA GTGCCAAACA AAGACAGCAA
601  TTCAAAGGAA AAGATTTTCT CCCGCTGTCT CACTTCTTAC CCATGATCAA CACTGTGCCA
661  GTGGAGGTGA CAGACTTTGG TGAATATGGT GATTACAGCC AGGCTTTTGA GCCAGAGGTC
721  TACTCATCGC CTCTCGAAAC GGACAGCATG GATCCCTTTG GGATCACTTC CAAACTGTCT
781  CCAGTGAAGA GCCCCAGCTT TCAGAAATGA
```

*Taeniopygia guttata* gene coding sequence (zebra finch) FGF19 (SEQ ID NO: 78) (GenBank Accession No. XM_002194457, which is hereby incorporated by reference in its entirety)

```
  1  ATGGTTATCA TAAGCAATCT ATATCTGATG CAGAACGATG TTATGATGAA TATGAGGCGA
 61  GCACCCCTTC GCGTTCACGC TGCTCGCTCT TCGGCCACCC CTGCCTCCGC GCTGCCGCTG
121  CCGCCGCCCG ACGCCGGCCC GCACCTCAAA TACGGCTGGG GAGAGCCCAT CCGGCTGCGG
181  CACCTCTACA CCGCCAGCAA GCACGGGCTC TTCAGCTGCT TCCTGCGTAT CGGCGCTGAC
241  GGCCGGGTGG ACGCGGCCGG CAGCCAGAGC CCGCAGAGCC TGCTAGAGAT CCGCGCCGTG
301  GCCGTGCGCA CCGTGGCCAT CAAGGGCGTG GGGTACCTGT CATGGACGAG
361  GCGGGGCGGC TGCACGGGCA GCTCAGGAAT TCCACTGAAG ACTGCTCCTT TGAGGAGGAG
421  ATTCGCCCAG ACGGCTACAA TGTGTATAGA TCTAAAAAAC ATGGAATATC GGTGTCTTTG
481  AGCAGTGCCA AACAAAGACA GCAGTTCAAG GGGAAAGATT TCCTTCCCCT GTCTCACTTC
541  TTGCCCATGA TCAACACTGT GCCCATGGAG TGCAGACTT TTGGTGAATA TGGTGATTAC
601  AGCCAGGCCT TTGAGGCAGA GGCCTTCTCC TCACCTCTGG AGACGGACAG CATGGACCCC
661  TTTGGCATCG CCTCCAAACT GTCCCTAGTG AAGAGCCCTA GCTTCCAAAA CTGA
```

*Danio rerio* gene coding sequence (zebrafish) FGF19 (SEQ ID NO: 79) (GenBank Accession No. NM_001012246, which is hereby incorporated by reference in its entirety)

```
  1  ATGCTCCTCT TACTCTTTGT CACTGTTTGT GGAAGTATCG GCGTGGAGAG CCTCCCGTTG
 61  CCCGACTCTG GTCCACATTT GGCAAATGAC TGGAGTGAAG CCGTCCGGCT ACGACATCTG
121  TACGCAGCCA GACATGGCTT ACATCTGCAA ATAAACACAG ACGGAGAAAT CATTGGATCC
181  ACATGCAAAG CTCGGACAGT AAGTTTGATG GAGATATGGC CGGTGGACAC AGGCTGCGTA
241  GCCATTAAGG GAGTTGCAAG CTCCCGATTT CTTTGCATGG AAAGACTGGG AAACCTGTAC
301  GGATCGCACA TTTACACTAA AGAGGACTGC TCTTTTTTGG AACGCATCCT TCCAGACGGC
361  TACAACGTCT ACTTCTCGAG CAAACACGGA GCTCTTGTGA CTTTAAGTGG TGCGAAAAAC
421  AAGTTGCACA GTAACGATGG GACTTCTGCA TCCCAGTTCC TCCCCATGAT CAACACACTT
481  TCAGAGGAAC ACACTAAACA GCACTCAGGG AACAGCACT CTTCTGTTAA CCATGGACAG
541  GACCATCAGT TGGGCCTTGA AATAGACAGT ATGGACCCTT TCGGAAAGAT CTCTCAAATA
601  GTGATCCAGA GTCCCAGCTT CAACAAAAGA TGA
```

*Xenopus (Silurana) tropicalis* gene coding sequence (Western clawed frog) FGF19 (SEQ ID NO: 80) (GenBank Accession No. NM_001142825, which is hereby incorporated by reference in its entirety)

```
  1  ATGTGGAAGA CCCTGCCTTG GATTTTGGTT CCCATGATGG TGGCCGTGCT GTATTTCCTC
 61  GGAGGGGCGG AAAGTCTGCC GCTTTTTGAT GCCGGGCCGC ACATGCAGAA CGGCTGGGGG
121  GAGTCGATCA GAATTCGGCA CCTGTATACG GCCAGGAGGT TCGGGCACGA CAGCTACTAC
181  CTCCGGATAC ACGAGGATGG CAGAGTCGAT GGTGACAGGC AACAAAGCAT GCACAGTTTA
241  TTGGAAATCA GAGCAATTGC AGTTGGAATT GTTGCCATTA AAGGGTATCG CAGCTCTCTG
301  TACCTGTGCA TGGGGTCCGA GGGAAAACTC TATGGAATGC ACAGTTACTC CCAGGATGAT
361  TGCTCTTTTG AAGAGGAGCT TCTCCCGGAT GGATACAACA TGTATAAATC AAGGAAACAT
421  GGCGTTGCTG TCTCCCTAAG CAAGGAGAAG CAGAAGCAAC AATACAAAGG AAAGGGCTAC
481  CTCCCGTTGT CCCATTTCCT ACCCGTGATA AGCTGGGTGC CCATGGAGCC CACCGGAGAT
541  GTAGAAGATG ATATCTACAG GTTTCCATTC AATACGGACA CAAAAGTGT CATTGACAGC
601  CTTGATACCC TGGGACTAAT GGATTTTTCG AGTTATCACA AGAAATAG
```

*Otolemur garnettii* (bushbaby) FGF19 gene coding sequence (SEQ ID NO: 81) (Ensembl accession no. ENS0GAT00000031686, which is hereby incorporated by reference in its entirety)

```
  1  ATGCCCAGCG GGCTGAGAGG GCGTGTGGTA GCCGGCGCCC TGGCCCTGGC CAGCTTCTGG
 61  CTGGCCGTGG CCGGGCGCCC GCTGGCCTTC TCGGATGCCG GCCCTCACGT GCACTACGGC
121  TGGGGTGAGC CCATCCGCCT GCGACACCTG TACACCGCCG GCCCCACGG CCTCTCCAGC
181  TGCTTCCTGC GCGTACGCAC CGACGGTGCG GTAGACTGCG CGCGGGGCCA GAGCGCACAC
241  AGTTTGCTGG AAATCAGGGC CGTCGCTCTC CGGACCGTGG CCATCAAAGG CGTGCACAGC
301  GCGCGGTACC TCTGCATGGG CGCCGACGGC AGGATGCAGG GGCTGCCTCA GTACTCGGAG
361  GAAGACTGTG CCTTTGAGGA GGAGATCCGG CCAGACGGCT ACAACGTCTA CTGGTCTGAG
421  AAGCACCGCC TGCCGGTGTC TCTGAGCAGT GCCCGGCAGA GGCAGCTGTA CAAGGGCAGG
481  GGCTTTCTGC CGCTCTCTCA CTTCCTGCCC ATGCTGCCTG TGACCCCAGC CGAGCCCGGG
541  GACCTCAGAG ACCACCTGGA ATCCGACATG TTCTCTTTGC CCCTGGAAAC TGACAGCATG
601  GATCCATTTG GGATCGCCAC CAGACTGGGC GTGGTGAAGA GTCCCAGCTT TCAGAAATGA
```

*Felis catus* (cat) FGF19 gene coding sequence (SEQ ID NO: 82) (Ensembl accession no. ENSFCAT00000026317, which is hereby incorporated by reference in its entirety)

```
  1  ATGCGGAGCG CGCCGAGCCA GTGCGCGGTA ACCCGCGCCC TGGTCCTAGC CGGTCTCTGG
 61  CTGGCAGCAG CCGGGCGCCC CCTAGCCTTC TCGGACGCGG GGCCTCACGT GCACTACGGC
121  TGGGGTGAGC CCATCCGCCT GCGGCACCTG TACACCGCCG GCCCCCACGG CCTCTCCAGC
181  TGCTTCCTGC GCATCCGAGC CGACGGGGGG GTTGACTGCG CGCGGAGCCA GAGCGCGCAC
241  AGTTTGGTGG AGATCAGGGC AGTCGCTCTG CGGACCGTGG CCATCAAGGG CGTGCACAGC
301  GTCCGGTACC TCTGCATGGG CGCCGACGGC AGGATGCAAG GGCTGCTTCA GTACTCTGCT
361  GGGGACTGTG CCTTCCAAGA GGAGATCCGC CCCGACGGCT ACAATGTGTA CCGGTCCGAG
421  AAGCACCGTC TCCCCGTCTC TTTGAGTAGT GCCATACGA GGCAGCTGTA CAAGGGCAGA
```

TABLE 2-continued

```
481 GGGTTTTTGC CCCTGTCCCA TTTCTTGCCC ATGCTGCCCG GCAGCCCAGC AGAGCCCAGG
541 GACCTCCAGG ACCACGTGGA GTCGGAGAGG TTTTCTTCAC CCCTGGAAAC AGACAGCATG
601 GACCCTTTTG GGATTGCCAC CAAAATGGGG TTAGTGAAGA GTCCCAGCTT CCAAAAGTAA
```

*Pelodiscus sinensis* (Chinese softshell turtle) FGF19 gene coding
sequence (SEQ ID NO: 83) (Ensembl accession no. ENSPSIT00000010427,
which is hereby incorporated by reference in its entirety)

```
241                      ATGTGGAG GAGCCTGTGC AAATCTCACA
301 CGTCTCTGGC TCTGCTGGGA CTCTGCTTTG CGGTGGTCGT GAGATCTCTG CCTTTCTCGG
361 ATGCAGGGCC ACATGTGAAC TATGGCTGGG GGAGCCTAT TCGATTAAGG CACCTATACA
421 CCGCCAGCAG ACACGGGCTG TTCAATTACT TCCTGAGGAT CAGCAGTGAT GGCAAAGTGG
481 ATGGCACCAG CATTCAGAGT CCTCACAGTC TGCTGGAAAT CAGGGCTGTG GCAGTTCGCA
541 CGGTGGCGAT CAAGGGCGTC CACAGTTCCC GGTACCTCTG CATGGAAGAA GACGGGAAGC
601 TGCATGGACT TCTCAGGTAT TCTACAGAAG ATTGCTCCTT TGAAGAGGAG ATACGCCCAG
661 ATGGCTACAA TGTATATAAA TCAAAGAAAT ATGGAATCTC TGTGTCCTTA AGTAGTGCCA
721 AACAAAGACA ACAATTCAAA GGAAAAGACT TCTTCCATT GTCTCACTTC TTGCCTATGA
781 TCAATACAGT ACCTGTGGAG TCAATGGATT TTGGAGAATA TGGTGATTAT AGTCATACTT
841 TTGAATCAGA TCTATTCTCT TCACCTCTCG AAACTGACAG CATGGATCCC TTTGGAATCA
901 CCTCTAAAAT ATCTCCAGTG AAGAGCCCCA GCTTTCAGAA ATAA
```

*Latimeria chalumnae* (coelacanth) FGF19 gene coding sequence (SEQ ID
NO: 84) (Ensembl accession no. ENSLACT00000014697, which is hereby
incorporated by reference in its entirety)

```
  1 ATGTTACAGG CACTGTACAA TCTCTGTACA GCTCTAGTTT TGTTTAAGCT TCCTTTTGCA
 61 ATGGTGGGGT ACACCCTGCC TTCTGCCAAT GAAGGGCCCC ATCTGAACTA TGACTGGGGA
121 GAATCTGTAA GACTCAAACA TCTGTACACA TCTAGCAAGC ATGGATTGAT CAGTTACTTT
181 TTACAGATCA ATGATGATGG CAAAGTAGAT GGGACCACTA CACGAAGCTG TTATAGTTTG
241 CTCGAAATAA AATCAGTGGG GCCAGGAGTT TTGGCAATTA AAGGCATACA GAGCTCCAGA
301 TACCTTTGTG TCGAGAAGGA TGGAAAATTG CATGGATCGC GCACTTATTC AGCAGACGAT
361 TGCTCCTTCA AAGAGGATAT ACTCCCAGAT GGTTACACTA TCTACGTGTC AAAGAAACAT
421 GGATCTGTTG TTAATCTGAG CAACCACAAA CAGAAACGTC AGAGAAATCG CAGAACCCTG
481 CCTCCATTTT CTCAGTTCCT ACCGCTTATG GACACCATTC GTGTGGAGTG CATGAACTGC
541 GGGGAGCACT GTGACGACAA CCTGCATGAC GAGCTAGAAA CAGGACTGTC CATGGATCCC
601 TTTGAAAGTA CATCCAAAAA ATCCTTTCAG AGTCCAGCT TTCACAATAG ATAA
```

*Mustela putorius furo* (ferret) FGF19 gene coding sequence (SEQ ID NO:
85) (Ensembl accession no. ENSMPUT00000004650, which is hereby
incorporated by reference in its entirety)

```
421       ATGCGG AGCGCCGCGA GTCGGTGCGC GGTAGCCCGC GCGCTGGTCC TAGCCGGCCT
481 TTGGCTGGCC GCAGCCGGGC GCCCCCTAGC CTTCTCGGAC GCGGGGCCGC ACGTGCACTA
541 TGGCTGGGGT GAGCCCATCC GCCTACGGCA CCTGTACACC GCCGGCCCCC ACGGCCTCTC
601 CAGCTGCTTC CTGCGCATCC GTGCCGACGG CGGGGTTGAC TGCGCGCGGG GCCAGAGCGC
661 GCACAGTTTG GTGGAGATCC GGGCAGTCGC TCTGCGGACG GTGGCCATCA AGGGCGTGTA
721 CAGCGACCGC TATCTCTGCA TGGGTGCGGA CGGCAGGATG CAAGGGCTGC CTCAGTACTC
781 CGCCGGAGAC TGTGCTTTCG AGGAGGAGAT CCGCCCTGAT GGCTACAACG TGTACCGGTC
841 CAAGAAGCAC CGTCTCCCCG TCTCCCTGAG CAGTGCGAAA CAAAGGCAGC TGTACAAGGA
901 CCGGGGCTTT TTGCCTCTGT CCCATTTCTT GCCCATGCTG CCCGGGAGCC TGGCGGAGCC
961 CAGGGACCTC CAGGACCACG TGGAGGCTGA TGGGTTTTCT GCCCCCCTAG AAACAGACAG
1021 CATGGACCCT TTTGGGATTG CCACCAAAAT GGGACTAGTG AAGAGTCCCA GCTTCCAAAA
1081 ATGA
```

*Takifugu rubripes* (fugu) FGF19 gene coding sequence (SEQ ID NO: 86)
(Ensembl accession no. ENSTRUT00000007155, which is hereby
incorporated by reference in its entirety)

```
  1 TCATCTACAA GGATTAGTGG AAACATGGTT CTCCTCATGC TCCCCATCAC CGTTGCAAAC
 61 CTCTTCCTCT GTGCTGGAGT TCTCTCCTTG CCTTTGTTGG ATCAAGGGTC TCATTTTCCC
121 CAAGGCTGGG AACAGGTAGT CCGCTTCAGG CACCTGTATG CTGCCAGTGC AGGGCTGCAC
181 CTGCTGATCA CTGAAGAGGG CTCGATCCAA GGCTCTGCAG ATCCAACTTT ATACAGCCTG
241 ATGGAGATCC GTCCGGTGGA CCCAGGCTGT GTTGTCATTA GAGGAGCAGC AACCACACGC
301 TTCCTCTGCA TAGAAGGTGC TGGAAGACTG TACTCATCAC AGACCTACAG CCAGACGAC
361 TGTACCTTCA GAGAGCAAAT CCTAGCAGAC GGCTACAGCC TCTACAGATC TGTCGGACAC
421 GGAGCTCTGG TCAGTCTGGG AAACTACCGG CAGCAGCTGA GGGGGGAGGA CTGGAGCGTT
481 CCGACACTGG CTCAGTTCCT CCCCAGAATA AGTTCACTGG ATCAGGACTT TAAAGCTGCT
541 CTTGACGAGA CTGAGAAGCC AGAACAAACT GCACCTCAAA GATCGGAACC TGTCGACATG
601 GTGGACTCAT TTGGAAAGCT CTCTCAGATC ATCCACAGTC CAGTTTTCA CAAG
```

*Equus caballus* (horse) FGF19 gene coding sequence (SEQ ID NO: 87)
(Ensembl accession no. ENSECAT00000021494, which is hereby
incorporated by reference in its entirety) (1-216, excluding 1-19 and
114-216)

```
  1 ---------- ---------- ---------- ---------- ---------- -------GCG
  4 GCCGGGCGCC CCCTAGCCTT GTCCGACGCT GGGCCGCACG TGCACTACGG CTGGGGCGAG
 64 CCGATCCGCC TGCGGCACCT GTACACCGCC GGCCCCCACG GCCTCTCCAG CTGCTTCCTG
124 CGCATCCGCG CCGATGCGCG CGTGGACTGC GCGCGGGGCC AGAGCGCGCA CAGTTTGGTG
184 GAGATCAGAG CAGTCGCTCT GCGCACCGTG GCCATCAAGG GCGTGCACAC CGTCCGGTAC
244 CTCTGCATGG GCGCCGACGG CAGGATGCAA GGGCTGGTA
```

TABLE 2-continued

*Oryzias latipes* (medaka) FGF19 gene coding sequence (SEQ ID NO: 88) (Ensembl accession no. ENSORLT00000000352, which is hereby incorporated by reference in its entirety)

```
  1 ACCATGCTGC TCATTGTGGT CACCATTTCC ACAATGGTGT TTTCTGACTC TGGAGTTTCC
 61 AGCATGCCGC TCTCTGATCA TGGACCCCAC ATCACTCACA GCTGGAGCCA AGTGGTCCGC
121 CTCCGGCACC TGTACGCGGT CAAGCCTGGA CAACATGTCC AGATCAGAGA GGATGGACAC
181 ATCCACGGCT CAGCAGAACA AACTCTGAAC AGCCTGCTGG AGATCCGTCC GGTTGCTCCG
241 GGACGGGTGG TCTTCAGAGG AGTAGCCACC TCAAGGTTTC TGTGCATGGA GAGCGACGGC
301 AGACTCTTCT CCTCACACAC ATTTGACAAG GACAACTGCG TCTTCAGAGA GCAGATCTTG
361 GCAGACGGCT ACAACATCTA CATTTCAGAT CAGCATGAA CCCTGCTTAG TTTGGGAAAC
421 CACCGGCAAA GGCAGCAGGG TTTAGACCGG GATGTTCCAG CCCTGGCTCA GTTCCTCCCC
481 AGGATCAGCA CCCTGCAGCA GGGCGTGTAC CCAGTGCCAG ACCCCCCCA CCAGATGAGA
541 ACAATGCAAA CAGAGAAGAC TCTAGATGCC ACGGACACAT TTGGGCAACT CTCTAAAATC
601 ATTCACAGTC CCAGCTTCAA CAAAAGATGA
```

*Xiphophorus maculatus* (platyfish) FGF19 gene coding sequence (SEQ ID NO: 89) (Ensembl accession no. ENSXMAT00000001519, which is hereby incorporated by reference in its entirety)

```
  1                                                               ATG
  4 TTTGTGTTCA TTCTATGCAT TGCTGGTGAA CTTTTTACTC TGGGAGTATT TTGCATGCCA
 64 ATGATGGACC AGGGGCCACT TGTCACCCAT GGCTGGGGCC AGGTGGTCCG GCACCGGCAT
124 CTGTATGCAG CCAAGCCAGG ACTGCACCTA CTGATCAGTG AGGATGGACA AATCCACGGT
184 TCCGCAGATC AAACTCTTTA CAGCCTGCTG GAGATCAAC CTGTTGGCCC CGGACGTGTT
244 GTGATCAAAG GAGTGGCAAC CACACGCTTC CTCTGCATGG AGAGCGACGG CAGATTGTAC
304 TCAACTGAAA CATACAGCAG AGCTGACTGC ACCTTCAGAG AACAGATCCA GGCAGACGGC
364 TACAACGTCT ACACCTCTGA TAGCCATGGA GCCCTCCTCA GTTGGGAAA CAACCAGCAA
424 AGACACAGCG GCTCAGACCG TGGTGTTCCA GCTCTGGCCC GCTTTCTTCC CAGGTTAAAC
484 ACCCTTCAGC AGGCCGTCCC CACAGAGCCG GATGTTCCTG ATCAGCTCAG TCCAGAGAAA
544 GTACAACAGA CTGTGGACAT GGTGGCCTCC TTTGGCAAGC TCTCTCATAT AATTCACAGT
604 CCCAGCTTCC ATAAGAGATG A
```

*Ictidomys tridecemlineatus* (squirrel) FGF19 gene coding sequence (SEQ ID NO: 90) (Ensembl accession no. ENSSTOT00000026298, which is hereby incorporated by reference in its entirety)

```
  1 ATGCGGAGCG CGCCGAGCGG ACGTGCCTTA GCCCGCGCCC TGGTGCTGGC CAGCCTCTGG
 61 TTGGCAGTGG CCGGACGACC CCTGGCCCGG CGCTCTCTGG CTCTCTCCGA CCAGGGGCCA
121 CACTTGTACT ATGGCTGGGA TCAGCCCATC CGCCTCCGGC ACCTGTACGC CGCGGGCCCC
181 TACGGCTTCT CCAACTGTTT CCTGCGCATC CGCACCGACG GCGCCGTGGA CTGCGAGGAG
241 AAGCAGAGCG AGCGTAGTTT GATGGAGATC AGGGCGGTCG CTCTGGAGAC TGTGGCCATC
301 AAGGACATAA ACAGCGTCCG GTACCTCTGC ATGGGCGCCG ACGGCAGGAT ACAGGGACTG
361 CCTCGGTACT CGGAGGAAGA GTGCACGTTC AAGGAGGAGA TCAGCTATGA CGGCTACAG
421 GTGTACCGGT CCCAGAAGTA CCACCTTCCC GTGGTGCTCA GCAGTGCCAA GCAGCGGCAG
481 CTGTACCAGA GCAAGGGCGT GGTTCCCCTG TCCTACTTCC TGCCCATGCT GCCCCTGGCC
541 TCTGCGGAGA CCAGGGACCG CTTGGAATCC GATGTGTTCT CTTTACCTCT GGAAACTGAC
601 AGCATGGACC CGTTTGGGAT GGCCAGTGAA GTGGGCCTGA AGAGCCCCAG CTTCCAGAAG
661 TAA
```

*Gasterosteus aculeatus* (stickleback) FGF19 gene coding sequence (SEQ ID NO: 91) (Ensembl accession no. ENSGACT00000018770, which is hereby incorporated by reference in its entirety)

```
  1 ATGCTGCTGC TGCTGGTCCC CGCGTACGTT GCCAGTGTGT TTTTAGCTCT CGGGGTTGTT
 61 TGCTTGCCCC TAACAGATCA GGGTCTCCAC ATGGCCGACG ACTGGGGCCA GTCGGTCCGA
121 CTCAAGCACC TGTACGCCGC CAGCCGGGA CTCCACCTGC TGATCGGGGA GGATGGTCGG
181 ATCCAAGGCT CGGCGCAGCA AAGCCCCTAC AGCCTGCTGG AGATCAGTGC AGTGGATCCG
241 GGCTGTGTGG TCATCAGAGG AGTAGCAACC GCACGGTTTC TCTGCATCGA AGGCGATGGA
301 AGACTGTACT CATCGGACAC CTACAGCAGA GACGACTGCA CCTTCAGGGA GCAGATCCTC
361 CCGGACGGCT ACAGCGTCTA CGTCTCCCAT GGACACGGGG CCCTGCTCAG CCTGGGGAAC
421 CACAGGCAGA GGCTGCAGGG TCGAGACCAC GGCGTGCCGG CTCTGGCCCA GTTCCTCCCG
481 AGGGTCAGCA CCATGGATCA GGCCTCGGCC CCCGACGCGC CGGGCAGAC CGCCACCGAG
541 ACGGAAGAGC CCGTGGACTC GTTTGGAAAG CTCTCTCAGA TCATTCACAG TCCCAGCTTC
601 CACGAGAGAT GA
```

*Oreochromis niloticus* (tilapia) FGF19 gene coding sequence (SEQ ID NO: 92) (Ensembl accession no. ENSONIT00000022816, which is hereby incorporated by reference in its entirety)

```
 55                                                            ATGCTG
 61 CTGCTCCTCA TCGTATCCAT TGTCAATATG CTTTTTGGTG TTGGAATGGT TTGCATGCCC
121 CTGTCAGACA ACGGGCCCCA CATCGCCCAC GGCTGGGCCC AGGTGGTCCG GCTCAGGCAC
181 CTTTACGCCA CCAGACCGGG AATGCACCTG CTGATCAGTG AGGGTGGACA GATCCGTGGT
241 TCTGCCGTCC AGACTCTGCA CAGCCTAATG GAGATTCGTC CAGTCGGTCC AGGCCGTGTT
301 GTCATCAGAG GGGTAGCAAC CGCAAGGTTT CTCTGCATAG AAGACGACGG CACACTGTAC
361 TCATCGCACG CCTACAGCAG AGAGGACTGC ATCTTCAGAG AGCAGATCTT GCCAGATGTG
421 TACAACATCT ACATCTCTGA CAGACATGGA GTCCTGCTCA GTCTGGGAAA CCACCGGCAA
481 AGACTGCAGG GCTTAGACCG AGGAGATCCA GCCCTGGCCC AGTTCCTCCC CAGGATCAGC
541 ACTCTGAATC AAATCCCTTC CCCTGGGGCA ACATCGGTG ACCACATGAA AGTAGCAAAA
601 ACAGAAGAAC CTGTGGACAC AATAGATTCA TTTGGAAAGT CTCTCAGAT CATTGACAGT
607 CCCAGCTTCC ATAAGAGATG A
```

TABLE 2-continued

*Meleagris gallopavo* (turkey) FGF19 gene coding sequence (SEQ ID NO: 93) (Ensembl accession no. ENSMGAT00000011114, which is hereby incorporated by reference in its entirety) (1-216, excluding 1-70)
```
  1 GTAGGCAATC AATCACCACA GAGCATCCTT GAAATAACTG CTGTTGATGT CGGGATCGTC
 61 GCTATCAAGG GCTTGTTCTC TGGCAGATAC CTGGCCATGA ACAAAAGGGG CAGGCTTTAT
121 GCATCACTCA GCTATTCCAT TGAGGACTGT TCCTTTGAAG AGGAGATTCG TCCAGATGGC
181 TATAACGTGT ATAAATCAAA GAAATACGGA ATATCAGTGT CTTTGAGCAG TGCCAAACAA
241 AGACAACAAT TCAAAGGAAA AGATTTTCTC CCACTGTCTC ACTTCTTACC CATGATCAAC
301 ACTGTGCCAG TGGAGGTGAC AGACTTTGGT GAATACGGTG ATTACAGCCA GGCTTTTGAG
361 CCAGAGGTCT ACTCATCGCC TCTCGAAACG GACAGCATGG ATCCCTTTGG GATCACTTCC
421 AAACTGTCTC CAGTGAAGAG CCCCAGCTTT CAGAAA
```

*Papio anubis* (olive baboon) FGF19 gene coding sequence (SEQ ID NO: 94) (GenBank accession no. XM_003909422, which is hereby incorporated by reference in its entirety)
```
                                         758 ATG AGGAGCGGGT GTGTGGTGGT
 781 CCACGCCTGG ATCCTGGCCA GCCTCTGGCT GGCCGTGGCC GGGCGTCCCC TCGCCTTCTC
 841 GGACGCGGGG CCCCACGTGC ACTACGGCTG GGGCGACCCC ATCCGCCTGC GGCACCTGTA
 901 CACCTCCGGC CCCCACGGGC TCTCCAGCTG CTTCCTGCGC ATCCGCACCG ACGGCGTCGT
 961 GGACTGCGCG CGGGGCCAAA GCGCGCACAG TTTGCTGGAG ATCAAGGCAG TAGCTCTGCG
1021 GACCGTGGCC ATCAAGGGCG TGCACAGCGT GCGGTACCTC TGCATGGGCG CCGACGGCAA
1081 GATGCAGGGG CTGCTTCAGT ACTCAGAGGA AGACTGTGCT TTCGAGGAGG AGATCCGCCC
1141 TGATGGCTAC AATGTATACC GATCCCAGAA GCACCGCCTC CCGGTCTCCC TGAGCAGTGC
1201 CAAACAGCGG CAGCTGTACA AGAACAGAGG CTTTCTTCCG CTGTCTCATT TCCTGCCCAT
1261 GCTGCCCATG GCCCCAGAGG AGCCTGAGGA CCTCAGGGGC CCCTTGGAAT CTGACATGTT
1321 CTCTTCGCCC TGGAGACTG ACAGCATGGA CCCATTTGGG CTTGTCACCG ACTGGAGGC
1381 GGTGAGGAGT CCCAGCTTTG AGAAATAA
```

*Saimiri boliviensis boliviensis* (Bolivian squirrel monkey) FGF19 gene coding sequence (SEQ ID NO: 95) (GenBank accession no. XM_003941165, which is hereby incorporated by reference in its entirety)
```
                                                    231 ATGCGGAGCG
241 GGTGTGTGGT GGTCCACGCC TGGATCCTGG CTGGCCTCTG GCTGGCTGTG GTCGGGCGCC
301 CCCTCGCCTT CTCCGATGCG GGGCCGCATG TGCATTACGG CTGGGGCGAC CCCATTCGCC
361 TGCGGCACCT GTACACCTCC AGCCCCACG GCCTCTCCAG CTGCTTCCTG CGCATCCGCA
421 GCGACGGCGT CGTGGACTGC GCGCGGGGCC AGAGCGCGCA CAGTTTGCTG GAGATCAAGG
481 CAGTCGCTCT AAGGACCGTG GCCATCAAGG GCGTGCACAG CTCGCGGTAC CTCTGCATGG
541 GCGCCGACGG CAGGCTGCAG GGGCTGTTCC AGTACTCGGA GGAAGACTGT GCTTTCGAGG
601 AGGAGATCCG CCCCGACGGC TACAATGTGT ACCTATCCGA GAAGCACCGC CTCCCGGTCT
661 CCCTGAGCAG CGCCAAACAG CGGCAGCTGT ACAAGAAACG AGGCTTTCTT CCGCTGTCCC
721 ATTTCCTGCC CATGCTGCCC AGAGCCCCAG AGGAGCCTGA TGACCTCAGG GGCCCACTTGG
781 AATCTGACGT GTTCTCTTCA CCCCTGGAGA CTGATAGCAT GGACCCATTT GGGCTTGTCA
841 CGGGACTGGA GGCGGTGAAC AGTCCCAGCT TGAGAAGTA A
```

*Pteropus alecto* (black flying fox) FGF19 gene coding sequence (SEQ ID NO: 96) (generated using SMS Reverse Translate tool on the ExPASy Bioinformatics Resource website (www.expasy.org))
```
  1 ATGCGCAGCC CGTGCGCGGT GGCGCGCGCG CTGGTGCTGG CGGGCCTGTG GCTGGCGAGC
 61 GCGGCGGGCC CGCTGGCGCT GAGCGATGCG GGCCCGCATG TGCATTATGG CTGGGGCGAA
121 GCGATTCGCC TGCGCCATCT GTATACCGCG GGCCCGCATG GCCCGAGCAG CTGCTTTCTG
181 CGCATTCGCG CGGATGGCGC GGTGGATTGC GCGCGCGGCC AGAGCGCGCA TAGCCTGGTG
241 GAAATTCGCG CGGTGGCGCT GCGCAACGTG GCGATTAAAG GCGTGCATAG CGTGCGCTAT
301 CTGTGCATGG GCGCGGATGG CCGCATGCTG GCCTGCTGCA GTATAGCGC GGATGATTGC
361 GCGTTTGAAG AAGAAATTCG CCCCGGATGGC TATAACGTGT ATCATAGCAA AAAACATCAT
421 CTGCCGGTGA GCCTGAGCAG CGCGAAACAG CGCCAGCTGT ATAAAGATCG CGGCTTTCTG
481 CCGCTGAGCC ATTTTCTGCC GATGCTGCCG CGCAGCCCGA CCGAACCGGA AAACTTTGAA
541 GATCATCTGG AAGCGGATAC CTTTAGCAGC CCGCTGGAAA CCGATGATAT GGATCCGTTT
601 GGCATTGCGA GCAAACTGGG CCTGGAAGAA AGCCCGAGCT TTCAGAAA
```

*Myotis davidii* (David's myotis) FGF19 gene coding sequence (SEQ ID NO: 97) (generated using SMS Reverse Translate tool on the ExPASy Bioinformatics Resource website (www.expasy.org))
```
  1 ATGAGCGGCC AGAACAGCGG CCGCCATGGC AGCCGCCCGG GCCTGGATGA AGAACCGGAA
 61 CCGGGCCCGC TGGAACTGCG CGCGCTGGGC AGCACCCGCG CGGATCCGCA GCTGTGCGAT
121 TTTCTGGAAA ACCATTTTCT GGGCTATACC TGCCTGGAAC TGGATATTTG CCTGGCGACC
181 TATCTGGGCG TGAGCCATTG GGGCGAAAGC ATTGCCTGC GCCATCTGTA TACCAGCGGC
241 CCGCATGGCC CGAGCAGCTG CTTTCTGCGC ATTCGCGTGG ATGGCGCGGT GGATTGCGCG
301 CGCGGCCAGA GCGCGCATAG CCTGGTGGAA ATCCGCGCAG TGGCGCTGCG CAAGTGCGG
361 ATTAAAGGCG TGCATAGCGC GCTGTATCTG TGCATGGAAG GCGATGGCCG CATGCGCGGC
421 CTGCCGCAGT TTAGCCCGGA AGATTGCGCG TTTGAAGAAG AAATTCGCCC GGATGGCTAT
481 AACGTGTATC GCAGCCAGAA ACATCAGCTG CCGGTGAGCC TGAGCAGCGC GCGCCAGCGC
541 CAGCTGTTTA AAGCGCGCG CTTTCTGCCG CTGAGCCATT TTCTGCCGAT GCTGCCGAGC
601 AGCCCGGCGG AACCGGTGCA TCGCGAACGC CCGCTGGAAC CGGATGCGTT TAGCAGCCCG
661 CTGGAAACCG ATAGCATGGA TCCGTTTGGC ATTGCGAACA ACCTGCGCCT GGTGAAAAGC
721 CCGAGCTTTC AGAAA
```

TABLE 2-continued

Tupaia chinensis (Chinese tree shrew) FGF19 gene coding sequence (SEQ ID NO: 98) (generated using SMS Reverse Translate tool on the ExPASy Bioinformatics Resource website (www.expasy.org)) (1-257, excluding 13-19)

```
  1 ATGCGCCGCA CCTGGAGCGG CTTTGCGGTG GCGACC---- ---------- ----CGCGCG
 61 GGCAGCCCGC TGGCGCTGGC GGATGCGGGC CCGCATGTGA ACTATGGCTG GGATGAAAGC
121 ATTCGCCTGC GCCATCTGTA TACCGCGAGC CTGCATGGCA GCACCAGCTG CTTTCTGCGC
181 ATTCGCGATG ATGGCAGCGT GGGCTGCGCG CGCGGCCAGA GCATGCATAG CCTGCTGGAA
241 ATTAAAGCGG TGGCGCTGCA GACCGTGGCG ATTAAAGGCG TGTATAGCGT GCGCTATCTG
301 TGCATGGATA CCGATGGCCG CATGCAGGGC CTGCCGCAGT ATAGCGAAGA AGATTGCACC
361 TTTGAAGAAG AAATTCGCAG CGATGGCCAT AACGTGTATC GCAGCAAAAA ACATGGCCTG
421 CCGGTGAGCC TGAGCAGCGC GAAACAGCGC CAGCTGTATA AAGGCCGCGG CTTTCTGAGC
481 CTGAGCCATT TTCTGCTGAT GATGCCGAAA ACCAGCGCGG GCCCGGGCAA CCCGCGCGAT
541 CAGCGCAACC CGCGCGATCA GCGCGATCCG AACACCTTTA GCCTGCCGCT GGAAACCGAT
601 AGCATGGATC CGTTTGGCAT GACCACCCGC CATGCCTGC TGCTGGATAG CTGCTGCGCG
661 AGCCTGGTGC TGCTGAACAT TAGCACCGAT GGCGAATTTA GCCCGTATGG CAACATTCTG
721 CGCCCGAGCT TTCGCTTTAA ACTGTTTAAA ATGAAAAAAG TGACCAAC
```

Heterocephalus glaber (naked mole-rat) FGF19 gene coding sequence (SEQ ID NO: 99) (generated using SMS Reverse Translate tool on the ExPASy Bioinformatics Resource website (www.expasy.org))

```
  1 ATGCGCTTTA GCAAAAGCAC CTGCGGCTTT TTTAACCATC AGCGCCTGCA GGCGCTGTGG
 61 CTGAGCCTGA GCAGCGTGAA ATGGGTGCTG GATGCGGCGG TGGAAGGCCG CCCGATTCGC
121 CTGCGCCATC TGTATGCGGC GGGCCCGTAT GGCCGCAGCC GCTGCTTTCT GCGCATTCAT
181 ACCGATGGCG CGGTGGATTG CGTGGAAGAA CAGAGCGAAC ATTGCCTGCT GGAAATTCGC
241 GCGGTGGCGC TGGAAACCGT GGCGATTAAA GATATTAACA GCGTGCGCTA TCTGTGCATG
301 GGCCCGGATG GCCGCATGCA GGGCCTGCCG TGGTATAGCG AAGAAGATTG CGCGTTTAAA
361 GAAGAAATTA GCTATCCGGG CTATAGCGTG TATCGCAGCC AGAAACATCA TCTGCCGATT
421 GTGCTGAGCA GCGTGAAACA GCGCCAGCAG TATCAGAGCA AAGGCGTGGT GCCGCTGAGC
481 TATTTTCTGC CGATGCTGCC GAAAGCGAGC GTGGAACCGG GCGATGAAGA AGAAAGCGCG
541 TTTAGCCTGC CGCTGAAAAC CGATAGCATG GATCCGTTTG GCATGGCGAG CGAAATTGGC
601 CTGGCGAAAA GCCCGAGCTT TCAGAAA
```

Another member of the FGF19 subfamily, FGF21, is expressed primarily by the pancreas (Fon Tacer et al., "Research Resource: Comprehensive Expression Atlas of the Fibroblast Growth Factor System in Adult Mouse," *Mol Endocrinol* 24(10):2050-2063 (2010), which is hereby incorporated by reference in its entirety) and has metabolic effects similar to that of FGF19, such as increased energy metabolism, weight loss, lowered blood glucose levels, and resistance to obesity and diabetes (Kharitonenkov et al., "FGF-21 as a Novel Metabolic Regulator," *J Clin Invest* 115(6), 1627-1635 (2005); Coskun et al., "Fibroblast growth factor 21 corrects obesity in mice," *Endocrinology* 149(12): 6018-6027 (2008), which are hereby incorporated by reference in their entirety). Transgenic mice overexpressing FGF21 are also resistant to diet-induced obesity (Kharitonenkov et al., "FGF-21 as a Novel Metabolic Regulator," *J Clin Invest* 115(6), 1627-1635 (2005), which is hereby incorporated by reference in its entirety). Moreover, in diabetic rodent models, FGF21 administration lowers blood glucose and triglyceride levels (Kharitonenkov et al., "FGF-21 as a Novel Metabolic Regulator," *J Clin Invest* 115(6), 1627-1635 (2005), which is hereby incorporated by reference in its entirety).

In one embodiment of the present invention, the FGF21 portion of the chimeric protein of the present invention is from human FGF21 protein having an amino acid sequence of SEQ ID NO: 100 (GenBank Accession No. NP_061986, which is hereby incorporated by reference in its entirety) or a portion thereof, as follows:

In one embodiment of the present invention, the N-terminal portion of FGF21 of the chimeric protein of the present invention comprises an amino acid sequence spanning residues corresponding to residues from position 29 to 167 of SEQ ID NO: 100, from position 29 to 190 of SEQ ID NO: 100, or from position 29 to 197 of SEQ ID NO: 100.

In one embodiment of the present invention, the N-terminal portion of the chimeric protein according to the present invention is or is derived from a mammalian FGF21. In one embodiment of the present invention, the N-terminal portion of the chimeric protein according to the present invention is or is derived from a vertebrate FGF21. In one embodiment, the N-terminal portion of the chimeric protein according to the present invention is derived from a non-human vertebrate FGF21. It will be understood that this includes orthologs of human FGF21, or a polypeptide or protein obtained from one species that is the functional counterpart of a polypeptide or protein from a different species. In one embodiment of the present invention, the N-terminal portion of FGF21 of the chimeric protein according to the present invention is derived from human, *pongo abelii, pan troglodytes, canis lupus familiaris, bos taurus, equus caballus, ailuropoda melanoleuca, oryctolagus cuniculus, gorilla gorilla, nomascus leucogenys, procavia capensis, cavia porcellus, tupaia belangeri, sorex araneus, ictidomys tridecemlineatus, loxodonta africana, sus scrofa, felis catus, otolemur garnettii, rattus norvegicus, mus mus-*

(SEQ ID NO: 100)

```
  1 MDSDETGFEH SGLWVSVLAG LLLGACQAHP IPDSSPLLQF GGQVRQRYLY TDDAQQTEAH
 61 LEIREDGTVG GAADQSPESL LQLKALKPGV IQILGVKTSR FLCQRPDGAL YGSLHFDPEA
121 CSFRELLLED GYNVYQSEAH GLPLHLPGNK SPHRDPAPRG PARFLPLPGL PPALPEPPGI
181 LAPQPPDVGS SDPLSMVGPS QGRSPSYAS
```

*culus, vicugna pacos, anolis carolinensis, gadus morhua, latimeria chalumnae, tursiops truncatus, mustela putorius furo, takifugu rubripes, dipodomys ordii, echinops telfairi, macaca mulatta, microcebus murinus, ochotona princeps, xiphosphorus maculatus, gasterosteus aculeatus, sarcophilus harrisii, macropus eugenii, xenopus tropicalis, danio rerio, bos grunniens mutus, saimiri boliviensis boliviensis, callithrix jacchus, tupaia chinensis, papio anubis, pteropus alecto, heterocephalus glaber, cricetulus griseus, ovies aries, pan paniscus, macaca fascicularis, mesocricetus auratus,* or *oreochromis niloticus.*

Figure 9:
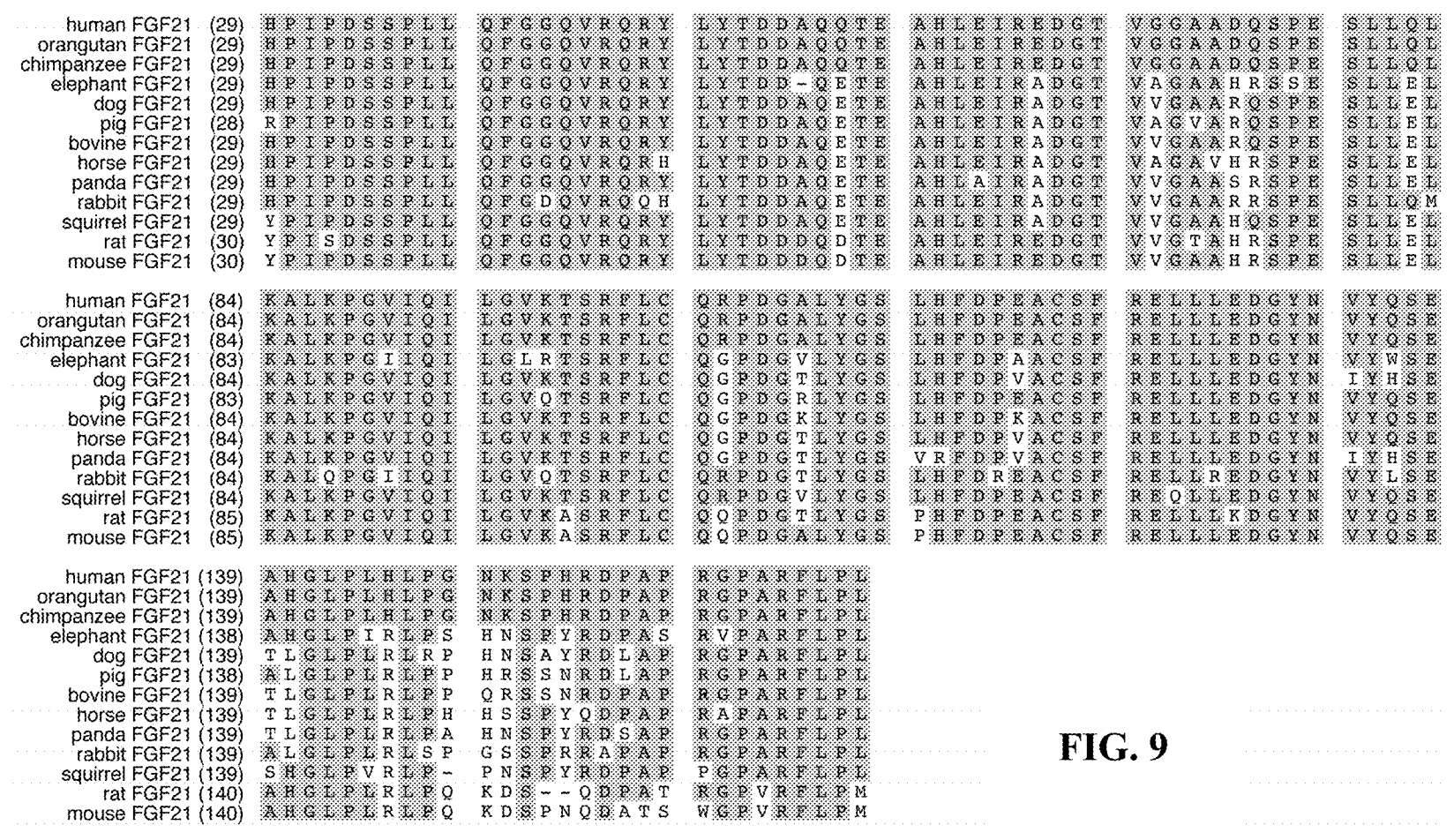

In one embodiment of the present invention, the portion of FGF21 of the chimeric protein of the present invention is from an ortholog of human FGF21 having an amino acid sequence as shown in Table 3. The portions of an ortholog of human FGF21 of a chimeric protein according to the present invention include portions corresponding to the above-identified amino acid sequences of human FGF21. Corresponding portions may be determined by, for example, sequence analysis and structural analysis. The high degree of FGF21 sequence conservation among mammals is shown in FIG. 9.

TABLE 3

*Pongo abelii* (Sumatran orangutan) FGF21 (GenBank Accession No. XP_002829565, which is hereby incorporated by reference in its entirety) (SEQ ID NO: 101)

```
  1 MDSDETGFEH SGLWVPVLAG LLLGACQAHP IPDSSPLLQF GGQVRQRYLY TDDAQQTEAH

61 LEIREDGTVG GAADQSPESL LQLKALKPGV IQILGVKTSR FLCQRPDGAL YGSLHFDPEA

121 CSFRELLLED GYNVYQSEAH GLPLHLPGNK SPHRDPAPRG PARFLPLPGL PPAPPEPPGI

181 LAPQPPDVGS SDPLSMVGPS QGRSPSYAS
```

*Pan troglodytes* (chimpanzee) FGF21 (GenBank Accession No. XP_524333, which is hereby incorporated by reference in its entirety) (SEQ ID NO: 102)

```
  1 MDSDETGFEH SGLWVSVLAG LLLGACQAHP IPDSSPLLQF GGQVRQRYLY TDDAQQTEAH

61 LEIREDGTVG GAADQSPESL LQLKALKPGV IQILGVKTSR FLCQRPDGAL YGSLHFDPEA

121 CSFRELLLED GYNVYQSEAH GLPLHLPGNK SPHRDPAPRG PARFLPLPGL PPAPPEPPGI

181 LAPQPPDVGS SDPLSMVGPS QGRSPSYTS
```

*Canis lupus familiaris* (dog) FGF21 (GenBank Accession No. XP_541510, which is hereby incorporated by reference in its entirety) (SEQ ID NO: 103)

```
  1 MGWAEAGFEH LGLWVPVLAV LLLEACRAHP IPDSSPLLQF GGQVRQRYLY TDDAQETEAH

61 LEIRADGTVV GAARQSPESL LELKALKPGV IQILGVKTSR FLCQGPDGTL YGSLHFDPVA

121 CSFRELLLED GYNIYHSETL GLPLRLRPHN SAYRDLAPRG PARFLPLPGL LPAPPEPPGI

181 LAPEPPDVGS SDPLSMVGPS QGRSPSYAS
```

*Bos taurus* (bovine) FGF21 (GenBank Accession No. XP_001789639, which is hereby incorporated by reference in its entirety) (SEQ ID NO: 104)

```
  1 MGWDEAKFKH LGLWVPVLAV LLLGTCRAHP IPDSSPLLQF GGQVRQRYLY TDDAQETEAH

61 LEIRADGTVV GAARQSPESL LELKALKPGV IQILGVKTSR FLCQGPDGKL YGSLHFDPKA

121 CSFRELLLED GYNVYQSETL GLPLRLPPQR SSNRDPAPRG PARFLPLPGL PAAPPDPPGI

181 LAPEPPDVGS SDPLSMVGPS YGRSPSYTS
```

*Equus caballus* (horse) FGF21 (GenBank Accession No. XP_001489202, which is hereby incorporated by reference in its entirety) (SEQ ID NO: 105)

```
  1 MDWDKTGFKY QGLWVPVLAV LLLGACQSHP IPDSSPLLQF GGQVRQRHLY TDDAQETEAH

61 LEIRADGTVA GAVHRSPESL LELKALKPGV IQILGVKTSR FLCQGPDGTL YGSLHFDPVA

121 CSFRELLLED GYNVYQSETL GLPLRLPHHS SPYQDPAPRA PARFLPLPGF PPAPPEPPGI

181 PAPEPPDVGS SDPLSMVGPS RSRSPSYTS
```

*Ailuropoda melanoleuca* (giant panda) FGF21 (GenBank Accession No. XP_002917910, which is hereby incorporated by reference in its entirety) (SEQ ID NO: 106)

```
  1 MGWDEARSEQ LGLWVPVLAV LLLEACQAHP IPDSSPLLQF GGQVRQRYLY TDDAQETEAH

61 LAIRADGTVV GAASRSPESL LELKALKPGV IQILGVKTSR FLCQGPDGTL YGSVRFDPVA

121 CSFRELLLED GYNIYHSETL GLPLRLPAHN SPYRDSAPRG PARFLPLPGL LPVPPDPPGI

181 LGPEPPDVGS SDPLSMVGPS QGRSPSYAS
```

TABLE 3-continued

*Oryctolagus cuniculus* (rabbit) FGF21 (GenBank Accession No.
XP_002723745, which is hereby incorporated by reference
in its entirety) (SEQ ID NO: 107)
```
  1 MDWGKAKCRP PGLWVPALAA LLLGACQAHP IPDSSPLLQF GDQVRQQHLY TDDAQETEAH

61 LEIRADGTVV GAARRSPESL LQMKALQPGI IQILGVQTSR FLCQRPDGTL YGSLHFDREA

121 CSFRELLRED GYNVYLSEAL GLPLRLSPGS SPRRAPAPRG PARFLPLPGL PPDLPEPPGL

181 LAAAPPDVDS PDPLSMVQPA LDQSPSYTS
```

*Gorilla gorilla* (gorilla) FGF21 (Ensembl Accession No.
ENSGGOP00000001229, which is hereby incorporated by
reference in its entirety) (SEQ ID NO: 108)
```
  1 MDSDETGFEH SGLWVSVLAG LLLGACQAHP IPDSSPLLQF GGQVRQRYLY TDDAQQTEAH

61 LEIREDGTVG GAADQSPESL LQLKALKPGV IQILGVKTSR FLCQRPDGAL YGSLHFDPEA

121 CSFRELLLED GYNVYQSEAH GLPLHLPGNK SPHRDPAPRG PARFLPLPGL PPAPPEPPGI

181 LAPQPPDVGS SDPLSMVGPS QGRSPSYAS
```

*Nomascus leucogenys* (Northern white-cheeked gibbon) FGF21
(Ensembl Accession No. ENSNLEP00000005639, which is hereby
incorporated by reference in its entirety) (SEQ ID NO: 109)
```
  1 MDSDETGFEH SGLWVPVLAG LLLGACQAHP IPDSSPLLQF GGQVRQRYLY TDDAQQTEAH

61 LEIREDGTVG GAADQSPESL LQLKALKPGV IQILGVKTSR FLCQRPDGAL YGSLHFDPEA

121 CSFRELLLED GYNVYQSEAH GLPLHLPGNK SPHRDPAPRG PARFLPLPGL PPAPPEPPGI

181 LAPQPPDVGS SDPLSMVGPS QGRSPSYAS
```

*Procavia capensis* (hyrax) FGF21 (Ensembl Accession No.
ENSOGAG00000001210, which is hereby incorporated by
reference in its entirety) (SEQ ID NO: 110)
```
  1 MDWAKFGIEH PGLWVPVMAV LLLGACQGYP IPDSSPLLQF GGQVRQRYLY TDDAQETEAH

61 LEIRADGTVV GAAHRSPESL LELKALKPGI IQILGVKTSR FLCQGPDGVL YGSLRFDPVA

121 CSFRELLLED GYNVYQSEAH GLPLRLPSHN SPQRDLASRV PARFLPLPGR LTVLPEPSGV

181 LGPEPPDVDS SDPLSMVGPS QGRSPSYAS
```

*Cavia porcellus* (guinea pig) FGF21 (Ensembl Accession No.
ENSCPOP00000000237, which is hereby incorporated by
reference in its entirety) (SEQ ID NO: 111)
```
  1 MDWARTECER PRLWVSMLAI LLVGACQAHP IPDSSPLLQF GGQVRQRYLY TDDAQDTEVH

61 LEIRADGSVR GIAHRSPESL LELKALKPGV IQILGIRTSR FLCQRPDGSL YGSLHFDPEA

121 CSFRELLLAD GYNVYKSEAH GLPLHLLRGD SLSQEPAPPG PARFLPLPGL PATPPEPPRM

181 LPPGPPDVGS SDPLSMVGPL WDRSPSYTS
```

*Tupaia belangeri* (tree shrew) FGF21 (Ensembl Accession No.
ENSTBEP00000013946, which is hereby incorporated by
reference in its entirety) (SEQ ID NO: 112)
```
  1 MGWDKARFEH LGAWAPVLAV LLLGACQAYP IPDSSPLLQF GGQVRQRYLY TDDTQDTEAH

61 LEIRADGTVV GAAHQSPESL LELKALKPGV IQILGVKTSR FLCQRPDGAL YGSLHFDPEA

121 CSFRELLLED GYNIYQSEAR GLPLRLPPHD SPHRDRTPRG PARFLPLPGL PLVPPELPGV

181 LALEPPDVGS SDPLSMMGPS QGQSPSYAS
```

*Sorex araneus* (shrew) FGF21 (Ensembl Accession No.
ENSSARP00000002784, which is hereby incorporated by reference
in its entirety) (SEQ ID NO: 113)
```
  1 MVWDKARGQQ LGLWAPMLLG LLLGACQAHP LPDSSPLLQF GGQVRLRFLY TDDAQRTGAH

61 LEIRADGTVQ GAAHRTPECL LELKALKPGV IQILGVSTSR FLCQRPDGVL YGSLRFDPEA

121 CSFRELLLQD GYNVYQSEAL GLPLYLHPPS APVSQEPASR GAVRFLPLPG LPPASLEPPR

181 PPAPVPPDVG SSDPLSMVGP PERHSPSYTS
```

TABLE 3-continued

*Ictidomys tridecemlineatus* (squirrel) FGF21 (SEQ ID NO: 114)
1 MDWVKAKLEP LGLWVLVLAA LVLGACQAYP IPDSSPLLQF GGQVRQRYLY TDDAQETEAH

61 LEIRADGTVV GAAHQSPESL LELKALKPGV IQILGVKTSR FLCQRPDGVL YGSLHFDPEA

121 CSFREQLLED GYNVYQSESH GLPVRLPPNS PYRDPAPPGP ARFLPLPGLP PAALEPPGIL

181 GPEPPDVGSS DPLSMVGPLQ GRSPSYAS

*Loxodonta africana* (elephant) FGF21 (Ensembl Accession
No. ENSLAFP00000016854, which is hereby incorporated
by reference in its entirety) (SEQ ID NO: 115)
1 MDWAKFGLE HPGLWVPVMA VLLLGACQGH PIPDSSPLLQ FGGQVRQRYL YTDDQETEAH

60 LEIRADGTVA GAAHRSSESL LELKALKPGI IQILGVKTSR FLCQGPDGVL YGSLHFDPAA

120 CSFRELLLED GYNVYWSEAH GLPIRLPSHN SPYRDPASRV PARFLPLPGL LPMLQEPPGV

180 LAPEPPDVDS SDPLSMVGPS QGRSPSYAS

*Sus scrofa* (pig) FGF21 (GenBank Accession No.
NP_001156882, which is hereby incorporated by reference
in its entirety) (SEQ ID NO: 116)
1 MGWAEAKFER LGLWVPVLAV LLGACQARPI PDSSPLLQFG GQVRQRYLYT DDAQETEAHL

61 EIRADGTVAG VARQSPESLL ELKALKPGVI QILGVQTSRF LCQGPDGRLY GSLHFDPEAC

121 SFRELLLEDG YNVYQSEALG LPLRLPPHRS SNRDLAPRGP ARFLPLPGLP PAPPEPPGIL

181 APEPPDVGSS DPLSMVGPSH GRSPSYTS

*Felis catus* (cat) FGF21 (Ensembl Accession No.
ENSFCAP00000006832, which is hereby incorporated by
reference in its entirety) (SEQ ID NO: 117)
1 MDWDEAGSQ RLGLWVVLGV LLPEACQAHP IPDSSPLLQF GGQVRQRFLY TDDAQETEVH

60 LEIKADGTVV GTARRSPESL LELKALKPGV IQILGVKTSR FLCQGPDGTL YGSLRFDPAA

120 CSFRELLLED GYNIYHSETL GLPLRLPPHN SPYRDLAPRA PARFLPLPGL LPAPPEPPGI

180 LAPEPPDVGS SDPLSMVGPS QGRSPSYAS

*Otolemur garnettii* (bushbaby) FGF21 (Ensembl Accession
No. ENSOGAG00000003581, which is hereby incorporated
by reference in its entirety) (SEQ ID NO: 118)
1 DKARTGFKH PGPWFPLLAV LLLGACQAHP IPDSSPLLQF GGQVRQRYLY TDDAQETEAH

60 LEIREDGTVV GAAQQSPESL LELKALKPGV IQILGVKTSR FLCQRPDGGL YGSLYFDPKA

120 CSFRELLLED GYNVYWSETY GLPLHLPPAN SPYWGPSLRS PARFLPLPGP PAASPELPGI

180 LALEPPDVGS SDPLSMVGPS QGRSPSYAS

*Rattus norvegicus* (Norway rat) FGF21 (GenBank Accession No.
NP_570108, which is hereby incorporated by reference
in its entirety) (SEQ ID NO: 119)
1 MDWMKSRVGA PGLWVCLLLP VFLLGVCEAY PISDSSPLLQ FGGQVRQRYL YTDDDQDTEA

61 HLEIREDGTV VGTAHRSPES LLELKALKPG VIQILGVKAS RFLCQQPDGT LYGSPHFDPE

121 ACSFRELLLK DGYNVYQSEA HGLPLRLPQK DSQDPATRGP VRFLPMPGLP HEPQEQPGVL

181 PPEPPDVGSS DPLSMVEPLQ GRSPSYAS

*Mus musculus* (house mouse) FGF21 (GenBank Accession No.
NP_064397, which is hereby incorporated by reference
in its entirety) (SEQ ID NO: 120)
1 MEWMRSRVGT LGLWVRLLLA VFLLGVYQAY PIPDSSPLLQ FGGQVRQRYL YTDDDQDTEA

61 HLEIREDGTV VGAAHRSPES LLELKALKPG VIQILGVKAS RFLCQQPDGA LYGSPHFDPE

121 ACSFRELLLE DGYNVYQSEA HGLPLRLPQK DSPNQDATSW GPVRFLPMPG LLHEPQDQAG

181 FLPPEPPDVG SSDPLSMVEP LQGRSPSYAS

TABLE 3-continued

*Vicugna pacos* (alpaca) FGF21 (Ensembl Accession No.
ENSVPAP00000005562, which is hereby incorporated by
reference in its entirety) (SEQ ID NO: 121); partial
sequence corresponding to human FGF21 residues 1 to
78, 169 to 171, and 183 to 209

```
  1 MDWDEAKFEH RGLWVPVLTV LLLGACQARP IPDSSPLLQF GGQVRQRYLY TDDAQETEAH

61 LEIRADGTVV GVARQPE--- ---------- ---------- ---------- ----------

121 ---------- ---------- ---------- ---------- --------GI P---------

181 --PEPPDVGS SDPLSMVGPS YSRSPSYTS
```

*Anolis carolinensis* (anole lizard) FGF21 (Ensembl
Accession No. ENSACAP00000016895, which is hereby
incorporated by reference in its entirety)
(SEQ ID NO: 122)

```
  1 CKSKGGGKGG ERMWVDLVFW AALLRTAPAL PLRNSNPIYQ FDGQVRLRHL YTADEQTHLH

61 LEILPDGTVG GSRFQNPFSL MEIKAVKPGV IRMQAKKTSR FLCMKPNGRL YGSLFYSEEA

121 CNFHEKVLSD GYNLYYSENY NIPVSLSSAG NLGQSRQLPP FSQFLPLVNK IPLEPVLEDF

181 DFYGHQLDVE SADPLSILGQ NPGFMSPSYV F
```

*Gadus morhua* (cod) FGF21 (Ensembl Accession No.
ENSGMOP00000013789, which is hereby incorporated
by reference in its entirety) (SEQ ID NO: 123)

```
  1 LLLATLLHIG LSFYVPDSGP LLWLGDQVRE RHLYTAESHR RGLFLEMSPD GQVTGSAAQT

61 PLSVLELRSV RAGDTVIRAR LSSLYLCVDR AGHLTGQRQY TESDCTFREV ILEDGYTHFL

121 SVHHGLPISL APRHSPGRQG LRFSRFLPLR SSLSEDRVAE PPDSPLNLDS EDPLGMGLGS

181 LLSPAFSM
```

*Latimeria chalumnae* (coelacanth) FGF21 (Ensembl
Accession No. ENSLACP00000003781, which is
hereby incorporated by reference in its entirety)
(SEQ ID NO: 124)

```
  1 MLCQSFVILS QKFIFGLFLT GLGLTGLAWT RPFQDSNPIL QYSDSIRLRH LYTASESRHL

61 HLQINSDGQV GGTTKQSPYS LLEMKAVKTG FVVIRGKKSA RYLCMERSGR LYGSLQYTEK

121 DCTFKEVVLA DGYNLYVSEE HQATVTLSPM RARIAQGKKI PPFSHFLPMV NKVPVEDVAA

181 EMEFVQVLRE MTADVDSPDP FGMTWEESVH SPSFFA
```

*Tursiops truncatus* (dolphin) FGF21 (Ensembl Accession
No. ENSTTRP00000013808, which is hereby incorporated
by reference in its entirety) (SEQ ID NO: 125)

```
  1 MGWDKTKLEH LGLWVPVLAV LLGPCQAHPI PDSSPLLQFG GQVRQRYLYT DDAQETEAHL

61 EIRADGTVVG TARRSPEGVK TSRFLCQGPE GRLYGSLHFN PQACSFRELL LEDGYNVYQS

121 EALGIPLRLP PHRSSNWDLA PRGPARFLPL PGFLPPPLEP PGILAPEPPN VGSSDPLSMV

181 GPSHGRSPSY TS
```

*Mustela putorius* furo (ferret) FGF21 (Ensembl Accession
No. ENSMPUP00000003687, which is hereby incorporated
by reference in its entirety) (SEQ ID NO: 126)

```
  1 MGWEEARSEH LGLWVPVLAV LLLGACQAYP IPDSSPLLQF GGQVRQRYLY TDDAQETEAH

61 LEIRADGTVV GAARRSPESL LELKALKPGV IQILGVKTSR FLCQGPNGTL YGSFHFDPVA

121 CSFREVLLED GYNIYHSETL GLPLRLPPHN SPHRDLAPRG PARFLPLPGL LPATPESRGI

181 PAPEPPNVGS SDPLSMVGPL QGQSPSYTS
```

*Takifugu rubripes* (fugu) FGF21 (Ensembl Accession
No. ENSTRUP00000033950, which is hereby incorporated
by reference in its entirety) (SEQ ID NO: 127)

```
  1 FIYLFIQTAL FSPSKWFNFY LPDSNPLLSF DSHGRGIHLY TDNQRRGMYL QMSTDGSVSG

61 SDVQTANSVL ELKSVRNGHV VIRGKSSSLF LCMDSRGRLW GQRHPTEADC TFREVLLADG

121 YTRFLSLHNG TPVSLAPKQS PDQHTVPFTR FLPLRNTLAE ESMSEPPSNQ QRYFNIDSDD

181 LLGMDLNAMV SPQFSGDK
```

TABLE 3-continued

*Dipodomys ordii* (kangaroo rat) FGF21 (Ensembl Accession
No.ENSDORP00000001155, which is hereby incorporated
by reference in its entirety) (SEQ ID NO: 128)

```
  1 MDQAKTRVGA RGLGGLVLAV IILGACKARP IPDSSPLLQF GGQVRLRHLY TDDTQETEAH

61 LEIRADGTVV GTAHRSPESL LELKALKPGV IQILGIKTSR FLCQRPDGTL YGSLHFDPEV

121 CSFQELLLED GYNIYRSEAL GLPLRLSPDP APWGPARFLP LPGVPPAPPE PPGILAPEPP

181 DVGSSDPLSM VGLLQGRSPS YAS
```

*Echinops telfairi* (lesser hedgehog tenrec) FGF21 (Ensembl
Accession No. ENSETEP00000008707, which is hereby
incorporated by reference in its entirety) (SEQ ID NO: 129)

```
  1 MGCTKSGWKS PGLWVPVLAS LLLGGCGAHP IPDSSPLLQF GGQVRQRYLY TDDAQTTEAH

61 LEIRADGTVG GVAHQSPEKF LSQWREKPLR SLHFDPAACS FREKLLEDGY NLYHSETHGL

121 PLRLPPRGGD PSSQPGARFP PLPGQLPQLQ ETPGVLAPEP PDVGSSDPLS MVGPWRGQSP

181 SYAS
```

*Macaca mulatta* (rhesus monkey) FGF21 (Ensembl Accession
No. ENSMMUP00000031540, which is hereby incorporated by
reference in its entirety) (SEQ ID NO: 130)

```
  1 MDSDETGFEH SGLWVPVLAG LLLGACQAHP IPDSSPLLQF GGQVRQRYLY TDDAQQTEAH

61 LEIREDGTVG GAAHQSPESE CGPEPGSEGG GAVGGAEGPG LLGLREAGLG PGSWLHFDPE

121 ACSFRELLLE NGYNVYQSEA HGLPLHLPGN KSPHRDPASQ GPARFLPLPG LPPAPPEPPG

181 ILAPQPPDVG SSDPLSMVGP SQARSPSYAS
```

*Microcebus murinus* (mouse lemur) FGF21 (Ensembl Accession
No. ENSMICP00000012089, which is hereby incorporated by
reference in its entirety) (SEQ ID NO: 131)

```
  1 MGWDEAGAGF EHPGLWFPML GVLLLGACQA YPIPDSSPLL QFGGQVRQRH LYTDDIQETE

61 AHLEIRADGT VVGAARQSPE LELKALKPGV IQILGVKTSR FLCQRPDGAL YGSLHFDPEC

121 SFRELLLEDG YNVYCPYLPL HLSPRIELAG SRSALPLPPA PERRILAPEP PDGSSDPLSM

181 VGPSQGRSPS YAS
```

*Ochotona princeps* (pika) FGF21 (Ensembl Accession No.
ENSOPRP00000006754, which is hereby incorporated by
reference in its entirety) (SEQ ID NO: 132)

```
  1 KDMDGLQPPG LRVPVLAALL LGVGQARPIP DSSPLLQFGG QVRQRHLYTD DAQESEVHLE

61 IRADGTVAGT ARRSPESLLE MKALKPGVIQ ILGVHTSRFL CQRPDGTLYG SLHFDHKACS

121 FREQLLEDGY NVYHSETHGL PLRLSPDRAP RGPARFLPLP GPPPDLLVPP LPPDVLAPEP

181 PDVDSPDPLS MVGPLQGQSP SYTS
```

*Xiphophorus maculatus* (platyfish) FGF21 (Ensembl
Accession No. ENSXMAP00000001576, which is hereby
incorporated by reference in its entirety)
(SEQ ID NO: 133)

```
  1 CPFPFLFLIL SLPFFSSSFY IPESNPIFAF RNQLREVHLY TENHRRGLYV EIHLDGRVTG

61 SDAQSPYSVL QIKSVKPGHV VIKGQTSSLF LCMDDSGNLR GQTTYDEADC SFRELLLADG

121 YTRFLNSQHG VPLSLASRNS PDRHSVPFTR FLPLRNTLTV SEESTKTQRD FNLDSDDLLG

181 MG
```

*Gasterosteus aculeatus* (stickleback) FGF21 (Ensembl
Accession No. ENSGACP00000010703, which is hereby
incorporated by reference in its entirety)
(SEQ ID NO: 134)

```
  1 SLLLMVPLPF CSSFYLTDSS PLLPFNNQVK EVHLYTAENH RRAMYLQIAL DGSVSGSDAR

61 STYSVLQLKS IQPGHVVIRG KASSMFLCVD SGGRLRGQGP YSEADCSFRE LLLGDGYTRF

121 LSSQHGSPLS LASRPSPDPN SVPFTRFLPI RTAPEAESVI EEPPSNQRYV NVDSEDLLGM

181 GLNTVVSPQF SA
```

TABLE 3-continued

*Sarcophilus harrisii* (tasmanian devil) FGF21 (Ensembl
Accession No. ENSSHAP00000005963, which is hereby
incorporated by reference in its entirety)
(SEQ ID NO: 135); partial sequence corresponding to
human FGF21 residues 3 to 172

```
  1 VSAMGLRERA PRYLAPLLSL LLACRASGHP LPDSSPMLLF GGQVRLRHLY TDVGQEAEAH

61 VELASDGTVR AAARRSPNSL LELKAVKPGI VRILAVHSSR FLCMRPNGEL YGAIHYDPSA

121 CNFRERLLGD GYNVYESEAH GRTLRLPPKA APGPAGPSRF LPLPG
```

*Macropus eugenii* (wallaby) FGF21 (Ensembl Accession
No. ENSMEUP00000013936, which is hereby incorporated
by reference in its entirety) (SEQ ID NO: 136)

```
  1 TEEPSTGSRH LGQWAPGLPG PLLSLLLAYR GWGSPIPDSS PMLLFGGQVR LRHLYTDDGQ

61 DTEAHVELGP DGVVRAVAER SPNSLLELKA VKPGVIRILA VQSSRFLCMR PNGELYGAVH

121 YDPSACNFRE HLLGDGYNVY ESETHRRTLR LSPSLGQAGP SRFLPLPGDW LPGPDPPWAQ

181 GPEPPDVGSA DPLSMVGAVQ GLSPSYSS
```

*Xenopus tropicalis* (Western clawed frog) FGF21 (Ensembl
Accession No. ENSXETP00000009917, which is hereby
incorporated by reference in its entirety) (SEQ ID
NO: 137); partial sequence corresponding to human
FGF21 residues 1 to 169

```
  1 RGGRTKKKTL LRKWLCLLAI MLSRSRFSLA NPIQNSNPIL SDNDQVRTQY LYTDNNNMHL

61 YLQITHNGVV TGTEEKNDYG VLEIKAVKAG VVVIKGIRSN LYLCMDSRHQ LYASAYDKDD

121 CHFHEKITPD NYNMYSSEKH SEYVSLAPLK GSQMARFLPI
```

*Danio rerio* (zebrafish) FGF21 (Ensembl Accession No.
ENSDARP00000094287, which is hereby incorporated by
reference in its entirety) (SEQ ID NO: 138)

```
  1 MLLACFFIFF ALFPHLRWCM YVPAQNVLLQ FGTQVRERLL YTDGLFLEMN PDGSVKGSPE

61 KNLNCVLELR SVKAGETVIQ SAATSLYLCV DDQDKLKGQH HYSALDCTFQ ELLLDGYSFF

121 LSPHTNLPVS LLSKRQKHGN PLSRFLPVSR AEDSRTQEVK QYIQDINLDS DDPLGMGHRS

181 HLQTVFSPSL HTKK
```

*Bos grunniens mutus* (yak) FGF21 (GenBank Accession No.
ELR56628, which is hereby incorporated by reference
in its entirety) (SEQ ID NO: 139)

```
  1 MGWDEAKFKH LGLWVPVLAV LLLGTCRAHP IPDSSPLLQF GGQVRQRYLY TDDAQETEAH

61 LEIRADGTVV GAARQSPESL LELKALKPGV IQILGVKTSR FLCQGPDGKL YGSLHFDPKA

121 CSFRELLLED GYNVYQSETL GLPLRLPPQR SSNRDPAPRG PARFLPLPGL PAEPPDPPGI

181 LAPEPPDVGS SDPLSMVGPS YGRSPSYTS
```

*Saimiri boliviensis boliviensis* (Bolivian squirrel monkey)
FGF21 (GenBank Accession No. XP_003940375, which is hereby
incorporated by reference in its entirety) (SEQ ID NO: 140)

```
  1 MGSEEVALER PALWVSVLAG LLLGTCQAYP IPDSSPLLQF GGQVRQRYLY TDDAQQTEAH

61 LEIREDGTVA GAAHQSPESL LQLKALKPGV IQILGVKTSR FLCQRPDGAL YGSLYFDPEA

121 CSFRELLLED GYNVYQSVAH SLPLHLPGGR SPPWDPAPRG PARFLPLPGL PPEPPEAPGI

181 LAPEPPDVGS SDPLSMVGPS QGQSPSYTS
```

*Callithrix jacchus* (white-tufted-ear marmoset) FGF21 (GenBank
Accession No. XP_003735669, which is hereby incorporated by
reference in its entirety) (SEQ ID NO: 141)

```
  1 MGSEEVGLEH PALWVSVLAG LLLGTCQAHP IPDSSPLLQF GGQVRQRYLY TDDAQQKEAH

61 LEIXEDGTVA GAATKVPKVS LLQLKALKPG VIQILGVKTS RFLCQRPDGA LYGSLHFDPE

121 ACSFRELLLE DGYNVYQSVA HGLPLHLPES RSPPRDPAPR GPARFLPLPG LPPEPPEPPG

181 ILAPEPPDVG SSDPLSMVGP SQGQSPSYAS
```

TABLE 3-continued

*Tupaia chinensis* (Chinese tree shrew) FGF21 (GenBank
Accession No. ELW47159, which is hereby incorporated
by reference in its entirety) (SEQ ID NO: 142)

```
  1 MGWDKARFEH LGAWAPVLAV LLLGACQAYP IPDSSPLLQF GGQVRQRYLY TDDTQDTEAH

61 LEIRADGTVV GAAHQSPESL LELKALKPGV IQILGVKTSR FLCQRPDGAL YGSLHFDPEA

121 CSFRELLLED GYNIYQSEAR GLPLRLPPHD SPHRDRTPQG PARFLPLPGL PLVPPELPGV

181 LALEPPDVGS SDPLSMMGPS QGQSPSYAS
```

*Papio anubis* (olive baboon) FGF21 (GenBank Accession No.
XP_003915900, which is hereby incorporated by reference
in its entirety) (SEQ ID NO: 143)

```
  1 MDSDETGFEH SGLWVPVLAG LLLGACQAHP IPDSSPLLQF GGQVRQRYLY TDDAQQTEAH

61 LEIREDGTVG GAAHQSPESK CGPEPGSEGG GALHFDPEAC SFRELLLENG YNVYQSEAHG

121 LPLHLPGNKS PHRDPASRGP ARFLPLPGLP PAPPEPPGIL APQPPDVGSS DPLSMVGPSQ

181 ARSPSYAS
```

*Pteropus alecto* (black flying fox) FGF21 (GenBank
Accession No. ELK18566, which is hereby incorporated
by reference in its entirety) (SEQ ID NO: 144)

```
  1 MGWGKARLQH PGLWGPVLAV LLGACQAHPI LDSSPLFQFG SQVRRRYLYT DDAQDTEAHL

61 EIRADGTVAG AARRSPESLL ELKALKPGVI QVLGVKTSRF LCQRPDGTLY GSLHFDPAAC

121 SFRELLLKDG YNVYQSEALA RPLRLPPYSS PSSDPARRGP ARFLPLPGPP PEPPQPPGRL

181 APEPPDVGSS DPLSMVWPSR GRSPSYTS
```

*Heterocephalus glaber* (naked mole-rat) FGF21 (GenBank
Accession No. EHB06286, which is hereby incorporated
by reference in its entirety) (SEQ ID NO: 145)

```
  1 MDWARAESER PGLWVPAVLA VLLLGACQAH PIPDSSPLLQ FGGQVRQRHL YTDDAQDTEV

61 HLEIRADGSV GGAAHRSPES LLELKALKPG VIQILGVRTS RFLCQRPDGT LYGSLHFDPE

121 ACSFRELLLA DGYNIYQSEA YGLPLRMLPS DSASRDPVPP GPARFLPLPG LHPPPLEPPG

181 MLPPEPPDVG SSDPLSMVGP LQGRSPSYAF
```

*Cricetulus griseus* (Chinese hamster) FGF21 (GenBank
Accession No. XP_003508726, which is hereby incorporated
by reference in it sentirety) (SEQ ID NO: 146)

```
  1 MDWMKSGVGV PGLWVPLLPI FLLGVSQAHP IPDSSPLLQF GGQVRHRHLY TDDNQETEVH

61 LEIRQDGTVI GTTHRSPESL LELKALKPEV IPVLGVKASR FLCQQPDGTL YGSPHFDPEA

121 CSFRELLLED GYNVYQSEVH GLPLRLPQRD SPNQAPASWG PVPPLPVPGL HQPQELPGF

181 LAPEPPDVGS SDPLSMVGPL QGRSPSYAS
```

*Ovis aries* (sheep) FGF21 (GenBank Accession No.
XP_004015845, which is hereby incorporated by
reference in its entirety) (SEQ ID NO: 147)

```
  1 MGWDEAKFKH LGLWVPVLAV LLLGTCRAHP IPDSSPLLQF GGQVRQRYLY TDDAQETEAH

61 LEIRADGTVV GAARQSPESL LELKALKPGV IQIFGVKTSR FLCQGPDGKL YGSLHFDPKA

121 CSFRELLLED GYNVYQSETL GLPLRLPPQR SSNRDPAPRG PPKPQLHFLK TSAVQYWPRY

181 EKVPAFLHPF PG
```

*Pan paniscus* (pygmy chimpanzee) FGF21 (GenBank Accession
No. XP_003814163, which is hereby incorporated by
reference in its entirety) (SEQ ID NO: 148); partial
sequence corresponding to human FGF21 residues 1 to
116 and 195 to 201

```
  1 MDSDETGFEH SGLWVSVLAG LLLGACQAHP IPDSSPLLQF GGQVRQRYLY TDDAQQTEAH

61 LEIREDGTVG GAADQSPESL LQLKALKPGV IQILGVKTSR FLCQRPDGAL YGSVSF----

121 ---------- ---------- ---------- ----Q----- ---------- -----DPP--

181 --HHPP---C S---SYMSPS Q---PG---
```

TABLE 3-continued

*Macaca fascicularis* (crab-eating macaque) FGF21(GenBank
Accession No. EHH59757, which is hereby incorporated by
reference in its entirety) (SEQ ID NO: 149); partial
sequence corresponding to human FGF21 residues 1 to 116

```
  1 MDSDETGFEH SGLWVPVLAG LLLGACQAHP IPDSSPLLQF GGQVRQRYLY TDDAQQTEAH

61 LEIREDGTVG GAAHQSPESL LQLKALKPGV IQILGVKTSR FLCQKPDGAL YGSVSF
```

*Mesocricetus auratus* (golden hamster) FGF21 (GenBank
Accession No. ACB30542, which is hereby incorporated
by reference in its entirety) (SEQ ID NO: 150); partial
sequence corresponding to human FGF21 residues 90 to 193

```
  1 VIQILGVKAA RFPCQQPDGS LYGSPHFDPE ACSFRELLLE DGYNVYQSEA HGLPLRLPQR

61 DAPSQPPASW GPVRFLPVPG LFQPPHDLPG RPAPEPPDVG SSDP
```

*Oreochromis niloticus* (Nile tilapia) FGF21
(GenBank Accession No. XP_003438516, which is hereby
incorporated by reference in its entirety) (SEQ ID
NO: 151); partial sequence corresponding to human
FGF21 residues 59 to 209

```
  1 MYLQMNMDGR VTGSDAQTPY SLMQLKSVKP GHVIIKGPSS SLFLCVDSEG NLRGQSHYSE

61 TSCTFREMLL ADGYTRFISS QYGFPMSLAS RHSPDRHALP FTRFLPLRNN LKTDSVSEQL

121 PNNQRLFNVD SDDLLGMGLN SMGSPQFSMD K
```

In one embodiment of the present invention, the N-terminal portion of FGF21 of the chimeric protein of the present invention comprises an amino acid residue substitution to strengthen or increase the stability of the FGF21 core domain compared to wild type FGF21. In one embodiment of the present invention, the N-terminal portion of FGF21 of the chimeric protein of the present invention comprises an amino acid residue substitution to strengthen or increase the stability of the FGF21 core domain compared to that of SEQ ID NO: 100. In one particular embodiment, the N-terminal portion of FGF21 comprises a substitution at a residue corresponding to residue 104 of SEQ ID NO: 100. In one embodiment, the substitution is a glutamine to methionine substitution (i.e., Q104M).

The N-terminal portion of the chimeric protein according to the present invention may include a core domain, also referred to as, for example, an FGF21 core domain. In one embodiment, the core domain is the FGF β-trefoil core domain. In one embodiment, this region corresponds to H29 to L167 of human FGF21 of SEQ ID NO: 100.

In one embodiment, increasing the stability of the core domain includes an increase in thermal stability of the protein as compared to either wild type protein or a chimeric protein in which such a substitution is not made. In one embodiment, increasing the stability includes increasing the half-life of the protein in the blood circulation as compared to either wild type protein or a chimeric protein in which such a substitution is not made.

Based on the inventors' extensive knowledge of the structures of FGF ligands, including the structures of FGF19 and FGF23, Q104 of FGF21 was selected for mutagenesis. Replacing Q104 with methionine, which is found in all other FGF ligands at the corresponding position (Mohammadi et al., "Structural Basis for Fibroblast Growth Factor Receptor Activation," *Cytokine & Growth Factor Rev* 16(2):107-137 (2005), which is hereby incorporated by reference in its entirety), increases the stability of FGF21 without affecting ligand-binding affinity for receptor.

In one embodiment of the present invention, FGF21 has an amino acid sequence corresponding to human FGF21 harboring a mutation at Q104. In one embodiment of the present invention, FGF21 has an amino acid sequence corresponding to human FGF21 harboring a Q104M mutation. In one embodiment the FGF21 having an amino acid sequence corresponding to human FGF21 and harboring a Q104M mutation, has the amino acid sequence of SEQ ID NO: 152, as follows:

```
                                                                  (SEQ ID NO: 152)
  1 MDSDETGFEH SGLWVSVLAG LLLGACQAHP IPDSSPLLQF GGQVRQRYLY TDDAQQTEAH

61 LEIREDGTVG GAADQSPESL LQLKALKPGV IQILGVKTSR FLCMRPDGAL YGSLHFDPEA

121 CSFRELLLED GYNVYQSEAH GLPLHLPGNK SPHRDPAPRG PARFLPLPGL PPALPEPPGI

181 LAPQPPDVGS SDPLSMVGPS QGRSPSYAS
```

In one embodiment according to the present invention, the chimeric FGF21 protein comprises an N-terminal portion of FGF21 that contains at least one amino acid residue substitution to increase stability of the FGF21 core domain as compared to a sequence corresponding to SEQ ID NO: 100. In one embodiment of the present invention, the N-terminal portion of FGF21 comprises an amino acid sequence spanning residues corresponding to residues selected from the group consisting of from position 29 to 167 of SEQ ID NO: 152, from position 29 to 190 of SEQ ID NO: 152, or from position 29 to 197 of SEQ ID NO: 152. Exemplary chimeric proteins include those of SEQ ID NOs: 312-336.

In one particular embodiment of the present invention, the N-terminal portion of FGF21 of the chimeric protein of the present invention is a modified N-terminal portion of the FGF21 protein. In one embodiment, the N-terminal portion of the chimeric protein of the present invention comprises an amino acid sequence at least 85% identical to the amino acid sequence corresponding to residues from position 29 to 197 of SEQ ID NO: 100, from position 29 to 190 of SEQ ID NO: 100, or from position 29 to 167 of SEQ ID NO: 100. In one embodiment, the N-terminal portion of FGF21 of the chimeric protein of the present invention is derived from a modified FGF21 protein, where the N-terminal portion of the chimeric protein of the present invention comprises an amino acid sequence that has at least 80%, at least 85%, at least 90%, at least 95%, at least 97% or at least 99% amino acid sequence identity to the amino acid sequence corresponding to residues from position 29 to 197 of SEQ ID NO: 100, from position 29 to 190 of SEQ ID NO: 100, or from position 29 to 167 of SEQ ID NO: 100. In one embodiment, the N-terminal portion having such amino acid sequence similarity will maintain the activity of the corresponding naturally occurring N-terminal portion of FGF21. In one embodiment, the N-terminal portion of the chimeric protein of the present invention comprises an amino acid sequence at least 85% homologous to the amino acid sequence corresponding to residues from position 29 to 197 of SEQ ID NO: 100, from position 29 to 190 of SEQ ID NO: 100, or from position 29 to 167 of SEQ ID NO: 100. In one embodiment, the N-terminal portion of FGF21 of the chimeric protein of the present invention is derived from a modified FGF21 protein, where the N-terminal portion of the chimeric protein of the present invention comprises an amino acid sequence that has at least 80%, at least 85%, at least 90%, at least 95%, at least 97% or at least 99% amino acid sequence homology to the amino acid sequence corresponding to residues from position 29 to 197 of SEQ ID NO: 100, from position 29 to 190 of SEQ ID NO: 100, or from position 29 to 167 of SEQ ID NO: 100. In one embodiment, the N-terminal portion having such amino acid sequence homology will maintain the activity of the corresponding naturally occurring N-terminal portion of FGF21.

In one embodiment of the present invention, the N-terminal portion of FGF21 of the chimeric protein of the present invention is a modified N-terminal portion of the FGF21 protein. In one embodiment, the N-terminal portion of FGF21 of the chimeric protein of the present invention comprises an amino acid sequence at least 85% identical to the amino acid sequence corresponding to residues from position 29 to 167 of SEQ ID NO: 152, from position 29 to 190 of SEQ ID NO: 152, or from position 29 to 197 of SEQ ID NO: 152. In one embodiment, the N-terminal portion of FGF21 of the chimeric protein of the present invention comprises an amino acid sequence at least 85% homologous to the amino acid sequence corresponding to residues from position 29 to 167 of SEQ ID NO: 152, from position 29 to 190 of SEQ ID NO: 152, or from position 29 to 197 of SEQ ID NO: 152.

It will be understood that the portion of FGF21 of the chimeric protein of the present invention may be derived from a nucleotide sequence that encodes a vertebrate or a non-vertebrate FGF21 protein. In one embodiment, the portion of FGF21 of the chimeric protein of the present invention may be derived a nucleotide sequence that encodes a mammalian FGF21 protein. Nucleotide sequences encoding a vertebrate FGF21 protein according to the present invention may include, but are not limited to, those shown in Table 4.

TABLE 4

```
Human FGF21 gene coding sequence (SEQ ID NO: 153) (GenBank
Accession No. NM_019113, which is hereby incorporated by
reference in its entirety)
  151 ATGGACTCGG ACGAGACCGG GTTCGAGCAC TCAGGACTGT GGGTTTCTGT GCTGGCTGGT

211 CTTCTGCTGG GAGCCTGCCA GGCACACCCC ATCCCTGACT CCAGTCCTCT CCTGCAATTC

271 GGGGGCCAAG TCCGGCAGCG GTACCTCTAC ACAGATGATG CCCAGCAGAC AGAAGCCCAC

331 CTGGAGATCA GGGAGGATGG GACGGTGGGG GGCGCTGCTG ACCAGAGCCC CGAAAGTCTC

391 CTGCAGCTGA AAGCCTTGAA GCCGGGAGTT ATTCAAATCT TGGGAGTCAA GACATCCAGG

451 TTCCTGTGCC AGCGGCCAGA TGGGGCCCTG TATGGATCGC TCCACTTTGA CCCTGAGGCC

511 TGCAGCTTCC GGGAGCTGCT TCTTGAGGAC GGATACAATG TTTACCAGTC CGAAGCCCAC

571 GGCCTCCCGC TGCACCTGCC AGGGAACAAG TCCCCACACC GGGACCCTGC ACCCCGAGGA

631 CCAGCTCGCT TCCTGCCACT ACCAGGCCTG CCCCCCGCAC TCCCGGAGCC ACCCGGAATC

691 CTGGCCCCCC AGCCCCCCGA TGTGGGCTCC TCGGACCCTC TGAGCATGGT GGGACCTTCC

751 CAGGGCCGAA GCCCCAGCTA CGCTTCCTGA

Pongo abelii (Sumatran orangutan) FGF21 gene coding sequence
(SEQ ID NO: 154) (GenBank Accession No. XM_002829519, which
is hereby incorporated by reference in its entirety)
  165      ATGGAC TCGGACGAGA CCGGGTTCGA GCACTCAGGA CTGTGGGTTC CTGTGCTGGC

221 TGGTCTTCTG CTGGGAGCCT GCCAGGCACA CCCCATCCCT GACTCCAGTC CTCTCCTGCA

281 ATTCGGGGGC CAAGTCCGGC AGCGGTACCT CTACACAGAT GATGCCCAGC AGACAGAAGC

341 CCACCTGGAG ATCAGGGAGG ATGGGACGGT GGGGGGCGCT GCTGACCAGA GCCCCGAAAG

401 TCTCCTGCAG CTGAAAGCCT TGAAGCCGGG AGTTATTCAA ATCTTGGGAG TCAAGACATC

461 CAGGTTCCTG TGCCAGAGGC CAGATGGGGC CCTGTATGGA TCGCTCCACT TTGACCCTGA
```

TABLE 4-continued

```
521 GGCCTGCAGC TTCCGGGAGC TGCTTCTTGA GGACGGATAC AATGTTTATC AGTCCGAGGC

581 CCATGGCCTC CCGCTGCACC TGCCGGGAAA CAAGTCCCCA CACCGGGACC CTGCACCCCG

641 AGGACCAGCT CGCTTCCTGC CACTACCAGG CCTGCCCCCC GCACCCCCAG AGCCGCCCGG

701 AATCCTGGCC CCCCAGCCCC CCGATGTGGG CTCCTCGGAC CCTCTGAGCA TGGTGGGACC

761 TTCCCAGGGC CGAAGCCCCA GCTATGCTTC CTGA
```

Pan troglodytes (chimpanzee) FGF21 gene coding sequence
(SEQ ID NO: 155) (GenBank Accession No. XM_524333, which
is hereby incorporated by reference in its entirety)

```
573      ATGGACTC GGACGAGACC GGGTTCGAGC ACTCAGGACT GTGGGTTTCT GTGCTGGCTG

631 GTCTTCTGCT AGGAGCCTGC AGGCACACC CCATCCCTGA CTCCAGTCCT CTCCTGCAAT

691 TCGGGGCCA AGTCCGGCAG CGGTACCTCT ACACAGATGA TGCCCAGCAG ACAGAAGCCC

751 ACCTGGAGAT CAGGGAGGAT GGGACGGTGG GGGGCGCTGC TGACCAGAGC CCCGAAAGTC

811 TCCTGCAGCT GAAAGCCTTG AAGCCGGGAG TTATTCAAAT CTTGGGAGTC AAGACATCCA

871 GGTTCCTGTG CCAGAGGCCA GATGGGGCCC TGTATGGATC GCTCCACTTT GACCCTGAGG

931 CCTGCAGCTT CCGGGAGCTG CTTCTTGAGG ACGGATACAA TGTTTACCAG TCCGAGGCCC

991 ACGGCCTCCC GCTGCACCTG CCGGGGAACA AGTCCCCACA CCGGGACCCT GCACCCCGAG

1051 GACCAGCTCG CTTCCTGCCA CTACCAGGCC TGCCCCCCGC ACCCCGGAG CCACCCGGAA

1111 TCCTGGCCCC CCAGCCCCCC GATGTGGGCT CCTCAGACCC TCTGAGCATG GTGGGACCTT

1171 CCCAGGGCCG AAGCCCCAGC TACACTTCCT GA
```

Canis lupus familiaris (dog) FGF21 gene coding sequence
(SEQ ID NO: 156) (GenBank Accession No. XM_541510, which
is hereby incorporated by reference in its entirety)

```
  1 ATGGGCTGGG CCGAGGCCGG GTTCGAGCAC CTGGGACTGT GGGTCCCTGT GCTGGCTGTG

61 CTTTTGCTGG AAGCCTGCCG GGCACATCCG ATCCCTGACT CCAGCCCCCT CCTACAATTT

121 GGAGGTCAAG TTCGACAGCG GTACCTCTAC ACCGACGATG CCCAGGAGAC AGAGGCCCAC

181 CTAGAGATCA GGGCCGATGG CACAGTGGTG GGGGCTGCCC GCCAGAGCCC TGAAAGTCTC

241 CTGGAGCTGA AAGCCCTAAA GCCAGGGGTC ATTCAAATCT TGGGAGTCAA ACATCCAGG

301 TTCCTGTGCC AGGGCCCAGA TGGGACACTA TATGGCTCGC TCCATTTCGA CCCTGTGGCC

361 TGCAGTTTCC GAGAACTGCT TCTTGAGGAT GGGTACAACA TCTACCACTC CGAGACCCTT

421 GGTCTCCCGC TTCGCCTGCG CCCCCACAAC TCCGCATACC GGGACTTGGC ACCCCGCGGG

481 CCTGCCCGCT TCCTGCCACT GCCAGGCCTG CTTCCAGCAC CCCAGAGCC TCCAGGGATC

541 CTGGCCCCGG AGCCTCCTGA CGTGGGCTCC TCGGACCCTC TGAGCATGGT GGGGCCTTCA

601 CAGGGCCGGA GTCCCAGCTA TGCTTCCTAA
```

Bos taurus (bovine) FGF21 gene coding sequence (SEQ ID
NO: 157) (GenBank Accession No. XP_001789587, which is
hereby incorporated by reference in its entirety)

```
  1 ATGGGCTGGG ACGAGGCCAA GTTCAAGCAC TTGGGACTGT GGGTCCCTGT GCTGGCTGTC

61 CTCCTGCTAG GAACCTGCCG GGCGCATCCC ATTCCAGACT CCAGCCCCCT CCTCCAGTTT

121 GGGGGCCAAG TCCGCCAGCG GTACCTCTAC ACGGATGATG CCCAGGAGAC AGAGGCCCAC

181 CTGGAGATCA GGGCCGATGG CACAGTGGTG GGGGCAGCCC GCCAGAGCCC CGAAAGTCTC

241 TTGGAGCTGA AAGCCCTGAA GCCAGGCGTC ATTCAGATCT TGGGAGTTAA ACATCCAGG

301 TTTCTCTGCC AGGGGCCAGA TGGGAAGCTG TACGGATCGC TGCACTTTGA CCCCAAAGCC

361 TGCAGCTTTC GGGAGCTGCT TCTTGAAGAT GGATACAACG TCTACCAGTC GGAGACCCTG

421 GGCCTTCCAC TCCGCCTGCC CCCCCAGCGC TCGTCCAACC GGGACCCGGC CCCGCGGGGA
```

TABLE 4-continued

```
481 CCTGCTCGCT TCCTTCCACT GCCGGGCCTG CCCGCGGCGC CCCCGGATCC TCCAGGGATC

541 TTGGCCCCCG AGCCTCCCGA CGTGGGCTCC TCGGATCCCC TGAGTATGGT GGGACCCTCG

601 TATGGCCGAA GCCCCAGCTA CACTTCTTGA
```

*Equus caballus* (horse) FGF21 gene coding sequence (SEQ ID NO: 158) (GenBank Accession No. XM_001489152, which is hereby incorporated by reference in its entirety)

```
  1 ATGGACTGGG ACAAGACGGG GTTCAAGTAC CAGGGACTGT GGGTCCCTGT GCTGGCTGTC

61 CTTCTGCTGG GAGCCTGCCA GTCACACCCC ATCCCTGACT CCAGTCCCCT CCTCCAATTC

121 GGGGGCCAAG TCAGGCAGCG CCACCTCTAC ACAGATGATG CCCAGGAGAC AGAGGCGCAC

181 CTGGAGATCA GGGCTGACGG CACTGTGGCA GGGGCTGTCC ACCGGAGCCC AGAAAGTCTC

241 TTGGAGCTGA AGCCCTGAA GCCAGGGGTA ATTCAAATCT GGGAGTCAA GACATCCAGG

301 TTTCTGTGCC AGGGGCCAGA CGGGACGCTG TACGGATCGC TCCACTTCGA CCCCGTGGCC

361 TGCAGCTTCC GGGAGCTGCT TCTCGAAGAC GGCTACAACG TTTACCAGTC TGAGACCCTT

421 GGCCTCCCAC TCCGCCTGCC CCACCACAGC TCCCCATACC AGGATCCGGC CCCTCGGGCA

481 CCCGCCCGCT TCCTGCCGCT GCCAGGCTTT CCCCCAGCAC CCCCGGAGCC TCCAGGGATC

541 CCGGCCCCCG AGCCCCCGGA CGTGGGCTCC TCGGACCCCC TGAGCATGGT GGGGCCTTCA

601 CGCAGCCGGA GCCCCAGCTA CACTTCCTGA
```

*Ailuropoda melanoleuca* (giant panda) FGF21 gene coding sequence (SEQ ID NO: 159) (GenBank Accession No. XM_002917864, which is hereby incorporated by reference in its entirety)

```
  1 ATGGGCTGGG ACGAGGCCAG GTCCGAGCAG CTGGGGCTGT GGGTCCCTGT GCTGGCTGTC

61 CTTTTGCTGG AAGCTTGCCA GGCACACCCT ATCCCTGACT CCAGCCCCCT CCTCCAATTC

121 GGAGGCCAAG TTCGACAGCG GTACCTCTAC ACGGACGATG CCCAGGAGAC AGAGGCCCAC

181 CTAGCGATCA GGGCTGATGG CACAGTGGTG GGGGCTGCCA GCCGGAGCCC AGAAAGTCTC

241 TTGGAGCTGA AGCCCTGAA ACCGGGGGTC ATTCAAATCC TGGGAGTGAA ACATCTAGG

301 TTCCTGTGCC AGGGCCCAGA TGGGACACTG TACGGATCGG TCCGCTTCGA CCCCGTAGCC

361 TGCAGCTTCC GGGAACTGCT CCTGGAGGAT GGGTACAACA TCTACCACTC TGAGACCCTC

421 GGCCTCCCAC TTCGCCTGCC CGCCCACAAC TCTCCATACC GGGACTCGGC GCCCCGGGGG

481 CCTGCCCGCT TCCTGCCCCT GCCAGGCCTG CTTCCGGTCC CCCCGGACCC CCAGGGATC

541 CTGGGCCCCG AGCCTCCCGA CGTGGGCTCC TCGGACCCCC TGAGCATGGT GGGGCCTTCA

601 CAGGGCCGAA GTCCCAGCTA CGCTTCCTGA
```

*Oryctolagus cuniculus* (rabbit) FGF21 gene coding sequence (SEQ ID NO: 160) (GenBank Accession No. XM_002723699, which is hereby incorporated by reference in its entirety)

```
  1 ATGGACTGGG GCAAGGCCAA GTGCCGGCCC CCGGGGCTGT GGGTCCCCGC GCTCGCTGCC

61 CTGCTGCTGG GGGCCTGCCA GGCACACCCC ATCCCCGACT CCAGCCCCCT CCTCCAGTTT

121 GGGGACCAAG TGCGGCAGCA GCACCTGTAC ACGGACGATG CGCAGGAAAC AGAAGCCCAC

181 CTGGAGATCA GGGCGGATGG CACGGTGGTG GGGGCTGCCC GGAGGAGCCC AGAAAGTCTC

241 TTGCAGATGA AGCCCTTACA ACCGGGGATC ATTCAGATCT GGGGGTCCA GACGTCCAGG

301 TTCCTCTGCC AGAGGCCGGA TGGCACGCTC TACGGCTCGC TCCACTTCGA CCGCGAGGCC

361 TGCAGCTTCC GGGAGCTGCT GCGTGAGGAT GGGTACAACG TTTACCTCTC GGAGGCCCTG

421 GGCCTGCCCC TGCGCCTGTC CCCCGGCAGC TCCCACGCA GGGCGCCGGC CCCCCGGGGA

481 CCAGCCCGCT TCCTGCCGCT GCCCGGCCTG CCGCCAGACC TTCCGGAACC GCCAGGCCTC
```

TABLE 4-continued

541 CTGGCCGCCG CGCCCCCCGA TGTCGACTCC CCGGACCCCC TGAGCATGGT GCAGCCTGCG

601 CTGGACCAGA GCCCCAGCTA CACCTCCTGA

*Gorilla gorilla* (gorilla) FGF21 gene coding sequence
(SEQ ID NO: 161) (Ensembl Accession No. ENSGGOT00000001253,
which is hereby incorporated by reference in its entirety)
151 ATGGACTCGG ACGAGACCGG GTTCGAGCAC TCAGGACTGT GGGTTTCTGT GCTGGCTGGT

211 CTTCTGCTGG AGCCTGCCA GGCACACCCC ATCCCTGACT CCAGTCCTCT CCTGCAATTC

271 GGGGGCCAAG TCCGGCAGCG GTACCTCTAC ACAGATGATG CCCAGCAGAC AGAAGCCCAC

331 CTGGAGATCA GGGAGGATGG GACGGTGGGG GGTGCTGCTG ACCAGAGCCC TGAAAGTCTC

391 CTGCAGCTGA AAGCCTTGAA GCCGGGAGTT ATTCAAATCT TGGGAGTCAA GACATCCAGG

451 TTCCTGTGCC AGAGGCCAGA TGGGGCCCTG TATGGATCGC TCCACTTTGA CCCTGAGGCC

511 TGCAGCTTCC GGGAGCTGCT TCTTGAGGAC GGATACAATG TTTACCAGTC CGAGGCCCAC

571 GGCCTCCCGC TGCACCTGCC GGGGAACAAG TCCCCACACC GGGACCCTGC ACCCCGAGGA

631 CCAGCTCGCT TCCTGCCACT ACCAGGCCTG CCCCCCGCAC CCCCGGAGCC ACCCGGAATC

691 CTGGCCCCCC AGCCCCCCGA TGTGGGCTCC TCGGACCCTC TGAGCATGGT GGGACCTTCC

751 CAGGGCCGAA GCCCCAGCTA CGCTTCCTGA

*Nomascus leucogenys* (Northern white-cheeked gibbon) FGF21
gene coding sequence (SEQ ID NO: 162) (Ensembl Accession
No. ENSNLET00000005931, which is hereby incorporated by
reference in its entirety)
587         ATGG ACTCGGACGA GACCGGGTTC GAGCACTCAG GACTGTGGGT TCCTGTGCTG

647 GCTGGTCTTC TGCTGGGAGC CTGCCAGGCA CACCCCATCC TGACTCCAG TCCTCTCCTG

707 CAATTCGGGG GCCAAGTCCG GCAGCGGTAC CTCTACACAG ATGATGCCCA GCAGACAGAA

767 GCCCACCTGG AGATCAGGGA GGATGGGACG GTGGGGGGCG CTGCTGACCA GAGCCCTGAA

831 AGTCTCCTGC AGCTGAAAGC CTTGAAGCCG GGAGTTATTC AAATCTTGGG AGTCAAGACA

891 TCCAGGTTCC TATGCCAGAG GCCAGATGGG GCCCTGTATG GATCGCTCCA CTTTGACCCT

951 GAGGCCTGCA GCTTCCGGGA GCTGCTTCTT GAGGACGGAT ACAATGTTTA CCAGTCCGAG

1011 GCCCATGGCC TCCCGCTGCA CCTGCCGGGG AACAAGTCCC CACACCGGGA CCCTGCACCC

1071 CGAGGACCAG CTCGCTTCCT GCCACTACCA GGCCTGCCCC CTGCACCCCC AGAGCCGCCC

1131 GGAATCCTGG CCCCCCAGCC CCCCGATGTG GGCTCCTCGG ACCCTCTGAG CATGGTGGGA

1191 CCTTCCCAGG GCCGAAGCCC CAGCTACGCT TCCTGA

*Procavia capensis* (hyrax) FGF21 gene coding sequence (SEQ
ID NO: 163) (Ensembl Accession No. ENSPCAT00000001288,
which is hereby incorporated by reference in its entirety)
1 ATGGACTGGG CCAAGTTTGG GATCGAGCAC CCGGGACTGT GGGTCCCGGT GATGGCAGTA

61 CTTCTGCTGG AGCCTGCCA AGGATACCCT ATTCCTGACT CCAGCCCCCT TCTCCAATTC

121 GGAGGCCAGG TCCGGCAACG TTACCTCTAC ACAGATGACG CGCAGGAGAC CGAGGCCCAC

181 CTGGAGATCC GAGCAGACGG CACGGTGGTG GGGGCTGCCC ACCGGAGCCC CGAGAGTCTC

241 TTGGAGCTGA AAGCTTTGAA GCCCGGCATA ATTCAGATCT TGGGAGTCAA GACATCCAGA

301 TTCCTCTGCC AGGGTCCTGA TGGGGTGCTG TATGGATCGC TCCGTTTTGA CCCAGTGGCC

361 TGCAGCTTCC GGGAGCTGCT TCTTGAAGAT GGATACAATG TTTACCAGTC TGAGGCCCAC

421 GGCCTCCCGC TTCGCCTACC ATCCCACAAT TCCCCACAGA GGGACCTGGC GTCCCGGGTG

481 CCAGCCCGCT TCCTGCCACT GCCAGGCCGG CTCACGGTGC TCCCAGAACC TTCGGGGGTC

541 CTGGGCCCTG AGCCCCCCGA TGTGGACTCC TCAGACCCCC TGAGCATGGT GGGGCCTTCG

601 CAGGGCCGAA GCCCCAGTTA CGCCTCCTGA

TABLE 4-continued

*Cavia porcellus* (guinea pig) FGF21 gene coding sequence
(SEQ ID NO: 164) (Ensembl Accession No. ENSCPOT00000000273,
which is hereby incorporated by reference in its entirety)
```
  1 ATGGACTGGG CCCGGACTGA GTGTGAGCGC CCAAGGCTGT GGGTCTCCAT GCTGGCCATC

61 CTTCTGGTGG GAGCCTGCCA GGCACACCCT ATCCCTGACT CCAGCCCCCT CCTCCAGTTT

121 GGGGGCCAGG TCCGGCAGCG GTACCTCTAC ACAGATGATG CTCAGGACAC TGAAGTGCAC

181 CTGGAGATCA GGGCCGATGG CTCAGTACGG GCATTGCCC  ACAGGAGCCC TGAAAGTCTC

241 CTGGAGCTGA AAGCCTTGAA GCCAGGAGTC ATTCAGATCT TGGGAATCAG GACTTCCAGG

301 TTCCTGTGCC AGAGGCCCGA TGGGAGTCTG TATGGATCAC TCCACTTTGA TCCTGAGGCC

361 TGCAGCTTCC GGGAGCTGCT GCTTGCTGAT GGCTACAATG TCTACAAGTC TGAAGCCCAC

421 GGCCTCCCTC TGCACCTGCT GCGCGGTGAC TCTCTATCGC AGGAACCAGC ACCCCCAGGA

481 CCAGCCCGAT TTCTGCCACT ACCAGGCCTG CCCGCAACAC CCCCGGAGCC ACCCAGGATG

541 CTGCCCCCAG GCCCCCAGA  TGTGGGCTCC TCGGACCCTT TGAGCATGGT GGGGCCTTTA

601 TGGGACCGAA GCCCCAGCTA TACTTCCTGA
```

*Tupaia belangeri* (tree shrew) FGF21 gene coding sequence
(SEQ ID NO: 165) (Ensembl Accession No. ENSTBET00000016056,
which is hereby incorporated by reference in its entirety)
```
  1 ATGGGCTGGG ACAAGGCCCG GTTCGAGCAC CTGGGAGCGT GGGCTCCTGT GCTGGCTGTC

61 CTCCTCCTGG GAGCCTGCCA GGCATACCCC ATCCCTGACT CCAGCCCCCT CCTACAATTC

121 GGGGGCCAGG TCCGGCAGCG GTACCTCTAC ACGGACGACA CGCAGGACAC AGAAGCCCAC

181 CTTGAGATCA GGGCCGACGG CACCGTGGTG GGGGCCGCCC ACCAAAGCCC GGAAAGTCTC

241 CTGGAGCTGA AAGCCTTGAA GCCGGGGGTC ATTCAAATCC TGGGAGTCAA GACCTCCAGG

301 TTCCTGTGCC AGAGGCCAGA CGGGGCCCTG TACGGGTCGC TTCACTTCGA CCCCGAGGCC

361 TGCAGCTTCC GGGAGCTGCT TCTCGAGGAT GGATACAACA TTTACCAGTC TGAGGCTCGT

421 GGCCTCCCCC TGCGCCTGCC GCCCCACGAC TCCCCACATC GGGACCGGAC CCCTCGGGGA

481 CCAGCTCGTT TCCTGCCGCT GCCTGGCCTG CCCCTGGTTC CTCCAGAGCT GCCAGGGGTC

541 CTGGCCCTTG AGCCCCCCGA CGTGGGCTCC TCAGACCCGC TGA
```

*Sorex araneus* (shrew) FGF21 gene coding sequence (SEQ ID
NO: 166) (Ensembl Accession No. ENSSART00000003074,
which is hereby incorporated by reference in its entirety)
```
  1 ATGGTCTGGG ACAAGGCCAG GGGGCAGCAG TTGGGACTGT GGGCCCCCAT GCTGCTGGGC

61 TTGCTGCTGG GTGCCTGCCA GGCACACCCC CTCCCTGACT CCAGCCCCCT CCTCCAATTT

121 GGGGGCCAAG TCCGACTGAG GTTCCTGTAC ACCGACGATG CCCAGAGGAC AGGGGCGCAC

181 CTGGAGATCA GGGCCGACGG CACAGTGCAG GGTGCGGCCC ACAGGACCCC AGAATGTCTC

241 CTGGAGCTGA AAGCCTTGAA GCCAGGCGTA ATTCAAATCC TTGGGGTCAG CACATCCAGA

301 TTCCTGTGCC AGCGGCCCGA TGGGGTCCTG TATGGATCGC TTCGCTTTGA CCCAGAGGCC

361 TGCAGTTTCC GGGAACTTCT TCTCCAGGAT GGATATAACG TTTACCAGTC TGAGGCCCTG

421 GGTCTCCCGC TCTACCTACA CCCGCCCAGT GCCCCAGTGT CCCAGGAACC AGCCTCACGG

481 GGCGCCGTCC GCTTCCTGCC ACTGCCAGGA CTGCCACCTG CCTCCCTGGA GCCCCCCAGG

541 CCCCCCGCCC CGGTGCCTCC AGACGTGGGT TCCTCAGACC CCCTGA
```

*Ictidomys tridecemlineatus* (squirrel) FGF21 gene coding
sequence (SEQ ID NO: 167)
```
  1 ATGTACCCCA TCCCTGACTC AAGCCCCCTC CTCCAATTTG GGGGCAAGT  CCGGCAGCGG

61 TACCTGTACA CAGATGATGC CCAGGAGACT GAGGCCCACC TGGAGATCAG GGCTGATGGC

121 ACCGTGGTGG GGGCTGCCCA TCAAAGCCCG GAAAGTCTCT TGGAACTGAA AGCCTTGAAG
```

TABLE 4-continued

```
181 CCTGGGGTCA TTCAAATCTT GGGGGTCAAA ACATCCAGGT TCCTGTGCCA GAGGCCAGAT

241 GGAGTGCTGT ATGGATCGCT CCACTTTGAC CCTGAGGCCT GCAGCTTCCG GGAGCAGCTT

301 CTGGAGGACG GGTACAACGT TTACCAGTCA GAATCCCACG GCCTCCCCGT GCGCCTGCCC

361 CCTAACTCAC CATACCGGGA CCCAGCGCCG CCAGGACCAG CCCGCTTCCT TCCACTGCCA

421 GGCCTGCCCC CAGCAGCCCT GGAGCCGCCA GGGATCCTGG GCCCTGAGCC CCTGATGTG

481 GGCTCCTCCG ACCCACTCAG CATGGTGGGG CCTTTGCAGG GCCGAAGCCC CAGTTACGCT

541 TCCTGA
```

*Loxodonta africana* (elephant) FGF21 gene coding sequence
(SEQ ID NO: 168) (Ensembl Accession No. ENSLAFT00000022429,
which is hereby incorporated by reference in its entirety)

```
  1 ATGGACTGGG CCAAGTTTGG GTTGGAGCAC CCAGGACTGT GGGTCCCTGT GATGGCTGTC

61 CTTCTGCTGG GAGCCTGCCA GGACACCCC ATCCCTGACT CCAGCCCCCT CCTCCAATTC

121 GGGGGCCAGG TCCGGCAACG TTACCTCTAC ACAGATGATC AGGAGACCGA GGCCCACCTG

181 GAGATCAGAG CAGATGGCAC AGTGGCGGGA GCCGCTCACC GGAGCTCTGA GAGTCTCTTG

241 GAGCTGAAAG CTTTGAAGCC TGGAATAATT CAGATCTTGG GGGTCAAGAC ATCCCGGTTC

301 CTGTGCCAGG GGCCTGATGG GGTGCTGTAC GGATCGCTCC ATTTCGACCC AGCCGCCTGC

361 AGCTTCCGGG AGCTGCTTCT TGAAGATGGA TACAATGTTT ACTGGTCCGA GGCCCATGGA

421 CTCCCAATCC GCCTGCCCTC CCACAACTCC CCATATAGGG ACCCAGCATC CCGGGTACCA

481 GCCCGCTTCC TGCCACTGCC AGGCCTGCTC CCAATGCTCC AAGAACCTCC AGGGGTCCTG

541 GCCCCTGAGC CCCCTGATGT GGACTCCTCA GACCCCCTGA GCATGGTGGG GCCTTCACAG

601 GGCCGAAGCC CCAGCTATGC CTCCTGA
```

*Sus scrofa* (pig) FGF21 gene coding sequence) (SEQ ID
NO: 169) (GenBank Accession No. NM_001163410, which
is hereby incorporated by reference in its entirety)

```
131 ATGGGCTGGG CCGAGGCCAA GTTCGAGCGC TTGGGACTGT GGGTCCCTGT GCTGGCTGTC

191 CTGCTGGGAG CCTGCCAGGC ACGTCCCATT CCTGACTCCA GCCCCTCCT CCAATTTGGG

251 GGCCAAGTGC GCCAACGATA CCTCTACACG GATGATGCCC AGGAAACTGA AGCCCACCTG

311 GAGATCAGAG CTGATGGCAC CGTGGCAGGG GTAGCCCGCC AGAGCCCTGA AAGTCTCTTG

371 GAGCTGAAAG CCCTGAAGCC AGGGGTCATT CAAATTTTGG GAGTCCAGAC ATCCCGGTTC

431 CTGTGCCAGG GGCCAGACGG GAGACTGTAC GGATCGCTCC ACTTCGACCC TGAGGCCTGC

491 AGCTTCCGGG AGCTGCTTCT TGAGGATGGC TACAACGTTT ACCAGTCTGA GGCCCTTGGC

551 CTCCCACTCC GGCTGCCTCC GCACCGCTCC TCCAACCGGG ACCTGGCCCC CGGGGACCT

611 GCTCGCTTCC TGCCACTGCC AGGCCTGCCC CCGGCACCCC GGAGCCGCC AGGGATCTTG

671 GCCCCTGAAC CTCCCGACGT GGGCTCCTCG GACCCCCTGA GCATGGTGGG GCCTTCACAC

731 GGCCGGAGCC CCAGCTACAC TTCTTGA
```

*Felis catus* (cat) FGF21 gene coding sequence (SEQ ID
NO: 170) (Ensembl Accession No. ENSFCAT00000007367,
which is hereby incorporated by reference in its entirety)

```
  1 ATGGGCTGGG ACGAGGCCGG GTCCCAGCGC CTGGGACTGT GGGTCGTGCT GGGGGTCCTT

61 TTGCCGGAAG CCTGCCAGGC ACACCCTATC CCTGACTCCA GCCCCTCCT CCAATTCGGG

121 GGCCAAGTTC GACAGCGGTT CCTCTACACG GACGACGCCC AGGAGACAGA GGTCCACCTC

181 GAGATCAAGG CTGATGGCAC AGTGGTGGGG ACCGCTCGCC GGAGCCCTGA GAGTCTCTTG

241 GAGCTAAAAG CCCTGAAGCC GGGGGTAATT CAAATCTTGG GGGTCAAAAC GTCCAGGTTC

301 CTGTGCCAGG GCCCAGATGG GACACTGTAT GGATCGCTCC GCTTTGACCC CGCAGCCTGC

361 AGCTTCCGGG AACTGCTCCT GGAGGACGGA TACAACATCT ACCACTCGGA GACCTCGGG
```

TABLE 4-continued

```
421 CTCCCACTCC GCCTGCCCCC CCACAACTCC CCATACCGGG ACTTGGCCCC CCGGGCACCT

481 GCCCGCTTCC TGCCGCTGCC AGGCCTGCTT CCGGCACCCC CGGAGCCTCC AGGGATCCTG

541 GCCCCCGAGC CCCCGGACGT GGGCTCCTCG GACCCTCTGA GCATGGTGGG GCCTTCCCAG

601 GGCCGAAGTC CCAGCTACGC TTCCTGA
```

*Otolemur garnettii* (bushbaby) FGF21 gene coding sequence
(SEQ ID NO: 171) (Ensembl Accession No. ENSOGAT00000003585,
which is hereby incorporated by reference in its entirety)

```
  1 GACAAGGCCA GGACTGGGTT CAAGCACCCA GGACCATGGT TTCCCCTGCT GGCTGTACTT

61 TTGTTGGGAG CCTGCCAGGC ACACCCTATC CCTGACTCCA GCCCCCTACT CCAGTTTGGT

121 GGCCAAGTCC GGCAGCGGTA CCTCTACACA GATGATGCCC AGGAGACAGA AGCCCACCTG

181 GAGATCAGGG AAGATGGCAC AGTGGTGGGG CTGCACAAC AGAGCCCTGA AGTCTCTTG

241 GAGCTGAAAG CTTTAAAGCC AGGGGTCATT CAAATCTTGG GAGTCAAGAC ATCCAGGTTC

301 CTGTGCCAGA GGCCAGATGG GGGCCTATAT GGATCGCTCT ACTTTGACCC CAAGGCCTGC

361 AGTTTCCGGG AGCTGCTTCT TGAGGATGGA TACAACGTTT ACTGGTCTGA GACCTATGGC

421 CTCCCACTGC ACCTGCCTCC TGCCAATTCC CCATACTGGG GCCCATCCCT TCGGAGCCCA

481 GCCCGCTTCC TGCCACTGCC AGGCCCTCCT GCAGCATCCC CAGAGCTGCC GGGGATCTTG

541 GCCCTGGAAC CCCCCGATGT GGGCTCCTCG GACCCTCTGA GCATGGTGGG GCCTTCGCAG

601 GGCCGAAGCC CCAGCTATGC TTCCTGA
```

*Rattus norvegicus* (Norway rat) FGF21 gene coding sequence
(SEQ ID NO: 172) (GenBank Accession No. NM_130752, which
is hereby incorporated by reference in its entirety)

```
  1 ATGGACTGGA TGAAATCTAG AGTTGGGGCC CCGGGACTGT GGGTCTGTCT CCTGCTGCCT

61 GTCTTCCTGC TGGGGGTGTG CGAGGCATAC CCCATCTCTG ACTCCAGCCC CCTCCTCCAG

121 TTTGGGGGTC AAGTCCGACA GAGGTATCTC TACACAGATG ACGACCAGGA CACCGAAGCC

181 CACCTGGAGA TCAGGGAGGA CGGAACAGTG GTGGGCACAG CACACCGCAG TCCAGAAAGT

241 CTCCTGGAGC TCAAAGCCTT GAAGCCAGGG GTCATTCAAA TCCTGGGTGT CAAAGCCTCT

301 AGGTTTCTTT GCCAACAACC AGATGGAACT CTCTATGGAT CGCCTCACTT TGATCCTGAG

361 GCCTGCAGTT TCAGAGAGCT GCTGCTTAAG GACGGATACA ATGTGTACCA GTCTGAGGCC

421 CATGGCCTGC CCCTGCGTCT GCCCCAGAAG GACTCCCAGG ATCCAGCAAC CCGGGGACCT

481 GTGCGCTTCC TGCCCATGCC AGGCCTGCCC CACGAGCCCC AAGAGCAACC AGGAGTCCTT

541 CCCCCAGAGC CCCCAGATGT GGGTTCCTCC GACCCCCTGA GCATGGTAGA GCCTTTGCAA

601 GGCCGAAGCC CCAGCTATGC ATCTTGA
```

*Mus musculus* (house mouse) FGF21 gene coding sequence
(SEQ ID NO: 173) (GenBank Accession No. NM_020013, which
is hereby incorporated by reference in its entirety)

```
185     ATGGAA TGGATGAGAT CTAGAGTTGG GACCCTGGGA CTGTGGGTCC GACTGCTGCT

241 GGCTGTCTTC CTGCTGGGGG TCTACCAAGC ATACCCCATC CCTGACTCCA GCCCCCTCCT

301 CCAGTTTGGG GGTCAAGTCC GGCAGAGGTA CCTCTACACA GATGACGACC AAGACACTGA

361 AGCCCACCTG GAGATCAGGG AGGATGGAAC AGTGGTAGGC GCAGCACACC GCAGTCCAGA

421 AAGTCTCCTG GAGCTCAAAG CCTTGAAGCC AGGGGTCATT CAAATCCTGG GTGTCAAAGC

481 CTCTAGGTTT CTTTGCCAAC AGCCAGATGG AGCTCTCTAT GGATCGCCTC ACTTTGATCC

541 TGAGGCCTGC AGCTTCAGAG AACTGCTGCT GGAGGACGGT ACAATGTGT ACCAGTCTGA

601 AGCCCATGGC CTGCCCCTGC GTCTGCCTCA GAAGGACTCC CCAAACCAGG ATGCAACATC

661 CTGGGGACCT GTGCGCTTCC TGCCCATGCC AGGCCTGCTC CACGAGCCCC AAGACCAAGC
```

TABLE 4-continued

721 AGGATTCCTG CCCCCAGAGC CCCCAGATGT GGGCTCCTCT GACCCCCTGA GCATGGTAGA

781 GCCTTTACAG GGCCGAAGCC CCAGCTATGC GTCCTGA

*Vicugna pacos* (alpaca) FGF21 gene coding sequence (SEQ ID
NO: 174) (Ensembl accession no. ENSVPAT00000005993,
which is hereby incorporated by reference in its entirety)
(1-209, excluding 79-168 and 172-182)
  1 ATGGACTGGG ACGAGGCCAA GTTCGAGCAT CGGGGACTGT GGGTCCCAGT GCTCACTGTC

61 CTTCTGCTGG GAGCCTGCCA GGCACGCCCC ATTCCTGACT CCAGCCCCCT CCTCCAATTC

121 GGGGGCCAAG TCCGGCAGCG GTACCTCTAC ACGGATGACG CCCAGGAGAC AGAAGCCCAC

181 CTGGAGATCA GGGCTGATGG CACAGTGGTG GGGGTGGCCC GCCAG---CC CGAA------

241 ---------- ---------- ---------- ---------- ---------- ----------

301 ---------- ---------- ---------- ---------- ---------- ----------

361 ---------- ---------- ---------- ---------- ---------- ----------

421 ---------- ---------- ---------- ---------- ---------- ----------

481 ---------- ---------- ----GGAATT CCT------- ---------- ----------

541 ------CCCG AGCCTCCTGA CGTGGGCTCC TCAGACCCCC TGAGCATGGT GGGGCCTTCA

601 TACAGCAGAA GCCCCAGCTA CACTTCCTGA

*Anolis carolinensis* (anole lizard) FGF21 gene coding
sequence (SEQ ID NO: 175) (Ensembl accession no.
ENSACAT00000017230, which is hereby incorporated by
reference in its entirety)
  1 TGTAAAAGCA AGGGAGGAGG GAAGGGGGGA GAGAGGATGT GGGTAGACCT AGTTTTCTGG

61 GCTGCCTTGC TCCGCACAGC TCCTGCTCTT CCCTTGCGGA ATTCCAACCC CATCTACCAA

121 TTTGATGGGC AGGTCCGGCT TCGGCACCTC TACACAGCAG ATGAACAGAC GCACCTCCAC

181 TTGGAGATCT TGCCAGACGG TACCGTGGGT GGATCCAGGT TTCAGAATCC CTTCAGTTTG

241 ATGGAGATCA AAGCTGTGAA GCCAGGAGTC ATTCGCATGC AGGCCAAGAA GACCTCTAGA

301 TTTCTCTGTA TGAAACCCAA TGGACGACTG TATGGCTCGC TGTTCTACTC TGAGGAGGCA

361 TGCAACTTCC ATGAGAAGGT TCTCAGCGAT GGCTACAACC TCTACTATTC TGAAAACTAC

421 AACATACCTG TCAGCCTCAG CTCGGCAGGG AACCTGGGTC AGAGCCGTCA GTTGCCTCCC

481 TTCTCCCAAT TCCTGCCGTT AGTCAACAAA ATTCCTCTTG AGCCTGTGCT TGAAGACTTT

541 GACTTCTATG GACATCAATT GGATGTTGAA TCAGCTGATC CTTTGAGCAT TTTAGGACAA

601 AACCCTGGTT TCATGAGTCC GAGCTATGTC TTC

*Gadus morhua* (cod) FGF21 gene coding sequence (SEQ ID
NO: 176) (Ensembl accession no. ENSGMOT00000014151,
which is hereby incorporated by reference in its entirety)
  1 CTCCTCCTCG CCACCCTCCT CCACATCGGC CTCTCCTTCT ACGTCCCCGA CTCCGGCCCC

61 CTGCTGTGGC TGGGCGACCA GGTCAGGGAG AGACACCTCT ACACAGCAGA GAGCCACCGG

121 AGGGGGCTGT TCCTGGAGAT GAGCCCGGAC GGTCAGGTGA CAGGAAGTGC TGCTCAGACG

181 CCGCTCAGTG TTCTGGAGCT GAGGTCGGTC AGAGCAGGAG ATACGGTCAT CAGAGCGCGC

241 CTCTCCTCTC TCTACCTGTG TGTGGACAGG GCAGGTCACC TGACAGGACA GAGACAGTAC

301 ACAGAGTCCG ACTGCACCTT CAGAGAGGTC ATCCTTGAGG ACGGCTACAC CCACTTCCTG

361 TCCGTGCACC ACGGACTTCC TATTTCGCTG GCGCCGAGAC ACTCCCCAGG GAGACAGGGG

421 CTGCGCTTCA GCAGGTTCCT CCCGCTGAGG AGCAGTCTGT CAGAGGATAG GGTCGCCGAG

481 CCCCCAGACA GCCCACTGAA CCTGGACTCT GAAGACCCCC TGGGGATGGG TCTGGGTTCG

541 CTCCTCAGCC CGGCCTTCTC CATG

TABLE 4-continued

*Latimeria chalumnae* (coelacanth) FGF21 gene coding sequence
(SEQ ID NO: 177) (Ensembl accession no. ENSLACT00000003815,
which is hereby incorporated by reference in its entirety)
```
  1 ATGTTATGCC AGAGTTTTGT GATATTAAGT CAGAAATTCA TTTTTGGGCT CTTTTTGACT

61 GGATTGGGGC TAACAGGATT GGCTTGGACA AGGCCCTTCC AGGATTCCAA TCCCATCCTG

121 CAGTATTCCG ATTCCATCCG GCTCCGACAT CTGTACACTG CCAGTGAGAG TCGGCACCTT

181 CACCTACAAA TCAACTCGGA TGGACAGGTG GGAGGGACAA CCAAGCAAAG CCCTTACAGT

241 CTGTTGGAGA TGAAGGCGGT GAAGACAGGT TTTGTGGTCA TCAGGGGCAA GAAAAGCGCC

301 CGTTACCTCT GTATGGAACG TAGTGGACGG CTCTATGGAT CGCTGCAGTA TACAGAAAAA

361 GACTGCACCT TCAAAGAGGT TGTGTTGGCA GATGGATACA ACCTGTATGT CTCAGAGGAA

421 CACCAGGCCA CAGTGACGCT GAGCCCCATG AGGGCGAGGA TAGCGCAAGG GAAAAAGATC

481 CCACCCTTTT CCCATTTCCT TCCAATGGTG AACAAGGTGC CTGTGGAGGA TGTTGCCGCT

541 GAGATGGAGT TTGTCCAGGT GCTGCGGAA ATGACGGCCG ACGTGGACTC TCCGGATCCC

601 TTTGGAATGA CCTGGGAAGA ATCGGTTCAC AGTCCGAGCT TTTTTGCC
```

*Tursiops truncatus* (dolphin) FGF21 gene coding sequence
(SEQ ID NO: 178) (Ensembl accession no. ENSTTRT00000014561,
which is hereby incorporated by reference in its entirety)
```
  1 ATGGGCTGGG ACAAGACCAA ACTCGAGCAC CTGGGACTGT GGGTCCCTGT GCTAGCTGTC

61 CTGCTGGGAC CCTGCCAGGC ACATCCCATT CCTGACTCCA GCCCCTCCT CCAATTTGGG

121 GGCCAAGTCC GCCAGCGATA CCTCTACACG GATGACGCCC AGGAGACGGA GGCCCACCTG

181 GAGATCAGGG CTGATGGCAC AGTGGTGGGG ACGGCCCGCC GGAGCCCCGA AGGAGTTAAA

241 ACATCCAGGT TCCTGTGCCA GGGGCCAGAG GGGAGGCTGT ATGGATCGCT CCACTTCAAC

301 CCCCAGGCCT GCAGCTTCCG GGAGCTGCTT CTTGAGGATG GATACAACGT TTACCAGTCT

361 GAGGCTCTTG GCATTCCCCT CCGCCTGCCC CCGCACCGCT CCTCCAACTG GACCTGGCC

421 CCCCGGGGAC CTGCTCGCTT CCTGCCGCTG CCAGGCTTCC TCCCGCCACC CCTGGAGCCT

481 CCAGGGATCT TGGCCCCCGA GCCTCCCAAC GTAGGTTCCT CGGACCCCTT GAGCATGGTG

541 GGACCTTCAC ATGGCCGAAG CCCCAGCTAC ACTTCCTGA
```

*Mustela putorius* furo (ferret) FGF21 gene coding sequence
(SEQ ID NO: 179) (Ensembl accession no. ENSMPUT00000003755,
which is hereby incorporated by reference in its entirety)
```
188        ATG GCTGGGAAG AGGCCAGGTC CGAGCACCTG GGGCTGTGGG TCCCTGTGCT

241 GGCGGTCCTT TTGCTGGGAG CCTGCCAGGC ATACCCTATT CCTGACTCCA GCCCCCTCCT

301 CCAATTTGGA GGCCAAGTTC GACAGCGGTA CCTCTACACA GACGACGCTC AGGAGACGGA

361 GGCCCACCTA GAGATCAGGG CTGATGGCAC GGTGGTGGGG GCTGCCCGCC GGAGCCCCGA

421 AAGTCTCTTG GAGCTGAAAG CCCTGAAGCC AGGGGTCATT CAGATCTTGG GAGTGAAAAC

481 ATCCAGGTTC CTGTGCCAGG GCCCGAATGG GACACTGTAC GGATCGTTCC ACTTCGACCC

541 CGTAGCCTGC AGCTTCCGGG AAGTGCTTCT GGAAGATGGA TACAACATCT ACCACTCTGA

601 GACCCTGGGC CTCCCACTGC GCCTGCCCCC CCACAACTCC CCACACAGGG ACCTGGCGCC

661 CCGGGGGCCT GCCCGCTTCC TGCCCCTGCC AGGCCTGCTT CCGGCCACCC CGGAGTCCCG

721 GGGGATCCCA GCCCCCGAGC CTCCCAACGT GGGCTCCTCA GACCCCCTGA GCATGGTGGG

781 GCCTTTGCAG GGTCAAAGTC CCAGCTACAC TTCCTGA
```

*Takifugu rubripes* (fugu) FGF21 gene coding sequence (SEQ
ID NO: 180) (Ensembl accession no. ENSTRUT00000034076,
which is hereby incorporated by reference in its entirety)
```
  1 TTTATTTATT TATTTATTCA AACTGCACTT TTTTCCCCTT CCAAATGGTT CAACTTTTAT

61 CTCCCTGACT CCAACCCGCT CTTATCCTTT GACAGTCATG GCAGAGGCAT CCACCTCTAC
```

TABLE 4-continued

```
121 ACAGATAATC AAAGGCGAGG GATGTATCTG CAGATGAGCA CAGATGGAAG CGTTTCCGGG

181 AGTGATGTCC AGACGGCGAA CAGTGTGCTG GAACTGAAGT CAGTCAGAAA CGGCCACGTC

241 GTCATCCGAG GAAAATCGTC TTCTCTGTTT CTCTGTATGG ACAGCAGAGG CCGTTTATGG

301 GGGCAGAGGC ACCCCACTGA GGCCGACTGC ACTTTCAGGG AAGTGTTGCT GGCAGATGGA

361 TACACTCGCT TCCTGTCCCT GCACAACGGA ACTCCTGTGT CTCTGGCACC TAAACAATCT

421 CCAGACCAGC ACACAGTCCC CTTCACTCGT TTCCTGCCGC TCAGGAATAC ACTGGCAGAG

481 GAGAGCATGT CTGAACCACC ATCAAACCAA CAGAGATATT TTAACATTGA CTCTGATGAT

541 CTTCTTGGAA TGGATTTAAA TGCGATGGTC AGTCCTCAGT TTTCAGGGGA CAAGTGA
```

Dipodomys ordii (kangaroo rat) FGF21 gene coding sequence
(SEQ ID NO: 181) (Ensembl accession no. ENSDORT00000001234,
which is hereby incorporated by reference in its entirety)

```
  1 ATGGACCAGG CAAAGACCAG GGTTGGGGCC CGGGGGCTGG GGGGCCTTGT GCTGGCTGTC

61 ATAATTCTGG GAGCATGCAA GGCACGGCCT ATCCCTGACT CCAGCCCCCT CCTCCAATTT

121 GGGGGTCAAG TTCGGCTTCG GCACCTCTAC ACAGATGACA CTCAGGAGAC GGAAGCCCAT

181 CTGGAGATCA GGGCAGATGG CACGGTAGTG GGGACTGCCC ACCGGAGCCC TGAAAGTCTC

241 TTGGAGCTGA AAGCCTTGAA GCCAGGAGTC ATTCAAATCT TAGGGATCAA GACATCCAGA

301 TTCTTATGCC AGAGACCAGA CGGGACACTG TATGGATCAC TCCACTTTGA CCCTGAGGTT

361 TGCAGCTTCC AGGAGCTGCT TCTGGAAGAT GGATACAACA TTTACCGTTC TGAAGCCCTG

421 GGTCTCCCCC TGCGCCTGTC CCCAGATCCA GCACCCTGGG GGCCAGCCCG CTTCCTGCCC

481 CTGCCTGGTG TGCCCCCCGC ACCGCCGGAG CCCCCCGGGA TCCTGGCTCC CGAACCCCCT

541 GATGTCGGCT CCTCCGACCC TCTGAGTATG GTGGGACTGT TGCAGGGCCG AAGCCCCAGC

601 TATGCATCCT GA
```

Echinops telfairi (lesser hedgehog tenrec) FGF21 gene
coding sequence (SEQ ID NO: 182) (Ensembl accession no.
ENSETET00000010721, which is hereby incorporated by
reference in its entirety)

```
  1 ATGGGTTGCA CCAAATCTGG GTGGAAGTCC CCGGGACTGT GGGTCCCTGT GCTGGCCAGC

61 CTTCTGCTGG GAGGCTGCGG AGCACACCCC ATCCCTGACT CCAGCCCCCT CCTCCAATTC

121 GGGGGCCAAG TCCGGCAGCG ATACCTCTAT ACGGATGACG CCCAGACCAC CGAGGCCCAC

181 CTGGAGATCA GAGCGGATGG CACAGTGGGG GGCGTCGCCC ACCAGAGCCC AGAGAAGTTC

241 CTGAGTCAAT GGCGTGAAAA GCCCCTGAGA TCACTCCATT TCGACCCAGC CGCCTGCAGC

301 TTCCGGGAGA AGCTTCTAGA AGACGGATAC AACTTGTACC ACTCTGAGAC CCACGGCCTC

361 CCCCTCCGCC TCCCACCCCG TGGGGCGAC CCCTCTTCTC AGCCTGGGGC CGCTTCCCA

421 CCGCTGCCGG GCCAGCTCCC ACAACTCCAA GAGACGCCAG GGGTCCTCGC CCCCGAACCC

481 CCCGACGTGG GCTCTTCAGA CCCCCTGAGC ATGGTGGGGC CTTGGCGAGG GCAAAGTCCC

541 AGTTATGCCT CCTGA
```

Macaca mulatta (rhesus monkey) FGF21 gene coding sequence
(SEQ ID NO: 183) (Ensembl accession no. ENSMMUT00000038440,
which is hereby incorporated by reference in its entirety)

```
  1 ATGGACTCGG ACGAGACCGG GTTCGAGCAC TCAGGACTGT GGGTTCCTGT GCTGGCTGGT

61 CTTCTGCTGG GAGCCTGCCA GGCACACCCC ATCCCTGACT CCAGTCCTCT CCTGCAATTC

121 GGGGGCCAAG TCCGGCAACG GTACCTCTAC ACAGATGATG CCCAGCAGAC AGAAGCCCAC

181 CTGGAGATCA GGGAGGATGG GACAGTGGGG GGCGCTGCTC ACCAGAGCCC CGAAAGTGAG

241 TGTGGGCCAG AGCCTGGGTC TGAGGGAGGA GGGGCTGTGG GAGGTGCTGA GGGACCTGGA

301 CTCCTGGGTC TGAGGGAGGC AGGGCTGGGG CCTGGATCCT GGCTCCACTT TGACCCTGAG
```

```
361 GCCTGCAGCT TCCGGGAGCT GCTTCTTGAG AACGGATACA ATGTTTACCA GTCCGAGGCC

421 CACGGCCTCC CACTGCACCT GCCGGGAAAC AAGTCCCCAC ACCGGGACCC TGCATCCCAA

481 GGACCAGCTC GCTTCCTGCC ACTACCAGGC CTGCCCCCCG CACCCCCGGA GCCGCCAGGA

541 ATCCTCGCCC CCCAGCCCCC CGATGTGGGC TCCTCGGACC CTCTGAGCAT GGTGGGACCT

601 TCCCAGGCCC GAAGCCCCAG CTATGCTTCC TGA
```

Microcebus murinus (mouse lemur) FGF21 gene coding sequence
(SEQ ID NO: 184) (Ensembl accession no. ENSMICT00000013258,
which is hereby incorporated by reference in its entirety)
```
  1 ATGGGCTGGG ACGAGGCCGG CGCCGGGTTC GAGCACCCAG GACTGTGGTT TCCCATGCTG

61 GGTGTCCTGC TGCTGGGAGC CTGCCAGGCG TACCCCATCC CTGACTCCAG CCCCCTCCTC

121 CAATTTGGCG GCCAAGTCCG GCAGCGGCAC CTCTACACAG ACGATATCCA GGAGACAGAA

181 GCCCACCTGG AGATCAGGGC GGACGGCACA GTGGTGGGGG CCGCCCGACA GAGCCCTGAG

241 TTGGAGCTGA AAGCCTTAAA GCCAGGGGTC ATTCAAATCT GGGAGTCAA GACCTCCAGG

301 TTCCTGTGCC AGAGGCCAGA CGGGGCCCTG TACGGATCGC TCCACTTTGA CCCCGAGTGC

361 AGCTTCCGGG AGCTGCTTCT TGAGGATGGA TACAACGTCT ACTGTCCCTA CCTCCCGCTG

421 CACCTGTCCC CACGCATCGA ACTGGCCGGA TCACGCTCTG CGCTGCCACT GCCCCCAGCA

481 CCTGAACGCA GGATTTTGGC CCCGGAGCCC CCGGATGGCT CCTCGGACCC TCTGAGCATG

541 GTGGGGCCTT CGCAGGGCCG AAGTCCCAGC TATGCTTCCT GA
```

Ochotona princeps (pika) FGF21 gene coding sequence (SEQ
ID NO: 185) (Ensembl accession no. ENSOPRT00000007373,
which is hereby incorporated by reference in its entirety)
```
  1 AAAGACATGG ACGGGCTCCA GCCTCCGGGG CTGCGGGTTC CTGTGCTGGC TGCCCTGCTT

61 TTGGGAGTTG GCCAGGCACG CCCCATCCCT GATTCTAGCC CTCTCCTCCA ATTCGGGGGC

121 CAGGTCCGGC AGAGGCACCT CTACACGGAT GACGCCCAGG AATCGGAAGT ACACCTGGAG

181 ATCCGGGCAG ACGGCACCGT GGCAGGGACT GCCCGCCGGA GCCCTGAAAG TCTCTTAGAA

241 ATGAAAGCGT TGAAGCCAGG CGTCATTCAG ATCCTGGGGG TCCACACATC CAGGTTCCTG

301 TGCCAGAGAC CAGACGGGAC GCTGTACGGC TCGCTCCACT TCGACCACAA GGCCTGCAGC

361 TTCCGGGAGC AGCTGCTGGA GGATGGGTAC AACGTGTACC ACTCAGAGAC ACACGGCCTC

421 CCGCTGCGCC TGTCTCCAGA CCGAGCCCCC CGGGGCCCAG CCCGCTTCCT GCCACTGCCA

481 GGCCCTCCTC CTGACCTCCT GGTGCCACCC CTGCCACCGG ACGTCCTAGC CCCTGAGCCC

541 CCCGACGTGG ACTCCCCAGA CCCCCTGAGC ATGGTGGGGC CCTTGCAGGG CCAAAGCCCC

601 AGCTACACTT CCTGA
```

Xiphophorus maculatus (platyfish) FGF21 gene coding sequence
(SEQ ID NO: 186) (Ensembl accession no. ENSXMAT00000001579,
which is hereby incorporated by reference in its entirety)
```
  1 TGCCCGTTCC CCTTCCTTTT CTTAATCCTC TCTCTTCCCT TTTTCTCTTC CTCGTTTTAC

61 ATCCCAGAAT CCAACCCAAT CTTTGCCTTC AGGAATCAGC TCAGAGAGGT GCATCTCTAC

121 ACAGAAAATC ACAGACGGGG TTTGTATGTG GAGATACATC TGGATGGGAG AGTGACTGGA

181 AGTGATGCTC AGAGTCCTTA TAGTGTGTTG CAGATAAAGT CTGTTAAACC GGGTCATGTG

241 GTCATAAAGG GACAGACATC GTCCCTGTTC CTCTGCATGG ACGACTCCGG GAATCTAAGA

301 GGACAGACAA CCTATGACGA GGCTGACTGC TCCTTCAGGG AACTGCTGCT GGCCGATGGC

361 TACACCCGTT TCCTGAACTC ACAACATGGC GTTCCTTTAT CACTGGCATC CAGAAACTCT

421 CCAGATCGAC ACTCCGTTCC TTTCACAAGA TTTTTACCTC TCAGGAATAC TTTAACGGTT
```

TABLE 4-continued

```
481 TCAGAAGAAT CAACAAAAAC TCAGAGGGAC TTCAACCTGG ACTCGGACGA CCTTCTCGGG

541 ATGGGA
```

*Gasterosteus aculeatus* (stickleback) FGF21 gene coding
sequence (SEQ ID NO: 187) (Ensembl accession no.
ENSGACT00000010725, which is hereby incorporated by
reference in its entirety)

```
  1 TCTCTCCTCC TCATGGTCCC ACTTCCTTTC TGTTCATCCT TTTATCTCAC TGACTCCAGC

61 CCACTTCTAC CCTTCAATAA TCAAGTCAAA GAGGTGCACC TCTACACAGC AGAGAATCAC

121 AGAAGAGCGA TGTACCTGCA GATCGCTCTG GACGGGAGCG TGTCGGGAAG CGACGCTCGG

181 TCCACTTACA GTGTGCTGCA GCTGAAATCT ATCCAGCCGG CCACGTGGT CATCAGAGGG

241 AAGGCCTCCT CCATGTTCCT CTGCGTGGAC AGCGGGGCC GTTTGAGAGG ACAGGGGCCG

301 TACTCAGAGG CCGACTGCAG CTTCAGGGAG CTGCTGCTGG GGATGGCTA CACCCGGTTC

361 CTGTCCTCGC AGCACGGGTC CCCGCTGTCT CTGGCGTCGA GGCCTTCCCC GGATCCCAAC

421 TCGGTGCCCT TCACTCGATT CCTACCCATC CGGACCGCCC CCGAGGCTGA GAGCGTGATC

481 GAAGAGCCAC CGAGCAATCA GAGATACGTC AACGTGGACT CCGAGGATCT TCTTGGAATG

541 GGCCTGAACA CTGTGGTCAG TCCTCAGTTC TCGGCG
```

*Sarcophilus harrisii* (Tasmanian devil) FGF21 gene coding
sequence (SEQ ID NO: 188) (Ensembl accession no.
ENSSHAT00000006017, which is hereby incorporated by
reference in its entirety) (1-209, excluding 1-2 and
173-209)

```
132           GTGTCTGCC ATGGGCCTGA GGGAGCGAGC TCCCAGGTAC CTGGCCCCGC

181 TGCTGTCCTT GCTCTTGGCC TGCAGGGCCT CGGGTCACCC CCTCCCGGAT CCAGCCCCA

241 TGCTCCTGTT TGGGGGGCAG GTCCGCCTCC GGCACCTCTA CACGGATGTG GGCCAGGAGG

301 CCGAGGCCCA CGTGGAACTG GCGTCCGACG GCACAGTCCG GGCGGCAGCG CGGAGGAGTC

361 CCAACAGTCT CCTGGAGCTG AAGGCTGTGA AGCCGGGCAT CGTCCGAATC CTGGCCGTCC

421 ACAGCTCTCG GTTTCTGTGT ATGAGGCCCA ACGGGGAGCT GTACGGAGCG ATACACTACG

481 ACCCTTCCGC CTGCAACTTT CGGGAGCGCC TGCTGGGGGA CGGCTACAAC GTGTACGAGT

541 CCGAGGCTCA CGGGAGGACC CTCCGCCTGC CCCCCAAGGC CGCACCGGGA CCCGCCGGAC

601 CTTCTCGCTT CCTGCCGCTC CCCGGC
```

*Macropus eugenii* (wallaby) FGF21 gene coding sequence
(SEQ ID NO: 189) (Ensembl accession no. ENSMEUT00000015309,
which is hereby incorporated by reference in its entirety)

```
  1 ACAGAGGAGC CTTCTACTGG GTCCAGGCAC CTGGGACAAT GGGCTCCCGG GCTGCCTGGT

61 CCTCTGCTGT CCTTGCTCCT GGCCTACAGG GGCTGGGGCT CCCCCATCCC TGATTCCAGC

121 CCCATGCTCC TGTTTGGTGG CCAGGTCCGC CTCCGACACC TGTACACAGA TGATGGCCAG

181 GACACGGAGG CCCATGTGGA GCTGGGGCCA GATGGAGTGG TTCGAGCTGT GGCTGAGAGG

241 AGCCCCAACA GTCTTCTGGA ACTGAAGGCG GTGAAGCCTG GAGTCATCCG AATCCTCGCT

301 GTCCAGAGCT CTCGGTTTCT GTGTATGAGG CCCAACGGGG AACTGTATGG AGCGGTACAC

361 TATGACCCTT CTGCCTGCAA CTTTCGGGAA CATCTGCTGG GGATGGTTA TAATGTGTAT

421 GAATCAGAGA CTCACAGAAG GACCCTCCGT CTGTCCCAT CCCTGGGTCA GGCTGGCCCC

481 TCTCGCTTCC TGCCACTTCC AGGCGACTGG CTGCCCGGCC CTGATCCACC TTGGGCACAG

541 GGCCCTGAGC CCCCAGACGT GGGCTCTGCA GACCCCCTGA GCATGGTGGG GGCCGTGCAG

601 GGCCTCAGCC CCAGCTACTC CTCCTGA
```

TABLE 4-continued

*Xenopus tropicalis* (Western clawed frog) FGF21 gene
coding sequence (SEQ ID NO: 190) (Ensembl accession no.
ENSXETT00000009917, which is hereby incorporated by
reference in its entirety) (1-209, excluding 170-209)

```
  1 AGAGGGGGTA GGACCAAAAA AAAGACGTTA CTCAGGAAAT GGCTTTGCCT TTTAGCCATT

61 ATGTTGAGTA GGTCAAGGTT TTCTTTAGCA ATCCTATCC AGAATTCGAA CCCAATCTTA

121 TCCAACGACA ACCAAGTACG GACTCAGTAT TTATACACAG ATAACAATAA CATGCACCTG

181 TATCTTCAGA TCACCCACAA TGGAGTAGTA ACTGGTACCG AAGAAAAGAA TGACTATGGT

241 GTGCTGGAAA TAAAGGCAGT AAAAGCTGGG GTTGTAGTTA TAAAAGGAAT TCGAAGCAAT

301 CTCTACCTAT GCATGGATTC TAGACACCAA TTGTATGCGT CGGCATATGA TAAAGATGAC

361 TGCCATTTCC ATGAAAAGAT CACACCAGAT AATTACAACA TGTATAGCTC AGAGAAGCAT

421 TCAGAATACG TGTCCTTAGC TCCATTAAAA GGAAGCCAGA TGGCTCGTTT TCTACCTATA
```

*Danio rerio* (zebrafish) FGF21 gene coding sequence (SEQ
ID NO: 191) (Ensembl accession no. ENSDART00000103511,
which is hereby incorporated by reference in its entirety)

```
 30                         A TGCTTCTTGC CTGCTTTTTT ATATTTTTG

61 CTCTTTTTCC TCATCTTCGG TGGTGTATGT ATGTTCCTGC ACAGAACGTG CTTCTGCAGT

121 TTGGCACACA AGTCAGGGAA CGCCTGCTTT ACACAGATGG GTTGTTTCTT GAAATGAATC

181 CAGATGGCTC CGTCAAAGGC TCTCCTGAAA AGAATCTAAA TTGTGTGCTG GAGCTGCGTT

241 CAGTCAAAGC GGGTGAAACC GTCATCCAGA GTGCAGCTAC ATCTCTCTAC CTCTGCGTCG

301 ATGATCAAGA CAAGCTGAAA GGACAGCATC ATTACTCTGC ACTAGACTGC ACCTTTCAGG

361 AATTGCTACT GGATGGATAT TCGTTTTTCC TTTCTCCACA CACTAATCTT CCCGTATCGC

421 TCCTCTCGAA ACGTCAGAAA CACGGCAATC CTCTTTCTCG CTTCCTCCCT GTTAGCAGAG

481 CAGAGGACAG CCGGACACAG GAGGTGAAAC AGTATATTCA GGATATAAAC CTGGACTCTG

541 ACGACCCACT AGGAATGGGA CATCGGTCAC ACTTACAGAC CGTCTTCAGT CCCAGTCTGC

572 ATACTAAAAA ATGA
```

*Bos grunniens mutus* (yak) FGF21 gene coding sequence
(SEQ ID NO: 192) (generated using SMS Reverse Translate
tool on the ExPASy Bioinformatics Resource website
(www.expasy.org))

```
  1 ATGGGCTGGG ATGAAGCGAA ATTTAAACAT CTGGGCCTGT GGGTGCCGGT GCTGGCGGTG

61 CTGCTGCTGG GCACCTGCCG CGCGCATCCG ATTCCGGATA GCAGCCCGCT GCTGCAGTTT

121 GGCGGCCAGG TGCGCCAGCG CTATCTGTAT ACCGATGATG CGCAGGAAAC CGAAGCGCAT

181 CTGGAAATTC GCGCGGATGG CACCGTGGTG GGCGCGGCGC GCCAGAGCCC GGAAAGCCTG

241 CTGGAACTGA AAGCGCTGAA ACCGGGCGTG ATTCAGATTC TGGGCGTGAA AACCAGCCGC

301 TTTCTGTGCC AGGGCCCGGA TGGCAAACTG TATGGCAGCC TGCATTTTGA TCCGAAAGCG

361 TGCAGCTTTC GCGAACTGCT GCTGGAAGAT GGCTATAACG TGTATCAGAG CGAAACCCTG

421 GGCCTGCCGC TGCGCCTGCC GCCGCAGCGC AGCAGCAACC GCGATCCGGC GCCGCGCGGC

481 CCGGCGCGCT TTCTGCCGCT GCCGGGCCTG CCGGCGGAAC CGCCGGATCC GCCGGGCATT

541 CTGGCGCCGG AACCGCCGGA TGTGGGCAGC AGCGATCCGC TGAGCATGGT GGGCCCGAGC

601 TATGGCCGCA GCCCGAGCTA TACCAGCTAA
```

*Saimiri boliviensis boliviensis* (Bolivian squirrel monkey)
FGF21 gene coding sequence (SEQ ID NO: 193) (GenBank
accession no. XM_003940326, which is hereby incorporated
by reference in its entirety)

```
163                                        atgggctc ggaggaggtc

181 GCGTTGGAGC GCCCTGCACT GTGGGTCTCT GTGTTGGCTG GTCTCCTGCT GGGAACCTGC

241 CAGGCATACC CCATCCCTGA CTCTAGTCCC CTCCTGCAAT TTGGAGGCCA AGTCCGGCAG
```

TABLE 4-continued

```
301 CGGTACCTCT ACACAGATGA CGCTCAGCAG ACAGAAGCCC ACCTGGAGAT CAGGGAAGAT

361 GGCACGGTGG CGGGGGCTGC CCACCAGAGC CCCGAAAGTC TCTTGCAGCT GAAAGCCTTA

421 AAGCCAGGGG TTATTCAAAT CTTGGGAGTC AAGACCTCCA GGTTCCTGTG CCAGAGGCCG

481 GACGGGGCCC TGTACGGATC GCTCTACTTT GACCCCGAGG CCTGCAGCTT CCGGGAGCTG

541 CTTCTTGAGG ACGGATACAA TGTGTACCAG TCCGTGGCCC ACAGCCTCCC GCTGCACCTG

601 CCAGGGGGCA GGTCCCCACC CTGGGACCCT GCACCTCGAG GACCAGCTCG CTTCCTGCCG

661 CTACCAGGCC TGCCCCCCGA ACCCCCCGAG GCGCCAGGAA TCCTGGCCCC GAGCCCCCC

721 GATGTGGGCT CCTCAGACCC TCTGAGCATG GTGGGGCCTT CCCAAGGCCA AAGCCCCAGC

781 TACACTTCCT GA
```

*Callithrix jacchus* (white-tufted-ear marmoset) FGF21 gene
coding sequence (SEQ ID NO: 194) (GenBank accession no.
XM_003735621, which is hereby incorporated by reference
in its entirety)

```
  1 ATGGGCTCGG AGGAGGTCGG GTTGGAGCAC CCTGCACTGT GGGTTTCTGT GCTGGCTGGT

61 CTCCTGCTGG GAACCTGCCA GGCGCACCCC ATCCCTGACT CCAGTCCCCT CCTGCAATTT

121 GGAGGCCAAG TCCGGCAGCG GTACCTCTAC ACAGATGACG CCCAGCAGAA AGAAGCCCAC

181 CTGGAGATCN AGGAAGATGG CACAGTGGCC GGGGCTGCCA CCAAAGTCCC GAAAGTGAGT

241 CTCTTGCAGC TGAAAGCCTT AAAGCCAGGG GTTATTCAAA TCTTGGGAGT CAAGACATCC

301 AGGTTCCTGT GCCAGAGGCC AGACGGGGCG CTGTATGGAT CGCTCCACTT TGACCCCGAG

361 GCCTGCAGCT TCCGGGAGCT GCTTCTTGAG GACGGATACA ATGTGTACCA GTCTGTGGCC

421 CACGGCCTCC CGCTGCACCT GCCAGAGAGC AGGTCACCAC CCCGGGACCC TGCACCCCGA

481 GGACCAGCTC GCTTCCTGCC ACTACCAGGC CTGCCCCCTG AACCCCCAGA GCCGCCAGGA

541 ATCCTGGCCC CTGAGCCCCC CGACGTGGGC TCCTCAGACC CTCTGAGCAT GGTGGGGCCT

601 TCCCAAGGCC AAAGCCCCAG CTACGCTTCC TGA
```

*Tupaia chinensis* (Chinese tree shrew) FGF21 gene coding
sequence (SEQ ID NO: 195) (generated using SMS Reverse
Translate tool on the ExPASy Bioinformatics Resource
website (www.expasy.org))

```
  1 ATGGCTGGG ATAAAGCGCG CTTTGAACAT CTGGGCGCGT GGGCGCCGGT GCTGGCGGTG

61 CTGCTGCTGG GCGCGTGCCA GGCGTATCCG ATTCCGGATA GCAGCCCGCT GCTGCAGTTT

121 GGCGGCCAGG TGCGCCAGCG CTATCTGTAT ACCGATGATA CCCAGGATAC CGAAGCGCAT

181 CTGGAAATTC GCGCGGATGG CACCGTGGTG GGCGCGGCGC ATCAGAGCCC GGAAAGCCTG

241 CTGGAACTGA AAGCGCTGAA ACCGGGCGTG ATTCAGATTC TGGGCGTGAA AACCAGCCGC

301 TTTCTGTGCC AGCGCCCGGA TGGCGCGCTG TATGGCAGCC TGCATTTTGA TCCGGAAGCG

361 TGCAGCTTTC GCGAACTGCT GCTGGAAGAT GGCTATAACA TTTATCAGAG CGAAGCGCGC

421 GGCCTGCCGC TGCGCCTGCC GCCGCATGAT AGCCCGCATC GCGATCGCAC CCGCAGGGC

481 CCGGCGCGCT TTCTGCCGCT GCCGGGCCTG CCGCTGGTGC CGCCGGAACT GCCGGGCGTG

541 CTGGCGCTGG AACCGCCGGA TGTGGGCAGC AGCGATCCGC TGAGCATGAT GGGCCCGAGC

601 CAGGGCCAGA GCCCGAGCTA TGCGAGCTAA
```

*Papio anubis* (olive baboon) FGF21 gene coding sequence
(SEQ ID NO: 196) (GenBank accession no. XM_003915851,
which is hereby incorporated by reference in its entirety)

```
  1 ATGGACTCGG ACGAGACCGG GTTCGAGCAC TCAGGACTGT GGGTTCCTGT GCTGGCTGGT

61 CTTCTGCTGG GAGCCTGCCA GGCACACCCC ATCCCTGACT CCAGTCCTCT CCTGCAATTC

121 GGGGGCCAAG TCCGGCAACG GTACCTCTAC ACAGATGATG CCCAGCAGAC AGAAGCCCAC
```

TABLE 4-continued

```
181 CTGGAGATCA GGGAGGATGG GACAGTGGGG GGCGCTGCTC ACCAGAGCCC CGAAAGTAAG

241 TGTGGGCCAG AGCCTGGGTC TGAGGGAGGA GGGGCTCTCC ACTTTGACCC TGAGGCCTGC

301 AGCTTCCGCG AGCTGCTTCT TGAGAACGGA TACAATGTTT ACCAGTCCGA GGCCCACGGC

361 CTCCCACTGC ACCTGCCGGG AAACAAGTCC CCACACCGGG ACCCTGCATC CCGAGGACCA

421 GCTCGCTTCC TGCCACTACC AGGCCTGCCC CCCGCACCCC CAGAGCCACC AGGAATCCTC

481 GCCCCCCAGC CCCCCGATGT GGGCTCCTCG ACCCTCTGA GCATGGTGGG ACCTTCCCAG

541 GCCCGAAGCC CTAGCTACGC TTCCTGA
```

*Pteropus alecto* (black flying fox) FGF21 gene coding sequence (SEQ ID NO: 197) (generated using SMS Reverse Translate tool on the ExPASy Bioinformatics Resource website (www.expasy.org))

```
  1 ATGGGCTGGG GCAAAGCGCG CCTGCAGCAT CCGGGCCTGT GGGCCCCGGT GCTGGCGGTG

61 CTGCTGGGCG CGTGCCAGGC GCATCCGATT CTGGATAGCA GCCCGCTGTT TCAGTTTGGC

121 AGCCAGGTGC GCCGCCGCTA TCTGTATACC GATGATGCGC AGGATACCGA AGCGCATCTG

181 GAAATTCGCG CGGATGGCAC CGTGGCGGGC GCGGCGCGCC GCAGCCCGGA AAGCCTGCTG

241 GAACTGAAAG CGCTGAAACC GGGCGTGATT CAGGTGCTGG CGTGAAAAC CAGCCGCTTT

301 CTGTGCCAGC GCCCGGATGG CACCCTGTAT GGCAGCCTGC ATTTTGATCC GGCGGCGTGC

361 AGCTTTCGCG AACTGCTGCT GAAAGATGGC TATAACGTGT ATCAGAGCGA AGCGCTGGCG

421 CGCCCGCTGC GCCTGCCGCC GTATAGCAGC CCGAGCAGCG ATCCGGCGCG CCGCGGCCCG

481 GCGCGCTTTC TGCCGCTGCC GGGCCCGCCG CCGGAACCGC CGCAGCCGCC GGGCCGCCTG

541 GCGCCGGAAC CGCCGGATGT GGGCAGCAGC GATCCGCTGA GCATGGTGTG GCCGAGCCGC

601 GGCCGCAGCC CGAGCTATAC CAGCTAA
```

*Heterocephalus glaber* (naked mole-rat) FGF21 gene coding sequence (SEQ ID NO: 198) (generated using SMS Reverse Translate tool on the ExPASy Bioinformatics Resource website (www.expasy.org))

```
  1 ATGGATTGGG CGCGCGCGGA AAGCGAACGC CCGGGCCTGT GGGTGCCGGC GGTGCTGGCG

61 GTGCTGCTGC TGGGCGCGTG CCAGGCGCAT CCGATTCCGG ATAGCAGCCC GCTGCTGCAG

121 TTTGGCGGCC AGGTGCGCCA GCGCCATCTG TATACCGATG ATGCGCAGGA TACCGAAGTG

181 CATCTGGAAA TTCGCGCGGA TGGCAGCGTG GGCGGCGCGG CGCATCGCAG CCCGGAAAGC

241 CTGCTGGAAC TGAAAGCGCT GAAACCGGGC GTGATTCAGA TTCTGGGCGT GCGCACCAGC

301 CGCTTTCTGT GCCAGCGCCC GGATGGCACC CTGTATGGCA GCCTGCATTT TGATCCGGAA

361 GCGTGCAGCT TTCGCGAACT GCTGCTGGCG GATGGCTATA ACATTTATCA GAGCGAAGCG

421 TATGGCCTGC CGCTGCGCAT GCTGCCGAGC GATAGCGCGA CCGCGATCC GGTGCCGCCG

481 GGCCCGGCGC GCTTTCTGCC GCTGCCGGGC CTGCATCCGC CGCCGCTGGA ACCGCCGGGC

541 ATGCTGCCGC CGGAACCGCC GGATGTGGGC AGCAGCGATC CGCTGAGCAT GGTGGGCCCG

601 CTGCAGGGCC GCAGCCCGAG CTATGCGTTT TAA
```

*Cricetulus griseus* (Chinese hamster) FGF21 gene coding sequence (SEQ ID NO: 199) (GenBank accession no. XM_003508678, which is hereby incorporated by reference in its entirety)

```
  1 ATGGACTGGA TGAAATCTGG AGTTGGGGTC CCGGGACTGT GGGTCCCTCT GCTGCCTATC

61 TTCCTGCTGG GGGTCTCCCA GGCACACCCC ATCCCTGACT CCAGCCCCCT CCTCCAGTTT

121 GGGGGTCAAG TCCGGCACAG GCACCTCTAC ACAGATGACA ACCAGGAAAC TGAAGTCCAC

181 CTGGAGATTA GCAGGATGG CACGGTGATA GGGACCACAC ACCGCAGCCC AGAAAGTCTC

241 CTGGAGCTCA AAGCCTTGAA GCCAGAGGTC ATCCCAGTGC TGGGTGTCAA GGCCTCCAGG
```

TABLE 4-continued

```
301 TTTCTTTGCC AACAACCAGA CGGAACCCTG TATGGATCGC CTCACTTTGA TCCTGAGGCC

361 TGCAGTTTCA GGGAGCTCTT GCTTGAGGAT GGATACAATG TGTACCAATC TGAAGTCCAT

421 GGCCTGCCCC TGCGCCTGCC CCAGAGGGAC TCTCCAAACC AGGCCCCAGC ATCCTGGGGA

481 CCTGTGCCCC CCTGCCAGT GCCAGGACTG CTCCACCAGC CCCAGGAGCT ACCAGGGTTC

541 CTGGCCCCAG AACCTCCAGA TGTGGGCTCC TCTGACCCAC TGAGCATGGT GGGACCTTTG

601 CAGGGCCGAA GCCCCAGCTA TGCTTCCTGA
```

Ovis aries (sheep) FGF21 gene coding sequence (SEQ ID NO: 200) (GenBank accession no. XM_004015796, which is hereby incorporated by reference in its entirety)

```
  1 ATGGGCTGGG ACGAGGCCAA GTTCAAGCAC TTGGGACTGT GGGTCCCTGT GCTGGCTGTC

61 CTCCTGCTAG GAACCTGCCG GGCGCATCCA ATTCCAGACT CCAGCCCCCT CCTCCAGTTT

121 GGGGGCCAAG TCCGCCAGCG GTACCTCTAC ACGGATGATG CCCAGGAGAC AGAGGCCCAC

181 CTGGAGATCA GGGCCGATGG CACAGTGGTG GGGGCGGCCC GCCAGAGTCC CGAAAGTCTC

241 TTGGAGCTGA AAGCCCTGAA GCCAGGAGTC ATTCAGATCT TGGGAGTTAA ACATCCAGG

301 TTCCTGTGCC AGGGGCCAGA TGGGAAGCTG TATGGATCGC TGCACTTTGA CCCCAAAGCC

361 TGCAGCTTCC GGGAGCTGCT TCTTGAAGAT GGGTACAATG TCTACCAGTC GGAGACCCTG

421 GGCCTTCCAC TCCGCCTGCC GCCGCAGCGC TCATCCAACC GGGACCCGGC CCCGCGGGGA

481 CCTCCGAAGC CCCAGCTACA CTTCTTGAAG ACGTCCGCTG TGCAGTACTG GCCACGTTAT

541 GAGAAGGTCC CAGCTTTTCT GCACCCCTTC CCCGGCTGA
```

Pan paniscus (pygmy chimpanzee) FGF21 gene coding sequence (SEQ ID NO: 201) (GenBank accession no. XM_003814115, which is hereby incorporated by reference in its entirety) (1-209, excluding 117-194 and 202-209)

```
573                                         ATGGACTC GGACGAGACC GGGTTCGAGC

601 ACTCAGGACT GTGGGTTTCT GTGCTGGCTG GTCTTCTGCT GGGAGCCTGC CAGGCACACC

661 CCATCCCTGA CTCCAGTCCT CTCCTGCAAT TCGGGGCCA AGTCCGGCAG CGGTACCTCT

721 ACACAGATGA TGCCCAGCAG ACAGAAGCCC ACCTGGAGAT CAGGGAGGAT GGGACGGTGG

781 GGGGCGCTGC TGACCAGAGC CCCGAAAGTC TCCTGCAGCT GAAAGCCTTG AAGCCGGGAG

841 TTATTCAAAT CTTGGGAGTC AAGACATCCA GGTTCCTGTG CCAGAGGCCA GATGGGGCCC

901 TGTATGGATC GGTGAGTTTC ---------- ---------- ---------- ----------

---------- ---------- ---------- ---------- ---------- ----------

921 ---------- ----CAG--- ---------- ---------- ---------- ----------

924 ---------- -------GAC CCTCCT---- --------CA CCACCCACCA ---------T

946 GCTCC----- ----TCCTAT ATGTCGCCCTCACAG------ ---CCTGGG
```

Macaca fascicularis (crab-eating macaque) FGF21 gene coding sequence (SEQ ID NO: 202) (generated using SMS Reverse Translate tool on the ExPASy Bioinformatics Resource website (www.expasy.org)) (1-209, excluding 117-209)

```
  1 ATGGATAGCG ATGAAACCGG CTTTGAACAT AGCGGCCTGT GGGTGCCGGT GCTGGCGGGC

61 CTGCTGCTGG GCGCGTGCCA GGCGCATCCG ATTCCGGATA GCAGCCCGCT GCTGCAGTTT

121 GGCGGCCAGG TGCGCCAGCG CTATCTGTAT ACCGATGATG CGCAGCAGAC CGAAGCGCAT

181 CTGGAAATTC GCGAAGATGG CACCGTGGGC GGCGCGGCGC ATCAGAGCCC GGAAAGCCTG

241 CTGCAGCTGA AAGCGCTGAA ACCGGGCGTG ATTCAGATTC TGGGCGTGAA AACCAGCCGC

301 TTTCTGTGCC AGAAACCGGA TGGCGCGCTG TATGGCAGCG TGAGCTTTTA A
```

TABLE 4-continued

*Mesocricetus auratus* (golden hamster) FGF21 gene coding sequence (SEQ ID NO: 203) (GenBank accession no. EU497769, which is hereby incorporated by reference in its entirety) (1-209, excluding 1-89 and 194-209)

```
  1 GGTCATCCAA ATCCTGGGTG TCAAGGCTGC TAGGTTTCCT TGCCAGCAAC CAGACGGAAG

61 CCTGTACGGA TCGCCTCACT TCGATCCCGA GGCCTGCAGT TTCCGGGAGC TCCTGCTTGA

121 GGATGGATAC AATGTGTACC AGTCGGAAGC CCACGGCCTG CCCCTGCGCC TGCCCCAGAG

181 GGACGCTCCG AGCCAGCCCC CAGCATCCTG GGGACCGGTG CGCTTCCTGC CAGTGCCCGG

241 ACTGTTCCAG CCGCCCCACG ACCTCCCAGG GCGCCCGGCC CCAGAGCCTC CGGACGTGGG

301 CTCCTCCGAC CCAC
```

*Nile tilapia* FGF21 gene coding sequence (SEQ ID NO: 204) (GenBank accession no. XM_003438468, which is hereby incorporated by reference in its entirety) (1-209, excluding 1-58)

```
  1 ATGTATTTGC AGATGAACAT GGATGGGAGA GTCACAGGAA GTGATGCTCA GACACCTTAC

61 AGTTTGATGC AGCTGAAATC AGTTAAACCA GGCCATGTAA TCATTAAAGG ACCATCATCA

121 TCTCTTTTTC TCTGTGTGGA CAGCGAAGGC AATCTGAGAG GCAGAGTCA CTACTCAGAA

181 ACCAGCTGCA CCTTCAGAGA AATGCTGCTG GCTGACGGAT ACACCCGTTT CATTTCCTCA

241 CAATATGGAT TTCCCATGTC ACTGGCATCA AGACATTCCC CAGATCGACA CGCGCTTCCC

301 TTTACGCGGT TCCTACCACT GAGGAATAAC TTGAAAACGG ATAGCGTATC AGAGCAGCTG

361 CCAAACAATC AGAGACTCTT CAACGTGGAC TCTGATGACC TTCTTGGAAT GGGTCTAAAT

421 TCTATGGGCA GTCCTCAGTT TTCTATGGAC AAATAA
```

In one embodiment, the chimeric protein of the present invention comprises the amino acid sequence of SEQ ID NO: 205, SEQ ID NO: 206, SEQ ID NO: 207, SEQ ID NO: 208, SEQ ID NO: 209, or SEQ ID NO: 210, as shown in Table 5.

TABLE 5

Description of Chimeric Protein Sequence

| | |
|---|---|
| Amino acid sequence of a FGF21/19 chimera composed of residues H29 to V197 of human FGF21 and residues T204 to K216 of human FGF19 (bold) | SEQ ID NO: 205<br>HP IPDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLPGL PPALPEPPGI LAPQPPDVGS SDPLSMVTGL EAVRSPSFEK |
| Amino acid sequence of a FGF21/19 chimera composed of residues H29 to S190 of human FGF21 and residues M197 to K216 of human FGF19 (bold) | SEQ ID NO: 206<br>HP IPDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLPGL PPALPEPPGI LAPQPPDVGS MDPFGLVTGL EAVRSPSFEK |
| Amino acid sequence of a FGF21/19 chimera composed of the β-trefoil core domain of human FGF21 (residues H29 to L167) and the C-terminal tail of human FGF19 (residues L169 to K216) (bold) | SEQ ID NO: 207<br>HP IPDSSPLLQF GGQVRQRYLY TDDAQQTEAH LEIREDGTVG GAADQSPESL LQLKALKPGV IQILGVKTSR FLCQRPDGAL YGSLHFDPEA CSFRELLLED GYNVYQSEAH GLPLHLPGNK SPHRDPAPRG PARFLPLLPM VPEEPEDLRG HLESDMFSSP LETDSMDPFG LVTGLEAVRS PSFEK |
| Amino acid sequence of a FGF21/19 chimera composed of residues H29 to V197 of human FGF21 harboring Q104M mutation and residues T204 to | SEQ ID NO: 208<br>HP IPDSSPLLQF GGQVRQRYLY TDDAQQTEAH LEIREDGTVG GAADQSPESL LQLKALKPGV IQILGVKTSR FLCMRPDGAL YGSLHFDPEA CSFRELLLED GYNVYQSEAH GLPLHLPGNK |

TABLE 5-continued

Description of Chimeric Protein Sequence

| | |
|---|---|
| K216 of human FGF19 (bold) | SPHRDPAPRG PARFLPLPGL PPALPEPPGI<br>LAPQPPDVGS SDPLSMVTGL EAVRSPSFEK |
| Amino acid sequence of a FGF21/19 chimera composed of residues H29 to S190 of human FGF21 harboring Q104M mutation and residues M197 to K216 of human FGF19 (bold) | SEQ ID NO: 209<br>HP IPDSSPLLQF GGQVRQRYLY TDDAQQTEAH<br>LEIREDGTVG GAADQSPESL LQLKALKPGV<br>IQILGVKTSR FLCMRPDGAL YGSLHFDPEA<br>CSFRELLLED GYNVYQSEAH GLPLHLPGNK<br>SPHRDPAPRG PARFLPLPGL PPALPEPPGI<br>LAPQPPDVGS MDPFGLVTGL EAVRSPSFEK |
| Amino acid sequence of a FGF21/19 chimera composed of the β-trefoil core domain of human FGF21 (residues H29 to L167) harboring Q104M mutation and the C-terminal tail of human FGF19 (residues L169 to K216) (bold) | SEQ ID NO: 210<br>HP IPDSSPLLQF GGQVRQRYLY TDDAQQTEAH<br>LEIREDGTVG GAADQSPESL LQLKALKPGV<br>IQILGVKTSR FLCMRPDGAL YGSLHFDPEA<br>CSFRELLLED GYNVYQSEAH GLPLHLPGNK<br>SPHRDPAPRG PARFLPLLPM VPEEPEDLRG<br>HLESDMFSSP LETDSMDPFG LVTGLEAVRS<br>PSFEK |

Figure 11:
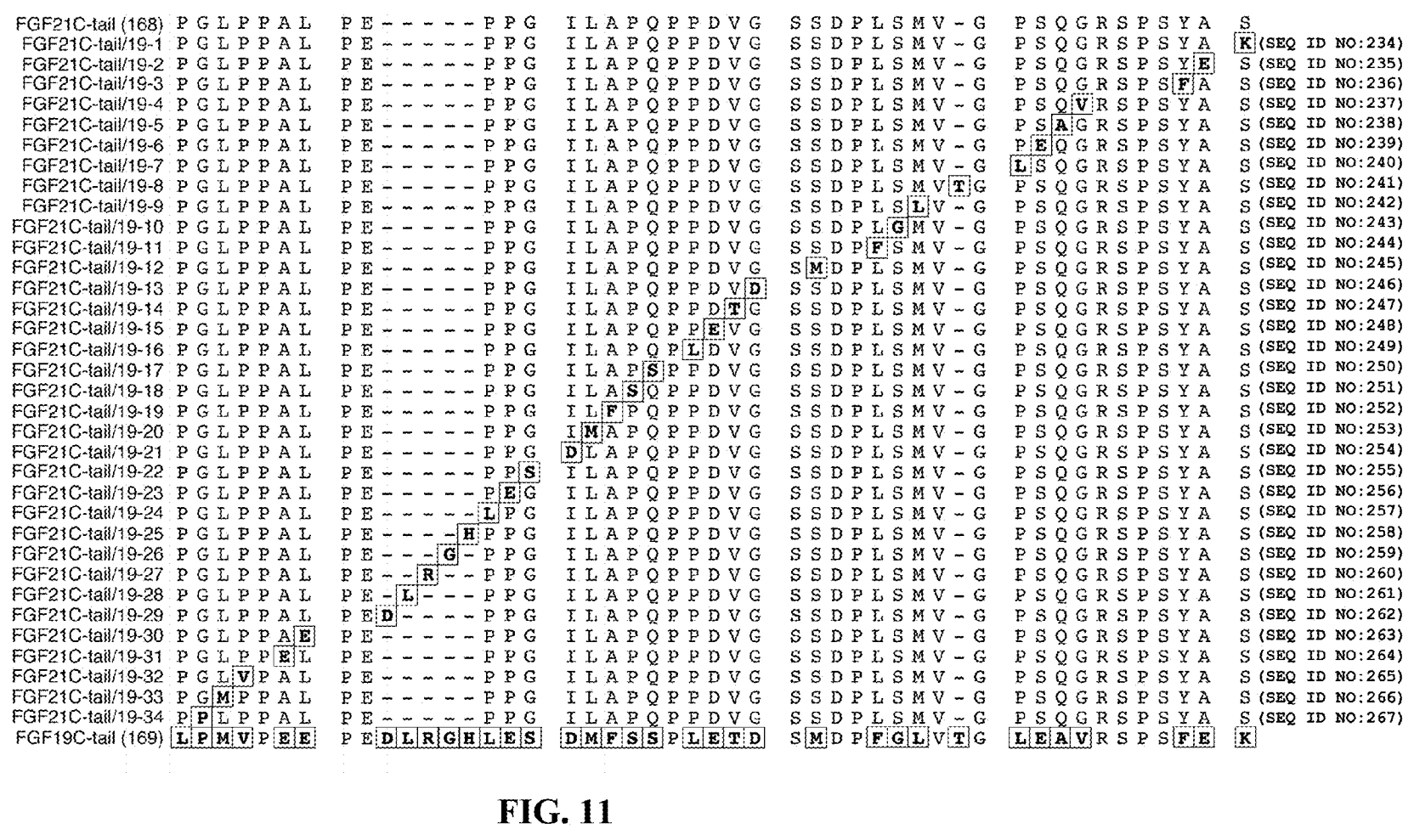
Figure 12:
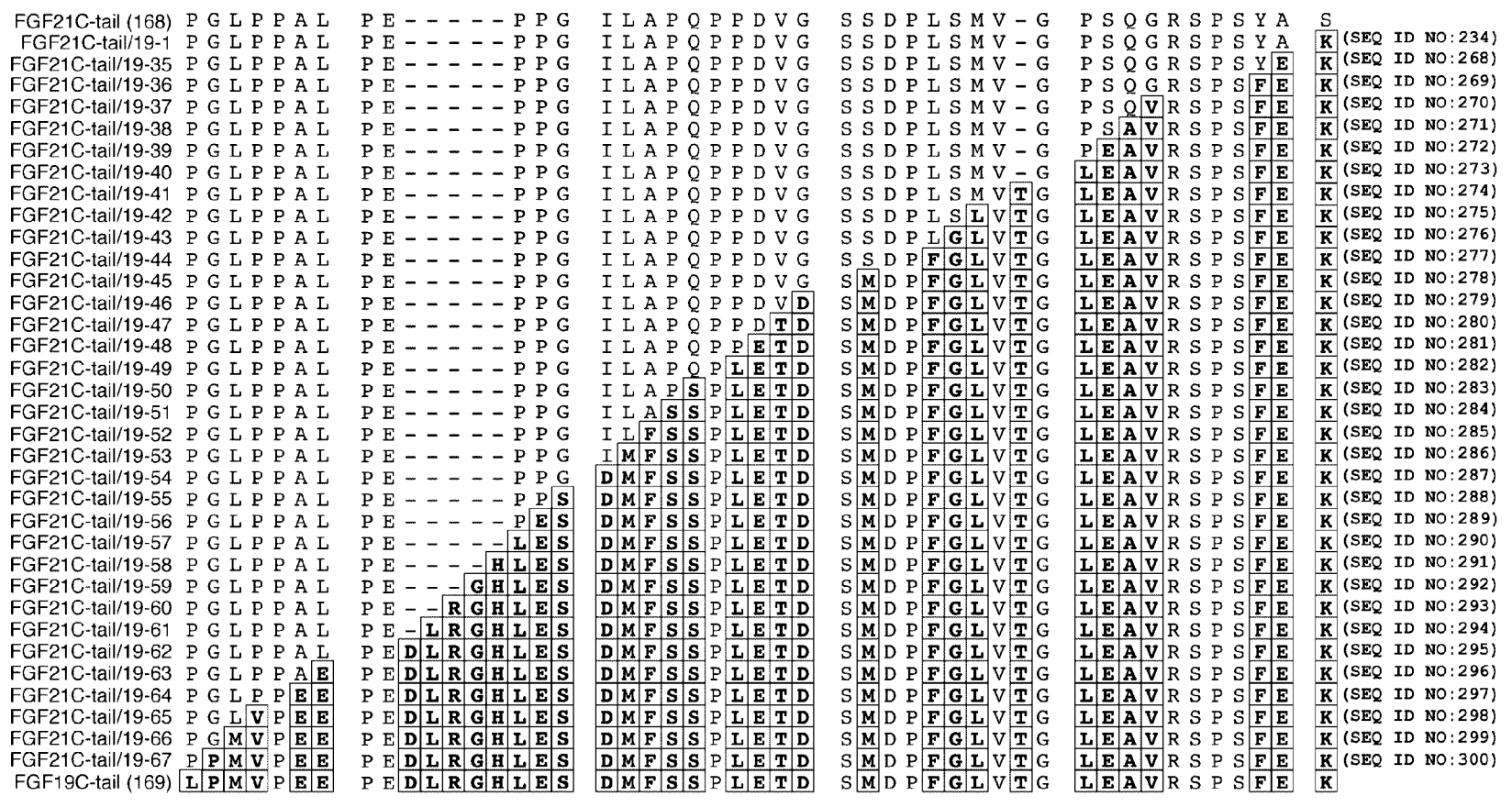

In one embodiment of the present invention, the chimeric protein may include one or more substitutions for or additions of amino acids from another FGF molecule. In one embodiment, the C-terminal portion from FGF19 includes a modification that includes a substitution for or addition of amino acid residues from an FGF21 molecule. Exemplary substitutions and additions of such residues are shown in FIGS. 11, 12, and 13.

In one embodiment, the C-terminal portion from FGF19 comprises a modification that includes a substitution of amino acid residues from an FGF21 molecule. In one embodiment, the modification comprises a substitution for or addition of amino acid residues 168 to 209 of SEQ ID NO: 100. In one embodiment, the modification is a substitution of amino acid residues from SEQ ID NO: 100 for corresponding amino acid residues of SEQ ID NO: 1. As shown in FIGS. 5A, 8B, 11, 12, and 13, the corresponding residues of FGF molecules may be identified by sequence analysis and/or structural analysis. In one embodiment, the modification includes a substitution of a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or 42 amino acid residues 168 to 209 of SEQ ID NO: 100 for the corresponding contiguous stretch of amino acid residues of SEQ ID NO: 1. In one embodiment, amino acid residues 169 to 173, 169 to 196, or 169 to 203 of SEQ ID NO: 1 are substituted with the corresponding amino acid residues selected from the sequence comprising amino acid residues 168 to 209 of SEQ ID NO: 100.

In one embodiment, the modification includes a substitution of one or more individual amino acid residues from residues 168 to 209 of SEQ ID NO: 100 for the corresponding amino acid residues of SEQ ID NO: 1. In one embodiment, the C-terminal portion includes substitutions of one or more of amino acid residues 169, 170, 171, 172, 174, 175, 183, 184, 185, 186, 187, 188, 189, 190, 192, 193, 194, 195, 197, 200, 201, 202, 206, 207, 208, 209, 214, 215, or 216 of SEQ ID NO: 1 for the corresponding amino acid residues of SEQ ID NO: 100.

In one embodiment of the present invention, the C-terminal portion from FGF19 includes a modification that includes a deletion of amino acid residues that are absent in the corresponding C-terminal portion from FGF21. As shown in FIGS. 5A, 8B, 11, 12, and 13, FGF19 residues that are absent in the corresponding C-terminal portion of FGF21 may be identified by sequence analysis and/or structural analysis. In one embodiment, the modification comprises a deletion of amino acid residues selected from residues 204 to 216, 197 to 216, 174 to 216, or 169 to 216 of SEQ ID NO: 1. In one embodiment, the modification comprises a deletion corresponding to amino acid residue 204 of SEQ ID NO: 1. In one embodiment, the modification includes a deletion of amino acid residues 178, 179, 180, 181, and/or 182 of SEQ ID NO: 1 individually or in combination.

Chimeric proteins according to the present invention may be isolated proteins or polypeptides. The isolated chimeric proteins of the present invention may be prepared for use in the above described methods of the present invention using standard methods of synthesis known in the art, including solid phase peptide synthesis (Fmoc or Boc strategies) or solution phase peptide synthesis. Alternatively, peptides of the present invention may be prepared using recombinant expression systems.

Accordingly, another aspect of the present invention relates to an isolated nucleic acid molecule encoding a chimeric protein according to the present invention. In one embodiment, the nucleic acid molecule comprises the nucleotide sequence of SEQ ID NO: 211, SEQ ID NO: 212, SEQ ID NO: 213, SEQ ID NO: 214, SEQ ID NO: 215, or SEQ ID NO: 216 (as shown in Table 6). Another aspect of the present invention relates to a nucleic acid construct comprising a nucleic acid molecule encoding a chimeric protein according to the present invention, a 5' DNA promoter sequence, and a 3' terminator sequence. The nucleic acid molecule, the promoter, and the terminator are operatively coupled to permit transcription of the nucleic acid molecule.

TABLE 6

Description of Chimeric Protein Sequence

| | |
|---|---|
| Nucleotide sequence of a FGF21/19 chimera composed of | SEQ ID NO: 211<br>caccccc atccctgact ccagtcctct |

TABLE 6-continued

| Description of Chimeric Protein Sequence | | |
|---|---|---|
| residues H29 to V197 of human FGF21 and residues T204 to K216 of human FGF19 (bold) | | cctgcaattc gggggccaag tccggcagcg gtacctctac acagatgatg cccagcagac agaagcccac ctggagatca ggggaggatgg gacggtgggg ggcgctgctg accagagccc cgaaagtctc ctgcagctga aagccttgaa gccgggagtt attcaaatct tgggagtcaa gacatccagg ttcctgtgcc agcggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact accaggcctg ccccccgcac tcccggagcc acccggaatc ctggccccccc agccccccga tgtgggctcc tcggaccctc tgagcatggt gggactggag gccgtgagga gtcccagctt tgagaagtaa |
| Nucleotide sequence of a FGF21/19 chimera composed of residues H29 to S190 of human FGF21 and residues M197 to K216 of human FGF19 (bold) | SEQ ID NO: 212 | cacccc atccctgact ccagtcctct cctgcaattc gggggccaag tccggcagcg gtacctctac acagatgatg cccagcagac agaagcccac ctggagatca ggggaggatgg gacggtgggg ggcgctgctg accagagccc cgaaagtctc ctgcagctga aagccttgaa gccgggagtt attcaaatct tgggagtcaa gacatccagg ttcctgtgcc agcggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact accaggcctg ccccccgcac tcccggagcc acccggaatc ctggccccccc agccccccga tgtgggctcc atggacccat ttgggcttgt caccggactg gaggccgtga ggagtcccag ctttgagaag taa |
| Nucleotide sequence of a FGF21/19 chimera composed of the β-trefoil core domain of human FGF21 (residues H29 to L167) and the C-terminal tail of human FGF19 (residues L169 to K216) (bold) | SEQ ID NO: 213 | cacccc atccctgact ccagtcctct cctgcaattc gggggccaag tccggcagcg gtacctctac acagatgatg cccagcagac agaagcccac ctggagatca ggggaggatgg gacggtgggg ggcgctgctg accagagccc cgaaagtctc ctgcagctga aagccttgaa gccgggagtt attcaaatct tgggagtcaa gacatccagg ttcctgtgcc agcggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact actgcccatg gtcccagagg agcctgagga cctcaggggc cacttggaat ctgacatgtt ctcttcgccc ctggagaccg acagcatgga cccatttggg cttgtcaccg gactggaggc cgtgaggagt cccagctttg agaagtaa |
| Nucleotide sequence of a FGF21/19 chimera composed of residues H29 to V197 of human FGF21 harboring Q104M mutation and residues T204 to K216 of human FGF19 (bold) | SEQ ID NO: 214 | cacccc atccctgact ccagtcctct cctgcaattc gggggccaag tccggcagcg gtacctctac acagatgatg cccagcagac agaagcccac ctggagatca ggggaggatgg gacggtgggg ggcgctgctg accagagccc cgaaagtctc ctgcagctga aagccttgaa gccgggagtt attcaaatct tgggagtcaa gacatccagg ttcctgtgcc aatggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact accaggcctg ccccccgcac tcccggagcc acccggaatc ctggccccccc agccccccga |

TABLE 6-continued

Description of Chimeric Protein Sequence

| | |
|---|---|
| | tgtgggctcc tcggaccctc tgagcatggt gggactggag gccgtgagga gtcccagctt tgagaagtaa |
| Nucleotide sequence of a FGF21/19 chimera composed of residues H29 to S190 of human FGF21 harboring Q104M mutation and residues M197 to K216 of human FGF19 (bold) | SEQ ID NO: 215<br>caccccc atccctgact ccagtcctct cctgcaattc gggggccaag tccggcagcg gtacctctac acagatgatg cccagcagac agaagcccac ctggagatca gggaggatgg gacggtgggg ggcgctgctg accagagccc cgaaagtctc ctgcagctga aagccttgaa gccgggagtt attcaaatct tgggagtcaa gacatccagg ttcctgtgcc aatggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact accaggcctg cccccgcac tcccggagcc acccggaatc ctggcccccc agcccccga tgtgggctcc atggacccat ttgggcttgt caccggactg gaggccgtga ggagtcccag ctttgagaag taa |
| Nucleotide sequence of a FGF21/19 chimera composed of the β-trefoil core domain of human FGF21 (residues H29 to L167) harboring Q104M mutation and the C-terminal tail of human FGF19 (residues L169 to K216) (bold) | SEQ ID NO: 216<br>caccccc atccctgact ccagtcctct cctgcaattc gggggccaag tccggcagcg gtacctctac acagatgatg cccagcagac agaagcccac ctggagatca gggaggatgg gacggtgggg ggcgctgctg accagagccc cgaaagtctc ctgcagctga aagccttgaa gccgggagtt attcaaatct tgggagtcaa gacatccagg ttcctgtgcc aatggccaga tggggccctg tatggatcgc tccactttga ccctgaggcc tgcagcttcc gggagctgct tcttgaggac ggatacaatg tttaccagtc cgaagcccac ggcctcccgc tgcacctgcc agggaacaag tccccacacc gggaccctgc accccgagga ccagctcgct tcctgccact actgccatg gtcccagagg agcctgagga cctcaggggc cacttggaat ctgacatgtt ctcttcgccc ctggagaccg acagcatgga cccatttggg cttgtcaccg gactggaggc cgtgaggagt cccagctttg agaagtaa |

Also encompassed are vectors or expression vectors comprising such nucleic acid molecules and host cells comprising such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize protein production. For the purposes of expressing a cloned nucleic acid sequence encoding a desired protein, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus E1a, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize protein production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination *In Vitro*," *Methods in Enzymology* 68:473-82 (1979), which is hereby incorporated by reference in its entirety.

A nucleic acid molecule encoding an isolated protein of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999); and U.S. Pat. No. 4,237,224 to Cohen and Boyer, which are hereby incorporated by reference in their entirety.

Once the nucleic acid molecule encoding the protein has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK et al., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified proteins may be obtained by several methods readily known in the art, including ion exchange chromatography, hydrophobic interaction chromatography, affinity chromatography, gel filtration, and reverse phase chromatography. The protein is preferably produced in purified form (preferably at least about 80% or 85% pure, more preferably at least about 90% or 95% pure) by conventional techniques. Depending on whether the recombinant host cell is made to secrete the protein into growth medium (see U.S. Pat. No. 6,596,509 to Bauer et al., which is hereby incorporated by reference in its entirety), the protein can be isolated and purified by centrifugation (to separate cellular components from supernatant containing the secreted protein) followed by sequential ammonium sulfate precipitation of the supernatant. The fraction containing the protein is subjected to gel filtration in an appropriately sized dextran or polyacrylamide column to separate the protein of interest from other proteins. If necessary, the protein fraction may be further purified by HPLC.

Another aspect of the present invention relates to a pharmaceutical composition that includes a chimeric protein according to the present invention and a pharmaceutically acceptable carrier.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "pharmaceutically acceptable" means it is, within the scope of sound medical judgment, suitable for use in contact with the cells of humans and lower animals without undue toxicity, irritation, allergic response, and the like, and is commensurate with a reasonable benefit/risk ratio.

In one embodiment, the chimeric protein of the present invention or a pharmaceutical composition thereof is administered in a therapeutically effective amount in combination with a therapeutically effective amount of a second agent. In one embodiment, the chimeric protein of the present invention or pharmaceutical composition thereof is administered in conjunction with the second agent, i.e., the respective periods of administration are part of a single administrative regimen. In one embodiment, the chimeric protein of the present invention or pharmaceutical composition thereof and the second agent are administered concurrently, i.e., the respective periods of administration overlap each other. In one embodiment, the chimeric protein of the present invention or pharmaceutical composition thereof and the second agent are administered non-concurrently, i.e., the respective periods of administration do not overlap each other. In one embodiment, the chimeric protein of the present invention or pharmaceutical composition thereof and the second agent are administered sequentially, i.e., the chimeric protein of the present invention or pharmaceutical composition thereof is administered prior to and/or after the administration of the second agent. In one embodiment, the chimeric protein of the present invention or pharmaceutical composition thereof and the second agent are administered simultaneously as separate compositions. In one embodiment, the chimeric protein of the present invention or pharmaceutical composition thereof and the second agent are administered simultaneously as part of the same compositions.

In one embodiment, the second agent is an anti-inflammatory agent, an antihypertensive agent, an anti-diabetic agent, and/or cholesterol-lowering drug such as a drug of the "statin" class. In one embodiment, the second agent is insulin. In one embodiment, the insulin is rapid acting, short acting, regular acting, intermediate acting, or long acting insulin. In one embodiment, the insulin is and/or comprises Humalog, Lispro, Novolog, Apidra, Humulin, Aspart, regular insulin, NPH, Lente, Ultralente, Lantus, Glargine, Levemir, or Detemir. In one embodiment, the second agent is a statin. In one embodiment, the statin is and/or comprises Atorvastatin (e.g., Lipitor or Torvast), Cerivastatin (e.g., Lipobay or Baycol), Fluvastatin (e.g., Lescol or Lescol), Lovastatin (e.g., Mevacor, Altocor, or Altoprev) Mevastatin, Pitavastatin (e.g., Livalo or Pitava), Pravastatin (e.g., Pravachol, Selektine, or Lipostat) Rosuvastatin (e.g., Crestor), Simvastatin (e.g., Zocor or Lipex), Vytorin, Advicor, Besylate Caduet or Simcor.

In one embodiment of the present invention, the pharmaceutical composition according to the present invention is administered with an anti-inflammatory agent, an antifibrotic agent, an antihypertensive agent, an antidiabetic agent, a triglyceride-lowering agent, and/or a cholesterol-lowering agent.

Another aspect of the present invention relates to a method of treating a subject suffering from diabetes, obesity, or metabolic syndrome. This method includes selecting a subject suffering from diabetes, obesity, or metabolic syndrome and administering to this selected subject a therapeutically effective amount of a chimeric protein according to the present invention.

In one embodiment, the selected subject is a mammal. In one particular embodiment, the selected subject is a human. In another embodiment, the selected subject is a rodent.

In one embodiment the selected subject has diabetes. As used herein, diabetes includes, but is not limited to, type I diabetes, type II diabetes, gestational diabetes, and drug-induced diabetes. In one embodiment, the subject has obesity. In one embodiment, the subject has metabolic syndrome.

The pharmaceutical compositions comprising a chimeric protein of the present invention provided herein can be used to treat a number of conditions. Preferably, the condition is one which the therapeutic outcome includes a decrease in blood glucose, a decrease in blood fructosamine, an increase in energy expenditure, an increase in fat utilization, a decrease in body weight, a decrease in body fat, a decrease in triglycerides, a decrease in free fatty acids, an increase in fat excretion, an improvement, or even a preservation, of pancreatic β-cell function and mass, a decrease in total blood cholesterol, a decrease in blood low-density lipoprotein cholesterol, an increase in blood high-density lipoprotein cholesterol, an increase in blood adiponectin, an increase in insulin sensitivity, an increase in leptin sensitivity, a decrease in blood insulin, a decrease in blood leptin, a decrease in blood glucagon, an increase in glucose uptake by adipocytes, a decrease in fat accumulation in hepatocytes, and/or an increase in fat oxidation in hepatocytes. Each of these parameters can be measured by standard methods, for example, by measuring oxygen consumption to determine metabolic rate, using scales to determine weight, and measuring lean body mass composition or mass to determine fat. Moreover, the presence and amount of triglycerides, free fatty acids, glucose and leptin can be determined by standard methods (e.g., blood test).

Additional conditions that are treatable in accordance with the present invention include one or more of type 1 diabetes, type 2 diabetes, gestational diabetes, drug-induced diabetes, high blood glucose, metabolic syndrome, lipodystrophy syndrome, dyslipidemia, insulin resistance, leptin resistance, atherosclerosis, vascular disease, inflammatory disease, fibrotic disease, hypercholesterolemia, hypertriglyceridemia, non-alcoholic fatty liver disease, overweight, and obesity.

The pharmaceutical composition according to the present invention can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes. The most suitable route may depend on the condition and disorder of the recipient. The formulations may conveniently be presented in unit dosage form and may be prepared by any of the methods well known in the art of pharmacy.

Dosages and desired drug concentrations of pharmaceutical compositions of the present invention may vary depending on the particular use envisioned. The determination of the appropriate dosage or route of administration is well within the skill of an ordinary physician. Those skilled in the art can readily optimize pharmaceutically effective dosages and administration regimens for therapeutic compositions comprising the chimeric protein according to the present invention, as determined by good medical practice and the clinical condition of the individual patient.

When in vivo administration of a chimeric protein of the present invention or is employed, normal dosage amounts may vary from, for example, about 10 ng/kg to up to 100 mg/kg of mammal body weight or more per day. In one embodiment, the dosage may be from about 1 mg/kg/day to 10 mg/kg/day, depending upon the route of administration. In one embodiment, the chimeric protein according to the present invention is administered at a dose of about 0.1 to 10 mg/kg once or twice daily. In one embodiment, the chimeric protein according to the present invention is administered at a dose of about 1 to 9, 1 to 8, 1 to 7, 1 to 6, 1 to 5, 1 to 4, 1 to 3, or 1 to 2 mg/kg. In one embodiment, the dosage is the same as that of a native FGF21 therapeutic. In one embodiment, the dosage is less than that of a native FGF21 therapeutic, but having the same effect as a higher dosage of a native FGF21 therapeutic. Guidance as to particular dosages and methods of delivery of proteins is provided in the literature; see, for example, U.S. Pat. Nos. 4,657,760; 5,206,344; or 5,225,212, which are hereby incorporated by reference in their entirety. It is anticipated that different formulations will be effective for different treatment compounds and different disorders, that administration targeting one organ or tissue, for example, may necessitate delivery in a manner different from that to another organ or tissue.

Where sustained-release administration of a chimeric protein of the present invention is desired in a formulation with release characteristics suitable for the treatment of any disease or disorder requiring administration of the chimeric protein of the present invention, microencapsulation is contemplated. Microencapsulation of recombinant proteins for sustained release has been successfully performed with human growth hormone (rhGH), interferon- (rhIFN-), interleukin-2, and MN rgp120. Johnson et al., "Preparation and Characterization of Poly(D,L-lactide-co-glycolide) Microspheres for Controlled Release of Human Growth Hormone," *Nat. Med.* 2:795-799 (1996); Yasuda, "Sustained Release Formulation of Interferon," *Biomed. Ther.* 27:1221-1223 (1993); Hora et al., "Controlled Release of Interleukin-2 from Biodegradable Microspheres," *Nat. Biotechnol.* 8:755-758 (1990); Cleland, "Design and Production of Single Immunization Vaccines Using Polylactide Polyglycolide Microsphere Systems," in VACCINE DESIGN: THE SUBUNIT AND ADJUVANT APPROACH 439-462 (Powell and Newman, eds. 1995); WO 97/03692; WO 96/40072; WO 96/07399; and U.S. Pat. No. 5,654,010, which are hereby incorporated by reference in their entirety. The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: BIODEGRADABLE POLYMERS AS DRUG DELIVERY SYSTEMS 1-41 (M. Chasin and R. Langer eds. 1990), which is hereby incorporated by reference in its entirety.

The compositions according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. For other patients, it will be necessary to prescribe not more than one or two doses per day.

Another aspect of the present invention relates to a method of treating a subject in need of increased FGF21-βKlotho-FGF receptor ("FGFR") complex formation. This method includes selecting a subject in need of increased FGF21-βKlotho-FGFR complex formation and administering to the selected subject a chimeric FGF21 protein, where the chimeric FGF21 protein includes an FGF21 core domain and a C-terminal portion of FGF19, thereby treating a subject in need of increased FGF21-βKlotho-FGFR complex formation.

Suitable chimeric FGF21 proteins include chimeric proteins according to the present invention, as described above and throughout the present application.

FGF21 depends on the co-receptor βKlotho to activate its cognate FGFR (FGFR1c) in its target tissues including white adipose tissue (Ogawa et al., "BetaKlotho is Required for Metabolic Activity of Fibroblast Growth Factor 21," *Proc. Natl. Acad. Sci. USA* 104(18):7432-7437 (2007), which is hereby incorporated by reference in its entirety). In the course of deciphering the molecular details of how FGF21 forms a signaling complex on the cell surface with FGFR1c and βKlotho, two discoveries were made that provided the basis for the rational design of an FGF21 agonist. It was found that βKlotho promotes binding of FGF21 to its cognate FGFR by engaging ligand and receptor simultaneously through two distinct binding sites. βKlotho plays the same role in promoting binding of FGF19, an endocrine regulator of bile acid homeostasis, to its cognate FGFR. The binding site for βKlotho was mapped on FGF21 and FGF19 to the C-terminal region of each ligand that follows the β-trefoil core domain. In the course of these studies, it was found that the C-terminal tail peptides of FGF21 and FGF19 share a common binding site on βKlotho, and that the C-terminal tail of FGF 19 binds tighter than the C-terminal tail of FGF21 to this site. Based on these findings, chimeric FGF21 proteins were made in which C-terminal sequences in FGF21 were replaced with the corresponding sequences of FGF 19 in order to confer greater binding affinity to βKlotho, and enhance agonistic properties.

In one embodiment according to the present invention, βKlotho is mammalian βKlotho. In one embodiment, βKlotho is human or mouse βKlotho. In one particular embodiment of the present invention, βKlotho is human or mouse βKlotho comprising the amino acid sequence of SEQ ID NO: 217 (i.e., GenBank Accession No. NP_783864, which is hereby incorporated by reference in its entirety) or SEQ ID NO: 218 (i.e., GenBank Accession No. NP_112457, which is hereby incorporated by reference in its entirety), respectively, as follows:

```
SEQ ID NO: 217:
   1 MKPGCAAGSP GNEWIFFSTD EITTRYRNTM SNGGLQRSVI LSALILLRAV TGFSGDGRAI

61 WSKNPNFTPV NESQLFLYDT FPKNFFWGIG TGALQVEGSW KKDGKGPSIW DHFIHTHLKN

121 VSSTNGSSDS YIFLEKDLSA LDFIGVSFYQ FSISWPRLFP DGIVTVANAK GLQYYSTLLD

181 ALVLRNIEPI VTLYHWDLPL ALQEKYGGWK NDTIIDIFND YATYCFQMFG DRVKYWITIH

241 NPYLVAWHGY GTGMHAPGEK GNLAAVYTVG HNLIKAHSKV WHNYNTHFRP HQKGWLSITL

301 GSHWIEPNRS ENTMDIFKCQ QSMVSVLGWF ANPIHGDGDY PEGMRKKLFS VLPIFSEAEK

361 HEMRGTADFF AFSFGPNNFK PLNTMAKMGQ NVSLNLREAL NWIKLEYNNP RILIAENGWF

421 TDSRVKTEDT TAIYMMKNFL SQVLQAIRLD EIRVFGYTAW SLLDGFEWQD AYTIRRGLFY

481 VDFNSKQKER KPKSSAHYYK QIIRENGFSL KESTPDVQGQ FPCDFSWGVT ESVLKPESVA

541 SSPQFSDPHL YVWNATGNRL LHRVEGVRLK TRPAQCTDFV NIKKQLEMLA RMKVTHYRFA

601 LDWASVLPTG NLSAVNRQAL RYYRCVVSEG LKLGISAMVT LYYPTHAHLG LPEPLLHADG

661 WLNPSTAEAF QAYAGLCFQE LGDLVKLWIT INEPNRLSDI YNRSGNDTYG AAHNLLVAHA

721 LAWRLYDRQF RPSQRGAVSL SLHADWAEPA NPYADSHWRA AERFLQFEIA WFAEPLFKTG

781 DYPAAMREYI ASKHRRGLSS SALPRLTEAE RRLLKGTVDF CALNHFTTRF VMHEQLAGSR

841 YDSDRDIQFL QDITRLSSPT RLAVIPWGVR KLLRWVRRNY GDMDIYITAS GIDDQALEDD

901 RLRKYYLGKY LQEVLKAYLI DKVRIKGYYA FKLAEEKSKP RFGFFTSDFK AKSSIQFYNK

961 VISSRGFPFE NSSSRCSQTQ ENTECTVCLF LVQKKPLIFL GCCFFSTLVL LLSIAIFQRQ

1021 KRRKFWKAKN LQHIPLKKGK RVVS
```

SEQ ID NO: 218:
```
  1 MKTGCAAGSP GNEWIFFSSD ERNTRSRKTM SNRALQRSAV LSAFVLLRAV TGFSGDGKAI

61 WDKKQYVSPV NPSQLFLYDT FPKNFSWGVG TGAFQVEGSW KTDGRGPSIW DRYVYSHLRG

121 VNGTDRSTDS YIFLEKDLLA LDFLGVSFYQ FSISWPRLFP NGTVAAVNAQ GLRYYRALLD

181 SLVLRNIEPI VTLYHWDLPL TLQEEYGGWK NATMIDLFND YATYCFQTFG DRVKYWITIH

241 NPYLVAWHGF GTGMHAPGEK GNLTAVYTVG HNLIKAHSKV WHNYDKNFRP HQKGWLSITL

301 GSHWIEPNRT DNMEDVINCQ HSMSSVLGWF ANPIHGDGDY PEFMKTGAMI PEFSEAEKEE

361 VRGTADFFAF SFGPNNFRPS NTVVKMGQNV SLNLRQVLNW IKLEYDDPQI LISENGWFTD

421 SYIKTEDTTA IYMMKNFLNQ VLQAIKFDEI RVFGYTAWTL LDGFEWQDAY TTRRGLFYVD

481 FNSEQKERKP KSSAHYYKQI IQDNGFPLKE STPDMKGRFP CDFSWGVTES VLKPEFTVSS

541 PQFTDPHLYV WNVTGNRLLY RVEGVRLKTR PSQCTDYVSI KKRVEMLAKM KVTHYQFALD

601 WTSILPTGNL SKVNRQVLRY YRCVVSEGLK LGVFPMVTLY HPTHSHLGLP LPLLSSGGWL

661 NMNTAKAFQD YAELCFRELG DLVKLWITIN EPNRLSDMYN RTSNDTYRAA HNLMIAHAQV

721 WHLYDRQYRP VQHGAVSLSL HCDWAEPANP FVDSHWKAAE RFLQFEIAWF ADPLFKTGDY

781 PSVMKEYIAS KNQRGLSSSV LPRFTAKESR LVKGTVDFYA LNHFTTRFVI HKQLNTNRSV

841 ADRDVQFLQD ITRLSSPSRL AVTPWGVRKL LAWIRRNYRD RDIYITANGI DDLALEDDQI

901 RKYYLEKYVQ EALKAYLIDK VKIKGYYAFK LTEEKSKPRF GFFTSDFRAK SSVQFYSKLI

961 SSSGLPAENR SPACGQPAED TDCTICSFLV EKKPLIFFGC CFISTLAVLL SITVFHHQKR

1021 RKFQKARNLQ NIPLKKGHSR VFS
```

In one particular embodiment of the present invention, βKlotho is human or mouse βKlotho encoded by a nucleotide sequence comprising the nucleotide sequences of SEQ ID NO: 219 (GenBank Accession No. NM_175737, which is hereby incorporated by reference in its entirety) and SEQ ID NO: 220 (GenBank Accession No. NM_031180, which is hereby incorporated by reference in its entirety), as follows:

```
SEQ ID NO: 219 (Human βKlotho gene coding sequence):
  98      atg aagccaggct gtgcggcagg atctccaggg aatgaatgga ttttcttcag 151 cactgatgaa ataaccacac gctataggaa tacaatgtcc aacgggggat tgcaaagatc 211 tgtcatcctg tcagcactta ttctgctacg agctgttact ggattctctg gagatggaag 271 agctatatgg tctaaaaatc ctaattttac tccggtaaat gaaagtcagc tgtttctcta 331 tgacactttc cctaaaaact ttttctgggg tattgggact ggagcattgc aagtggaagg 391 gagttggaag aaggatgaaa aggaccttta tatgggat catttcatcc acacacacct 451 taaaaatgtc agcagcacga atggttccag tgacagttat attttctgg aaaaagactt 511 atcagccctg gattttatag gagtttcttt ttatcaattt tcaatttcct ggccaaggct 571 tttccccgat ggaatagtaa cagttgccaa cgcaaaaggt ctgcagtact acagtactct 631 tctggacgct ctagtgctta gaaacattga acctatagtt actttatacc actgggattt 691 gccctttggca ctacaagaaa aatatggggg gtggaaaaat gataccataa tagatatctt 751 caatgactat gccacatact gtttccagat gtttggggac cgtgtcaaat attggattac 811 aattcacaac ccatatctag tggcttggca tgggtatggg acaggtatgc atgcccctgg 871 agagaaggga aatttagcag ctgtctacac tgtgggacac aacttgatca aggctcactc 931 gaaagtttgg cataactaca cacacatttt ccgcccacat cagaagggtt ggttatcgat 991 cacgttggga tctcattgga tcgagccaaa ccggtcggaa aacacgatgg atatattcaa 1051 atgtcaacaa tccatggttt ctgtgcttgg atggtttgcc aacccctatc atgggatgg
```

```
1111  cgactatcca gaggggatga gaaagaagtt gttctccgtt ctacccattt tctctgaagc 1171  agagaagcat gagatgagag gcacagctga tttctttgcc ttttcttttg gacccaacaa 1231  cttcaagccc ctaaacacca tggctaaaat gggacaaaat gtttcactta atttaagaga 1291  agcgctgaac tggattaaac tggaatacaa caaccctcga atcttgattg ctgagaatgg 1351  ctggttcaca gacagtcgtg tgaaaacaga agacaccacg gccatctaca tgatgaagaa 1411  tttcctcagc caggtgcttc aagcaataag gttagatgaa atacgagtgt ttggttatac 1471  tgcctggtct ctcctggatg gctttgaatg gcaggatgct tacaccatcc gccgaggatt 1531  attttatgtg gattttaaca gtaaacagaa agagcggaaa cctaagtctt cagcacacta 1591  ctacaaacag atcatacgag aaaatggttt ttctttaaaa gagtccacgc cagatgtgca 1651  gggccagttt ccctgtgact ctcctgggg tgtcactgaa tctgttctta agcccgagtc 1711  tgtggcttcg tccccacagt tcagcgatcc tcatctgtac gtgtggaacg ccactggcaa 1771  cagactgttg caccgagtgg aaggggtgag gctgaaaaca cgacccgctc aatgcacaga 1831  ttttgtaaac atcaaaaaac aacttgagat gttggcaaga atgaaagtca cccactaccg 1891  gtttgctctg gattgggcct cggtccttcc cactggcaac ctgtccgcgg tgaaccgaca 1951  ggccctgagg tactacaggt gcgtggtcag tgaggggctg aagcttggca tctccgcgat 2011  ggtcaccctg tattatccga cccacgccca cctaggcctc cccgagcctc tgttgcatgc 2071  cgacgggtgg ctgaacccat cgacggccga ggccttccag gcctacgctg ggctgtgctt 2131  ccaggagctg ggggacctgg tgaagctctg gatcaccatc aacgagccta accggctaag 2191  tgacatctac aaccgctctg gcaacgacac ctacggggcg gcgcacaacc tgctggtggc 2251  ccacgccctg gcctggcgcc tctacgaccg gcagttcagg ccctcacagc gcgggcccgt 2311  gtcgctgtcg ctgcacgcgg actgggcgga acccgccaac ccctatgctg actcgcactg 2371  gagggcggcc gagcgcttcc tgcagttcga gatcgcctgg ttcgccgagc cgctcttcaa 2431  gaccggggac taccccgcgg ccatgaggga atacattgcc tccaagcacc gacggggct 2491  ttccagctcg gccctgccgc gcctcaccga ggccgaaagg aggctgctca agggcacggt 2551  cgacttctgc gcgctcaacc acttcaccac taggttcgtg atgcacgagc agctggccgg 2611  cagccgctac gactcggaca gggacatcca gtttctgcag gacatcaccc gcctgagctc 2671  ccccacgcgc ctggctgtga ttccctgggg ggtgcgcaag ctgctgcggt gggtccggag 2731  gaactacggc gacatggaca tttacatcac cgccagtggc atcgacgacc aggctctgga 2791  ggatgaccgg ctccggaagt actacctagg gaagtacctt caggaggtgc tgaaagcata 2851  cctgattgat aaagtcagaa tcaaaggcta ttatgcattc aaactggctg aagagaaatc 2911  taaacccaga tttggattct tcacatctga ttttaaagct aaatcctcaa tacaatttta 2971  caacaaagtg atcagcagca ggggcttccc ttttgagaac agtagttcta gatgcagtca 3031  gacccaagaa aatacagagt gcactgtctg cttattcctt gtgcagaaga aaccactgat 3091  attcctgggt tgttgcttct tctccaccct ggttctactc ttatcaattg ccatttttca 3151  aaggcagaag agaagaaagt tttggaaagc aaaaaactta caacacatac cattaaagaa 3211  aggcaagaga gttgttagct aa SEQ ID NO: 220 (House mouse βKlotho gene coding sequence):
   2  atgaagaca ggctgtgcag cagggtctcc ggggaatgaa tggattttct tcagctctga 61  tgaaagaaac acacgctcta ggaaaacaat gtccaacagg gcactgcaaa gatctgccgt 121  gctgtctgcg tttgttctgc tgcgagctgt taccggcttc tccggagacg ggaaagcaat 181  atgggataaa aaacagtacg tgagtccggt aaacccaagt cagctgttcc tctatgacac
```

-continued

```
 241 tttccctaaa aacttttcct ggggcgttgg gaccggagca tttcaagtgg aagggagttg 301 gaagacagat ggaagaggac cctcgatctg ggatcggtac gtctactcac acctgagagg 361 tgtcaacggc acagacagat ccactgacag ttacatcttt ctggaaaaag acttgttggc 421 tctggatttt ttaggagttt cttttatca gttctcaatc tcctgccac ggttgtttcc 481 caatggaaca gtagcagcag tgaatgcgca aggtctccgg tactaccgtg cacttctgga 541 ctcgctggta cttaggaata tcgagcccat tgttaccttg taccattggg atttgcctct 601 gacgctccag gaagaatatg ggggctggaa aaatgcaact atgatagatc tcttcaacga 661 ctatgccaca tactgcttcc agacctttgg agaccgtgtc aaatattgga ttacaattca 721 caacccttac cttgttgctt ggcatgggtt tggcacaggt atgcatgcac caggagagaa 781 gggaaattta acagctgtct acactgtggg acacaacctg atcaaggcac attcgaaagt 841 gtggcataac tacgacaaaa acttccgccc tcatcagaag ggttggctct ccatcacctt 901 ggggtcccat tggatagagc caaacagaac agacaacatg gaggacgtga tcaactgcca 961 gcactccatg tcctctgtgc ttggatggtt cgccaacccc atccacgggg acggcgacta 1021 ccctgagttc atgaagacgg gcgccatgat ccccgagttc tctgaggcag agaaggagga 1081 ggtgaggggc acggctgatt tctttgcctt ttccttcggg cccaacaact tcaggccctc 1141 aaacaccgtg gtgaaaatgg acaaaatgt atcactcaac ttaaggcagg tgctgaactg 1201 gattaaactg gaatacgatg accctcaaat cttgatttcg gagaacggct ggttcacaga 1261 tagctatata aagacagagg acaccacggc catctacatg atgaagaatt cctaaaacca 1321 ggttcttcaa gcaataaaat ttgatgaaat ccgcgtgttt ggttatacgg cctggactct 1381 cctggatggc tttgagtggc aggatgccta tacgacccga cgagggctgt tttatgtgga 1441 ctttaacagt gagcagaaag agaggaaacc caagtcctcg gctcattact acaagcagat 1501 catacaagac aacggcttcc ctttgaaaga gtccacgcca gacatgaagg gtcggttccc 1561 ctgtgatttc tcttggggag tcactgagtc tgttcttaag cccgagttta cggtctcctc 1621 cccgcagttt accgatcctc acctgtatgt gtggaatgtc actggcaaca gattgctcta 1681 ccgagtggaa ggggtaaggc tgaaaacaag accatcccag tgcacagatt atgtgagcat 1741 caaaaaacga gttgaaatgt tggcaaaaat gaaagtcacc cactaccagt ttgctctgga 1801 ctggaccctct atccttccca ctggcaatct gtccaaagtt aacagacaag tgttaaggta 1861 ctataggtgt gtggtgagcg aaggactgaa gctgggcgtc ttccccatgg tgacgttgta 1921 ccacccaacc cactcccatc tcggcctccc cctgccactt ctgagcagtg ggggtggct 1981 aaacatgaac acagccaagg ccttccagga ctacgctgag ctgtgcttcc gggagttggg 2041 ggacttggtg aagctctgga tcaccatcaa tgagcctaac aggctgagtg acatgtacaa 2101 ccgcacgagt aatgacacct accgtgcagc ccacaacctg atgatcgccc atgcccaggt 2161 ctggcacctc tatgataggc agtataggcc ggtccagcat ggggctgtgt cgctgtcctt 2221 acattgcgac tgggcagaac ctgccaaccc ctttgtggat tcacactgga aggcagccga 2281 gcgcttcctc cagtttgaga tcgcctggtt tgcagatccg ctcttcaaga ctggcgacta 2341 tccatcggtt atgaaggaat acatcgcctc caagaaccag cgagggctgt ctagctcagt 2401 cctgccgcgc ttcaccgcga aggagagcag gctggtgaag ggtaccgtcg acttctacgc 2461 actgaaccac ttcactacga ggttcgtgat acacaagcag ctgaacacca accgctcagt 2521 tgcagacagg gacgtccagt tcctgcagga catcacccgc taagctcgc cagccgcct 2581 ggctgtaaca ccctggggag tgcgcaagct ccttgcgtgg atccggagga actacagaga 2641 cagggatatc tacatcacag ccaatggcat cgatgacctg gctctagagg atgatcagat
```

```
2701 ccgaaagtac tacttggaga agtatgtcca ggaggctctg aaagcatatc tcattgacaa 2761 ggtcaaaatc aaaggctact atgcattcaa actgactgaa gagaaatcta agcctagatt 2821 tggattttc acctctgact tcagagctaa gtcctctgtc cagttttaca gcaagctgat 2881 cagcagcagt ggcctcccg ctgagaacag aagtcctgcg tgtggtcagc ctgcggaaga 2941 cacagactgc accatttgct catttctcgt ggagaagaaa ccactcatct tcttcggttg 3001 ctgcttcatc tccactctgg ctgtactgct atccatcacc gtttttcatc atcaaaagag 3061 aagaaaattc cagaaagcaa ggaacttaca aaatatacca ttgaagaaag gccacagcag 3121 agttttcagc taa
```

In one embodiment of the present invention, the FGF receptor is FGFR1c receptor. In one particular embodiment, the FGFR1c receptor is the human FGFR1c receptor comprising the amino acid sequence of SEQ ID NO: 221 (GenBank Accession No. NP_075598, which is hereby incorporated by reference in its entirety), as follows:

```
  1 MWSWKCLLFW AVLVTATLCT ARPSPTLPEQ AQPWGAPVEV ESFLVHPGDL LQLRCRLRDD

61 VQSINWLRDG VQLAESNRTR ITGEEVEVQD SVPADSGLYA CVTSSPSGSD TTYFSVNVSD

121 ALPSSEDDDD DDDSSSEEKE TDNTKPNRMP VAPYWTSPEK MEKKLHAVPA AKTVKFKCPS

181 SGTPNPTLRW LKNGKEFKPD HRIGGYKVRY ATWSIIMDSV VPSDKGNYTC IVENEYGSIN

241 HTYQLDVVER SPHRPILQAG LPANKTVALG SNVEFMCKVY SDPQPHIQWL KHIEVNGSKI

301 GPDNLPYVQI LKTAGVNTTD KEMEVLHLRN VSFEDAGEYT CLAGNSIGLS HHSAWLTVLE

361 ALEERPAVMT SPLYLEIIIY CTGAFLISCM VGSVIVYKMK SGTKKSDFHS QMAVHKLAKS

421 IPLRRQVTVS ADSSASMNSG VLLVRPSRLS SSGTPMLAGV SEYELPEDPR WELPRDRLVL

481 GKPLGEGCFG QVVLAEAIGL DKDKPNRVTK VAVKMLKSDA TEKDLSDLIS EMEMMKMIGK

541 HKNIINLLGA CTQDGPLYVI VEYASKGNLR EYLQARRPPG LEYCYNPSHN PEEQLSSKDL

601 VSCAYQVARG MEYLASKKCI HRDLAARNVL VTEDNVMKIA DFGLARDIHH IDYYKKTTNG

661 RLPVKWMAPE ALFDRIYTHQ SDVWSFGVLL WEIFTLGGSP YPGVPVEELF KLLKEGHRMD

721 KPSNCTNELY MMMRDCWHAV PSQRPTFKQL VEDLDRIVAL TSNQEYLDLS MPLDQYSPSF

781 PDTRSSTCSS GEDSVFSHEP LPEEPCLPRH PAQLANGGLK RR
```

In one particular embodiment of the present invention, the FGFR1c receptor is the human FGFR1c receptor encoded by a nucleotide sequence comprising the nucleotide sequence of SEQ ID NO: 222 (GenBank Accession No. NM_023110, which is hereby incorporated by reference in its entirety), as follows:

```
SEQ ID NO: 222 (Human FGFR1c gene coding sequence):
 943    atgtggag ctggaagtgc ctcctcttct gggctgtgct ggtcacagcc acactctgca 1001 ccgctaggcc gtccccgacc ttgcctgaac aagcccagcc ctggggagcc cctgtggaag 1061 tggagtcctt cctggtccac cccggtgacc tgctgcagct tcgctgtcgg ctgcgggacg 1121 atgtgcagag catcaactgg ctgcgggacg gggtgcagct ggcggaaagc aaccgcaccc 1181 gcatcacagg ggaggaggtg gaggtgcagg actccgtgcc cgcagactcc ggcctctatg 1241 cttgcgtaac cagcagcccc tcgggcagtg acaccaccta cttctccgtc aatgtttcag 1301 atgctctccc ctcctcggag gatgatgatg atgatgatga ctcctcttca gaggagaaag 1361 aaacagataa caccaaacca aaccgtatgc ccgtagctcc atattggaca tccccagaaa 1421 agatggaaaa gaaattgcat gcagtgccgg ctgccaagac agtgaagttc aaatgccctt
```

```
-continued
1481 ccagtgggac cccaaacccc acactgcgct ggttgaaaaa tggcaaagaa ttcaaacctg 1541 accacagaat tggaggctac aaggtccgtt atgccacctg gagcatcata atggactctg 1601 tggtgccctc tgacaagggc aactacacct gcattgtgga gaatgagtac ggcagcatca 1661 accacacata ccagctggat gtcgtggagc ggtcccctca ccggcccatc ctgcaagcag 1721 ggttgcccgc caacaaaaca gtggccctgg gtagcaacgt ggagttcatg tgtaaggtgt 1781 acagtgaccc gcagccgcac atccagtggc taaagcacat cgaggtgaat gggagcaaga 1841 ttggcccaga caacctgcct tatgtccaga tcttgaagac tgctggagtt aataccaccg 1901 acaaagagat ggaggtgctt cacttaagaa atgtctcctt tgaggacgca ggggagtata 1961 cgtgcttggc gggtaactct atcggactct cccatcactc tgcatggttg accgttctgg 2021 aagccctgga agagaggccg gcagtgatga cctcgcccct gtacctggag atcatcatct 2081 attgcacagg ggccttcctc atctcctgca tggtggggtc ggtcatcgtc tacaagatga 2141 agagtggtac caagaagagt gacttccaca gccagatggc tgtgcacaag ctggccaaga 2201 gcatccctct gcgcagacag gtaacagtgt ctgctgactc cagtgcatcc atgaactctg 2261 gggttcttct ggttcggcca tcacggctct cctccagtgg gactcccatg ctagcagggg 2301 tctctgagta tgagcttccc gaagaccctc gctgggagct gcctcgggac agactggtct 2361 taggcaaacc cctgggagag ggctgctttg gcaggtggt gttggcagag gctatcgggc 2421 tggacaagga caaacccaac cgtgtgacca aagtggctgt gaagatgttg aagtcggacg 2481 caacagagaa agacttgtca gacctgatct cagaaatgga gatgatgaag atgatcggga 2541 agcataagaa tatcatcaac ctgctggggg cctgcacgca ggatggtccc ttgtatgtca 2601 tcgtggagta tgcctccaag ggcaacctgc gggagtacct gcaggccggg aggccccag 2661 ggctggaata ctgctacaac cccagccaca acccagagga gcagctctcc tccaaggacc 2721 tggtgtcctg cgcctaccag gtggcccgag gcatggagta tctggcctcc aagaagtgca 2781 tacaccgaga cctggcagcc aggaatgtcc tggtgacaga ggacaatgtg atgaagatag 2841 cagactttgg cctcgcacgg gacattcacc acatcgacta ctataaaaag acaaccaacg 2901 gccgactgcc tgtgaagtgg atggcacccg aggcattatt tgaccggatc tacacccacc 2961 agagtgatgt gtggtctttc ggggtgctcc tgtgggagat cttcactctg gcggctccc 3021 catacccgg tgtgcctgtg gaggaacttt tcaagctgct gaaggagggt caccgcatgg 3081 acaagcccag taactgcacc aacgagctgt acatgatgat gcgggactgc tggcatgcag 3141 tgccctcaca gagacccacc ttcaagcagc tggtggaaga cctggaccgc atcgtggcct 3201 tgacctccaa ccaggagtac ctggacctgt ccatgccct ggaccagtac tcccccagct 3261 ttcccgacac ccggagctct acgtgctcct caggggagga ttccgtcttc tctcatgagc 3321 cgctgcccga ggagccctgc ctgccccgac acccagccca gcttgccaat ggcggactca 3381 aacgccgctg a
```

The FGFR1, transcript variant 1 protein is a member of the FGFR family, where amino acid sequences are highly conserved between members and throughout evolution. FGFR family members differ from one another in their ligand affinities and tissue distribution. A full-length representative protein consists of an extracellular region, composed of three immunoglobulin-like domains, a single hydrophobic membrane-spanning segment, and a cytoplasmic tyrosine kinase domain. The extracellular portion of the protein interacts with fibroblast growth factors, setting in motion a cascade of downstream signals, ultimately influencing a myriad of biological processes including mitogenesis and differentiation. This particular family member binds both acidic and basic fibroblast growth factors and is involved in limb induction. Mutations in this gene have been associated with Pfeiffer syndrome, Jackson-Weiss syndrome, Antley-Bixler syndrome, osteoglophonic dysplasia, and autosomal dominant Kallmann syndrome. See, e.g., Dode et al., "Kallmann Syndrome: Fibroblast Growth Factor Signaling Insufficiency?" *J Mol Med* 82(11):725-34 (2004); Coumoul et al., "Roles of FGF Receptors in Mammalian Development and Congenital Diseases," *Birth Defects Res C Embryo Today* 69(4):286-304 (2003), which are hereby incorporated by reference in their entirety. Alternatively spliced variants, which encode different protein isoforms, have been described; however, not all variants have been fully characterized.

The nucleic acid and amino acid sequences for FGFR1 variants 2-6 may be found using the following reference sequence ID numbers on GenBank: FGFR1, transcript variant 2 (GenBank Accession No. NM_015850), FGFR1, transcript variant 3 (GenBank Accession No. NM_023105), FGFR1, transcript variant 4 (GenBank Accession No. NM_023106), FGFR1, transcript variant 5 (GenBank Accession No. NM_023107), FGFR1, transcript variant 6 (GenBank Accession No. NM_023108), and FGFR1, transcript variant 9, (GenBank Accession No. NM_023111). These sequences are hereby incorporated by reference in their entirety.

Yet another aspect of the present invention relates to a method of causing increased FGF21 receptor agonist-βKlotho-FGFR complex formation. This method comprises providing a cell comprising βKlotho and an FGFR and providing an FGF21 receptor agonist, where the agonist comprises a chimeric protein comprising a C-terminal portion of FGF19. This method also includes contacting the cell and the FGF21 receptor agonist under conditions effective to cause increased FGF21 receptor agonist-βKlotho-FGFR complex formation relative to contacting the cell with FGF21 alone, where the FGF21 has a core domain.

With respect to the FGF21 agonist, suitable chimeric proteins include those chimeric proteins according to the present invention that are described above and throughout the present application. Suitable N-terminal portions of FGF21 and C-terminal portions of FGF19 are also described above and throughout the present application.

In one embodiment, the method of causing increased FGF21 receptor agonist-βKlotho-FGFR complex formation is carried out in vitro. In one embodiment, the method is carried out in an adipocyte.

In one embodiment, the method of causing increased FGF21 receptor agonist-βKlotho-FGFR complex formation is carried out in vivo. In one embodiment, the method is carried out in a mammal. In one particular embodiment, the mammal is a mouse.

A further aspect of the present invention relates to a method of screening for compounds with enhanced binding affinity for βKlotho suitable for fusion to the C-terminus of an N-terminal portion of FGF21 to generate an FGF21 agonist. The method includes providing FGF21, providing βKlotho, and providing one or more candidate compounds; combining the FGF21, the βKlotho, and the candidate compounds under conditions effective for FGF21 and βKlotho to form a binary complex if present by themselves; and identifying the candidate compounds which diminish binary complex formation, compared to when the candidate compound is absent, as being potentially suitable for fusion to the C-terminus of an N-terminal portion of FGF21 to generate an FGF21 agonist. In one embodiment, the candidate compound out-competes FGF21 for binding to the βKlotho.

Yet a further aspect of the present invention relates to a method of screening for compounds with enhanced binding affinity for the βKlotho-FGFR complex suitable for treatment of diabetes, obesity, or related metabolic disorders. This method includes providing FGF21, providing a binary βKlotho-FGFR complex, and providing one or more candidate compounds. This method also includes combining the FGF21, the binary βKlotho-FGFR complex, and the candidate compounds under conditions effective for the FGF21 and the βKlotho-FGFR complex to form a ternary complex if present by themselves and identifying the candidate compounds which diminish ternary complex formation compared to when the candidate compound is absent as being potentially suitable for treatment of diabetes, obesity, or related metabolic disorders. In one embodiment, the candidate compound out-competes FGF21 for binding to the βKlotho-FGFR complex.

In one embodiment of the screening aspects of the present invention, the FGF21 has the amino acid sequence of SEQ ID NO: 100.

In one embodiment of the screening aspects of the present invention, βKlotho has the amino acid sequence of SEQ ID NO: 217 or SEQ ID NO: 218.

In one embodiment of the screening aspects of the present invention, the FGF receptor is FGFR1c. In one particular embodiment, the FGFR1c receptor has the amino acid sequence of SEQ ID NO: 221.

In one embodiment of the screening aspects of the present invention, a plurality of compounds is tested. In one embodiment, the candidate compounds are biomolecules. In one embodiment, the biomolecules are proteins. In one embodiment, the biomolecules are peptides. In one particular embodiment, the peptides are synthetic peptides. In one embodiment, the compounds are small organic molecules.

In one embodiment of the screening aspects of the present invention, the method is carried out using a cell-based assay. In one embodiment, the identifying is carried out using a cell-based assay.

In one embodiment of the screening aspects of the present invention, the method is carried out using a binding assay. In one embodiment, the binding assay is a direct binding assay. In one embodiment, the binding assay is a competition-binding assay. In one embodiment, the binding assay is carried out using surface plasmon resonance spectroscopy. In one embodiment, the identifying is carried out using a binding assay. In one embodiment, the identifying is carried out using surface plasmon resonance spectroscopy.

In one embodiment of the screening aspects of the present invention, the cell-based assay is carried out with adipocytes. In one embodiment, the cell-based assay is carried out with skeletal muscle cells. In one embodiment, stimulation of glucose uptake is the assay readout. In one embodiment, induction of glucose transporter 1 gene expression is the assay readout. In one embodiment, a dose-response curve is generated for the stimulation of glucose uptake by a candidate compound to determine potency and efficacy of the candidate compound. In one embodiment, a dose-response curve is generated for the induction of glucose transporter 1 gene expression by a candidate compound to determine potency and efficacy of the candidate compound. For example, if the dose-response curve is shifted to the left compared to that obtained for native FGF21, the candidate compound has greater potency than native FGF21. In one embodiment, an $IC_{50}$ value is derived from the dose-response curve of a candidate compound to determine potency of the candidate compound. An $IC_{50}$ value smaller than that obtained for native FGF21 identifies a candidate compound as more potent than native FGF21.

In one embodiment of the screening aspects of the present invention, the cell-based assay is carried out with mammalian cells ectopically expressing βKlotho. In one particular embodiment, the cells are HEK293 cells. In one embodiment, activation of FGF receptor is the assay readout. In one embodiment, tyrosine phosphorylation of an FGF receptor substrate is used as readout for FGF receptor activation. In one particular embodiment, the FGF receptor substrate is FGF receptor substrate 2α. In one embodiment, activation of downstream mediators of FGF signaling is used as readout for (or an indicator of) FGF receptor activation. In one particular embodiment, the downstream mediator of FGF signaling is 44/42 mitogen-activated protein kinase. In one embodiment, the downstream mediator of FGF signaling is a transcription factor. In one particular embodiment, the transcription factor is early growth response 1. In one embodiment, a dose-response curve is generated for βKlotho-dependent activation of FGF receptor by a candidate compound to determine potency and efficacy of the candidate compound. For example, if the dose-response curve is shifted to the left compared to that obtained for native FGF21, the candidate compound is more potent than native FGF21. In one embodiment, an $IC_{50}$ value is derived from the dose-response curve of a candidate compound to determine potency of the candidate compound. An $IC_{50}$ value smaller than that obtained for native FGF21 identifies a candidate compound as more potent than native FGF21.

In one embodiment of the screening aspects of the present invention, the surface plasmon resonance spectroscopy-based assay is carried out using FGF21 as ligand coupled to a biosensor chip. In one embodiment, mixtures of βKlotho ectodomain with increasing concentrations of a candidate compound are passed over a biosensor chip containing FGF21. In one embodiment, mixtures of the binary complex of FGFR ligand-binding domain and βKlotho ectodomain with increasing concentrations of a candidate compound are passed over a biosensor chip containing FGF21. In one particular embodiment, the FGFR ligand-binding domain is the FGFR1c ligand-binding domain. In one embodiment, an inhibition-binding curve is plotted for a candidate compound to determine potency of the candidate compound. For example, if the inhibition-binding curve is shifted to the left compared to that obtained for native FGF21, the candidate compound has greater potency than native FGF21. In one embodiment, an $IC_{50}$ value is derived from the inhibition-binding curve of a candidate compound to determine potency of the candidate compound. An $IC_{50}$ value smaller than that obtained for native FGF21 identifies a candidate compound as more potent than native FGF21. In one embodiment, the inhibition constant $K_i$ is determined for a candidate compound to determine potency of the candidate compound. A $K_i$ value smaller than that obtained for native FGF21 identifies a candidate compound as more potent than native FGF21.

In one embodiment of the screening aspects of the present invention, the method is carried out in vivo. In one embodiment, the method is carried out in a mammal. In one particular embodiment, the mammal is a mouse. In one embodiment, the ability of a candidate compound to potentiate the hypoglycemic effect of insulin is used as readout for FGF21-like metabolic activity. This involves fasting the mammal for a period of time prior to insulin injection and measuring fasting blood glucose levels. The mammal is then injected with insulin alone or co-injected with insulin plus a candidate compound. Blood glucose levels are measured at several time points after the injection. If a candidate compound potentiates the hypoglycemic effect of insulin to a greater degree than native FGF21 does, the candidate compound exhibits enhanced efficacy. Likewise, if a candidate compound potentiates the hypoglycemic effect of insulin to a similar degree than native FGF21 does but at a lower dose compared to that of FGF21 and/or for a longer period of time compared to FGF21, the candidate compound has enhanced agonistic properties.

EXAMPLES

The following examples are provided to illustrate embodiments of the present invention but are by no means intended to limit its scope.
Materials and Methods used in Examples 1-8
Purification of FGF19, FGF21, FGF23, FGFR, αKlotho, and βKlotho Proteins and Purification of FGF19, FGF21, and FGF23 Peptides The three endocrine FGF ligands, and mutants, chimeras, and C-terminal peptides thereof, as well as the ligand-binding domain of FGFRs were expressed in *E. coli* BL21 (DE3) cells. The secreted, bioactive form of human FGF19 (R23 to K216 of SEQ ID NO: 1), human FGF21 (H29 to S209 of SEQ ID NO: 100), and human FGF23 (Y25 to I251 of SEQ ID NO: 223) was refolded in vitro from inclusion bodies, and purified by published protocols (Ibrahimi et al., "Biochemical Analysis of Pathogenic Ligand-dependent FGFR2 Mutations Suggests Distinct Pathophysiological Mechanisms for Craniofacial and Limb Abnormalities," *Hum Mol Genet.* 13(19):2313-2324 (2004), Plotnikov et al., "Crystal Structures of Two FGF-FGFR Complexes Reveal the Determinants of Ligand-receptor Specificity," *Cell* 101 (4):413-424 (2000), which are hereby incorporated by reference in their entirety). In order to minimize proteolysis of FGF23, arginine residues 176 and 179 of the proteolytic cleavage site $^{176}$RXXR$^{179}$ (with reference to SEQ ID NO: 223) were replaced with glutamine as it occurs in the phosphate wasting disorder "autosomal dominant hypophosphatemic rickets" (Anonymous, "Autosomal Dominant Hypophosphataemic Rickets is Associated with Mutations in FGF23," *Nat Genet* 26(3):345-348 (2000); White et al., "Autosomal-dominant Hypophosphatemic Rickets (ADHR) Mutations Stabilize FGF-23," *Kidney Int* 60(6):2079-2086 (2001), which are hereby incorporated by reference in their entirety).

Chimeras composed of a N-terminal portion of human FGF21 (H29 to V197, H29 to S190, or H29 to L167 of SEQ ID NO: 100) and a C-terminal portion of human FGF19 (T204 to K216, M197 to K216, or L169 to K216 of SEQ ID NO: 1), termed FGF21$^{29-197}$/FGF19$^{204-216}$ (SEQ ID NO: 205), FGF21$^{29-190}$/FGF19$^{197-216}$ (SEQ ID NO: 206), and FGF21$^{29-167}$/FGF19$^{169-216}$ (SEQ ID NO: 207), respectively, were purified from inclusion bodies by the same protocol as the wild-type protein.

Likewise, two single mutants (Q104M and Y207F, SEQ ID NOs: 152 and 232, respectively) and one triple mutant (Y207F/A208E/S209K, SEQ ID NO: 233) of human FGF21 were purified by the same protocol as the wild-type protein. The C-terminal tail peptide of human FGF19 (M171 to K216 of SEQ ID NO: 1, termed FGF19$^{C\text{-}tail}$) and the C-terminal tail peptide of human FGF21 (P168 to S209 of SEQ ID NO: 100, termed FGF21$^{C\text{-}tail}$) were expressed as fusion peptides with a 50 residue-long N-terminal tag including a hexahistidine tag, and purified from the soluble cell lysate fraction by nickel affinity- and ion exchange chromatographies.

The N-terminally hexahistidine-tagged C-terminal tail peptide of human FGF23 (S180 to I251 of SEQ ID NO: 223, termed FGF23$^{C\text{-}tail}$) was expressed and purified as described previously (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety).

A single mutant (M96T) of human FGF23 (SEQ ID NO: 224) was purified by the same protocol as the wild-type protein. The proteolytic cleavage site $^{176}$RXXR$^{179}$ was not mutated in the M96T mutant protein. The wild-type FGF23 protein used as a control in the experiments with the M96T mutant also did not contain mutations at the proteolytic cleavage site.

Full-length human FGF homologous factor 1B (FHF1B; M1 to T181), which was used as a negative control for surface plasmon resonance (SPR) spectroscopy, was purified by a published protocol (Olsen et al., "Fibroblast Growth Factor (FGF) Homologous Factors Share Structural but not Functional Homology with FGFs," *J Biol Chem* 278(36): 34226-34236 (2003), which is hereby incorporated by reference in its entirety).

The ligand-binding domain of each of the seven principal human FGFRs, namely FGFR1b (D142 to E374 of SEQ ID NO: 225), FGFR1c (D142 to R365 of SEQ ID NO: 221), FGFR2b (A140 to E366 of SEQ ID NO: 227), FGFR2c (N149 to E368 of SEQ ID NO: 226), FGFR3b (D147 to H358 of SEQ ID NO: 229), FGFR3c (D147 to E365 of SEQ ID NO: 228), and FGFR4 (Q144 to D355 of SEQ ID NO: 230), was refolded in vitro from inclusion bodies, and purified as described previously (Ibrahimi et al., "Biochemical Analysis of Pathogenic Ligand-dependent FGFR2 Mutations Suggests Distinct Pathophysiological Mechanisms for Craniofacial and Limb Abnormalities," *Hum Mol Genet.* 13(19):2313-2324 (2004); Plotnikov et al., "Crystal Structures of Two FGF-FGFR Complexes Reveal the Determinants of Ligand-receptor Specificity," *Cell* 101(4):413-424 (2000), which are hereby incorporated by reference in their entirety).

The ectodomain of murine αKlotho (A35 to K982 of SEQ ID NO: 231) was purified from culture media of a HEK293 cell line ectopically expressing the αKlotho ectodomain as a fusion protein with a C-terminal FLAG tag (Kurosu et al., "Regulation of Fibroblast Growth Factor-23 Signaling by Klotho," *J Biol Chem* 281(10):6120-6123 (2006); Kurosu et al., "Suppression of Aging in Mice by the Hormone Klotho," *Science* 309(5742):1829-1833 (2005), which are hereby incorporated by reference in their entirety). Similarly, the ectodomain of murine βKlotho (F53 to L995 of SEQ ID NO: 218) was expressed in HEK293 cells as a fusion protein with a C-terminal FLAG tag and purified using the same protocol as for the αKlotho ectodomain. Purified bovine β-glucuronidase was obtained from Sigma-Aldrich.

Analysis of Ternary Complex Formation Between FGF19/FGF21, FGFR, and βKlotho by Size-Exclusion Chromatography Size-exclusion chromatography experiments were performed on a HiLoad™ 16/60 Superdex™ 200 prep grade column (GE Healthcare) mounted on an ÄKTApurifier (GE Healthcare). Because of poor solubility of the ligand-binding domain of FGFR1c in low salt buffer, the experiments were carried out with 25 mM HEPES-NaOH buffer, pH7.5, containing 1.0 M NaCl. Sample injection volume was 0.9 to 2.0 ml, and the flow rate was 1.0 ml min$^{-1}$. Protein retention times were determined by absorbance at 280 nm. The column was calibrated with ferritin (440 kDa), immunoglobulin G (150 kDa), albumin (69.3 kDa), ovalbumin (44.3 kDa), carbonic anhydrase (28.8 kDa), and ribonuclease A (13.7 kDa). The void volume was determined using blue dextran 2,000, and the column volume was measured with acetone. To examine ternary complex formation between FGF21, FGFR1c, and βKlotho, 2.72 μmol of the 1:1 binary complex of FGFR1c ligand-binding domain and βKlotho ectodomain were mixed with 9.25 μmol of FGF21, and the mixture was applied to the size-exclusion column. The retention time of the FGFR1c-βKlotho complex alone served as a reference point. To examine ternary complex formation between FGF19, FGFR4, and βKlotho, 2.46 μmol of the 1:1 binary complex of FGFR4 ligand-binding domain and βKlotho ectodomain were mixed with 8.51 μmol of FGF19, and the mixture was applied to the size-exclusion column. The retention time of the FGFR4-βKlotho complex alone served as a reference point. Proteins of column peak fractions were resolved on 14% SDS-polyacrylamide gels, and then stained with Coomassie Brilliant Blue R-250.

Analysis of Mutant and Wild-Type FGF23 Proteins by Size-Exclusion Chromatography Size-exclusion chromatography experiments were performed on a HiLoad™ 16/60 Superdex™ 75 prep grade column (GE Healthcare). Because of poor solubility of FGF23 in low salt buffer, the experiments were carried out with 25 mM HEPES-NaOH buffer, pH7.5, containing 1.0 M NaCl. Sample injection volume was 1.5 to 3.8 ml, and the flow rate was 1.0 ml min$^{-1}$. Protein retention times were determined by absorbance at 280 nm. The column was calibrated with albumin (69.3 kDa), ovalbumin (44.3 kDa), carbonic anhydrase (28.8 kDa), ribonuclease A (13.7 kDa), and aprotinin (6.5 kDa). The void volume was determined using blue dextran 2,000, and the column volume was measured with acetone. To assess stability of FGF23 harboring the M96T mutation, equal amounts of mutant protein were injected onto the column at different times after affinity purification of the mutant protein. As a control, the elution profile of wild-type FGF23 was studied.

Analysis of FGF19/21/23-α/βKlotho, FGFR-βKlotho, and FGF21-FGFR1c-βKlotho Interactions by Surface Plasmon Resonance Spectroscopy SPR experiments were performed on a Biacore 2000 instrument (Biacore AB), and all the protein-protein and protein-peptide interactions were studied at 25° C. in HBS-EP buffer (10 mM HEPES-NaOH, pH 7.4, 150 mM NaCl, 3 mM EDTA, 0.005% (v/v) polysorbate 20). Proteins were immobilized by amine coupling on flow channels of research grade CM5 chips (Biacore AB). Proteins were injected over a CM5 chip at a flow rate of 50 μl min$^{-1}$, and at the end of each protein injection (180 s), HBS-EP buffer (50 μl min$^{-1}$) was flowed over the chip to monitor dissociation for 180 s. In experiments where βKlotho binding to FGFR was analyzed, the chip surface was then regenerated by injecting 50 μl of 2.0 M NaCl in 10 mM sodium/potassium phosphate, pH 6.5. In experiments where α/βKlotho binding to FGF19/21/23 or binding of the FGFR1c-βKlotho complex to FGF21 was studied, 2.0 M NaCl in 10 mM sodium acetate, pH 4.5 was used for chip regeneration. To control for nonspecific binding in experiments where the ectodomain of αKlotho or βKlotho was immobilized on the chip, β-glucuronidase was coupled to the control flow channel of the chip (~43-68 fmol/mm$^2$). Like αKlotho and βKlotho, β-glucuronidase is a member of family 1 glycosidases (carbohydrate-active enzymes database at cazy's online website; Cantarel et al., "The Carbohydrate-Active EnZymes Database (CAZy): an Expert Resource for Glycogenomics," *Nucleic Acids Res* 37:D233-238 (2009), which is hereby incorporated by reference in its entirety), and hence structurally related to each of the two extracellular glycosidase-like domains of αKlotho and βKlotho, respectively. In experiments where an FGF ligand was immobilized on the chip, FHF1B, which shares structural similarity with FGFs, but does not exhibit any FGFR binding (Olsen et al., "Fibroblast Growth Factor (FGF) Homologous Factors Share Structural but not Functional Homology with FGFs," *J Biol Chem* 278(36):34226-34236 (2003), which is hereby incorporated by reference in its entirety), was coupled to the control flow channel of the chip (~17-101 fmol/mm$^2$). The data were processed with BiaEvaluation software (Biacore AB). For each protein injection over a chip onto which αKlotho or βKlotho had been immobilized, the nonspecific responses from the β-glucuronidase control flow channel were subtracted from the responses recorded for the α/βKlotho flow channel. Similarly, for each protein injection over a FGF chip, the nonspecific responses from the FHF1B control flow channel were subtracted from the responses recorded for the FGF flow channel. Each set of experiments was repeated at least twice.

To analyze FGF21 binding to the binary FGFR1c-βKlotho complex, FGF21 was immobilized on a chip (~20 fmol/mm$^2$ of flow channel), and increasing concentrations of 1:1 complex of FGFR1c ligand-binding domain and βKlotho ectodomain in HBS-EP buffer were passed over the chip. To test the specificity of the interaction between FGF21 and the FGFR1c-βKlotho complex, two concentrations of 1:1 complex of FGFR1c ligand-binding domain and αKlotho ectodomain in HBS-EP buffer were passed over the FGF21 chip. The results are shown in FIGS. 1C and 1D.

To measure binding of βKlotho to each of the seven principal FGFRs, the ectodomain of βKlotho was immobilized on a chip (~42-46 fmol/mm$^2$ of flow channel). Increasing concentrations of the ligand-binding domain of FGFR1b, FGFR1c, FGFR2b, FGFR2c, FGFR3b, FGFR3c, or FGFR4 in HBS-EP buffer were passed over the chip. Maximal equilibrium binding responses were plotted against the concentrations of FGFR ligand-binding domain, and from the fitted saturation binding curve the equilibrium dissociation constant ($K_D$) was calculated. The fitted binding curve was judged to be accurate based on the distribution of the residuals (even and near zero) and $\chi^2$ (<10% of $R_{max}$). The results are shown in FIGS. 3A to 3G.

To analyze binding of βKlotho to FGF19 and FGF21, FGF19 and FGF21 were coupled to two flow channels of a chip (~30 fmol/mm$^2$ of flow channel). As a control, FGF23 was also coupled to the chip (~29 fmol/mm$^2$ of flow channel). Increasing concentrations of the ectodomain of βKlotho in HBS-EP buffer were injected over the chip. As an additional control, binding of αKlotho to FGF19 and FGF21 was studied. The results are shown in FIGS. 4A to 4E.

To examine whether the isolated C-terminal tail peptide of FGF19 or FGF21 can compete with full-length FGF19 or FGF21 for binding to βKlotho, FGF19 and FGF21 were immobilized on two flow channels of a chip (~18-29 fmol/mm$^2$ of flow channel). Increasing concentrations of either FGF19$^{C\text{-}tail}$ (0-20 nM) or FGF21$^{C\text{-}tail}$ (0-200 nM) were mixed with a fixed concentration of βKlotho (10 nM) in HBS-EP buffer, and the mixtures were passed over the chip. To test the specificity of the interaction between βKlotho and the C-terminal tail of FGF19 or FGF21, βKlotho ectodomain was mixed with a 2-fold molar excess of FGF23$^{C\text{-}tail}$, and the mixture was injected over the chip. The results are shown in FIGS. 5B to 5G.

To examine whether mutants of FGF21 or chimeras composed of a N-terminal portion of FGF21 and a C-terminal portion of FGF19 can compete with wild-type ligand for binding to the FGFR1c-βKlotho complex, FGF21 was immobilized on a chip (~30 fmol/mm$^2$ of flow channel). Increasing concentrations of FGF21 mutant or chimera (0-60 nM) were mixed with a fixed concentration of 1:1 complex of FGFR1c ligand-binding domain and βKlotho ectodomain (10 nM), and the mixtures were passed over the chip. As a control, competition of FGF21 in solution with immobilized FGF21 for binding to the FGFR1c-βKlotho complex was studied. The results are shown in FIGS. 14A to 14D and 15A to 15F.

Figures 7A, 7B, 7C:
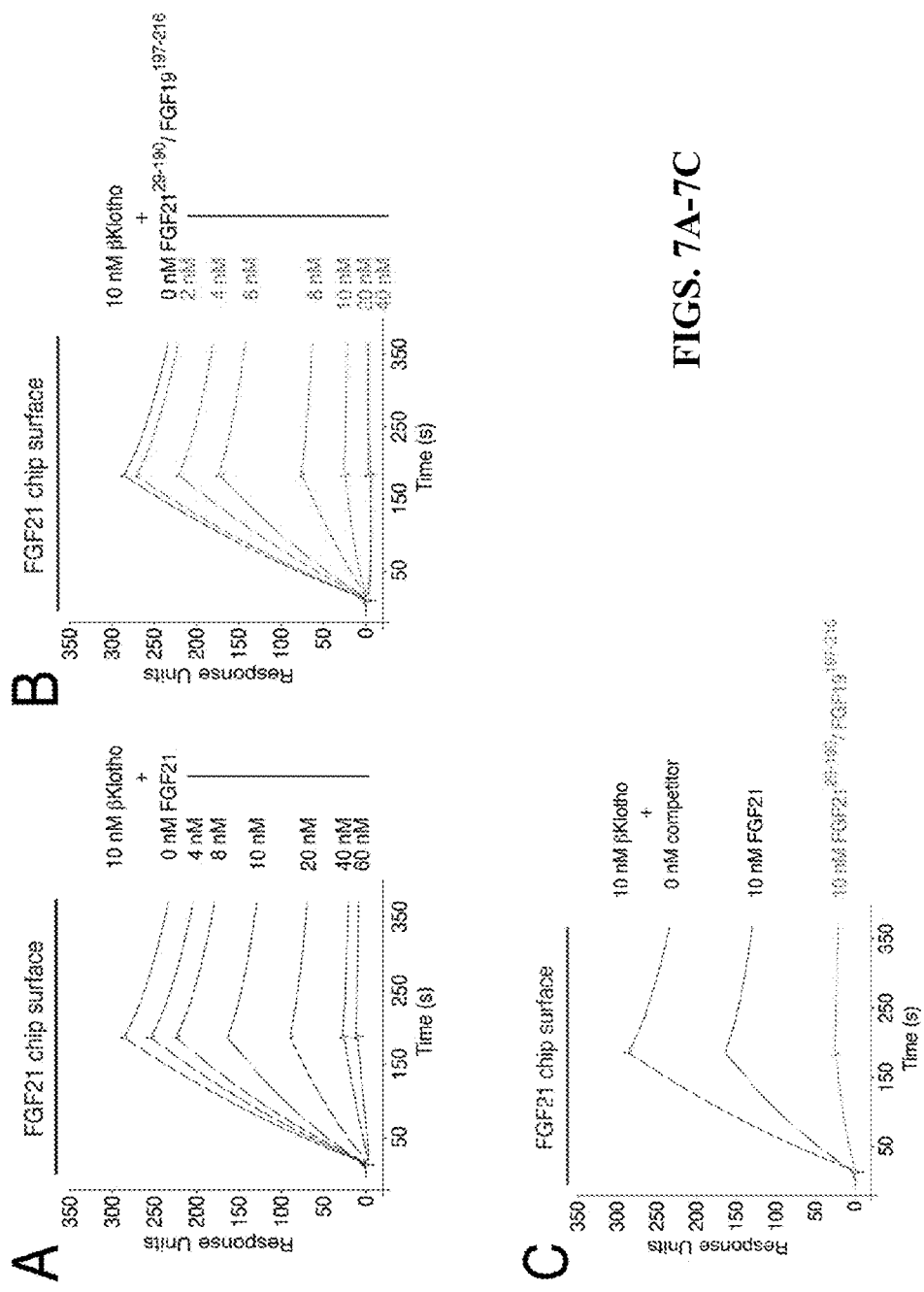
FIGS. 7A-7C show that a FGF21/FGF19 chimera has enhanced binding affinity for βKlotho.

To examine whether a chimera composed of a N-terminal portion of FGF21 and a C-terminal portion of FGF19 can compete with wild-type FGF21 for binding to βKlotho, FGF21 was immobilized on a chip (~29 fmol/mm$^2$ of flow channel). Increasing concentrations of chimera (0-40 nM) were mixed with a fixed concentration of βKlotho ectodomain (10 nM), and the mixtures were injected over the chip. As a control, competition of FGF21 in solution with immobilized FGF21 for binding to βKlotho was studied. The results are shown in FIGS. 7A to 7C.

Analysis of Phosphorylation of FRS2α and 44/42 MAP Kinase in a Hepatoma Cell Line To test whether the C-terminal tail peptides of FGF19 and FGF21 are interchangeable in inhibiting the signaling of FGF19, H4IIE rat hepatoma cells, which endogenously express βKlotho and FGFR4, were serum starved overnight and then pretreated for 60 min with either FGF19$^{C\text{-}tail}$ (10 to 1000 ng ml$^{-1}$) or FGF21$^{C\text{-}tail}$ (10 to 1000 ng ml$^{-1}$) prior to stimulation with FGF19 (30 ng ml$^{-1}$) for 10 min. Cell stimulation with FGF19 (3 to 300 ng ml$^{-1}$), FGF19$^{C\text{-}tail}$ (10 to 1000 ng ml$^{-1}$), or FGF21$^{C\text{-}tail}$ (10 to 1000 ng ml$^{-1}$) alone served as controls.

Figures 6A, 6B:
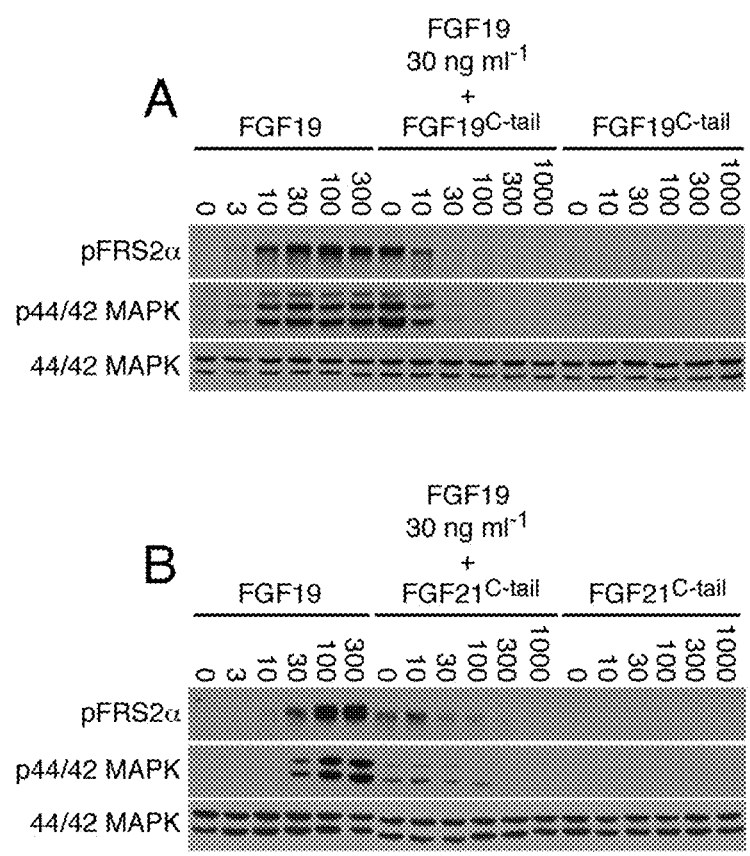
FIGS. 6A-6B show that the C-terminal tail peptides of FGF19 and FGF21 are interchangeable in inhibiting the signaling of FGF19.

After stimulation, the cells were lysed (Kurosu et al, "Suppression of Aging in Mice by the Hormone Klotho," *Science* 309(5742):1829-1833 (2005), which is hereby incorporated by reference in its entirety), and cellular proteins were resolved on SDS-polyacrylamide gels and transferred to nitrocellulose membranes. The protein blots were probed with an antibody to phosphorylated FGFR substrate-2α (FRS2α), and with antibodies recognizing only phosphorylated 44/42 MAP kinase or both phosphorylated and nonphosphorylated (total) 44/42 MAP kinase. All antibodies were from Cell Signaling Technology. The results are shown in FIGS. 6A and 6B.

Analysis of Egr1 Protein Expression in an Epithelial Cell Line

Figures 17A, 17B, 17C:
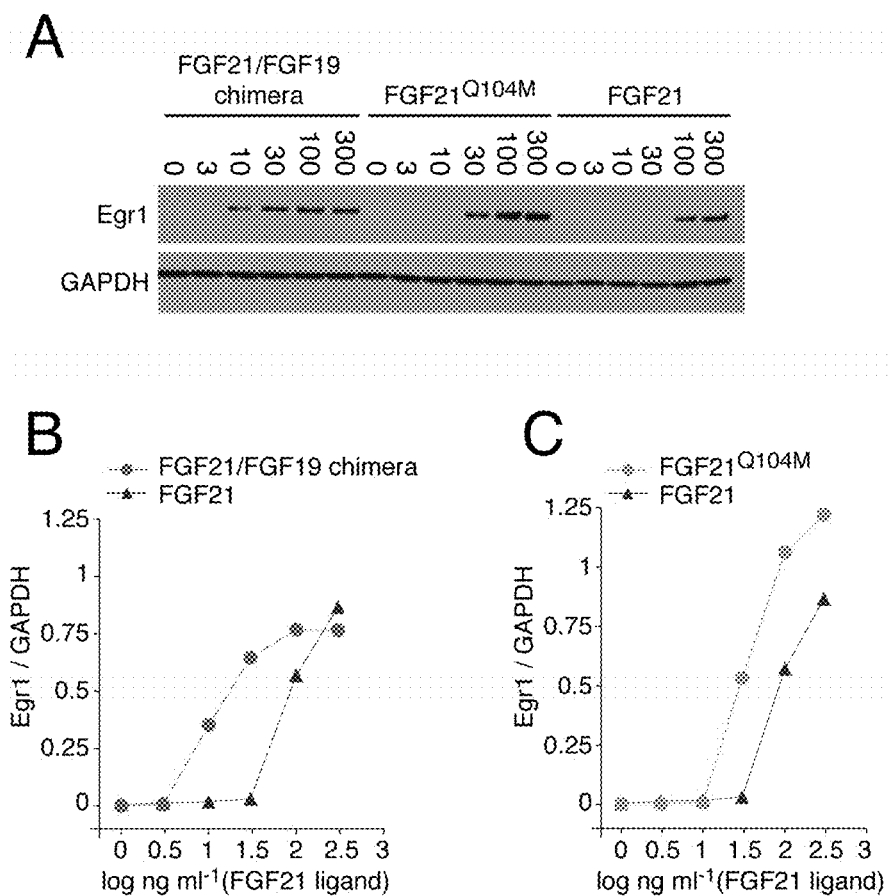
FIGS. 17A-17C show that a FGF21/FGF19 chimera and a single mutant of FGF21 harboring Q104M substitution in the core domain act as FGF21 agonists in a cell-based assay.

The ability of a single mutant of FGF21 and an FGF21/FGF19 chimera to activate FGFR1c in a βKlotho-dependent fashion was studied using induction of Egr1 expression as readout for FGFR1c activation. HEK293 cells, which endogenously express FGFR1c (Kurosu et al, "Regulation of Fibroblast Growth Factor-23 Signaling by Klotho," *J Biol Chem* 281:6120-6123 (2006), which is hereby incorporated by reference in its entirety), were transiently transfected with murine βKlotho. βKlotho HEK293 transfectants were serum starved overnight and then stimulated for 90 min with FGF21 mutant, chimera, or wild-type protein (3 to 300 ng ml$^{-1}$ each). After stimulation, the cells were lysed (Kurosu et al, "Suppression of Aging in Mice by the Hormone Klotho," *Science* 309(5742):1829-1833 (2005), which is hereby incorporated by reference in its entirety), and cellular proteins were resolved on SDS-polyacrylamide gels and transferred to nitrocellulose membranes. The protein blots were probed with antibodies to Egr1 and GAPDH. The intensity of the protein bands on the immunoblots was quantified and the ratio of Egr1 to GAPDH was calculated. The ratio of Egr1 to GAPDH was then plotted as a function of FGF21 ligand concentration. The anti-Egr1 antibody was from Cell Signaling Technology and the anti-GAPDH antibody was from Abcam. The results are shown in FIGS. 17A to 17C.

Insulin Tolerance Test in Mice

The metabolic activity of a single mutant of FGF21 and an FGF21/FGF19 chimera was studied in C57BL/6 mice.

The ability of FGF21 mutant or chimera to potentiate the hypoglycemic effect of insulin was used as readout for FGF21-like metabolic activity (Ohnishi et al., "Dietary and Genetic Evidence for Enhancing Glucose Metabolism and Reducing Obesity by Inhibiting Klotho Functions," *FASEB J* 25, 2031-2039 (2011), which is hereby incorporated by reference in its entirety). Mice were kept on normal chow. On the day of the insulin tolerance test, mice were fasted for 4 h and then bled from the cheek pouch for measuring fasting blood glucose levels. Thereafter, mice were administered intraperitoneally insulin (0.5 units per kilogram body weight) alone or insulin (0.5 units per kilogram body weight) plus either FGF21 mutant or FGF21/FGF19 chimera (0.3 mg per kilogram body weight). As controls, mice were injected with vehicle alone or co-injected with insulin plus FGF21. At the indicated time points after the injection (FIGS. 18A-18C), blood was drawn from the tail vein. Glucose concentrations in the blood samples were determined using Bayer Contour® blood glucose test strips (Bayer Corp.).

Example 1

Figure 2A:
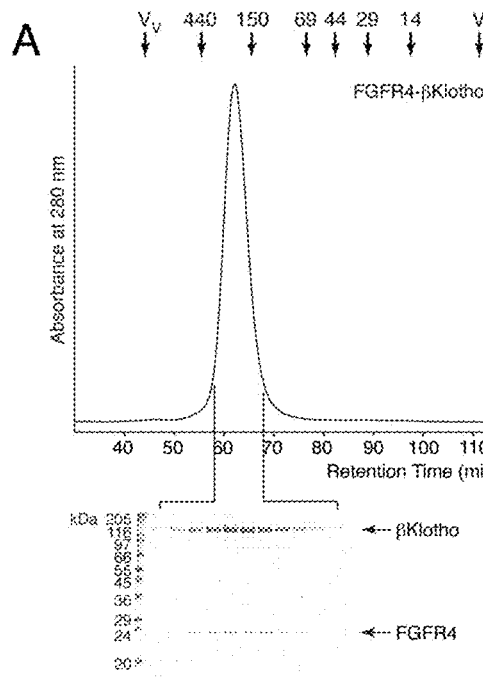
FIGS. 2A-2B show that the ternary complex of FGF19 with its cognate FGFR and βKlotho coreceptor can be reconstituted in solution using the ectodomains of βKlotho and FGFR4.
Figure 2B:
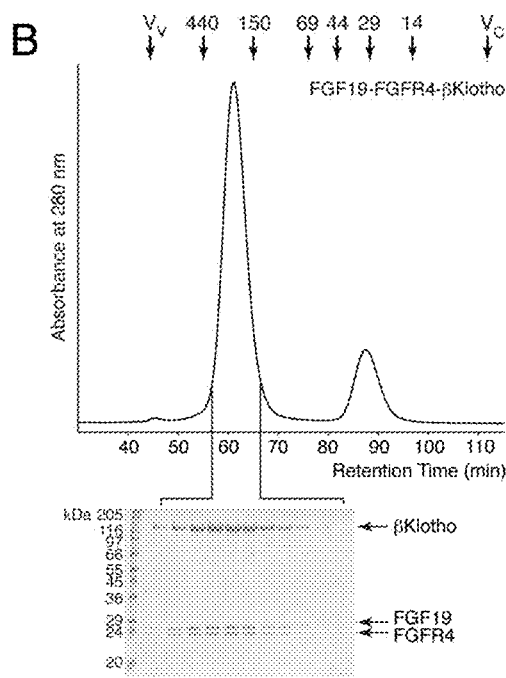

Klotho Co-Receptors Use Different Mechanisms to Promote Binding of Endocrine FGF Ligands to Cognate FGFRs The protein-protein interactions leading to the formation of the ternary complex between FGF23, FGFR1c, and αKlotho were previously characterized (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety). It was shown that the ectodomain of αKlotho possesses a high-affinity binding site for the ligand-binding domain of FGFR1c but not for the FGF23 ligand (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety), and that the preformed binary FGFR1c-αKlotho complex binds avidly to FGF23 (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety). It was concluded that FGF23 binds to a de novo binding site generated at the composite FGFR1c-αKlotho interface. The region on FGF23 that binds to this site was mapped to the C-terminal tail that follows the β-trefoil core domain (Goetz et al., "Isolated C-terminal Tail of FGF23 Alleviates Hypophosphatemia by Inhibiting FGF23-FGFR-Klotho Complex Formation," *Proc Natl Acad Sci USA* 107(1):407-412 (2010), which is hereby incorporated by reference in its entirety). Here it was explored whether βKlotho uses the same mechanism to promote binding of FGF19 and FGF21 to FGFR4 and FGFR1c, the principal cognate FGFRs of these ligands. It was first examined whether the FGF21-FGFR1c-βKlotho ternary complex can be reconstituted in solution in the same manner as the FGF23-FGFR1c-αKlotho complex. To form FGFR1c-βKlotho binary complex, conditioned media from a HEK293 cell line ectopically expressing murine βKlotho ectodomain (F53 to L995 of SEQ ID NO: 218) was applied to an affinity column containing the ligand-binding domain of FGFR1c (D142 to R365 of SEQ ID NO: 221). The FGFR1c-βKlotho complex eluted from the column was purified further by size-exclusion chromatography (FIG. 1A). To examine ternary complex formation, the FGFR1c-βKlotho complex was mixed with FGF21 (H29 to S209 of SEQ ID NO: 100), and the mixture was applied to a size-exclusion column. As shown in FIG. 1B, FGF21 coeluted with FGFR1c-βKlotho, demonstrating that, similar to FGF23, FGF21 forms a stable ternary complex with the ectodomain of βKlotho and the ligand-binding domain of FGFR1c. Consistent with the gel filtration data, analysis of ternary complex formation by SPR spectroscopy also showed that FGF21 binds the binary FGFR1c-βKlotho complex (FIG. 1C). The SPR analysis further showed that FGF21 does not interact with the FGFR1c-αKlotho complex demonstrating that the interaction between FGF21 and the FGFR1c-βKlotho complex is specific (FIG. 1D). Similar to FGF21, the ternary complex of FGF19 with its cognate receptor (FGFR4) and βKlotho co-receptor could be reconstituted in solution using the ectodomain of βKlotho and the ligand-binding domain of FGFR4 (FIGS. 2A and 2B).

Since the ectodomain of βKlotho forms stable binary complexes with the ligand-binding domains of FGFR1c and FGFR4, it was reasoned that it must contain a high affinity binding site for FGFR1c and FGFR4. To substantiate this and to measure the binding affinity of βKlotho for each of the two receptors, SPR spectroscopy was employed. βKlotho ectodomain was immobilized on a biosensor chip, and increasing concentrations of the ligand-binding domain of either FGFR1c or FGFR4 were passed over the chip. βKlotho bound both receptors with comparably high affinity (FIGS. 3A and 3D), demonstrating that similar to αKlotho, βKlotho contains a high-affinity binding site for its cognate FGFRs.

Figures 4A, 4B, 4C, 4D, 4E:
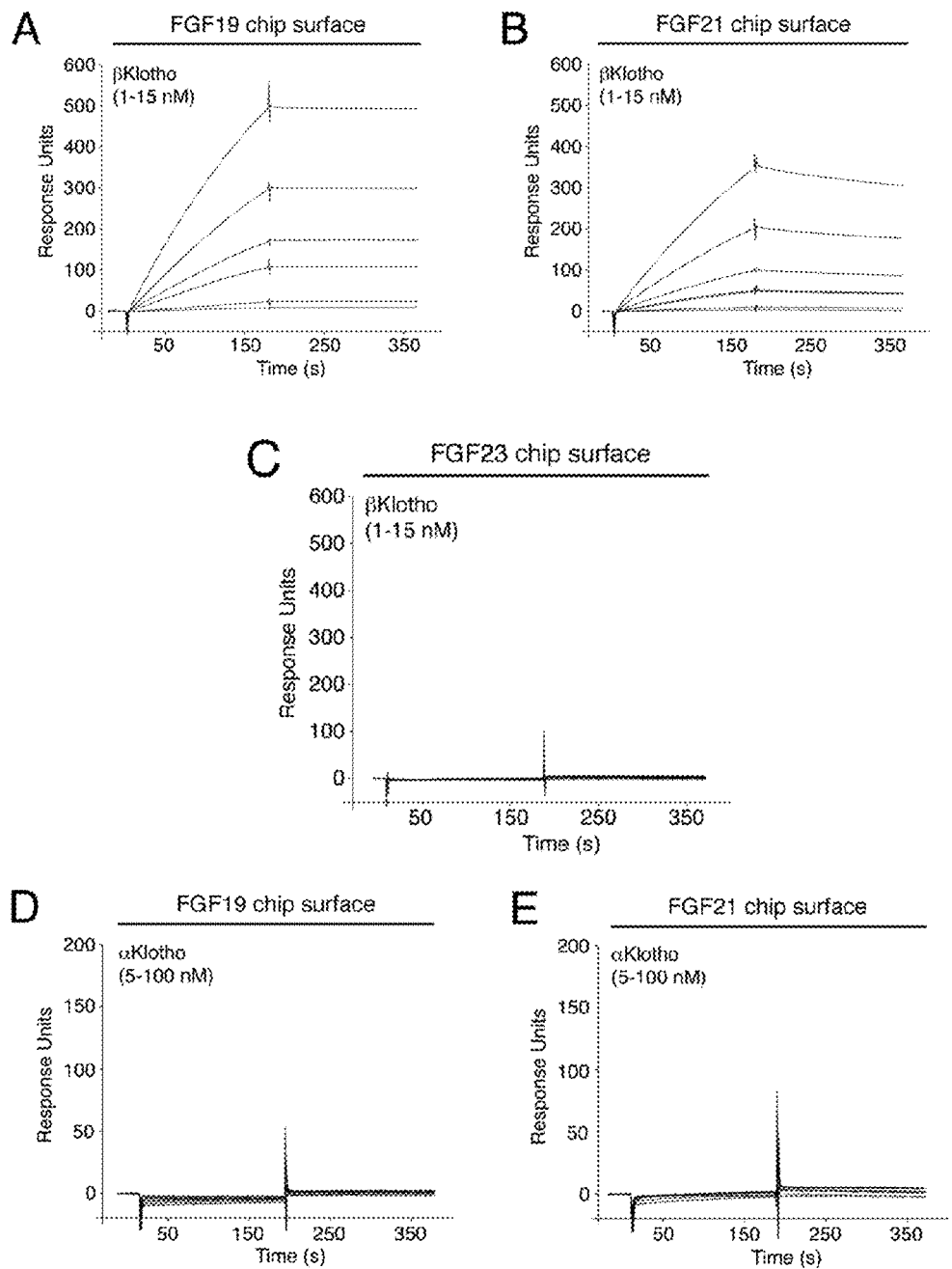
FIGS. 4A-4E show that βKlotho contains a high affinity binding site for FGF19 and FGF21.

For ternary complex formation with FGF19 or FGF21, two possible mechanisms remained open: one was that a de novo binding site for the ligand was generated in the context of the binary βKlotho-FGFR complex as in the case of ternary complex formation between αKlotho, FGF23, and FGFR; the other possibility was that βKlotho contained a distinct high affinity binding site for the ligand. In order to distinguish between these two mechanisms, it was examined, by SPR spectroscopy, whether βKlotho directly binds to FGF 19 and FGF21, respectively. FGF19 and FGF21 and as a specificity control, FGF23 were immobilized on a biosensor chip, and increasing concentrations of the ectodomain of βKlotho were passed over the chip. Both FGF19 and FGF21 bound strongly to βKlotho (FIGS. 4A and 4B), whereas no interaction was observed between FGF23 and βKlotho (FIG. 4C). To further confirm the specificity of the interaction, increasing concentrations of the ectodomain of αKlotho were passed over the chip. Neither FGF19 nor FGF21 bound to αKlotho (FIGS. 4D and 4E). Together, the data show that in contrast to αKlotho, βKlotho possesses distinct high-affinity binding sites for cognate endocrine FGF ligand and FGFR, indicating that βKlotho promotes ternary complex formation by engaging FGF ligand and FGFR simultaneously.

Figure 5A:
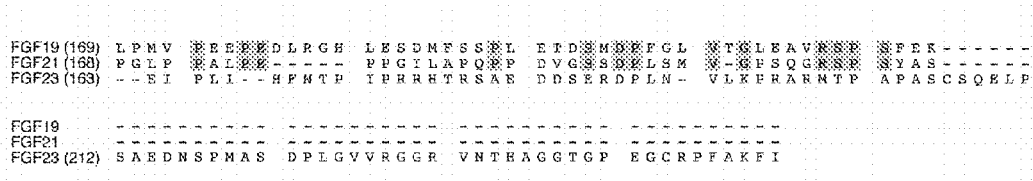
FIGS. 5A-5G show that the C-terminal tail peptides of FGF19 and FGF21 share a common binding site on βKlotho, and that the C-terminal tail peptide of FGF19 has greater affinity for this site than the C-terminal tail peptide of FGF21.
Figure 5B:
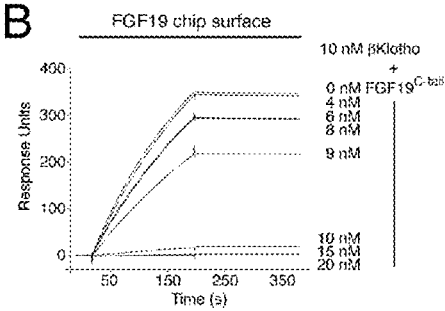
Figure 5C:
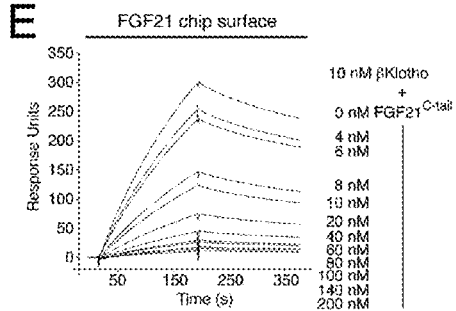
Figure 5D:
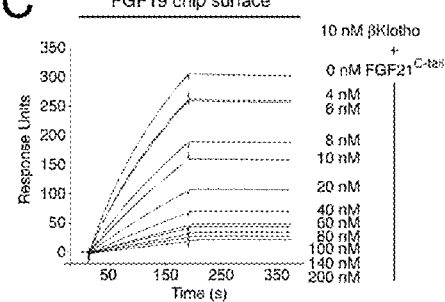
Figure 5E:
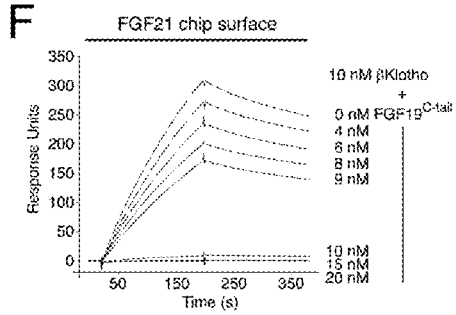
Figure 5F:
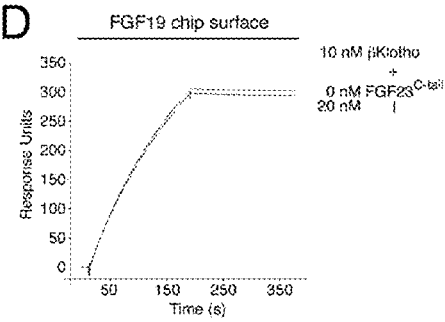
Figure 5G:
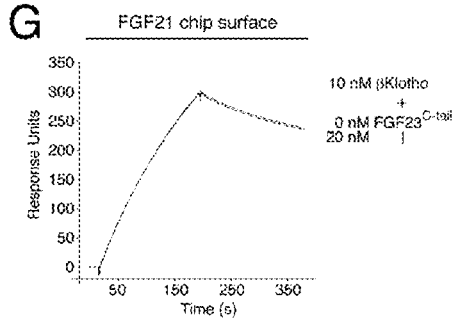

Example 2

βKlotho Binding Site on FGF19 and FGF21 Maps to the C-Terminal Region of Each Ligand It was next investigated which sequences of FGF19 and FGF21 bind to βKlotho. A clue to the location of the βKlotho binding site on FGF19 and FGF21 came from the previous finding that the binding site on FGF23 for the binary FGFR-αKlotho complex resides in the C-terminal region of FGF23 that follows the β-trefoil core domain (Goetz et al., "Molecular Insights into the Klotho-Dependent, Endocrine Mode of Action of Fibroblast Growth Factor 19 Subfamily Members," *Mol Cell Biol* 27(9):3417-3428 (2007), which is hereby incorporated by reference in its entirety). Subsequent studies suggested that the same region in FGF19 and FGF21 mediates binding of these ligands to βKlotho. Specifically, it was shown that a chimera of FGF19 with the C-terminal tail of FGF21 was able to bind βKlotho and gradual deletion of C-terminal residues of FGF21 resulted in progressively reduced binding affinity for βKlotho (Wu et al., "C-terminal Tail of FGF19 Determines its Specificity Toward Klotho Co-receptors," *J Biol Chem* 283(48):33304-33309 (2008); Yie et al., "FGF21 N- and C-termini Play Different Roles in Receptor Interaction and Activation," *FEBS Lett* 583(1):19-24 (2009); Micanovic et al., "Different Roles of N- and C-termini in the Functional Activity of FGF21," *J Cell Physiol* 219(2):227-234 (2009), which are hereby incorporated by reference in their entirety). In order to unambiguously demonstrate that the βKlotho-binding site on FGF19 and FGF21 resides in the C-terminal region of each ligand, the C-terminal tail peptides of FGF 19 (FGF19$^{C\text{-}tail}$; M171 to K216 of SEQ ID NO: 1) and FGF21 (FGF21$^{C\text{-}tail}$; P168 to S209 of SEQ ID NO: 100) were expressed and purified. It was then examined, by SPR spectroscopy, whether each peptide can compete with full-length ligand for binding to βKlotho. FGF19 and FGF21 were immobilized on a biosensor chip, and mixtures of a fixed concentration of βKlotho ectodomain with increasing concentrations of either FGF19$^{C\text{-}tail}$ or FGF21$^{C\text{-}tail}$ were passed over the chip. As shown in FIG. 5B, FGF19$^{C\text{-}tail}$ competed, in a dose-dependent fashion, with FGF19 for binding to βKlotho. Similarly, FGF21$^{C\text{-}tail}$ competed with FGF21 for binding to βKlotho (FIG. 5E). To confirm that the interaction between βKlotho and the C-terminal tail of FGF19 or FGF21 is specific, βKlotho ectodomain was mixed with a 2-fold molar excess of the C-terminal tail peptide of FGF23 (FGF23$^{C\text{-}tail}$), and the mixture was passed over the FGF19/21 chip. As expected, FGF23$^{C\text{-}tail}$ did not interfere with βKlotho binding to immobilized FGF19 or FGF21 (FIGS. 5D and 5G). Together, the data conclusively show that the C-terminal region of FGF19 and FGF21 contains the βKlotho-binding site.

Example 3

FGF19 and FGF21 Share a Common Binding Site on βKlotho

Since both FGF19 and FGF21 bind to βKlotho, it raised the question whether these ligands bind to a shared site on βKlotho or whether each ligand has its own distinct binding site. To answer this, an SPR-based competition binding assay as described above was employed to examine whether the isolated C-terminal tail peptide of FGF19 can compete with full-length FGF21 for binding to βKlotho, and conversely, whether the C-terminal tail peptide of FGF21 can compete with full-length FGF19 for binding to βKlotho. As shown in FIG. 5F, FGF19$^{C\text{-}tail}$ effectively competed with FGF21 for binding to βKlotho. Similarly, FGF21$^{C\text{-}tail}$ was capable of inhibiting βKlotho binding to FGF19 (FIG. 5C). These data show that FGF19 and FGF21 have overlapping binding sites on βKlotho.

To provide biological evidence for the in vitro finding that FGF19 and FGF21 bind to a shared binding site on βKlotho, it was next examined whether the FGF19$^{C\text{-}tail}$ peptide and the FGF21$^{C\text{-}tail}$ peptide are both able to block FGF19 signaling in cells. H4IIE hepatoma cells, which endogenously express βKlotho and FGFR4 (Kurosu et al., "Tissue-specific Expression of betaKlotho and Fibroblast Growth Factor (FGF) Receptor Isoforms Determines Metabolic Activity of FGF19 and FGF21," *J Biol Chem* 282:26687-26695 (2007), which is hereby incorporated by reference in its entirety), were pretreated with FGF19$^{C\text{-}tail}$ or FGF21$^{C\text{-}tail}$ and then stimulated with FGF19. As shown in FIGS. 6A and 6B, both FGF19$^{C\text{-}tail}$ and FGF21$^{C\text{-}tail}$ inhibited, in a dose-dependent fashion, FGF19-induced tyrosine phosphorylation of FRS2a and downstream activation of MAP kinase cascade. As expected, neither of the two peptides elicited any signaling response when applied alone (FIGS. 6A and 6B). These data show that the C-terminal tail peptides of FGF19 and FGF21 are interchangeable in inhibiting the signaling of FGF19, and provide cell-based evidence that FGF19 and FGF21 share a common binding site on βKlotho. Importantly, the binding site overlap may provide a molecular mechanism for why transgenic expression or therapeutic administration of FGF 19 produces beneficial effects on glucose and lipid metabolism resembling those elicited by FGF21 (Fu et al., "Fibroblast Growth Factor 19 Increases Metabolic Rate and Reverses Dietary and Leptin-deficient Diabetes," *Endocrinology* 145:2594-2603 (2004); Tomlinson et al., "Transgenic Mice Expressing Human Fibroblast Growth Factor-19 Display Increased Metabolic Rate and Decreased Adiposity," *Endocrinology* 143:1741-1747 (2002), which are hereby incorporated by reference in their entirety).

Example 4

FGF19 Binds βKlotho with Greater Affinity than FGF21

It was next asked whether FGF19 and FGF21 bind with similar affinity to the common site on βKlotho or whether the two ligands have different binding affinities for βKlotho. A quantitative analysis of the SPR data shows that the FGF 19 C-terminal tail peptide is more potent than the FGF21 C-terminal tail peptide at inhibiting binding of βKlotho to full-length FGF 19 or FGF21. Specifically, an equimolar amount of FGF19$^{C\text{-}tail}$ relative to βKlotho already yielded nearly complete inhibition of βKlotho binding to FGF19 or FGF21 (FIGS. 5B and 5F), whereas a 10- to 20-fold molar excess of FGF21$^{C\text{-}tail}$ over βKlotho was needed to achieve a similar effect (FIGS. 5C and 5E). These data indicate that the C-terminal tail of FGF19 binds βKlotho with greater affinity than the C-terminal tail of FGF21 suggesting that primary sequence differences at this region account for the observed difference in binding affinity of the two ligands for βKlotho.

Comparison of the C-terminal tail sequences of FGF19 and FGF21 shows a significant degree of sequence similarity (40% amino acid identity) only in the last twenty residues (FIG. 5A; see also FIG. 8B), pointing to these residues as the major binding epitope for βKlotho. To test this possibility, the nineteen most C-terminal residues in FGF21 were swapped with the corresponding residues of FGF19, including a one-residue insertion (FIG. 12, FGF21$^{C\text{-}tail}$ variant 19-45), and it was examined, by SPR spectroscopy, whether the chimeric FGF21 protein (termed FGF21$^{29\text{-}190}$/FGF19$^{197\text{-}216}$; SEQ ID NO: 206) is more potent than wild-type FGF21 at inhibiting binding of βKlotho to immobilized FGF21. As shown in FIGS. 7B and 7C, an equimolar amount of FGF21$^{29\text{-}190}$/FGF19$^{197\text{-}216}$ chimera relative to βKlotho yielded nearly complete inhibition of βKlotho binding to immobilized FGF21, whereas the same molar ratio of wild-type FGF21 to βKlotho produced at best half-maximum inhibition (FIGS. 7A and 7C). These data show that the exchange of unique residues in the distal portion of the C-terminal tail of FGF21 for the corresponding residues of FGF 19 confers increased binding affinity to βKlotho on FGF21. In other words, the sequence from M197 to K216 of FGF19 contains residues that contribute to the higher βKlotho-binding affinity of FGF19 compared to FGF21.

The biological significance of the differential binding affinities of FGF19 and FGF21 for βKlotho was next explored. Since FGF19 binds βKlotho with greater affinity than FGF21 does, FGF19 would out-compete FGF21 for βKlotho if both FGF ligands were present in target tissue at the same time. Under physiological conditions, FGF19 and FGF21 do not appear to equally coexist in the blood circulation (Badman et al., "Hepatic Fibroblast Growth Factor 21 is Regulated by PPARalpha and is a Key Mediator of Hepatic Lipid Metabolism in Ketotic States," *Cell Metab* 5:426-437 (2007); Galman et al., "The Circulating Metabolic Regulator FGF21 is Induced by Prolonged Fasting and PPARalpha Activation in Man," *Cell Metab* 8:169-174 (2008); Holt et al., "Definition of a Novel Growth Factor-dependent Signal Cascade for the Suppression of Bile Acid Biosynthesis," *Genes Dev* 17:1581-1591 (2003); Inagaki et al., "Fibroblast Growth Factor 15 Functions as an Enterohepatic Signal to Regulate Bile Acid Homeostasis," *Cell Metab* 2:217-225 (2005); Inagaki et al., "Endocrine Regulation of the Fasting Response by PPARalpha-mediated Induction of Fibroblast Growth Factor 21," *Cell Metab* 5:415-425 (2007); Tong et al., "Transcriptional Repressor E4-binding Protein 4 (E4BP4) Regulates Metabolic Hormone Fibroblast Growth Factor 21 (FGF21) During Circadian Cycles and Feeding," *J Biol Chem* 285:36401-36409 (2010), which are hereby incorporated by reference in their entirety). It was speculated that the high affinity interaction between FGF19 and βKlotho, together with the binding preference of βKlotho for FGFR4, ensure that most of the postprandially secreted FGF19 acts on the liver (and the gall bladder) and hence becomes trapped in the enterohepatic circulation. Importantly, these findings have provided for the rational design of an FGF21 agonist, as follows.

Example 5

Figures 8A, 8B:
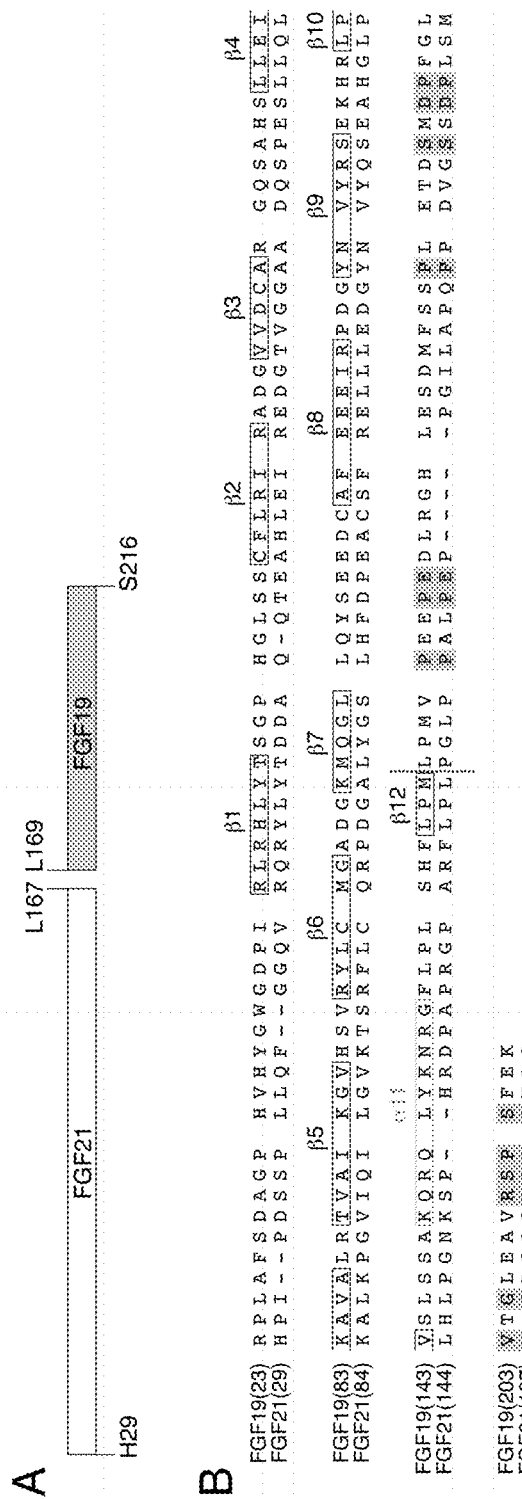
FIGS. 8A-8B show a schematic of one of the FGF21/FGF19 chimeras claimed in this invention and an alignment of the primary sequences of FGF19 and FGF21.

Chimera Composed of a N-terminal Portion of FGF21 and a C-Terminal Portion of FGF19 Exhibits Enhanced Binding Affinity for the FGFR1c-βKlotho Complex Based on these findings, it was reasoned that variants of FGF21 in which C-terminal residues unique to FGF21 were replaced with the corresponding residues of FGF19 should have enhanced binding affinity for βKlotho compared to native FGF21, and hence agonist potency. To begin to explore this, residues located in the distal portion of the C-terminal tail of FGF21 were progressively mutated, namely residues within the sequence from S191 to S209, since this region is essential in determining the ligand's binding affinity for βKlotho (FIG. 7). Specifically, a single mutant of FGF21 (Y207F; FIG. 11, FGF21$^{C\text{-}tail}$ variant 19-3), a triple mutant of FGF21 (Y207F/A208E/S209K; FIG. 12, FGF21$^{C\text{-}tail}$ variant 19-36), and a chimeric FGF21 protein in which the twelve most C-terminal residues in FGF21 were swapped with the corresponding residues of FGF19, including a one-residue insertion, (termed FGF21$^{29\text{-}197}$/FGF19$^{204\text{-}216}$; SEQ ID NO: 205; FIG. 12, FGF21$^{C\text{-}tail}$ variant 19-41) were made. The FGF21$^{29\text{-}190}$/FGF19$^{197\text{-}216}$ chimera (SEQ ID NO: 206; see FIG. 12, FGF21$^{C\text{-}tail}$ variant 19-45), which is discussed above, was also included in these studies. In this chimera, the entire sequence from S191 to S209 of FGF21 is replaced by the corresponding sequence of FGF19 (FIG. 12, FGF21$^{C\text{-}tail}$ variant 19-45), and it was shown that this chimera exhibits enhanced binding affinity for βKlotho compared to native FGF21 (FIG. 7). A chimera in which the entire C-terminal tail of FGF21 was exchanged for the corresponding region of FGF 19 (termed FGF21$^{29\text{-}167}$/FGF19$^{169\text{-}216}$; SEQ ID NO: 207; FIG. 8A) was used as a control.

To test whether the FGF21 mutant or chimeric proteins exhibit agonist potency, a SPR-based competition binding assay was employed. A competition binding assay was selected over a direct binding assay because its binding data are not confounded by the effects that the coupling of one binding partner to the chip might have. Specifically, it was examined whether a mutant or chimera can compete with native FGF21 for binding to the FGFR1c-βKlotho complex. If a mutant or chimera had greater affinity for the FGFR1c-βKlotho complex than native FGF21, and hence agonist potency, it would out-compete native FGF21 for binding to FGFR1c-βKlotho. FGF21 was immobilized on a biosensor chip, and mixtures of a fixed concentration of FGFR1c-βKlotho complex with increasing concentrations of either FGF21 mutant or FGF21/FGF19 chimera were passed over the chip. As a control, competition of FGF21 in solution with immobilized FGF21 for binding to the FGFR1c-βKlotho complex was studied.

Figures 14A, 14B, 14C, 14D:
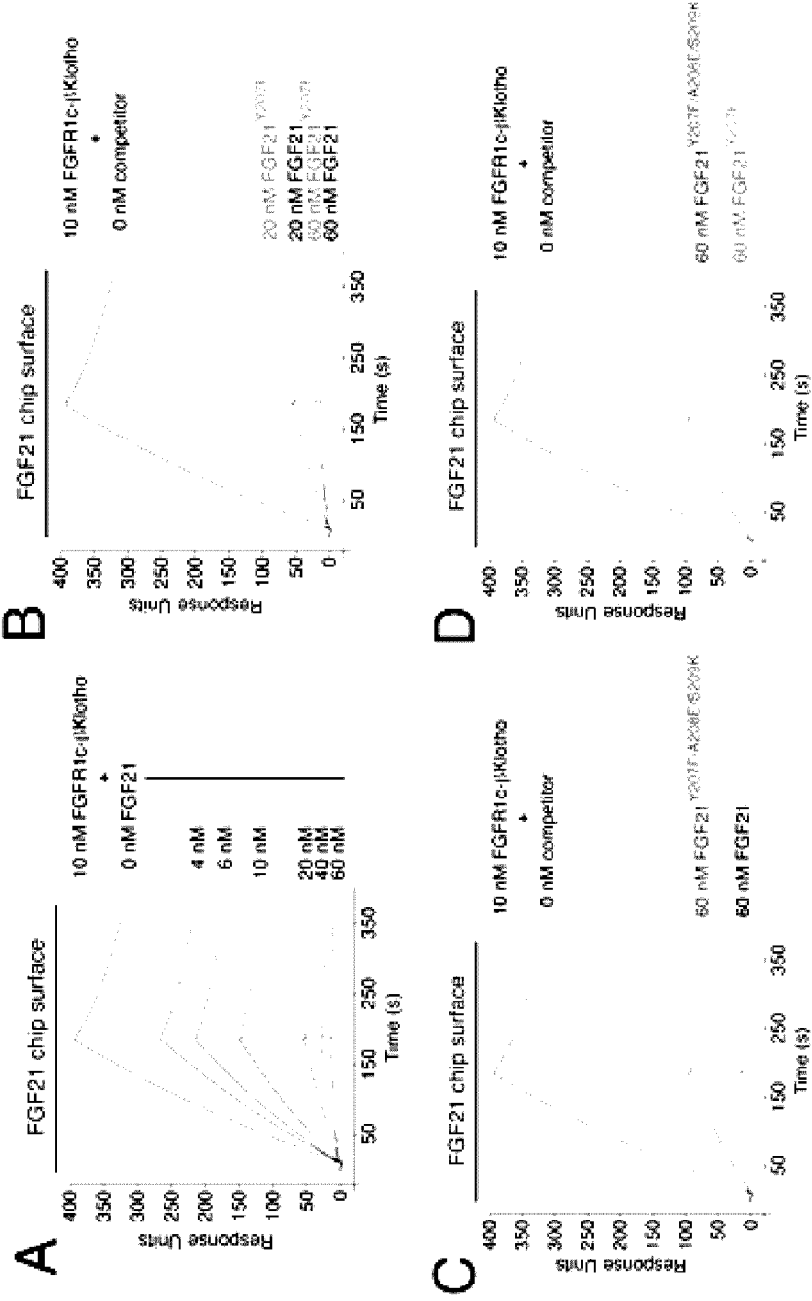
FIGS. 14A-14D show that substitution of the last three residues at the C-terminus of FGF21 for the corresponding residues of FGF 19 reduces the binding affinity of FGF21 for the FGFR1c-βKlotho complex.
Figures 15A, 15B, 15C, 15D, 15E, 15F:
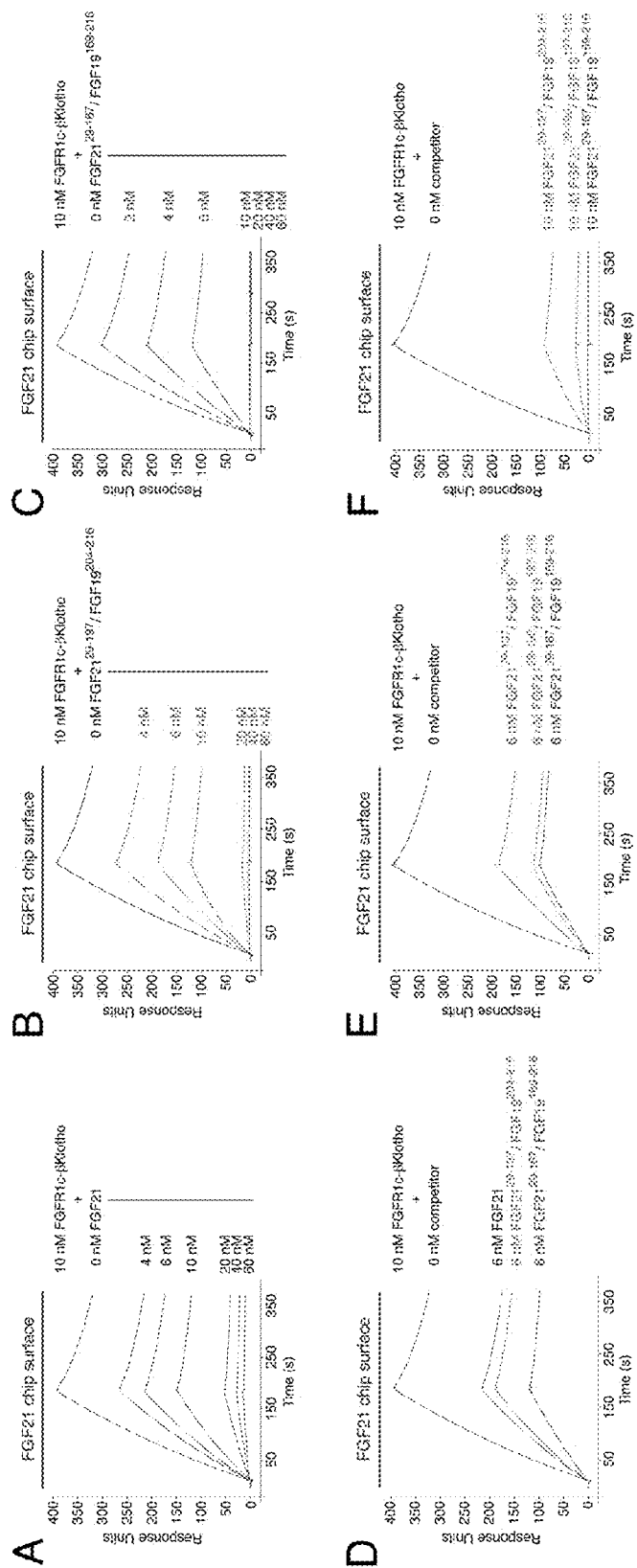
FIGS. 15A-15F show that FGF21/FGF19 chimeras have enhanced binding affinity for the FGFR1c-βKlotho complex.

As expected, FGF21 in solution competed, in a dose-dependent fashion, with immobilized FGF21 for binding to the FGFR1c-βKlotho complex (FIGS. 14A and 15A). The Y207F mutant of FGF21 was a weaker competitor than wild-type FGF21 for binding to the FGFR1c-βKlotho complex (FIG. 14B), suggesting that the mutant had reduced affinity for FGFR1c-βKlotho compared to wild-type FGF21. The Y207F/A208E/S209K triple mutant of FGF21 was even less potent than the Y207F single mutant at inhibiting binding of the FGFR1c-βKlotho complex to immobilized wild-type FGF21 (FIGS. 14C and 14D). These data indicate that the triple mutation causes an even greater loss in binding affinity of FGF21 for FGFR1c-βKlotho than the single mutation.

Based on these findings, it was concluded that replacing Y207 in FGF21 with phenylalanine of FGF19 reduces rather than enhances the binding affinity of FGF21 for βKlotho, and the combined replacement of Y207, A208, and S209 for the corresponding residues of FGF19 has an even greater negative impact on the binding affinity of FGF21 for βKlotho. In contrast to those two mutants of FGF21, all three FGF21/FGF19 chimeras proved to be more potent competitors than native FGF21 for binding to the FGFR1c-βKlotho complex (FIGS. 15A-15F). At any given concentration tested, the FGF21$^{29\text{-}197}$/FGF19$^{204\text{-}216}$ chimera caused greater inhibition of FGFR1c-βKlotho binding to the FGF21 chip surface than native FGF21 did (FIGS. 15A, 15B, and 15D), suggesting that it has increased affinity for FGFR1c-βKlotho compared to native FGF21. The FGF21$^{29\text{-}190}$/FGF19$^{197\text{-}216}$ chimera, which harbors four additional amino acid substitutions in the distal portion of the C-terminal tail of FGF21 compared to the FGF21$^{29\text{-}197}$/FGF19$^{204\text{-}216}$ chimera (FIG. 12), exhibited a further increased binding affinity for FGFR1c-βKlotho; at any given dose, it inhibited binding of FGFR1c-βKlotho to immobilized FGF21 to a substantially greater degree than the FGF21$^{29\text{-}197}$/FGF19$^{204\text{-}216}$ chimera (FIGS. 15E and 15F). For example, an equimolar amount of FGF21$^{29\text{-}190}$/FGF19$^{197\text{-}216}$ chimera relative to FGFR1c-βKlotho complex yielded nearly complete inhibition of FGFR1c-βKlotho binding to immobilized FGF21, whereas the same molar ratio of FGF21$^{29-197}$/FGF19$^{204-216}$ chimera to FGFR1c-βKlotho produced at best 75% inhibition (FIG. 15F). These data show that a substantial further increase in binding affinity for FGFR1c-βKlotho was achieved by introducing four amino acid substitutions in the FGF21 sequence from S191 to V197 in addition to replacing the unique residues C-terminal to V197 with the analogous residues of FGF19. The FGF21$^{29-167}$/FGF19$^{169-216}$ chimera in which the entire C-terminal tail of FGF21 was exchanged for the corresponding region of FGF19 was only slightly more potent than the FGF21$^{29-190}$/FGF19$^{197-216}$ chimera at inhibiting binding of FGFR1c-βKlotho to immobilized FGF21 (FIGS. 15E and 15F). Thus, the major increase in binding affinity for FGFR1c-βKlotho was obtained by replacing the C-terminal sequence from S191 to S209 in FGF21 with the analogous sequence of FGF19.

Together, the data show that an FGF21 agonist can be engineered by replacing C-terminal sequences in FGF21 with the corresponding sequences of FGF19. Increased binding affinity for βKlotho underlies the agonist potency of an FGF21/FGF19 chimera. Based on the findings with the triple mutant of FGF21, it was speculated that replacing the sequence from S191 to S206 in FGF21 with the analogous sequence of FGF19 might be sufficient to confer similar binding affinity for βKlotho on FGF21 as FGF19 has. Moreover, it is thought that replacing poorly conserved residues in the C-terminal region of FGF19 might further enhance the binding affinity of FGF19 itself for βKlotho (FIGS. 10 and 13).

Example 6

Chimera Composed of a N-Terminal Portion of FGF21 and a C-Terminal Portion of FGF19 Acts as an FGF21 Agonist in a Cell-Based Assay The FGF21$^{29-167}$/FGF19$^{169-216}$ chimera, which has proved the most potent among the three FGF21/FGF19 chimeras in the competition binding experiments, was then selected for analysis of agonist potency and efficacy in a cell-based assay. Specifically, the ability of the chimera to activate FGFR1c in a βKlotho-dependent fashion in HEK293 cells co-expressing FGFR1c and βKlotho was examined. Induction of protein expression of Egr1, a known downstream mediator of FGF signaling, was used as readout for FGFR1c activation. As shown in FIG. 17A, the FGF21$^{29-167}$/FGF19$^{169-216}$ chimera induced, in a dose-dependent fashion, Egr1 protein expression. The effect became evident at a 10-fold lower concentration of chimera than native FGF21 (FIG. 17A). The dose-response curve for the FGF21$^{29-167}$/FGF19$^{169-216}$ chimera obtained from quantitative analysis of the data shown in FIG. 17A was markedly shifted to the left compared to the dose-response curve for native FGF21 (FIG. 17B). The maximum signaling responses were similar, however. These data show that the FGF21/FGF19 chimera exhibits greater potency than native FGF21, which is consistent with the SPR results.

Example 7

Figures 18A, 18B, 18C:
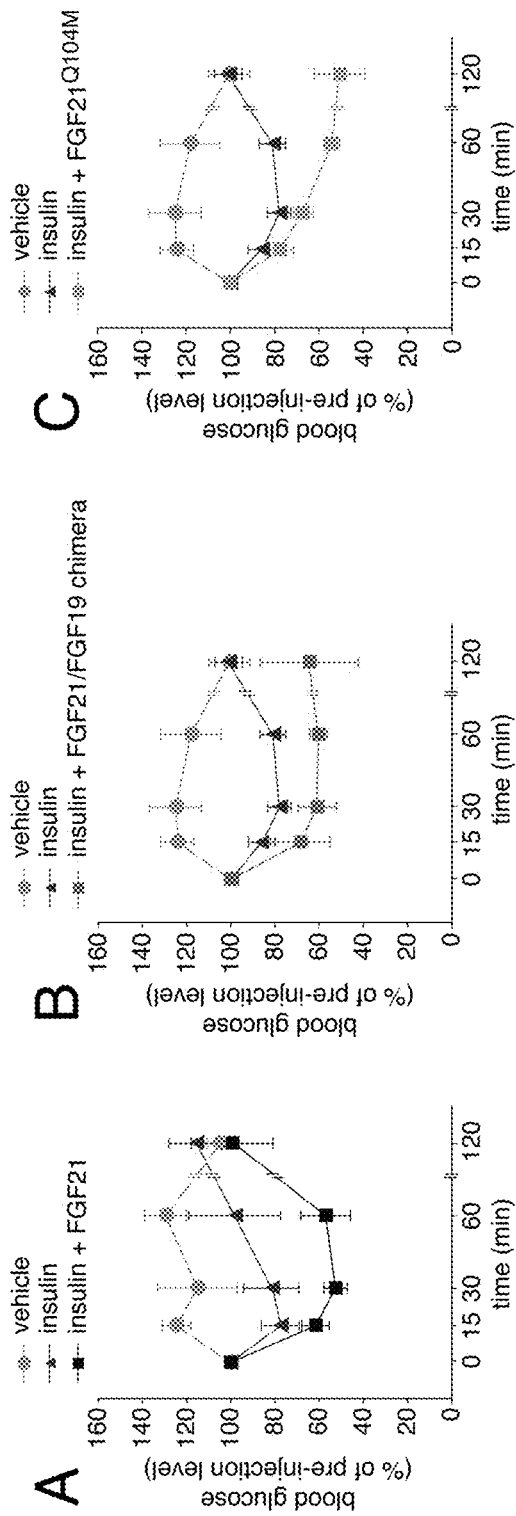
FIGS. 18A-18C show that a FGF21/FGF19 chimera and a single mutant of FGF21 harboring Q104M substitution in the core domain exhibit prolonged potentiating effects on insulin-induced hypoglycemia.

Chimera Composed of a N-Terminal Portion of FGF21 and a C-Terminal Portion of FGF19 Acts as an FGF21 Agonist In Vivo These findings prompted examination of whether the FGF21$^{29-167}$/FGF19$^{169-216}$ chimera exhibits FGF21 agonist activity in vivo. Specifically, insulin tolerance was used as pharmacodynamic marker, and it was analyzed whether the chimera can potentiate the hypoglycemic effect of exogenous insulin in mice. As shown in FIGS. 18A and 18B, the FGF21$^{29-167}$/FGF19$^{169-216}$ chimera increased the hypoglycemic effect of insulin to a similar degree as native FGF21 did. However, the effect of the chimera persisted for at least twice as long as that of native FGF21 (FIGS. 18A and 18B). These data show that compared to native FGF21, the FGF21/FGF19 chimera has a prolonged potentiating effect on insulin-induced hypoglycemia, which is indicative of agonist potency.

Example 8

Mutant FGF21 Harboring Q104M Substitution in the Core Domain Acts as an FGF21 Agonist IN VITRO and In Vivo In a second approach of engineering an FGF21 agonist, glutamine at position 104 in FGF21 was mutated to methionine in order to increase the thermal stability of the β-trefoil core domain of FGF21 (FGF21$^{Q104M}$, SEQ ID NO: 152). Except for FGF21, all FGF ligands have a methionine residue at the position analogous to Q104 of FGF21 (Mohammadi et al., "Structural Basis for Fibroblast Growth Factor Receptor Activation," *Cytokine & Growth Factor Rev* 16(2):107-137 (2005), which is hereby incorporated by reference in its entirety). Together with other hydrophobic residues, the methionine forms the interior hydrophobic core of an FGF ligand's β-trefoil core domain. The key role the methionine plays in providing stabilizing interactions in the hydrophobic core is evidenced by the fact that its replacement with threonine as it naturally occurs in FGF23 dramatically reduces protein stability (FIGS. 16A-E), and leads to disease (Chefetz et al., "A Novel Homozygous Missense Mutation in FGF23 Causes Familial Tumoral Calcinosis Associated with Disseminated Visceral Calcification," *Hum Genet.* 118(2):261-266 (2005), which is hereby incorporated by reference in its entirety).

Figures 16A, 16B, 16C, 16D, 16E:
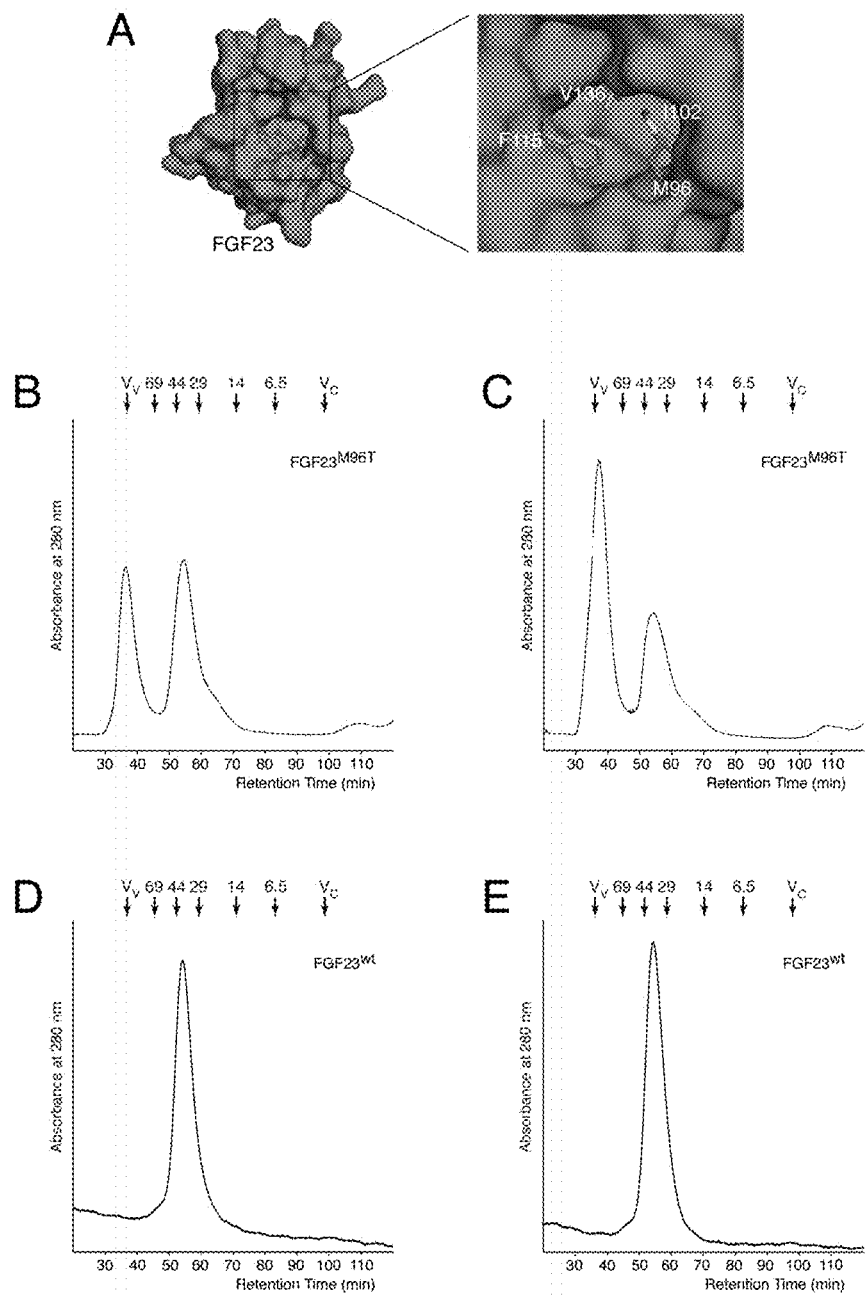
FIGS. 16A-16E show that substitution of methionine at position 96 for threonine in FGF23 (SEQ ID NO: 224), as it occurs in Familial Tumoral Calcinosis (Chefetz et al., "A Novel Homozygous Missense Mutation in FGF23 Causes Familial Tumoral Calcinosis Associated with Disseminated Visceral Calcification," *Hum Genet.* 118(2):261-266 (2005), which is hereby incorporated by reference in its entirety), destabilizes the FGF23 protein.

In particular, as shown in FIGS. 16A-E, substitution of methionine at position 96 for threonine in FGF23 (SEQ ID NO: 224), as it occurs in Familial Tumoral Calcinosis (Chefetz et al., "A Novel Homozygous Missense Mutation in FGF23 Causes Familial Tumoral Calcinosis Associated with Disseminated Visceral Calcification," *Hum Genet.* 118 (2):261-266 (2005), which is hereby incorporated by reference in its entirety), destabilizes the FGF23 protein. FIG. 16A shows a molecular surface representation of the FGF23 crystal structure (PDB ID: 2P39; Goetz et al., "Molecular Insights into the Klotho-Dependent, Endocrine Mode of Action of Fibroblast Growth Factor 19 Subfamily Members," *Mol Cell Biol* 27:3417-3428 (2007), which is hereby incorporated by reference in its entirety). A close-up view into the hydrophobic interior core of FGF23's β-trefoil core domain showing some of the key hydrophobic side chains is shown on the right, and a view of the whole structure is shown on the left. Note that M96 makes numerous hydrophobic contacts with its neighboring residues such as I102, F115, and V136 in the β-trefoil core of FGF23. The M96T substitution would weaken these hydrophobic contacts leading to thermal instability of the FGF23 protein. FIG. 16B shows a size-exclusion chromatogram of the M96T mutant of FGF23 analyzed immediately after Ni-chelating affinity purification. FIG. 16C shows a size-exclusion chromatogram of the M96T mutant of FGF23 analyzed following incubation at 4° C. for 24 hours. FIG. 16D shows a size-exclusion chromatogram of wild-type FGF23 immediately following protein purification. FIG. 16E shows a size-exclusion chromatogram of purified wild-type FGF23 following incubation at 4° C. for 24 hours. Arrows in FIGS. 16B-E indicate the retention times of molecular size standards, the void volume ($V_v$) and the column volume ($V_c$). Note that, in contrast to wild-type FGF23, there is a substantial increase in the portion of M96T mutant protein eluting in the void volume indicating that the mutant protein unfolds over time.

Thus, it was reasoned that substituting Q104 of FGF21 for methionine would confer greater stability on FGF21, and hence increase the half-life of the FGF21 protein in the blood circulation. Owing to its increased half-life compared to wild-type FGF21, the Q104M mutant might exhibit agonist potency.

To test this, a cell-based assay was first employed. Specifically, it was analyzed whether the mutant protein can activate FGFR1c in a βKlotho-dependent fashion in HEK293 cells co-expressing FGFR1c and βKlotho. Induction of protein expression of Egr1, a known downstream mediator of FGF signaling, was used as readout for FGFR1c activation. As shown in FIG. 17A, the Q104M mutant of FGF21 induced, in a dose-dependent fashion, Egr1 protein expression. The induction of Egr1 protein expression by the FGF21 mutant was already detectable at a concentration of 30 ng ml$^{-1}$, whereas a more than 3-fold greater concentration of wild-type FGF21 was needed to see a similar effect (FIG. 17A). The dose-response curve for the FGF21 mutant obtained from quantitative analysis of the data shown in FIG. 17A was shifted to the left compared to the dose-response curve for wild-type FGF21, and the maximum response for the mutant was greater than that for wild-type FGF21 (FIG. 17C). These data show that the Q104M mutant of FGF21 exhibits greater potency and efficacy than native FGF21.

These findings prompted examination of whether the Q104M mutant of FGF21 acts as an FGF21 agonist in vivo. Insulin tolerance was used as pharmacodynamic marker, and it was tested whether the mutant can potentiate the hypoglycemic effect of exogenous insulin in mice. As shown in FIGS. 18A and 18C, the Q104M mutant of FGF21 increased the hypoglycemic effect of insulin to a similar degree as wild-type FGF21 did. However, the effect of the mutant persisted for at least twice as long as that of wild-type FGF21, and tended to further increase with time (FIGS. 18A and 18C). These data show that compared to wild-type FGF21, the Q104M mutant of FGF21 has a prolonged potentiating effect on insulin-induced hypoglycemia, which is indicative of agonist potency.

Although the invention has been described in detail for the purposes of illustration, it is understood that such detail is solely for that purpose, and variations can be made therein by those skilled in the art without departing from the spirit and scope of the invention, which is defined by the following claims.

What is claimed:

1. An isolated chimeric protein comprising:
an N-terminus coupled to a C-terminus, wherein the N-terminus comprises an N-terminal portion of fibroblast growth factor (FGF) 21, and the C-terminus comprises a C-terminal portion of FGF19, wherein the N-terminal portion of FGF21 comprises an amino acid sequence beginning at residue 29 and ending at any one of residues 167-197 of SEQ ID NO:152, wherein the C-terminal portion of FGF21 beginning at any one of residues 167-197 and ending at residue 209 of SEQ ID NO: 152 is progressively replaced with a C-terminal portion of FGF19 beginning at any one of residues 169-204 and ending at residue 216 of SEQ ID NO:1.

2. The chimeric protein of claim 1, wherein the chimeric protein comprises the amino acid sequence of SEQ ID NO: 208, SEQ ID NO: 209, or SEQ ID NO: 210.

3. A pharmaceutical composition comprising:
the chimeric protein of claim 1 and
a pharmaceutically-acceptable carrier.

4. The pharmaceutical composition of claim 3 further comprising:
an anti-inflammatory agent, an antifibrotic agent, an antihypertensive agent, an antidiabetic agent, a triglyceride-lowering agent, and/or a cholesterol-lowering agent.

5. The chimeric protein according to claim 1, wherein the chimeric protein consists of the amino acid sequence of SEQ ID NO: 208, SEQ ID NO: 209, or SEQ ID NO: 210.

6. The chimeric protein according to claim 1, wherein the chimeric protein comprises the amino acid sequence of SEQ ID NO:312, SEQ ID NO:313, SEQ ID NO:314, SEQ ID NO:315, SEQ ID NO:316, SEQ ID NO:317, SEQ ID NO:318, SEQ ID NO:319, SEQ ID NO:320, SEQ ID NO:321, SEQ ID NO:322, SEQ ID NO:323, SEQ ID NO:324, SEQ ID NO:325, SEQ ID NO:326, SEQ ID NO:327, SEQ ID NO:328, SEQ ID NO:329, SEQ ID NO:330, SEQ ID NO:331, SEQ ID NO:332, SEQ ID NO:333, SEQ ID NO:334, SEQ ID NO:335, or SEQ ID NO:336.

7. A method for decreasing blood glucose level in a subject, said method comprising:
selecting a subject and
administering to said selected subject an effective amount of the chimeric protein of claim 1 to decrease blood glucose level in the selected subject.

8. The method according to claim 7, wherein the selected subject has diabetes, obesity, or metabolic syndrome.

9. The method according to claim 8, wherein the chimeric protein is administered with a pharmaceutically-acceptable carrier.

10. The method according to claim 8, wherein the selected subject is a mammal.

11. The method according to claim 10, wherein the selected subject is a human.

12. The method according to claim 8, wherein the selected subject has diabetes.

13. The method according to claim 12, wherein the selected subject has type II diabetes, gestational diabetes, or drug-induced diabetes.

14. The method according to claim 12, wherein the selected subject has type I diabetes.

15. The method according to claim 8, wherein the selected subject has obesity.

16. The method according to claim 8, wherein the selected subject has metabolic syndrome.

17. The method according to claim 7, wherein said administering is carried out parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

18. The method according to claim 7, wherein the chimeric protein comprises the amino acid sequence of SEQ ID NO: 208, SEQ ID NO: 209, or SEQ ID NO: 210.

19. The method according to claim 7, wherein the chimeric protein consists of the amino acid sequence of SEQ ID NO: 208, SEQ ID NO: 209, or SEQ ID NO: 210.

20. The method according to claim 7, wherein the chimeric protein comprises the amino acid sequence of SEQ ID NO:312, SEQ ID NO:313, SEQ ID NO:314, SEQ ID NO:315, SEQ ID NO:316, SEQ ID NO:317, SEQ ID NO:318, SEQ ID NO:319, SEQ ID NO:320, SEQ ID NO:321, SEQ ID NO:322, SEQ ID NO:323, SEQ ID NO:324, SEQ ID NO:325, SEQ ID NO:326, SEQ ID NO:327, SEQ ID NO:328, SEQ ID NO:329, SEQ ID NO:330, SEQ ID NO:331, SEQ ID NO:332, SEQ ID NO:333, SEQ ID NO:334, SEQ ID NO:335, or SEQ ID NO:336.

* * * * *

UNITED STATES PATENT AND TRADEMARK OFFICE
CERTIFICATE OF CORRECTION

PATENT NO. : 9,475,856 B2
APPLICATION NO. : 13/784289
DATED : October 25, 2016
INVENTOR(S) : Mohammadi et al.

Page 1 of 1

It is certified that error appears in the above-identified patent and that said Letters Patent is hereby corrected as shown below:

In the Specification

Column 1 at Lines 10-13, delete "This invention was made with U.S. government support under DE13686, DK077276, AG019712, DK091392, and DK067158 awarded by the National Institutes of Health. The Government has certain rights in the invention." and insert in its place --This invention was made with government support under DE013686, DK077276, AG019712, DK091392, and DK067158 awarded by National Institutes of Health. The government has certain rights in the invention.--

Signed and Sealed this
Twentieth Day of August, 2019

Andrei Iancu
*Director of the United States Patent and Trademark Office*

SEQUENCE LISTING

```
<160> NUMBER OF SEQ ID NOS: 336

<210> SEQ ID NO 1
<211> LENGTH: 216
<212> TYPE: PRT
<213> ORGANISM: Homo sapiens

<400> SEQUENCE: 1

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
                100                 105                 110

Leu Gln Tyr Ser Glu Glu Asp Cys Ala Phe Glu Glu Glu Ile Arg Pro
            115                 120                 125

Asp Gly Tyr Asn Val Tyr Arg Ser Glu Lys His Arg Leu Pro Val Ser
        130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175
```

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 2
<211> LENGTH: 216
<212> TYPE: PRT
<213> ORGANISM: Gorilla gorilla

<400> SEQUENCE: 2

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 3
<211> LENGTH: 216
<212> TYPE: PRT
<213> ORGANISM: Pan troglodytes

<400> SEQUENCE: 3

Met Arg Asn Gly Cys Val Val His Val Trp Ile Leu Ala Gly Leu
1               5                   10                  15

Trp Leu Ala Val Ala Gly Arg Pro Leu Ala Phe Ser Asp Ala Gly Arg
            20                  25                  30

His Val His Tyr Cys Trp Gly Asp Pro Ile Pro Leu Arg His Leu Tyr
        35                  40                  45

Thr Ser Gly Pro His Gly Leu Ser Ser Cys Phe Leu Arg Ile Pro Ala
    50                  55                  60

Asn Cys Val Met Asn Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 4
<211> LENGTH: 216
<212> TYPE: PRT
<213> ORGANISM: Macaca mulatta

<400> SEQUENCE: 4

Met Arg Ser Gly Cys Val Val His Ala Trp Ile Leu Ala Ser Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Thr
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Ala Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 5
<211> LENGTH: 216
<212> TYPE: PRT
<213> ORGANISM: Pongo abelii

<400> SEQUENCE: 5

Met Arg Ser Gly Cys Val Val His Ala Trp Ile Leu Ala Gly Leu
1               5                   10                  15

Trp Leu Ala Val Ala Gly Arg Pro Leu Ala Phe Ser Asp Ser Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Glu Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Arg His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 6
<211> LENGTH: 216
<212> TYPE: PRT
<213> ORGANISM: Nomascus leucogenys

<400> SEQUENCE: 6

Met Arg Ser Glu Cys Val Val His Ala Trp Ile Leu Ala Gly Leu
1               5                   10                  15

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Ala
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

```
Leu Gln Tyr Ser Glu Glu Asp Cys Ala Phe Glu Glu Ile Arg Pro
            115                 120                 125

Asp Gly Tyr Asn Val Tyr Arg Ser Glu Lys His Arg Leu Pro Val Ser
        130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Pro
                165                 170                 175

Glu Asp Leu Arg Gly His Leu Glu Ser Asp Met Phe Ser Ser Pro Leu
                180                 185                 190

Glu Thr Asp Ser Met Asp Pro Phe Gly Leu Val Thr Gly Leu Glu Ala
                195                 200                 205

Val Arg Ser Pro Ser Phe Glu Lys
    210                 215

<210> SEQ ID NO 7
<211> LENGTH: 142
<212> TYPE: PRT
<213> ORGANISM: Callithrix jacchus

<400> SEQUENCE: 7

Met Trp Lys Ala Thr Ala Gly Gln Gln Gly Gln Ser Glu Ala Gln
1               5                   10                  15

Met Ser Thr Cys Pro His Val Pro Arg Pro Leu Trp Ile Ala Gln Ser
            20                  25                  30

Cys Leu Phe Ser Leu Gln Leu Gln Tyr Ser Glu Glu Asp Cys Ala Phe
            35                  40                  45

Glu Glu Glu Ile Arg Pro Asp Gly Tyr Asn Val Tyr Trp Ser Glu Lys
        50                  55                  60

His Arg Leu Pro Val Ser Leu Ser Ser Ala Lys Gln Arg Gln Leu Tyr
65                  70                  75                  80

Lys Lys Arg Gly Phe Leu Pro Leu Ser His Phe Leu Pro Met Leu Pro
                85                  90                  95

Ile Ala Pro Glu Glu Pro Glu Asp Leu Arg Gly His Leu Glu Ser Asp
            100                 105                 110

Val Phe Ser Ser Pro Leu Glu Thr Asp Ser Met Asp Pro Phe Gly Leu
            115                 120                 125

Val Thr Gly Leu Glu Ala Val Asn Ser Pro Ser Phe Glu Lys
            130                 135                 140

<210> SEQ ID NO 8
<211> LENGTH: 219
<212> TYPE: PRT
<213> ORGANISM: Microcebus murinus

<400> SEQUENCE: 8

Met Pro Ser Gly Gln Ser Gly Cys Val Ala Ala Arg Ala Leu Ile Leu
1               5                   10                  15

Ala Gly Leu Trp Leu Thr Ala Ala Gly Arg Pro Leu Ala Phe Ser Asp
            20                  25                  30

Ala Gly Pro His Val His Tyr Gly Trp Gly Glu Pro Ile Arg Leu Arg
            35                  40                  45

His Leu Tyr Thr Ala Gly Pro His Gly Leu Ser Ser Cys Phe Leu Arg
        50                  55                  60

Ile Arg Ala Asp Gly Ser Val Asp Cys Ala Arg Gly Gln Ser Ala His
65                  70                  75                  80
```

```
Ser Leu Leu Glu Ile Arg Ala Val Ala Leu Arg Thr Val Ala Ile Lys
                85                  90                  95

Gly Val His Ser Val Arg Tyr Leu Cys Met Gly Ala Asp Gly Arg Met
            100                 105                 110

Gln Gly Leu Leu Arg Tyr Ser Glu Glu Asp Cys Ala Phe Glu Glu Glu
        115                 120                 125

Ile Arg Pro Asp Gly Tyr Asn Val Tyr Arg Ser Glu Lys His Arg Leu
    130                 135                 140

Pro Val Ser Leu Ser Ser Ala Arg Gln Arg Gln Leu Tyr Lys Gly Arg
145                 150                 155                 160

Gly Phe Leu Pro Leu Ser His Phe Leu Pro Met Leu Pro Val Thr Pro
                165                 170                 175

Ala Glu Thr Gly Asp Leu Arg Asp His Leu Glu Ser Asp Met Phe Ala
            180                 185                 190

Ser Pro Leu Glu Thr Asp Ser Met Asp Pro Phe Gly Ile Ala Thr Arg
        195                 200                 205

Leu Gly Val Val Lys Ser Pro Ser Phe Gln Lys
    210                 215

<210> SEQ ID NO 9
<211> LENGTH: 138
<212> TYPE: PRT
<213> ORGANISM: Choloepus hoffmanni

<400> SEQUENCE: 9

Leu Leu Glu Met Lys Ala Val Ala Leu Arg Ala Val Ala Ile Lys Gly
1               5                   10                  15

Val His Ser Ala Leu Tyr Leu Cys Met Asn Ala Asp Gly Ser Leu His
            20                  25                  30

Gly Leu Pro Arg Tyr Ser Ala Glu Asp Cys Ala Phe Glu Glu Glu Ile
        35                  40                  45

Arg Pro Asp Gly Tyr Asn Val Tyr Trp Ser Arg Lys His Gly Leu Pro
    50                  55                  60

Val Ser Leu Ser Ser Ala Lys Gln Arg Gln Leu Tyr Lys Gly Arg Gly
65                  70                  75                  80

Phe Leu Pro Leu Ser His Phe Leu Pro Met Leu Pro Met Thr Pro Ala
                85                  90                  95

Glu Pro Ala Asp Pro Gly Asp Val Glu Ser Asp Met Phe Ser Ser
            100                 105                 110

Pro Leu Glu Thr Asp Ser Met Asp Pro Phe Gly Ile Ala Ser Arg Leu
        115                 120                 125

Glu Leu Val Asn Ser Pro Ser Phe Gln Thr
    130                 135

<210> SEQ ID NO 10
<211> LENGTH: 205
<212> TYPE: PRT
<213> ORGANISM: Ailuropoda melanoleuca

<400> SEQUENCE: 10

Val Leu Ala Gly Leu Cys Leu Val Ala Gly Arg Pro Leu Ala Phe
1               5                   10                  15

Ser Asp Ala Gly Pro His Val His Tyr Gly Trp Gly Glu Pro Ile Arg
            20                  25                  30

Leu Arg His Leu Tyr Thr Ala Gly Pro His Gly Leu Ser Ser Cys Phe
        35                  40                  45
```

```
Leu Arg Ile Arg Ala Asp Gly Val Asp Cys Ala Arg Gly Gln Ser
 50                  55                  60

Ala His Ser Leu Val Glu Ile Arg Ala Val Ala Leu Arg Thr Val Ala
 65                  70                  75                  80

Ile Lys Gly Val His Ser Val Arg Tyr Leu Cys Met Gly Ala Asp Gly
                 85                  90                  95

Arg Met Gln Gly Leu Pro Gln Tyr Ser Ala Gly Asp Cys Ala Phe Glu
            100                 105                 110

Glu Glu Ile Arg Pro Asp Gly Tyr Asn Val Tyr Arg Ser Lys Lys His
        115                 120                 125

Arg Leu Pro Val Ser Leu Ser Gly Ala Lys Gln Arg Gln Leu Tyr Lys
    130                 135                 140

Asp Arg Gly Phe Leu Pro Leu Ser His Phe Leu Pro Met Leu Pro Gly
145                 150                 155                 160

Ser Pro Ala Glu Pro Arg Asp Leu Gln Asp His Ala Glu Ser Asp Gly
                165                 170                 175

Phe Ser Ala Pro Leu Glu Thr Asp Ser Met Asp Pro Phe Gly Ile Ala
            180                 185                 190

Thr Lys Met Gly Leu Val Lys Ser Pro Ser Phe Gln Lys
        195                 200                 205

<210> SEQ ID NO 11
<211> LENGTH: 218
<212> TYPE: PRT
<213> ORGANISM: Sus scrofa

<400> SEQUENCE: 11

Met Arg Ser Ala Pro Ser Arg Cys Ala Val Val Arg Ala Leu Val Leu
 1               5                  10                  15

Ala Gly Leu Trp Leu Ala Ala Ala Gly Arg Pro Leu Ala Phe Ser Asp
                 20                  25                  30

Ala Gly Pro His Val His Tyr Gly Trp Gly Glu Ser Val Arg Leu Arg
             35                  40                  45

His Leu Tyr Thr Ala Ser Pro His Gly Val Ser Ser Cys Phe Leu Arg
 50                  55                  60

Ile His Ser Asp Gly Pro Val Asp Cys Ala Pro Gly Gln Ser Ala His
 65                  70                  75                  80

Ser Leu Met Glu Ile Arg Ala Val Ala Leu Ser Thr Val Ala Ile Lys
                 85                  90                  95

Gly Glu Arg Ser Arg Tyr Leu Cys Met Gly Ala Asp Gly Lys Met Gln
            100                 105                 110

Gly Gln Thr Gln Tyr Ser Asp Glu Asp Cys Ala Phe Glu Glu Glu Ile
        115                 120                 125

Arg Pro Asp Gly Tyr Asn Val Tyr Trp Ser Lys Lys His His Leu Pro
    130                 135                 140

Val Ser Leu Ser Ser Ala Arg Gln Arg Gln Leu Tyr Lys Gly Arg Gly
145                 150                 155                 160

Phe Leu Pro Leu Ser His Phe Leu Pro Met Leu Ser Thr Leu Pro Ala
                165                 170                 175

Glu Pro Glu Asp Leu Gln Asp Pro Phe Lys Ser Asp Leu Phe Ser Leu
            180                 185                 190

Pro Leu Glu Thr Asp Ser Met Asp Pro Phe Arg Ile Ala Ala Lys Leu
        195                 200                 205

Gly Ala Val Lys Ser Pro Ser Phe Tyr Lys
    210                 215
```

-continued

```
            210                 215

<210> SEQ ID NO 12
<211> LENGTH: 218
<212> TYPE: PRT
<213> ORGANISM: Bos Taurus

<400> SEQUENCE: 12

Met Arg Ser Ala Pro Ser Arg Cys Ala Val Ala Arg Ala Leu Val Leu
1               5                   10                  15

Ala Gly Leu Trp Leu Ala Ala Gly Arg Pro Leu Ala Phe Ser Asp
            20                  25                  30

Ala Gly Pro His Val His Tyr Gly Trp Gly Glu Ser Val Arg Leu Arg
            35                  40                  45

His Leu Tyr Thr Ala Gly Pro Gln Gly Leu Tyr Ser Cys Phe Leu Arg
        50                  55                  60

Ile His Ser Asp Gly Ala Val Asp Cys Ala Gln Val Gln Ser Ala His
65                  70                  75                  80

Ser Leu Met Glu Ile Arg Ala Val Ala Leu Ser Thr Val Ala Ile Lys
                85                  90                  95

Gly Glu Arg Ser Val Leu Tyr Leu Cys Met Asp Ala Asp Gly Lys Met
            100                 105                 110

Gln Gly Leu Thr Gln Tyr Ser Ala Glu Asp Cys Ala Phe Glu Glu Glu
        115                 120                 125

Ile Arg Pro Asp Gly Tyr Asn Val Tyr Trp Ser Arg Lys His His Leu
    130                 135                 140

Pro Val Ser Leu Ser Ser Arg Gln Arg Gln Leu Phe Lys Ser Arg
145                 150                 155                 160

Gly Phe Leu Pro Leu Ser His Phe Leu Pro Met Leu Ser Thr Ile Pro
                165                 170                 175

Ala Glu Pro Glu Asp Leu Gln Glu Pro Leu Lys Pro Asp Phe Phe Leu
            180                 185                 190

Pro Leu Lys Thr Asp Ser Met Asp Pro Phe Gly Leu Ala Thr Lys Leu
        195                 200                 205

Gly Ser Val Lys Ser Pro Ser Phe Tyr Asn
    210                 215

<210> SEQ ID NO 13
<211> LENGTH: 192
<212> TYPE: PRT
<213> ORGANISM: Canis lupus familiaris

<400> SEQUENCE: 13

Leu Ala Phe Ser Asp Ala Gly Pro His Val His Ser Phe Trp Gly Glu
1               5                   10                  15

Pro Ile Arg Leu Arg His Leu Tyr Thr Ala Gly Pro His Gly Leu Ser
            20                  25                  30

Ser Cys Phe Leu Arg Ile Arg Ala Asp Gly Gly Val Asp Cys Ala Arg
        35                  40                  45

Gly Gln Ser Ala His Ser Leu Met Glu Met Arg Ala Val Ala Leu Arg
    50                  55                  60

Thr Val Ala Ile Lys Gly Val His Ser Gly Arg Tyr Leu Cys Met Gly
65                  70                  75                  80

Ala Asp Gly Arg Met Gln Gly Leu Pro Gln Tyr Ser Ala Gly Asp Cys
                85                  90                  95

Thr Phe Glu Glu Glu Ile Arg Pro Asp Gly Tyr Asn Val Tyr Trp Ser
```

```
                    100                 105                 110
Lys Lys His His Leu Pro Ile Ser Leu Ser Ser Ala Lys Gln Arg Gln
        115                 120                 125

Leu Tyr Lys Gly Arg Gly Phe Leu Pro Leu Ser His Phe Leu Pro Ile
        130                 135                 140

Leu Pro Gly Ser Pro Thr Glu Pro Arg Asp Leu Glu Asp His Val Glu
145                 150                 155                 160

Ser Asp Gly Phe Ser Ala Ser Leu Glu Thr Asp Ser Met Asp Pro Phe
                165                 170                 175

Gly Ile Ala Thr Lys Ile Gly Leu Val Lys Ser Pro Ser Phe Gln Lys
                180                 185                 190

<210> SEQ ID NO 14
<211> LENGTH: 218
<212> TYPE: PRT
<213> ORGANISM: Oryctolagus cuniculus

<400> SEQUENCE: 14

Met Arg Arg Ala Pro Ser Gly Gly Ala Ala Arg Ala Leu Val Leu
1               5                   10                  15

Ala Gly Leu Trp Leu Ala Ala Ala Arg Pro Leu Ala Leu Ser Asp
                20                  25                  30

Ala Gly Pro His Leu His Tyr Gly Trp Gly Glu Pro Val Arg Leu Arg
                35                  40                  45

His Leu Tyr Ala Thr Ser Ala His Gly Val Ser His Cys Phe Leu Arg
        50                  55                  60

Ile Arg Ala Asp Gly Ala Val Asp Cys Glu Arg Ser Gln Ser Ala His
65                  70                  75                  80

Ser Leu Leu Glu Ile Arg Ala Val Ala Leu Arg Thr Val Ala Phe Lys
                85                  90                  95

Gly Val His Ser Ser Arg Tyr Leu Cys Met Gly Ala Asp Gly Arg Met
                100                 105                 110

Arg Gly Gln Leu Gln Tyr Ser Glu Glu Asp Cys Ala Phe Gln Glu Glu
        115                 120                 125

Ile Ser Ser Gly Tyr Asn Val Tyr Arg Ser Thr Thr His His Leu Pro
        130                 135                 140

Val Ser Leu Ser Ser Ala Lys Gln Arg His Leu Tyr Lys Thr Arg Gly
145                 150                 155                 160

Phe Leu Pro Leu Ser His Phe Leu Pro Val Leu Pro Leu Ala Ser Glu
                165                 170                 175

Glu Thr Ala Ala Leu Gly Asp His Pro Glu Ala Asp Leu Phe Ser Pro
                180                 185                 190

Pro Leu Glu Thr Asp Ser Met Asp Pro Phe Gly Met Ala Thr Lys Leu
        195                 200                 205

Gly Pro Val Lys Ser Pro Ser Phe Gln Lys
    210                 215

<210> SEQ ID NO 15
<211> LENGTH: 215
<212> TYPE: PRT
<213> ORGANISM: Pteropus vampyrus

<400> SEQUENCE: 15

Met Arg Ser Pro Cys Ala Val Ala Arg Ala Leu Val Leu Ala Gly Leu
1               5                   10                  15

Trp Leu Ala Ser Ala Ala Gly Pro Leu Ala Leu Ser Asp Ala Gly Pro
```

```
                     20                  25                  30
His Val His Tyr Gly Trp Gly Glu Ala Ile Arg Leu Arg His Leu Tyr
             35                  40                  45
Thr Ala Gly Pro His Gly Pro Ser Ser Cys Phe Leu Arg Ile Arg Ala
 50                  55                  60
Asp Gly Ala Val Asp Cys Ala Arg Gly Gln Ser Ala His Ser Leu Val
 65                  70                  75                  80
Glu Ile Arg Ala Val Ala Leu Arg Asn Val Ala Ile Lys Gly Val His
                 85                  90                  95
Ser Val Arg Tyr Leu Cys Met Gly Ala Asp Gly Arg Met Leu Gly Leu
            100                 105                 110
Leu Gln Tyr Ser Ala Asp Asp Cys Ala Phe Glu Glu Glu Ile Arg Pro
            115                 120                 125
Asp Gly Tyr Asn Val Tyr His Ser Lys Lys His Leu Pro Val Ser
        130                 135                 140
Leu Ser Ser Ala Lys Gln Arg Gln Leu Tyr Lys Asp Arg Gly Phe Leu
145                 150                 155                 160
Pro Leu Ser His Phe Leu Pro Met Leu Pro Arg Ser Pro Thr Glu Pro
                165                 170                 175
Glu Asn Phe Glu Asp His Leu Glu Ala Asp Thr Phe Ser Ser Leu Glu
            180                 185                 190
Thr Asp Asp Met Asp Pro Phe Gly Ile Ala Ser Lys Leu Gly Leu Glu
            195                 200                 205
Glu Ser Pro Ser Phe Gln Lys
        210                 215

<210> SEQ ID NO 16
<211> LENGTH: 219
<212> TYPE: PRT
<213> ORGANISM: Tursiops truncates

<400> SEQUENCE: 16

Met Arg Ser Ala Pro Ser Arg Cys Ala Val Ala Arg Ala Leu Val Leu
 1               5                  10                  15
Ala Gly Leu Trp Leu Ala Ala Gly Arg Pro Leu Ala Phe Ser Asp
                 20                  25                  30
Ala Gly Pro His Val His Tyr Gly Trp Gly Glu Ser Val Arg Leu Arg
             35                  40                  45
His Leu Tyr Thr Ala Gly Pro Gln Gly Leu Ser Ser Cys Phe Leu Arg
 50                  55                  60
Ile His Ser Asp Gly Ala Val Asp Cys Ala Pro Val Gln Ser Ala His
 65                  70                  75                  80
Ser Leu Met Glu Ile Arg Ala Val Ala Leu Ser Thr Val Ala Ile Lys
                 85                  90                  95
Gly Glu Arg Ser Val Leu Tyr Leu Cys Met Gly Ala Asp Gly Lys Met
            100                 105                 110
Gln Gly Leu Ser Gln Tyr Ser Ala Glu Asp Cys Ala Phe Glu Glu Glu
            115                 120                 125
Ile Arg Pro Asp Gly Tyr Asn Val Tyr Trp Ser Lys Lys His His Leu
        130                 135                 140
Pro Val Ser Leu Ser Ser Ala Arg Gln Arg Gln Leu Phe Lys Gly Arg
145                 150                 155                 160
Gly Phe Leu Pro Leu Ser His Phe Leu Pro Met Leu Ser Thr Ile Pro
                165                 170                 175
```

Thr Glu Pro Asp Glu Ile Gln Asp His Leu Lys Pro Asp Leu Phe Ala
            180                 185                 190

Leu Pro Leu Lys Thr Asp Ser Met Asp Pro Phe Gly Leu Ala Thr Lys
            195                 200                 205

Leu Gly Val Val Lys Ser Pro Ser Phe Tyr Lys
            210                 215

<210> SEQ ID NO 17
<211> LENGTH: 219
<212> TYPE: PRT
<213> ORGANISM: Myotis lucifugus

<400> SEQUENCE: 17

Met Gln Ser Ala Trp Ser Arg Arg Val Val Ala Arg Ala Leu Val Leu
1               5                   10                  15

Ala Ser Leu Gly Leu Ala Ser Ala Gly Gly Pro Leu Gly Leu Ser Asp
            20                  25                  30

Ala Gly Pro His Val His Tyr Gly Trp Gly Glu Ser Ile Arg Leu Arg
            35                  40                  45

His Leu Tyr Thr Ser Gly Pro His Gly Pro Ser Ser Cys Phe Leu Arg
    50                  55                  60

Ile Arg Ala Asp Gly Ala Val Asp Cys Ala Arg Gly Gln Ser Ala His
65                  70                  75                  80

Ser Leu Val Glu Ile Arg Ala Val Ala Leu Arg Lys Val Ala Ile Lys
                85                  90                  95

Gly Val His Ser Ala Leu Tyr Leu Cys Met Gly Gly Asp Gly Arg Met
            100                 105                 110

Leu Gly Leu Pro Gln Phe Ser Pro Glu Asp Cys Ala Phe Glu Glu Glu
            115                 120                 125

Ile Arg Pro Asp Gly Tyr Asn Val Tyr Arg Ser Gln Lys His Gln Leu
            130                 135                 140

Pro Val Ser Leu Ser Ser Ala Arg Gln Arg Gln Leu Phe Lys Ala Arg
145                 150                 155                 160

Gly Phe Leu Pro Leu Ser His Phe Leu Pro Met Leu Pro Ser Ser Pro
                165                 170                 175

Ala Gly Pro Val Pro Arg Glu Arg Pro Ser Glu Pro Asp Glu Phe Ser
            180                 185                 190

Ser Pro Leu Glu Thr Asp Ser Met Asp Pro Phe Gly Ile Ala Asn Asn
            195                 200                 205

Leu Arg Leu Val Arg Ser Pro Ser Phe Gln Glu
            210                 215

<210> SEQ ID NO 18
<211> LENGTH: 185
<212> TYPE: PRT
<213> ORGANISM: Ornithorhynchus anatinus

<400> SEQUENCE: 18

Met Leu Ser Cys Val Val Leu Pro Ser Leu Leu Glu Ile Lys Ala Val
1               5                   10                  15

Ala Val Arg Thr Val Ala Ile Lys Gly Val His Ile Ser Arg Tyr Leu
            20                  25                  30

Cys Met Glu Glu Asp Gly Lys Thr Pro Trp Ala Arg Leu Leu Glu Ile
            35                  40                  45

Lys Ala Val Ala Val Arg Thr Val Ala Ile Lys Gly Val His Ser Ser
    50                  55                  60

```
Arg Tyr Leu Cys Met Glu Glu Asp Gly Lys Leu His Gly Gln Ile Trp
 65                  70                  75                  80

Tyr Ser Ala Glu Asp Cys Ala Phe Glu Glu Ile Arg Pro Asp Gly
                 85                  90                  95

Tyr Asn Val Tyr Lys Ser Lys Lys Tyr Gly Val Pro Val Ser Leu Ser
                100                 105                 110

Ser Ala Lys Gln Arg Gln Gln Phe Lys Gly Arg Asp Phe Leu Pro Leu
            115                 120                 125

Ser Arg Phe Leu Pro Met Ile Asn Thr Val Pro Val Glu Pro Ala Glu
        130                 135                 140

Phe Gly Asp Tyr Ala Asp Tyr Phe Glu Ser Asp Ile Phe Ser Ser Pro
145                 150                 155                 160

Leu Glu Thr Asp Ser Met Asp Pro Phe Arg Ile Ala Pro Lys Leu Ser
                165                 170                 175

Pro Val Lys Ser Pro Ser Phe Gln Lys
            180                 185

<210> SEQ ID NO 19
<211> LENGTH: 212
<212> TYPE: PRT
<213> ORGANISM: Monodelphis domestica

<400> SEQUENCE: 19

Met Ala Gln Leu Leu Ala Pro Leu Leu Thr Leu Ala Ala Leu Trp Leu
 1               5                  10                  15

Ala Pro Thr Ala Arg Ala Arg Pro Leu Val Asp Ala Gly Pro His Val
                20                  25                  30

Tyr Tyr Gly Trp Gly Glu Pro Ile Arg Leu Arg His Leu Tyr Thr Ala
             35                  40                  45

Asn Arg His Gly Leu Ala Ser Phe Ser Phe Leu Arg Ile His Arg Asp
 50                  55                  60

Gly Arg Val Asp Gly Ser Arg Ser Gln Ser Ala Leu Ser Leu Leu Glu
 65                  70                  75                  80

Ile Lys Ala Val Ala Leu Arg Met Val Ala Ile Lys Gly Val His Ser
                 85                  90                  95

Ser Arg Tyr Leu Cys Met Gly Asp Ala Gly Lys Leu Gln Gly Ser Val
                100                 105                 110

Arg Phe Ser Ala Glu Asp Cys Thr Phe Glu Glu Gln Ile Arg Pro Asp
            115                 120                 125

Gly Tyr Asn Val Tyr Gln Ser Pro Lys Tyr Asn Leu Pro Val Ser Leu
        130                 135                 140

Cys Thr Asp Lys Gln Arg Gln Ala His Gly Lys Glu His Leu Pro
145                 150                 155                 160

Leu Ser His Phe Leu Pro Met Ile Asn Ala Ile Pro Leu Glu Ala Glu
                165                 170                 175

Glu Pro Glu Gly Pro Arg Met Leu Ala Ala Pro Leu Glu Thr Asp Ser
            180                 185                 190

Met Asp Pro Phe Gly Leu Thr Ser Lys Leu Leu Pro Val Lys Ser Pro
        195                 200                 205

Ser Phe Gln Lys
        210

<210> SEQ ID NO 20
<211> LENGTH: 220
<212> TYPE: PRT
<213> ORGANISM: Anolis carolinensis
```

<400> SEQUENCE: 20

```
Met Cys Arg Arg Ala Leu Pro Leu Leu Gly Ala Leu Leu Gly Leu Ala
1               5                   10                  15

Ala Val Ala Ser Arg Ala Leu Pro Leu Thr Asp Ala Gly Pro His Val
            20                  25                  30

Ser Tyr Gly Trp Gly Glu Pro Val Arg Leu Arg His Leu Tyr Thr Ala
        35                  40                  45

Gly Arg Gln Gly Leu Phe Ser Gln Phe Leu Arg Ile His Ala Asp Gly
    50                  55                  60

Arg Val Asp Gly Ala Gly Ser Gln Asn Arg Gln Ser Leu Leu Glu Ile
65                  70                  75                  80

Arg Ala Val Ser Leu Arg Ala Val Ala Leu Lys Gly Val His Ser Ser
                85                  90                  95

Arg Tyr Leu Cys Met Glu Glu Asp Gly Arg Leu Arg Gly Met Leu Arg
            100                 105                 110

Tyr Ser Ala Glu Asp Cys Ser Phe Glu Glu Met Arg Pro Asp Gly
        115                 120                 125

Tyr Asn Ile Tyr Lys Ser Lys Lys Tyr Gly Val Leu Val Ser Leu Ser
    130                 135                 140

Asn Ala Arg Gln Arg Gln Gln Phe Lys Gly Lys Asp Phe Leu Pro Leu
145                 150                 155                 160

Ser His Phe Leu Pro Met Ile Asn Thr Val Pro Val Glu Ser Ala Asp
                165                 170                 175

Phe Gly Glu Tyr Gly Asp Thr Arg Gln His Tyr Glu Ser Asp Ile Phe
            180                 185                 190

Ser Ser Arg Leu Glu Thr Asp Ser Met Asp Pro Phe Gly Leu Thr Ser
        195                 200                 205

Glu Val Ser Ser Val Gln Ser Pro Ser Phe Gly Lys
    210                 215                 220
```

<210> SEQ ID NO 21
<211> LENGTH: 179
<212> TYPE: PRT
<213> ORGANISM: Ochotona princeps

<400> SEQUENCE: 21

```
Val Arg Ser Arg Gly Ala Met Ala Arg Ala Leu Val Leu Ala Thr Leu
1               5                   10                  15

Trp Leu Ala Ala Thr Gly Arg Pro Leu Ala Leu Ser Asp Ala Gly Pro
            20                  25                  30

His Leu His Tyr Gly Trp Gly Glu Pro Ile Arg Leu Arg His Leu Tyr
        35                  40                  45

Ala Thr Ser Ala His Gly Leu Ser His Cys Phe Leu Arg Ile Arg Thr
    50                  55                  60

Asp Gly Thr Val Asp Cys Glu Arg Ser Gln Ser Ala His Leu Gln Tyr
65                  70                  75                  80

Ser Glu Glu Asp Cys Ala Phe Glu Glu Ile Ser Ser Gly Tyr Asn
                85                  90                  95

Val Tyr Arg Ser Arg Arg Tyr Gln Leu Pro Val Ser Leu Gly Ser Ala
            100                 105                 110

Arg Gln Arg Gln Leu Gln Arg Ser Arg Gly Phe Leu Pro Leu Ser His
        115                 120                 125

Phe Leu Pro Val Leu Pro Ala Ala Ser Glu Glu Val Ala Ala Pro Ala
    130                 135                 140
```

Asp His Pro Gln Ala Asp Pro Phe Ser Pro Leu Glu Thr Asp Ser Met
145                 150                 155                 160

Asp Pro Phe Gly Met Ala Thr Lys Arg Gly Leu Val Lys Ser Pro Ser
                165                 170                 175

Phe Gln Lys

<210> SEQ ID NO 22
<211> LENGTH: 221
<212> TYPE: PRT
<213> ORGANISM: Cavia porcellus

<400> SEQUENCE: 22

Met Trp Ser Ala Pro Ser Gly Cys Val Val Ile Arg Ala Leu Val Leu
1               5                   10                  15

Ala Gly Leu Trp Leu Ala Val Ala Gly Arg Pro Leu Ala Arg Arg Ser
                20                  25                  30

Leu Ala Leu Ser Asp Gln Gly Pro His Leu Tyr Tyr Gly Trp Asp Gln
            35                  40                  45

Pro Ile Arg Leu Arg His Leu Tyr Ala Ala Gly Pro Tyr Gly Arg Ser
50                  55                  60

Arg Cys Phe Leu Arg Ile His Thr Asp Gly Ala Val Asp Cys Val Glu
65                  70                  75                  80

Glu Gln Ser Glu His Cys Leu Leu Glu Ile Arg Ala Val Ala Leu Glu
                85                  90                  95

Thr Val Ala Ile Lys Asp Ile Asn Ser Val Arg Tyr Leu Cys Met Gly
            100                 105                 110

Pro Asp Gly Arg Met Arg Gly Leu Pro Trp Tyr Ser Glu Glu Asp Cys
        115                 120                 125

Ala Phe Lys Glu Glu Ile Ser Tyr Pro Gly Tyr Ser Val Tyr Arg Ser
    130                 135                 140

Gln Lys His His Leu Pro Ile Val Leu Ser Ser Val Lys Gln Arg Gln
145                 150                 155                 160

Gln Tyr Gln Ser Lys Gly Val Val Pro Leu Ser Tyr Phe Leu Pro Met
                165                 170                 175

Leu Pro Lys Ala Ser Val Glu Pro Ser Asp Glu Glu Ser Ser Val
            180                 185                 190

Phe Ser Leu Pro Leu Lys Thr Asp Ser Met Asp Pro Phe Gly Met Ala
            195                 200                 205

Ser Glu Ile Gly Leu Val Lys Ser Pro Ser Phe Gln Lys
210                 215                 220

<210> SEQ ID NO 23
<211> LENGTH: 196
<212> TYPE: PRT
<213> ORGANISM: Tupaia belangeri

<400> SEQUENCE: 23

Met Arg Arg Thr Pro Ser Gly Phe Ala Val Ala Arg Val Leu Phe Leu
1               5                   10                  15

Gly Ser Leu Trp Leu Ala Ala Ala Gly Ser Pro Leu Ala Leu Ser Asp
                20                  25                  30

Ala Gly Pro His Val Asn Tyr Gly Trp Asp Glu Ser Ile Arg Leu Arg
            35                  40                  45

His Leu Tyr Thr Ala Ser Pro His Gly Ser Thr Ser Cys Phe Leu Arg
        50                  55                  60

```
Ile Arg Asp Asp Gly Ser Val Asp Cys Ala Arg Gly Gln Ser Leu His
 65                  70                  75                  80

Ser Leu Leu Glu Ile Lys Ala Val Ala Leu Gln Thr Val Ala Ile Lys
                 85                  90                  95

Gly Val Tyr Ser Val Arg Tyr Leu Cys Met Asp Ala Asp Gly Arg Met
            100                 105                 110

Gln Gly Leu Ser Thr Lys His Gly Leu Pro Val Ser Leu Ser Ser Ala
        115                 120                 125

Lys Gln Arg Gln Leu Leu Thr Val Arg Gly Phe Pro Ser Leu Pro His
130                 135                 140

Phe Leu Leu Met Met Ala Lys Thr Ser Ala Gly Pro Gly Asn Pro Arg
145                 150                 155                 160

Asp His Pro Gly Ser Asn Thr Phe Ser Leu Pro Leu Glu Thr Asp Ser
                165                 170                 175

Met Asp Pro Phe Gly Met Thr Thr Arg His Gly Leu Val Lys Ser Pro
            180                 185                 190

Ser Phe Gln Asn
        195

<210> SEQ ID NO 24
<211> LENGTH: 218
<212> TYPE: PRT
<213> ORGANISM: Rattus norvegicus

<400> SEQUENCE: 24

Met Ala Arg Lys Trp Ser Gly Arg Ile Val Ala Arg Ala Leu Val Leu
 1               5                  10                  15

Ala Thr Leu Trp Leu Ala Val Ser Gly Arg Pro Leu Val Gln Gln Ser
                 20                  25                  30

Gln Ser Val Ser Asp Glu Gly Pro Leu Phe Leu Tyr Gly Trp Gly Lys
            35                  40                  45

Ile Thr Arg Leu Gln Tyr Leu Tyr Ser Ala Gly Pro Tyr Val Ser Asn
        50                  55                  60

Cys Phe Leu Arg Ile Arg Ser Asp Gly Ser Val Asp Cys Glu Glu Asp
 65                  70                  75                  80

Gln Asn Glu Arg Asn Leu Leu Glu Phe Arg Ala Val Ala Leu Lys Thr
                 85                  90                  95

Ile Ala Ile Lys Asp Val Ser Ser Val Arg Tyr Leu Cys Met Ser Ala
            100                 105                 110

Asp Gly Lys Ile Tyr Gly Leu Ile Arg Tyr Ser Glu Glu Asp Cys Thr
        115                 120                 125

Phe Arg Glu Glu Met Asp Cys Leu Gly Tyr Asn Gln Tyr Arg Ser Met
130                 135                 140

Lys His His Leu His Ile Ile Phe Ile Lys Ala Lys Pro Arg Glu Gln
145                 150                 155                 160

Leu Gln Gly Gln Lys Pro Ser Asn Phe Ile Pro Ile Phe His Arg Ser
                165                 170                 175

Phe Phe Glu Ser Thr Asp Gln Leu Arg Ser Lys Met Phe Ser Leu Pro
            180                 185                 190

Leu Glu Ser Asp Ser Met Asp Pro Phe Arg Met Val Glu Asp Val Asp
        195                 200                 205

His Leu Val Lys Ser Pro Ser Phe Gln Lys
210                 215

<210> SEQ ID NO 25
```

<211> LENGTH: 218
<212> TYPE: PRT
<213> ORGANISM: Mus musculus

<400> SEQUENCE: 25

```
Met Ala Arg Lys Trp Asn Gly Arg Ala Val Arg Ala Leu Val Leu
1               5                   10                  15

Ala Thr Leu Trp Leu Ala Val Ser Gly Arg Pro Leu Ala Gln Gln Ser
            20                  25                  30

Gln Ser Val Ser Asp Glu Asp Pro Leu Phe Leu Tyr Gly Trp Gly Lys
        35                  40                  45

Ile Thr Arg Leu Gln Tyr Leu Tyr Ser Ala Gly Pro Tyr Val Ser Asn
    50                  55                  60

Cys Phe Leu Arg Ile Arg Ser Asp Gly Ser Val Asp Cys Glu Glu Asp
65                  70                  75                  80

Gln Asn Glu Arg Asn Leu Leu Glu Phe Arg Ala Val Ala Leu Lys Thr
                85                  90                  95

Ile Ala Ile Lys Asp Val Ser Ser Val Arg Tyr Leu Cys Met Ser Ala
            100                 105                 110

Asp Gly Lys Ile Tyr Gly Leu Ile Arg Tyr Ser Glu Glu Asp Cys Thr
        115                 120                 125

Phe Arg Glu Glu Met Asp Cys Leu Gly Tyr Asn Gln Tyr Arg Ser Met
    130                 135                 140

Lys His His Leu His Ile Ile Phe Ile Gln Ala Lys Pro Arg Glu Gln
145                 150                 155                 160

Leu Gln Asp Gln Lys Pro Ser Asn Phe Ile Pro Val Phe His Arg Ser
                165                 170                 175

Phe Phe Glu Thr Gly Asp Gln Leu Arg Ser Lys Met Phe Ser Leu Pro
            180                 185                 190

Leu Glu Ser Asp Ser Met Asp Pro Phe Arg Met Val Glu Asp Val Asp
        195                 200                 205

His Leu Val Lys Ser Pro Ser Phe Gln Lys
    210                 215
```

<210> SEQ ID NO 26
<211> LENGTH: 227
<212> TYPE: PRT
<213> ORGANISM: Gallus gallus

<400> SEQUENCE: 26

```
Met Gly Pro Ala Arg Pro Ala Ala Pro Gly Ala Ala Leu Ala Leu Leu
1               5                   10                  15

Gly Ile Ala Ala Ala Ala Ala Ala Arg Ser Leu Pro Leu Pro Asp
            20                  25                  30

Val Gly Gly Pro His Val Asn Tyr Gly Trp Gly Pro Ile Arg Leu
        35                  40                  45

Arg His Leu Leu His Arg Pro Gly Lys His Gly Leu Phe Ser Cys Phe
    50                  55                  60

Leu Arg Ile Gly Gly Asp Gly Arg Val Asp Ala Val Gly Ser Gln Ser
65                  70                  75                  80

Pro Gln Ser Leu Leu Glu Ile Arg Ala Val Ala Val Arg Thr Val Ala
                85                  90                  95

Ile Lys Gly Val Gln Ser Ser Arg Tyr Leu Cys Met Asp Glu Ala Gly
            100                 105                 110

Arg Leu His Gly Gln Leu Ser Tyr Ser Ile Glu Asp Cys Ser Phe Glu
        115                 120                 125
```

```
Glu Glu Ile Arg Pro Asp Gly Tyr Asn Val Tyr Lys Ser Lys Lys Tyr
            130                 135                 140

Gly Ile Ser Val Ser Leu Ser Ser Ala Lys Gln Arg Gln Gln Phe Lys
145                 150                 155                 160

Gly Lys Asp Phe Leu Pro Leu Ser His Phe Leu Pro Met Ile Asn Thr
                165                 170                 175

Val Pro Val Glu Val Thr Asp Phe Gly Glu Tyr Gly Asp Tyr Ser Gln
                180                 185                 190

Ala Phe Glu Pro Glu Val Tyr Ser Ser Pro Leu Glu Thr Asp Ser Met
            195                 200                 205

Asp Pro Phe Gly Ile Thr Ser Lys Leu Ser Pro Val Lys Ser Pro Ser
    210                 215                 220

Phe Gln Lys
225

<210> SEQ ID NO 27
<211> LENGTH: 237
<212> TYPE: PRT
<213> ORGANISM: Taeniopygia guttata

<400> SEQUENCE: 27

Met Val Ile Ile Ser Asn Leu Tyr Leu Met Gln Asn Asp Val Met Met
1               5                   10                  15

Asn Met Arg Arg Ala Pro Leu Arg Val His Ala Ala Arg Ser Ser Ala
            20                  25                  30

Thr Pro Ala Ser Ala Leu Pro Leu Pro Pro Asp Ala Gly Pro His
        35                  40                  45

Leu Lys Tyr Gly Trp Gly Glu Pro Ile Arg Leu Arg His Leu Tyr Thr
    50                  55                  60

Ala Ser Lys His Gly Leu Phe Ser Cys Phe Leu Arg Ile Gly Ala Asp
65                  70                  75                  80

Gly Arg Val Asp Ala Ala Gly Ser Gln Ser Pro Gln Ser Leu Leu Glu
                85                  90                  95

Ile Arg Ala Val Ala Val Arg Thr Val Ala Ile Lys Gly Val Gln Ser
            100                 105                 110

Ser Arg Tyr Leu Cys Met Asp Glu Ala Gly Arg Leu His Gly Gln Leu
        115                 120                 125

Arg Asn Ser Thr Glu Asp Cys Ser Phe Glu Glu Ile Arg Pro Asp
    130                 135                 140

Gly Tyr Asn Val Tyr Arg Ser Lys Lys His Gly Ile Ser Val Ser Leu
145                 150                 155                 160

Ser Ser Ala Lys Gln Arg Gln Gln Phe Lys Gly Lys Asp Phe Leu Pro
                165                 170                 175

Leu Ser His Phe Leu Pro Met Ile Asn Thr Val Pro Met Glu Ser Ala
            180                 185                 190

Asp Phe Gly Glu Tyr Gly Asp Tyr Ser Gln Ala Phe Glu Ala Glu Ala
        195                 200                 205

Phe Ser Ser Pro Leu Glu Thr Asp Ser Met Asp Pro Phe Gly Ile Ala
    210                 215                 220

Ser Lys Leu Ser Leu Val Lys Ser Pro Ser Phe Gln Asn
225                 230                 235

<210> SEQ ID NO 28
<211> LENGTH: 210
<212> TYPE: PRT
```

<213> ORGANISM: Danio rerio

<400> SEQUENCE: 28

```
Met Leu Leu Leu Phe Val Thr Val Cys Gly Ser Ile Gly Val Glu
1               5                   10                  15

Ser Leu Pro Leu Pro Asp Ser Gly Pro His Leu Ala Asn Asp Trp Ser
            20                  25                  30

Glu Ala Val Arg Leu Arg His Leu Tyr Ala Ala Arg His Gly Leu His
        35                  40                  45

Leu Gln Ile Asn Thr Asp Gly Glu Ile Ile Gly Ser Thr Cys Lys Ala
    50                  55                  60

Arg Thr Val Ser Leu Met Glu Ile Trp Pro Val Asp Thr Gly Cys Val
65                  70                  75                  80

Ala Ile Lys Gly Val Ala Ser Ser Arg Phe Leu Cys Met Glu Arg Leu
                85                  90                  95

Gly Asn Leu Tyr Gly Ser His Ile Tyr Thr Lys Glu Asp Cys Ser Phe
            100                 105                 110

Leu Glu Arg Ile Leu Pro Asp Gly Tyr Asn Val Tyr Phe Ser Ser Lys
        115                 120                 125

His Gly Ala Leu Val Thr Leu Ser Gly Ala Lys Asn Lys Leu His Ser
    130                 135                 140

Asn Asp Gly Thr Ser Ala Ser Gln Phe Leu Pro Met Ile Asn Thr Leu
145                 150                 155                 160

Ser Glu Glu His Thr Lys Gln His Ser Gly Glu Gln His Ser Ser Val
                165                 170                 175

Asn His Gly Gln Asp His Gln Leu Gly Leu Glu Ile Asp Ser Met Asp
            180                 185                 190

Pro Phe Gly Lys Ile Ser Gln Ile Val Ile Gln Ser Pro Ser Phe Asn
        195                 200                 205

Lys Arg
    210
```

<210> SEQ ID NO 29
<211> LENGTH: 215
<212> TYPE: PRT
<213> ORGANISM: Xenopus (Silurana) tropicalis

<400> SEQUENCE: 29

```
Met Trp Lys Thr Leu Pro Trp Ile Leu Val Pro Met Met Val Ala Val
1               5                   10                  15

Leu Tyr Phe Leu Gly Gly Ala Glu Ser Leu Pro Leu Phe Asp Ala Gly
            20                  25                  30

Pro His Met Gln Asn Gly Trp Gly Glu Ser Ile Arg Ile Arg His Leu
        35                  40                  45

Tyr Thr Ala Arg Arg Phe Gly His Asp Ser Tyr Tyr Leu Arg Ile His
    50                  55                  60

Glu Asp Gly Arg Val Asp Gly Asp Arg Gln Gln Ser Met His Ser Leu
65                  70                  75                  80

Leu Glu Ile Arg Ala Ile Ala Val Gly Ile Val Ala Ile Lys Gly Tyr
                85                  90                  95

Arg Ser Ser Leu Tyr Leu Cys Met Gly Ser Glu Gly Lys Leu Tyr Gly
            100                 105                 110

Met His Ser Tyr Ser Gln Asp Asp Cys Ser Phe Glu Glu Glu Leu Leu
        115                 120                 125

Pro Asp Gly Tyr Asn Met Tyr Lys Ser Arg Lys His Gly Val Ala Val
```

```
            130                 135                 140
Ser Leu Ser Lys Glu Lys Gln Lys Gln Gln Tyr Lys Gly Lys Gly Tyr
145                 150                 155                 160

Leu Pro Leu Ser His Phe Leu Pro Val Ile Ser Trp Val Pro Met Glu
                165                 170                 175

Pro Thr Gly Asp Val Glu Asp Asp Ile Tyr Arg Phe Pro Phe Asn Thr
            180                 185                 190

Asp Thr Lys Ser Val Ile Asp Ser Leu Asp Thr Leu Gly Leu Met Asp
            195                 200                 205

Phe Ser Ser Tyr His Lys Lys
    210                 215

<210> SEQ ID NO 30
<211> LENGTH: 219
<212> TYPE: PRT
<213> ORGANISM: Otolemur garnettii

<400> SEQUENCE: 30

Met Pro Ser Gly Leu Arg Gly Arg Val Val Ala Gly Ala Leu Ala Leu
1               5                   10                  15

Ala Ser Phe Trp Leu Ala Val Ala Gly Arg Pro Leu Ala Phe Ser Asp
            20                  25                  30

Ala Gly Pro His Val His Tyr Gly Trp Gly Glu Pro Ile Arg Leu Arg
        35                  40                  45

His Leu Tyr Thr Ala Gly Pro His Gly Leu Ser Ser Cys Phe Leu Arg
    50                  55                  60

Val Arg Thr Asp Gly Ala Val Asp Cys Ala Arg Gly Gln Ser Ala His
65                  70                  75                  80

Ser Leu Leu Glu Ile Arg Ala Val Ala Leu Arg Thr Val Ala Ile Lys
                85                  90                  95

Gly Val His Ser Ala Arg Tyr Leu Cys Met Gly Ala Asp Gly Arg Met
            100                 105                 110

Gln Gly Leu Pro Gln Tyr Ser Glu Glu Asp Cys Ala Phe Glu Glu Glu
        115                 120                 125

Ile Arg Pro Asp Gly Tyr Asn Val Tyr Trp Ser Glu Lys His Arg Leu
    130                 135                 140

Pro Val Ser Leu Ser Ser Ala Arg Gln Arg Gln Leu Tyr Lys Gly Arg
145                 150                 155                 160

Gly Phe Leu Pro Leu Ser His Phe Leu Pro Met Leu Pro Val Thr Pro
                165                 170                 175

Ala Glu Pro Gly Asp Leu Arg Asp His Leu Glu Ser Asp Met Phe Ser
            180                 185                 190

Leu Pro Leu Glu Thr Asp Ser Met Asp Pro Phe Gly Ile Ala Thr Arg
            195                 200                 205

Leu Gly Val Val Lys Ser Pro Ser Phe Gln Lys
    210                 215

<210> SEQ ID NO 31
<211> LENGTH: 219
<212> TYPE: PRT
<213> ORGANISM: Felis catus

<400> SEQUENCE: 31

Met Arg Ser Ala Pro Ser Gln Cys Ala Val Thr Arg Ala Leu Val Leu
1               5                   10                  15

Ala Gly Leu Trp Leu Ala Ala Ala Gly Arg Pro Leu Ala Phe Ser Asp
```

```
            20                  25                  30
Ala Gly Pro His Val His Tyr Gly Trp Gly Glu Pro Ile Arg Leu Arg
            35                  40                  45
His Leu Tyr Thr Ala Gly Pro His Gly Leu Ser Ser Cys Phe Leu Arg
        50                  55                  60
Ile Arg Ala Asp Gly Val Asp Cys Ala Arg Ser Gln Ser Ala His
 65                  70                  75                  80
Ser Leu Val Glu Ile Arg Ala Val Ala Leu Arg Thr Val Ala Ile Lys
                85                  90                  95
Gly Val His Ser Val Arg Tyr Leu Cys Met Gly Ala Asp Gly Arg Met
            100                 105                 110
Gln Gly Leu Leu Gln Tyr Ser Ala Gly Asp Cys Ala Phe Gln Glu Glu
            115                 120                 125
Ile Arg Pro Asp Gly Tyr Asn Val Tyr Arg Ser Glu Lys His Arg Leu
            130                 135                 140
Pro Val Ser Leu Ser Ser Ala Ile Gln Arg Gln Leu Tyr Lys Gly Arg
145                 150                 155                 160
Gly Phe Leu Pro Leu Ser His Phe Leu Pro Met Leu Pro Gly Ser Pro
                165                 170                 175
Ala Glu Pro Arg Asp Leu Gln Asp His Val Glu Ser Glu Arg Phe Ser
            180                 185                 190
Ser Pro Leu Glu Thr Asp Ser Met Asp Pro Phe Gly Ile Ala Thr Lys
            195                 200                 205
Met Gly Leu Val Lys Ser Pro Ser Phe Gln Lys
    210                 215

<210> SEQ ID NO 32
<211> LENGTH: 223
<212> TYPE: PRT
<213> ORGANISM: Pelodiscus sinensis

<400> SEQUENCE: 32

Met Trp Arg Ser Leu Cys Lys Ser His Thr Ser Leu Ala Leu Leu Gly
 1               5                  10                  15
Leu Cys Phe Ala Val Val Val Arg Ser Leu Pro Phe Ser Asp Ala Gly
                20                  25                  30
Pro His Val Asn Tyr Gly Trp Gly Glu Pro Ile Arg Leu Arg His Leu
            35                  40                  45
Tyr Thr Ala Ser Arg His Gly Leu Phe Asn Tyr Phe Leu Arg Ile Ser
        50                  55                  60
Ser Asp Gly Lys Val Asp Gly Thr Ser Ile Gln Ser Pro His Ser Leu
 65                  70                  75                  80
Leu Glu Ile Arg Ala Val Ala Val Arg Thr Val Ala Ile Lys Gly Val
                85                  90                  95
His Ser Ser Arg Tyr Leu Cys Met Glu Glu Asp Gly Lys Leu His Gly
            100                 105                 110
Leu Leu Arg Tyr Ser Thr Glu Asp Cys Ser Phe Glu Glu Ile Arg
            115                 120                 125
Pro Asp Gly Tyr Asn Val Tyr Lys Ser Lys Tyr Gly Ile Ser Val
            130                 135                 140
Ser Leu Ser Ser Ala Lys Gln Arg Gln Phe Lys Gly Lys Asp Phe
145                 150                 155                 160
Leu Pro Leu Ser His Phe Leu Pro Met Ile Asn Thr Val Pro Val Glu
                165                 170                 175
```

```
Ser Met Asp Phe Gly Glu Tyr Gly Asp Tyr Ser His Thr Phe Glu Ser
            180                 185                 190

Asp Leu Phe Ser Ser Pro Leu Glu Thr Asp Ser Met Asp Pro Phe Gly
            195                 200                 205

Ile Thr Ser Lys Ile Ser Pro Val Lys Ser Pro Ser Phe Gln Lys
        210                 215                 220

<210> SEQ ID NO 33
<211> LENGTH: 217
<212> TYPE: PRT
<213> ORGANISM: Latimeria chalumnae

<400> SEQUENCE: 33

Met Leu Gln Ala Leu Tyr Asn Leu Cys Thr Ala Leu Val Leu Phe Lys
1               5                   10                  15

Leu Pro Phe Ala Met Val Gly Tyr Thr Leu Pro Ser Ala Asn Glu Gly
            20                  25                  30

Pro His Leu Asn Tyr Asp Trp Gly Glu Ser Val Arg Leu Lys His Leu
        35                  40                  45

Tyr Thr Ser Ser Lys His Gly Leu Ile Ser Tyr Phe Leu Gln Ile Asn
    50                  55                  60

Asp Asp Gly Lys Val Asp Gly Thr Thr Arg Ser Cys Tyr Ser Leu
65                  70                  75                  80

Leu Glu Ile Lys Ser Val Gly Pro Gly Val Leu Ala Ile Lys Gly Ile
                85                  90                  95

Gln Ser Ser Arg Tyr Leu Cys Val Gln Lys Asp Gly Lys Leu His Gly
            100                 105                 110

Ser Arg Thr Tyr Ser Ala Asp Asp Cys Ser Phe Lys Glu Asp Ile Leu
        115                 120                 125

Pro Asp Gly Tyr Thr Ile Tyr Val Ser Lys Lys His Gly Ser Val Val
    130                 135                 140

Asn Leu Ser Asn His Lys Gln Lys Arg Gln Asn Arg Arg Thr Leu
145                 150                 155                 160

Pro Pro Phe Ser Gln Phe Leu Pro Leu Met Asp Thr Ile Arg Val Glu
                165                 170                 175

Cys Met Asn Cys Gly Glu His Cys Asp Asp Asn Leu His Asp Glu Leu
            180                 185                 190

Glu Thr Gly Leu Ser Met Asp Pro Phe Glu Ser Thr Ser Lys Lys Ser
        195                 200                 205

Phe Gln Ser Pro Ser Phe His Asn Arg
    210                 215

<210> SEQ ID NO 34
<211> LENGTH: 219
<212> TYPE: PRT
<213> ORGANISM: Mustela putorius furo

<400> SEQUENCE: 34

Met Arg Ser Ala Ala Ser Arg Cys Ala Val Ala Arg Ala Leu Val Leu
1               5                   10                  15

Ala Gly Leu Trp Leu Ala Ala Gly Arg Pro Leu Ala Phe Ser Asp
            20                  25                  30

Ala Gly Pro His Val His Tyr Gly Trp Gly Glu Pro Ile Arg Leu Arg
        35                  40                  45

His Leu Tyr Thr Ala Gly Pro His Gly Leu Ser Ser Cys Phe Leu Arg
    50                  55                  60
```

```
Ile Arg Ala Asp Gly Gly Val Asp Cys Ala Arg Gly Gln Ser Ala His
 65                  70                  75                  80

Ser Leu Val Glu Ile Arg Ala Val Ala Leu Arg Thr Val Ala Ile Lys
                 85                  90                  95

Gly Val Tyr Ser Asp Arg Tyr Leu Cys Met Gly Ala Asp Gly Arg Met
            100                 105                 110

Gln Gly Leu Pro Gln Tyr Ser Ala Gly Asp Cys Ala Phe Glu Glu Glu
        115                 120                 125

Ile Arg Pro Asp Gly Tyr Asn Val Tyr Arg Ser Lys Lys His Arg Leu
    130                 135                 140

Pro Val Ser Leu Ser Ser Ala Lys Gln Arg Gln Leu Tyr Lys Asp Arg
145                 150                 155                 160

Gly Phe Leu Pro Leu Ser His Phe Leu Pro Met Leu Pro Gly Ser Leu
                165                 170                 175

Ala Glu Pro Arg Asp Leu Gln Asp His Val Glu Ala Asp Gly Phe Ser
            180                 185                 190

Ala Pro Leu Glu Thr Asp Ser Met Asp Pro Phe Gly Ile Ala Thr Lys
        195                 200                 205

Met Gly Leu Val Lys Ser Pro Ser Phe Gln Lys
    210                 215

<210> SEQ ID NO 35
<211> LENGTH: 218
<212> TYPE: PRT
<213> ORGANISM: Takifugu rubripes

<400> SEQUENCE: 35

Ser Ser Thr Arg Ile Ser Gly Asn Met Val Leu Leu Met Leu Pro Ile
  1               5                  10                  15

Thr Val Ala Asn Leu Phe Leu Cys Ala Gly Val Leu Ser Leu Pro Leu
             20                  25                  30

Leu Asp Gln Gly Ser His Phe Pro Gln Gly Trp Glu Gln Val Val Arg
         35                  40                  45

Phe Arg His Leu Tyr Ala Ala Ser Ala Gly Leu His Leu Leu Ile Thr
 50                  55                  60

Glu Glu Gly Ser Ile Gln Gly Ser Ala Asp Pro Thr Leu Tyr Ser Leu
 65                  70                  75                  80

Met Glu Ile Arg Pro Val Asp Pro Gly Cys Val Val Ile Arg Gly Ala
                 85                  90                  95

Ala Thr Thr Arg Phe Leu Cys Ile Glu Gly Ala Gly Arg Leu Tyr Ser
            100                 105                 110

Ser Gln Thr Tyr Ser Lys Asp Asp Cys Thr Phe Arg Glu Gln Ile Leu
        115                 120                 125

Ala Asp Gly Tyr Ser Val Tyr Arg Ser Val Gly His Gly Ala Leu Val
    130                 135                 140

Ser Leu Gly Asn Tyr Arg Gln Gln Leu Arg Gly Glu Asp Trp Ser Val
145                 150                 155                 160

Pro Thr Leu Ala Gln Phe Leu Pro Arg Ile Ser Ser Leu Asp Gln Asp
                165                 170                 175

Phe Lys Ala Ala Leu Asp Glu Thr Glu Lys Pro Glu Gln Thr Ala Pro
            180                 185                 190

Gln Arg Ser Glu Pro Val Asp Met Val Asp Ser Phe Gly Lys Leu Ser
        195                 200                 205

Gln Ile Ile His Ser Pro Ser Phe His Lys
    210                 215
```

<210> SEQ ID NO 36
<211> LENGTH: 94
<212> TYPE: PRT
<213> ORGANISM: Equus caballus

<400> SEQUENCE: 36

Ala Ala Gly Arg Pro Leu Ala Leu Ser Asp Ala Gly Pro His Val His
1               5                   10                  15

Tyr Gly Trp Gly Glu Pro Ile Arg Leu Arg His Leu Tyr Thr Ala Gly
            20                  25                  30

Pro His Gly Leu Ser Ser Cys Phe Leu Arg Ile Arg Ala Asp Gly Ala
        35                  40                  45

Val Asp Cys Ala Arg Gly Gln Ser Ala His Ser Leu Val Glu Ile Arg
50                  55                  60

Ala Val Ala Leu Arg Thr Val Ala Ile Lys Gly Val His Ser Val Arg
65                  70                  75                  80

Tyr Leu Cys Met Gly Ala Asp Gly Arg Met Gln Gly Leu Val
                85                  90

<210> SEQ ID NO 37
<211> LENGTH: 209
<212> TYPE: PRT
<213> ORGANISM: Oryzias latipes

<400> SEQUENCE: 37

Thr Met Leu Leu Ile Val Val Thr Ile Ser Thr Met Val Phe Ser Asp
1               5                   10                  15

Ser Gly Val Ser Ser Met Pro Leu Ser Asp His Gly Pro His Ile Thr
            20                  25                  30

His Ser Trp Ser Gln Val Val Arg Leu Arg His Leu Tyr Ala Val Lys
        35                  40                  45

Pro Gly Gln His Val Gln Ile Arg Glu Asp Gly His Ile His Gly Ser
    50                  55                  60

Ala Glu Gln Thr Leu Asn Ser Leu Leu Glu Ile Arg Pro Val Ala Pro
65                  70                  75                  80

Gly Arg Val Val Phe Arg Gly Val Ala Thr Ser Arg Phe Leu Cys Met
                85                  90                  95

Glu Ser Asp Gly Arg Leu Phe Ser Ser His Thr Phe Asp Lys Asp Asn
            100                 105                 110

Cys Val Phe Arg Glu Gln Ile Leu Ala Asp Gly Tyr Asn Ile Tyr Ile
        115                 120                 125

Ser Asp Gln His Gly Thr Leu Leu Ser Leu Gly Asn His Arg Gln Arg
    130                 135                 140

Gln Gln Gly Leu Asp Arg Asp Val Pro Ala Leu Ala Gln Phe Leu Pro
145                 150                 155                 160

Arg Ile Ser Thr Leu Gln Gln Gly Val Tyr Pro Val Pro Asp Pro Pro
                165                 170                 175

His Gln Met Arg Thr Met Gln Thr Glu Lys Thr Leu Asp Ala Thr Asp
            180                 185                 190

Thr Phe Gly Gln Leu Ser Lys Ile Ile His Ser Pro Ser Phe Asn Lys
        195                 200                 205

Arg

<210> SEQ ID NO 38
<211> LENGTH: 207

<212> TYPE: PRT
<213> ORGANISM: Xiphophorus maculates

<400> SEQUENCE: 38

```
Met Phe Val Phe Ile Leu Cys Ile Ala Gly Glu Leu Phe Thr Leu Gly
1               5                   10                  15

Val Phe Cys Met Pro Met Met Asp Gln Gly Pro Leu Val Thr His Gly
            20                  25                  30

Trp Gly Gln Val Val Arg His Arg His Leu Tyr Ala Ala Lys Pro Gly
        35                  40                  45

Leu His Leu Leu Ile Ser Glu Asp Gly Gln Ile His Gly Ser Ala Asp
    50                  55                  60

Gln Thr Leu Tyr Ser Leu Leu Glu Ile Gln Pro Val Gly Pro Gly Arg
65                  70                  75                  80

Val Val Ile Lys Gly Val Ala Thr Thr Arg Phe Leu Cys Met Glu Ser
                85                  90                  95

Asp Gly Arg Leu Tyr Ser Thr Glu Thr Tyr Ser Arg Ala Asp Cys Thr
            100                 105                 110

Phe Arg Glu Gln Ile Gln Ala Asp Gly Tyr Asn Val Tyr Thr Ser Asp
        115                 120                 125

Ser His Gly Ala Leu Leu Ser Leu Gly Asn Asn Gln Gln Arg His Ser
    130                 135                 140

Gly Ser Asp Arg Gly Val Pro Ala Leu Ala Arg Phe Leu Pro Arg Leu
145                 150                 155                 160

Asn Thr Leu Gln Gln Ala Val Pro Thr Glu Pro Asp Val Pro Asp Gln
                165                 170                 175

Leu Ser Pro Glu Lys Val Gln Gln Thr Val Asp Met Val Ala Ser Phe
            180                 185                 190

Gly Lys Leu Ser His Ile Ile His Ser Pro Ser Phe His Lys Arg
        195                 200                 205
```

<210> SEQ ID NO 39
<211> LENGTH: 220
<212> TYPE: PRT
<213> ORGANISM: Ictidomys tridecemlineatus

<400> SEQUENCE: 39

```
Met Arg Ser Ala Pro Ser Gly Arg Ala Leu Arg Ala Leu Val Leu
1               5                   10                  15

Ala Ser Leu Trp Leu Ala Val Ala Gly Arg Pro Leu Ala Arg Arg Ser
            20                  25                  30

Leu Ala Leu Ser Asp Gln Gly Pro His Leu Tyr Tyr Gly Trp Asp Gln
        35                  40                  45

Pro Ile Arg Leu Arg His Leu Tyr Ala Ala Gly Pro Tyr Gly Phe Ser
    50                  55                  60

Asn Cys Phe Leu Arg Ile Arg Thr Asp Gly Ala Val Asp Cys Glu Glu
65                  70                  75                  80

Lys Gln Ser Glu Arg Ser Leu Met Glu Ile Arg Ala Val Ala Leu Glu
                85                  90                  95

Thr Val Ala Ile Lys Asp Ile Asn Ser Val Arg Tyr Leu Cys Met Gly
            100                 105                 110

Ala Asp Gly Arg Ile Gln Gly Leu Pro Arg Tyr Ser Glu Glu Glu Cys
        115                 120                 125

Thr Phe Lys Glu Glu Ile Ser Tyr Asp Gly Tyr Asn Val Tyr Arg Ser
    130                 135                 140
```

```
Gln Lys Tyr His Leu Pro Val Val Leu Ser Ser Ala Lys Gln Arg Gln
145                 150                 155                 160

Leu Tyr Gln Ser Lys Gly Val Val Pro Leu Ser Tyr Phe Leu Pro Met
                165                 170                 175

Leu Pro Leu Ala Ser Ala Glu Thr Arg Asp Arg Leu Glu Ser Asp Val
            180                 185                 190

Phe Ser Leu Pro Leu Glu Thr Asp Ser Met Asp Pro Phe Gly Met Ala
        195                 200                 205

Ser Glu Val Gly Leu Lys Ser Pro Ser Phe Gln Lys
    210                 215                 220

<210> SEQ ID NO 40
<211> LENGTH: 203
<212> TYPE: PRT
<213> ORGANISM: Gasterosteus aculeatus

<400> SEQUENCE: 40

Met Leu Leu Leu Val Pro Ala Tyr Val Ala Ser Val Phe Leu Ala
1               5                   10                  15

Leu Gly Val Val Cys Leu Pro Leu Thr Asp Gln Gly Leu His Met Ala
                20                  25                  30

Asp Asp Trp Gly Gln Ser Val Arg Leu Lys His Leu Tyr Ala Ala Ser
            35                  40                  45

Pro Gly Leu His Leu Leu Ile Gly Glu Asp Gly Arg Ile Gln Gly Ser
        50                  55                  60

Ala Gln Gln Ser Pro Tyr Ser Leu Leu Glu Ile Ser Ala Val Asp Pro
65                  70                  75                  80

Gly Cys Val Val Ile Arg Gly Val Ala Thr Ala Arg Phe Leu Cys Ile
                85                  90                  95

Glu Gly Asp Gly Arg Leu Tyr Ser Ser Asp Thr Tyr Ser Arg Asp Asp
                100                 105                 110

Cys Thr Phe Arg Glu Gln Ile Leu Pro Asp Gly Tyr Ser Val Tyr Val
            115                 120                 125

Ser His Gly His Gly Ala Leu Leu Ser Leu Gly Asn His Arg Gln Arg
130                 135                 140

Leu Gln Gly Arg Asp His Gly Val Pro Ala Leu Ala Gln Phe Leu Pro
145                 150                 155                 160

Arg Val Ser Thr Met Asp Gln Ala Ser Ala Pro Asp Ala Pro Gly Gln
                165                 170                 175

Thr Ala Thr Glu Thr Glu Glu Pro Val Asp Ser Phe Gly Lys Leu Ser
            180                 185                 190

Gln Ile Ile His Ser Pro Ser Phe His Glu Arg
        195                 200

<210> SEQ ID NO 41
<211> LENGTH: 208
<212> TYPE: PRT
<213> ORGANISM: Oreochromis niloticus

<400> SEQUENCE: 41

Met Leu Leu Leu Leu Ile Val Ser Ile Val Asn Met Leu Phe Gly Val
1               5                   10                  15

Gly Met Val Cys Met Pro Leu Ser Asp Asn Gly Pro His Ile Ala His
                20                  25                  30

Gly Trp Ala Gln Val Val Arg Leu Arg His Leu Tyr Ala Thr Arg Pro
            35                  40                  45
```

```
Gly Met His Leu Leu Ile Ser Glu Gly Gly Gln Ile Arg Gly Ser Ala
    50                  55                  60

Val Gln Thr Leu His Ser Leu Met Glu Ile Arg Pro Val Gly Pro Gly
65                  70                  75                  80

Arg Val Val Ile Arg Gly Val Ala Thr Ala Arg Phe Leu Cys Ile Glu
                85                  90                  95

Asp Asp Gly Thr Leu Tyr Ser Ser His Ala Tyr Ser Arg Glu Asp Cys
            100                 105                 110

Ile Phe Arg Glu Gln Ile Leu Pro Asp Gly Tyr Asn Ile Tyr Ile Ser
        115                 120                 125

Asp Arg His Gly Val Leu Leu Ser Leu Gly Asn His Arg Gln Arg Leu
    130                 135                 140

Gln Gly Leu Asp Arg Gly Asp Pro Ala Leu Ala Gln Phe Leu Pro Arg
145                 150                 155                 160

Ile Ser Thr Leu Asn Gln Ile Pro Ser Pro Gly Ala Asn Ile Gly Asp
                165                 170                 175

His Met Lys Val Ala Lys Thr Glu Glu Pro Val Asp Thr Ile Asp Ser
            180                 185                 190

Phe Gly Lys Phe Ser Gln Ile Ile Asp Ser Pro Ser Phe His Lys Arg
        195                 200                 205

<210> SEQ ID NO 42
<211> LENGTH: 152
<212> TYPE: PRT
<213> ORGANISM: Meleagris gallopavo

<400> SEQUENCE: 42

Val Gly Asn Gln Ser Pro Gln Ser Ile Leu Glu Ile Thr Ala Val Asp
1               5                   10                  15

Val Gly Ile Val Ala Ile Lys Gly Leu Phe Ser Gly Arg Tyr Leu Ala
                20                  25                  30

Met Asn Lys Arg Gly Arg Leu Tyr Ala Ser Leu Ser Tyr Ser Ile Glu
            35                  40                  45

Asp Cys Ser Phe Glu Glu Ile Arg Pro Asp Gly Tyr Asn Val Tyr
    50                  55                  60

Lys Ser Lys Lys Tyr Gly Ile Ser Val Ser Leu Ser Ser Ala Lys Gln
65                  70                  75                  80

Arg Gln Gln Phe Lys Gly Lys Asp Phe Leu Pro Leu Ser His Phe Leu
                85                  90                  95

Pro Met Ile Asn Thr Val Pro Val Glu Val Thr Asp Phe Gly Glu Tyr
            100                 105                 110

Gly Asp Tyr Ser Gln Ala Phe Glu Pro Glu Val Tyr Ser Ser Pro Leu
        115                 120                 125

Glu Thr Asp Ser Met Asp Pro Phe Gly Ile Thr Ser Lys Leu Ser Pro
    130                 135                 140

Val Lys Ser Pro Ser Phe Gln Lys
145                 150

<210> SEQ ID NO 43
<211> LENGTH: 216
<212> TYPE: PRT
<213> ORGANISM: Papio anubis

<400> SEQUENCE: 43

Met Arg Ser Gly Cys Val Val Val His Ala Trp Ile Leu Ala Ser Leu
1               5                   10                  15
```

Trp Leu Ala Val Ala Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Gly Pro His Gly Leu Ser Ser Cys Phe Leu Arg Ile Arg Thr
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Glu Ile Arg Pro
        115                 120                 125

Asp Gly Tyr Asn Val Tyr Arg Ser Gln Lys His Arg Leu Pro Val Ser
    130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Ala Pro Glu Glu Pro
                165                 170                 175

Glu Asp Leu Arg Gly Pro Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 44
<211> LENGTH: 216
<212> TYPE: PRT
<213> ORGANISM: Saimiri boliviensis boliviensis

<400> SEQUENCE: 44

Met Arg Ser Gly Cys Val Val His Ala Trp Ile Leu Ala Gly Leu
1               5                   10                  15

Trp Leu Ala Val Val Gly Arg Pro Leu Ala Phe Ser Asp Ala Gly Pro
            20                  25                  30

His Val His Tyr Gly Trp Gly Asp Pro Ile Arg Leu Arg His Leu Tyr
        35                  40                  45

Thr Ser Ser Pro His Gly Leu Ser Ser Cys Phe Leu Arg Ile Arg Ser
    50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Ser Arg Tyr Leu Cys Met Gly Ala Asp Gly Arg Leu Gln Gly Leu
            100                 105                 110

Phe Gln Tyr Ser Glu Glu Asp Cys Ala Phe Glu Glu Glu Ile Arg Pro
        115                 120                 125

Asp Gly Tyr Asn Val Tyr Leu Ser Glu Lys His Arg Leu Pro Val Ser
    130                 135                 140

Leu Ser Ser Ala Lys Gln Arg Gln Leu Tyr Lys Lys Arg Gly Phe Leu
145                 150                 155                 160

Pro Leu Ser His Phe Leu Pro Met Leu Pro Arg Ala Pro Glu Glu Pro
                165                 170                 175

```
Asp Asp Leu Arg Gly His Leu Glu Ser Asp Val Phe Ser Ser Pro Leu
            180                 185                 190

Glu Thr Asp Ser Met Asp Pro Phe Gly Leu Val Thr Gly Leu Glu Ala
        195                 200                 205

Val Asn Ser Pro Ser Phe Glu Lys
    210                 215

<210> SEQ ID NO 45
<211> LENGTH: 216
<212> TYPE: PRT
<213> ORGANISM: Pteropus alecto

<400> SEQUENCE: 45

Met Arg Ser Pro Cys Ala Val Ala Arg Ala Leu Val Leu Ala Gly Leu
1               5                   10                  15

Trp Leu Ala Ser Ala Ala Gly Pro Leu Ala Leu Ser Asp Ala Gly Pro
            20                  25                  30

His Val His Tyr Gly Trp Gly Glu Ala Ile Arg Leu Arg His Leu Tyr
        35                  40                  45

Thr Ala Gly Pro His Gly Pro Ser Ser Cys Phe Leu Arg Ile Arg Ala
    50                  55                  60

Asp Gly Ala Val Asp Cys Ala Arg Gly Gln Ser Ala His Ser Leu Val
65                  70                  75                  80

Glu Ile Arg Ala Val Ala Leu Arg Asn Val Ala Ile Lys Gly Val His
                85                  90                  95

Ser Val Arg Tyr Leu Cys Met Gly Ala Asp Gly Arg Met Leu Gly Leu
            100                 105                 110

Leu Gln Tyr Ser Ala Asp Asp Cys Ala Phe Glu Glu Glu Ile Arg Pro
        115                 120                 125

Asp Gly Tyr Asn Val Tyr His Ser Lys Lys His His Leu Pro Val Ser
    130                 135                 140

Leu Ser Ser Ala Lys Gln Arg Gln Leu Tyr Lys Asp Arg Gly Phe Leu
145                 150                 155                 160

Pro Leu Ser His Phe Leu Pro Met Leu Pro Arg Ser Pro Thr Glu Pro
                165                 170                 175

Glu Asn Phe Glu Asp His Leu Glu Ala Asp Thr Phe Ser Ser Pro Leu
            180                 185                 190

Glu Thr Asp Asp Met Asp Pro Phe Gly Ile Ala Ser Lys Leu Gly Leu
        195                 200                 205

Glu Glu Ser Pro Ser Phe Gln Lys
    210                 215

<210> SEQ ID NO 46
<211> LENGTH: 245
<212> TYPE: PRT
<213> ORGANISM: Myotis davidii

<400> SEQUENCE: 46

Met Ser Gly Gln Asn Ser Gly Arg His Gly Ser Arg Pro Gly Leu Asp
1               5                   10                  15

Glu Glu Pro Glu Pro Gly Pro Leu Glu Leu Arg Ala Leu Gly Ser Thr
            20                  25                  30

Arg Ala Asp Pro Gln Leu Cys Asp Phe Leu Glu Asn His Phe Leu Gly
        35                  40                  45

Tyr Thr Cys Leu Glu Leu Asp Ile Cys Leu Ala Thr Tyr Leu Gly Val
    50                  55                  60
```

```
Ser His Trp Gly Glu Ser Ile Arg Leu Arg His Leu Tyr Thr Ser Gly
 65                  70                  75                  80

Pro His Gly Pro Ser Ser Cys Phe Leu Arg Ile Arg Val Asp Gly Ala
                 85                  90                  95

Val Asp Cys Ala Arg Gly Gln Ser Ala His Ser Leu Val Glu Ile Arg
            100                 105                 110

Ala Val Ala Leu Arg Lys Val Ala Ile Lys Gly Val His Ser Ala Leu
        115                 120                 125

Tyr Leu Cys Met Glu Gly Asp Gly Arg Met Arg Gly Leu Pro Gln Phe
    130                 135                 140

Ser Pro Glu Asp Cys Ala Phe Glu Glu Glu Ile Arg Pro Asp Gly Tyr
145                 150                 155                 160

Asn Val Tyr Arg Ser Gln Lys His Gln Leu Pro Val Ser Leu Ser Ser
                165                 170                 175

Ala Arg Gln Arg Gln Leu Phe Lys Ala Arg Gly Phe Leu Pro Leu Ser
            180                 185                 190

His Phe Leu Pro Met Leu Pro Ser Ser Pro Ala Glu Pro Val His Arg
        195                 200                 205

Glu Arg Pro Leu Glu Pro Asp Ala Phe Ser Ser Pro Leu Glu Thr Asp
    210                 215                 220

Ser Met Asp Pro Phe Gly Ile Ala Asn Asn Leu Arg Leu Val Lys Ser
225                 230                 235                 240

Pro Ser Phe Gln Lys
                245

<210> SEQ ID NO 47
<211> LENGTH: 250
<212> TYPE: PRT
<213> ORGANISM: Tupaia chinensis

<400> SEQUENCE: 47

Met Arg Arg Thr Trp Ser Gly Phe Ala Val Ala Thr Arg Ala Gly Ser
  1               5                  10                  15

Pro Leu Ala Leu Ala Asp Ala Gly Pro His Val Asn Tyr Gly Trp Asp
             20                  25                  30

Glu Ser Ile Arg Leu Arg His Leu Tyr Thr Ala Ser Leu His Gly Ser
         35                  40                  45

Thr Ser Cys Phe Leu Arg Ile Arg Asp Asp Gly Ser Val Gly Cys Ala
     50                  55                  60

Arg Gly Gln Ser Met His Ser Leu Leu Glu Ile Lys Ala Val Ala Leu
 65                  70                  75                  80

Gln Thr Val Ala Ile Lys Gly Val Tyr Ser Val Arg Tyr Leu Cys Met
                 85                  90                  95

Asp Thr Asp Gly Arg Met Gln Gly Leu Pro Gln Tyr Ser Glu Glu Asp
            100                 105                 110

Cys Thr Phe Glu Glu Glu Ile Arg Ser Asp Gly His Asn Val Tyr Arg
        115                 120                 125

Ser Lys Lys His Gly Leu Pro Val Ser Leu Ser Ser Ala Lys Gln Arg
    130                 135                 140

Gln Leu Tyr Lys Gly Arg Gly Phe Leu Ser Leu Ser His Phe Leu Leu
145                 150                 155                 160

Met Met Pro Lys Thr Ser Ala Gly Pro Gly Asn Pro Arg Asp Gln Arg
                165                 170                 175

Asn Pro Arg Asp Gln Arg Asp Pro Asn Thr Phe Ser Leu Pro Leu Glu
```

```
                180                 185                 190
Thr Asp Ser Met Asp Pro Phe Gly Met Thr Thr Arg His Gly Leu Leu
            195                 200                 205

Leu Asp Ser Cys Cys Ala Ser Leu Val Leu Leu Asn Ile Ser Thr Asp
        210                 215                 220

Gly Glu Phe Ser Pro Tyr Gly Asn Ile Leu Arg Pro Ser Phe Arg Phe
225                 230                 235                 240

Lys Leu Phe Lys Met Lys Lys Val Thr Asn
                245                 250

<210> SEQ ID NO 48
<211> LENGTH: 209
<212> TYPE: PRT
<213> ORGANISM: Heterocephalus glaber

<400> SEQUENCE: 48

Met Arg Phe Ser Lys Ser Thr Cys Gly Phe Phe Asn His Gln Arg Leu
1               5                   10                  15

Gln Ala Leu Trp Leu Ser Leu Ser Ser Val Lys Trp Val Leu Asp Ala
            20                  25                  30

Ala Val Glu Gly Arg Pro Ile Arg Leu Arg His Leu Tyr Ala Ala Gly
        35                  40                  45

Pro Tyr Gly Arg Ser Arg Cys Phe Leu Arg Ile His Thr Asp Gly Ala
    50                  55                  60

Val Asp Cys Val Glu Glu Gln Ser Glu His Cys Leu Leu Glu Ile Arg
65                  70                  75                  80

Ala Val Ala Leu Glu Thr Val Ala Ile Lys Asp Ile Asn Ser Val Arg
                85                  90                  95

Tyr Leu Cys Met Gly Pro Asp Gly Arg Met Gln Gly Leu Pro Trp Tyr
            100                 105                 110

Ser Glu Glu Asp Cys Ala Phe Lys Glu Glu Ile Ser Tyr Pro Gly Tyr
        115                 120                 125

Ser Val Tyr Arg Ser Gln Lys His His Leu Pro Ile Val Leu Ser Ser
    130                 135                 140

Val Lys Gln Arg Gln Gln Tyr Gln Ser Lys Gly Val Val Pro Leu Ser
145                 150                 155                 160

Tyr Phe Leu Pro Met Leu Pro Lys Ala Ser Val Glu Pro Gly Asp Glu
                165                 170                 175

Glu Glu Ser Ala Phe Ser Leu Pro Leu Lys Thr Asp Ser Met Asp Pro
            180                 185                 190

Phe Gly Met Ala Ser Glu Ile Gly Leu Ala Lys Ser Pro Ser Phe Gln
        195                 200                 205

Lys

<210> SEQ ID NO 49
<211> LENGTH: 13
<212> TYPE: PRT
<213> ORGANISM: Artificial
<220> FEATURE:
<223> OTHER INFORMATION: C-terminal Portion of FGF19 of the Chimeric
      Protein
<220> FEATURE:
<221> NAME/KEY: MISC_FEATURE
<222> LOCATION: (7)..(7)
<223> OTHER INFORMATION: Xaa at position 7 is R or N

<400> SEQUENCE: 49

Thr Gly Leu Glu Ala Val Xaa Ser Pro Ser Phe Glu Lys
```

<210> SEQ ID NO 50
<211> LENGTH: 20
<212> TYPE: PRT
<213> ORGANISM: Artificial
<220> FEATURE:
<223> OTHER INFORMATION: C-terminal Portion of FGF19 of the Chimeric
      Protein
<220> FEATURE:
<221> NAME/KEY: MISC_FEATURE
<222> LOCATION: (14)..(14)
<223> OTHER INFORMATION: Xaa at position 14 is R or N

<400> SEQUENCE: 50

Met Asp Pro Phe Gly Leu Val Thr Gly Leu Glu Ala Val Xaa Ser Pro
1               5                   10                  15

Ser Phe Glu Lys
            20

<210> SEQ ID NO 51
<211> LENGTH: 48
<212> TYPE: PRT
<213> ORGANISM: Artificial
<220> FEATURE:
<223> OTHER INFORMATION: C-terminal Portion of FGF19 of the Chimeric
      Protein
<220> FEATURE:
<221> NAME/KEY: MISC_FEATURE
<222> LOCATION: (3)..(3)
<223> OTHER INFORMATION: Xaa at position 3 is M or I
<220> FEATURE:
<221> NAME/KEY: MISC_FEATURE
<222> LOCATION: (4)..(4)
<223> OTHER INFORMATION: Xaa at position 4 is V or A
<220> FEATURE:
<221> NAME/KEY: MISC_FEATURE
<222> LOCATION: (13)..(13)
<223> OTHER INFORMATION: Xaa at position 13 is G or R
<220> FEATURE:
<221> NAME/KEY: MISC_FEATURE
<222> LOCATION: (19)..(19)
<223> OTHER INFORMATION: Xaa at position 19 is M or V
<220> FEATURE:
<221> NAME/KEY: MISC_FEATURE
<222> LOCATION: (42)..(42)
<223> OTHER INFORMATION: Xaa at position 42 is R or N

<400> SEQUENCE: 51

Leu Pro Xaa Xaa Pro Glu Glu Pro Glu Asp Leu Arg Xaa His Leu Glu
1               5                   10                  15

Ser Asp Xaa Phe Ser Ser Pro Leu Glu Thr Asp Ser Met Asp Pro Phe
            20                  25                  30

Gly Leu Val Thr Gly Leu Glu Ala Val Xaa Ser Pro Ser Phe Glu Lys
        35                  40                  45

<210> SEQ ID NO 52
<211> LENGTH: 651
<212> TYPE: DNA
<213> ORGANISM: Homo sapiens

<400> SEQUENCE: 52
atgcggagcg ggtgtgtggt ggtccacgta tggatcctgg ccggcctctg gctggccgtg     60
gccgggcgcc ccctcgcctt ctcggacgcg gggccccacg tgcactacgg ctggggcgac    120
cccatccgcc tgcggcacct gtacacctcc ggccccacg ggctctccag ctgcttcctg    180
cgcatccgtg ccgacggcgt cgtggactgc gcgcggggcc agagcgcgca cagtttgctg    240

```
gagatcaagg cagtcgctct gcggaccgtg gccatcaagg gcgtgcacag cgtgcggtac      300
ctctgcatgg gcgccgacgg caagatgcag gggctgcttc agtactcgga ggaagactgt      360
gctttcgagg aggagatccg cccagatggc tacaatgtgt accgatccga gaagcaccgc      420
ctcccggtct ccctgagcag tgccaaacag cggcagctgt acaagaacag aggctttctt      480
ccactctctc atttcctgcc catgctgccc atggtcccag aggagcctga ggacctcagg      540
ggccacttgg aatctgacat gttctcttcg cccctggaga ccgacagcat ggacccattt      600
gggcttgtca ccggactgga ggccgtgagg agtcccagct ttgagaagta a               651
```

<210> SEQ ID NO 53
<211> LENGTH: 651
<212> TYPE: DNA
<213> ORGANISM: Gorilla

<400> SEQUENCE: 53

```
atgcggagcg ggtgtgtggt ggtccacgtc tggatcctgg ccggcctctg gctggccgtg       60
gccgggcgcc ccctcgcctt ctcggacgcg gggccccacg tgcactacgg ctggggcgac      120
cccatccgcc tgcggcacct gtacacctcc ggcccccacg gctctccag ctgcttcctg       180 cgcatccgtg ccgacggcgt cgtggactgc gcgcggggcc agagcgcgca cagtttgctg      240
gagatcaagg cagtcgctct gcggaccgtg gccatcaagg gcgtgcacag cgtgcggtac      300
ctctgcatgg gcgccgacgg caagatgcag gggctgcttc agtactcgga ggaagactgt      360
gctttcgagg aggagatccg cccagatggc tacaatgtgt accgatctga gaagcaccgc      420
ctcccggtct ccctgagcag tgccaaacag cggcagctgt acaagaacag aggctttctt      480
ccgctctctc atttcctgcc catgctgccc atggtcccag aggagcctga ggacctcagg      540
ggccacttgg aatctgacat gttctcttca cccctggaga ccgacagcat ggacccattt      600
gggcttgtca ccggactgga ggccgtgagg agtcctagct ttgagaagta a               651
```

<210> SEQ ID NO 54
<211> LENGTH: 651
<212> TYPE: DNA
<213> ORGANISM: Pan troglodytes

<400> SEQUENCE: 54

```
atgcggaacg ggtgtgtggt ggtccacgtc tggatcctgg ccggcctctg gctggccgtg       60
gccgggcgcc ccctcgcctt ctcggacgcg gggcgccacg tgcactactg ctggggcgac      120
cccatccccc tgcggcacct gtacacctcc ggcccccatg gctctccag ctgcttcctg       180 cgcatccctg cgaactgcgt catgaactgc gcgcggggcc agagcgcgca cagtttgctg      240
gagatcaagg cagtcgctct gcggaccgtg gccatcaagg gcgtgcacag cgtgcggtac      300
ctctgcatgg gcgccgacgg caagatgcag gggctgcttc agtactcgga ggaagactgt      360
gctttcgagg aggagatccg cccagatggc tacaatgtgt accgatccga gaagcaccgc      420
ctcccggtct ccctgagcag tgccaaacag cggcagctgt acaagaacag aggctttctt      480
ccactctctc atttcctgcc catgctgccc atggtcccag aggagcctga ggacctcagg      540
ggccacttgg aatctgacat gttctcttcg cccctggaga ccgacagcat ggacccattt      600
gggcttgtca ccggactgga ggccgtgagg agtcccagct ttgagaagta a               651
```

<210> SEQ ID NO 55
<211> LENGTH: 651
<212> TYPE: DNA
<213> ORGANISM: Macaca mulatta

<400> SEQUENCE: 55

```
atgaggagcg ggtgtgtggt ggtccacgcc tggatcctgg ccagcctctg gctggccgtg      60
gccgggcgtc ccctcgcctt ctcggacgcg gggccccacg tgcactacgg ctggggcgac     120
cccatccgct gcggcacct gtacacctcc ggcccccatg gctctccag ctgcttcctg      180
cgcatccgca ccgacggcgt cgtggactgc gcgcggggcc aaagcgcgca cagtttgctg     240
gagatcaagg cagtagctct gcggaccgtg gccatcaagg gcgtgcacag cgtgcggtac     300
ctctgcatgg gcgccgacgg caagatgcag gggctgcttc agtactcaga ggaagactgt     360
gctttcgagg aggagatccg ccctgatggc tacaatgtat accgatccga aagcaccgc      420
ctcccggtct ctctgagcag tgccaaacag aggcagctgt acaagaacag aggctttctt     480
ccgctctctc atttcctacc catgctgccc atggccccag aggagcctga ggacctcagg     540
ggccacttgg aatctgacat gttctcttcg cccctggaga ctgacagcat ggacccattt     600
gggcttgtca ccggactgga ggcggtgagg agtcccagct ttgagaaata a              651
```

<210> SEQ ID NO 56
<211> LENGTH: 651
<212> TYPE: DNA
<213> ORGANISM: Pongo abelii

<400> SEQUENCE: 56

```
atgcggagcg ggtgtgtggt ggtccacgcc tggatcctgg ccggcctctg gctggccgtg      60
gccgggcgcc ccctcgcctt ctcggactcg gggccccacg tgcactacgg ctggggcgac     120
cccatccgcc tgcggcacct gtacacctcc ggcccccacg gctctccag ctgcttcctg      180
cgcatccgtg ccgacggcgt cgtggactgc gcgcggggcc agagcgcgca cagtttgctg     240
gagatcaagg cagtcgctct gcggaccgtg gccatcaagg gcgtgcacag cgtgcggtac     300
ctctgcatgg gcgccgacgg caagatgcag gggctgcttc agtactcgga ggaagactgt     360
gctttcgagg aggagatccg cccagatggc tacaatgtgt accgatccga agcaccgc       420
ctcccggtct ccctgagcag tgccaaacag cggcagctgt acaagaacag ggctttctt     480
ccgctctctc atttcctgcc catgctgccc atggtcccag aggagcctga ggacctcagg     540
cgccacttgg aatccgacat gttctcttcg cccctggaga ccgacagcat ggacccattt     600
gggcttgtca ccggactgga ggccgtgagg agtcccagct ttgagaaata a              651
```

<210> SEQ ID NO 57
<211> LENGTH: 651
<212> TYPE: DNA
<213> ORGANISM: Nomascus leucogenys

<400> SEQUENCE: 57

```
atgcggagcg agtgtgtggt ggtccacgcc tggatcctgg ccggcctctg gctggcagtg      60
gccgggcgcc ccctcgcctt ttcggacgcg gggccccacg tgcactacgg ctggggcgac     120
cccatccgtc tgcggcacct gtacacctcc ggcccccacg gctctccag ctgcttcctg      180
cgcatccgtg ccgacggcgt cgtggactgc gcgcggggcc agagcgcgca cagtttgctg     240
gagatcaagg cagtcgctct gcggaccgtg gccataaagg gcgtgcacag cgtgcggtac     300
ctctgcatgg gcgccgacgg caagatgcag gggctgcttc agtattcgga ggaagactgt     360
gctttcgagg aggagatccg cccagatggc tacaatgtgt accgatccga agcaccgc       420
ctccccgtct ccctgagcag tgccaaacag cggcagctgt ataagaacag aggctttctt     480
```

```
ccactctctc atttcctgcc catgctgccc atggtcccag aggagcctga ggacctcagg      540
ggccacttgg aatctgacat gttctcttcg cccctggaga ccgacagcat ggacccattt      600
gggcttgtca ccggactgga ggccgtgagg agtcccagct ttgagaaata a               651

<210> SEQ ID NO 58
<211> LENGTH: 429
<212> TYPE: DNA
<213> ORGANISM: Callithrix jacchus

<400> SEQUENCE: 58
atgtggaagg ccaccgctgg tggccagcag ggacagtccg aagcacaaat gtccacatgt       60
ccccatgttc ctcgtcctct gtggattgct cagagctgcc tgttttctct gcagctccag      120
tactcggagg aagactgtgc tttcgaggag agatccgccc tgatggctaa caatgtgtac      180
tggtccgaga agcaccgcct cccggtctcc ctgagcagcc caaacagcg gcagctgtac       240 aagaaacgag gctttcttcc actgtcccat ttcctgccca tgctgcccat agccccagaa      300
gagcctgagg acctcagggg cacctgaa tctgacgtgt ctcttcacc cctggagact         360 gacagcatgg acccatttgg gcttgtcacg ggactggagg cggtgaacag tcccagcttt      420
gagaagtaa                                                              429

<210> SEQ ID NO 59
<211> LENGTH: 660
<212> TYPE: DNA
<213> ORGANISM: Microcebus murinus

<400> SEQUENCE: 59
atgccgagcg ggcaaagcgg ttgtgtggcg gcccgcgccc tgatcctggc cggcctctgg       60
ctgaccgcgg ccgggcgccc gctggccttc tccgacgcgg cccgcacgt gcactacggc       120 tggggcgagc ccatccgcct gcggcacctg tacaccgccg cccccacgg cctctccagc       180 tgcttcctgc gcatccgcgc agacggctcc gtggactgcg cgcggggcca gagcgcacac      240
agtttgctgg agatcagggc ggtcgctctt cggactgtgg ccatcaaggg cgtgcacagc      300
gtgcggtacc tctgcatggg cgcagacggc aggatgcagg ggctgctccg gtactcggag      360
gaagactgtg ccttcgagga ggagatccgc cccgatggct acaacgtgta ccggtctgag      420
aagcaccgcc tgccggtgtc tctgagcagc gccaggcaga ggcagctgta caagggcagg      480
ggcttcctgc cgctctctca cttcctgccc atgctgcccg tgaccccggc agagaccggg      540
gacctcaggg accacttgga gtccgacatg ttcgcttcgc ccctggagac cgacagcatg      600
gacccgtttg ggatcgccac cagacttggg gtggtgaaga gtcccagctt tcagaaatga      660

<210> SEQ ID NO 60
<211> LENGTH: 415
<212> TYPE: DNA
<213> ORGANISM: Choloepus hoffmanni

<400> SEQUENCE: 60
ttgctcgaaa tgaaggcagt ggcgctgcgg gccgtggcca tcaagggcgt gcacagtgct       60
ctgtacctct gcatgaacgc cgacggcagt ctgcacgggc tgcctcggta ctctgcagaa      120
gactgtgctt ttgaggagga aatccgcccc gacggctaca atgtgtactg gtctaggaag      180
cacggcctcc ctgtctcttt gagcagtgca aaacagaggc agctgtacaa aggcagaggc      240
tttctgcccc tgtcccactt cctgcccatg ctgcccatga cgccgccga gcccgcagac      300 cccggggatg acgtggagtc ggacatgttc tcttcacctc tggaaaccga cagcatggat      360
```

```
ccttttggaa ttgcctccag acttgagctt gtgaacagtc cagcttcag cataa        415
```

<210> SEQ ID NO 61
<211> LENGTH: 619
<212> TYPE: DNA
<213> ORGANISM: Ailuropoda melanoleuca

<400> SEQUENCE: 61

```
ggtcctagcc ggcctctgcc tggcggtagc cgggcgcccc ctagccttct cggacgcggg    60
gccgcacgtg cactacggct ggggtgagcc catccgccta cggcacctgt acaccgccgg   120
cccccacggc ctctccagct gcttcctgcg catccgtgcc gacggcgggg ttgactgcgc   180
gcggggccag agcgcgcaca gtttggtgga gatcagggca gtcgctctgc ggaccgtggc   240
catcaagggt gtgcacagcg tccggtacct ctgcatgggc gcggacggca ggatgcaagg   300
gctgcctcag tactctgcag gggactgtgc tttcgaggag gagatccgcc ccgacggcta   360
caatgtgtac cggtccaaga agcaccgtct ccccgtctct ctgagcggtg ccaaacagag   420
gcagctttac aaagacagag ctttctgcc cctgtcccac ttcttgccca tgctgcccgg   480
gagcccagca gagcccaggg acctccagga ccatgcggag tcggacgggt tttctgcacc   540
cctagaaaca gacagcatgg acccttttgg gatcgccacc aaaatgggac tagtgaagag   600
tcccagcttc cagaaataa                                               619
```

<210> SEQ ID NO 62
<211> LENGTH: 660
<212> TYPE: DNA
<213> ORGANISM: Sus scrofa

<400> SEQUENCE: 62

```
atgcggagcg ctccgagccg gtgcgcggtg gtccgcgccc tggtcctggc cggcctctgg    60
ctggccgcag ccgggcgccc cctagccttc tcggatgctg ggccgcacgt gcactacggc   120
tggggcgagt cggtccgcct gcggcacctg tacactgcga gtcccacgg cgtctccagc   180
tgcttcctgc gcatccactc agacggcccc gtggactgcg cgccgggaca gagcgcgcac   240
agtttgatgg agatcagggc agtcgcgctg agtaccgtgg cgatcaaggg cgagcgcagc   300
ggccgttacc tctgcatggg cgccgacggc aagatgcaag gcagactca gtactcggat   360
gaggactgtg ctttcgagga ggagatccgc cctgatggct acaacgtgta ctggtccaag   420
aaacaccatc tgcccgtctc tctgagcagc gccaggcaga ggcagctgta caaaggcagg   480
ggcttcctgc cgctgtccca ctttctgccc atgctgtcca ctctcccagc cgagccggag   540
gacctccagg acccccttcaa gtccgacctg ttttctttgc ccctggaaac ggacagcatg   600
gaccctttcc ggatcgccgc caaactggga gcggtgaaga gtcccagctt ctataaataa   660
```

<210> SEQ ID NO 63
<211> LENGTH: 657
<212> TYPE: DNA
<213> ORGANISM: Bos taurus

<400> SEQUENCE: 63

```
atgcggagcg ctccgagccg gtgcgccgtg gcccgcgccc tggtcctggc tggcctctgg    60
ctggccgcag ccgggcgccc cctggccttc tcggatgcgg ggccgcacgt gcactacggc   120
tggggcgagt cggttcgctt gcggcacctg tataccgcgg gccgcaggg cctctacagc   180
tgctttctgc gcatccactc cgacggcgcc gtggactgcg cgcaggtcca gagcgcgcac   240
```

```
agtttgatgg agatcagggc ggtcgctctg agcaccgtag ccatcaaggg cgagcgcagc    300
gtgctgtacc tctgcatgga cgccgacggc aagatgcaag gactgaccca gtactcagcc    360
gaggactgtg ctttcgagga ggagatccgt cctgacggct acaacgtgta ctggtccagg    420
aagcaccatc tcccggtctc cctgagcagc tccaggcaga ggcagctgtt caaaagcagg    480
ggcttcctgc cgctgtctca cttcctgccc atgctgtcca ccatcccagc cgaacctgaa    540
gacctccagg aaccectgaa gcctgatttc tttctgcccc tgaaaacaga tagcatggac    600
cctttcgggc tcgccaccaa actgggatcg gtgaagagtc ccagcttcta taattaa      657
```

<210> SEQ ID NO 64
<211> LENGTH: 579
<212> TYPE: DNA
<213> ORGANISM: Canis lupus familiaris

<400> SEQUENCE: 64

```
ctagccttct ccgacgcggg gccgcacgtg cactccttct gggggagcc catccgcctg      60 cggcacctgt acaccgccgg cccccacggc ctctccagct gcttcctgcg catccgcgcc    120
gacggcgggg tggactgcgc gcggggccag agcgcgcaca gtctgatgga gatgagggcg    180
gtcgctctgc ggaccgtggc catcaagggc gtgcacagcg gccggtacct ctgcatgggc    240
gccgacggca ggatgcaagg gctgcctcag tactccgccg agactgtac tttcgaggag    300 gagatccgtc ccgatggcta caatgtgtac tggtccaaga agcaccatct ccccatctct    360
ctgagtagtg ccaaacagag gcagctctac aagggcaggg gcttttttgcc cctgtcccac    420 ttcttaccta tcttgcccgg gagcccaaca gagcccaggg acctgaaaga ccatgtggag    480
tctgacgggt tttctgcatc cctggaaaca gacagcatgg accctttggg atcgccacc    540 aaaattggac tagtgaagag tcccagtttc caaaaataa                          579
```

<210> SEQ ID NO 65
<211> LENGTH: 657
<212> TYPE: DNA
<213> ORGANISM: Oryctolagus cuniculus

<400> SEQUENCE: 65

```
atgcgccgcg cgccgagcgg aggtgccgcg gcccgcgcct tggtcctggc cggcctctgg     60
ctggccgcgg ccgcgcgccc cttggccttg tccgacgcgg gccgcatct gcactacggc    120 tggggcgagc ccgtccgcct gcggcacctg tacgccacca gcgcccacgg cgtctcgcac    180
tgcttcctgc gtatacgcgc cgacggcgcc gtggactgcg agcggagcca gagcgcacac    240
agcttgctgg agatccgagc ggtcgccctg cgcaccgtgg cctcaaggg cgtgcacagc    300 tcccgctacc tctgcatggg cgccgacggc aggatgcggg ggcagctgca gtactcggag    360
gaggactgtg ccttccagga ggagatcagc tccggctaca cgtgtaccg ctccacgacg    420 caccacctgc ccgtgtctct gagcagtgcc aagcagagac acctgtacaa gaccagaggc    480
ttcctgcccc tctcccactt cctgcccgtg ctgcccctgg cctccgagga gaccgcggcc    540
ctcggcgacc accctgaagc cgacctgttc tccccgcccc tggaaaccga cagcatggac    600
cccttcggca tggccaccaa gctcgggccg gtgaagagcc ccagctttca gaagtag      657
```

<210> SEQ ID NO 66
<211> LENGTH: 651
<212> TYPE: DNA
<213> ORGANISM: Pteropus vampyrus

<400> SEQUENCE: 66

```
atgcggagcc cgtgcgctgt ggcccgcgcc ttggtcctgg ccggcctctg gctggcctca    60
gctgcgggcc ccctcgccct ctcggacgcg gggccgcacg tgcactacgg ctggggcgag   120
gccatccgcc tgcggcacct gtacaccgcc ggccccacg gcccctccag ctgcttcctg    180
cgcatccgcg cggatggggc ggtggactgc gcgcggggcc agagcgcgca cagtttggtg   240
gaaatccggg ctgtcgccct gcggaacgtg gctatcaagg gcgtgcacag cgtccgatac   300
ctctgcatgg gagccgacgg caggatgcta gggctgcttc agtactccgc tgacgactgc   360
gccttcgagg aggagatccg cccggacggc tacaacgtgt accactccaa gaagcaccac   420
ctcccggtct ctctgagcag tgccaagcag aggcaactgt acaaggacag ggcttcctg    480 cccctgtccc atttcctgcc catgctgccc aggagcccga cagagcccga aacttcgaa    540 gaccacttgg aggccgacac gttttcctcg cccctggaga cagacgacat ggaccctttt    600
gggattgcca gtaaattggg gctggaggaa agtcccagct tccagaagta a             651
```

<210> SEQ ID NO 67
<211> LENGTH: 660
<212> TYPE: DNA
<213> ORGANISM: Tursiops truncatus

<400> SEQUENCE: 67

```
atgcggagcg ctccgagccg gtgcgccgtg gcccgcgccc tggtcctggc cggcctctgg    60
ctggctgcag ccgggcgccc cctagccttc tcggatgccg ggccgcacgt gcactacggc   120
tggggcgagt ccgtccgcct gcggcacctg tacaccgcgg tccccaggg cctctccagc   180 tgcttcctgc gcatccactc agacggcgcc gtggactgcg cgccggttca gagcgcgcac   240
agtttgatgg agatcagggc agtcgctctg agtaccgtgg ccatcaaggg cgaacgcagc   300
gtcctgtacc tctgcatggg cgccgacggc aaaatgcaag ggctgagtca gtactcagct   360
gaggactgtg cctttgagga ggaaatccgt ccggacggct acaacgtgta ctggtccaag   420
aaacaccacc tcccggtgtc cctgagcagc gccaggcagc ggcagctgtt caaaggcagg   480
ggtttcctgc cgctgtctca cttccttccc atgctgtcca ccatcccac agagcccgat   540 gaaatccagg accacttgaa gcccgatttg tttgctttgc ccctgaaaac agatagcatg   600
gacccatttg ggctcgccac caaactggga gtggtgaaga gtcccagctt ctataagtaa   660
```

<210> SEQ ID NO 68
<211> LENGTH: 660
<212> TYPE: DNA
<213> ORGANISM: Myotis lucifugus

<400> SEQUENCE: 68

```
atgcaaagcg cgtggagccg acgcgttgtg gcccgagccc tggtcttggc cagcctcggg    60
ctggcctcag ccgggggggcc cctcggtctt tcggacgctg gccgcacgt gcactacggc    120 tgggggagt ccatccgcct gcgccacctg tacacctccg gccccacgg cccatccagc    180 tgcttcctgc gcatccgcgc tgacggcgca gtggactgcg cgcggggcca gagcgcgcac   240
agtttggtgg agatcagggc cgtcgccttg cggaaagtgg ccatcaaggg cgtgcacagc   300
gccctgtacc tctgcatggg aggcgacggc aggatgctgg ggctgcctca gttctcgccc   360
gaggactgtg ctttcgagga ggagatccgc ccggacggct acaacgtgta ccggtcccag   420
aagcaccagc tgcccgtctc gctgagcagt gcccggcaga ggcagctgtt caaggcccgg   480
ggcttcctgc cgctgtccca cttcctgccc atgctgccca gcagcccgc gggaccgtg    540
```

```
cccgagagc gcccctcgga gccggacgag ttctcttcgc ccctggaaac agacagcatg    600
gacccttttg ggattgccaa caacctgagg ctggtgagaa gtcccagctt tcaggaataa    660
```

<210> SEQ ID NO 69
<211> LENGTH: 558
<212> TYPE: DNA
<213> ORGANISM: Ornithorhynchus anatinus

<400> SEQUENCE: 69

```
atgctttcct gtgtggtttt gcctagtctg ctggagatca aggcggtggc cgtgcgcacg     60
gtggccatca aggggtcca catctctcgg tacctctgca tggaagagga tgggaaaact    120
ccatgggcac gtctgctgga gatcaaggcg gtggccgtgc gcacggtggc catcaaaggg    180
gtccacagct ctcggtacct ctgcatggaa gaggatggaa actccatgg gcagatttgg     240 tattctgcag aagactgtgc ttttgaagag gaaatacgtc agatggcta caatgtgtat    300 aaatctaaga aatatggtgt tcctgtttct ttaagcagcg ccaaacaaag gcagcaattc    360
aaaggaagag actttctgcc tctttctcgt ttcttgccaa tgatcaacac agtgcctgtg    420
gagccagcag agtttgggga ctatgccgat tactttgaat cagatatatt ttcctcacct    480
ctggaaactg acagcatgga cccatttaga attgcccta aactgtcccc tgtaaagagc    540
cccagctttc agaaataa                                                  558
```

<210> SEQ ID NO 70
<211> LENGTH: 639
<212> TYPE: DNA
<213> ORGANISM: Monodelphis domestica

<400> SEQUENCE: 70

```
atggcccagc tcctggcccc gctcctcacc ctggctgctc tctggctggc cccgacggcg     60
cgtgcccgac cgctggtgga cgccgggcct cacgtctact acggctgggg ggagcccatt    120
cgtctgcgga tctctacac ggccaatcgg cacgggctcg ccagcttctc cttcctccgg    180
atccaccgcg acggccgcgt ggacggcagc cggagtcaga gcgcgctcag tttgctggag    240 atcaaggcg tagctcttcg gatggtggcg atcaaaggtg tccatagctc tcggtacctg    300
tgtatgggag acgccgggaa actccaggga tcggtgaggt tctcggccga ggactgcacc    360
ttcgaggagc agattcgccc cgacggctac aacgtgtacc agtcccccaa gtacaacctc    420
cccgtctcgc tctgcactga caagcagagg cagcaggccc acggcaagga gcacctgccc    480
ctgtcccact tcctgcccat gatcaatgct attcctttgg aggccgagga gcccgagggc    540
cccaggatgt tggcggcgcc tctggagacg gacagcatgg acccccttcgg cctcacctcc    600 aagctgttgc cggtcaagag ccccagcttt cagaaataa                           639
```

<210> SEQ ID NO 71
<211> LENGTH: 663
<212> TYPE: DNA
<213> ORGANISM: Anolis carolinensis

<400> SEQUENCE: 71

```
atgtgtcggc gggcgttgcc tctgctgggg gcccttctgg gcttggcggc cgtggcctcc     60
cgcgccctcc cgctcaccga cgccgggccc cacgtcagct acggctgggg ggagcccgtc    120
cggctcaggc acctctacac cgcggggcgg cagggcctct tcagccagtt cctccgcatc    180
cacgccgacg ggagagtcga cggcgccggc agccagaacc ggcagagttt gctggagatc    240
cgcgcggtct cgttgcgcgc cgtggccctc aaaggcgtgc acagctcccg ctacctctgc    300
```

```
atggaggagg acggccggct ccgcgggatg ctcagatatt ctgcagaaga ctgttccttt    360
gaagaggaga tgcgtccaga tggctacaat atctacaagt caaagaaata cggagttttg    420
gtctccctaa gtaatgccag acaaagacag caattcaaag ggaaagattt tcttcctttg    480
tctcatttct tgccgatgat caacactgtg ccagtggagt ctgcagactt ggagagtat     540 ggtgacacca ggcagcatta tgaatcggat attttcagtt cacgtcttga aactgacagc    600 atggacccctt ttggcctcac ttcagaagtg tcatcagtac aaagtcctag ctttgggaaa    660
taa                                                                    663
```

<210> SEQ ID NO 72
<211> LENGTH: 541
<212> TYPE: DNA
<213> ORGANISM: Ochotona princeps

<400> SEQUENCE: 72

```
gtgcggagca ggggagccat ggcccgcgct ctggttctag ccactctctg gctggccgcg     60
acggggcggc cgctggcctt gtccgacgcg ggccgcacc tgcactacgg ctggggcgag    120
cccatccgcc tgcggcacct gtacgccacc agcgcccacg gcctctcgca ctgcttttg     180 cgcatccgta ccgacggcac cgtggactgc gagcgcagcc agagcgcgca cactacagta    240
ctcggaggag gactgcgcct tcgaagagga gatcagctct ggctataacg tgtaccgctc    300
caggaggtac cagctgcccg tgtccctggg cagcgccagg cagaggcagc tgcagcggag    360
ccgtggcttc ctgccctgt cccacttcct gccggtgctg cccgcggcct cggaggaggt    420
ggcggccccc gctgaccacc gcaagcaga cccttctctcg cccctggaga ccgacagcat    480
ggacccattt ggaatggcca ccaagcgggg gctggtgaag agcccagct tccagaagtg    540 a                                                                    541
```

<210> SEQ ID NO 73
<211> LENGTH: 666
<212> TYPE: DNA
<213> ORGANISM: Cavia porcellus

<400> SEQUENCE: 73

```
atgtggagtg cgccgagcgg atgtgtggtg atccgcgccc tggtcctggc tggcctgtgg     60
ctggcggtgg cggggcgccc cctgcccggg cggtctctcg cgctatctga ccaggggccg    120
cacttgtact acggctggga ccagccgatc cgccttcggc acctgtacgc cgcgggcccc    180
tacgccgcgt cgcgctgctt cctgcgcatt cacacggacg cgcgcggtgga ctgcgtcgag    240 gaacagagcg agcactgttt gctggagatc agagcagtcg ctctggagac cgtggccatc    300
aaggacataa acagcgtccg gtacctgtgc atggccccg acggcaggat gcggggcctg    360
ccctggtatt cggaggagga ctgtgccttc aaggaagaga tcagctaccc gggctacagc    420
gtgtaccgct cccagaagca ccacctcccc atcgtgctga gcagtgtcaa gcagaggcag    480
cagtaccaga gcaaggggt ggtgcccctg tcctacttcc tgcccatgct gcccaaggcc    540
tctgtggagc ccagcgacga ggaggaatcc agcgtgttct cgttgccct gaagacggac    600 agcatggacc cctttgggat ggccagtgag atcgggctgg tgaagagtcc cagctttcag    660
aagtaa                                                                666
```

<210> SEQ ID NO 74
<211> LENGTH: 593
<212> TYPE: DNA

```
<213> ORGANISM: Tupaia belangeri

<400> SEQUENCE: 74
atgaggagaa caccgagcgg gtttgcagtg gcccgtgtcc tcttcctggg cagcctttgg      60
ctggccgcag ccgggagccc cttggccctg tccgacgccg ggccgcatgt gaactacggc     120
tgggatgagt ccatacgcct gcgacacttg tacaccgcca gcccgcacgg ctccaccagc     180
tgcttcttgc gcatccgtga cgacggctca gtggactgcg cgcggggcca gagtttgcac     240
agtttgctgg agatcaaggc agtcgctttg cagaccgtgg ccatcaaagg cgtgtacagt     300
gtccgctacc tctgcatgga cgccgacggc aggatgcagg ggctgggtcc acgaagcacg     360
gcctcccagt ctccctgagc agtgccaagc agaggcagct gttaacggtt aggggctttc     420
cttcccttcc ccacttcctg ctcatgatgg ccaagacttc agcagggcct ggaaacccca     480
gggaccaccc agggtctaac actttctcgt tgcccctgga aactgatagc atggacccat     540
ttgggatgac caccagacat gggctggtga agagtcccag ctttcaaaac taa           593

<210> SEQ ID NO 75
<211> LENGTH: 657
<212> TYPE: DNA
<213> ORGANISM: Rattus norvegicus

<400> SEQUENCE: 75
atggcgagaa agtggagtgg gcgtattgtg gcccgagctc tggtcctggc cactctgtgg      60
ctggccgtgt ctgggcgtcc cctggtccag caatcccagt ctgtgtcgga tgaaggtcca     120
ctctttctct atggctgggg caagattacc cgcctgcagt acctgtactc tgctggtccc     180
tacgtctcca actgcttcct gcgtatccgg agtgacggct ctgtggactg cgaggaggac     240
cagaacgaac gaaatctgtt ggagttccgc gcggttgctc tgaagacaat tgccatcaag     300
gacgtcagca gcgtgcggta cctctgcatg agcgccgacg gcaagatata cgggctgatt     360
cgctactcgg aggaagactg taccttcagg gaggaaatgg actgtttggg ctacaaccag     420
tacaggtcca tgaagcacca cctccacatc atcttcatca aggccaagcc cagagagcag     480
ctccagggcc agaaaccttc aaactttatc cccatatttc accggtcttt ctttgaatcc     540
acggaccagc tgaggtctaa aatgttctct ctgcccctgg agagcgacag catggatccg     600
ttcagaatgg tggaggatgt ggaccaccta gtgaagagtc ccagcttcca gaaatga        657

<210> SEQ ID NO 76
<211> LENGTH: 657
<212> TYPE: DNA
<213> ORGANISM: Mus musculus

<400> SEQUENCE: 76
atggcgagaa agtggaacgg gcgtgcggtg gcccgagccc tggtcctggc cactctgtgg      60
ctggctgtgt ctgggcgtcc cctggctcag caatcccagt ctgtgtcaga tgaagatcca     120
ctctttctct acggctgggg caagattacc cgcctgcagt acctgtactc cgctggtccc     180
tatgtctcca actgcttcct ccgaatccgg agcgacggct ctgtggactg cgaggaggac     240
caaaacgaac gaaatttgtt ggaattccgc gcggtcgctc tgaagacgat tgccatcaag     300
gacgtcagca gcgtgcggta cctctgcatg agcgcggacg gcaagatata cgggctgatt     360
cgctactcgg aggaagactg taccttcagg gaggaaatgg actgtttagg ctacaaccag     420
tacagatcca tgaagcacca ctccatatc atcttcatcc aggccaagcc cagagaacag     480
ctccaggacc agaaaccctc aaactttatc cccgtgtttc accgctcctt ctttgaaacc     540
```

```
ggggaccagc tgaggtctaa aatgttctcc ctgcccctgg agagtgacag catggatccg    600
ttcaggatgg tggaggatgt agaccaccta gtgaagagtc ccagcttcca gaaatga      657

<210> SEQ ID NO 77
<211> LENGTH: 684
<212> TYPE: DNA
<213> ORGANISM: Gallus gallus

<400> SEQUENCE: 77
atggggccgg cccgccccgc cgcacccggc gctgccctgg cgctgctggg gatcgccgcc    60
gccgccgccg ccgccaggtc cctgccgctg cccgacgtcg ggggtccgca cgtcaactac   120 ggctggggg aacccatccg gctgcggcac ctactacacc gcccaggcaa gcacgggctc   180
ttcagctgct cctgcgcat cggcggcgac ggccgggtgg acgctgtcgg tagccagagc    240
ccgcagagtc tgttggagat ccgcgccgtg gcggtgcgca ccgtggccat caagggcgtg   300
cagagctccc gctacctctg catggacgag gcggggcggc tgcacgggca gctcagctat   360
tccattgagg actgttcctt tgaagaggag attcgtccag acggctacaa cgtgtataaa   420
tcaaagaaat acgggatatc ggtgtctttg agcagtgcca aacaaagaca gcaattcaaa   480
ggaaaagatt ttctcccgct gtctcacttc ttacccatga tcaacactgt gccagtggag   540
gtgacagact tggtgaata tggtgattac agccaggctt ttgagccaga ggtctactca   600
tcgcctctcg aaacggacag catggatccc tttgggatca cttccaaact gtctccagtg   660
aagagcccca gctttcagaa atga                                          684

<210> SEQ ID NO 78
<211> LENGTH: 714
<212> TYPE: DNA
<213> ORGANISM: Taeniopygia guttata

<400> SEQUENCE: 78
atggttatca taagcaatct atatctgatg cagaacgatg ttatgatgaa tatgaggcga    60
gcaccccttc gcgttcacgc tgctcgctct tcggccaccc ctgcctccgc gctgccgctg   120
ccgccgcccg acgccggccc gcacctcaaa tacggctggg gagagcccat ccggctgcgg   180
cacctctaca ccgccagcaa gcacgggctc ttcagctgct cctgcgtat cggcgctgac   240 ggccgggtgg acgcggccgg cagccagagc ccgcagagcc tgctagagat ccgcgccgtg   300
gccgtgcgca ccgtggccat caagggcgtg cagagctccc ggtacctgtg catggacgag   360
gcggggcggc tgcacgggca gctcaggaat tccactgaag actgctcctt tgaggaggag   420
attcgcccag acggctacaa tgtgtataga tctaaaaaac atggaatatc ggtgtctttg   480
agcagtgcca aacaaagaca gcagttcaag gggaaagatt tccttcccct gtctcacttc   540
ttgcccatga tcaacactgt gcccatggag tcagcagact tggtgaata tggtgattac    600 agccaggcct ttgaggcaga ggccttctcc tcacctctgg agacggacag catggacccc   660
tttggcatcg cctccaaact gtccctagtg aagagcccta gcttccaaaa ctga         714

<210> SEQ ID NO 79
<211> LENGTH: 633
<212> TYPE: DNA
<213> ORGANISM: Danio rerio

<400> SEQUENCE: 79
atgctcctct tactctttgt cactgtttgt ggaagtatcg gcgtggagag cctcccgttg    60
```

| | |
|---|---|
| cccgactctg gtccacattt ggcaaatgac tggagtgaag ccgtccggct acgacatctg | 120 |
| tacgcagcca gacatggctt acatctgcaa ataaacacag acggagaaat cattggatcc | 180 |
| acatgcaaag ctcggacagt aagtttgatg gagatatggc cggtggacac aggctgcgta | 240 |
| gccattaagg gagttgcaag ctcccgattt ctttgcatgg aaagactggg aaacctgtac | 300 |
| ggatcgcaca tttacactaa agaggactgc tcttttttgg aacgcatcct tccagacggc | 360 |
| tacaacgtct acttctcgag caaacacgga gctcttgtga ctttaagtgg tgcgaaaaac | 420 |
| aagttgcaca gtaacgatgg gacttctgca tcccagttcc tccccatgat caacacactt | 480 |
| tcagaggaac acactaaaca gcactcaggg gaacagcact cttctgttaa ccatggacag | 540 |
| gaccatcagt tgggccttga aatagacagt atggacccct tcggaaagat ctctcaaata | 600 |
| gtgatccaga gtcccagctt caacaaaaga tga | 633 |

<210> SEQ ID NO 80
<211> LENGTH: 648
<212> TYPE: DNA
<213> ORGANISM: Xenopus (Silurana) tropicalis

<400> SEQUENCE: 80

| | |
|---|---|
| atgtggaaga ccctgccttg gattttggtt cccatgatgg tggccgtgct gtatttcctc | 60 |
| ggaggggcgg aaagtctgcc gcttttttgat gccgggccgc acatgcagaa cggctggggg | 120 |
| gagtcgatca gaattcggca cctgtatacg gccaggaggt cgggcacga cagctactac | 180 |
| ctccggatac acgaggatgg cagagtcgat ggtgacaggc aacaaagcat gcacagttta | 240 |
| ttggaaatca gagcaattgc agttggaatt gttgccatta aagggtatcg cagctctctg | 300 |
| tacctgtgca tggggtccga gggaaaactc tatggaatgc acagttactc ccaggatgat | 360 |
| tgctcttttg aagaggagct tctcccggat ggatacaaca tgtataaatc aaggaaacat | 420 |
| ggcgttgctg tctcccctaag caaggagaag cagaagcaac aatacaaagg aaagggctac | 480 |
| ctcccgttgt cccatttcct acccgtgata agctgggtgc ccatggagcc caccggagat | 540 |
| gtagaagatg atatctacag gtttccattc aatacggaca caaaaagtgt cattgacagc | 600 |
| cttgataccc tgggactaat ggattttcg agttatcaca agaaatag | 648 |

<210> SEQ ID NO 81
<211> LENGTH: 660
<212> TYPE: DNA
<213> ORGANISM: Otolemur garnettii

<400> SEQUENCE: 81

| | |
|---|---|
| atgcccagcg ggctgagagg gcgtgtggta gccggcgccc tggccctggc cagcttctgg | 60 |
| ctggccgtgg ccgggcgccc gctggccttc tcggatgccg ccctcacgt gcactacggc | 120 |
| tggggtgagc ccatccgcct gcgacacctg tacaccgccg gccccacgg cctctccagc | 180 |
| tgcttcctgc gcgtacgcac cgacggtgcg gtagactgcg cgcggggcca gagcgcacac | 240 |
| agtttgctgg aaatcagggc cgtcgctctc cggaccgtgg ccatcaaagg cgtgcacagc | 300 |
| gcgcggtacc tctgcatggg cgccgacggc aggatgcagg gctgcctca gtactcggag | 360 |
| gaagactgtg cctttgagga ggagatccgg ccagacggct acaacgtcta ctggtctgag | 420 |
| aagcaccgcc tgccggtgtc tctgagcagt gcccggcaga ggcagctgta caagggcagg | 480 |
| ggctttctgc cgctctctca cttcctgccc atgctgcctg tgaccccagc cgagcccggg | 540 |
| gacctcagag accacctgga atccgacatg ttctctttgc ccctgaaaac tgacagcatg | 600 |
| gatccatttg ggatcgccac cagactgggc gtggtgaaga gtcccagctt tcagaaatga | 660 |

<210> SEQ ID NO 82
<211> LENGTH: 660
<212> TYPE: DNA
<213> ORGANISM: Felis catus

<400> SEQUENCE: 82

| | | | | | |
|---|---|---|---|---|---|
| atgcggagcg | cgccgagcca | gtgcgcggta | acccgcgccc | tggtcctagc | cggtctctgg | 60 |
| ctggcagcag | ccgggcgccc | cctagccttc | tcggacgcgg | ggcctcacgt | gcactacggc | 120 |
| tggggtgagc | ccatccgcct | gcggcacctg | tacaccgccg | gcccccacgg | cctctccagc | 180 |
| tgcttcctgc | gcatccgagc | cgacgggggg | gttgactgcg | cgcggagcca | gagcgcgcac | 240 |
| agtttggtgg | agatcagggc | agtcgctctg | cggaccgtgg | ccatcaaggg | cgtgcacagc | 300 |
| gtccggtacc | tctgcatggg | cgccgacggc | aggatgcaag | gctgcttca | gtactctgct | 360 |
| ggggactgtg | ccttccaaga | ggagatccgc | cccgacggct | acaatgtgta | ccggtccgag | 420 |
| aagcaccgtc | tccccgtctc | tttgagtagt | gccatacaga | ggcagctgta | caagggcaga | 480 |
| gggttttgc | ccctgtccca | tttcttgccc | atgctgcccg | gcagcccagc | agagcccagg | 540 |
| gacctccagg | accacgtgga | gtcggagagg | ttttcttcac | ccctggaaac | agacagcatg | 600 |
| gaccctttg | ggattgccac | caaaatgggg | ttagtgaaga | gtcccagctt | ccaaaagtaa | 660 |

<210> SEQ ID NO 83
<211> LENGTH: 672
<212> TYPE: DNA
<213> ORGANISM: Pelodiscus sinensis

<400> SEQUENCE: 83

| | | | | | |
|---|---|---|---|---|---|
| atgtggagga | gcctgtgcaa | atctcacacg | tctctggctc | tgctgggact | ctgctttgcg | 60 |
| gtggtcgtga | gatctctgcc | tttctcggat | gcagggccac | atgtgaacta | tggctggggg | 120 |
| gagcctattc | gattaaggca | cctatacacc | gccagcagac | acgggctgtt | caattacttc | 180 |
| ctgaggatca | gcagtgatgg | caaagtggat | ggcaccagca | ttcagagtcc | tcacagtctg | 240 |
| ctggaaatca | gggctgtggc | agttcgcacg | gtggcgatca | agggcgtcca | cagttcccgg | 300 |
| tacctctgca | tggaagaaga | cgggaagctg | catggacttc | tcaggtattc | tacagaagat | 360 |
| tgctcctttg | aagaggagat | acgcccagat | ggctacaatg | tatataaatc | aaagaaatat | 420 |
| ggaatctctg | tgtccttaag | tagtgccaaa | caaagacaac | aattcaaagg | aaaagacttt | 480 |
| cttccattgt | ctcacttctt | gcctatgatc | aatacagtac | ctgtggagtc | aatggatttt | 540 |
| ggagaatatg | tgattatag | tcatactttt | gaatcagatc | tattctcttc | acctctcgaa | 600 |
| actgacagca | tggatcccctt | tggaatcacc | tctaaaatat | ctccagtgaa | gagccccagc | 660 |
| tttcagaaat | aa | | | | | 672 |

<210> SEQ ID NO 84
<211> LENGTH: 654
<212> TYPE: DNA
<213> ORGANISM: Latimeria chalumnae

<400> SEQUENCE: 84

| | | | | | |
|---|---|---|---|---|---|
| atgttacagg | cactgtacaa | tctctgtaca | gctctagttt | tgtttaagct | tccttttgca | 60 |
| atggtggggt | acaccctgcc | ttctgccaat | gaagggcccc | atctgaacta | tgactgggga | 120 |
| gaatctgtaa | gactcaaaca | tctgtacaca | tctagcaagc | atggattgat | cagttacttt | 180 |
| ttacagatca | atgatgatgg | caaagtagat | gggaccacta | cacgaagctg | ttatagtttg | 240 |

```
ctcgaaataa aatcagtggg gccaggagtt ttggcaatta aaggcataca gagctccaga    300
tacctttgtg tcgagaagga tggaaaattg catggatcgc gcacttattc agcagacgat    360
tgctccttca aagaggatat actcccagat ggttacacta tctacgtgtc aaagaaacat    420
ggatctgttg ttaatctgag caaccacaaa cagaaacgtc agagaaatcg cagaaccctg    480
cctccatttt ctcagttcct accgcttatg gacaccattc gtgtggagtg catgaactgc    540
ggggagcact gtgacgacaa cctgcatgac gagctagaaa caggactgtc catggatccc    600
tttgaaagta catccaaaaa atcctttcag agtcccagct tcacaatag ataa             654
```

\<210\> SEQ ID NO 85
\<211\> LENGTH: 660
\<212\> TYPE: DNA
\<213\> ORGANISM: Mustela putorius

\<400\> SEQUENCE: 85

```
atgcggagcg ccgcgagtcg gtgcgcggta gcccgcgcgc tggtcctagc cggcctttgg     60
ctggccgcag ccgggcgccc cctagccttc tcggacgcgg ggccgcacgt gcactatggc    120
tggggtgagc ccatccgcct acggcacctg taccgcccg ccccacgg cctctccagc       180 tgcttcctgc gcatccgtgc cgacggcggg gttgactgcg cgcggggcca gagcgcgcac    240
agtttggtgg agatccgggc agtcgctctg cggacggtgg ccatcaaggg cgtgtacagc    300
gaccgctatc tctgcatggg tgcggacggc aggatgcaag gctgcctca gtactccgcc    360 ggagactgtg ctttcgagga ggagatccgc cctgatggct acaacgtgta ccggtccaag    420
aagcaccgtc tccccgtctc cctgagcagt gcgaaacaaa ggcagctgta caaggaccgg    480 ggcttttgc ctctgtccca tttcttgccc atgctgcccg ggagcctggc ggagcccagg     540
gacctccagg accacgtgga ggctgatggg ttttctgccc ccctagaaac agacagcatg    600
gaccctttgg ggattgccac caaaatggga ctagtgaaga gtcccagctt ccaaaaatga    660
```

\<210\> SEQ ID NO 86
\<211\> LENGTH: 654
\<212\> TYPE: DNA
\<213\> ORGANISM: Takifugu rubripes

\<400\> SEQUENCE: 86

```
tcatctacaa ggattagtgg aaacatggtt ctcctcatgc tccccatcac cgttgcaaac     60
ctcttcctct gtgctggagt tctctccttg cctttgttgg atcaagggtc tcattttccc    120
caaggctggg aacaggtagt ccgcttcagg cacctgtatg ctgccagtgc agggctgcac    180
ctgctgatca ctgaagaggg ctcgatccaa ggctctgcag atccaacttt atacagcctg    240
atggagatcc gtccggtgga cccaggctgt gttgtcatta gggagcagc aaccacacgc     300 ttcctctgca tagaaggtgc tggaagactg tactcatcac agacctacag caaagacgac    360
tgtaccttca gagagcaaat cctagcagac ggctacagcg tctacagatc tgtcggacac    420
ggagctctgg tcagtctggg aaactaccgg cagcagctga gggggagga ctggagcgtt     480 ccgacactgg ctcagttcct ccccagaata agttcactgg atcaggactt taaagctgct    540
cttgacgaga ctgagaagcc agaacaaact gcacctcaaa gatcggaacc tgtcgacatg    600
gtggactcat ttggaaagct ctctcagatc atccacagtc ccagttttca caag            654
```

\<210\> SEQ ID NO 87
\<211\> LENGTH: 282
\<212\> TYPE: DNA
\<213\> ORGANISM: Equus caballus

<400> SEQUENCE: 87

```
gcggccgggc gcccctagc cttgtccgac gctgggccgc acgtgcacta cggctggggc    60
gagccgatcc gcctgcggca cctgtacacc gccggcccc acggcctctc cagctgcttc    120
ctgcgcatcc gcgccgatgg cgccgtgac tgcgcgcggg gccagagcgc gcacagtttg    180
gtggagatca gagcagtcgc tctgcgcacc gtggccatca agggcgtgca cagcgtccgg    240
tacctctgca tgggcgccga cggcaggatg caagggctgg ta                      282
```

<210> SEQ ID NO 88
<211> LENGTH: 630
<212> TYPE: DNA
<213> ORGANISM: Oryzias latipes

<400> SEQUENCE: 88

```
accatgctgc tcattgtggt caccattcc acaatggtgt ttctgactc tggagttcc      60
agcatgccgc tctctgatca tggacccac atcactcaca gctggagcca agtggtccgc    120
ctccggcacc tgtacgcggt caagcctgga caacatgtcc agatcagaga ggatggacac    180
atccacggct cagcagaaca aactctgaac agcctgctgg atccgtcc ggttgctccg     240
ggacgggtgg tcttcagagg agtagccacc tcaaggtttc tgtgcatgga gagcgacggc    300
agactcttct cctcacacac atttgacaag acaactgcg tcttcagaga gcagatcttg    360
gcagacggct acaacatcta catttcagat cagcatggaa ccctgcttag tttgggaaac    420
caccggcaaa ggcagcaggg tttagaccgg gatgttccag ccctggctca gttcctcccc    480
aggatcagca ccctgcagca gggcgtgtac ccagtgccag accccccca ccagatgaga    540
acaatgcaaa cagagaagac tctagatgcc acggacacat ttgggcaact ctctaaaatc    600
attcacagtc ccagcttcaa caaaagatga                                    630
```

<210> SEQ ID NO 89
<211> LENGTH: 624
<212> TYPE: DNA
<213> ORGANISM: Xiphophorus maculatus

<400> SEQUENCE: 89

```
atgtttgtgt tcattctatg cattgctggt gaactttta ctctgggagt attttgcatg     60
ccaatgatgg accaggggcc acttgtcacc catggctggg gccaggtggt ccggcaccgg    120
catctgtatg cagccaagcc aggactgcac ctactgatca gtgaggatgg acaaatccac    180
ggttccgcag atcaaactct ttacagcctg ctggagatcc aacctgttgg ccccggacgt    240
gttgtgatca aggagtggc aaccacacgc ttcctctgca tggagagcga cggcagattg    300
tactcaactg aaacatacag cagagctgac tgcaccttca gagaacagat ccaggcagac    360
ggctacaacg tctacaccct tgatagccat ggagccctcc tcagtttggg aaacaaccag    420
caaagacaca gcggctcaga ccgtggtgtt ccagctctgg cccgctttct tcccaggtta    480
aacacccttc agcaggccgt ccccacagag ccggatgttc ctgatcagct cagtccagag    540
aaagtacaac agactgtgga catggtggcc tcctttggca agctctctca tataattcac    600
agtcccagct tccataagag atga                                          624
```

<210> SEQ ID NO 90
<211> LENGTH: 663
<212> TYPE: DNA
<213> ORGANISM: Ictidomys tridecemlineatus

<400> SEQUENCE: 90

```
atgcggagcg cgccgagcgg acgtgcctta gcccgcgccc tggtgctggc cagcctctgg      60
ttggcagtgg ccggacgacc cctggcccgg cgctctctgg ctctctccga ccaggggcca     120
cacttgtact atggctggga tcagcccatc cgcctccggc acctgtacgc cgcgggcccc     180
tacggcttct ccaactgttt cctgcgcatc cgcaccgacg gcgccgtgga ctgcgaggag     240
aagcagagcg agcgtagttt gatggagatc agggcggtcg ctctggagac tgtgccatc     300
aaggacataa acagcgtccg gtacctctgc atgggcgccg acggcaggat acagggactg     360
cctcggtact cggaggaaga gtgcacgttc aaggaggaga tcagctatga cggctacaac     420
gtgtaccggt cccagaagta ccacttccc gtggtgctca gcagtgccaa gcagcggcag     480
ctgtaccaga gcaagggcgt ggttcccctg tcctacttcc tgcccatgct gcccctggcc     540
tctgcggaga ccagggaccg cttggaatcc gatgtgttct ctttacctct ggaaactgac     600
agcatggacc cgtttgggat ggccagtgaa gtgggcctga gagccccag cttccagaag     660
taa                                                                   663
```

<210> SEQ ID NO 91
<211> LENGTH: 612
<212> TYPE: DNA
<213> ORGANISM: Gasterosteus aculeatus

<400> SEQUENCE: 91

```
atgctgctgc tgctggtccc cgcgtacgtt gccagtgtgt ttttagctct cggggttgtt      60
tgcttgcccc taacagatca gggtctccac atggccgacg actggggcca gtcggtccga     120
ctcaagcacc tgtacgccgc cagcccggga ctccacctgc tgatcgggga ggatggtcgg     180
atccaaggct cggcgcagca aagccctac agcctgctgg agatcagtgc agtggatccg     240
ggctgtgtgg tcatcagagg agtagcaacc gcacggtttc tctgcatcga aggcgatgga     300
agactgtact catcggacac ctacagcaga gacgactgca ccttcaggga gcagatcctc     360
ccggacggct acagcgtcta cgtctcccat ggacacgggg ccctgctcag cctggggaac     420
cacaggcaga ggctgcaggg tcgagaccac ggcgtgccgg ctctggccca gttcctcccg     480
agggtcagca ccatggatca ggcctcggcc ccgacgcgc ccgggcagac cgccaccgag     540
acggaagagc ccgtggactc gtttggaaag ctctctcaga tcattcacag tcccagcttc     600
cacgagagat ga                                                         612
```

<210> SEQ ID NO 92
<211> LENGTH: 627
<212> TYPE: DNA
<213> ORGANISM: Oreochromis niloticus

<400> SEQUENCE: 92

```
atgctgctgc tcctcatcgt atccattgtc aatatgcttt ttggtgttgg aatggtttgc      60
atgcccctgt cagacaacgg gccccacatc gcccacggct gggcccaggt ggtccggctc     120
aggcaccttt acgccaccag accgggaatg cacctgctga tcagtgaggg tggacagatc     180
cgtggttctg ccgtccagac tctgcacagc ctaatggaga ttcgtccagt cggtccaggc     240
cgtgttgtca tcagaggggt agcaaccgca aggtttctct gcatagaaga cgacggcaca     300
ctgtactcat cgcacgccta cagcagagag gactgcatct tcagagagca gatcttgcca     360
gatgggtaca acatctacat ctctgacaga catggagtcc tgctcagtct gggaaaccac     420
cggcaaagac tgcagggctt agaccgagga gatccagccc tggcccagtt cctccccagg     480
```

| | |
|---|---|
| atcagcactc tgaatcaaat cccttcccct ggggcaaaca tcggtgacca catgaaagta | 540 |
| gcaaaaacag aagaacctgt ggacacaata gattcatttg gaaagttctc tcagatcatt | 600 |
| gacagtccca gcttccataa gagatga | 627 |

<210> SEQ ID NO 93
<211> LENGTH: 456
<212> TYPE: DNA
<213> ORGANISM: Meleagris gallopavo

<400> SEQUENCE: 93

| | |
|---|---|
| gtaggcaatc aatcaccaca gagcatcctt gaaataactg ctgttgatgt cgggatcgtc | 60 |
| gctatcaagg gcttgttctc tggcagatac ctggccatga acaaaagggg caggctttat | 120 |
| gcatcactca gctattccat tgaggactgt tcctttgaag aggagattcg tccagatggc | 180 |
| tataacgtgt ataaatcaaa gaaatacgga atatcagtgt ctttgagcag tgccaaacaa | 240 |
| agacaacaat tcaaaggaaa agattttctc ccactgtctc acttcttacc catgatcaac | 300 |
| actgtgccag tggaggtgac agactttggt gaatacggtg attacagcca ggcttttgag | 360 |
| ccagaggtct actcatcgcc tctcgaaacg gacagcatgg atccctttgg gatcacttcc | 420 |
| aaactgtctc cagtgaagag ccccagcttt cagaaa | 456 |

<210> SEQ ID NO 94
<211> LENGTH: 651
<212> TYPE: DNA
<213> ORGANISM: Papio anubis

<400> SEQUENCE: 94

| | |
|---|---|
| atgaggagcg ggtgtgtggt ggtccacgcc tggatcctgg ccagcctctg gctggccgtg | 60 |
| gccgggcgtc ccctcgcctt ctcggacgcg ggccccacg tgcactacgg ctggggcgac | 120 |
| cccatccgcc tgcggcacct gtacacctcg gcccccacg gctctccag ctgcttcctg | 180 |
| cgcatccgca ccgacggcgt cgtggactgc gcgcggggcc aaagcgcgca cagtttgctg | 240 |
| gagatcaagg cagtagctct gcggaccgtg gccatcaagg gcgtgcacag cgtgcggtac | 300 |
| ctctgcatgg gcgccgacgg caagatgcag gggctgcttc agtactcaga ggaagactgt | 360 |
| gctttcgagg aggagatccg ccctgatggc tacaatgtat accgatccca gaagcaccgc | 420 |
| ctcccggtct ccctgagcag tgccaaacag cggcagctgt acaagaacag aggctttctt | 480 |
| ccgctgtctc atttcctgcc catgctgccc atggccccag aggagcctga ggacctcagg | 540 |
| ggccccttgg aatctgacat gttctcttcg ccctggaga ctgacagcat ggacccattt | 600 |
| gggcttgtca ccggactgga ggcggtgagg agtcccagct ttgagaaata a | 651 |

<210> SEQ ID NO 95
<211> LENGTH: 651
<212> TYPE: DNA
<213> ORGANISM: Saimiri boliviensis boliviensis

<400> SEQUENCE: 95

| | |
|---|---|
| atgcggagcg ggtgtgtggt ggtccacgcc tggatcctgg ctggcctctg gctggctgtg | 60 |
| gtcgggcgcc ccctcgcctt ctccgatgcg ggccgcatg tgcattacgg ctggggcgac | 120 |
| cccattcgcc tgcggcacct gtacacctcc agccccacg gcctctccag ctgcttcctg | 180 |
| cgcatccgca gcgacggcgt cgtggactgc gcgcggggcc agagcgcgca cagtttgctg | 240 |
| gagatcaagg cagtcgctct aaggaccgtg gccatcaagg gcgtgcacag ctcgcggtac | 300 |

```
ctctgcatgg gcgccgacgg caggctgcag gggctgttcc agtactcgga ggaagactgt    360
gctttcgagg aggagatccg ccccgacggc tacaatgtgt acctatccga gaagcaccgc    420
ctcccggtct ccctgagcag cgccaaacag cggcagctgt acaagaaacg aggctttctt    480
ccgctgtccc atttcctgcc catgctgccc agagccccag aggagcctga tgacctcagg    540
ggccacttgg aatctgacgt gttctcttca cccctggaga ctgatagcat ggacccattt    600
gggcttgtca cgggactgga ggcggtgaac agtcccagct ttgagaagta a             651

<210> SEQ ID NO 96
<211> LENGTH: 648
<212> TYPE: DNA
<213> ORGANISM: Pteropus alecto

<400> SEQUENCE: 96
atgcgcagcc cgtgcgcggt ggcgcgcgcg ctggtgctgg cgggcctgtg gctggcgagc     60
gcggcgggcc cgctggcgct gagcgatgcg ggcccgcatg tgcattatgg ctggggcgaa    120
gcgattcgcc tgcgccatct gtataccgcg ggcccgcatg cccgagcag ctgctttctg     180 cgcattcgcg cggatggcgc ggtggattgc gcgcgcggcc agagcgcgca tagcctggtg    240
gaaattcgcg cggtggcgct gcgcaacgtg gcgattaaag gcgtgcatag cgtgcgctat    300
ctgtgcatgg gcgcgatggg ccgcatgctg ggcctgctgc agtatagcgc ggatgattgc    360
gcgtttgaag aagaaattcg cccggatggc tataacgtgt atcatagcaa aaacatcat    420 ctgccggtga gcctgagcag cgcgaaacag cgccagctgt ataaagatcg cggctttctg    480
ccgctgagcc atttttctgcc gatgctgccg cgcagcccga ccgaaccgga aaactttgaa    540
gatcatctgg aagcggatac ctttagcagc ccgctggaaa ccgatgatat ggatccgttt    600
ggcattgcga gcaaactggg cctggaagaa agcccgagct ttcagaaa                 648

<210> SEQ ID NO 97
<211> LENGTH: 735
<212> TYPE: DNA
<213> ORGANISM: Myotis davidii

<400> SEQUENCE: 97
atgagcggcc agaacagcgg ccgccatggc agccgcccgg gcctggatga agaaccggaa     60 ccgggccccgc tggaactgcg cgcgctgggc agcaccccgcg cggatccgca gctgtgcgat    120
tttctggaaa accattttct gggctatacc tgcctggaac tggatatttg cctggcgacc    180
tatctgggcg tgagccattg gggcgaaagc attcgcctgc ccatctgta taccagcggc    240 ccgcatggcc cgagcagctg ctttctgcgc attcgcgtgg atggcgcggt ggattgcgcg    300
cgcggccaga gcgcgcatag cctggtggaa attcgcgcgg tggcgctgcg caaagtggcg    360
attaaaggcg tgcatagcgc gctgtatctg tgcatggaag gcgatggccg catgcgcggc    420
ctgccgcagt ttagcccgga agattgcgcg tttgaagaag aaattcgccc ggatggctat    480
aacgtgtatc gcagccagaa acatcagctg ccggtgagcc tgagcagcgc gcgccagcgc    540
cagctgttta agcgcgcgg ctttctgccg ctgagccatt ttctgccgat gctgccgagc    600
agcccggcgg aaccggtgca tcgcgaacgc ccgctggaac cggatgcgtt tagcagcccg    660
ctggaaaccg atagcatgga tccgtttggc attgcgaaca acctgcgcct ggtgaaaagc    720
ccgagctttc agaaa                                                     735

<210> SEQ ID NO 98
<211> LENGTH: 750
```

```
<212> TYPE: DNA
<213> ORGANISM: Tupaia chinensis

<400> SEQUENCE: 98
atgcgccgca cctggagcgg ctttgcggtg gcgacccgcg cgggcagccc gctggcgctg      60
gcggatgcgg gcccgcatgt gaactatggc tgggatgaaa gcattcgcct gcgccatctg     120
tataccgcga gcctgcatgg cagcaccagc tgctttctgc gcattcgcga tgatggcagc     180
gtgggctgcg cgcgcggcca gagcatgcat agcctgctgg aaattaaagc ggtggcgctg     240
cagaccgtgg cgattaaagg cgtgtatagc gtgcgctatc tgtgcatgga taccgatggc     300
cgcatgcagg gcctgccgca gtatagcgaa gaagattgca cctttgaaga gaaaattcgc     360
agcgatggcc ataacgtgta tcgcagcaaa aaacatggcc tgccggtgag cctgagcagc     420
gcgaaacagc gccagctgta taaaggccgc ggctttctga gcctgagcca ttttctgctg     480
atgatgccga aaccagcgc gggcccgggc aacccgcgcg atcagcgcaa cccgcgcgat     540
cagcgcgatc cgaacacctt tagcctgccg ctggaaaccg atagcatgga tccgtttggc     600
atgaccaccc gccatggcct gctgctggat agctgctgcg cgagcctggt gctgctgaac     660
attagcaccg atgcgaatt tagcccgtat ggcaacattc tgcgcccgag ctttcgcttt     720
aaactgttta aaatgaaaaa agtgaccaac                                      750

<210> SEQ ID NO 99
<211> LENGTH: 627
<212> TYPE: DNA
<213> ORGANISM: Heterocephalus glaber

<400> SEQUENCE: 99
atgcgcttta gcaaaagcac ctgcggcttt tttaaccatc agcgcctgca ggcgctgtgg      60
ctgagcctga gcagcgtgaa atgggtgctg gatgcggcgg tggaaggccg cccgattcgc     120
ctgcgccatc tgtatgcggc gggcccgtat ggccgcagcc gctgctttct gcgcattcat     180
accgatggcg cggtggattg cgtggaagaa cagagcgaac attgcctgct ggaaattcgc     240
gcggtggcgc tggaaaccgt ggcgattaaa gatattaaca gcgtgcgcta tctgtgcatg     300
ggcccggatg gccgcatgca gggcctgccg tggtatagcg aagaagattg cgcgtttaaa     360
gaagaaatta gctatccggg ctatagcgtg tatcgcagcc agaaacatca tctgccgatt     420
gtgctgagca gcgtgaaaca gcgccagcag tatcagagca aaggcgtggt gccgctgagc     480
tattttctgc cgatgctgcc gaaagcgagc gtggaaccgg gcgatgaaga agaaagcgcg     540
tttagcctgc cgctgaaaac cgatagcatg gatccgtttg gcatggcgag cgaaattggc     600
ctggcgaaaa gcccgagctt tcagaaa                                         627

<210> SEQ ID NO 100
<211> LENGTH: 209
<212> TYPE: PRT
<213> ORGANISM: Homo sapiens

<400> SEQUENCE: 100

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
```

```
                    50                  55                  60
Glu Asp Gly Thr Val Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
                130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
                195                 200                 205

Ser
```

<210> SEQ ID NO 101
<211> LENGTH: 209
<212> TYPE: PRT
<213> ORGANISM: Pongo abelii

<400> SEQUENCE: 101

```
Met Asp Ser Asp Glu Thr Gly Phe Glu His Ser Gly Leu Trp Val Pro
 1               5                  10                  15

Val Leu Ala Gly Leu Leu Leu Gly Ala Cys Gln Ala His Pro Ile Pro
                 20                  25                  30

Asp Ser Ser Pro Leu Leu Gln Phe Gly Gly Gln Val Arg Gln Arg Tyr
                 35                  40                  45

Leu Tyr Thr Asp Asp Ala Gln Gln Thr Glu Ala His Leu Glu Ile Arg
 50                  55                  60

Glu Asp Gly Thr Val Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
                130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
                195                 200                 205

Ser
```

<210> SEQ ID NO 102
<211> LENGTH: 209
<212> TYPE: PRT
<213> ORGANISM: Pan troglodytes

<400> SEQUENCE: 102

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Thr
        195                 200                 205

Ser

<210> SEQ ID NO 103
<211> LENGTH: 209
<212> TYPE: PRT
<213> ORGANISM: Canis lupus familiaris

<400> SEQUENCE: 103

Met Gly Trp Ala Glu Ala Gly Phe Glu His Leu Gly Leu Trp Val Pro
1               5                   10                  15

Val Leu Ala Val Leu Leu Glu Ala Cys Arg Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
            100                 105                 110

```
Ser Leu His Phe Asp Pro Val Ala Cys Ser Phe Arg Glu Leu Leu Leu
            115                 120                 125

Glu Asp Gly Tyr Asn Ile Tyr His Ser Glu Thr Leu Gly Leu Pro Leu
        130                 135                 140

Arg Leu Arg Pro His Asn Ser Ala Tyr Arg Asp Leu Ala Pro Arg Gly
145                 150                 155                 160

Pro Ala Arg Phe Leu Pro Leu Pro Gly Leu Leu Pro Ala Pro Pro Glu
                165                 170                 175

Pro Pro Gly Ile Leu Ala Pro Glu Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 104
<211> LENGTH: 209
<212> TYPE: PRT
<213> ORGANISM: Bos Taurus

<400> SEQUENCE: 104

Met Gly Trp Asp Glu Ala Lys Phe Lys His Leu Gly Leu Trp Val Pro
1               5                   10                  15

Val Leu Ala Val Leu Leu Gly Thr Cys Arg Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Lys Leu Tyr Gly
            100                 105                 110

Ser Leu His Phe Asp Pro Lys Ala Cys Ser Phe Arg Glu Leu Leu Leu
            115                 120                 125

Glu Asp Gly Tyr Asn Val Tyr Gln Ser Glu Thr Leu Gly Leu Pro Leu
        130                 135                 140

Arg Leu Pro Pro Gln Arg Ser Ser Asn Arg Asp Pro Ala Pro Arg Gly
145                 150                 155                 160

Pro Ala Arg Phe Leu Pro Leu Pro Gly Leu Pro Ala Ala Pro Pro Asp
                165                 170                 175

Pro Pro Gly Ile Leu Ala Pro Glu Pro Pro Asp Val Gly Ser Ser Asp
            180                 185                 190

Pro Leu Ser Met Val Gly Pro Ser Tyr Gly Arg Ser Pro Ser Tyr Thr
        195                 200                 205

Ser

<210> SEQ ID NO 105
<211> LENGTH: 209
<212> TYPE: PRT
<213> ORGANISM: Equus caballus

<400> SEQUENCE: 105

Met Asp Trp Asp Lys Thr Gly Phe Lys Tyr Gln Gly Leu Trp Val Pro
1               5                   10                  15
```

```
Val Leu Ala Val Leu Leu Gly Ala Cys Gln Ser His Pro Ile Pro
            20                  25                  30

Asp Ser Ser Pro Leu Leu Gln Phe Gly Gly Gln Val Arg Gln Arg His
        35                  40                  45

Leu Tyr Thr Asp Asp Ala Gln Glu Thr Glu Ala His Leu Glu Ile Arg
    50                  55                  60

Ala Asp Gly Thr Val Ala Gly Ala Val His Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
                100                 105                 110

Ser Leu His Phe Asp Pro Val Ala Cys Ser Phe Arg Glu Leu Leu Leu
                115                 120                 125

Glu Asp Gly Tyr Asn Val Tyr Gln Ser Glu Thr Leu Gly Leu Pro Leu
    130                 135                 140

Arg Leu Pro His His Ser Ser Pro Tyr Gln Asp Pro Ala Pro Arg Ala
145                 150                 155                 160

Pro Ala Arg Phe Leu Pro Leu Pro Gly Phe Pro Pro Ala Pro Pro Glu
                165                 170                 175

Pro Pro Gly Ile Pro Ala Pro Glu Pro Pro Asp Val Gly Ser Ser Asp
                180                 185                 190

Pro Leu Ser Met Val Gly Pro Ser Arg Ser Arg Ser Pro Ser Tyr Thr
                195                 200                 205

Ser

<210> SEQ ID NO 106
<211> LENGTH: 209
<212> TYPE: PRT
<213> ORGANISM: Ailuropoda melanoleuca

<400> SEQUENCE: 106

Met Gly Trp Asp Glu Ala Arg Ser Glu Gln Leu Gly Leu Trp Val Pro
1               5                   10                  15

Val Leu Ala Val Leu Leu Glu Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Ala Ile Arg
    50                  55                  60

Ala Asp Gly Thr Val Val Gly Ala Ala Ser Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asp Gly Thr Leu Tyr Gly
                100                 105                 110

Ser Val Arg Phe Asp Pro Val Ala Cys Ser Phe Arg Glu Leu Leu Leu
                115                 120                 125

Glu Asp Gly Tyr Asn Ile Tyr His Ser Glu Thr Leu Gly Leu Pro Leu
    130                 135                 140

Arg Leu Pro Ala His Asn Ser Pro Tyr Arg Asp Ser Ala Pro Arg Gly
145                 150                 155                 160

Pro Ala Arg Phe Leu Pro Leu Pro Gly Leu Leu Pro Val Pro Pro Asp
                165                 170                 175
```

```
Pro Pro Gly Ile Leu Gly Pro Glu Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 107
<211> LENGTH: 209
<212> TYPE: PRT
<213> ORGANISM: Oryctolagus cuniculus

<400> SEQUENCE: 107

Met Asp Trp Gly Lys Ala Lys Cys Arg Pro Gly Leu Trp Val Pro
1               5                   10                  15

Ala Leu Ala Ala Leu Leu Leu Gly Ala Cys Gln Ala His Pro Ile Pro
            20                  25                  30

Asp Ser Ser Pro Leu Leu Gln Phe Gly Asp Gln Val Arg Gln Gln His
            35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Arg Ser Pro Glu Ser Leu
65                  70                  75                  80

Leu Gln Met Lys Ala Leu Gln Pro Gly Ile Ile Gln Ile Leu Gly Val
                85                  90                  95

Gln Thr Ser Arg Phe Leu Cys Gln Arg Pro Asp Gly Thr Leu Tyr Gly
            100                 105                 110

Ser Leu His Phe Asp Arg Glu Ala Cys Ser Phe Arg Glu Leu Leu Arg
            115                 120                 125

Glu Asp Gly Tyr Asn Val Tyr Leu Ser Glu Ala Leu Gly Leu Pro Leu
        130                 135                 140

Arg Leu Ser Pro Gly Ser Pro Arg Arg Ala Pro Ala Pro Arg Gly
145                 150                 155                 160

Pro Ala Arg Phe Leu Pro Leu Pro Gly Leu Pro Pro Asp Leu Pro Glu
                165                 170                 175

Pro Pro Gly Leu Leu Ala Ala Pro Pro Asp Val Asp Ser Pro Asp
            180                 185                 190

Pro Leu Ser Met Val Gln Pro Ala Leu Asp Gln Ser Pro Ser Tyr Thr
            195                 200                 205

Ser

<210> SEQ ID NO 108
<211> LENGTH: 209
<212> TYPE: PRT
<213> ORGANISM: Gorilla gorilla

<400> SEQUENCE: 108

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
```

```
             65                  70                  75                  80
Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
            130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
                195                 200                 205

Ser
```

<210> SEQ ID NO 109
<211> LENGTH: 209
<212> TYPE: PRT
<213> ORGANISM: Nomascus leucogenys

<400> SEQUENCE: 109

```
Met Asp Ser Asp Glu Thr Gly Phe Glu His Ser Gly Leu Trp Val Pro
1               5                   10                  15

Val Leu Ala Gly Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
                115                 120                 125

Glu Asp Gly Tyr Asn Val Tyr Gln Ser Glu Ala His Gly Leu Pro Leu
            130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Ala Pro Pro Glu
                165                 170                 175

Pro Pro Gly Ile Leu Ala Pro Gln Pro Pro Asp Val Gly Ser Ser Asp
                180                 185                 190

Pro Leu Ser Met Val Gly Pro Ser Gln Gly Arg Ser Pro Ser Tyr Ala
                195                 200                 205

Ser
```

<210> SEQ ID NO 110

<211> LENGTH: 209
<212> TYPE: PRT
<213> ORGANISM: Procavia capensis

<400> SEQUENCE: 110

Met Asp Trp Ala Lys Phe Gly Ile Glu His Pro Gly Leu Trp Val Pro
1               5                   10                  15

Val Met Ala Val Leu Leu Gly Ala Cys Gln Gly Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
50                  55                  60

Ala Asp Gly Thr Val Val Gly Ala Ala His Arg Ser Pro Glu Ser Leu
65                  70                  75                  80

Leu Glu Leu Lys Ala Leu Lys Pro Gly Ile Ile Gln Ile Leu Gly Val
                85                  90                  95

Lys Thr Ser Arg Phe Leu Cys Gln Gly Pro Asp Gly Val Leu Tyr Gly
            100                 105                 110

Ser Leu Arg Phe Asp Pro Val Ala Cys Ser Phe Arg Glu Leu Leu Leu
        115                 120                 125

Glu Asp Gly Tyr Asn Val Tyr Gln Ser Glu Ala His Gly Leu Pro Leu
130                 135                 140

Arg Leu Pro Ser His Asn Ser Pro Gln Arg Asp Leu Ala Ser Arg Val
145                 150                 155                 160

Pro Ala Arg Phe Leu Pro Leu Pro Gly Arg Leu Thr Val Leu Pro Glu
                165                 170                 175

Pro Ser Gly Val Leu Gly Pro Glu Pro Pro Asp Val Asp Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 111
<211> LENGTH: 209
<212> TYPE: PRT
<213> ORGANISM: Cavia porcellus

<400> SEQUENCE: 111

Met Asp Trp Ala Arg Thr Glu Cys Glu Arg Pro Arg Leu Trp Val Ser
1               5                   10                  15

Met Leu Ala Ile Leu Leu Val Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Asp Thr Glu Val His Leu Glu Ile Arg
50                  55                  60

Ala Asp Gly Ser Val Arg Gly Ile Ala His Arg Ser Pro Glu Ser Leu
65                  70                  75                  80

Leu Glu Leu Lys Ala Leu Lys Pro Gly Val Ile Gln Ile Leu Gly Ile
                85                  90                  95

Arg Thr Ser Arg Phe Leu Cys Gln Arg Pro Asp Gly Ser Leu Tyr Gly
            100                 105                 110

Ser Leu His Phe Asp Pro Glu Ala Cys Ser Phe Arg Glu Leu Leu Leu
        115                 120                 125

```
Ala Asp Gly Tyr Asn Val Tyr Lys Ser Glu Ala His Gly Leu Pro Leu
    130                 135                 140

His Leu Leu Arg Gly Asp Ser Leu Ser Gln Glu Pro Ala Pro Pro Gly
145                 150                 155                 160

Pro Ala Arg Phe Leu Pro Leu Pro Gly Leu Pro Ala Thr Pro Pro Glu
                165                 170                 175

Pro Pro Arg Met Leu Pro Pro Gly Pro Pro Asp Val Gly Ser Ser Asp
            180                 185                 190

Pro Leu Ser Met Val Gly Pro Leu Trp Asp Arg Ser Pro Ser Tyr Thr
            195                 200                 205

Ser

<210> SEQ ID NO 112
<211> LENGTH: 209
<212> TYPE: PRT
<213> ORGANISM: Tupaia belangeri

<400> SEQUENCE: 112

Met Gly Trp Asp Lys Ala Arg Phe Glu His Leu Gly Ala Trp Ala Pro
1               5                   10                  15

Val Leu Ala Val Leu Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Thr Gln Asp Thr Glu Ala His Leu Glu Ile Arg
50                  55                  60

Ala Asp Gly Thr Val Val Gly Ala Ala His Gln Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Ile Tyr Gln Ser Glu Ala Arg Gly Leu Pro Leu
    130                 135                 140

Arg Leu Pro Pro His Asp Ser Pro His Arg Asp Arg Thr Pro Arg Gly
145                 150                 155                 160

Pro Ala Arg Phe Leu Pro Leu Pro Gly Leu Pro Leu Val Pro Pro Glu
                165                 170                 175

Leu Pro Gly Val Leu Ala Leu Glu Pro Pro Asp Val Gly Ser Ser Asp
            180                 185                 190

Pro Leu Ser Met Met Gly Pro Ser Gln Gly Gln Ser Pro Ser Tyr Ala
            195                 200                 205

Ser

<210> SEQ ID NO 113
<211> LENGTH: 210
<212> TYPE: PRT
<213> ORGANISM: Sorex araneus

<400> SEQUENCE: 113

Met Val Trp Asp Lys Ala Arg Gly Gln Gln Leu Gly Leu Trp Ala Pro
1               5                   10                  15

Met Leu Leu Gly Leu Leu Leu Gly Ala Cys Gln Ala His Pro Leu Pro
            20                  25                  30
```

Asp Ser Ser Pro Leu Leu Gln Phe Gly Gly Gln Val Arg Leu Arg Phe
            35                  40                  45

Leu Tyr Thr Asp Asp Ala Gln Arg Thr Gly Ala His Leu Glu Ile Arg
 50                  55                  60

Ala Asp Gly Thr Val Gln Gly Ala Ala His Arg Thr Pro Glu Cys Leu
 65                  70                  75                  80

Leu Glu Leu Lys Ala Leu Lys Pro Gly Val Ile Gln Ile Leu Gly Val
                85                  90                  95

Ser Thr Ser Arg Phe Leu Cys Gln Arg Pro Asp Gly Val Leu Tyr Gly
            100                 105                 110

Ser Leu Arg Phe Asp Pro Glu Ala Cys Ser Phe Arg Glu Leu Leu Leu
            115                 120                 125

Gln Asp Gly Tyr Asn Val Tyr Gln Ser Glu Ala Leu Gly Leu Pro Leu
130                 135                 140

Tyr Leu His Pro Pro Ser Ala Pro Val Ser Gln Glu Pro Ala Ser Arg
145                 150                 155                 160

Gly Ala Val Arg Phe Leu Pro Leu Pro Gly Leu Pro Pro Ala Ser Leu
                165                 170                 175

Glu Pro Pro Arg Pro Pro Ala Pro Val Pro Pro Asp Val Gly Ser Ser
            180                 185                 190

Asp Pro Leu Ser Met Val Gly Pro Pro Glu Arg His Ser Pro Ser Tyr
            195                 200                 205

Thr Ser
    210

<210> SEQ ID NO 114
<211> LENGTH: 208
<212> TYPE: PRT
<213> ORGANISM: Ictidomys tridecemlineatus

<400> SEQUENCE: 114

Met Asp Trp Val Lys Ala Lys Leu Glu Pro Leu Gly Leu Trp Val Leu
 1               5                  10                  15

Val Leu Ala Ala Leu Val Leu Gly Ala Cys Gln Ala Tyr Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Glu Thr Glu Ala His Leu Glu Ile Arg
 50                  55                  60

Ala Asp Gly Thr Val Val Gly Ala Ala His Gln Ser Pro Glu Ser Leu
 65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Val Leu Tyr Gly
            100                 105                 110

Ser Leu His Phe Asp Pro Glu Ala Cys Ser Phe Arg Glu Gln Leu Leu
            115                 120                 125

Glu Asp Gly Tyr Asn Val Tyr Gln Ser Glu Ser His Gly Leu Pro Val
130                 135                 140

Arg Leu Pro Pro Asn Ser Pro Tyr Arg Asp Ala Pro Pro Gly Pro
145                 150                 155                 160

Ala Arg Phe Leu Pro Leu Pro Gly Leu Pro Pro Ala Ala Leu Glu Pro
                165                 170                 175

Pro Gly Ile Leu Gly Pro Glu Pro Pro Asp Val Gly Ser Ser Asp Pro

```
                  180                 185                 190

Leu Ser Met Val Gly Pro Leu Gln Gly Arg Ser Pro Ser Tyr Ala Ser
            195                 200                 205

<210> SEQ ID NO 115
<211> LENGTH: 208
<212> TYPE: PRT
<213> ORGANISM: Loxodonta Africana

<400> SEQUENCE: 115

Met Asp Trp Ala Lys Phe Gly Leu Glu His Pro Gly Leu Trp Val Pro
1               5                   10                  15

Val Met Ala Val Leu Leu Gly Ala Cys Gln Gly His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Gln Glu Thr Glu Ala His Leu Glu Ile Arg Ala
    50                  55                  60

Asp Gly Thr Val Ala Gly Ala Ala His Arg Ser Ser Glu Ser Leu Leu
65                  70                  75                  80

Glu Leu Lys Ala Leu Lys Pro Gly Ile Ile Gln Ile Leu Gly Val Lys
                85                  90                  95

Thr Ser Arg Phe Leu Cys Gln Gly Pro Asp Gly Val Leu Tyr Gly Ser
            100                 105                 110

Leu His Phe Asp Pro Ala Ala Cys Ser Phe Arg Glu Leu Leu Leu Glu
        115                 120                 125

Asp Gly Tyr Asn Val Tyr Trp Ser Glu Ala His Gly Leu Pro Ile Arg
    130                 135                 140

Leu Pro Ser His Asn Ser Pro Tyr Arg Asp Pro Ala Ser Arg Val Pro
145                 150                 155                 160

Ala Arg Phe Leu Pro Leu Pro Gly Leu Leu Pro Met Leu Gln Glu Pro
                165                 170                 175

Pro Gly Val Leu Ala Pro Glu Pro Pro Asp Val Asp Ser Ser Asp Pro
            180                 185                 190

Leu Ser Met Val Gly Pro Ser Gln Gly Arg Ser Pro Ser Tyr Ala Ser
        195                 200                 205

<210> SEQ ID NO 116
<211> LENGTH: 208
<212> TYPE: PRT
<213> ORGANISM: Sus scrofa

<400> SEQUENCE: 116

Met Gly Trp Ala Glu Ala Lys Phe Glu Arg Leu Gly Leu Trp Val Pro
1               5                   10                  15

Val Leu Ala Val Leu Leu Gly Ala Cys Gln Ala Arg Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Glu Thr Glu Ala His Leu Glu Ile Arg Ala
    50                  55                  60

Asp Gly Thr Val Ala Gly Val Ala Arg Gln Ser Pro Glu Ser Leu Leu
65                  70                  75                  80

Glu Leu Lys Ala Leu Lys Pro Gly Val Ile Gln Ile Leu Gly Val Gln
                85                  90                  95

Thr Ser Arg Phe Leu Cys Gln Gly Pro Asp Gly Arg Leu Tyr Gly Ser
```

```
                      100                 105                 110
Leu His Phe Asp Pro Glu Ala Cys Ser Phe Arg Glu Leu Leu Leu Glu
            115                 120                 125

Asp Gly Tyr Asn Val Tyr Gln Ser Glu Ala Leu Gly Leu Pro Leu Arg
        130                 135                 140

Leu Pro Pro His Arg Ser Ser Asn Arg Asp Leu Ala Pro Arg Gly Pro
145                 150                 155                 160

Ala Arg Phe Leu Pro Leu Pro Gly Leu Pro Ala Pro Pro Glu Pro
                165                 170                 175

Pro Gly Ile Leu Ala Pro Glu Pro Pro Asp Val Gly Ser Ser Asp Pro
            180                 185                 190

Leu Ser Met Val Gly Pro Ser His Gly Arg Ser Pro Ser Tyr Thr Ser
        195                 200                 205

<210> SEQ ID NO 117
<211> LENGTH: 208
<212> TYPE: PRT
<213> ORGANISM: Felis catus

<400> SEQUENCE: 117

Met Asp Trp Asp Glu Ala Gly Ser Gln Arg Leu Gly Leu Trp Val Val
1               5                   10                  15

Leu Gly Val Leu Leu Pro Glu Ala Cys Gln Ala His Pro Ile Pro Asp
                20                  25                  30

Ser Ser Pro Leu Leu Gln Phe Gly Gly Gln Val Arg Gln Arg Phe Leu
            35                  40                  45

Tyr Thr Asp Asp Ala Gln Glu Thr Glu Val His Leu Glu Ile Lys Ala
        50                  55                  60

Asp Gly Thr Val Val Gly Thr Ala Arg Arg Ser Pro Glu Ser Leu Leu
65                  70                  75                  80

Glu Leu Lys Ala Leu Lys Pro Gly Val Ile Gln Ile Leu Gly Val Lys
                85                  90                  95

Thr Ser Arg Phe Leu Cys Gln Gly Pro Asp Gly Thr Leu Tyr Gly Ser
                100                 105                 110

Leu Arg Phe Asp Pro Ala Ala Cys Ser Phe Arg Glu Leu Leu Leu Glu
            115                 120                 125

Asp Gly Tyr Asn Ile Tyr His Ser Glu Thr Leu Gly Leu Pro Leu Arg
        130                 135                 140

Leu Pro Pro His Asn Ser Pro Tyr Arg Asp Leu Ala Pro Arg Ala Pro
145                 150                 155                 160

Ala Arg Phe Leu Pro Leu Pro Gly Leu Leu Pro Ala Pro Pro Glu Pro
                165                 170                 175

Pro Gly Ile Leu Ala Pro Glu Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205

<210> SEQ ID NO 118
<211> LENGTH: 208
<212> TYPE: PRT
<213> ORGANISM: Otolemur garnettii

<400> SEQUENCE: 118

Asp Lys Ala Arg Thr Gly Phe Lys His Pro Gly Pro Trp Phe Pro Leu
1               5                   10                  15

Leu Ala Val Leu Leu Leu Gly Ala Cys Gln Ala His Pro Ile Pro Asp
```

```
                    20                  25                  30
Ser Ser Pro Leu Leu Gln Phe Gly Gly Gln Val Arg Gln Arg Tyr Leu
            35                  40                  45
Tyr Thr Asp Asp Ala Gln Glu Thr Glu Ala His Leu Glu Ile Arg Glu
        50                  55                  60
Asp Gly Thr Val Val Gly Ala Ala Gln Gln Ser Pro Glu Ser Leu Leu
65                  70                  75                  80
Glu Leu Lys Ala Leu Lys Pro Gly Val Ile Gln Ile Leu Gly Val Lys
                85                  90                  95
Thr Ser Arg Phe Leu Cys Gln Arg Pro Asp Gly Gly Leu Tyr Gly Ser
            100                 105                 110
Leu Tyr Phe Asp Pro Lys Ala Cys Ser Phe Arg Glu Leu Leu Leu Glu
        115                 120                 125
Asp Gly Tyr Asn Val Tyr Trp Ser Glu Thr Tyr Gly Leu Pro Leu His
        130                 135                 140
Leu Pro Pro Ala Asn Ser Pro Tyr Trp Gly Pro Ser Leu Arg Ser Pro
145                 150                 155                 160
Ala Arg Phe Leu Pro Leu Pro Gly Pro Pro Ala Ala Ser Pro Glu Leu
                165                 170                 175
Pro Gly Ile Leu Ala Leu Glu Pro Pro Asp Val Gly Ser Ser Asp Pro
            180                 185                 190
Leu Ser Met Val Gly Pro Ser Gln Gly Arg Ser Pro Ser Tyr Ala Ser
        195                 200                 205

<210> SEQ ID NO 119
<211> LENGTH: 208
<212> TYPE: PRT
<213> ORGANISM: Rattus norvegicus

<400> SEQUENCE: 119

Met Asp Trp Met Lys Ser Arg Val Gly Ala Pro Gly Leu Trp Val Cys
1               5                   10                  15
Leu Leu Leu Pro Val Phe Leu Leu Gly Val Cys Glu Ala Tyr Pro Ile
                20                  25                  30
Ser Asp Ser Ser Pro Leu Leu Gln Phe Gly Gly Gln Val Arg Gln Arg
            35                  40                  45
Tyr Leu Tyr Thr Asp Asp Gln Asp Thr Glu Ala His Leu Glu Ile
        50                  55                  60
Arg Glu Asp Gly Thr Val Val Gly Thr Ala His Arg Ser Pro Glu Ser
65                  70                  75                  80
Leu Leu Glu Leu Lys Ala Leu Lys Pro Gly Val Ile Gln Ile Leu Gly
                85                  90                  95
Val Lys Ala Ser Arg Phe Leu Cys Gln Gln Pro Asp Gly Thr Leu Tyr
            100                 105                 110
Gly Ser Pro His Phe Asp Pro Glu Ala Cys Ser Phe Arg Glu Leu Leu
        115                 120                 125
Leu Lys Asp Gly Tyr Asn Val Tyr Gln Ser Glu Ala His Gly Leu Pro
        130                 135                 140
Leu Arg Leu Pro Gln Lys Asp Ser Gln Asp Pro Ala Thr Arg Gly Pro
145                 150                 155                 160
Val Arg Phe Leu Pro Met Pro Gly Leu Pro His Glu Pro Gln Glu Gln
                165                 170                 175
Pro Gly Val Leu Pro Pro Glu Pro Pro Asp Val Gly Ser Ser Asp Pro
            180                 185                 190
```

Leu Ser Met Val Glu Pro Leu Gln Gly Arg Ser Pro Ser Tyr Ala Ser
         195                 200                 205

<210> SEQ ID NO 120
<211> LENGTH: 210
<212> TYPE: PRT
<213> ORGANISM: Mus musculus

<400> SEQUENCE: 120

Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
            20                  25                  30

Pro Asp Ser Ser Pro Leu Leu Gln Phe Gly Gly Gln Val Arg Gln Arg
        35                  40                  45

Tyr Leu Tyr Thr Asp Asp Gln Asp Thr Glu Ala His Leu Glu Ile
    50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
        115                 120                 125

Leu Glu Asp Gly Tyr Asn Val Tyr Gln Ser Glu Ala His Gly Leu Pro
    130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
        195                 200                 205

Ala Ser
    210

<210> SEQ ID NO 121
<211> LENGTH: 107
<212> TYPE: PRT
<213> ORGANISM: Vicugna pacos

<400> SEQUENCE: 121

Met Asp Trp Asp Glu Ala Lys Phe Glu His Arg Gly Leu Trp Val Pro
1               5                   10                  15

Val Leu Thr Val Leu Leu Leu Gly Ala Cys Gln Ala Arg Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Val Ala Arg Gln Pro Glu Gly Ile Pro
65                  70                  75                  80

Pro Glu Pro Pro Asp Val Gly Ser Ser Asp Pro Leu Ser Met Val Gly
                85                  90                  95

```
Pro Ser Tyr Ser Arg Ser Pro Ser Tyr Thr Ser
            100                 105
```

<210> SEQ ID NO 122
<211> LENGTH: 211
<212> TYPE: PRT
<213> ORGANISM: Anolis carolinensis

<400> SEQUENCE: 122

```
Cys Lys Ser Lys Gly Gly Lys Gly Gly Glu Arg Met Trp Val Asp
 1               5                  10                  15

Leu Val Phe Trp Ala Ala Leu Leu Arg Thr Ala Pro Ala Leu Pro Leu
                20                  25                  30

Arg Asn Ser Asn Pro Ile Tyr Gln Phe Asp Gly Gln Val Arg Leu Arg
                35                  40                  45

His Leu Tyr Thr Ala Asp Glu Gln Thr His Leu His Leu Glu Ile Leu
    50                  55                  60

Pro Asp Gly Thr Val Gly Ser Arg Phe Gln Asn Pro Phe Ser Leu
65                  70                  75                  80

Met Glu Ile Lys Ala Val Lys Pro Gly Val Ile Arg Met Gln Ala Lys
                85                  90                  95

Lys Thr Ser Arg Phe Leu Cys Met Lys Pro Asn Gly Arg Leu Tyr Gly
                100                 105                 110

Ser Leu Phe Tyr Ser Glu Glu Ala Cys Asn Phe His Glu Lys Val Leu
                115                 120                 125

Ser Asp Gly Tyr Asn Leu Tyr Tyr Ser Glu Asn Tyr Asn Ile Pro Val
            130                 135                 140

Ser Leu Ser Ser Ala Gly Asn Leu Gly Gln Ser Arg Gln Leu Pro Pro
145                 150                 155                 160

Phe Ser Gln Phe Leu Pro Leu Val Asn Lys Ile Pro Leu Glu Pro Val
                165                 170                 175

Leu Glu Asp Phe Asp Phe Tyr Gly His Gln Leu Asp Val Glu Ser Ala
                180                 185                 190

Asp Pro Leu Ser Ile Leu Gly Gln Asn Pro Gly Phe Met Ser Pro Ser
            195                 200                 205

Tyr Val Phe
    210
```

<210> SEQ ID NO 123
<211> LENGTH: 188
<212> TYPE: PRT
<213> ORGANISM: Gadus morhua

<400> SEQUENCE: 123

```
Leu Leu Leu Ala Thr Leu Leu His Ile Gly Leu Ser Phe Tyr Val Pro
 1               5                  10                  15

Asp Ser Gly Pro Leu Leu Trp Leu Gly Asp Gln Val Arg Glu Arg His
                20                  25                  30

Leu Tyr Thr Ala Glu Ser His Arg Arg Gly Leu Phe Leu Glu Met Ser
                35                  40                  45

Pro Asp Gly Gln Val Thr Gly Ser Ala Ala Gln Thr Pro Leu Ser Val
    50                  55                  60

Leu Glu Leu Arg Ser Val Arg Ala Gly Asp Thr Val Ile Arg Ala Arg
65                  70                  75                  80

Leu Ser Leu Tyr Leu Cys Val Asp Arg Ala Gly His Leu Thr Gly
                85                  90                  95
```

-continued

```
Gln Arg Gln Tyr Thr Glu Ser Asp Cys Thr Phe Arg Glu Val Ile Leu
            100                 105                 110

Glu Asp Gly Tyr Thr His Phe Leu Ser Val His His Gly Leu Pro Ile
        115                 120                 125

Ser Leu Ala Pro Arg His Ser Pro Gly Arg Gln Gly Leu Arg Phe Ser
    130                 135                 140

Arg Phe Leu Pro Leu Arg Ser Ser Leu Ser Glu Asp Arg Val Ala Glu
145                 150                 155                 160

Pro Pro Asp Ser Pro Leu Asn Leu Asp Ser Glu Asp Pro Leu Gly Met
                165                 170                 175

Gly Leu Gly Ser Leu Leu Ser Pro Ala Phe Ser Met
            180                 185

<210> SEQ ID NO 124
<211> LENGTH: 216
<212> TYPE: PRT
<213> ORGANISM: Latimeria chalumnae

<400> SEQUENCE: 124

Met Leu Cys Gln Ser Phe Val Ile Leu Ser Gln Lys Phe Ile Phe Gly
1               5                   10                  15

Leu Phe Leu Thr Gly Leu Gly Leu Thr Gly Leu Ala Trp Thr Arg Pro
            20                  25                  30

Phe Gln Asp Ser Asn Pro Ile Leu Gln Tyr Ser Asp Ser Ile Arg Leu
        35                  40                  45

Arg His Leu Tyr Thr Ala Ser Glu Ser Arg His Leu His Leu Gln Ile
    50                  55                  60

Asn Ser Asp Gly Gln Val Gly Gly Thr Thr Lys Gln Ser Pro Tyr Ser
65                  70                  75                  80

Leu Leu Glu Met Lys Ala Val Lys Thr Gly Phe Val Val Ile Arg Gly
                85                  90                  95

Lys Lys Ser Ala Arg Tyr Leu Cys Met Glu Arg Ser Gly Arg Leu Tyr
            100                 105                 110

Gly Ser Leu Gln Tyr Thr Glu Lys Asp Cys Thr Phe Lys Glu Val Val
        115                 120                 125

Leu Ala Asp Gly Tyr Asn Leu Tyr Val Ser Glu Glu His Gln Ala Thr
    130                 135                 140

Val Thr Leu Ser Pro Met Arg Ala Arg Ile Ala Gln Gly Lys Lys Ile
145                 150                 155                 160

Pro Pro Phe Ser His Phe Leu Pro Met Val Asn Lys Val Pro Val Glu
                165                 170                 175

Asp Val Ala Ala Glu Met Glu Phe Val Gln Val Leu Arg Glu Met Thr
            180                 185                 190

Ala Asp Val Asp Ser Pro Asp Pro Phe Gly Met Thr Trp Glu Glu Ser
        195                 200                 205

Val His Ser Pro Ser Phe Phe Ala
    210                 215

<210> SEQ ID NO 125
<211> LENGTH: 192
<212> TYPE: PRT
<213> ORGANISM: Tursiops truncates

<400> SEQUENCE: 125

Met Gly Trp Asp Lys Thr Lys Leu Glu His Leu Gly Leu Trp Val Pro
1               5                   10                  15
```

```
Val Leu Ala Val Leu Leu Gly Pro Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Glu Thr Glu Ala His Leu Glu Ile Arg Ala
    50                  55                  60

Asp Gly Thr Val Val Gly Thr Ala Arg Arg Ser Pro Glu Gly Val Lys
65                  70                  75                  80

Thr Ser Arg Phe Leu Cys Gln Gly Pro Glu Gly Arg Leu Tyr Gly Ser
                85                  90                  95

Leu His Phe Asn Pro Gln Ala Cys Ser Phe Arg Glu Leu Leu Leu Glu
            100                 105                 110

Asp Gly Tyr Asn Val Tyr Gln Ser Glu Ala Leu Gly Ile Pro Leu Arg
        115                 120                 125

Leu Pro Pro His Arg Ser Ser Asn Trp Asp Leu Ala Pro Arg Gly Pro
    130                 135                 140

Ala Arg Phe Leu Pro Leu Pro Gly Phe Leu Pro Pro Leu Glu Pro
145                 150                 155                 160

Pro Gly Ile Leu Ala Pro Glu Pro Pro Asn Val Gly Ser Ser Asp Pro
                165                 170                 175

Leu Ser Met Val Gly Pro Ser His Gly Arg Ser Pro Ser Tyr Thr Ser
            180                 185                 190

<210> SEQ ID NO 126
<211> LENGTH: 209
<212> TYPE: PRT
<213> ORGANISM: Mustela putorius furo

<400> SEQUENCE: 126

Met Gly Trp Glu Glu Ala Arg Ser Glu His Leu Gly Leu Trp Val Pro
1               5                   10                  15

Val Leu Ala Val Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Glu Thr Glu Ala His Leu Glu Ile Arg
    50                  55                  60

Ala Asp Gly Thr Val Val Gly Ala Ala Arg Arg Ser Pro Glu Ser Leu
65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Gly Pro Asn Gly Thr Leu Tyr Gly
            100                 105                 110

Ser Phe His Phe Asp Pro Val Ala Cys Ser Phe Arg Glu Val Leu Leu
        115                 120                 125

Glu Asp Gly Tyr Asn Ile Tyr His Ser Glu Thr Leu Gly Leu Pro Leu
    130                 135                 140

Arg Leu Pro Pro His Asn Ser Pro His Arg Asp Leu Ala Pro Arg Gly
145                 150                 155                 160

Pro Ala Arg Phe Leu Pro Leu Pro Gly Leu Leu Pro Ala Thr Pro Glu
                165                 170                 175

Ser Arg Gly Ile Pro Ala Pro Glu Pro Pro Asn Val Gly Ser Ser Asp
            180                 185                 190

Pro Leu Ser Met Val Gly Pro Leu Gln Gly Gln Ser Pro Ser Tyr Thr
        195                 200                 205
```

Ser

<210> SEQ ID NO 127
<211> LENGTH: 198
<212> TYPE: PRT
<213> ORGANISM: Takifugu rubripes

<400> SEQUENCE: 127

```
Phe Ile Tyr Leu Phe Ile Gln Thr Ala Leu Phe Ser Pro Ser Lys Trp
1               5                   10                  15

Phe Asn Phe Tyr Leu Pro Asp Ser Asn Pro Leu Leu Ser Phe Asp Ser
            20                  25                  30

His Gly Arg Gly Ile His Leu Tyr Thr Asp Asn Gln Arg Arg Gly Met
        35                  40                  45

Tyr Leu Gln Met Ser Thr Asp Gly Ser Val Ser Gly Ser Asp Val Gln
    50                  55                  60

Thr Ala Asn Ser Val Leu Glu Leu Lys Ser Val Arg Asn Gly His Val
65                  70                  75                  80

Val Ile Arg Gly Lys Ser Ser Leu Phe Leu Cys Met Asp Ser Arg
                85                  90                  95

Gly Arg Leu Trp Gly Gln Arg His Pro Thr Glu Ala Asp Cys Thr Phe
            100                 105                 110

Arg Glu Val Leu Leu Ala Asp Gly Tyr Thr Arg Phe Leu Ser Leu His
        115                 120                 125

Asn Gly Thr Pro Val Ser Leu Ala Pro Lys Gln Ser Pro Asp Gln His
    130                 135                 140

Thr Val Pro Phe Thr Arg Phe Leu Pro Leu Arg Asn Thr Leu Ala Glu
145                 150                 155                 160

Glu Ser Met Ser Glu Pro Pro Ser Asn Gln Gln Arg Tyr Phe Asn Ile
                165                 170                 175

Asp Ser Asp Asp Leu Leu Gly Met Asp Leu Asn Ala Met Val Ser Pro
            180                 185                 190

Gln Phe Ser Gly Asp Lys
        195
```

<210> SEQ ID NO 128
<211> LENGTH: 203
<212> TYPE: PRT
<213> ORGANISM: Dipodomys ordii

<400> SEQUENCE: 128

```
Met Asp Gln Ala Lys Thr Arg Val Gly Ala Arg Gly Leu Gly Gly Leu
1               5                   10                  15

Val Leu Ala Val Ile Ile Leu Gly Ala Cys Lys Ala Arg Pro Ile Pro
            20                  25                  30

Asp Ser Ser Pro Leu Leu Gln Phe Gly Gly Gln Val Arg Leu Arg His
        35                  40                  45

Leu Tyr Thr Asp Asp Thr Gln Glu Thr Glu Ala His Leu Glu Ile Arg
    50                  55                  60

Ala Asp Gly Thr Val Val Gly Thr Ala His Arg Ser Pro Glu Ser Leu
65                  70                  75                  80

Leu Glu Leu Lys Ala Leu Lys Pro Gly Val Ile Gln Ile Leu Gly Ile
                85                  90                  95

Lys Thr Ser Arg Phe Leu Cys Gln Arg Pro Asp Gly Thr Leu Tyr Gly
            100                 105                 110
```

Ser Leu His Phe Asp Pro Glu Val Cys Ser Phe Gln Glu Leu Leu Leu
            115                 120                 125

Glu Asp Gly Tyr Asn Ile Tyr Arg Ser Glu Ala Leu Gly Leu Pro Leu
        130                 135                 140

Arg Leu Ser Pro Asp Pro Ala Pro Trp Gly Pro Ala Arg Phe Leu Pro
145                 150                 155                 160

Leu Pro Gly Val Pro Pro Ala Pro Pro Glu Pro Pro Gly Ile Leu Ala
                165                 170                 175

Pro Glu Pro Pro Asp Val Gly Ser Ser Asp Pro Leu Ser Met Val Gly
            180                 185                 190

Leu Leu Gln Gly Arg Ser Pro Ser Tyr Ala Ser
        195                 200

<210> SEQ ID NO 129
<211> LENGTH: 184
<212> TYPE: PRT
<213> ORGANISM: Echinops telfairi

<400> SEQUENCE: 129

Met Gly Cys Thr Lys Ser Gly Trp Lys Ser Gly Leu Trp Val Pro
1               5                   10                  15

Val Leu Ala Ser Leu Leu Gly Gly Cys Gly Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Thr Thr Glu Ala His Leu Glu Ile Arg
50                  55                  60

Ala Asp Gly Thr Val Gly Val Ala His Gln Ser Pro Glu Lys Phe
65                  70                  75                  80

Leu Ser Gln Trp Arg Glu Lys Pro Leu Arg Ser Leu His Phe Asp Pro
                85                  90                  95

Ala Ala Cys Ser Phe Arg Glu Lys Leu Leu Glu Asp Gly Tyr Asn Leu
            100                 105                 110

Tyr His Ser Glu Thr His Gly Leu Pro Leu Arg Leu Pro Pro Arg Gly
        115                 120                 125

Gly Asp Pro Ser Ser Gln Pro Gly Ala Arg Phe Pro Pro Leu Pro Gly
    130                 135                 140

Gln Leu Pro Gln Leu Gln Glu Thr Pro Gly Val Leu Ala Pro Glu Pro
145                 150                 155                 160

Pro Asp Val Gly Ser Ser Asp Pro Leu Ser Met Val Gly Pro Trp Arg
                165                 170                 175

Gly Gln Ser Pro Ser Tyr Ala Ser
            180

<210> SEQ ID NO 130
<211> LENGTH: 210
<212> TYPE: PRT
<213> ORGANISM: Macaca mulatta

<400> SEQUENCE: 130

Met Asp Ser Asp Glu Thr Gly Phe Glu His Ser Gly Leu Trp Val Pro
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

```
Leu Tyr Thr Asp Asp Ala Gln Gln Thr Glu Ala His Leu Glu Ile Arg
         50                  55                  60

Glu Asp Gly Thr Val Gly Gly Ala Ala His Gln Ser Pro Glu Ser Glu
 65                  70                  75                  80

Cys Gly Pro Glu Pro Gly Ser Glu Gly Gly Ala Val Gly Gly Ala
                 85                  90                  95

Glu Gly Pro Gly Leu Leu Gly Leu Arg Glu Ala Gly Leu Gly Pro Gly
            100                 105                 110

Ser Trp Leu His Phe Asp Pro Glu Ala Cys Ser Phe Arg Glu Leu Leu
            115                 120                 125

Leu Glu Asn Gly Tyr Asn Val Tyr Gln Ser Glu Ala His Gly Leu Pro
        130                 135                 140

Leu His Leu Pro Gly Asn Lys Ser Pro His Arg Asp Pro Ala Ser Gln
145                 150                 155                 160

Gly Pro Ala Arg Phe Leu Pro Leu Pro Gly Leu Pro Ala Pro Pro
                165                 170                 175

Glu Pro Pro Gly Ile Leu Ala Pro Gln Pro Pro Asp Val Gly Ser Ser
            180                 185                 190

Asp Pro Leu Ser Met Val Gly Pro Ser Gln Ala Arg Ser Pro Ser Tyr
        195                 200                 205

Ala Ser
    210

<210> SEQ ID NO 131
<211> LENGTH: 193
<212> TYPE: PRT
<213> ORGANISM: Microcebus murinus

<400> SEQUENCE: 131

Met Gly Trp Asp Glu Ala Gly Ala Gly Phe Glu His Pro Gly Leu Trp
 1               5                  10                  15

Phe Pro Met Leu Gly Val Leu Leu Gly Ala Cys Gln Ala Tyr Pro
                20                  25                  30

Ile Pro Asp Ser Ser Pro Leu Leu Gln Phe Gly Gly Gln Val Arg Gln
             35                  40                  45

Arg His Leu Tyr Thr Asp Asp Ile Gln Glu Thr Glu Ala His Leu Glu
         50                  55                  60

Ile Arg Ala Asp Gly Thr Val Val Gly Ala Ala Arg Gln Ser Pro Glu
 65                  70                  75                  80

Leu Glu Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Cys Ser Phe Arg Glu Leu Leu Leu Glu
            115                 120                 125

Asp Gly Tyr Asn Val Tyr Cys Pro Tyr Leu Pro Leu His Leu Ser Pro
        130                 135                 140

Arg Ile Glu Leu Ala Gly Ser Arg Ser Ala Leu Pro Leu Pro Pro Ala
145                 150                 155                 160

Pro Glu Arg Arg Ile Leu Ala Pro Glu Pro Asp Gly Ser Ser Asp
                165                 170                 175

Pro Leu Ser Met Val Gly Pro Ser Gln Gly Arg Ser Pro Ser Tyr Ala
            180                 185                 190

Ser
```

<210> SEQ ID NO 132
<211> LENGTH: 204
<212> TYPE: PRT
<213> ORGANISM: Ochotona princeps

<400> SEQUENCE: 132

Lys Asp Met Asp Gly Leu Gln Pro Pro Gly Leu Arg Val Pro Val Leu
1               5                   10                  15

Ala Ala Leu Leu Leu Gly Val Gly Gln Ala Arg Pro Ile Pro Asp Ser
            20                  25                  30

Ser Pro Leu Leu Gln Phe Gly Gly Gln Val Arg Gln Arg His Leu Tyr
        35                  40                  45

Thr Asp Asp Ala Gln Glu Ser Glu Val His Leu Glu Ile Arg Ala Asp
    50                  55                  60

Gly Thr Val Ala Gly Thr Ala Arg Arg Ser Pro Glu Ser Leu Leu Glu
65                  70                  75                  80

Met Lys Ala Leu Lys Pro Gly Val Ile Gln Ile Leu Gly Val His Thr
                85                  90                  95

Ser Arg Phe Leu Cys Gln Arg Pro Asp Gly Thr Leu Tyr Gly Ser Leu
            100                 105                 110

His Phe Asp His Lys Ala Cys Ser Phe Arg Glu Gln Leu Leu Glu Asp
        115                 120                 125

Gly Tyr Asn Val Tyr His Ser Glu Thr His Gly Leu Pro Leu Arg Leu
    130                 135                 140

Ser Pro Asp Arg Ala Pro Arg Gly Pro Ala Arg Phe Leu Pro Leu Pro
145                 150                 155                 160

Gly Pro Pro Pro Asp Leu Leu Val Pro Pro Leu Pro Asp Val Leu
                165                 170                 175

Ala Pro Glu Pro Pro Asp Val Asp Ser Pro Asp Pro Leu Ser Met Val
            180                 185                 190

Gly Pro Leu Gln Gly Gln Ser Pro Ser Tyr Thr Ser
        195                 200

<210> SEQ ID NO 133
<211> LENGTH: 182
<212> TYPE: PRT
<213> ORGANISM: Xiphophorus maculates

<400> SEQUENCE: 133

Cys Pro Phe Pro Phe Leu Phe Leu Ile Leu Ser Leu Pro Phe Phe Ser
1               5                   10                  15

Ser Ser Phe Tyr Ile Pro Glu Ser Asn Pro Ile Phe Ala Phe Arg Asn
            20                  25                  30

Gln Leu Arg Glu Val His Leu Tyr Thr Glu Asn His Arg Arg Gly Leu
        35                  40                  45

Tyr Val Glu Ile His Leu Asp Gly Arg Val Thr Gly Ser Asp Ala Gln
    50                  55                  60

Ser Pro Tyr Ser Val Leu Gln Ile Lys Ser Val Lys Pro Gly His Val
65                  70                  75                  80

Val Ile Lys Gly Gln Thr Ser Ser Leu Phe Leu Cys Met Asp Asp Ser
                85                  90                  95

Gly Asn Leu Arg Gly Gln Thr Thr Tyr Asp Glu Ala Asp Cys Ser Phe
            100                 105                 110

Arg Glu Leu Leu Leu Ala Asp Gly Tyr Thr Arg Phe Leu Asn Ser Gln
        115                 120                 125

His Gly Val Pro Leu Ser Leu Ala Ser Arg Asn Ser Pro Asp Arg His
            130                 135                 140

Ser Val Pro Phe Thr Arg Phe Leu Pro Leu Arg Asn Thr Leu Thr Val
145                 150                 155                 160

Ser Glu Glu Ser Thr Lys Thr Gln Arg Asp Phe Asn Leu Asp Ser Asp
                165                 170                 175

Asp Leu Leu Gly Met Gly
            180

<210> SEQ ID NO 134
<211> LENGTH: 192
<212> TYPE: PRT
<213> ORGANISM: Gasterosteus aculeatus

<400> SEQUENCE: 134

Ser Leu Leu Leu Met Val Pro Leu Pro Phe Cys Ser Ser Phe Tyr Leu
1               5                   10                  15

Thr Asp Ser Ser Pro Leu Leu Pro Phe Asn Asn Gln Val Lys Glu Val
            20                  25                  30

His Leu Tyr Thr Ala Glu Asn His Arg Arg Ala Met Tyr Leu Gln Ile
        35                  40                  45

Ala Leu Asp Gly Ser Val Ser Gly Ser Asp Ala Arg Ser Thr Tyr Ser
    50                  55                  60

Val Leu Gln Leu Lys Ser Ile Gln Pro Gly His Val Val Ile Arg Gly
65                  70                  75                  80

Lys Ala Ser Ser Met Phe Leu Cys Val Asp Ser Gly Gly Arg Leu Arg
                85                  90                  95

Gly Gln Gly Pro Tyr Ser Glu Ala Asp Cys Ser Phe Arg Glu Leu Leu
            100                 105                 110

Leu Gly Asp Gly Tyr Thr Arg Phe Leu Ser Ser Gln His Gly Ser Pro
        115                 120                 125

Leu Ser Leu Ala Ser Arg Pro Ser Pro Asp Pro Asn Ser Val Pro Phe
    130                 135                 140

Thr Arg Phe Leu Pro Ile Arg Thr Ala Pro Glu Ala Glu Ser Val Ile
145                 150                 155                 160

Glu Glu Pro Pro Ser Asn Gln Arg Tyr Val Asn Val Asp Ser Glu Asp
                165                 170                 175

Leu Leu Gly Met Gly Leu Asn Thr Val Val Ser Pro Gln Phe Ser Ala
            180                 185                 190

<210> SEQ ID NO 135
<211> LENGTH: 165
<212> TYPE: PRT
<213> ORGANISM: Sarcophilus harrisii

<400> SEQUENCE: 135

Val Ser Ala Met Gly Leu Arg Glu Arg Ala Pro Arg Tyr Leu Ala Pro
1               5                   10                  15

Leu Leu Ser Leu Leu Ala Cys Arg Ala Ser Gly His Pro Leu Pro
            20                  25                  30

Asp Ser Ser Pro Met Leu Leu Phe Gly Gly Gln Val Arg Leu Arg His
        35                  40                  45

Leu Tyr Thr Asp Val Gly Gln Glu Ala Glu Ala His Val Glu Leu Ala
    50                  55                  60

Ser Asp Gly Thr Val Arg Ala Ala Arg Arg Ser Pro Asn Ser Leu
65                  70                  75                  80

```
Leu Glu Leu Lys Ala Val Lys Pro Gly Ile Val Arg Ile Leu Ala Val
                85                  90                  95

His Ser Ser Arg Phe Leu Cys Met Arg Pro Asn Gly Glu Leu Tyr Gly
            100                 105                 110

Ala Ile His Tyr Asp Pro Ser Ala Cys Asn Phe Arg Glu Arg Leu Leu
        115                 120                 125

Gly Asp Gly Tyr Asn Val Tyr Glu Ser Glu Ala His Gly Arg Thr Leu
    130                 135                 140

Arg Leu Pro Pro Lys Ala Ala Pro Gly Pro Ala Gly Pro Ser Arg Phe
145                 150                 155                 160

Leu Pro Leu Pro Gly
            165

<210> SEQ ID NO 136
<211> LENGTH: 208
<212> TYPE: PRT
<213> ORGANISM: Macropus eugenii

<400> SEQUENCE: 136

Thr Glu Glu Pro Ser Thr Gly Ser Arg His Leu Gly Gln Trp Ala Pro
1               5                   10                  15

Gly Leu Pro Gly Pro Leu Leu Ser Leu Leu Ala Tyr Arg Gly Gly Trp
            20                  25                  30

Gly Ser Pro Ile Pro Asp Ser Ser Pro Met Leu Leu Phe Gly Gly Gln
        35                  40                  45

Val Arg Leu Arg His Leu Tyr Thr Asp Asp Gly Gln Asp Thr Glu Ala
    50                  55                  60

His Val Glu Leu Gly Pro Asp Gly Val Val Arg Ala Val Ala Glu Arg
65                  70                  75                  80

Ser Pro Asn Ser Leu Leu Glu Leu Lys Ala Val Lys Pro Gly Val Ile
            85                  90                  95

Arg Ile Leu Ala Val Gln Ser Ser Arg Phe Leu Cys Met Arg Pro Asn
            100                 105                 110

Gly Glu Leu Tyr Gly Ala Val His Tyr Asp Pro Ser Ala Cys Asn Phe
        115                 120                 125

Arg Glu His Leu Leu Gly Asp Gly Tyr Asn Val Tyr Glu Ser Glu Thr
    130                 135                 140

His Arg Arg Thr Leu Arg Leu Ser Pro Ser Leu Gly Gln Ala Gly Pro
145                 150                 155                 160

Ser Arg Phe Leu Pro Leu Pro Gly Asp Trp Leu Pro Gly Pro Asp Pro
            165                 170                 175

Pro Trp Ala Gln Gly Pro Glu Pro Pro Asp Val Gly Ser Ala Asp Pro
        180                 185                 190

Leu Ser Met Val Gly Ala Val Gln Gly Leu Ser Pro Ser Tyr Ser Ser
    195                 200                 205

<210> SEQ ID NO 137
<211> LENGTH: 160
<212> TYPE: PRT
<213> ORGANISM: Xenopus tropicalis

<400> SEQUENCE: 137

Arg Gly Gly Arg Thr Lys Lys Thr Leu Leu Arg Lys Trp Leu Cys
1               5                   10                  15

Leu Leu Ala Ile Met Leu Ser Arg Ser Arg Phe Ser Leu Ala Asn Pro
            20                  25                  30
```

```
Ile Gln Asn Ser Asn Pro Ile Leu Ser Asn Asp Asn Gln Val Arg Thr
             35                  40                  45

Gln Tyr Leu Tyr Thr Asp Asn Asn Met His Leu Tyr Leu Gln Ile
 50                  55                  60

Thr His Asn Gly Val Val Thr Gly Thr Glu Glu Lys Asn Asp Tyr Gly
 65                  70                  75                  80

Val Leu Glu Ile Lys Ala Val Lys Ala Gly Val Val Ile Lys Gly
                 85                  90                  95

Ile Arg Ser Asn Leu Tyr Leu Cys Met Asp Ser Arg His Gln Leu Tyr
                100                 105                 110

Ala Ser Ala Tyr Asp Lys Asp Asp Cys His Phe His Glu Lys Ile Thr
                115                 120                 125

Pro Asp Asn Tyr Asn Met Tyr Ser Ser Glu Lys His Ser Glu Tyr Val
130                 135                 140

Ser Leu Ala Pro Leu Lys Gly Ser Gln Met Ala Arg Phe Leu Pro Ile
145                 150                 155                 160
```

<210> SEQ ID NO 138
<211> LENGTH: 194
<212> TYPE: PRT
<213> ORGANISM: Danio rerio

<400> SEQUENCE: 138

```
Met Leu Leu Ala Cys Phe Phe Ile Phe Phe Ala Leu Phe Pro His Leu
 1               5                  10                  15

Arg Trp Cys Met Tyr Val Pro Ala Gln Asn Val Leu Leu Gln Phe Gly
             20                  25                  30

Thr Gln Val Arg Glu Arg Leu Leu Tyr Thr Asp Gly Leu Phe Leu Glu
             35                  40                  45

Met Asn Pro Asp Gly Ser Val Lys Gly Ser Pro Glu Lys Asn Leu Asn
 50                  55                  60

Cys Val Leu Glu Leu Arg Ser Val Lys Ala Gly Glu Thr Val Ile Gln
 65                  70                  75                  80

Ser Ala Ala Thr Ser Leu Tyr Leu Cys Val Asp Asp Gln Asp Lys Leu
                 85                  90                  95

Lys Gly Gln His His Tyr Ser Ala Leu Asp Cys Thr Phe Gln Glu Leu
                100                 105                 110

Leu Leu Asp Gly Tyr Ser Phe Phe Leu Ser Pro His Thr Asn Leu Pro
                115                 120                 125

Val Ser Leu Leu Ser Lys Arg Gln Lys His Gly Asn Pro Leu Ser Arg
130                 135                 140

Phe Leu Pro Val Ser Arg Ala Glu Asp Ser Arg Thr Gln Glu Val Lys
145                 150                 155                 160

Gln Tyr Ile Gln Asp Ile Asn Leu Asp Ser Asp Pro Leu Gly Met
                165                 170                 175

Gly His Arg Ser His Leu Gln Thr Val Phe Ser Pro Ser Leu His Thr
                180                 185                 190

Lys Lys
```

<210> SEQ ID NO 139
<211> LENGTH: 209
<212> TYPE: PRT
<213> ORGANISM: Bos grunniens mutus

<400> SEQUENCE: 139

```
Met Gly Trp Asp Glu Ala Lys Phe Lys His Leu Gly Leu Trp Val Pro
```

-continued

```
                1               5                   10                  15
        Val Leu Ala Val Leu Leu Gly Thr Cys Arg Ala His Pro Ile Pro
                        20                  25                  30
        Asp Ser Ser Pro Leu Leu Gln Phe Gly Gly Gln Val Arg Gln Arg Tyr
                        35                  40                  45
        Leu Tyr Thr Asp Asp Ala Gln Glu Thr Glu Ala His Leu Glu Ile Arg
                    50                  55                  60
        Ala Asp Gly Thr Val Val Gly Ala Ala Arg Gln Ser Pro Glu Ser Leu
         65                 70                  75                  80
        Leu Glu Leu Lys Ala Leu Lys Pro Gly Val Ile Gln Ile Leu Gly Val
                            85                  90                  95
        Lys Thr Ser Arg Phe Leu Cys Gln Gly Pro Asp Gly Lys Leu Tyr Gly
                        100                 105                 110
        Ser Leu His Phe Asp Pro Lys Ala Cys Ser Phe Arg Glu Leu Leu Leu
                        115                 120                 125
        Glu Asp Gly Tyr Asn Val Tyr Gln Ser Glu Thr Leu Gly Leu Pro Leu
                        130                 135                 140
        Arg Leu Pro Pro Gln Arg Ser Ser Asn Arg Asp Pro Ala Pro Arg Gly
        145                 150                 155                 160
        Pro Ala Arg Phe Leu Pro Leu Pro Gly Leu Pro Ala Glu Pro Pro Asp
                        165                 170                 175
        Pro Pro Gly Ile Leu Ala Pro Glu Pro Pro Asp Val Gly Ser Ser Asp
                        180                 185                 190
        Pro Leu Ser Met Val Gly Pro Ser Tyr Gly Arg Ser Pro Ser Tyr Thr
                        195                 200                 205
        Ser
```

<210> SEQ ID NO 140
<211> LENGTH: 209
<212> TYPE: PRT
<213> ORGANISM: Saimiri boliviensis boliviensis

<400> SEQUENCE: 140

```
        Met Gly Ser Glu Glu Val Ala Leu Glu Arg Pro Ala Leu Trp Val Ser
         1               5                   10                  15
        Val Leu Ala Gly Leu Leu Gly Thr Cys Gln Ala Tyr Pro Ile Pro
                        20                  25                  30
        Asp Ser Ser Pro Leu Leu Gln Phe Gly Gly Gln Val Arg Gln Arg Tyr
                        35                  40                  45
        Leu Tyr Thr Asp Asp Ala Gln Gln Thr Glu Ala His Leu Glu Ile Arg
                    50                  55                  60
        Glu Asp Gly Thr Val Ala Gly Ala Ala His Gln Ser Pro Glu Ser Leu
         65                 70                  75                  80
        Leu Gln Leu Lys Ala Leu Lys Pro Gly Val Ile Gln Ile Leu Gly Val
                            85                  90                  95
        Lys Thr Ser Arg Phe Leu Cys Gln Arg Pro Asp Gly Ala Leu Tyr Gly
                        100                 105                 110
        Ser Leu Tyr Phe Asp Pro Glu Ala Cys Ser Phe Arg Glu Leu Leu Leu
                        115                 120                 125
        Glu Asp Gly Tyr Asn Val Tyr Gln Ser Val Ala His Ser Leu Pro Leu
                        130                 135                 140
        His Leu Pro Gly Gly Arg Ser Pro Pro Trp Asp Pro Ala Pro Arg Gly
        145                 150                 155                 160
        Pro Ala Arg Phe Leu Pro Leu Pro Gly Leu Pro Pro Glu Pro Pro Glu
```

-continued

```
                165                 170                 175
Ala Pro Gly Ile Leu Ala Pro Glu Pro Pro Asp Val Gly Ser Ser Asp
            180                 185                 190

Pro Leu Ser Met Val Gly Pro Ser Gln Gly Gln Ser Pro Ser Tyr Thr
        195                 200                 205

Ser

<210> SEQ ID NO 141
<211> LENGTH: 210
<212> TYPE: PRT
<213> ORGANISM: Callithrix jacchus
<220> FEATURE:
<221> NAME/KEY: misc_feature
<222> LOCATION: (64)..(64)
<223> OTHER INFORMATION: Xaa can be any naturally occurring amino acid

<400> SEQUENCE: 141

Met Gly Ser Glu Glu Val Gly Leu Glu His Pro Ala Leu Trp Val Ser
1               5                   10                  15

Val Leu Ala Gly Leu Leu Leu Gly Thr Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Lys Glu Ala His Leu Glu Ile Xaa
    50                  55                  60

Glu Asp Gly Thr Val Ala Gly Ala Ala Thr Lys Val Pro Lys Val Ser
65                  70                  75                  80

Leu Leu Gln Leu Lys Ala Leu Lys Pro Gly Val Ile Gln Ile Leu Gly
                85                  90                  95

Val Lys Thr Ser Arg Phe Leu Cys Gln Arg Pro Asp Gly Ala Leu Tyr
            100                 105                 110

Gly Ser Leu His Phe Asp Pro Glu Ala Cys Ser Phe Arg Glu Leu Leu
        115                 120                 125

Leu Glu Asp Gly Tyr Asn Val Tyr Gln Ser Val Ala His Gly Leu Pro
    130                 135                 140

Leu His Leu Pro Glu Ser Arg Ser Pro Arg Asp Pro Ala Pro Arg
145                 150                 155                 160

Gly Pro Ala Arg Phe Leu Pro Leu Pro Gly Leu Pro Pro Glu Pro Pro
                165                 170                 175

Glu Pro Pro Gly Ile Leu Ala Pro Gly Pro Pro Asp Val Gly Ser Ser
            180                 185                 190

Asp Pro Leu Ser Met Val Gly Pro Ser Gln Gly Gln Ser Pro Ser Tyr
        195                 200                 205

Ala Ser
    210

<210> SEQ ID NO 142
<211> LENGTH: 209
<212> TYPE: PRT
<213> ORGANISM: Tupaia chinensis

<400> SEQUENCE: 142

Met Gly Trp Asp Lys Ala Arg Phe Glu His Leu Gly Ala Trp Ala Pro
1               5                   10                  15

Val Leu Ala Val Leu Leu Gly Ala Cys Gln Ala Tyr Pro Ile Pro
            20                  25                  30

Asp Ser Ser Pro Leu Leu Gln Phe Gly Gly Gln Val Arg Gln Arg Tyr
```

```
              35                  40                  45
Leu Tyr Thr Asp Asp Thr Gln Asp Thr Glu Ala His Leu Glu Ile Arg
 50                  55                  60
Ala Asp Gly Thr Val Val Gly Ala Ala His Gln Ser Pro Glu Ser Leu
 65                  70                  75                  80
Leu Glu Leu Lys Ala Leu Lys Pro Gly Val Ile Gln Ile Leu Gly Val
                 85                  90                  95
Lys Thr Ser Arg Phe Leu Cys Gln Arg Pro Asp Gly Ala Leu Tyr Gly
                100                 105                 110
Ser Leu His Phe Asp Pro Glu Ala Cys Ser Phe Arg Glu Leu Leu Leu
            115                 120                 125
Glu Asp Gly Tyr Asn Ile Tyr Gln Ser Glu Ala Arg Gly Leu Pro Leu
            130                 135                 140
Arg Leu Pro Pro His Asp Ser Pro His Arg Asp Arg Thr Pro Gln Gly
145                 150                 155                 160
Pro Ala Arg Phe Leu Pro Leu Pro Gly Leu Pro Leu Val Pro Pro Glu
                165                 170                 175
Leu Pro Gly Val Leu Ala Leu Glu Pro Pro Asp Val Gly Ser Ser Asp
                180                 185                 190
Pro Leu Ser Met Met Gly Pro Ser Gln Gly Gln Ser Pro Ser Tyr Ala
            195                 200                 205
Ser

<210> SEQ ID NO 143
<211> LENGTH: 188
<212> TYPE: PRT
<213> ORGANISM: Papio anubis

<400> SEQUENCE: 143

Met Asp Ser Asp Glu Thr Gly Phe Glu His Ser Gly Leu Trp Val Pro
  1               5                  10                  15
Val Leu Ala Gly Leu Leu Leu Gly Ala Cys Gln Ala His Pro Ile Pro
                 20                  25                  30
Asp Ser Ser Pro Leu Leu Gln Phe Gly Gly Gln Val Arg Gln Arg Tyr
             35                  40                  45
Leu Tyr Thr Asp Asp Ala Gln Gln Thr Glu Ala His Leu Glu Ile Arg
 50                  55                  60
Glu Asp Gly Thr Val Gly Gly Ala Ala His Gln Ser Pro Glu Ser Lys
 65                  70                  75                  80
Cys Gly Pro Glu Pro Gly Ser Glu Gly Gly Ala Leu His Phe Asp
                 85                  90                  95
Pro Glu Ala Cys Ser Phe Arg Glu Leu Leu Leu Glu Asn Gly Tyr Asn
                100                 105                 110
Val Tyr Gln Ser Glu Ala His Gly Leu Pro Leu His Leu Pro Gly Asn
            115                 120                 125
Lys Ser Pro His Arg Asp Pro Ala Ser Arg Gly Pro Ala Arg Phe Leu
            130                 135                 140
Pro Leu Pro Gly Leu Pro Pro Ala Pro Glu Pro Pro Gly Ile Leu
145                 150                 155                 160
Ala Pro Gln Pro Pro Asp Val Gly Ser Ser Asp Pro Leu Ser Met Val
                165                 170                 175
Gly Pro Ser Gln Ala Arg Ser Pro Ser Tyr Ala Ser
            180                 185
```

<210> SEQ ID NO 144
<211> LENGTH: 208
<212> TYPE: PRT
<213> ORGANISM: Pteropus alecto

<400> SEQUENCE: 144

Met Gly Trp Gly Lys Ala Arg Leu Gln His Pro Gly Leu Trp Gly Pro
1               5                   10                  15

Val Leu Ala Val Leu Leu Gly Ala Cys Gln Ala His Pro Ile Leu Asp
            20                  25                  30

Ser Ser Pro Leu Phe Gln Phe Gly Ser Gln Val Arg Arg Arg Tyr Leu
        35                  40                  45

Tyr Thr Asp Asp Ala Gln Asp Thr Glu Ala His Leu Glu Ile Arg Ala
    50                  55                  60

Asp Gly Thr Val Ala Gly Ala Ala Arg Arg Ser Pro Glu Ser Leu Leu
65                  70                  75                  80

Glu Leu Lys Ala Leu Lys Pro Gly Val Ile Gln Val Leu Gly Val Lys
                85                  90                  95

Thr Ser Arg Phe Leu Cys Gln Arg Pro Asp Gly Thr Leu Tyr Gly Ser
            100                 105                 110

Leu His Phe Asp Pro Ala Ala Cys Ser Phe Arg Glu Leu Leu Leu Lys
        115                 120                 125

Asp Gly Tyr Asn Val Tyr Gln Ser Glu Ala Leu Ala Arg Pro Leu Arg
    130                 135                 140

Leu Pro Pro Tyr Ser Ser Pro Ser Ser Asp Pro Ala Arg Arg Gly Pro
145                 150                 155                 160

Ala Arg Phe Leu Pro Leu Pro Gly Pro Pro Glu Pro Pro Gln Pro
                165                 170                 175

Pro Gly Arg Leu Ala Pro Glu Pro Pro Asp Val Gly Ser Ser Asp Pro
            180                 185                 190

Leu Ser Met Val Trp Pro Ser Arg Gly Arg Ser Pro Ser Tyr Thr Ser
        195                 200                 205

<210> SEQ ID NO 145
<211> LENGTH: 210
<212> TYPE: PRT
<213> ORGANISM: Heterocephalus glaber

<400> SEQUENCE: 145

Met Asp Trp Ala Arg Ala Glu Ser Glu Arg Pro Gly Leu Trp Val Pro
1               5                   10                  15

Ala Val Leu Ala Val Leu Leu Gly Ala Cys Gln Ala His Pro Ile
            20                  25                  30

Pro Asp Ser Ser Pro Leu Leu Gln Phe Gly Gly Gln Val Arg Gln Arg
        35                  40                  45

His Leu Tyr Thr Asp Asp Ala Gln Asp Thr Glu Val His Leu Glu Ile
    50                  55                  60

Arg Ala Asp Gly Ser Val Gly Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Arg Thr Ser Arg Phe Leu Cys Gln Arg Pro Asp Gly Thr Leu Tyr
            100                 105                 110

Gly Ser Leu His Phe Asp Pro Glu Ala Cys Ser Phe Arg Glu Leu Leu
        115                 120                 125

Leu Ala Asp Gly Tyr Asn Ile Tyr Gln Ser Glu Ala Tyr Gly Leu Pro

```
                    130                 135                 140
Leu Arg Met Leu Pro Ser Asp Ser Ala Ser Arg Asp Pro Val Pro
145                 150                 155                 160

Gly Pro Ala Arg Phe Leu Pro Leu Pro Gly Leu His Pro Pro Leu
                165                 170                 175

Glu Pro Pro Gly Met Leu Pro Pro Glu Pro Pro Asp Val Gly Ser Ser
                180                 185                 190

Asp Pro Leu Ser Met Val Gly Pro Leu Gln Gly Arg Ser Pro Ser Tyr
                195                 200                 205

Ala Phe
    210

<210> SEQ ID NO 146
<211> LENGTH: 209
<212> TYPE: PRT
<213> ORGANISM: Cricetulus griseus

<400> SEQUENCE: 146

Met Asp Trp Met Lys Ser Gly Val Gly Val Pro Gly Leu Trp Val Pro
1               5                   10                  15

Leu Leu Pro Ile Phe Leu Leu Gly Val Ser Gln Ala His Pro Ile Pro
                20                  25                  30

Asp Ser Ser Pro Leu Leu Gln Phe Gly Gly Gln Val Arg His Arg His
                35                  40                  45

Leu Tyr Thr Asp Asp Asn Gln Glu Thr Glu Val His Leu Glu Ile Arg
    50                  55                  60

Gln Asp Gly Thr Val Ile Gly Thr Thr His Arg Ser Pro Glu Ser Leu
65                  70                  75                  80

Leu Glu Leu Lys Ala Leu Lys Pro Glu Val Ile Pro Val Leu Gly Val
                85                  90                  95

Lys Ala Ser Arg Phe Leu Cys Gln Gln Pro Asp Gly Thr Leu Tyr Gly
                100                 105                 110

Ser Pro His Phe Asp Pro Glu Ala Cys Ser Phe Arg Glu Leu Leu Leu
                115                 120                 125

Glu Asp Gly Tyr Asn Val Tyr Gln Ser Glu Val His Gly Leu Pro Leu
    130                 135                 140

Arg Leu Pro Gln Arg Asp Ser Pro Asn Gln Ala Pro Ala Ser Trp Gly
145                 150                 155                 160

Pro Val Pro Pro Leu Pro Val Pro Gly Leu Leu His Gln Pro Gln Glu
                165                 170                 175

Leu Pro Gly Phe Leu Ala Pro Glu Pro Pro Asp Val Gly Ser Ser Asp
                180                 185                 190

Pro Leu Ser Met Val Gly Pro Leu Gln Gly Arg Ser Pro Ser Tyr Ala
                195                 200                 205

Ser

<210> SEQ ID NO 147
<211> LENGTH: 192
<212> TYPE: PRT
<213> ORGANISM: Ovis aries

<400> SEQUENCE: 147

Met Gly Trp Asp Glu Ala Lys Phe Lys His Leu Gly Leu Trp Val Pro
1               5                   10                  15

Val Leu Ala Val Leu Leu Leu Gly Thr Cys Arg Ala His Pro Ile Pro
                20                  25                  30
```

```
Asp Ser Ser Pro Leu Leu Gln Phe Gly Gly Gln Val Arg Gln Arg Tyr
            35                  40                  45

Leu Tyr Thr Asp Asp Ala Gln Glu Thr Glu Ala His Leu Glu Ile Arg
 50                  55                  60

Ala Asp Gly Thr Val Val Gly Ala Ala Arg Gln Ser Pro Glu Ser Leu
 65                  70                  75                  80

Leu Glu Leu Lys Ala Leu Lys Pro Gly Val Ile Gln Ile Phe Gly Val
                85                  90                  95

Lys Thr Ser Arg Phe Leu Cys Gln Gly Pro Asp Gly Lys Leu Tyr Gly
                100                 105                 110

Ser Leu His Phe Asp Pro Lys Ala Cys Ser Phe Arg Glu Leu Leu Leu
            115                 120                 125

Glu Asp Gly Tyr Asn Val Tyr Gln Ser Glu Thr Leu Gly Leu Pro Leu
        130                 135                 140

Arg Leu Pro Pro Gln Arg Ser Ser Asn Arg Asp Pro Ala Pro Arg Gly
145                 150                 155                 160

Pro Pro Lys Pro Gln Leu His Phe Leu Lys Thr Ser Ala Val Gln Tyr
                165                 170                 175

Trp Pro Arg Tyr Glu Lys Val Pro Ala Phe Leu His Pro Phe Pro Gly
            180                 185                 190

<210> SEQ ID NO 148
<211> LENGTH: 135
<212> TYPE: PRT
<213> ORGANISM: Pan paniscus

<400> SEQUENCE: 148

Met Asp Ser Asp Glu Thr Gly Phe Glu His Ser Gly Leu Trp Val Ser
 1               5                  10                  15

Val Leu Ala Gly Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Val Ser Phe Gln Asp Pro Pro His His Pro Pro Cys Ser Ser Tyr
            115                 120                 125

Met Ser Pro Ser Gln Pro Gly
        130                 135

<210> SEQ ID NO 149
<211> LENGTH: 116
<212> TYPE: PRT
<213> ORGANISM: Macaca fascicularis

<400> SEQUENCE: 149

Met Asp Ser Asp Glu Thr Gly Phe Glu His Ser Gly Leu Trp Val Pro
 1               5                  10                  15

Val Leu Ala Gly Leu Leu Gly Ala Cys Gln Ala His Pro Ile Pro
                20                  25                  30
```

```
Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
 50                  55                  60

Glu Asp Gly Thr Val Gly Gly Ala Ala His Gln Ser Pro Glu Ser Leu
 65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Lys Pro Asp Gly Ala Leu Tyr Gly
                100                 105                 110

Ser Val Ser Phe
        115

<210> SEQ ID NO 150
<211> LENGTH: 104
<212> TYPE: PRT
<213> ORGANISM: Mesocricetus auratus

<400> SEQUENCE: 150

Val Ile Gln Ile Leu Gly Val Lys Ala Ala Arg Phe Pro Cys Gln Gln
 1               5                  10                  15

Pro Asp Gly Ser Leu Tyr Gly Ser Pro His Phe Asp Pro Glu Ala Cys
                20                  25                  30

Ser Phe Arg Glu Leu Leu Leu Glu Asp Gly Tyr Asn Val Tyr Gln Ser
        35                  40                  45

Glu Ala His Gly Leu Pro Leu Arg Leu Pro Gln Arg Asp Ala Pro Ser
 50                  55                  60

Gln Pro Pro Ala Ser Trp Gly Pro Val Arg Phe Leu Pro Val Pro Gly
 65                  70                  75                  80

Leu Phe Gln Pro Pro His Asp Leu Pro Gly Arg Pro Ala Pro Glu Pro
                85                  90                  95

Pro Asp Val Gly Ser Ser Asp Pro
                100

<210> SEQ ID NO 151
<211> LENGTH: 151
<212> TYPE: PRT
<213> ORGANISM: Oreochromis niloticus

<400> SEQUENCE: 151

Met Tyr Leu Gln Met Asn Met Asp Gly Arg Val Thr Gly Ser Asp Ala
 1               5                  10                  15

Gln Thr Pro Tyr Ser Leu Met Gln Leu Lys Ser Val Lys Pro Gly His
                20                  25                  30

Val Ile Ile Lys Gly Pro Ser Ser Leu Phe Leu Cys Val Asp Ser
        35                  40                  45

Glu Gly Asn Leu Arg Gly Gln Ser His Tyr Ser Glu Thr Ser Cys Thr
 50                  55                  60

Phe Arg Glu Met Leu Leu Ala Asp Gly Tyr Thr Arg Phe Ile Ser Ser
 65                  70                  75                  80

Gln Tyr Gly Phe Pro Met Ser Leu Ala Ser Arg His Ser Pro Asp Arg
                85                  90                  95

His Ala Leu Pro Phe Thr Arg Phe Leu Pro Leu Arg Asn Asn Leu Lys
                100                 105                 110

Thr Asp Ser Val Ser Glu Gln Leu Pro Asn Asn Gln Arg Leu Phe Asn
                115                 120                 125
```

Val Asp Ser Asp Asp Leu Leu Gly Met Gly Leu Asn Ser Met Gly Ser
            130                 135                 140

Pro Gln Phe Ser Met Asp Lys
145                 150

<210> SEQ ID NO 152
<211> LENGTH: 209
<212> TYPE: PRT
<213> ORGANISM: Homo sapiens

<400> SEQUENCE: 152

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Met Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 153
<211> LENGTH: 630
<212> TYPE: DNA
<213> ORGANISM: Homo sapiens

<400> SEQUENCE: 153
atggactcgg acgagaccgg gttcgagcac tcaggactgt gggtttctgt gctggctggt      60
cttctgctgg gagcctgcca ggcacacccc atccctgact ccagtcctct cctgcaattc     120
gggggccaag tccggcagcg gtacctctac acagatgatg cccagcagac agaagcccac     180
ctggagatca gggaggatgg gacggtgggg gcgctgctg accagagccc cgaaagtctc      240
ctgcagctga agccttgaa gccgggagtt attcaaatct gggagtcaa gacatccagg      300 ttcctgtgcc agcggccaga tggggccctg tatggatcgc tccactttga ccctgaggcc     360
tgcagcttcc gggagctgct tcttgaggac ggatacaatg tttaccagtc cgaagcccac     420
ggcctcccgc tgcacctgcc agggaacaag tccccacacc gggaccctgc accccgagga     480

```
ccagctcgct tcctgccact accaggcctg ccccccgcac tcccggagcc acccggaatc    540 ctggccccc  agcccccga  tgtgggctcc tcggaccctc tgagcatggt gggaccttcc    600
cagggccgaa gccccagcta cgcttcctga                                     630
```

<210> SEQ ID NO 154
<211> LENGTH: 630
<212> TYPE: DNA
<213> ORGANISM: Pongo abelii

<400> SEQUENCE: 154

```
atggactcgg acgagaccgg gttcgagcac tcaggactgt gggttcctgt gctggctggt    60
cttctgctgg gagcctgcca ggcacacccc atccctgact ccagtcctct cctgcaattc   120
gggggccaag tccggcagcg gtacctctac acagatgatg cccagcagac agaagcccac   180
ctggagatca gggaggatgg gacggtgggg ggcgctgctg accagagccc cgaaagtctc   240
ctgcagctga aagccttgaa gccgggagtt attcaaatct gggagtcaa  gacatccagg   300 ttcctgtgcc agaggccaga tggggccctg tatggatcgc tccactttga ccctgaggcc   360
tgcagcttcc gggagctgct tcttgaggac ggatacaatg tttatcagtc cgaggcccat   420
ggcctcccgc tgcacctgcc gggaaacaag tccccacacc gggaccctgc accccgagga   480
ccagctcgct tcctgccact accaggcctg ccccccgcac ccccagagcc gcccggaatc   540 ctggccccc  agcccccga  tgtgggctcc tcggaccctc tgagcatggt gggaccttcc   600
cagggccgaa gccccagcta tgcttcctga                                    630
```

<210> SEQ ID NO 155
<211> LENGTH: 630
<212> TYPE: DNA
<213> ORGANISM: Pan troglodytes

<400> SEQUENCE: 155

```
atggactcgg acgagaccgg gttcgagcac tcaggactgt gggtttctgt gctggctggt    60
cttctgctag gagcctgcca ggcacacccc atccctgact ccagtcctct cctgcaattc   120
gggggccaag tccggcagcg gtacctctac acagatgatg cccagcagac agaagcccac   180
ctggagatca gggaggatgg gacggtgggg ggcgctgctg accagagccc cgaaagtctc   240
ctgcagctga aagccttgaa gccgggagtt attcaaatct gggagtcaa  gacatccagg   300 ttcctgtgcc agaggccaga tggggccctg tatggatcgc tccactttga ccctgaggcc   360
tgcagcttcc gggagctgct tcttgaggac ggatacaatg tttaccagtc cgaggcccac   420
ggcctcccgc tgcacctgcc ggggaacaag tccccacacc gggaccctgc accccgagga   480
ccagctcgct tcctgccact accaggcctg ccccccgcac ccccggagcc acccggaatc   540 ctggccccc  agcccccga  tgtgggctcc tcagaccctc tgagcatggt gggaccttcc   600
cagggccgaa gccccagcta cacttcctga                                    630
```

<210> SEQ ID NO 156
<211> LENGTH: 630
<212> TYPE: DNA
<213> ORGANISM: Canis lupus familiaris

<400> SEQUENCE: 156

```
atgggctggg ccgaggccgg gttcgagcac ctgggactgt gggtccctgt gctggctgtg    60
cttttgctgg aagcctgccg ggcacatccg atccctgact ccagcccct  cctacaattt   120
```

| | |
|---|---|
| ggaggtcaag ttcgacagcg gtacctctac accgacgatg cccaggagac agaggcccac | 180 |
| ctagagatca gggccgatgg cacagtggtg ggggctgccc gccagagccc tgaaagtctc | 240 |
| ctggagctga aagccctaaa gccaggggtc attcaaatct tgggagtcaa acatccagg | 300 |
| ttcctgtgcc agggcccaga tgggacacta tatggctcgc tccatttcga ccctgtggcc | 360 |
| tgcagtttcc gagaactgct tcttgaggat gggtacaaca tctaccactc cgagacccctt | 420 |
| ggtctcccgc ttcgcctgcg cccccacaac tccgcatacc gggacttggc accccgcggg | 480 |
| cctgcccgct tcctgccact gccaggcctg cttccagcac ccccagagcc tcagggatc | 540 |
| ctggccccgg agcctcctga cgtgggctcc tcggaccctc tgagcatggt ggggccttca | 600 |
| cagggccgga gtcccagcta tgcttcctaa | 630 |

<210> SEQ ID NO 157
<211> LENGTH: 630
<212> TYPE: DNA
<213> ORGANISM: Bos taurus

<400> SEQUENCE: 157

| | |
|---|---|
| atgggctggg acgaggccaa gttcaagcac ttgggactgt gggtccctgt gctggctgtc | 60 |
| ctcctgctag gaacctgccg ggcgcatccc attccagact ccagccccct cctccagttt | 120 |
| gggggccaag tccgccagcg gtacctctac acggatgatg cccaggagac agaggcccac | 180 |
| ctagagatca gggccgatgg cacagtggtg gggcagccc gccagagccc cgaaagtctc | 240 |
| ttggagctga aagccctgaa gccaggcgtc attcagatct tgggagttaa aacatccagg | 300 |
| tttctctgcc aggggccaga tgggaagctg tacggatcgc tgcactttga ccccaaagcc | 360 |
| tgcagctttc gggagctgct tcttgaagat ggatacaacg tctaccagtc ggagaccctg | 420 |
| ggccttccac tccgcctgcc ccccagcgc tcgtccaacc gggacccggc cccgcgggga | 480 |
| cctgctcgct tccttccact gccgggcctg cccgcggcgc cccggatcc tcagggatc | 540 |
| ttggccccg agcctcccga cgtgggctcc tcggatcccc tgagtatggt gggaccctcg | 600 |
| tatggccgaa gccccagcta cacttcttga | 630 |

<210> SEQ ID NO 158
<211> LENGTH: 630
<212> TYPE: DNA
<213> ORGANISM: Equus caballus

<400> SEQUENCE: 158

| | |
|---|---|
| atggactggg acaagacggg gttcaagtac cagggactgt gggtccctgt gctggctgtc | 60 |
| cttctgctgg gagcctgcca gtcacacccc atccctgact ccagtcccct cctccaattc | 120 |
| ggggccaag tcaggcagcg ccacctctac acagatgatg cccaggagac agaggcgcac | 180 |
| ctggagatca gggctgacgg cactgtggca ggggctgtcc accggagccc agaaagtctc | 240 |
| ttggagctga aagccctgaa gccagggggta attcaaatct tgggagtcaa gacatccagg | 300 |
| tttctgtgcc aggggccaga cgggacgctg tacggatcgc tccacttcga ccccgtggcc | 360 |
| tgcagcttcc gggagctgct tctcgaagac ggctacaacg tttaccagtc tgagacccctt | 420 |
| ggcctcccac tccgcctgcc ccaccacagc tccccatacc aggatccggc ccctcgggca | 480 |
| cccgcccgct tcctgccgct gccaggcttt ccccagcac cccggagcc tcagggatc | 540 |
| ccggcccccg agcctcccga cgtgggctcc tcggaccccc tgagcatggt ggggccttca | 600 |
| cgcagccgga gccccagcta cacttcctga | 630 |

<210> SEQ ID NO 159
<211> LENGTH: 630
<212> TYPE: DNA
<213> ORGANISM: Ailuropoda melanoleuca

<400> SEQUENCE: 159

```
atgggctggg acgaggccag gtccgagcag ctggggctgt gggtccctgt gctggctgtc     60
cttttgctgg aagcttgcca ggcacaccct atccctgact ccagccccct cctccaattc    120
ggaggccaag ttcgacagcg gtacctctac acggacgatg cccaggagac agaggcccac    180
ctagcgatca gggctgatgg cacagtggtg ggggctgcca gccggagccc agaaagtctc    240
ttggagctga aagccctgaa accggggtc attcaaatcc tgggagtgaa acatctagg      300
ttcctgtgcc agggcccaga tgggacactg tacggatcgg tccgcttcga ccccgtagcc    360
tgcagcttcc gggaactgct cctggaggat gggtacaaca tctaccactc tgagaccctc    420
ggcctcccac ttcgcctgcc cgcccacaac tctccatacc gggactcggc gccccggggg    480
cctgcccgct cctgcccct gcaggcctg cttccggtcc cccggaccc ccagggatc        540
ctgggccccg agcctcccga cgtgggctcc tcggacccc tgagcatggt ggggccttca    600
cagggccgaa gtcccagcta cgcttcctga                                    630
```

<210> SEQ ID NO 160
<211> LENGTH: 630
<212> TYPE: DNA
<213> ORGANISM: Oryctolagus cuniculus

<400> SEQUENCE: 160

```
atggactggg gcaaggccaa gtgccggccc ccggggctgt gggtccccgc gctcgctgcc     60
ctgctgctgg gggcctgcca ggcacacccc atccccgact ccagccccct cctccagttt    120
ggggaccaag tgcggcagca gcacctgtac acggacgatg cgcaggaaac agaagcccac    180
ctggagatca gggcggatgg cacggtggtg ggggctgccc ggaggagccc agaaagtctc    240
ttgcagatga aagccttaca accggggatc attcagatct gggggtcca gacgtccagg     300
ttcctctgcc agaggccgga tgcacgctc tacggctcgc tccacttcga ccgcgaggcc    360
tgcagcttcc gggagctgct gcgtgaggat gggtacaacg tttacctctc ggaggccctg    420
ggcctgcccc tgcgcctgtc ccccggcagc tccccacgca gggcgccggc ccccggga     480
ccagcccgct cctgccgct gccggcctg ccgccagacc ttccggaacc gccaggcctc     540
ctggccgccg cgccccccga tgtcgactcc ccggaccccc tgagcatggt gcagcctgcg    600
ctggaccaga gccccagcta cacctcctga                                    630
```

<210> SEQ ID NO 161
<211> LENGTH: 630
<212> TYPE: DNA
<213> ORGANISM: Gorilla gorilla

<400> SEQUENCE: 161

```
atggactcgg acgagaccgg gttcgagcac tcaggactgt gggtttctgt gctggctggt     60
cttctgctgg gagcctgcca ggcacacccc atccctgact ccagtcctct cctgcaattc    120
gggggccaag tccggcagcg gtacctctac acagatgatg cccagcagac agaagcccac    180
ctggagatca gggaggatgg gacggtgggg ggtgctgctg accagagccc tgaaagtctc    240
ctgcagctga aagccttgaa gccggggagtt attcaaatct tgggagtcaa gacatccagg   300
ttcctgtgcc agaggccaga tggggccctg tatggatcgc tccactttga ccctgaggcc    360
```

```
tgcagcttcc gggagctgct tcttgaggac ggatacaatg tttaccagtc cgaggcccac    420
ggcctcccgc tgcacctgcc ggggaacaag tccccacacc gggaccctgc accccgagga    480
ccagctcgct tcctgccact accaggcctg ccccccgcac ccccggagcc acccggaatc    540
ctggcccccc agccccccga tgtgggctcc tcggaccctc tgagcatggt gggaccttcc    600
cagggccgaa gccccagcta cgcttcctga                                     630
```

<210> SEQ ID NO 162
<211> LENGTH: 630
<212> TYPE: DNA
<213> ORGANISM: Nomascus leucogenys

<400> SEQUENCE: 162

```
atggactcgg acgagaccgg gttcgagcac tcaggactgt gggttcctgt gctggctggt     60
cttctgctgg agcctgcca ggcacacccc atccctgact ccagtcctct cctgcaattc    120
gggggccaag tccggcagcg gtacctctac acagatgatg cccagcagac agaagcccac    180
ctggagatca ggaggatgg gacggtgggg ggcgctgctg accagagccc tgaaagtctc    240
ctgcagctga aagccttgaa gccgggagtt attcaaatct tgggagtcaa gacatccagg    300
ttcctatgcc agaggccaga tggggccctg tatggatcgc tccactttga ccctgaggcc    360
tgcagcttcc gggagctgct tcttgaggac ggatacaatg tttaccagtc cgaggcccat    420
ggcctcccgc tgcacctgcc ggggaacaag tccccacacc gggaccctgc accccgagga    480
ccagctcgct tcctgccact accaggcctg cccctgcac cccagagcc gcccggaatc     540 ctggcccccc agccccccga tgtgggctcc tcggaccctc tgagcatggt gggaccttcc    600
cagggccgaa gccccagcta cgcttcctga                                     630
```

<210> SEQ ID NO 163
<211> LENGTH: 630
<212> TYPE: DNA
<213> ORGANISM: Procavia capensis

<400> SEQUENCE: 163

```
atggactggg ccaagtttgg gatcgagcac ccgggactgt gggtcccggt gatggcagta     60
cttctgctgg agcctgcca aggataccct attcctgact ccagccccct tctccaattc    120
ggaggccagg tccggcaacg ttacctctac acagatgacg cgcaggagac cgaggcccac    180
ctggagatcc gagcagacgg cacggtggtg ggggctgccc accggagccc cgagagtctc    240
ttggagctga aagctttgaa gcccggcata attcagatct tgggagtcaa gacatccaga    300
ttcctctgcc agggtcctga tggggtgctg tatggatcgc tccgttttga cccagtggcc    360
tgcagcttcc gggagctgct tcttgaagat ggatacaatg tttaccagtc tgaggcccac    420
ggcctcccgc ttcgcctacc atcccacaat tccccacaga gggacctggc gtcccgggtg    480
ccagcccgct tcctgccact gccaggccgg ctcacggtgc tcccagaacc ttcggggtc    540 ctgggccctg agccccccga tgtggactcc tcagaccccc tgagcatggt ggggccttcg    600
cagggccgaa gcccagtta cgcctcctga                                      630
```

<210> SEQ ID NO 164
<211> LENGTH: 630
<212> TYPE: DNA
<213> ORGANISM: Cavia porcellus

<400> SEQUENCE: 164

```
atggactggg cccggactga gtgtgagcgc ccaaggctgt gggtctccat gctggccatc     60
```

```
cttctggtgg gagcctgcca ggcacaccct atccctgact ccagcccct cctccagttt      120 ggggggccagg tccggcagcg gtacctctac acagatgatg ctcaggacac tgaagtgcac     180
ctggagatca gggccgatgg ctcagtacgg ggcattgccc acaggagccc tgaaagtctc     240
ctggagctga aagccttgaa gccaggagtc attcagatct gggaatcag acttccagg       300 ttcctgtgcc agaggcccga tgggagtctg tatggatcac ccactttga tcctgaggcc     360 tgcagcttcc gggagctgct gcttgctgat ggctacaatg tctacaagtc tgaagcccac    420
ggcctccctc tgcacctgct gcgcggtgac tctctatcgc aggaaccagc accccagga     480 ccagcccgat ttctgccact accaggcctg cccgcaacac cccggagcc acccaggatg     540 ctgcccccag ggcccccaga tgtgggctcc tcggacccct tgagcatggt ggggcctta    600 tgggaccgaa gccccagcta tacttcctga                                      630

<210> SEQ ID NO 165
<211> LENGTH: 583
<212> TYPE: DNA
<213> ORGANISM: Tupaia belangeri

<400> SEQUENCE: 165
atgggctggg acaaggcccg gttcgagcac ctgggagcgt gggctcctgt gctggctgtc      60
ctcctcctgg gagcctgcca ggcatacccc atccctgact ccagcccct cctacaattc    120 ggggggccagg tccggcagcg gtacctctac acggacgaca cgcaggacac agaagcccac   180
cttgagatca gggccgacgg caccgtggtg ggggccgccc accaaagccc ggaaagtctc    240
ctggagctga aagccttgaa gccgggggtc attcaaatcc tgggagtcaa gacctccagg    300
ttcctgtgcc agaggccaga cgggggcctg tacgggtcgc ttcacttcga ccccgaggcc    360
tgcagcttcc gggagctgct tctcgaggat ggatacaaca tttaccagtc tgaggctcgt    420
ggcctccccc tgcgcctgcc gccccacgac tccccacatc gggaccggac ccctcgggga    480
ccagctcgtt tcctgccgct gcctggcctg ccctggttc ctccagagct gccaggggtc     540
ctggcccttg agcccccgga cgtgggctcc tcagacccgc tga                      583

<210> SEQ ID NO 166
<211> LENGTH: 586
<212> TYPE: DNA
<213> ORGANISM: Sorex araneus

<400> SEQUENCE: 166
atggtctggg acaaggccag ggggcagcag ttgggactgt gggcccccat gctgctgggc      60
ttgctgctgg gtgcctgcca ggcacacccc ctccctgact ccagcccct cctccaattt    120 ggggggccaag tccgactgag gttcctgtac accgacgatg cccagaggac aggggcgcac    180
ctggagatca gggccgacgg cacagtgcag ggtgcggccc acaggacccc agaatgtctc    240
ctggagctga aagccttgaa gccaggcgta attcaaatcc ttggggtcag cacatccaga    300
ttcctgtgcc agcggcccga tggggtcctg tatggatcgc ttcgctttga cccagaggcc    360
tgcagtttcc gggaacttct tctccaggat ggatataacg tttaccagtc tgaggccctg    420
ggtctcccgc tctacctaca cccgcccagt gccccagtgt cccaggaacc agcctcacgg    480
ggcgccgtcc gcttcctgcc actgccagga ctgccacctg cctccctgga gccccccagg    540
ccccccgccc cggtgcctcc agacgtgggt tcctcagacc ccctga                    586

<210> SEQ ID NO 167
```

<210> SEQ ID NO 167
<211> LENGTH: 546
<212> TYPE: DNA
<213> ORGANISM: Ictidomys tridecemlineatus

<400> SEQUENCE: 167

```
atgtacccca tccctgactc aagcccctc ctccaatttg ggggccaagt ccggcagcgg      60
tacctgtaca cagatgatgc ccaggagact gaggcccacc tggagatcag ggctgatggc     120
accgtggtgg gggctgccca tcaaagcccg gaaagtctct tggaactgaa agccttgaag     180
cctggggtca ttcaaatctt gggggtcaaa acatccaggt tcctgtgcca gaggccagat     240
ggagtgctgt atggatcgct ccactttgac cctgaggcct gcagcttccg ggagcagctt     300
ctggaggacg ggtacaacgt ttaccagtca gaatcccacg gcctcccgt gcgcctgccc      360
cctaactcac ataccggga cccagcgccg ccaggaccag cccgcttcct tccactgcca      420
ggcctgcccc cagcagccct ggagccgcca gggatcctgg ccctgagcc cctgatgtg      480
ggctcctccg acccactcag catggtgggg cctttgcagg gccgaagccc cagttacgct     540
tcctga                                                                546
```

<210> SEQ ID NO 168
<211> LENGTH: 627
<212> TYPE: DNA
<213> ORGANISM: Loxodonta africana

<400> SEQUENCE: 168

```
atggactggg ccaagtttgg gttggagcac ccaggactgt gggtccctgt gatggctgtc      60
cttctgctgg gagcctgcca gggacacccc atccctgact ccagccccct cctccaattc     120
ggggggccagg tccggcaacg ttacctctac acagatgatc aggagaccga ggcccacctg     180
gagatcagag cagatggcac agtggcggga gccgctcacc ggagctctga gagtctcttg     240
gagctgaaag ctttgaagcc tggaataatt cagatcttgg gggtcaagac atcccggttc     300
ctgtgccagg gcctgatgg ggtgctgtac ggatcgctcc atttcgaccc agccgcctgc     360
agcttccggg agctgcttct tgaagatgga tacaatgttt actggtccga ggcccatgga     420
ctcccaatcc gcctgccctc ccacaactcc ccatataggg acccagcatc ccgggtacca     480
gcccgcttcc tgccactgcc aggcctgctc ccaatgctcc aagaacctcc aggggtcctg     540
gcccctgagc ccctgatgt ggactcctca gacccctga gcatggtggg gccttcacag     600
ggccgaagcc ccagctatgc ctcctga                                        627
```

<210> SEQ ID NO 169
<211> LENGTH: 627
<212> TYPE: DNA
<213> ORGANISM: Sus scrofa

<400> SEQUENCE: 169

```
atgggctggg ccgaggccaa gttcgagcgc ttgggactgt gggtccctgt gctggctgtc      60
ctgctgggag cctgccaggc acgtcccatt cctgactcca gccccctcct ccaatttggg     120
ggccaagtgc ccaacgata cctctacacg gatgatgccc aggaaactga agcccacctg     180
gagatcagag ctgatggcac cgtggcaggg gtagcccgcc agagccctga agtctcttg      240
gagctgaaag ccctgaagcc aggggtcatt caaattttgg gagtccagac atcccggttc     300
ctgtgccagg ggccagacgg gagactgtac ggatcgctcc acttcgaccc tgaggcctgc     360
agcttccggg agctgcttct tgaggatggc tacaacgttt accagtctga ggcccttggc     420
ctcccactcc ggctgcctcc gcaccgctcc tccaaccggg acctggcccc ccggggacct     480
```

```
gctcgcttcc tgccactgcc aggcctgccc ccggcacccc cggagccgcc agggatcttg    540 gccctgaac  ctcccgacgt gggctcctcg accccctga  gcatggtggg gccttcacac    600
ggccggagcc ccagctacac ttcttga                                        627
```

<210> SEQ ID NO 170
<211> LENGTH: 627
<212> TYPE: DNA
<213> ORGANISM: Felis catus

<400> SEQUENCE: 170

```
atgggctggg acgaggccgg gtcccagcgc ctgggactgt gggtcgtgct gggggtcctt    60
ttgccggaag cctgccaggc acaccctatc cctgactcca gcccctcct  ccaattcggg   120 ggccaagttc gacagcggtt cctctacacg gacgacgccc aggagacaga ggtccacctc   180
gagatcaagg ctgatggcac agtggtgggg accgctcgcc ggagccctga gagtctcttg   240
gagctaaaag ccctgaagcc gggggtaatt caaatcttgg gggtcaaaac gtccaggttc   300
ctgtgccagg gcccagatgg gacactgtat ggatcgctcc gctttgaccc cgcagcctgc   360
agcttccggg aactgctcct ggaggacgga tacaacatct accactcgga ccctcgggg   420 ctcccactcc gcctgcccc  ccacaactcc ccataccggg acttggcccc ccgggcacct   480
gcccgcttcc tgccgctgcc aggcctgctt ccggcacccc cggagcctcc agggatcctg   540
gcccccgagc cccggacgt  gggctcctcg  accctctga  gcatggtggg gccttcccag   600
ggccgaagtc ccagctacgc ttcctga                                        627
```

<210> SEQ ID NO 171
<211> LENGTH: 627
<212> TYPE: DNA
<213> ORGANISM: Otolemur garnettii

<400> SEQUENCE: 171

```
gacaaggcca ggactgggtt caagcaccca ggaccatggt ttcccctgct ggctgtactt    60
ttgttgggag cctgccaggc acaccctatc cctgactcca gcccctact  ccagtttggt   120 ggccaagtcc ggcagcggta cctctacaca gatgatgccc aggagacaga agcccacctg   180
gagatcaggg aagatggcac agtggtgggg gctgcacaac agagccctga aagtctcttg   240
gagctgaaag ctttaaagcc aggggtcatt caaatcttgg gagtcaagac atccaggttc   300
ctgtgccaga ggccagatgg gggcctatat ggatcgctct actttgaccc caaggcctgc   360
agtttccggg agctgcttct tgaggatgga tacaacgttt actggtctga gacctatggc   420
ctcccactgc acctgcctcc tgccaattcc ccatactggg gcccatccct tcggagccca   480
gcccgcttcc tgccactgcc aggccctcct gcagcatccc cagagctgcc ggggatcttg   540
gccctggaac ccccgatgt  gggctcctcg  accctctga  gcatggtggg gccttcgcag   600
ggccgaagcc ccagctatgc ttcctga                                        627
```

<210> SEQ ID NO 172
<211> LENGTH: 627
<212> TYPE: DNA
<213> ORGANISM: Rattus norvegicus

<400> SEQUENCE: 172

```
atggactgga tgaaatctag agttgggggcc ccgggactgt gggtctgtct cctgctgcct    60
gtcttcctgc tgggggtgtg cgaggcatac cccatctctg actccagccc cctcctccag   120
```

```
tttggggtc aagtccgaca gaggtatctc tacacagatg acgaccagga caccgaagcc    180
cacctggaga tcaggagga cggaacagtg gtgggcacag cacaccgcag tccagaaagt    240
ctcctggagc tcaaagcctt gaagccaggg gtcattcaaa tcctgggtgt caaagcctct    300
aggtttcttt gccaacaacc agatggaact ctctatggat cgcctcactt tgatcctgag    360
gcctgcagtt tcagagagct gctgcttaag gacggataca atgtgtacca gtctgaggcc    420
catggcctgc ccctgcgtct gccccagaag gactcccagg atccagcaac ccggggacct    480
gtgcgcttcc tgcccatgcc aggcctgccc cacgagcccc aagagcaacc aggagtcctt    540
cccccagagc cccagatgtg ggttcctcc gaccccctga gcatggtaga gcctttgcaa     600
ggccgaagcc ccagctatgc atcttga                                       627

<210> SEQ ID NO 173
<211> LENGTH: 633
<212> TYPE: DNA
<213> ORGANISM: Mus musculus

<400> SEQUENCE: 173
atggaatgga tgagatctag agttgggacc ctgggactgt gggtccgact gctgctggct    60
gtcttcctgc tggggtcta ccaagcatac cccatccctg actccagccc cctcctccag    120
tttgggggtc aagtccggca gaggtacctc tacacagatg acgaccaaga cactgaagcc    180
cacctggaga tcagggagga tggaacagtg gtaggcgcag cacaccgcag tccagaaagt    240
ctcctggagc tcaaagcctt gaagccaggg gtcattcaaa tcctgggtgt caaagcctct    300
aggtttcttt gccaacagcc agatggagct ctctatggat cgcctcactt tgatcctgag    360
gcctgcagct tcagagaact gctgctggag gacggttaca atgtgtacca gtctgaagcc    420
catggcctgc ccctgcgtct gcctcagaag gactccccaa accaggatgc aacatcctgg    480
ggacctgtgc gcttcctgcc catgccaggc ctgctccacg agccccaaga ccaagcagga    540
ttcctgcccc cagagccccc agatgtgggc tcctctgacc cctgagcat ggtagagcct    600 ttacagggcc gaagccccag ctatgcgtcc tga                                633

<210> SEQ ID NO 174
<211> LENGTH: 324
<212> TYPE: DNA
<213> ORGANISM: Vicugna pacos

<400> SEQUENCE: 174
atggactggg acgaggccaa gttcgagcat cggggactgt gggtcccagt gctcactgtc    60
cttctgctgg gagcctgcca ggcacgcccc attcctgact ccagcccct cctccaattc    120 gggggccaag tccggcagcg gtacctctac acgatgacg cccaggagac agaagcccac    180
ctggagatca gggctgatgg cacagtggtg ggggtggccc gccagcccga aggaattcct    240
cccgagcctc ctgacgtggg ctcctcagac cccctgagca tggtggggcc ttcatacagc    300
agaagcccca gctacacttc ctga                                          324

<210> SEQ ID NO 175
<211> LENGTH: 633
<212> TYPE: DNA
<213> ORGANISM: Anolis carolinensis

<400> SEQUENCE: 175
tgtaaaagca agggaggagg gaagggggga gagaggatgt gggtagacct agttttctgg    60
gctgccttgc tccgcacagc tcctgctctt cccttgcgga attccaaccc catctaccaa    120
```

```
tttgatgggc aggtccggct tcggcacctc tacacagcag atgaacagac gcacctccac    180
ttggagatct tgccagacgg taccgtgggt ggatccaggt ttcagaatcc cttcagtttg    240
atggagatca aagctgtgaa gccaggagtc attcgcatgc aggccaagaa gacctctaga    300
tttctctgta tgaaacccaa tggacgactg tatggctcgc tgttctactc tgaggaggca    360
tgcaacttcc atgagaaggt tctcagcgat ggctacaacc tctactattc tgaaaactac    420
aacatacctg tcagcctcag ctcggcaggg aacctgggtc agagccgtca gttgcctccc    480
ttctcccaat tcctgccgtt agtcaacaaa attcctcttg agcctgtgct tgaagacttt    540
gacttctatg acatcaatt ggatgttgaa tcagctgatc ctttgagcat tttaggacaa    600
aaccctggtt tcatgagtcc gagctatgtc ttc                                633

<210> SEQ ID NO 176
<211> LENGTH: 564
<212> TYPE: DNA
<213> ORGANISM: Gadus morhua

<400> SEQUENCE: 176
ctcctcctcg ccaccctcct ccacatcggc ctctccttct acgtccccga ctccggcccc     60
ctgctgtggc tgggcgacca ggtcagggag agacacctct acacagcaga gagccaccgg    120 aggggggctgt tcctggagat gagcccggac ggtcaggtga caggaagtgc tgctcagacg    180
ccgctcagtg ttctggagct gaggtcggtc agagcaggag atacggtcat cagagcgcgc    240
ctctcctctc tctacctgtg tgtggacagg gcaggtcacc tgacaggaca gagacagtac    300
acagagtccg actgcaccctt cagagaggtc atccttgagg acggctacac ccacttcctg    360
tccgtgcacc acggacttcc tatttcgctg gcgccgagac actccccagg agacaggggg    420
ctgcgcttca gcaggttcct cccgctgagg agcagtctgt cagaggatag ggtcgccgag    480
cccccagaca gcccactgaa cctggactct gaagaccccc tggggatggg tctgggttcg    540
ctcctcagcc cggccttctc catg                                          564

<210> SEQ ID NO 177
<211> LENGTH: 648
<212> TYPE: DNA
<213> ORGANISM: Latimeria chalumnae

<400> SEQUENCE: 177
atgttatgcc agagttttgt gatattaagt cagaaattca ttttggget cttttttgact      60 ggattggggc taacaggatt ggcttggaca aggcccttcc aggattccaa tcccatcctg    120
cagtattccg attccatccg gctccgacat ctgtacactg ccagtgagag tcggcacctt    180
cacctacaaa tcaactcgga tggacaggtg ggagggacaa ccaagcaaag cccttacagt    240
ctgttggaga tgaaggcggt gaagacaggt tttgtggtca tcaggggcaa gaaaagcgcc    300
cgttacctct gtatggaacg tagtggacgg ctctatggat cgctgcagta tacagaaaaa    360
gactgcacct tcaaagaggt tgtgttggca gatggataca acctgtatgt ctcagaggaa    420
caccaggcca cagtgacgct gagccccatg agggcgagga tagcgcaagg gaaaaagatc    480 ccacccttt cccatttcct tccaatggtg aacaaggtgc ctgtggagga tgttgccgct    540
gagatggagt ttgtccaggt gctgcgggaa atgacggccg acgtggactc tccggatccc    600
tttggaatga cctgggaaga atcggttcac agtccgagct ttttgcc                  648

<210> SEQ ID NO 178
```

```
<211> LENGTH: 579
<212> TYPE: DNA
<213> ORGANISM: Tursiops truncatus

<400> SEQUENCE: 178
atgggctggg acaagaccaa actcgagcac ctgggactgt gggtccctgt gctagctgtc      60
ctgctgggac cctgccaggc acatcccatt cctgactcca gcccctcct ccaatttggg      120
ggccaagtcc gccagcgata cctctacacg gatgacgccc aggagacgga ggcccacctg     180
gagatcaggg ctgatggcac agtggtgggg acggcccgcc ggagccccga aggagttaaa     240
acatccaggt tcctgtgcca ggggccgagg ggaggctgt atggatcgct ccacttcaac      300
ccccaggcct gcagcttccg ggagctgctt cttgaggatg gatacaacgt ttaccagtct     360
gaggctcttg gcattcccct ccgcctgccc ccgcaccgct cctccaactg ggacctggcc     420
ccccggggac ctgctcgctt cctgccgctg ccaggcttcc tcccgccacc cctggagcct     480
ccagggatct tggcccccga gcctcccaac gtaggttcct cggacccctt gagcatggtg     540
ggaccttcac atggccgaag ccccagctac acttcctga                            579

<210> SEQ ID NO 179
<211> LENGTH: 630
<212> TYPE: DNA
<213> ORGANISM: Mustela putorius furo

<400> SEQUENCE: 179
atgggctggg aagaggccag gtccgagcac ctggggctgt gggtccctgt gctggcggtc      60
cttttgctgg gagcctgcca ggcatacccc attcctgact ccagcccct cctccaattt      120
ggaggccaag ttcgacagcg gtacctctac acagacgacg ctcaggagac ggaggcccac     180
ctagagatca gggctgatgg cacggtggtg ggggctgccc gccggagccc cgaaagtctc     240
ttggagctga agccctgaa gccaggggtc attcagatct gggagtgaa acatccagg        300
ttcctgtgcc agggccccgaa tgggacactg tacggatcgt tccacttcga ccccgtagcc    360
tgcagcttcc gggaagtgct tctggaagat ggatacaaca tctaccactc tgagaccctg     420
ggcctcccac tgcgcctgcc ccccacaac tccccacaca gggacctggc gccccggggg      480
cctgcccgct tcctgcccct gccaggcctg cttccggcca cccggagtc ccggggggatc      540
ccagccccg agcctcccaa cgtgggctcc tcagaccccc tgagcatggt ggggccttg       600
cagggtcaaa gtcccagcta cacttcctga                                      630

<210> SEQ ID NO 180
<211> LENGTH: 597
<212> TYPE: DNA
<213> ORGANISM: Takifugu rubripes

<400> SEQUENCE: 180
tttatttatt tatttattca aactgcactt ttttcccctt ccaaatggtt caacttttat      60
ctccctgact ccaacccgct cttatccttt gacagtcatg gcagaggcat ccacctctac     120
acagataatc aaaggcgagg gatgtatctg cagatgagca cagatggaag cgtttccggg     180
agtgatgtcc agacggcgaa cagtgtgctg gaactgaagt cagtcagaaa cggccacgtc     240
gtcatccgag gaaaatcgtc ttctctgttt ctctgtatgg acagcagagg ccgtttatgg     300
gggcagaggc accccactga ggccgactgc actttcaggg aagtgttgct ggcagatgga     360
tacactcgct tcctgtccct gcacaacgga actcctgtgt ctctggcacc taaacaatct     420
ccagaccagc acacagtccc cttcactcgt ttcctgccgc tcaggaatac actggcagag     480
```

```
gagagcatgt ctgaaccacc atcaaaccaa cagagatatt ttaacattga ctctgatgat      540
cttcttggaa tggatttaaa tgcgatggtc agtcctcagt tttcagggga caagtga         597

<210> SEQ ID NO 181
<211> LENGTH: 612
<212> TYPE: DNA
<213> ORGANISM: Dipodomys ordii

<400> SEQUENCE: 181
atggaccagg caaagaccag ggttggggcc ggggggctgg ggggccttgt gctggctgtc       60
ataattctgg gagcatgcaa ggcacggcct atccctgact ccagcccct cctccaattt      120 gggggtcaag ttcggcttcg gcacctctac acagatgaca ctcaggagac ggaagcccat     180
ctggagatca gggcagatgg cacggtagtg gggactgccc accggagccc tgaaagtctc     240
ttggagctga aagccttgaa gccaggagtc attcaaatct tagggatcaa gacatccaga     300
ttcttatgcc agagaccaga cggacactg tatggatcac tccactttga ccctgaggtt     360
tgcagcttcc aggagctgct tctggaagat ggatacaaca tttaccgttc tgaagccctg     420
ggtctccccc tgcgcctgtc cccagatcca gcacctgggg gccagcccg cttcctgccc     480 ctgcctggtg tgccccccgc accgccggag ccccccggga tcctggctcc cgaacccct     540 gatgtcggct cctccgaccc tctgagtatg gtgggactgt tgcagggccg aagccccagc     600
tatgcatcct ga                                                        612

<210> SEQ ID NO 182
<211> LENGTH: 555
<212> TYPE: DNA
<213> ORGANISM: Echinops telfairi

<400> SEQUENCE: 182
atgggttgca ccaaatctgg gtggaagtcc ccgggactgt gggtccctgt gctggccagc       60
cttctgctgg gaggctgcgg agcacacccc atccctgact ccagcccct cctccaattc      120 ggggggccaag tccggcagcg atacctctat acggatgacg cccagaccac cgaggcccac    180
ctggagatca gagcggatgg cacagtgggg ggcgtcgccc accagagccc agagaagttc     240
ctgagtcaat ggcgtgaaaa gcccctgaga tcactccatt tcgacccagc cgcctgcagc     300
ttccgggaga agcttctaga agacggatac aacttgtacc actctgagac ccacggcctc     360
cccctccgcc tcccaccccg tggggcgac ccctcttctc agcctggggc ccgcttccca     420
ccgctgccgg gccagctccc acaactccaa gagacgccag gggtcctcgc ccccgaaccc     480
cccgacgtgg gctcttcaga cccctgagc atggtggggc cttggcgagg gcaaagtccc     540
agttatgcct cctga                                                    555

<210> SEQ ID NO 183
<211> LENGTH: 633
<212> TYPE: DNA
<213> ORGANISM: Macaca mulatta

<400> SEQUENCE: 183
atggactcgg acgagaccgg gttcgagcac tcaggactgt gggttcctgt gctggctggt       60
cttctgctgg gagcctgcca ggcacacccc atccctgact ccagtcctct cctgcaattc     120 ggggggccaag tccggcaacg gtacctctac acagatgatg cccagcagac agaagcccac    180
ctggagatca gggaggatgg gacagtgggg ggcgctgctc accagagccc cgaaagtgag    240
```

```
tgtgggccag agcctgggtc tgagggagga ggggctgtgg gaggtgctga gggacctgga    300
ctcctgggtc tgagggaggc agggctgggg cctggatcct ggctccactt tgaccctgag    360
gcctgcagct tccgggagct gcttcttgag aacggataca atgtttacca gtccgaggcc    420
cacggcctcc cactgcacct gccgggaaac aagtccccac accgggaccc tgcatcccaa    480
ggaccagctc gcttcctgcc actaccaggc ctgcccccg caccccgga gccgccagga     540 atcctcgccc ccagccccc cgatgtgggc tcctcggacc ctctgagcat ggtgggacct     600
tcccaggccc gaagccccag ctatgcttcc tga                                633
```

```
<210> SEQ ID NO 184
<211> LENGTH: 582
<212> TYPE: DNA
<213> ORGANISM: Microcebus murinus

<400> SEQUENCE: 184
atgggctggg acgaggccgg cgccgggttc gagcacccag gactgtggtt tcccatgctg    60
ggtgtcctgc tgctgggagc ctgccaggcg taccccatcc ctgactccag ccccctcctc   120
caatttggcg ccaagtccg gcagcggcac ctctacacag acgatatcca ggagacagaa    180
gcccacctgg agatcagggc ggacggcaca gtggtgggg ccgcccgaca gagccctgag    240
ttggagctga agccttaaa gccaggggtc attcaaatct tgggagtcaa gacctccagg   300
ttcctgtgcc agaggccaga cggggccctg tacggatcgc tccactttga ccccgagtgc   360
agcttccggg agctgcttct tgaggatgga tacaacgtct actgtcccta cctcccgctg   420
cacctgtccc cacgcatcga actggccgga tcacgctctg cgctgccact gccccagca    480 cctgaacgca ggattttggc cccggagccc ccggatggct cctcggaccc tctgagcatg   540
gtggggcctt cgcagggccg aagtcccagc tatgcttcct ga                     582
```

```
<210> SEQ ID NO 185
<211> LENGTH: 615
<212> TYPE: DNA
<213> ORGANISM: Ochotona princeps

<400> SEQUENCE: 185
aaagacatgg acgggctcca gcctccgggg ctgcgggttc ctgtgctggc tgccctgctt    60
ttgggagttg gccaggcacg ccccatccct gattctagcc ctctcctcca attcgggggc   120
caggtccggc agaggcacct ctacacggat gacgcccagg aatcggaagt acacctggag   180
atccgggcag acggcaccgt ggcagggact gcccgccgga gccctgaaag tctcttagaa   240
atgaaagcgt tgaagccagg cgtcattcag atcctggggg tccacacatc caggttcctg   300
tgccagagac cagacgggac gctgtacggc tcgctccact tcgaccacaa ggcctgcagc   360
ttccgggagc agctgctgga ggatgggtac aacgtgtacc actcagagac acacggcctc   420
ccgctgcgcc tgtctccaga ccgagccccc cggggcccag cccgcttcct gccactgcca   480
ggccctcctc ctgacctcct ggtgccaccc ctgccaccgg acgtcctagc ccctgagccc   540
cccgacgtgg actccccaga cccctgagc atggtggggc ccttgcaggg ccaaagcccc    600
agctacactt cctga                                                   615
```

```
<210> SEQ ID NO 186
<211> LENGTH: 546
<212> TYPE: DNA
<213> ORGANISM: Xiphophorus maculatus

<400> SEQUENCE: 186
```

```
tgcccgttcc ccttcctttt cttaatcctc tctcttccct tttctcttc ctcgttttac    60
atcccagaat ccaacccaat ctttgccttc aggaatcagc tcagagaggt gcatctctac   120
acagaaaatc acagacgggg tttgtatgtg gagatacatc tggatgggag agtgactgga   180
agtgatgctc agagtcctta tagtgtgttg cagataaagt ctgttaaacc gggtcatgtg   240
gtcataaagg gacagacatc gtccctgttc ctctgcatgg acgactccgg gaatctaaga   300
ggacagacaa cctatgacga ggctgactgc tccttcaggg aactgctgct ggccgatggc   360
tacacccgtt tcctgaactc acaacatggc gttcctttat cactggcatc cagaaactct   420
ccagatcgac actccgttcc tttcacaaga ttttacctc tcaggaatac tttaacggtt    480
tcagaagaat caacaaaaac tcagagggac ttcaacctgg actcggacga ccttctcggg   540
atggga                                                              546

<210> SEQ ID NO 187
<211> LENGTH: 576
<212> TYPE: DNA
<213> ORGANISM: Gasterosteus aculeatus

<400> SEQUENCE: 187
tctctcctcc tcatggtccc acttcctttc tgttcatcct tttatctcac tgactccagc    60
ccacttctac ccttcaataa tcaagtcaaa gaggtgcacc tctacacagc agagaatcac   120
agaagagcga tgtacctgca gatcgctctg gacgggagcg tgtcgggaag cgacgctcgg   180
tccacttaca gtgtgctgca gctgaaatct atccagccgg ccacgtggt catcagaggg    240
aaggcctcct ccatgttcct ctgcgtggac agcgggggcc gtttgagagg acaggggccg   300
tactcagagg ccgactgcag cttcaggagc tgctgctgg gggatggcta cacccggttc    360
ctgtcctcgc agcacgggtc cccgctgtct ctggcgtcga ggccttcccc ggatcccaac   420
tcggtgccct tcactcgatt cctacccatc cggaccgccc cgaggctga gagcgtgatc    480
gaagagccac cgagcaatca gagatacgtc aacgtggact ccgaggatct tcttggaatg   540
ggcctgaaca ctgtggtcag tcctcagttc tcggcg                             576

<210> SEQ ID NO 188
<211> LENGTH: 495
<212> TYPE: DNA
<213> ORGANISM: Sarcophilus harrisii

<400> SEQUENCE: 188
gtgtctgcca tgggcctgag ggagcgagct cccaggtacc tggccccgct gctgtccttg    60
ctcttggcct gcagggcctc gggtcacccc ctcccggatt ccagccccat gctcctgttt   120
ggggggcagg tccgcctccg gcacctctac acgatgtgg ccaggaggc cgaggcccac    180
gtggaactgg cgtccgacgg cacagtccgg gcggcagcgc ggaggagtcc caacagtctc   240
ctggagctga aggctgtgaa gccgggcatc gtccgaatcc tggccgtcca cagctctcgg   300
tttctgtgta tgaggcccaa cggggagctg tacggagcga tacactacga cccttccgcc   360
tgcaactttc gggagcgcct gctgggggac ggctacaacg tgtacgagtc cgaggctcac   420
gggaggaccc tccgcctgcc ccccaaggcc gcaccgggac ccgccggacc ttctcgcttc   480
ctgccgctcc ccggc                                                    495

<210> SEQ ID NO 189
<211> LENGTH: 627
<212> TYPE: DNA
```

<213> ORGANISM: Macropus eugenii

<400> SEQUENCE: 189

| | |
|---|---|
| acagaggagc cttctactgg gtccaggcac ctgggacaat gggctcccgg gctgcctggt | 60 |
| cctctgctgt ccttgctcct ggcctacagg ggctggggct cccccatccc tgattccagc | 120 |
| cccatgctcc tgtttggtgg ccaggtccgc ctccgacacc tgtacacaga tgatggccag | 180 |
| gacacgaggc ccatgtggag gctggggcca gatggagtgg ttcgagctgt ggctgagagg | 240 |
| agccccaaca gtcttctgga actgaaggcg gtgaagcctg gagtcatccg aatcctcgct | 300 |
| gtccagagct ctcggttttct gtgtatgagg cccaacgggg aactgtatgg agcggtacac | 360 |
| tatgacccttt ctgcctgcaa ctttcgggaa catctgctgg gggatggtta taatgtgtat | 420 |
| gaatcagaga ctcacagaag gaccctccgt ctgtccccat ccctgggtca ggctggcccc | 480 |
| tctcgcttcc tgccacttcc aggcgactgg ctgcccggcc ctgatccacc ttgggcacag | 540 |
| ggccctgagc cccagacgt gggctctgca gaccccctga gcatggtggg ggccgtgcag | 600 |
| ggcctcagcc ccagctactc ctcctga | 627 |

<210> SEQ ID NO 190
<211> LENGTH: 480
<212> TYPE: DNA
<213> ORGANISM: Xenopus tropicalis

<400> SEQUENCE: 190

| | |
|---|---|
| agaggggta ggaccaaaaa aaagacgtta ctcaggaaat ggctttgcct tttagccatt | 60 |
| atgttgagta ggtcaaggtt ttcttagca aatcctatcc agaattcgaa cccaatctta | 120 |
| tccaacgaca accaagtacg gactcagtat ttatacacag ataacaataa catgcacctg | 180 |
| tatcttcaga tcacccacaa tggagtagta actggtaccg aagaaaagaa tgactatggt | 240 |
| gtgctggaaa taaaggcagt aaaagctggg gttgtagtta taaaaggaat tcgaagcaat | 300 |
| ctctacctat gcatggattc tagacaccaa ttgtatgcgt cggcatatga taaagatgac | 360 |
| tgccattttcc atgaaaagat cacaccagat aattacaaca tgtatagctc agagaagcat | 420 |
| tcagaatacg tgtccttagc tccattaaaa ggaagccaga tggctcgttt tctacctata | 480 |

<210> SEQ ID NO 191
<211> LENGTH: 585
<212> TYPE: DNA
<213> ORGANISM: Danio rerio

<400> SEQUENCE: 191

| | |
|---|---|
| atgcttcttg cctgcttttt tatatttttt gctcttttc ctcatcttcg gtggtgtatg | 60 |
| tatgttcctg cacagaacgt gcttctgcag tttggcacac aagtcaggga acgcctgctt | 120 |
| tacacagatg ggttgttctt tgaaatgaat ccagatggct ccgtcaaagg ctctcctgaa | 180 |
| aagaatctaa attgtgtgct ggagctgcgt tcagtcaaag cgggtgaaac cgtcatccag | 240 |
| agtgcagcta catctctcta cctctgcgtc gatgatcaag acaagctgaa aggacagcat | 300 |
| cattactctg cactagactg cacctttcag gaattgctac tggatggata ttcgtttttc | 360 |
| ctttctccac acactaatct tcccgtatcg ctccctctcga aacgtcagaa acacggcaat | 420 |
| cctctttctc gcttcctccc tgttagcaga gcagaggaca gccggacaca ggaggtgaaa | 480 |
| cagtatattc aggatataaa cctggactct gacgacccac taggaatggg acatcggtca | 540 |
| cacttacaga ccgtcttcag tcccagtctg catactaaaa aatga | 585 |

```
<210> SEQ ID NO 192
<211> LENGTH: 630
<212> TYPE: DNA
<213> ORGANISM: Bos grunniens mutus

<400> SEQUENCE: 192
atgggctggg atgaagcgaa atttaaacat ctgggcctgt gggtgccggt gctggcggtg      60
ctgctgctgg gcacctgccg cgcgcatccg attccggata gcagcccgct gctgcagttt     120
ggcggccagg tgcgccagcg ctatctgtat accgatgatg cgcaggaaac cgaagcgcat     180
ctggaaattc gcgcggatgg caccgtggtg ggcgcggcgc gccagagccc ggaaagcctg     240
ctggaactga aagcgctgaa accgggcgtg attcagattc tgggcgtgaa aaccagccgc     300
tttctgtgcc agggcccgga tgcaaactg tatggcagcc tgcattttga tccgaaagcg     360
tgcagctttc gcgaactgct gctggaagat ggctataacg tgtatcagag cgaaaccctg     420
ggcctgccgc tgcgcctgcc gccgcagcgc agcagcaacc gcgatccggc cgcgcgcggc     480
ccggcgcgct ttctgccgct gccgggcctg ccggcggaac cgccggatcc gccgggcatt     540
ctggcgccgg aaccgccgga tgtgggcagc agcgatccgc tgagcatggt gggcccgagc     600
tatggccgca gcccgagcta taccagctaa                                      630

<210> SEQ ID NO 193
<211> LENGTH: 630
<212> TYPE: DNA
<213> ORGANISM: Saimiri boliviensis boliviensis

<400> SEQUENCE: 193
atgggctcgg aggaggtcgc gttggagcgc cctgcactgt gggtctctgt gttggctggt      60
ctcctgctgg gaacctgcca ggcataccc atccctgact ctagtcccct cctgcaattt     120
ggaggccaag tccggcagcg gtacctctac acagatgacg ctcagcagac agaagcccac     180
ctggagatca gggaagatgg cacggtggcg ggggctgccc accagagccc cgaaagtctc     240
ttgcagctga aagccttaaa gccagggggtt attcaaatct gggagtcaa gacctccagg     300 ttcctgtgcc agaggccgga cggggccctg tacggatcgc tctactttga ccccgaggcc     360
tgcagcttcc gggagctgct tcttgaggac ggatacaatg tgtaccagtc cgtggcccac     420
agcctcccgc tgcacctgcc agggggcagg tccccaccct gggaccctgc acctcgagga     480
ccagctcgct tctgccgct accaggcctg ccccccgaac ccccgaggc gccaggaatc     540 ctggcccccg agccccccga tgtgggctcc tcagaccctc tgagcatggt ggggccttcc     600
caaggccaaa gccccagcta cacttcctga                                      630

<210> SEQ ID NO 194
<211> LENGTH: 633
<212> TYPE: DNA
<213> ORGANISM: Callithrix jacchus
<220> FEATURE:
<221> NAME/KEY: misc_feature
<222> LOCATION: (190)..(190)
<223> OTHER INFORMATION: n is a, c, g, or t

<400> SEQUENCE: 194
atgggctcgg aggaggtcgg gttggagcac cctgcactgt gggtttctgt gctggctggt      60
ctcctgctgg gaacctgcca ggcgcacccc atccctgact ccagtcccct cctgcaattt     120
ggaggccaag tccggcagcg gtacctctac acagatgacg cccagcagaa agaagcccac     180
ctggagatcn aggaagatgg cacagtggcc ggggctgcca ccaaagtccc gaaagtgagt     240
```

```
ctcttgcagc tgaaagcctt aaagccaggg gttattcaaa tcttgggagt caagacatcc    300
aggttcctgt gccagaggcc agacggggcg ctgtatggat cgctccactt tgaccccgag    360
gcctgcagct tccgggagct gcttcttgag gacggataca atgtgtacca gtctgtggcc    420 cacgcctcc cgctgcacct gccagagagc aggtcaccac cccgggaccc tgcaccccga     480
ggaccagctc gcttcctgcc actaccaggc ctgccccctg aaccccccaga gccgccagga   540 atcctggccc ctgagccccc cgacgtgggc tcctcagacc ctctgagcat ggtggggcct    600
tcccaaggcc aaagccccag ctacgcttcc tga                                 633

<210> SEQ ID NO 195
<211> LENGTH: 630
<212> TYPE: DNA
<213> ORGANISM: Tupaia chinensis

<400> SEQUENCE: 195
atgggctggg ataaagcgcg ctttgaacat ctgggcgcgt gggcgccggt gctggcggtg    60
ctgctgctgg gcgcgtgcca ggcgtatccg attccggata gcagcccgct gctgcagttt   120
ggcggccagg tgcgccagcg ctatctgtat accgatgata cccaggatac cgaagcgcat   180
ctggaaattc gcgcggatgg caccgtggtg ggcgcggcgc atcagagccc ggaaagcctg   240
ctggaactga aagcgctgaa accgggcgtg attcagattc tgggcgtgaa aaccagccgc   300
tttctgtgcc agcgcccgga tggcgcgctg tatggcagcc tgcattttga tccggaagcg   360
tgcagctttc gcgaactgct gctggaagat ggctataaca tttatcagag cgaagcgcgc   420
ggcctgccgc tgcgcctgcc gccgcatgat agcccgcatc gcgatcgcac cccgcagggc   480
ccggcgcgct ttctgccgct gccgggcctg ccgctggtgc cgccggaact gccgggcgtg   540
ctggcgctgg aaccgccgga tgtgggcagc agcgatccgc tgagcatgat gggcccgagc   600
cagggccaga gcccgagcta tgcgagctaa                                    630

<210> SEQ ID NO 196
<211> LENGTH: 567
<212> TYPE: DNA
<213> ORGANISM: Papio anubis

<400> SEQUENCE: 196
atggactcgg acgagaccgg gttcgagcac tcaggactgt gggttcctgt gctggctggt    60
cttctgctgg gagcctgcca ggcacacccc atccctgact ccagtcctct cctgcaattc   120
gggggccaag tccggcaacg gtacctctac acagatgatg cccagcagac agaagcccac   180
ctggagatca gggaggatgg gacagtgggg ggcgctgctc accagagccc gaaagtaag    240 tgtgggccag agcctgggtc tgagggagga ggggctctcc actttgaccc tgaggcctgc   300
agcttccgcg agctgcttct tgagaacgga tacaatgttt accagtccga ggcccacggc   360
ctcccactgc acctgccggg aaacaagtcc ccacaccggg accctgcatc ccgaggacca   420
gctcgcttcc tgccactacc aggcctgccc ccgcaccccc agagccacc aggaatcctc    480 gcccccagc cccccgatgt gggctcctcg gaccctctga gcatggtggg accttcccag   540
gcccgaagcc ctagctacgc ttcctga                                       567

<210> SEQ ID NO 197
<211> LENGTH: 627
<212> TYPE: DNA
<213> ORGANISM: Pteropus alecto

<400> SEQUENCE: 197
```

```
atgggctggg gcaaagcgcg cctgcagcat ccgggcctgt ggggcccggt gctggcggtg      60
ctgctgggcg cgtgccaggc gcatccgatt ctggatagca gcccgctgtt tcagtttggc     120
agccaggtgc gccgccgcta tctgtatacc gatgatcgcg aggataccga agcgcatctg     180
gaaattcgcg cggatggcac cgtggcgggc gcggcgcgcc gcagcccgga aagcctgctg     240
gaactgaaag cgctgaaacc gggcgtgatt caggtgctgg cgtgaaaac cagccgcttt      300 ctgtgccagc gcccggatgg caccctgtat ggcagcctgc attttgatcc ggcggcgtgc     360
agctttcgcg aactgctgct gaaagatggc tataacgtgt atcagagcga agcgctggcg     420
cgcccgctgc cgctgccgcc gtatagcagc ccgagcagcg atccggcgcg ccgcggcccg     480
gcgcgctttc tgccgctgcc gggcccgccg ccggaaccgc cgcagccgcc gggccgcctg     540
gcgccggaac cgccggatgt gggcagcagc gatccgctga gcatggtgtg gccgagccgc     600
ggccgcagcc cgagctatac cagctaa                                         627

<210> SEQ ID NO 198
<211> LENGTH: 633
<212> TYPE: DNA
<213> ORGANISM: Heterocephalus glaber

<400> SEQUENCE: 198
atggattggg gcgcgcgcgga aagcgaacgc ccgggcctgt gggtgccggc ggtgctggcg     60
gtgctgctgc tgggcgcgtg ccaggcgcat ccgattccgg atagcagccc gctgctgcag    120
tttggcggcc aggtgcgcca cgccatctg tataccgatg atgcgcagga taccgaagtg     180
catctggaaa ttcgcgcgga tggcagcgtg ggcggcgcgg cgcatcgcag cccggaaagc    240
ctgctggaac tgaaagcgct gaaaccgggc gtgattcaga ttctgggcgt gcgcaccagc    300
cgctttctgt gccagcgccc ggatggcacc ctgtatggca gcctgcattt tgatccggaa    360
gcgtgcagct ttcgcgaact gctgctggcg gatggctata acatttatca gagcgaagcg    420
tatggcctgc cgctgcgcat gctgccgagc gatagcgcga gccgcgatcc ggtgccgccg    480
ggcccggcgc gctttctgcc gctgccgggc ctgcatccgc cgccgctgga accgccgggc    540
atgctgccgc cggaaccgcc ggatgtgggc agcagcgatc cgctgagcat ggtgggcccg    600
ctgcagggcc gcagcccgag ctatgcgttt taa                                 633

<210> SEQ ID NO 199
<211> LENGTH: 630
<212> TYPE: DNA
<213> ORGANISM: Cricetulus griseus

<400> SEQUENCE: 199
atggactgga tgaaatctgg agttgggggtc ccgggactgt gggtccctct gctgcctatc     60
ttcctgctgg gggtctccca ggcacacccc atccctgact ccagcccct cctccagttt     120 gggggtcaag tccggcacag gcacctctac acagatgaca accaggaaac tgaagtccac    180
ctggagatta ggcaggatgg cacggtgata gggaccacac accgcagccc agaaagtctc    240
ctggagctca aagccttgaa gccagaggtc atcccagtgc tggtgtcaa ggcctccagg     300 tttctttgcc aacaaccaga cggaaccctg tatggatcgc tcactttga tcctgaggcc     360 tgcagtttca gggagctctt gcttgaggat ggatacaatg tgtaccaatc tgaagtccat    420
ggcctgcccc tgcgcctgcc ccagagggac tctccaaacc aggccccagc atcctgggga    480
cctgtgcccc ccctgccagt gccaggactg ctccaccagc ccaggagct accagggttc    540
```

```
ctggccccag aacctccaga tgtgggctcc tctgacccac tgagcatggt gggacctttg      600
cagggccgaa gccccagcta tgcttcctga                                      630

<210> SEQ ID NO 200
<211> LENGTH: 579
<212> TYPE: DNA
<213> ORGANISM: Ovis aries

<400> SEQUENCE: 200
atgggctggg acgaggccaa gttcaagcac ttgggactgt gggtccctgt gctggctgtc      60
ctcctgctag gaacctgccg ggcgcatcca attccagact ccagcccct cctccagttt     120 ggggccaag tccgccagcg gtacctctac acggatgatg cccaggagac agaggcccac      180
ctggagatca gggccgatgg cacagtggtg ggggcggccc gccagagtcc cgaaagtctc     240
ttggagctga aagccctgaa gccaggagtc attcagatct ttggagttaa acatccagg      300 ttcctgtgcc aggggccaga tgggaagctg tatggatcgc tgcactttga ccccaaagcc     360
tgcagcttcc gggagctgct tcttgaagat gggtacaatg tctaccagtc ggagaccctg     420
ggccttccac tccgcctgcc gccgcagcgc tcatccaacc gggacccggc ccgcgggga     480 cctccgaagc cccagctaca cttcttgaag acgtccgctg tgcagtactg gccacgttat     540
gagaaggtcc cagcttttct gcacccttc cccggctga                             579

<210> SEQ ID NO 201
<211> LENGTH: 405
<212> TYPE: DNA
<213> ORGANISM: Pan paniscus

<400> SEQUENCE: 201
atggactcgg acgagaccgg gttcgagcac tcaggactgt gggtttctgt gctggctggt      60
cttctgctgg gagcctgcca ggcacacccc atccctgact ccagtcctct cctgcaattc     120 ggggccaag tccggcagcg gtacctctac acagatgatg cccagcagac agaagcccac      180
ctggagatca gggaggatgg gacggtgggg ggcgctgctg accagagccc gaaagtctc      240 ctgcagctga aagccttgaa gccgggagtt attcaaatct gggagtcaa gacatccagg      300 ttcctgtgcc agaggccaga tggggccctg tatggatcgg tgagtttcca ggaccctcct     360
caccacccac catgctcctc ctatatgtcg ccctcacagc ctggg                     405

<210> SEQ ID NO 202
<211> LENGTH: 351
<212> TYPE: DNA
<213> ORGANISM: Macaca fascicularis

<400> SEQUENCE: 202
atggatagcg atgaaaccgg ctttgaacat agcggcctgt gggtgccggt gctggcgggc      60
ctgctgctgg gcgcgtgcca ggcgcatccg attccggata gcagcccgct gctgcagttt     120
ggcggccagg tgcgccagcg ctatctgtat accgatgatg cgcagcagac cgaagcgcat     180
ctggaaattc gcgaagatgg caccgtgggc ggcgcggcgc atcagagccc ggaaagcctg     240
ctgcagctga aagcgctgaa accgggcgtg attcagattc tgggcgtgaa aaccagccgc     300
tttctgtgcc agaaaccgga tggcgcgctg tatggcagcg tgagctttta a              351

<210> SEQ ID NO 203
<211> LENGTH: 314
<212> TYPE: DNA
<213> ORGANISM: Mesocricetus auratus
```

<400> SEQUENCE: 203

```
ggtcatccaa atcctgggtg tcaaggctgc taggtttcct tgccagcaac cagacggaag      60
cctgtacgga tcgcctcact tcgatcccga ggcctgcagt ttccgggagc tcctgcttga     120
ggatggatac aatgtgtacc agtcggaagc cacggcctg cccctgcgcc tgccccagag      180
ggacgctccg agccagcccc cagcatcctg ggaccggtg cgcttcctgc agtgcccgg       240
actgttccag ccgccccacg acctcccagg gcgcccggcc ccagagcctc cggacgtggg     300
ctcctccgac ccac                                                       314
```

<210> SEQ ID NO 204
<211> LENGTH: 456
<212> TYPE: DNA
<213> ORGANISM: Nile tilapia

<400> SEQUENCE: 204

```
atgtatttgc agatgaacat ggatgggaga gtcacaggaa gtgatgctca gacaccttac      60
agtttgatgc agctgaaatc agttaaacca ggccatgtaa tcattaaagg accatcatca     120
tctcttttc tctgtgtgga cagcgaaggc aatctgagag gcagagtca ctactcagaa       180
accagctgca ccttcagaga aatgctgctg gctgacggat acaccgtttt catttcctca     240
caatatggat ttcccatgtc actggcatca agacattccc cagatcgaca cgcgcttccc     300
tttacgcggt tcctaccact gaggaataac ttgaaaacgg atagcgtatc agagcagctg     360
ccaaacaatc agagactctt caacgtggac tctgatgacc ttcttggaat gggtctaaat     420
tctatgggca gtcctcagtt ttctatggac aaataa                               456
```

<210> SEQ ID NO 205
<211> LENGTH: 182
<212> TYPE: PRT
<213> ORGANISM: Artificial
<220> FEATURE:
<223> OTHER INFORMATION: Chimeric Protein

<400> SEQUENCE: 205

```
His Pro Ile Pro Asp Ser Ser Pro Leu Leu Gln Phe Gly Gly Gln Val
  1               5                  10                  15

Arg Gln Arg Tyr Leu Tyr Thr Asp Asp Ala Gln Gln Thr Glu Ala His
             20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
     50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160
```

```
Gly Ser Ser Asp Pro Leu Ser Met Val Thr Gly Leu Glu Ala Val Arg
            165                 170                 175
Ser Pro Ser Phe Glu Lys
            180

<210> SEQ ID NO 206
<211> LENGTH: 182
<212> TYPE: PRT
<213> ORGANISM: Artificial
<220> FEATURE:
<223> OTHER INFORMATION: Chimeric Protein

<400> SEQUENCE: 206

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
Glu Leu Leu Leu Glu Asp Gly Tyr Asn Val Tyr Gln Ser Glu Ala His
            100                 105                 110
Gly Leu Pro Leu His Leu Pro Gly Asn Lys Ser Pro His Arg Asp Pro
        115                 120                 125
Ala Pro Arg Gly Pro Ala Arg Phe Leu Pro Leu Pro Gly Leu Pro Pro
    130                 135                 140
Ala Leu Pro Glu Pro Pro Gly Ile Leu Ala Pro Gln Pro Pro Asp Val
145                 150                 155                 160
Gly Ser Met Asp Pro Phe Gly Leu Val Thr Gly Leu Glu Ala Val Arg
                165                 170                 175
Ser Pro Ser Phe Glu Lys
            180

<210> SEQ ID NO 207
<211> LENGTH: 187
<212> TYPE: PRT
<213> ORGANISM: Artificial
<220> FEATURE:
<223> OTHER INFORMATION: Chimeric Protein

<400> SEQUENCE: 207

His Pro Ile Pro Asp Ser Ser Pro Leu Leu Gln Phe Gly Gly Gln Val
1               5                   10                  15
Arg Gln Arg Tyr Leu Tyr Thr Asp Asp Ala Gln Gln Thr Glu Ala His
            20                  25                  30
Leu Glu Ile Arg Glu Asp Gly Thr Val Gly Gly Ala Ala Asp Gln Ser
        35                  40                  45
Pro Glu Ser Leu Leu Gln Leu Lys Ala Leu Lys Pro Gly Val Ile Gln
    50                  55                  60
Ile Leu Gly Val Lys Thr Ser Arg Phe Leu Cys Gln Arg Pro Asp Gly
65                  70                  75                  80
Ala Leu Tyr Gly Ser Leu His Phe Asp Pro Glu Ala Cys Ser Phe Arg
                85                  90                  95
```

```
Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Met Val Pro
        130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 208
<211> LENGTH: 182
<212> TYPE: PRT
<213> ORGANISM: Artificial
<220> FEATURE:
<223> OTHER INFORMATION: Chimeric Protein

<400> SEQUENCE: 208

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Thr Gly Leu Glu Ala Val Arg
                165                 170                 175

Ser Pro Ser Phe Glu Lys
            180

<210> SEQ ID NO 209
<211> LENGTH: 182
<212> TYPE: PRT
<213> ORGANISM: Artificial
<220> FEATURE:
<223> OTHER INFORMATION: Chimeric Protein

<400> SEQUENCE: 209

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
```

```
                    20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Met Asp Pro Phe Gly Leu Val Thr Gly Leu Glu Ala Val Arg
                165                 170                 175

Ser Pro Ser Phe Glu Lys
            180

<210> SEQ ID NO 210
<211> LENGTH: 187
<212> TYPE: PRT
<213> ORGANISM: Artificial
<220> FEATURE:
<223> OTHER INFORMATION: Chimeric Protein

<400> SEQUENCE: 210

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Met Val Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185
```

<210> SEQ ID NO 211
<211> LENGTH: 546
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 211

| cacccatcc ctgactccag tcctctcctg caattcgggg gccaagtccg gcagcggtac | 60 |
| ctctacacag atgatgccca gcagacagaa gcccacctgg agatcaggga ggatgggacg | 120 |
| gtgggggcg ctgctgacca gagccccgaa agtctcctgc agctgaaagc cttgaagccg | 180 |
| ggagttattc aaatcttggg agtcaagaca tccaggttcc tgtgccagcg gccagatggg | 240 |
| gccctgtatg gatcgctcca cttttgaccct gaggcctgca gcttccggga gctgcttctt | 300 |
| gaggacggat acaatgttta ccagtccgaa gcccacggcc tcccgctgca cctgccaggg | 360 |
| aacaagtccc cacaccggga ccctgcaccc cgaggaccag ctcgcttcct gccactacca | 420 |
| ggcctgcccc ccgcactccc ggagccaccc ggaatcctgg ccccccagcc cccgatgtg | 480 |
| ggctcctcgg accctctgag catggtggga ctggaggccg tgaggagtcc cagctttgag | 540 |
| aagtaa | 546 |

<210> SEQ ID NO 212
<211> LENGTH: 549
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 212

| cacccatcc ctgactccag tcctctcctg caattcgggg gccaagtccg gcagcggtac | 60 |
| ctctacacag atgatgccca gcagacagaa gcccacctgg agatcaggga ggatgggacg | 120 |
| gtgggggcg ctgctgacca gagccccgaa agtctcctgc agctgaaagc cttgaagccg | 180 |
| ggagttattc aaatcttggg agtcaagaca tccaggttcc tgtgccagcg gccagatggg | 240 |
| gccctgtatg gatcgctcca cttttgaccct gaggcctgca gcttccggga gctgcttctt | 300 |
| gaggacggat acaatgttta ccagtccgaa gcccacggcc tcccgctgca cctgccaggg | 360 |
| aacaagtccc cacaccggga ccctgcaccc cgaggaccag ctcgcttcct gccactacca | 420 |
| ggcctgcccc ccgcactccc ggagccaccc ggaatcctgg ccccccagcc cccgatgtg | 480 |
| ggctccatgg acccatttgg gcttgtcacc ggactggagg ccgtgaggag tcccagcttt | 540 |
| gagaagtaa | 549 |

<210> SEQ ID NO 213
<211> LENGTH: 564
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 213

| cacccatcc ctgactccag tcctctcctg caattcgggg gccaagtccg gcagcggtac | 60 |
| ctctacacag atgatgccca gcagacagaa gcccacctgg agatcaggga ggatgggacg | 120 |
| gtgggggcg ctgctgacca gagccccgaa agtctcctgc agctgaaagc cttgaagccg | 180 |
| ggagttattc aaatcttggg agtcaagaca tccaggttcc tgtgccagcg gccagatggg | 240 |

```
gccctgtatg gatcgctcca ctttgaccct gaggcctgca gcttccggga gctgcttctt    300
gaggacggat acaatgttta ccagtccgaa gcccacggcc tcccgctgca cctgccaggg    360
aacaagtccc cacaccggga ccctgcaccc cgaggaccag ctcgcttcct gccactactg    420
cccatggtcc cagaggagcc tgaggacctc aggggccact ggaatctga catgttctct     480 tcgcccctgg agaccgacag catggaccca tttgggcttg tcaccggact ggaggccgtg    540
aggagtccca gctttgagaa gtaa                                           564
```

<210> SEQ ID NO 214
<211> LENGTH: 546
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 214

```
caccccatcc ctgactccag tcctctcctg caattcgggg gccaagtccg gcagcggtac     60
ctctacacag atgatgccca gcagacagaa gcccacctgg agatcaggga ggatgggacg    120 gtgggggggcg ctgctgacca gagccccgaa agtctcctgc agctgaaagc cttgaagccg    180
ggagttattc aaatcttggg agtcaagaca tccaggttcc tgtgccaatg ccagatgggg    240
gccctgtatg gatcgctcca ctttgaccct gaggcctgca gcttccggga gctgcttctt    300
gaggacggat acaatgttta ccagtccgaa gcccacggcc tcccgctgca cctgccaggg    360
aacaagtccc cacaccggga ccctgcaccc cgaggaccag ctcgcttcct gccactacca    420
ggcctgcccc ccgcactccc ggagccaccc ggaatcctgg cccccagcc cccgatgtg     480 ggctcctcgg accctctgag catggtggga ctggaggccg tgaggagtcc cagctttgag    540
aagtaa                                                               546
```

<210> SEQ ID NO 215
<211> LENGTH: 549
<212> TYPE: DNA
<213> ORGANISM: Artificial
<220> FEATURE:
<223> OTHER INFORMATION: Nucleic Acid Molecule Encoding a Chimeric
      Protein

<400> SEQUENCE: 215

```
caccccatcc ctgactccag tcctctcctg caattcgggg gccaagtccg gcagcggtac     60
ctctacacag atgatgccca gcagacagaa gcccacctgg agatcaggga ggatgggacg    120 gtgggggggcg ctgctgacca gagccccgaa agtctcctgc agctgaaagc cttgaagccg    180
ggagttattc aaatcttggg agtcaagaca tccaggttcc tgtgccaatg ccagatgggg    240
gccctgtatg gatcgctcca ctttgaccct gaggcctgca gcttccggga gctgcttctt    300
gaggacggat acaatgttta ccagtccgaa gcccacggcc tcccgctgca cctgccaggg    360
aacaagtccc cacaccggga ccctgcaccc cgaggaccag ctcgcttcct gccactacca    420
ggcctgcccc ccgcactccc ggagccaccc ggaatcctgg cccccagcc cccgatgtg     480 ggctccatgg acccatttgg gcttgtcacc ggactggagg ccgtgaggag tcccagcttt    540
gagaagtaa                                                            549
```

<210> SEQ ID NO 216
<211> LENGTH: 564
<212> TYPE: DNA

<213> ORGANISM: Artificial
<220> FEATURE:
<223> OTHER INFORMATION: Nucleic Acid Molecule Encoding a Chimeric Protein

<400> SEQUENCE: 216

```
cacccccatcc ctgactccag tcctctcctg caattcgggg gccaagtccg gcagcggtac    60
ctctacacag atgatgccca gcagacagaa gcccacctgg agatcaggga ggatgggacg   120
gtgggggggcg ctgctgacca gaccccgaa agtctcctgc agctgaaagc cttgaagccg   180
ggagttattc aaatcttggg agtcaagaca tccaggttcc tgtgccaatg ccagatggg    240
gccctgtatg gatcgctcca cttgtgaccct gaggcctgca gcttccggga gctgcttctt   300
gaggacggat acaatgttta ccagtccgaa gcccacggcc tcccgctgca cctgccaggg   360
aacaagtccc cacaccggga ccctgcaccc cgaggaccag ctcgcttcct gccactactg   420
cccatggtcc cagaggagcc tgaggacctc aggggccact ggaatctga catgttctct   480
tcgcccctgg agaccgacag catgaccca tttgggcttg tcaccggact ggaggccgtg   540
aggagtccca gctttgagaa gtaa                                           564
```

<210> SEQ ID NO 217
<211> LENGTH: 1044
<212> TYPE: PRT
<213> ORGANISM: Homo sapiens

<400> SEQUENCE: 217

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
                20                  25                  30

Gly Gly Leu Gln Arg Ser Val Ile Leu Ser Ala Leu Ile Leu Leu Arg
            35                  40                  45

Ala Val Thr Gly Phe Ser Gly Asp Gly Arg Ala Ile Trp Ser Lys Asn
        50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240
```

```
Asn Pro Tyr Leu Val Ala Trp His Gly Tyr Gly Thr Gly Met His Ala
            245                 250                 255

Pro Gly Glu Lys Gly Asn Leu Ala Ala Val Tyr Thr Val Gly His Asn
        260                 265                 270

Leu Ile Lys Ala His Ser Lys Val Trp His Asn Tyr Asn Thr His Phe
    275                 280                 285

Arg Pro His Gln Lys Gly Trp Leu Ser Ile Thr Leu Gly Ser His Trp
290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
            325                 330                 335

Asp Gly Asp Tyr Pro Glu Gly Met Arg Lys Lys Leu Phe Ser Val Leu
        340                 345                 350

Pro Ile Phe Ser Glu Ala Glu Lys His Glu Met Arg Gly Thr Ala Asp
    355                 360                 365

Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
            405                 410                 415

Asn Gly Trp Phe Thr Asp Ser Arg Val Lys Thr Glu Asp Thr Thr Ala
        420                 425                 430

Ile Tyr Met Met Lys Asn Phe Leu Ser Gln Val Leu Gln Ala Ile Arg
    435                 440                 445

Leu Asp Glu Ile Arg Val Phe Gly Tyr Thr Ala Trp Ser Leu Leu Asp
450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
            485                 490                 495

His Tyr Tyr Lys Gln Ile Ile Arg Glu Asn Gly Phe Ser Leu Lys Glu
        500                 505                 510

Ser Thr Pro Asp Val Gln Gly Gln Phe Pro Cys Asp Phe Ser Trp Gly
    515                 520                 525

Val Thr Glu Ser Val Leu Lys Pro Glu Ser Val Ala Ser Ser Pro Gln
530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
            565                 570                 575

Thr Asp Phe Val Asn Ile Lys Lys Gln Leu Glu Met Leu Ala Arg Met
        580                 585                 590

Lys Val Thr His Tyr Arg Phe Ala Leu Asp Trp Ala Ser Val Leu Pro
    595                 600                 605

Thr Gly Asn Leu Ser Ala Val Asn Arg Gln Ala Leu Arg Tyr Tyr Arg
610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
            645                 650                 655
```

-continued

```
His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
        675                 680                 685

Ile Thr Ile Asn Glu Pro Asn Arg Leu Ser Asp Ile Tyr Asn Arg Ser
    690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
        755                 760                 765

Ile Ala Trp Phe Ala Glu Pro Leu Phe Lys Thr Gly Asp Tyr Pro Ala
    770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Leu Leu Lys Gly
                805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
        835                 840                 845

Phe Leu Gln Asp Ile Thr Arg Leu Ser Ser Pro Thr Arg Leu Ala Val
    850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
                885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
        915                 920                 925

Tyr Ala Phe Lys Leu Ala Glu Glu Lys Ser Lys Pro Arg Phe Gly Phe
    930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Ser Arg Cys
                965                 970                 975

Ser Gln Thr Gln Glu Asn Thr Glu Cys Thr Val Cys Leu Phe Leu Val
            980                 985                 990

Gln Lys Lys Pro Leu Ile Phe Leu Gly Cys Cys Phe Phe Ser Thr Leu
        995                 1000                1005

Val Leu Leu Leu Ser Ile Ala Ile Phe Gln Arg Gln Lys Arg Arg
    1010                1015                1020

Lys Phe Trp Lys Ala Lys Asn Leu Gln His Ile Pro Leu Lys Lys
1025                1030                1035

Gly Lys Arg Val Val Ser
1040

<210> SEQ ID NO 218
<211> LENGTH: 1043
<212> TYPE: PRT
```

<213> ORGANISM: Mus musculus

<400> SEQUENCE: 218

```
Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
            20                  25                  30

Arg Ala Leu Gln Arg Ser Ala Val Leu Ser Ala Phe Val Leu Leu Arg
        35                  40                  45

Ala Val Thr Gly Phe Ser Gly Asp Gly Lys Ala Ile Trp Asp Lys Lys
    50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
    130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
        195                 200                 205

Trp Lys Asn Ala Thr Met Ile Asp Leu Phe Asn Asp Tyr Ala Thr Tyr
    210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
        275                 280                 285

Arg Pro His Gln Lys Gly Trp Leu Ser Ile Thr Leu Gly Ser His Trp
    290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Gly Ala Met Ile Pro Glu
            340                 345                 350

Phe Ser Glu Ala Glu Lys Glu Glu Val Arg Gly Thr Ala Asp Phe Phe
        355                 360                 365

Ala Phe Ser Phe Gly Pro Asn Asn Phe Arg Pro Ser Asn Thr Val Val
    370                 375                 380

Lys Met Gly Gln Asn Val Ser Leu Asn Leu Arg Gln Val Leu Asn Trp
385                 390                 395                 400
```

-continued

```
Ile Lys Leu Glu Tyr Asp Asp Pro Gln Ile Leu Ile Ser Glu Asn Gly
                405                 410                 415
Trp Phe Thr Asp Ser Tyr Ile Lys Thr Glu Asp Thr Thr Ala Ile Tyr
            420                 425                 430
Met Met Lys Asn Phe Leu Asn Gln Val Leu Gln Ala Ile Lys Phe Asp
        435                 440                 445
Glu Ile Arg Val Phe Gly Tyr Thr Ala Trp Thr Leu Leu Asp Gly Phe
    450                 455                 460
Glu Trp Gln Asp Ala Tyr Thr Thr Arg Arg Gly Leu Phe Tyr Val Asp
465                 470                 475                 480
Phe Asn Ser Glu Gln Lys Glu Arg Lys Pro Lys Ser Ser Ala His Tyr
                485                 490                 495
Tyr Lys Gln Ile Ile Gln Asp Asn Gly Phe Pro Leu Lys Glu Ser Thr
            500                 505                 510
Pro Asp Met Lys Gly Arg Phe Pro Cys Asp Phe Ser Trp Gly Val Thr
        515                 520                 525
Glu Ser Val Leu Lys Pro Glu Phe Thr Val Ser Ser Pro Gln Phe Thr
    530                 535                 540
Asp Pro His Leu Tyr Val Trp Asn Val Thr Gly Asn Arg Leu Leu Tyr
545                 550                 555                 560
Arg Val Glu Gly Val Arg Leu Lys Thr Arg Pro Ser Gln Cys Thr Asp
                565                 570                 575
Tyr Val Ser Ile Lys Lys Arg Val Glu Met Leu Ala Lys Met Lys Val
            580                 585                 590
Thr His Tyr Gln Phe Ala Leu Asp Trp Thr Ser Ile Leu Pro Thr Gly
        595                 600                 605
Asn Leu Ser Lys Val Asn Arg Gln Val Leu Arg Tyr Tyr Arg Cys Val
    610                 615                 620
Val Ser Glu Gly Leu Lys Leu Gly Val Phe Pro Met Val Thr Leu Tyr
625                 630                 635                 640
His Pro Thr His Ser His Leu Gly Leu Pro Leu Pro Leu Leu Ser Ser
                645                 650                 655
Gly Gly Trp Leu Asn Met Asn Thr Ala Lys Ala Phe Gln Asp Tyr Ala
            660                 665                 670
Glu Leu Cys Phe Arg Glu Leu Gly Asp Leu Val Lys Leu Trp Ile Thr
        675                 680                 685
Ile Asn Glu Pro Asn Arg Leu Ser Asp Met Tyr Asn Arg Thr Ser Asn
    690                 695                 700
Asp Thr Tyr Arg Ala Ala His Asn Leu Met Ile Ala His Ala Gln Val
705                 710                 715                 720
Trp His Leu Tyr Asp Arg Gln Tyr Arg Pro Val Gln His Gly Ala Val
                725                 730                 735
Ser Leu Ser Leu His Cys Asp Trp Ala Glu Pro Ala Asn Pro Phe Val
            740                 745                 750
Asp Ser His Trp Lys Ala Ala Glu Arg Phe Leu Gln Phe Glu Ile Ala
        755                 760                 765
Trp Phe Ala Asp Pro Leu Phe Lys Thr Gly Asp Tyr Pro Ser Val Met
    770                 775                 780
Lys Glu Tyr Ile Ala Ser Lys Asn Gln Arg Gly Leu Ser Ser Ser Val
785                 790                 795                 800
Leu Pro Arg Phe Thr Ala Lys Glu Ser Arg Leu Val Lys Gly Thr Val
                805                 810                 815
Asp Phe Tyr Ala Leu Asn His Phe Thr Thr Arg Phe Val Ile His Lys
```

```
          820             825              830
Gln Leu Asn Thr Asn Arg Ser Val Ala Asp Arg Asp Val Gln Phe Leu
            835              840             845

Gln Asp Ile Thr Arg Leu Ser Ser Pro Ser Arg Leu Ala Val Thr Pro
    850             855             860

Trp Gly Val Arg Lys Leu Leu Ala Trp Ile Arg Arg Asn Tyr Arg Asp
865             870             875                 880

Arg Asp Ile Tyr Ile Thr Ala Asn Gly Ile Asp Asp Leu Ala Leu Glu
                885             890                 895

Asp Asp Gln Ile Arg Lys Tyr Tyr Leu Glu Lys Tyr Val Gln Glu Ala
            900             905             910

Leu Lys Ala Tyr Leu Ile Asp Lys Val Lys Ile Lys Gly Tyr Tyr Ala
            915             920             925

Phe Lys Leu Thr Glu Glu Lys Ser Lys Pro Arg Phe Gly Phe Phe Thr
        930             935             940

Ser Asp Phe Arg Ala Lys Ser Ser Val Gln Phe Tyr Ser Lys Leu Ile
945             950             955                 960

Ser Ser Ser Gly Leu Pro Ala Glu Asn Arg Ser Pro Ala Cys Gly Gln
                965             970             975

Pro Ala Glu Asp Thr Asp Cys Thr Ile Cys Ser Phe Leu Val Glu Lys
            980             985             990

Lys Pro Leu Ile Phe Phe Gly Cys  Cys Phe Ile Ser Thr Leu Ala Val
        995             1000             1005

Leu Leu  Ser Ile Thr Val Phe  His His Gln Lys Arg  Arg Lys Phe
    1010             1015             1020

Gln Lys  Ala Arg Asn Leu Gln  Asn Ile Pro Leu Lys  Lys Gly His
    1025             1030             1035

Ser Arg  Val Phe Ser
    1040

<210> SEQ ID NO 219
<211> LENGTH: 3135
<212> TYPE: DNA
<213> ORGANISM: Homo sapiens

<400> SEQUENCE: 219
atgaagccag gctgtgcggc aggatctcca gggaatgaat ggattttctt cagcactgat      60
gaaataacca cacgctatag aatacaatg tccaacgggg gattgcaaag atctgtcatc     120
ctgtcagcac ttattctgct acgagctgtt actggattct ctggagatgg aagagctata     180
tggtctaaaa atcctaattt tactccggta atgaaagtc agctgttct ctatgacact      240 ttccctaaaa acttttttctg ggtattggg actggagcat gcaagtggaa agggagttgg     300
aagaaggatg gaaaaggacc ttctatatgg gatcatttca tccacacaca ccttaaaaat     360
gtcagcagca cgaatggttc cagtgacagt tatattttc tggaaaaaga cttatcagcc     420
ctggatttta taggagtttc tttttatcaa ttttcaattt cctggccaag gcttttcccc     480
gatggaatag taacagttgc caacgcaaaa ggtctgcagt actacagtac tcttctggac     540
gctctagtgc ttagaaacat tgaacctata gttactttat accactggga tttgcctttg     600
gcactacaag aaaaatatgg ggggtggaaa aatgatacca atagatat cttcaatgac      660 tatgccacat actgtttcca gatgtttggg gaccgtgtca atattggat tacaattcac      720 aacccatatc tagtggcttg gcatgggtat gggacaggta tgcatgcccc tggagagaag     780
ggaaatttag cagctgtcta cactgtggga cacaacttga tcaaggctca ctcgaaagtt     840
```

```
tggcataact acaacacaca tttccgccca catcagaagg gttggttatc gatcacgttg      900
ggatctcatt ggatcgagcc aaaccggtcg gaaaacacga tggatatatt caaatgtcaa      960
caatccatgg tttctgtgct tggatggttt gccaaccta tccatgggga tggcgactat     1020
ccagagggga tgagaaagaa gttgttctcc gttctaccca ttttctctga agcagagaag     1080
catgagatga gaggcacagc tgatttcttt gccttttctt ttggacccaa caacttcaag     1140
cccctaaaca ccatggctaa aatgggacaa aatgtttcac ttaatttaag agaagcgctg     1200
aactggatta aactggaata caacaaccct cgaatcttga ttgctgagaa tggctggttc     1260
acagacagtc gtgtgaaaac agaagacacc acggccatct acatgatgaa gaatttcctc     1320
agccaggtgc ttcaagcaat aaggttagat gaaatacgag tgtttggtta tactgcctgg     1380
tctctcctgg atggctttga atggcaggat gcttacacca tccgccgagg attattttat     1440
gtggatttta acagtaaaca gaaagagcgg aaacctaagt cttcagcaca ctactacaaa     1500
cagatcatac gagaaaatgg ttttctttta aaagagtcca cgccagatgt gcagggccag     1560
tttccctgtg acttctcctg gggtgtcact gaatctgttc ttaagcccga gtctgtggct     1620
tcgtccccac agttcagcga tcctcatctg tacgtgtgga acgccactgg caacagactg     1680
ttgcaccgag tggaagggt gaggctgaaa acacgacccg ctcaatgcac agattttgta     1740
aacatcaaaa acaacttga gatgttggca agaatgaaag tcacccacta ccggtttgct     1800
ctggattggg cctcggtcct tcccactggc aacctgtccg cggtgaaccg acaggccctg     1860
aggtactaca ggtgcgtggt cagtgagggg ctgaagcttg gcatctccgc gatggtcacc     1920
ctgtattatc cgacccacgc ccacctaggc ctccccgagc ctctgttgca tgccgacggg     1980
tggctgaacc catcgacggc cgaggccttc caggcctacg ctgggctgtg cttccaggag     2040
ctgggggacc tggtgaagct ctggatcacc atcaacgagc ctaaccggct aagtgacatc     2100
tacaaccgct ctggcaacga cacctacggg gcggcgcaca acctgctggt ggcccacgcc     2160
ctggcctggc gcctctacga ccggcagttc aggccctcac agcgcggggc cgtgtcgctg     2220
tcgctgcacg cggactgggc ggaacccgcc aaccccctatg ctgactcgca ctggagggcg     2280
gccgagcgct tcctgcagtt cgagatcgcc tggttcgccg agccgctctt caagaccggg     2340
gactaccccg cggccatgag ggaatacatt gcctccaagc accgacgggg gctttccagc     2400
tcggccctgc cgcgcctcac cgaggccgaa aggaggctgc tcaagggcac ggtcgacttc     2460
tgcgcgctca accacttcac cactaggttc gtgatgcacg agcagctggc cggcagccgc     2520
tacgactcgg acagggacat ccagtttctg caggacatca cccgcctgag ctcccccacg     2580
cgcctggctg tgattccctg ggggggtgcgc aagctgctgc ggtgggtccg gaggaactac     2640
ggcgacatgg acatttacat caccgccagt ggcatcgacg accaggctct ggaggatgac     2700
cggctccgga gtactacct agggaagtac cttcaggagg tgctgaaagc atacctgatt     2760
gataaagtca gaatcaaagg ctattatgca ttcaaactgg ctgaagagaa atctaaaccc     2820
agatttggat tcttcacatc tgattttaaa gctaaatcct caatacaatt ttacaacaaa     2880
gtgatcagca gcaggggctt cccttttgag aacagtagtt ctagatgcag tcagacccaa     2940
gaaaatacag agtgcactgt ctgcttattc cttgtgcaga gaaaccact gatattcctg     3000
ggttgttgct tcttctccac cctggttcta ctcttatcaa ttgccatttt tcaaaggcag     3060
aagagaagaa agttttggaa agcaaaaaaac ttacaacaca taccattaaa gaaaggcaag     3120
agagttgtta gctaa                                                      3135
```

<210> SEQ ID NO 220
<211> LENGTH: 3132
<212> TYPE: DNA
<213> ORGANISM: Mus musculus

<400> SEQUENCE: 220

| | | | | | | |
|---|---|---|---|---|---|---|
| atgaagacag | gctgtgcagc | agggtctccg | gggaatgaat | ggattttctt | cagctctgat | 60 |
| gaaagaaaca | cacgctctag | gaaaacaatg | tccaacaggg | cactgcaaag | atctgccgtg | 120 |
| ctgtctgcgt | tgttctgct | gcgagctgtt | accggcttct | ccggagacgg | gaaagcaata | 180 |
| tgggataaaa | aacagtacgt | gagtccggta | aacccaagtc | agctgttcct | ctatgacact | 240 |
| ttccctaaaa | acttttcctg | gggcgttggg | accggagcat | tcaagtgga | agggagttgg | 300 |
| aagacagatg | gaagaggacc | ctcgatctgg | gatcggtacg | tctactcaca | cctgagaggt | 360 |
| gtcaacggca | cagacagatc | cactgacagt | tacatctttc | tggaaaaaga | cttgttggct | 420 |
| ctggattttt | taggagtttc | ttttatcag | ttctcaatct | cctggccacg | gttgtttccc | 480 |
| aatggaacag | tagcagcagt | gaatgcgcaa | ggtctccggt | actaccgtgc | acttctggac | 540 |
| tcgctggtac | ttaggaatat | cgagcccatt | gttaccttgt | accattggga | tttgcctctg | 600 |
| acgctccagg | aagaatatgg | gggctggaaa | atgcaacta | tgatagatct | cttcaacgac | 660 |
| tatgccacat | actgcttcca | gacctttgga | gaccgtgtca | aatattggat | tacaattcac | 720 |
| aacccttacc | ttgttgcttg | gcatgggttt | ggcacaggta | tgcatgcacc | aggagagaag | 780 |
| ggaaatttaa | cagctgtcta | cactgtggga | cacaacctga | tcaaggcaca | ttcgaaagtg | 840 |
| tggcataact | acgacaaaaa | cttccgcccct | catcagaagg | gttggctctc | catcaccttg | 900 |
| gggtcccatt | ggatagagcc | aaacagaaca | gacaacatgg | aggacgtgat | caactgccag | 960 |
| cactccatgt | cctctgtgct | tggatggttc | gccaacccca | tccacgggga | cggcgactac | 1020 |
| cctgagttca | tgaagacggg | cgccatgatc | cccgagttct | ctgaggcaga | aaggaggag | 1080 |
| gtgaggggca | cggctgattt | ctttgccttt | tccttcgggc | caacaacttt | caggccctca | 1140 |
| aacaccgtgg | tgaaaatggg | acaaaatgta | tcactcaact | taaggcaggt | gctgaactgg | 1200 |
| attaaactgg | aatacgatga | ccctcaaatc | ttgatttcgg | agaacggctg | gttcacagat | 1260 |
| agctatataa | agacagagga | caccacggcc | atctacatga | tgaagaattt | cctaaaccag | 1320 |
| gttcttcaag | caataaaatt | tgatgaaatc | cgcgtgtttg | ttatacggc | ctggactctc | 1380 |
| ctggatggct | ttgagtggca | ggatgcctat | acgacccgac | gagggctgtt | ttatgtggac | 1440 |
| tttaacagtg | agcagaaaga | gaggaaaccc | aagtcctcgg | ctcattacta | caagcagatc | 1500 |
| atacaagaca | acggcttccc | tttgaaagag | tccacgccag | acatgaaggg | tcggttcccc | 1560 |
| tgtgatttct | cttggggagt | cactgagtct | gttcttaagc | ccgagtttac | ggtctcctcc | 1620 |
| ccgcagttta | ccgatcctca | cctgtatgtg | tggaatgtca | ctggcaacag | attgctctac | 1680 |
| cgagtggaag | gggtaaggct | gaaaacaaga | ccatcccagt | gcacagatta | tgtgagcatc | 1740 |
| aaaaaacgag | ttgaaatgtt | ggcaaaaatg | aaagtcaccc | actaccagtt | tgctctggac | 1800 |
| tggacctcta | tccttcccac | tggcaatctg | tccaaagtta | acagacaagt | gttaaggtac | 1860 |
| tataggtgtg | tggtgagcga | aggactgaag | ctgggcgtct | tccccatggt | gacgttgtac | 1920 |
| cacccaaccc | actcccatct | cggcctcccc | ctgccacttc | tgagcagtgg | ggggtggcta | 1980 |
| aacatgaaca | cagccaaggc | cttccaggac | tacgctgagc | tgtgcttccg | ggagttgggg | 2040 |
| gacttggtga | agctctggat | caccatcaat | gagcctaaca | ggctgagtga | catgtacaac | 2100 |
| cgcacgagta | atgacaccta | ccgtgcagcc | cacaacctga | tgatcgccca | tgcccaggtc | 2160 |

```
tggcacctct atgataggca gtataggccg gtccagcatg gggctgtgtc gctgtcctta    2220
cattgcgact gggcagaacc tgccaacccc tttgtggatt cacactggaa ggcagccgag    2280
cgcttcctcc agtttgagat cgcctggttt gcagatccgc tcttcaagac tggcgactat    2340
ccatcggtta tgaaggaata catcgcctcc aagaaccagc gagggctgtc tagctcagtc    2400
ctgccgcgct tcaccgcgaa ggagagcagg ctggtgaagg gtaccgtcga cttctacgca    2460
ctgaaccact tcactacgag gttcgtgata cacaagcagc tgaacaccaa ccgctcagtt    2520
gcagacaggg acgtccagtt cctgcaggac atcacccgcc taagctcgcc cagccgcctg    2580
gctgtaacac cctggggagt gcgcaagctc cttgcgtgga tccggaggaa ctacagagac    2640
agggatatct acatcacagc caatggcatc gatgacctgg ctctagagga tgatcagatc    2700
cgaaagtact acttggagaa gtatgtccag gaggctctga agcatatct cattgacaag    2760 gtcaaaatca aggctacta tgcattcaaa ctgactgaag agaaatctaa gcctagattt    2820 ggattttca cctctgactt cagagctaag tcctctgtcc agttttacag caagctgatc    2880
agcagcagtg gcctccccgc tgagaacaga agtcctgcgt gtggtcagcc tgcggaagac    2940
acagactgca ccatttgctc atttctcgtg gagaagaaac cactcatctt cttcggttgc    3000
tgcttcatct ccactctggc tgtactgcta tccatcaccg tttttcatca tcaaaagaga    3060
agaaaattcc agaaagcaag gaacttacaa aatataccat tgaagaaagg ccacagcaga    3120
gttttcagct aa                                                        3132
```

<210> SEQ ID NO 221
<211> LENGTH: 822
<212> TYPE: PRT
<213> ORGANISM: Homo sapiens

<400> SEQUENCE: 221

```
Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190
```

-continued

```
Asn Gly Lys Glu Phe Lys Pro Asp His Arg Ile Gly Tyr Lys Val
            195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
            245                 250                 255

Leu Gln Ala Gly Leu Pro Ala Asn Lys Thr Val Ala Leu Gly Ser Asn
                260                 265                 270

Val Glu Phe Met Cys Lys Val Tyr Ser Asp Pro Gln Pro His Ile Gln
            275                 280                 285

Trp Leu Lys His Ile Glu Val Asn Gly Ser Lys Ile Gly Pro Asp Asn
            290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
            355                 360                 365

Met Thr Ser Pro Leu Tyr Leu Glu Ile Ile Ile Tyr Cys Thr Gly Ala
            370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
            435                 440                 445

Leu Ser Ser Ser Gly Thr Pro Met Leu Ala Gly Val Ser Glu Tyr Glu
450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
            515                 520                 525

Ile Ser Glu Met Glu Met Met Lys Met Ile Gly Lys His Lys Asn Ile
530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
            565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
            595                 600                 605

Arg Gly Met Glu Tyr Leu Ala Ser Lys Lys Cys Ile His Arg Asp Leu
```

```
                610                615                620
Ala Ala Arg Asn Val Leu Val Thr Glu Asp Asn Val Met Lys Ile Ala
625                 630                635                640

Asp Phe Gly Leu Ala Arg Asp Ile His His Ile Asp Tyr Tyr Lys Lys
                645                650                655

Thr Thr Asn Gly Arg Leu Pro Val Lys Trp Met Ala Pro Glu Ala Leu
                660                665                670

Phe Asp Arg Ile Tyr Thr His Gln Ser Asp Val Trp Ser Phe Gly Val
            675                680                685

Leu Leu Trp Glu Ile Phe Thr Leu Gly Gly Ser Pro Tyr Pro Gly Val
            690                695                700

Pro Val Glu Glu Leu Phe Lys Leu Leu Lys Glu Gly His Arg Met Asp
705                710                715                720

Lys Pro Ser Asn Cys Thr Asn Glu Leu Tyr Met Met Met Arg Asp Cys
                725                730                735

Trp His Ala Val Pro Ser Gln Arg Pro Thr Phe Lys Gln Leu Val Glu
            740                745                750

Asp Leu Asp Arg Ile Val Ala Leu Thr Ser Asn Gln Glu Tyr Leu Asp
            755                760                765

Leu Ser Met Pro Leu Asp Gln Tyr Ser Pro Ser Phe Pro Asp Thr Arg
770                775                780

Ser Ser Thr Cys Ser Ser Gly Glu Asp Ser Val Phe Ser His Glu Pro
785                790                795                800

Leu Pro Glu Glu Pro Cys Leu Pro Arg His Pro Ala Gln Leu Ala Asn
                805                810                815

Gly Gly Leu Lys Arg Arg
                820

<210> SEQ ID NO 222
<211> LENGTH: 2469
<212> TYPE: DNA
<213> ORGANISM: Homo sapiens

<400> SEQUENCE: 222
atgtggagct ggaagtgcct cctcttctgg gctgtgctgg tcacagccac actctgcacc      60
gctaggccgt ccccgacctt gcctgaacaa gcccagccct ggggagcccc tgtggaagtg     120
gagtccttcc tggtccaccc cggtgacctg ctgcagcttc gctgtcggct gcgggacgat     180
gtgcagagca tcaactggct gcgggacggg gtgcagctgg cggaaagcaa ccgcacccgc     240
atcacagggg aggaggtgga ggtgcaggac tccgtgcccg cagactccgg cctctatgct     300
tgcgtaacca gcagcccctc gggcagtgac accacctact ctccgtcaa tgtttcagat     360 gctctcccct cctcggagga tgatgatgat gatgatgact cctcttcaga ggagaaagaa     420
acagataaca ccaaaccaaa ccgtatgccc gtagctccat attggacatc cccagaaaag     480
atggaaaaga aattgcatgc agtgccggct gccaagacag tgaagttcaa atgcccttcc     540
agtgggaccc caaaccccac actgcgctgg ttgaaaaatg gcaaagaatt caaacctgac     600
cacagaattg gaggctacaa ggtccgttat gccacctgga gcatcataat ggactctgtg     660
gtgccctctg acaagggcaa ctacacctgc attgtggaga tgagtacgg cagcatcaac     720 cacacatacc agctggatgt cgtggagcgg tcccctcacc ggcccatcct gcaagcaggg     780
ttgcccgcca acaaaacagt ggccctgggt agcaacgtgg agttcatgtg taaggtgtac     840
agtgacccgc agccgcacat ccagtggcta aagcacatcg aggtgaatgg gagcaagatt     900
```

```
ggcccagaca acctgcctta tgtccagatc ttgaagactg ctggagttaa taccaccgac    960
aaagagatgg aggtgcttca cttaagaaat gtctcctttg aggacgcagg ggagtatacg   1020
tgcttggcgg gtaactctat cggactctcc catcactctg catggttgac cgttctggaa   1080
gccctggaag agaggccggc agtgatgacc tcgcccctgt acctggagat catcatctat   1140
tgcacagggg ccttcctcat ctcctgcatg gtggggtcgg tcatcgtcta caagatgaag   1200
agtggtacca agaagagtga cttccacagc cagatggctg tgcacaagct ggccaagagc   1260
atccctctgc gcagacaggt aacagtgtct gctgactcca gtgcatccat gaactctggg   1320
gttcttctgg ttcggccatc acggctctcc tccagtggga ctcccatgct agcaggggtc   1380
tctgagtatg agcttcccga agaccctcgc tgggagctgc ctcgggacag actggtctta   1440
ggcaaacccc tgggagaggg ctgctttggg caggtggtgt tggcagaggc tatcgggctg   1500
gacaaggaca aacccaaccg tgtgaccaaa gtggctgtga agatgttgaa gtcggacgca   1560
acagagaaag acttgtcaga cctgatctca gaaatggaga tgatgaagat gatcgggaag   1620
cataagaata tcatcaacct gctgggggcc tgcacgcagg atggtccctt gtatgtcatc   1680
gtggagtatg cctccaaggg caacctgcgg gagtacctgc aggcccggag gccccagggg   1740
ctggaatact gctacaaccc cagccacaac ccagaggagc agctctcctc caaggacctg   1800
gtgtcctgcg cctaccaggt ggcccgaggc atggagtatc tggcctccaa gaagtgcata   1860
caccgagacc tggcagccag gaatgtcctg gtgacagagg acaatgtgat gaagatagca   1920
gactttggcc tcgcacggga cattcaccac atcgactact ataaaaagac aaccaacggc   1980
cgactgcctg tgaagtggat ggcacccgag gcattatttg accggatcta cacccaccag   2040
agtgatgtgt ggtctttcgg ggtgctcctg tgggagatct tcactctggg cggctcccca   2100
taccccggtg tgcctgtgga ggaacttttc aagctgctga aggagggtca ccgcatggac   2160
aagcccagta actgcaccaa cgagctgtac atgatgatgc gggactgctg gcatgcagtg   2220
ccctcacaga gacccacctt caagcagctg gtggaagacc tggaccgcat cgtgccttg   2280
acctccaacc aggagtacct ggacctgtcc atgcccctgg accagtactc ccccagcttt   2340
cccgacaccc ggagctctac gtgctcctca ggggaggatt ccgtcttctc tcatgagccg   2400
ctgcccgagg agccctgcct gccccgacac ccagcccagc ttgccaatgg cggactcaaa   2460
cgccgctga                                                          2469
```

<210> SEQ ID NO 223
<211> LENGTH: 251
<212> TYPE: PRT
<213> ORGANISM: Homo sapiens

<400> SEQUENCE: 223

Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Met
                85                  90                  95

```
Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
210                 215                 220

Gly Val Val Arg Gly Gly Arg Val Asn Thr His Ala Gly Gly Thr Gly
225                 230                 235                 240

Pro Glu Gly Cys Arg Pro Phe Ala Lys Phe Ile
                245                 250
```

<210> SEQ ID NO 224
<211> LENGTH: 251
<212> TYPE: PRT
<213> ORGANISM: Homo sapiens

<400> SEQUENCE: 224

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30

Gly Ser Ser Trp Gly Gly Leu Ile His Leu Tyr Thr Ala Thr Ala Arg
        35                  40                  45

Asn Ser Tyr His Leu Gln Ile His Lys Asn Gly His Val Asp Gly Ala
    50                  55                  60

Pro His Gln Thr Ile Tyr Ser Ala Leu Met Ile Arg Ser Glu Asp Ala
65                  70                  75                  80

Gly Phe Val Val Ile Thr Gly Val Met Ser Arg Arg Tyr Leu Cys Thr
                85                  90                  95

Asp Phe Arg Gly Asn Ile Phe Gly Ser His Tyr Phe Asp Pro Glu Asn
                100                 105                 110

Cys Arg Phe Gln His Gln Thr Leu Glu Asn Gly Tyr Asp Val Tyr His
            115                 120                 125

Ser Pro Gln Tyr His Phe Leu Val Ser Leu Gly Arg Ala Lys Arg Ala
        130                 135                 140

Phe Leu Pro Gly Met Asn Pro Pro Tyr Ser Gln Phe Leu Ser Arg
145                 150                 155                 160

Arg Asn Glu Ile Pro Leu Ile His Phe Asn Thr Pro Ile Pro Arg Arg
                165                 170                 175

His Thr Arg Ser Ala Glu Asp Asp Ser Glu Arg Asp Pro Leu Asn Val
            180                 185                 190

Leu Lys Pro Arg Ala Arg Met Thr Pro Ala Pro Ala Ser Cys Ser Gln
        195                 200                 205

Glu Leu Pro Ser Ala Glu Asp Asn Ser Pro Met Ala Ser Asp Pro Leu
```

```
                    210                 215                 220
Gly Val Val Arg Gly Arg Val Asn Thr His Ala Gly Gly Thr Gly
225                 230                 235                 240

Pro Glu Gly Cys Arg Pro Phe Ala Lys Phe Ile
                245                 250

<210> SEQ ID NO 225
<211> LENGTH: 825
<212> TYPE: PRT
<213> ORGANISM: Homo sapiens

<400> SEQUENCE: 225

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
        50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Val Pro Ile Asp Ala Leu Pro Ser Ser
        115                 120                 125

Glu Asp Asp Asp Asp Asp Asp Ser Ser Ser Glu Glu Lys Glu Thr
130                 135                 140

Asp Asn Thr Lys Pro Asn Pro Val Ala Pro Tyr Trp Thr Ser Pro Glu
145                 150                 155                 160

Lys Met Glu Lys Lys Leu His Ala Val Pro Ala Ala Lys Thr Val Lys
                165                 170                 175

Phe Lys Cys Pro Ser Ser Gly Thr Pro Asn Pro Thr Leu Arg Trp Leu
            180                 185                 190

Lys Asn Gly Lys Glu Phe Lys Pro Asp His Arg Ile Gly Gly Tyr Lys
        195                 200                 205

Val Arg Tyr Ala Thr Trp Ser Ile Ile Met Asp Ser Val Val Pro Ser
    210                 215                 220

Asp Lys Gly Asn Tyr Thr Cys Ile Val Glu Asn Glu Tyr Gly Ser Ile
225                 230                 235                 240

Asn His Thr Tyr Gln Leu Asp Val Val Glu Arg Ser Pro His Arg Pro
                245                 250                 255

Ile Leu Gln Ala Gly Leu Pro Ala Asn Lys Thr Val Ala Leu Gly Ser
            260                 265                 270

Asn Val Glu Phe Met Cys Lys Val Tyr Ser Asp Pro Gln Pro His Ile
        275                 280                 285

Gln Trp Leu Lys His Ile Glu Val Asn Gly Ser Lys Ile Gly Pro Asp
    290                 295                 300

Asn Leu Pro Tyr Val Gln Ile Leu Lys His Ser Gly Ile Asn Ser Ser
305                 310                 315                 320

Asp Ala Glu Val Leu Thr Leu Phe Asn Val Thr Glu Ala Gln Ser Gly
                325                 330                 335
```

-continued

Glu Tyr Val Cys Lys Val Ser Asn Tyr Ile Gly Glu Ala Asn Gln Ser
            340                 345                 350

Ala Trp Leu Thr Val Thr Arg Pro Val Ala Lys Ala Leu Glu Glu Arg
        355                 360                 365

Pro Ala Val Met Thr Ser Pro Leu Tyr Leu Glu Ile Ile Tyr Cys
    370                 375                 380

Thr Gly Ala Phe Leu Ile Ser Cys Met Val Gly Ser Val Ile Val Tyr
385                 390                 395                 400

Lys Met Lys Ser Gly Thr Lys Lys Ser Asp Phe His Ser Gln Met Ala
                405                 410                 415

Val His Lys Leu Ala Lys Ser Ile Pro Leu Arg Arg Gln Val Thr Val
            420                 425                 430

Ser Ala Asp Ser Ser Ala Ser Met Asn Ser Gly Val Leu Leu Val Arg
        435                 440                 445

Pro Ser Arg Leu Ser Ser Ser Gly Thr Pro Met Leu Ala Gly Val Ser
    450                 455                 460

Glu Tyr Glu Leu Pro Glu Asp Pro Arg Trp Glu Leu Pro Arg Asp Arg
465                 470                 475                 480

Leu Val Leu Gly Lys Pro Leu Gly Glu Gly Cys Phe Gly Gln Val Val
                485                 490                 495

Leu Ala Glu Ala Ile Gly Leu Asp Lys Asp Lys Pro Asn Arg Val Thr
            500                 505                 510

Lys Val Ala Val Lys Met Leu Lys Ser Asp Ala Thr Glu Lys Asp Leu
        515                 520                 525

Ser Asp Leu Ile Ser Glu Met Glu Met Met Lys Met Ile Gly Lys His
    530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Gln Ala Arg Arg Pro Pro Gly Leu Glu Tyr Cys Tyr Asn Pro Ser His
            580                 585                 590

Asn Pro Glu Glu Gln Leu Ser Ser Lys Asp Leu Val Ser Cys Ala Tyr
        595                 600                 605

Gln Val Ala Arg Gly Met Glu Tyr Leu Ala Ser Lys Lys Cys Ile His
    610                 615                 620

Arg Asp Leu Ala Ala Arg Asn Val Leu Val Thr Glu Asp Asn Val Met
625                 630                 635                 640

Lys Ile Ala Asp Phe Gly Leu Ala Arg Asp Ile His His Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Ile Tyr Thr His Gln Ser Asp Val Trp Ser
        675                 680                 685

Phe Gly Val Leu Leu Trp Glu Ile Phe Thr Leu Gly Gly Ser Pro Tyr
    690                 695                 700

Pro Gly Val Pro Val Glu Glu Leu Phe Lys Leu Leu Lys Glu Gly His
705                 710                 715                 720

Arg Met Asp Lys Pro Ser Asn Cys Thr Asn Glu Leu Tyr Met Met Met
                725                 730                 735

Arg Asp Cys Trp His Ala Val Pro Ser Gln Arg Pro Thr Phe Lys Gln
            740                 745                 750

Leu Val Glu Asp Leu Asp Arg Ile Val Ala Leu Thr Ser Asn Gln Glu

-continued

```
                755                 760                 765
Tyr Leu Asp Leu Ser Met Pro Leu Asp Gln Tyr Ser Pro Ser Phe Pro
770                 775                 780

Asp Thr Arg Ser Ser Thr Cys Ser Ser Gly Glu Asp Ser Val Phe Ser
785                 790                 795                 800

His Glu Pro Leu Pro Glu Glu Pro Cys Leu Pro Arg His Pro Ala Gln
                805                 810                 815

Leu Ala Asn Gly Gly Leu Lys Arg Arg
                820                 825

<210> SEQ ID NO 226
<211> LENGTH: 821
<212> TYPE: PRT
<213> ORGANISM: Homo sapiens

<400> SEQUENCE: 226

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300
```

```
Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
            325                 330                 335

Ala Gly Glu Tyr Thr Cys Leu Ala Gly Asn Ser Ile Gly Ile Ser Phe
            340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
            370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
                420                 425                 430

Glu Ser Ser Ser Ser Met Asn Ser Asn Thr Pro Leu Val Arg Ile Thr
                435                 440                 445

Thr Arg Leu Ser Ser Thr Ala Asp Thr Pro Met Leu Ala Gly Val Ser
450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
                500                 505                 510

Thr Val Ala Val Lys Met Leu Lys Asp Asp Ala Thr Glu Lys Asp Leu
                515                 520                 525

Ser Asp Leu Val Ser Glu Met Glu Met Met Lys Met Ile Gly Lys His
530                 535                 540

Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Pro Gly Met Glu Tyr Ser Tyr Asp Ile Asn Arg
                580                 585                 590

Val Pro Glu Glu Gln Met Thr Phe Lys Asp Leu Val Ser Cys Thr Tyr
                595                 600                 605

Gln Leu Ala Arg Gly Met Glu Tyr Leu Ala Ser Gln Lys Cys Ile His
                610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
                660                 665                 670

Glu Ala Leu Phe Asp Arg Val Tyr Thr His Gln Ser Asp Val Trp Ser
                675                 680                 685

Phe Gly Val Leu Met Trp Glu Ile Phe Thr Leu Gly Gly Ser Pro Tyr
                690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
```

-continued

```
                725                 730                 735
Arg Asp Cys Trp His Ala Val Pro Ser Gln Arg Pro Thr Phe Lys Gln
            740                 745                 750

Leu Val Glu Asp Leu Asp Arg Ile Leu Thr Leu Thr Thr Asn Glu Glu
        755                 760                 765

Tyr Leu Asp Leu Ser Gln Pro Leu Glu Gln Tyr Ser Pro Ser Tyr Pro
    770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 227
<211> LENGTH: 822
<212> TYPE: PRT
<213> ORGANISM: Homo sapiens

<400> SEQUENCE: 227

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270
```

-continued

```
Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
        290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
        355                 360                 365

Glu Ile Thr Ala Ser Pro Asp Tyr Leu Glu Ile Ala Ile Tyr Cys Ile
    370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
        435                 440                 445

Thr Thr Arg Leu Ser Ser Thr Ala Asp Thr Pro Met Leu Ala Gly Val
    450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
        515                 520                 525

Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Arg Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
```

```
                    690                 695                 700

Tyr Pro Gly Ile Pro Val Glu Leu Phe Lys Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
                740                 745                 750

Gln Leu Val Glu Asp Leu Asp Arg Ile Leu Thr Leu Thr Asn Glu
            755                 760                 765

Glu Tyr Leu Asp Leu Ser Gln Pro Leu Glu Gln Tyr Ser Pro Ser Tyr
            770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
                820

<210> SEQ ID NO 228
<211> LENGTH: 806
<212> TYPE: PRT
<213> ORGANISM: Homo sapiens

<400> SEQUENCE: 228

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
            115                 120                 125

Pro Ser Ser Gly Asp Asp Glu Asp Gly Glu Asp Glu Ala Glu Asp Thr
        130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240
```

```
Tyr Thr Leu Asp Val Leu Glu Arg Ser Pro His Arg Pro Ile Leu Gln
            245                 250                 255
Ala Gly Leu Pro Ala Asn Gln Thr Ala Val Leu Gly Ser Asp Val Glu
        260                 265                 270
Phe His Cys Lys Val Tyr Ser Asp Ala Gln Pro His Ile Gln Trp Leu
    275                 280                 285
Lys His Val Glu Val Asn Gly Ser Lys Val Gly Pro Asp Gly Thr Pro
290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Leu Val Glu Ala Asp Glu
        355                 360                 365
Ala Gly Ser Val Tyr Ala Gly Ile Leu Ser Tyr Gly Val Gly Phe Phe
    370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
        515                 520                 525
Met Lys Met Ile Gly Lys His Lys Asn Ile Ile Asn Leu Leu Gly Ala
    530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
        595                 600                 605
Ala Ser Gln Lys Cys Ile His Arg Asp Leu Ala Ala Arg Asn Val Leu
    610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
```

```
                    660                 665                 670
His Gln Ser Asp Val Trp Ser Phe Gly Val Leu Leu Trp Glu Ile Phe
            675                 680                 685

Thr Leu Gly Gly Ser Pro Tyr Pro Gly Ile Pro Val Glu Glu Leu Phe
        690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 229
<211> LENGTH: 808
<212> TYPE: PRT
<213> ORGANISM: Homo sapiens

<400> SEQUENCE: 229

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220
```

-continued

```
Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
        260                 265                 270

Phe His Cys Lys Val Tyr Ser Asp Ala Gln Pro His Ile Gln Trp Leu
    275                 280                 285

Lys His Val Glu Val Asn Gly Ser Lys Val Gly Pro Asp Gly Thr Pro
290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Leu Val Glu Ala
        355                 360                 365

Asp Glu Ala Gly Ser Val Tyr Ala Gly Ile Leu Ser Tyr Gly Val Gly
370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
        450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
        610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
```

```
              645                 650                 655
Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
            675                 680                 685

Ile Phe Thr Leu Gly Gly Ser Pro Tyr Pro Gly Ile Pro Val Glu Glu
            690                 695                 700

Leu Phe Lys Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
            755                 760                 765

Phe Glu Gln Tyr Ser Pro Gly Gly Gln Asp Thr Pro Ser Ser Ser Ser
            770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805

<210> SEQ ID NO 230
<211> LENGTH: 802
<212> TYPE: PRT
<213> ORGANISM: Homo sapiens

<400> SEQUENCE: 230

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205
```

```
Leu Val Met Glu Ser Val Val Pro Ser Asp Arg Gly Thr Tyr Thr Cys
    210                 215                 220
Leu Val Glu Asn Ala Val Gly Ser Ile Arg Tyr Asn Tyr Leu Leu Asp
225                 230                 235                 240
Val Leu Glu Arg Ser Pro His Arg Pro Ile Leu Gln Ala Gly Leu Pro
                245                 250                 255
Ala Asn Thr Thr Ala Val Val Gly Ser Asp Val Glu Leu Leu Cys Lys
                260                 265                 270
Val Tyr Ser Asp Ala Gln Pro His Ile Gln Trp Leu Lys His Ile Val
        275                 280                 285
Ile Asn Gly Ser Ser Phe Gly Ala Asp Gly Phe Pro Tyr Val Gln Val
    290                 295                 300
Leu Lys Thr Ala Asp Ile Asn Ser Ser Glu Val Glu Val Leu Tyr Leu
305                 310                 315                 320
Arg Asn Val Ser Ala Glu Asp Ala Gly Glu Tyr Thr Cys Leu Ala Gly
                325                 330                 335
Asn Ser Ile Gly Leu Ser Tyr Gln Ser Ala Trp Leu Thr Val Leu Pro
                340                 345                 350
Glu Glu Asp Pro Thr Trp Thr Ala Ala Ala Pro Glu Ala Arg Tyr Thr
                355                 360                 365
Asp Ile Ile Leu Tyr Ala Ser Gly Ser Leu Ala Leu Ala Val Leu Leu
370                 375                 380
Leu Leu Ala Gly Leu Tyr Arg Gly Gln Ala Leu His Gly Arg His Pro
385                 390                 395                 400
Arg Pro Pro Ala Thr Val Gln Lys Leu Ser Arg Phe Pro Leu Ala Arg
                405                 410                 415
Gln Phe Ser Leu Glu Ser Gly Ser Ser Gly Lys Ser Ser Ser Ser Leu
                420                 425                 430
Val Arg Gly Val Arg Leu Ser Ser Ser Gly Pro Ala Leu Leu Ala Gly
                435                 440                 445
Leu Val Ser Leu Asp Leu Pro Leu Asp Pro Leu Trp Glu Phe Pro Arg
        450                 455                 460
Asp Arg Leu Val Leu Gly Lys Pro Leu Gly Glu Gly Cys Phe Gly Gln
465                 470                 475                 480
Val Val Arg Ala Glu Ala Phe Gly Met Asp Pro Ala Arg Pro Asp Gln
                485                 490                 495
Ala Ser Thr Val Ala Val Lys Met Leu Lys Asp Asn Ala Ser Asp Lys
                500                 505                 510
Asp Leu Ala Asp Leu Val Ser Glu Met Glu Val Met Lys Leu Ile Gly
        515                 520                 525
Arg His Lys Asn Ile Ile Asn Leu Leu Gly Val Cys Thr Gln Glu Gly
    530                 535                 540
Pro Leu Tyr Val Ile Val Glu Cys Ala Ala Lys Gly Asn Leu Arg Glu
545                 550                 555                 560
Phe Leu Arg Ala Arg Arg Pro Pro Gly Pro Asp Leu Ser Pro Asp Gly
                565                 570                 575
Pro Arg Ser Ser Glu Gly Pro Leu Ser Phe Pro Val Leu Val Ser Cys
                580                 585                 590
Ala Tyr Gln Val Ala Arg Gly Met Gln Tyr Leu Glu Ser Arg Lys Cys
                595                 600                 605
Ile His Arg Asp Leu Ala Ala Arg Asn Val Leu Val Thr Glu Asp Asn
        610                 615                 620
Val Met Lys Ile Ala Asp Phe Gly Leu Ala Arg Gly Val His His Ile
```

-continued

```
                625                 630                 635                 640
Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
            675                 680                 685

Pro Tyr Pro Gly Ile Pro Val Glu Glu Leu Phe Ser Leu Leu Arg Glu
            690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
            755                 760                 765

Gly Asp Ala Ser Ser Thr Cys Ser Ser Ser Asp Ser Val Phe Ser His
        770                 775                 780

Asp Pro Leu Pro Leu Gly Ser Ser Ser Phe Pro Phe Gly Ser Gly Val
785                 790                 795                 800

Gln Thr
```

<210> SEQ ID NO 231
<211> LENGTH: 1014
<212> TYPE: PRT
<213> ORGANISM: Mus musculus

<400> SEQUENCE: 231

```
Met Leu Ala Arg Ala Pro Pro Arg Arg Pro Pro Arg Leu Val Leu Leu
1               5                   10                  15

Arg Leu Leu Leu Leu His Leu Leu Leu Leu Ala Leu Arg Ala Arg Cys
            20                  25                  30

Leu Ser Ala Glu Pro Gly Gln Gly Ala Gln Thr Trp Ala Arg Phe Ala
        35                  40                  45

Arg Ala Pro Ala Pro Glu Ala Ala Gly Leu Leu His Asp Thr Phe Pro
    50                  55                  60

Asp Gly Phe Leu Trp Ala Val Gly Ser Ala Ala Tyr Gln Thr Glu Gly
65                  70                  75                  80

Gly Trp Arg Gln His Gly Lys Gly Ala Ser Ile Trp Asp Thr Phe Thr
                85                  90                  95

His His Ser Gly Ala Ala Pro Ser Asp Ser Pro Ile Val Val Ala Pro
            100                 105                 110

Ser Gly Ala Pro Ser Pro Pro Leu Ser Ser Thr Gly Asp Val Ala Ser
        115                 120                 125

Asp Ser Tyr Asn Asn Val Tyr Arg Asp Thr Glu Gly Leu Arg Glu Leu
    130                 135                 140

Gly Val Thr His Tyr Arg Phe Ser Ile Ser Trp Ala Arg Val Leu Pro
145                 150                 155                 160

Asn Gly Thr Ala Gly Thr Pro Asn Arg Glu Gly Leu Arg Tyr Tyr Arg
                165                 170                 175

Arg Leu Leu Glu Arg Leu Arg Glu Leu Gly Val Gln Pro Val Val Thr
            180                 185                 190

Leu Tyr His Trp Asp Leu Pro Gln Arg Leu Gln Asp Thr Tyr Gly Gly
```

```
            195                 200                 205
Trp Ala Asn Arg Ala Leu Ala Asp His Phe Arg Asp Tyr Ala Glu Leu
210                 215                 220

Cys Phe Arg His Phe Gly Gly Gln Val Lys Tyr Trp Ile Thr Ile Asp
225                 230                 235                 240

Asn Pro Tyr Val Val Ala Trp His Gly Tyr Ala Thr Gly Arg Leu Ala
                245                 250                 255

Pro Gly Val Arg Gly Ser Ser Arg Leu Gly Tyr Leu Val Ala His Asn
                260                 265                 270

Leu Leu Leu Ala His Ala Lys Val Trp His Leu Tyr Asn Thr Ser Phe
            275                 280                 285

Arg Pro Thr Gln Gly Gly Arg Val Ser Ile Ala Leu Ser Ser His Trp
290                 295                 300

Ile Asn Pro Arg Arg Met Thr Asp Tyr Asn Ile Arg Glu Cys Gln Lys
305                 310                 315                 320

Ser Leu Asp Phe Val Leu Gly Trp Phe Ala Lys Pro Ile Phe Ile Asp
                325                 330                 335

Gly Asp Tyr Pro Glu Ser Met Lys Asn Asn Leu Ser Ser Leu Leu Pro
                340                 345                 350

Asp Phe Thr Glu Ser Glu Lys Arg Leu Ile Arg Gly Thr Ala Asp Phe
            355                 360                 365

Phe Ala Leu Ser Phe Gly Pro Thr Leu Ser Phe Gln Leu Leu Asp Pro
370                 375                 380

Asn Met Lys Phe Arg Gln Leu Glu Ser Pro Asn Leu Arg Gln Leu Leu
385                 390                 395                 400

Ser Trp Ile Asp Leu Glu Tyr Asn His Pro Pro Ile Phe Ile Val Glu
                405                 410                 415

Asn Gly Trp Phe Val Ser Gly Thr Thr Lys Arg Asp Asp Ala Lys Tyr
                420                 425                 430

Met Tyr Tyr Leu Lys Lys Phe Ile Met Glu Thr Leu Lys Ala Ile Arg
            435                 440                 445

Leu Asp Gly Val Asp Val Ile Gly Tyr Thr Ala Trp Ser Leu Met Asp
450                 455                 460

Gly Phe Glu Trp His Arg Gly Tyr Ser Ile Arg Arg Gly Leu Phe Tyr
465                 470                 475                 480

Val Asp Phe Leu Ser Gln Asp Lys Glu Leu Leu Pro Lys Ser Ser Ala
                485                 490                 495

Leu Phe Tyr Gln Lys Leu Ile Glu Asp Asn Gly Phe Pro Pro Leu Pro
            500                 505                 510

Glu Asn Gln Pro Leu Glu Gly Thr Phe Pro Cys Asp Phe Ala Trp Gly
            515                 520                 525

Val Val Asp Asn Tyr Val Gln Val Asp Thr Thr Leu Ser Gln Phe Thr
530                 535                 540

Asp Pro Asn Val Tyr Leu Trp Asp Val His His Ser Lys Arg Leu Ile
545                 550                 555                 560

Lys Val Asp Gly Val Val Ala Lys Lys Arg Lys Pro Tyr Cys Val Asp
                565                 570                 575

Phe Ser Ala Ile Arg Pro Gln Ile Thr Leu Leu Arg Glu Met Arg Val
            580                 585                 590

Thr His Phe Arg Phe Ser Leu Asp Trp Ala Leu Ile Leu Pro Leu Gly
            595                 600                 605

Asn Gln Thr Gln Val Asn His Thr Val Leu His Phe Tyr Arg Cys Met
            610                 615                 620
```

Ile Ser Glu Leu Val His Ala Asn Ile Thr Pro Val Ala Leu Trp
625                 630                 635                 640

Gln Pro Ala Ala Pro His Gln Gly Leu Pro His Ala Leu Ala Lys His
            645                 650                 655

Gly Ala Trp Glu Asn Pro His Thr Ala Leu Ala Phe Ala Asp Tyr Ala
        660                 665                 670

Asn Leu Cys Phe Lys Glu Leu Gly His Trp Val Asn Leu Trp Ile Thr
    675                 680                 685

Met Asn Glu Pro Asn Thr Arg Asn Met Thr Tyr Arg Ala Gly His His
690                 695                 700

Leu Leu Arg Ala His Ala Leu Ala Trp His Leu Tyr Asp Asp Lys Phe
705                 710                 715                 720

Arg Ala Ala Gln Lys Gly Lys Ile Ser Ile Ala Leu Gln Ala Asp Trp
            725                 730                 735

Ile Glu Pro Ala Cys Pro Phe Ser Gln Asn Asp Lys Glu Val Ala Glu
        740                 745                 750

Arg Val Leu Glu Phe Asp Ile Gly Trp Leu Ala Glu Pro Ile Phe Gly
    755                 760                 765

Ser Gly Asp Tyr Pro Arg Val Met Arg Asp Trp Leu Asn Gln Lys Asn
770                 775                 780

Asn Phe Leu Leu Pro Tyr Phe Thr Glu Asp Glu Lys Lys Leu Val Arg
785                 790                 795                 800

Gly Ser Phe Asp Phe Leu Ala Val Ser His Tyr Thr Thr Ile Leu Val
            805                 810                 815

Asp Trp Glu Lys Glu Asp Pro Met Lys Tyr Asn Asp Tyr Leu Glu Val
        820                 825                 830

Gln Glu Met Thr Asp Ile Thr Trp Leu Asn Ser Pro Ser Gln Val Ala
    835                 840                 845

Val Val Pro Trp Gly Leu Arg Lys Val Leu Asn Trp Leu Arg Phe Lys
850                 855                 860

Tyr Gly Asp Leu Pro Met Tyr Val Thr Ala Asn Gly Ile Asp Asp Asp
865                 870                 875                 880

Pro His Ala Glu Gln Asp Ser Leu Arg Ile Tyr Tyr Ile Lys Asn Tyr
            885                 890                 895

Val Asn Glu Ala Leu Lys Ala Tyr Val Leu Asp Asp Ile Asn Leu Cys
        900                 905                 910

Gly Tyr Phe Ala Tyr Ser Leu Ser Asp Arg Ser Ala Pro Lys Ser Gly
    915                 920                 925

Phe Tyr Arg Tyr Ala Ala Asn Gln Phe Glu Pro Lys Pro Ser Met Lys
930                 935                 940

His Tyr Arg Lys Ile Ile Asp Ser Asn Gly Phe Leu Gly Ser Gly Thr
945                 950                 955                 960

Leu Gly Arg Phe Cys Pro Glu Glu Tyr Thr Val Cys Thr Glu Cys Gly
            965                 970                 975

Phe Phe Gln Thr Arg Lys Ser Leu Leu Val Phe Ile Ser Phe Leu Val
        980                 985                 990

Phe Thr Phe Ile Ile Ser Leu Ala  Leu Ile Phe His Tyr  Ser Lys Lys
    995                 1000                1005

Gly Gln  Arg Ser Tyr Lys
    1010

<210> SEQ ID NO 232
<211> LENGTH: 209

```
<212> TYPE: PRT
<213> ORGANISM: Homo sapiens

<400> SEQUENCE: 232

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Phe Ala
            195                 200                 205

Ser

<210> SEQ ID NO 233
<211> LENGTH: 209
<212> TYPE: PRT
<213> ORGANISM: Homo sapiens

<400> SEQUENCE: 233

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
            35                  40                  45

Leu Tyr Thr Asp Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
```

```
                130             135             140
His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Phe Glu
        195                 200                 205

Lys

<210> SEQ ID NO 234
<211> LENGTH: 42
<212> TYPE: PRT
<213> ORGANISM: Artificial
<220> FEATURE:
<223> OTHER INFORMATION: FGF21 Variant

<400> SEQUENCE: 234

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
                20                  25                  30

Ser Gln Gly Arg Ser Pro Ser Tyr Ala Lys
        35                  40

<210> SEQ ID NO 235
<211> LENGTH: 42
<212> TYPE: PRT
<213> ORGANISM: Artificial
<220> FEATURE:
<223> OTHER INFORMATION: FGF21 Variant

<400> SEQUENCE: 235

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
                20                  25                  30

Ser Gln Gly Arg Ser Pro Ser Tyr Glu Ser
        35                  40

<210> SEQ ID NO 236
<211> LENGTH: 42
<212> TYPE: PRT
<213> ORGANISM: Artificial
<220> FEATURE:
<223> OTHER INFORMATION: FGF21 Variant

<400> SEQUENCE: 236

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
                20                  25                  30

Ser Gln Gly Arg Ser Pro Ser Phe Ala Ser
        35                  40

<210> SEQ ID NO 237
<211> LENGTH: 42
<212> TYPE: PRT
<213> ORGANISM: Artificial
<220> FEATURE:
```

<223> OTHER INFORMATION: FGF21 Variant

<400> SEQUENCE: 237

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Val Arg Ser Pro Ser Tyr Ala Ser
        35                  40

<210> SEQ ID NO 238
<211> LENGTH: 42
<212> TYPE: PRT
<213> ORGANISM: Artificial
<220> FEATURE:
<223> OTHER INFORMATION: FGF21 Variant

<400> SEQUENCE: 238

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Ala Gly Arg Ser Pro Ser Tyr Ala Ser
        35                  40

<210> SEQ ID NO 239
<211> LENGTH: 42
<212> TYPE: PRT
<213> ORGANISM: Artificial
<220> FEATURE:
<223> OTHER INFORMATION: FGF21 Variant

<400> SEQUENCE: 239

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Glu Gln Gly Arg Ser Pro Ser Tyr Ala Ser
        35                  40

<210> SEQ ID NO 240
<211> LENGTH: 42
<212> TYPE: PRT
<213> ORGANISM: Artificial
<220> FEATURE:
<223> OTHER INFORMATION: FGF21 Variant

<400> SEQUENCE: 240

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Leu
            20                  25                  30

Ser Gln Gly Arg Ser Pro Ser Tyr Ala Ser
        35                  40

<210> SEQ ID NO 241
<211> LENGTH: 43
<212> TYPE: PRT
<213> ORGANISM: Artificial
<220> FEATURE:
<223> OTHER INFORMATION: FGF21 Variant

<400> SEQUENCE: 241

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Thr Gly
            20                  25                  30

Pro Ser Gln Gly Arg Ser Pro Ser Tyr Ala Ser
        35                  40

<210> SEQ ID NO 242
<211> LENGTH: 42
<212> TYPE: PRT
<213> ORGANISM: Artificial
<220> FEATURE:
<223> OTHER INFORMATION: FGF21 Variant

<400> SEQUENCE: 242

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Leu Val Gly Pro
            20                  25                  30

Ser Gln Gly Arg Ser Pro Ser Tyr Ala Ser
        35                  40

<210> SEQ ID NO 243
<211> LENGTH: 42
<212> TYPE: PRT
<213> ORGANISM: Artificial
<220> FEATURE:
<223> OTHER INFORMATION: FGF21 Variant

<400> SEQUENCE: 243

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Gly Met Val Gly Pro
            20                  25                  30

Ser Gln Gly Arg Ser Pro Ser Tyr Ala Ser
        35                  40

<210> SEQ ID NO 244
<211> LENGTH: 42
<212> TYPE: PRT
<213> ORGANISM: Artificial
<220> FEATURE:
<223> OTHER INFORMATION: FGF21 Variant

<400> SEQUENCE: 244

Pro Gly Leu Pro Pro Ala Leu Pro Glu Pro Gly Ile Leu Ala Pro
1               5                   10                  15

Gln Pro Pro Asp Val Gly Ser Ser Asp Pro Phe Ser Met Val Gly Pro
            20                  25                  30

Ser Gln Gly Arg Ser Pro Ser Tyr Ala Ser
        35                  40

<210> SEQ ID NO 245
<211> LENGTH: 42
<212> TYPE: PRT
<213> ORGANISM: Artificial
<220> FEATURE:
<223> OTHER INFORMATION: FGF21 Variant

<400> SEQUENCE: 245

Pro Gly Leu Pro Pro Ala Leu Pro Glu Pro Gly Ile Leu Ala Pro
1               5                   10                  15

Gln Pro Pro Asp Val Gly Ser Met Asp Pro Leu Ser Met Val Gly Pro
            20                  25                  30

Ser Gln Gly Arg Ser Pro Ser Tyr Ala Ser
        35                  40

<210> SEQ ID NO 246
<211> LENGTH: 42
<212> TYPE: PRT
<213> ORGANISM: Artificial
<220> FEATURE:
<223> OTHER INFORMATION: FGF21 Variant

<400> SEQUENCE: 246

Pro Gly Leu Pro Pro Ala Leu Pro Glu Pro Pro Gly Ile Leu Ala Pro
1               5                   10                  15

Gln Pro Pro Asp Val Asp Ser Ser Asp Pro Leu Ser Met Val Gly Pro
            20                  25                  30

Ser Gln Gly Arg Ser Pro Ser Tyr Ala Ser
        35                  40

<210> SEQ ID NO 247
<211> LENGTH: 42
<212> TYPE: PRT
<213> ORGANISM: Artificial
<220> FEATURE:
<223> OTHER INFORMATION: FGF21 Variant

<400> SEQUENCE: 247

Pro Gly Leu Pro Pro Ala Leu Pro Glu Pro Pro Gly Ile Leu Ala Pro
1               5                   10                  15

Gln Pro Pro Asp Thr Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 248
<211> LENGTH: 42
<212> TYPE: PRT
<213> ORGANISM: Artificial
<220> FEATURE:
<223> OTHER INFORMATION: FGF21 Variant

<400> SEQUENCE: 248

Pro Gly Leu Pro Pro Ala Leu Pro Glu Pro Pro Gly Ile Leu Ala Pro
1               5                   10                  15

Gln Pro Pro Glu Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 249
<211> LENGTH: 42
<212> TYPE: PRT
<213> ORGANISM: Artificial
<220> FEATURE:
<223> OTHER INFORMATION: FGF21 Variant

<400> SEQUENCE: 249

Pro Gly Leu Pro Pro Ala Leu Pro Glu Pro Pro Gly Ile Leu Ala Pro
1               5                   10                  15

Gln Pro Leu Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 250
<211> LENGTH: 42
<212> TYPE: PRT
<213> ORGANISM: Artificial
<220> FEATURE:
<223> OTHER INFORMATION: FGF21 Variant

<400> SEQUENCE: 250

Pro Gly Leu Pro Pro Ala Leu Pro Glu Pro Pro Gly Ile Leu Ala Pro
1               5                   10                  15

Ser Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 251
<211> LENGTH: 42
<212> TYPE: PRT
<213> ORGANISM: Artificial
<220> FEATURE:
<223> OTHER INFORMATION: FGF21 Variant

<400> SEQUENCE: 251

Pro Gly Leu Pro Pro Ala Leu Pro Glu Pro Pro Gly Ile Leu Ala Ser
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 252
<211> LENGTH: 42
<212> TYPE: PRT
<213> ORGANISM: Artificial
<220> FEATURE:
<223> OTHER INFORMATION: FGF21 Variant

<400> SEQUENCE: 252

Pro Gly Leu Pro Pro Ala Leu Pro Glu Pro Pro Gly Ile Leu Phe Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 253
<211> LENGTH: 42
<212> TYPE: PRT
<213> ORGANISM: Artificial
<220> FEATURE:
<223> OTHER INFORMATION: FGF21 Variant

<400> SEQUENCE: 253

Pro Gly Leu Pro Pro Ala Leu Pro Glu Pro Pro Gly Ile Met Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 254
<211> LENGTH: 42
<212> TYPE: PRT
<213> ORGANISM: Artificial
<220> FEATURE:
<223> OTHER INFORMATION: FGF21 Variant

<400> SEQUENCE: 254

Pro Gly Leu Pro Pro Ala Leu Pro Glu Pro Pro Gly Asp Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 255
<211> LENGTH: 42
<212> TYPE: PRT
<213> ORGANISM: Artificial
<220> FEATURE:
<223> OTHER INFORMATION: FGF21 Variant

<400> SEQUENCE: 255

Pro Gly Leu Pro Pro Ala Leu Pro Glu Pro Pro Ser Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 256
<211> LENGTH: 42
<212> TYPE: PRT
<213> ORGANISM: Artificial
<220> FEATURE:
<223> OTHER INFORMATION: FGF21 Variant

<400> SEQUENCE: 256

Pro Gly Leu Pro Pro Ala Leu Pro Glu Pro Glu Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 257
<211> LENGTH: 42
<212> TYPE: PRT
<213> ORGANISM: Artificial
<220> FEATURE:
<223> OTHER INFORMATION: FGF21 Variant

<400> SEQUENCE: 257

Pro Gly Leu Pro Pro Ala Leu Pro Glu Leu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 258

<211> LENGTH: 43
<212> TYPE: PRT
<213> ORGANISM: Artificial
<220> FEATURE:
<223> OTHER INFORMATION: FGF21 Variant

<400> SEQUENCE: 258

Pro Gly Leu Pro Pro Ala Leu Pro Glu His Pro Pro Gly Ile Leu Ala
1               5                   10                  15
Pro Gln Pro Pro Asp Val Gly Ser Ser Asp Pro Leu Ser Met Val Gly
            20                  25                  30
Pro Ser Gln Gly Arg Ser Pro Ser Tyr Ala Ser
        35                  40

<210> SEQ ID NO 259
<211> LENGTH: 43
<212> TYPE: PRT
<213> ORGANISM: Artificial
<220> FEATURE:
<223> OTHER INFORMATION: FGF21 Variant

<400> SEQUENCE: 259

Pro Gly Leu Pro Pro Ala Leu Pro Glu Gly Pro Pro Gly Ile Leu Ala
1               5                   10                  15
Pro Gln Pro Pro Asp Val Gly Ser Ser Asp Pro Leu Ser Met Val Gly
            20                  25                  30
Pro Ser Gln Gly Arg Ser Pro Ser Tyr Ala Ser
        35                  40

<210> SEQ ID NO 260
<211> LENGTH: 43
<212> TYPE: PRT
<213> ORGANISM: Artificial
<220> FEATURE:
<223> OTHER INFORMATION: FGF21 Variant

<400> SEQUENCE: 260

Pro Gly Leu Pro Pro Ala Leu Pro Glu Arg Pro Pro Gly Ile Leu Ala
1               5                   10                  15
Pro Gln Pro Pro Asp Val Gly Ser Ser Asp Pro Leu Ser Met Val Gly
            20                  25                  30
Pro Ser Gln Gly Arg Ser Pro Ser Tyr Ala Ser
        35                  40

<210> SEQ ID NO 261
<211> LENGTH: 43
<212> TYPE: PRT
<213> ORGANISM: Artificial
<220> FEATURE:
<223> OTHER INFORMATION: FGF21 Variant

<400> SEQUENCE: 261

Pro Gly Leu Pro Pro Ala Leu Pro Glu Leu Pro Pro Gly Ile Leu Ala
1               5                   10                  15
Pro Gln Pro Pro Asp Val Gly Ser Ser Asp Pro Leu Ser Met Val Gly
            20                  25                  30
Pro Ser Gln Gly Arg Ser Pro Ser Tyr Ala Ser
        35                  40

<210> SEQ ID NO 262
<211> LENGTH: 43
<212> TYPE: PRT
<213> ORGANISM: Artificial

<220> FEATURE:
<223> OTHER INFORMATION: FGF21 Variant

<400> SEQUENCE: 262

Pro Gly Leu Pro Pro Ala Leu Pro Glu Asp Pro Gly Ile Leu Ala
1               5                   10                  15

Pro Gln Pro Pro Asp Val Gly Ser Ser Asp Pro Leu Ser Met Val Gly
            20                  25                  30

Pro Ser Gln Gly Arg Ser Pro Ser Tyr Ala Ser
        35                  40

<210> SEQ ID NO 263
<211> LENGTH: 42
<212> TYPE: PRT
<213> ORGANISM: Artificial
<220> FEATURE:
<223> OTHER INFORMATION: FGF21 Variant

<400> SEQUENCE: 263

Pro Gly Leu Pro Pro Ala Glu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 264
<211> LENGTH: 42
<212> TYPE: PRT
<213> ORGANISM: Artificial
<220> FEATURE:
<223> OTHER INFORMATION: FGF21 Variant

<400> SEQUENCE: 264

Pro Gly Leu Pro Pro Glu Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 265
<211> LENGTH: 42
<212> TYPE: PRT
<213> ORGANISM: Artificial
<220> FEATURE:
<223> OTHER INFORMATION: FGF21 Variant

<400> SEQUENCE: 265

Pro Gly Leu Val Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 266
<211> LENGTH: 42
<212> TYPE: PRT
<213> ORGANISM: Artificial
<220> FEATURE:
<223> OTHER INFORMATION: FGF21 Variant -continued

<400> SEQUENCE: 266

Pro Gly Met Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 267
<211> LENGTH: 42
<212> TYPE: PRT
<213> ORGANISM: Artificial
<220> FEATURE:
<223> OTHER INFORMATION: FGF21 Variant

<400> SEQUENCE: 267

Pro Pro Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 268
<211> LENGTH: 42
<212> TYPE: PRT
<213> ORGANISM: Artificial
<220> FEATURE:
<223> OTHER INFORMATION: FGF21 Variant

<400> SEQUENCE: 268

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Glu Lys
        35                  40

<210> SEQ ID NO 269
<211> LENGTH: 42
<212> TYPE: PRT
<213> ORGANISM: Artificial
<220> FEATURE:
<223> OTHER INFORMATION: FGF21 Variant

<400> SEQUENCE: 269

Pro Gly Leu Pro Pro Ala Leu Pro Glu Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Phe Glu Lys
        35                  40

<210> SEQ ID NO 270
<211> LENGTH: 42
<212> TYPE: PRT
<213> ORGANISM: Artificial
<220> FEATURE:
<223> OTHER INFORMATION: FGF21 Variant

<400> SEQUENCE: 270

Pro Gly Leu Pro Pro Ala Leu Pro Glu Pro Pro Gly Ile Leu Ala Pro

```
                1               5                   10                  15
Gln Pro Pro Asp Val Gly Ser Ser Asp Pro Leu Ser Met Val Gly Pro
            20                  25                  30

Ser Gln Val Arg Ser Pro Ser Phe Glu Lys
            35                  40
```

<210> SEQ ID NO 271
<211> LENGTH: 42
<212> TYPE: PRT
<213> ORGANISM: Artificial
<220> FEATURE:
<223> OTHER INFORMATION: FGF21 Variant

<400> SEQUENCE: 271

```
Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Ala Val Arg Ser Pro Ser Phe Glu Lys
            35                  40
```

<210> SEQ ID NO 272
<211> LENGTH: 42
<212> TYPE: PRT
<213> ORGANISM: Artificial
<220> FEATURE:
<223> OTHER INFORMATION: FGF21 Variant

<400> SEQUENCE: 272

```
Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Glu Ala Val Arg Ser Pro Ser Phe Glu Lys
            35                  40
```

<210> SEQ ID NO 273
<211> LENGTH: 42
<212> TYPE: PRT
<213> ORGANISM: Artificial
<220> FEATURE:
<223> OTHER INFORMATION: FGF21 Variant

<400> SEQUENCE: 273

```
Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Gly Leu
            20                  25                  30

Glu Ala Val Arg Ser Pro Ser Phe Glu Lys
            35                  40
```

<210> SEQ ID NO 274
<211> LENGTH: 42
<212> TYPE: PRT
<213> ORGANISM: Artificial
<220> FEATURE:
<223> OTHER INFORMATION: FGF21 Variant

<400> SEQUENCE: 274

```
Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Met Val Thr Gly
```

Leu Glu Ala Val Arg Ser Pro Phe Glu Lys
        35                  40

<210> SEQ ID NO 275
<211> LENGTH: 43
<212> TYPE: PRT
<213> ORGANISM: Artificial
<220> FEATURE:
<223> OTHER INFORMATION: FGF21 Variant

<400> SEQUENCE: 275

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Ser Leu Val Thr Gly
            20                  25                  30

Leu Glu Ala Val Arg Ser Pro Ser Phe Glu Lys
        35                  40

<210> SEQ ID NO 276
<211> LENGTH: 43
<212> TYPE: PRT
<213> ORGANISM: Artificial
<220> FEATURE:
<223> OTHER INFORMATION: FGF21 Variant

<400> SEQUENCE: 276

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Leu Gly Leu Val Thr Gly
            20                  25                  30

Leu Glu Ala Val Arg Ser Pro Ser Phe Glu Lys
        35                  40

<210> SEQ ID NO 277
<211> LENGTH: 43
<212> TYPE: PRT
<213> ORGANISM: Artificial
<220> FEATURE:
<223> OTHER INFORMATION: FGF21 Variant

<400> SEQUENCE: 277

Pro Gly Leu Pro Pro Ala Leu Pro Glu Pro Pro Gly Ile Leu Ala Pro
1               5                   10                  15

Gln Pro Pro Asp Val Gly Ser Ser Asp Pro Phe Gly Leu Val Thr Gly
            20                  25                  30

Leu Glu Ala Val Arg Ser Pro Ser Phe Glu Lys
        35                  40

<210> SEQ ID NO 278
<211> LENGTH: 43
<212> TYPE: PRT
<213> ORGANISM: Artificial
<220> FEATURE:
<223> OTHER INFORMATION: FGF21 Variant

<400> SEQUENCE: 278

Pro Gly Leu Pro Pro Ala Leu Pro Glu Pro Pro Gly Ile Leu Ala Pro
1               5                   10                  15

Gln Pro Pro Asp Val Gly Ser Met Asp Pro Phe Gly Leu Val Thr Gly
            20                  25                  30

Leu Glu Ala Val Arg Ser Pro Ser Phe Glu Lys

<210> SEQ ID NO 279
<211> LENGTH: 43
<212> TYPE: PRT
<213> ORGANISM: Artificial
<220> FEATURE:
<223> OTHER INFORMATION: FGF21 Variant

<400> SEQUENCE: 279

Pro Gly Leu Pro Pro Ala Leu Pro Glu Pro Pro Gly Ile Leu Ala Pro
1               5                   10                  15

Gln Pro Pro Asp Val Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 280
<211> LENGTH: 43
<212> TYPE: PRT
<213> ORGANISM: Artificial
<220> FEATURE:
<223> OTHER INFORMATION: FGF21 Variant

<400> SEQUENCE: 280

Pro Gly Leu Pro Pro Ala Leu Pro Glu Pro Pro Gly Ile Leu Ala Pro
1               5                   10                  15

Gln Pro Pro Asp Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 281
<211> LENGTH: 43
<212> TYPE: PRT
<213> ORGANISM: Artificial
<220> FEATURE:
<223> OTHER INFORMATION: FGF21 Variant

<400> SEQUENCE: 281

Pro Gly Leu Pro Pro Ala Leu Pro Glu Pro Pro Gly Ile Leu Ala Pro
1               5                   10                  15

Gln Pro Pro Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 282
<211> LENGTH: 43
<212> TYPE: PRT
<213> ORGANISM: Artificial
<220> FEATURE:
<223> OTHER INFORMATION: FGF21 Variant

<400> SEQUENCE: 282

Pro Gly Leu Pro Pro Ala Leu Pro Glu Pro Pro Gly Ile Leu Ala Pro
1               5                   10                  15

Gln Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

```
<210> SEQ ID NO 283
<211> LENGTH: 43
<212> TYPE: PRT
<213> ORGANISM: Artificial
<220> FEATURE:
<223> OTHER INFORMATION: FGF21 Variant

<400> SEQUENCE: 283

Pro Gly Leu Pro Pro Ala Leu Pro Glu Pro Pro Gly Ile Leu Ala Pro
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 284
<211> LENGTH: 43
<212> TYPE: PRT
<213> ORGANISM: Artificial
<220> FEATURE:
<223> OTHER INFORMATION: FGF21 Variant

<400> SEQUENCE: 284

Pro Gly Leu Pro Pro Ala Leu Pro Glu Pro Pro Gly Ile Leu Ala Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 285
<211> LENGTH: 43
<212> TYPE: PRT
<213> ORGANISM: Artificial
<220> FEATURE:
<223> OTHER INFORMATION: FGF21 Variant

<400> SEQUENCE: 285

Pro Gly Leu Pro Pro Ala Leu Pro Glu Pro Pro Gly Ile Leu Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 286
<211> LENGTH: 43
<212> TYPE: PRT
<213> ORGANISM: Artificial
<220> FEATURE:
<223> OTHER INFORMATION: FGF21 Variant

<400> SEQUENCE: 286

Pro Gly Leu Pro Pro Ala Leu Pro Glu Pro Pro Gly Ile Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 287
<211> LENGTH: 43
<212> TYPE: PRT
```

<213> ORGANISM: Artificial
<220> FEATURE:
<223> OTHER INFORMATION: FGF21 Variant

<400> SEQUENCE: 287

Pro Gly Leu Pro Pro Ala Leu Pro Glu Pro Gly Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 288
<211> LENGTH: 43
<212> TYPE: PRT
<213> ORGANISM: Artificial
<220> FEATURE:
<223> OTHER INFORMATION: FGF21 Variant

<400> SEQUENCE: 288

Pro Gly Leu Pro Pro Ala Leu Pro Glu Pro Pro Ser Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 289
<211> LENGTH: 43
<212> TYPE: PRT
<213> ORGANISM: Artificial
<220> FEATURE:
<223> OTHER INFORMATION: FGF21 Variant

<400> SEQUENCE: 289

Pro Gly Leu Pro Pro Ala Leu Pro Glu Pro Glu Ser Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 290
<211> LENGTH: 43
<212> TYPE: PRT
<213> ORGANISM: Artificial
<220> FEATURE:
<223> OTHER INFORMATION: FGF21 Variant

<400> SEQUENCE: 290

Pro Gly Leu Pro Pro Ala Leu Pro Glu Leu Glu Ser Asp Met Phe Ser
1               5                   10                  15

Ser Pro Leu Glu Thr Asp Ser Met Asp Pro Phe Gly Leu Val Thr Gly
            20                  25                  30

Leu Glu Ala Val Arg Ser Pro Ser Phe Glu Lys
        35                  40

<210> SEQ ID NO 291
<211> LENGTH: 44
<212> TYPE: PRT
<213> ORGANISM: Artificial
<220> FEATURE:
<223> OTHER INFORMATION: FGF21 Variant

<400> SEQUENCE: 291

Pro Gly Leu Pro Pro Ala Leu Pro Glu His Leu Glu Ser Asp Met Phe
1               5                   10                  15

Ser Ser Pro Leu Glu Thr Asp Ser Met Asp Pro Phe Gly Leu Val Thr
            20                  25                  30

Gly Leu Glu Ala Val Arg Ser Pro Ser Phe Glu Lys
        35                  40

<210> SEQ ID NO 292
<211> LENGTH: 45
<212> TYPE: PRT
<213> ORGANISM: Artificial
<220> FEATURE:
<223> OTHER INFORMATION: FGF21 Variant

<400> SEQUENCE: 292

Pro Gly Leu Pro Pro Ala Leu Pro Glu Gly His Leu Glu Ser Asp Met
1               5                   10                  15

Phe Ser Ser Pro Leu Glu Thr Asp Ser Met Asp Pro Phe Gly Leu Val
            20                  25                  30

Thr Gly Leu Glu Ala Val Arg Ser Pro Ser Phe Glu Lys
        35                  40                  45

<210> SEQ ID NO 293
<211> LENGTH: 46
<212> TYPE: PRT
<213> ORGANISM: Artificial
<220> FEATURE:
<223> OTHER INFORMATION: FGF21 Variant

<400> SEQUENCE: 293

Pro Gly Leu Pro Pro Ala Leu Pro Glu Arg Gly His Leu Glu Ser Asp
1               5                   10                  15

Met Phe Ser Ser Pro Leu Glu Thr Asp Ser Met Asp Pro Phe Gly Leu
            20                  25                  30

Val Thr Gly Leu Glu Ala Val Arg Ser Pro Ser Phe Glu Lys
        35                  40                  45

<210> SEQ ID NO 294
<211> LENGTH: 47
<212> TYPE: PRT
<213> ORGANISM: Artificial
<220> FEATURE:
<223> OTHER INFORMATION: FGF21 Variant

<400> SEQUENCE: 294

Pro Gly Leu Pro Pro Ala Leu Pro Glu Leu Arg Gly His Leu Glu Ser
1               5                   10                  15

Asp Met Phe Ser Ser Pro Leu Glu Thr Asp Ser Met Asp Pro Phe Gly
            20                  25                  30

Leu Val Thr Gly Leu Glu Ala Val Arg Ser Pro Ser Phe Glu Lys
        35                  40                  45

<210> SEQ ID NO 295
<211> LENGTH: 48
<212> TYPE: PRT
<213> ORGANISM: Artificial
<220> FEATURE:
<223> OTHER INFORMATION: FGF21 Variant

<400> SEQUENCE: 295

-continued

Pro Gly Leu Pro Pro Ala Leu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 296
<211> LENGTH: 48
<212> TYPE: PRT
<213> ORGANISM: Artificial
<220> FEATURE:
<223> OTHER INFORMATION: FGF21 Variant

<400> SEQUENCE: 296

Pro Gly Leu Pro Pro Ala Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 297
<211> LENGTH: 48
<212> TYPE: PRT
<213> ORGANISM: Artificial
<220> FEATURE:
<223> OTHER INFORMATION: FGF21 Variant

<400> SEQUENCE: 297

Pro Gly Leu Pro Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 298
<211> LENGTH: 48
<212> TYPE: PRT
<213> ORGANISM: Artificial
<220> FEATURE:
<223> OTHER INFORMATION: FGF21 Variant

<400> SEQUENCE: 298

Pro Gly Leu Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 299
<211> LENGTH: 48
<212> TYPE: PRT
<213> ORGANISM: Artificial
<220> FEATURE:
<223> OTHER INFORMATION: FGF21 Variant

<400> SEQUENCE: 299

Pro Gly Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 300
<211> LENGTH: 48
<212> TYPE: PRT
<213> ORGANISM: Artificial
<220> FEATURE:
<223> OTHER INFORMATION: FGF21 Variant

<400> SEQUENCE: 300

Pro Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 301
<211> LENGTH: 48
<212> TYPE: PRT
<213> ORGANISM: Artificial
<220> FEATURE:
<223> OTHER INFORMATION: FGF19 Variant

<400> SEQUENCE: 301

Leu Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Ala Lys
        35                  40                  45

<210> SEQ ID NO 302
<211> LENGTH: 48
<212> TYPE: PRT
<213> ORGANISM: Artificial
<220> FEATURE:
<223> OTHER INFORMATION: FGF19 Variant

<400> SEQUENCE: 302

Leu Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Ser Ala Val Arg Ser Pro Ser Phe Glu Lys
        35                  40                  45

<210> SEQ ID NO 303
<211> LENGTH: 48
<212> TYPE: PRT
<213> ORGANISM: Artificial
<220> FEATURE:
<223> OTHER INFORMATION: FGF19 Variant

<400> SEQUENCE: 303

Leu Pro Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

```
Gly Met Val Thr Gly Leu Glu Ala Val Arg Ser Pro Ser Phe Glu Lys
            35                  40                  45

<210> SEQ ID NO 304
<211> LENGTH: 48
<212> TYPE: PRT
<213> ORGANISM: Artificial
<220> FEATURE:
<223> OTHER INFORMATION: FGF19 Variant

<400> SEQUENCE: 304

Leu Pro Met Val Pro Glu Glu Pro Glu Asp Leu Arg Gly His Leu Glu
1               5                   10                  15

Ser Asp Leu Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
            35                  40                  45

<210> SEQ ID NO 305
<211> LENGTH: 48
<212> TYPE: PRT
<213> ORGANISM: Artificial
<220> FEATURE:
<223> OTHER INFORMATION: FGF19 Variant

<400> SEQUENCE: 305

Leu Pro Met Val Pro Glu Glu Pro Glu Asp Leu Arg Gly His Pro Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
            35                  40                  45

<210> SEQ ID NO 306
<211> LENGTH: 47
<212> TYPE: PRT
<213> ORGANISM: Artificial
<220> FEATURE:
<223> OTHER INFORMATION: FGF19 Variant

<400> SEQUENCE: 306

Leu Pro Met Val Pro Glu Glu Pro Glu Asp Leu Arg His Leu Glu Ser
1               5                   10                  15

Asp Met Phe Ser Ser Pro Leu Glu Thr Asp Ser Met Asp Pro Phe Gly
            20                  25                  30

Leu Val Thr Gly Leu Glu Ala Val Arg Ser Pro Ser Phe Glu Lys
            35                  40                  45

<210> SEQ ID NO 307
<211> LENGTH: 47
<212> TYPE: PRT
<213> ORGANISM: Artificial
<220> FEATURE:
<223> OTHER INFORMATION: FGF19 Variant

<400> SEQUENCE: 307

Leu Pro Met Val Pro Glu Glu Pro Glu Asp Leu Gly His Leu Glu Ser
1               5                   10                  15

Asp Met Phe Ser Ser Pro Leu Glu Thr Asp Ser Met Asp Pro Phe Gly
            20                  25                  30

Leu Val Thr Gly Leu Glu Ala Val Arg Ser Pro Ser Phe Glu Lys
            35                  40                  45
```

-continued

<210> SEQ ID NO 308
<211> LENGTH: 48
<212> TYPE: PRT
<213> ORGANISM: Artificial
<220> FEATURE:
<223> OTHER INFORMATION: FGF19 Variant

<400> SEQUENCE: 308

Leu Pro Met Val Pro Ala Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 309
<211> LENGTH: 48
<212> TYPE: PRT
<213> ORGANISM: Artificial
<220> FEATURE:
<223> OTHER INFORMATION: FGF19 Variant

<400> SEQUENCE: 309

Leu Pro Met Pro Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 310
<211> LENGTH: 48
<212> TYPE: PRT
<213> ORGANISM: Artificial
<220> FEATURE:
<223> OTHER INFORMATION: FGF19 Variant

<400> SEQUENCE: 310

Leu Pro Leu Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 311
<211> LENGTH: 48
<212> TYPE: PRT
<213> ORGANISM: Artificial
<220> FEATURE:
<223> OTHER INFORMATION: FGF19 Variant

<400> SEQUENCE: 311

Leu Gly Met Val Pro Glu Glu Pro Glu Asp Leu Arg Gly His Leu Glu
1               5                   10                  15

Ser Asp Met Phe Ser Ser Pro Leu Glu Thr Asp Ser Met Asp Pro Phe
            20                  25                  30

Gly Leu Val Thr Gly Leu Glu Ala Val Arg Ser Pro Ser Phe Glu Lys
        35                  40                  45

<210> SEQ ID NO 312
<211> LENGTH: 187

```
<212> TYPE: PRT
<213> ORGANISM: Artificial
<220> FEATURE:
<223> OTHER INFORMATION: Chimeric Protein

<400> SEQUENCE: 312

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro Met Val Pro
130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 313
<211> LENGTH: 187
<212> TYPE: PRT
<213> ORGANISM: Artificial
<220> FEATURE:
<223> OTHER INFORMATION: Chimeric Protein

<400> SEQUENCE: 313

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Met Val Pro
130                 135                 140
```

```
Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 314
<211> LENGTH: 187
<212> TYPE: PRT
<213> ORGANISM: Artificial
<220> FEATURE:
<223> OTHER INFORMATION: Chimeric Protein

<400> SEQUENCE: 314

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Val Pro
130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 315
<211> LENGTH: 187
<212> TYPE: PRT
<213> ORGANISM: Artificial
<220> FEATURE:
<223> OTHER INFORMATION: Chimeric Protein

<400> SEQUENCE: 315

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
```

```
                65                  70                  75                  80
Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Glu Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 316
<211> LENGTH: 187
<212> TYPE: PRT
<213> ORGANISM: Artificial
<220> FEATURE:
<223> OTHER INFORMATION: Chimeric Protein

<400> SEQUENCE: 316

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Glu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 317
<211> LENGTH: 187
<212> TYPE: PRT
<213> ORGANISM: Artificial
<220> FEATURE:
<223> OTHER INFORMATION: Chimeric Protein

<400> SEQUENCE: 317
```

```
His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Asp Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175

Leu Glu Ala Val Arg Ser Pro Ser Phe Glu Lys
            180                 185

<210> SEQ ID NO 318
<211> LENGTH: 187
<212> TYPE: PRT
<213> ORGANISM: Artificial
<220> FEATURE:
<223> OTHER INFORMATION: Chimeric Protein

<400> SEQUENCE: 318

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Leu Arg Gly His Leu Glu Ser Asp Met Phe Ser
145                 150                 155                 160

Ser Pro Leu Glu Thr Asp Ser Met Asp Pro Phe Gly Leu Val Thr Gly
                165                 170                 175
```

Leu Glu Ala Val Arg Ser Pro Ser Phe Glu Lys
            180                 185

<210> SEQ ID NO 319
<211> LENGTH: 186
<212> TYPE: PRT
<213> ORGANISM: Artificial
<220> FEATURE:
<223> OTHER INFORMATION: Chimeric Protein

<400> SEQUENCE: 319

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Arg Gly His Leu Glu Ser Asp Met Phe Ser Ser
145                 150                 155                 160

Pro Leu Glu Thr Asp Ser Met Asp Pro Phe Gly Leu Val Thr Gly Leu
                165                 170                 175

Glu Ala Val Arg Ser Pro Ser Phe Glu Lys
            180                 185

<210> SEQ ID NO 320
<211> LENGTH: 185
<212> TYPE: PRT
<213> ORGANISM: Artificial
<220> FEATURE:
<223> OTHER INFORMATION: Chimeric Protein

<400> SEQUENCE: 320

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

```
Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Glu Pro Gly His Leu Glu Ser Asp Met Phe Ser Ser Pro
145                 150                 155                 160

Leu Glu Thr Asp Ser Met Asp Pro Phe Gly Leu Val Thr Gly Leu Glu
                165                 170                 175

Ala Val Arg Ser Pro Ser Phe Glu Lys
            180                 185

<210> SEQ ID NO 321
<211> LENGTH: 184
<212> TYPE: PRT
<213> ORGANISM: Artificial
<220> FEATURE:
<223> OTHER INFORMATION: Chimeric Protein

<400> SEQUENCE: 321

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
    130                 135                 140

Ala Leu Pro Glu Pro His Leu Glu Ser Asp Met Phe Ser Ser Pro Leu
145                 150                 155                 160

Glu Thr Asp Ser Met Asp Pro Phe Gly Leu Val Thr Gly Leu Glu Ala
                165                 170                 175

Val Arg Ser Pro Ser Phe Glu Lys
            180

<210> SEQ ID NO 322
<211> LENGTH: 183
<212> TYPE: PRT
<213> ORGANISM: Artificial
<220> FEATURE:
<223> OTHER INFORMATION: Chimeric Protein

<400> SEQUENCE: 322

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
```

```
                35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Leu Glu Ser Asp Met Phe Ser Ser Pro Leu Glu
145                 150                 155                 160

Thr Asp Ser Met Asp Pro Phe Gly Leu Val Thr Gly Leu Glu Ala Val
                165                 170                 175

Arg Ser Pro Ser Phe Glu Lys
            180

<210> SEQ ID NO 323
<211> LENGTH: 182
<212> TYPE: PRT
<213> ORGANISM: Artificial
<220> FEATURE:
<223> OTHER INFORMATION: Chimeric Protein

<400> SEQUENCE: 323

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                 20                  25                  30

Leu Glu Ile Arg Glu Asp Gly Thr Val Gly Gly Ala Ala Asp Gln Ser
             35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
130                 135                 140

Ala Leu Pro Glu Pro Glu Ser Asp Met Phe Ser Ser Pro Leu Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 324
<211> LENGTH: 182
<212> TYPE: PRT
```

```
<213> ORGANISM: Artificial
<220> FEATURE:
<223> OTHER INFORMATION: Chimeric Protein

<400> SEQUENCE: 324

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Ser Asp Met Phe Ser Ser Pro Leu Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 325
<211> LENGTH: 182
<212> TYPE: PRT
<213> ORGANISM: Artificial
<220> FEATURE:
<223> OTHER INFORMATION: Chimeric Protein

<400> SEQUENCE: 325

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140
```

Ala Leu Pro Glu Pro Pro Gly Asp Met Phe Ser Ser Pro Leu Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 326
<211> LENGTH: 182
<212> TYPE: PRT
<213> ORGANISM: Artificial
<220> FEATURE:
<223> OTHER INFORMATION: Chimeric Protein

<400> SEQUENCE: 326

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Met Phe Ser Ser Pro Leu Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 327
<211> LENGTH: 182
<212> TYPE: PRT
<213> ORGANISM: Artificial
<220> FEATURE:
<223> OTHER INFORMATION: Chimeric Protein

<400> SEQUENCE: 327

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

```
Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Phe Ser Ser Pro Leu Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 328
<211> LENGTH: 182
<212> TYPE: PRT
<213> ORGANISM: Artificial
<220> FEATURE:
<223> OTHER INFORMATION: Chimeric Protein

<400> SEQUENCE: 328

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Ser Ser Pro Leu Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 329
<211> LENGTH: 182
<212> TYPE: PRT
<213> ORGANISM: Artificial
<220> FEATURE:
<223> OTHER INFORMATION: Chimeric Protein

<400> SEQUENCE: 329

His Pro Ile Pro Asp Ser Ser Pro Leu Leu Gln Phe Gly Gly Gln Val
```

```
            1               5                   10                  15
        Arg Gln Arg Tyr Leu Tyr Thr Asp Asp Ala Gln Gln Thr Glu Ala His
                        20                  25                  30

Leu Glu Ile Arg Glu Asp Gly Thr Val Gly Gly Ala Ala Asp Gln Ser
                        35                  40                  45

Pro Glu Ser Leu Leu Gln Leu Lys Ala Leu Lys Pro Gly Val Ile Gln
                        50                  55                  60

Ile Leu Gly Val Lys Thr Ser Arg Phe Leu Cys Met Arg Pro Asp Gly
        65                  70                  75                  80

Ala Leu Tyr Gly Ser Leu His Phe Asp Pro Glu Ala Cys Ser Phe Arg
                        85                  90                  95

Glu Leu Leu Glu Asp Gly Tyr Asn Val Tyr Gln Ser Glu Ala His
                        100                 105                 110

Gly Leu Pro Leu His Leu Pro Gly Asn Lys Ser Pro His Arg Asp Pro
                        115                 120                 125

Ala Pro Arg Gly Pro Ala Arg Phe Leu Pro Leu Pro Gly Leu Pro Pro
                        130                 135                 140

Ala Leu Pro Glu Pro Pro Gly Ile Leu Ala Pro Ser Pro Leu Glu Thr
        145                 150                 155                 160

Asp Ser Met Asp Pro Phe Gly Leu Val Thr Gly Leu Glu Ala Val Arg
                        165                 170                 175

Ser Pro Ser Phe Glu Lys
                        180

<210> SEQ ID NO 330
<211> LENGTH: 182
<212> TYPE: PRT
<213> ORGANISM: Artificial
<220> FEATURE:
<223> OTHER INFORMATION: Chimeric Protein

<400> SEQUENCE: 330

His Pro Ile Pro Asp Ser Ser Pro Leu Leu Gln Phe Gly Gly Gln Val
        1               5                   10                  15

Arg Gln Arg Tyr Leu Tyr Thr Asp Asp Ala Gln Gln Thr Glu Ala His
                        20                  25                  30

Leu Glu Ile Arg Glu Asp Gly Thr Val Gly Gly Ala Ala Asp Gln Ser
                        35                  40                  45

Pro Glu Ser Leu Leu Gln Leu Lys Ala Leu Lys Pro Gly Val Ile Gln
                        50                  55                  60

Ile Leu Gly Val Lys Thr Ser Arg Phe Leu Cys Met Arg Pro Asp Gly
        65                  70                  75                  80

Ala Leu Tyr Gly Ser Leu His Phe Asp Pro Glu Ala Cys Ser Phe Arg
                        85                  90                  95

Glu Leu Leu Glu Asp Gly Tyr Asn Val Tyr Gln Ser Glu Ala His
                        100                 105                 110

Gly Leu Pro Leu His Leu Pro Gly Asn Lys Ser Pro His Arg Asp Pro
                        115                 120                 125

Ala Pro Arg Gly Pro Ala Arg Phe Leu Pro Leu Pro Gly Leu Pro Pro
                        130                 135                 140

Ala Leu Pro Glu Pro Pro Gly Ile Leu Ala Pro Gln Pro Leu Glu Thr
        145                 150                 155                 160

Asp Ser Met Asp Pro Phe Gly Leu Val Thr Gly Leu Glu Ala Val Arg
                        165                 170                 175

Ser Pro Ser Phe Glu Lys
```

```
                180

<210> SEQ ID NO 331
<211> LENGTH: 182
<212> TYPE: PRT
<213> ORGANISM: Artificial
<220> FEATURE:
<223> OTHER INFORMATION: Chimeric Protein

<400> SEQUENCE: 331

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Glu Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 332
<211> LENGTH: 182
<212> TYPE: PRT
<213> ORGANISM: Artificial
<220> FEATURE:
<223> OTHER INFORMATION: Chimeric Protein

<400> SEQUENCE: 332

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110
```

Gly Leu Pro Leu His Leu Pro Gly Asn Lys Ser Pro His Arg Asp Pro
                115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Thr
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 333
<211> LENGTH: 182
<212> TYPE: PRT
<213> ORGANISM: Artificial
<220> FEATURE:
<223> OTHER INFORMATION: Chimeric Protein

<400> SEQUENCE: 333

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
                115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Asp Ser Met Asp Pro Phe Gly Leu Val Thr Gly Leu Glu Ala Val Arg
                165                 170                 175

Ser Pro Ser Phe Glu Lys
            180

<210> SEQ ID NO 334
<211> LENGTH: 182
<212> TYPE: PRT
<213> ORGANISM: Artificial
<220> FEATURE:
<223> OTHER INFORMATION: Chimeric Protein

<400> SEQUENCE: 334

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

```
Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Phe Gly Leu Val Thr Gly Leu Glu Ala Val Arg
                165                 170                 175

Ser Pro Ser Phe Glu Lys
            180

<210> SEQ ID NO 335
<211> LENGTH: 182
<212> TYPE: PRT
<213> ORGANISM: Artificial
<220> FEATURE:
<223> OTHER INFORMATION: Chimeric Protein

<400> SEQUENCE: 335

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
                 20                  25                  30

Leu Glu Ile Arg Glu Asp Gly Thr Val Gly Gly Ala Ala Asp Gln Ser
             35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Met Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
            130                 135                 140

Ala Leu Pro Glu Pro Pro Gly Ile Leu Ala Pro Gln Pro Pro Asp Val
145                 150                 155                 160

Gly Ser Ser Asp Pro Leu Gly Leu Val Thr Gly Leu Glu Ala Val Arg
                165                 170                 175

Ser Pro Ser Phe Glu Lys
            180

<210> SEQ ID NO 336
<211> LENGTH: 182
<212> TYPE: PRT
<213> ORGANISM: Artificial
```

```
<220> FEATURE:
<223> OTHER INFORMATION: Chimeric Protein

<400> SEQUENCE: 336

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
                20                  25                  30

Leu Glu Ile Arg Glu Asp Gly Thr Val Gly Gly Ala Ala Asp Gln Ser
            35                  40                  45

Pro Glu Ser Leu Leu Gln Leu Lys Ala Leu Lys Pro Gly Val Ile Gln
        50                  55                  60

Ile Leu Gly Val Lys Thr Ser Arg Phe Leu Cys Met Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
                100                 105                 110

Gly Leu Pro Leu His Leu Pro Gly Asn Lys Ser Pro His Arg Asp Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Leu Val Thr Gly Leu Glu Ala Val Arg
                165                 170                 175

Ser Pro Ser Phe Glu Lys
                180
```